US010308708B2

(12) United States Patent
Marks et al.

(10) Patent No.: US 10,308,708 B2
(45) Date of Patent: Jun. 4, 2019

(54) ANTIBODIES THAT NEUTRALIZE BOTULINUM NEUROTOXINS

(71) Applicant: The Regents of the University of California, Oakland, CA (US)

(72) Inventors: James D. Marks, Kensington, CA (US); Isin N. Geren, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/238,419

(22) Filed: Aug. 16, 2016

(65) Prior Publication Data

US 2017/0096474 A1 Apr. 6, 2017

Related U.S. Application Data

(62) Division of application No. 14/634,355, filed on Feb. 27, 2015, now Pat. No. 9,453,068, which is a division of application No. 13/055,436, filed as application No. PCT/US2009/052314 on Jul. 30, 2009, now Pat. No. 9,000,131.

(60) Provisional application No. 61/085,328, filed on Jul. 31, 2008.

(51) Int. Cl.
*A61K 39/00* (2006.01)
*C07K 16/12* (2006.01)

(52) U.S. Cl.
CPC .... *C07K 16/1282* (2013.01); *A61K 2039/505* (2013.01); *A61K 2039/507* (2013.01); *C07K 2317/21* (2013.01); *C07K 2317/52* (2013.01); *C07K 2317/54* (2013.01); *C07K 2317/55* (2013.01); *C07K 2317/565* (2013.01); *C07K 2317/622* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 4,689,299 | A | 8/1987 | Insel et al. | |
| 5,231,003 | A | 7/1993 | Coughlin et al. | |
| 5,306,730 | A | 4/1994 | Nagai et al. | |
| 5,599,539 | A | 2/1997 | Carroll et al. | |
| 5,719,267 | A | 2/1998 | Carroll et al. | |
| 5,731,161 | A | 3/1998 | Aoki et al. | |
| 5,807,741 | A | 9/1998 | Brown et al. | |
| 5,919,665 | A | 7/1999 | Williams | |
| 5,932,449 | A | 8/1999 | Emanuel et al. | |
| 6,331,402 | B1 | 12/2001 | Nussbaum et al. | |
| 6,416,947 | B1 | 7/2002 | Balasubramanian et al. | |
| 6,461,617 | B1 | 10/2002 | Shone et al. | |
| 6,495,143 | B2 | 12/2002 | Lee et al. | |
| 6,656,468 | B1 | 12/2003 | Carroll et al. | |
| 6,667,158 | B1 | 12/2003 | Bavari et al. | |
| 6,730,324 | B2 | 5/2004 | Troczynski et al. | |
| 6,762,280 | B2 | 7/2004 | Schmidt et al. | |
| 6,794,128 | B2 | 9/2004 | Marks et al. | |
| 6,841,156 | B2 | 1/2005 | Aoki et al. | |
| 6,932,449 | B2 | 8/2005 | Collins et al. | |
| 7,049,085 | B2 | 5/2006 | Bavari et al. | |
| 7,081,529 | B2 | 7/2006 | Smith et al. | |
| 7,157,562 | B1 | 1/2007 | Olsen, II et al. | |
| 7,192,596 | B2 | 3/2007 | Shone et al. | |
| 7,214,787 | B1 | 5/2007 | Smith et al. | |
| 7,244,826 | B1 | 7/2007 | Marks et al. | |
| 7,332,580 | B2 | 2/2008 | Adams et al. | |
| 7,332,585 | B2 | 2/2008 | Adams et al. | |
| 7,341,843 | B2 | 3/2008 | Atassi | |
| 7,563,874 | B2 * | 7/2009 | Marks ................ | C07K 16/1282 424/130.1 |
| 7,700,738 | B2 * | 4/2010 | Marks ................ | C07K 16/1282 424/130.1 |
| 7,999,079 | B2 * | 8/2011 | Marks ................ | C07K 16/1282 424/130.1 |
| 8,198,034 | B2 | 6/2012 | Fernandez-Salas et al. | |
| 8,263,747 | B2 * | 9/2012 | Marks ................ | C07K 16/1282 424/130.1 |
| 8,299,218 | B2 * | 10/2012 | Marks ................ | C07K 16/1282 435/7.1 |
| 8,329,873 | B2 | 12/2012 | Adams et al. | |

(Continued)

FOREIGN PATENT DOCUMENTS

| | | |
|---|---|---|
| EP | 0578515 | 1/1994 |
| WO | WO 1994010332 | 5/1994 |

(Continued)

OTHER PUBLICATIONS

U.S. Appl. No. 12/468,526, filed May 19, 2009, issued as U.S. Pat. No. 8,299,218.
U.S. Appl. No. 12/528,601, filed Nov. 12, 2009, issued as U.S. Pat. No. 8,598,321.
U.S. Appl. No. 13/614,771, filed Sep. 13, 2012, Marks, et al.
U.S. Appl. No. 13/175,628, filed Jul. 1, 2011, Marks, et al.
Dong et al. (2010) "A Single-Domain Llama Antibody Potently Inhibits the Enzymatic Activity of Botulinum Neurotoxin by Binding to the Non-Catalytic Alpha-Exosite Binding Region" *J Mol Biol* 397(4):1106-1118.
Gilsdorf et al. (2006) "Expression Purification, and Characterization of Clostridium Botulinum Type B Light Chain" *Protein Expr Purif* 46(2):256-267.

(Continued)

*Primary Examiner* — Nita M. Minnifield
(74) *Attorney, Agent, or Firm* — Carol L. Francis; Bozicevic, Field & Francis LLP

(57) ABSTRACT

This disclosure provides antibodies that specifically bind to and typically neutralize botulinum neurotoxins (e.g., BoNT/A, BoNT/B, BoNT/E, etc.) and the epitopes bound by those antibodies. The antibodies and derivatives thereof and/or other antibodies that specifically bind to the neutralizing epitopes provided herein can be used to neutralize botulinum neurotoxin and are therefore also useful in the treatment of botulism.

19 Claims, 19 Drawing Sheets

Specification includes a Sequence Listing.

(56) References Cited

U.S. PATENT DOCUMENTS

| | | | | |
|---|---|---|---|---|
| 8,476,024 | B2 | 7/2013 | Mahrhold et al. | |
| 8,598,321 | B2 * | 12/2013 | Marks | C07K 16/1282 424/130.1 |
| 8,821,879 | B2 * | 9/2014 | Babuka | A61K 39/39591 424/164.1 |
| 9,000,131 | B2 * | 4/2015 | Marks | C07K 16/1282 424/130.1 |
| 9,023,352 | B2 | 5/2015 | Shoemaker et al. | |
| 9,181,330 | B2 * | 11/2015 | Marks | C07K 16/1282 |
| 9,243,057 | B2 | 1/2016 | Marks | |
| 9,249,216 | B2 | 2/2016 | Fernandez-Salas | |
| 9,273,057 | B2 * | 3/2016 | Purandare | A61K 31/53 |
| 9,453,068 | B2 * | 9/2016 | Marks | C07K 16/1282 |
| 9,834,616 | B2 * | 12/2017 | Shoemaker | A61K 39/39591 |
| 9,902,780 | B2 * | 2/2018 | Marks | C07K 16/1282 |
| 9,902,781 | B2 * | 2/2018 | Marks | C07K 16/1282 |
| 2002/0155114 | A1 * | 10/2002 | Marks | C07K 16/1282 424/150.1 |
| 2004/0009172 | A1 | 1/2004 | Fischkoff et al. | |
| 2004/0137601 | A1 | 7/2004 | Von Eichel-Streiber et al. | |
| 2004/0175385 | A1 * | 9/2004 | Marks | C07K 16/1282 424/164.1 |
| 2004/0265935 | A1 | 12/2004 | Atassi | |
| 2005/0147610 | A1 | 7/2005 | Ghayur et al. | |
| 2006/0147471 | A1 | 7/2006 | Borodic et al. | |
| 2006/0177881 | A1 | 8/2006 | Bavari et al. | |
| 2006/0246071 | A1 | 11/2006 | Green et al. | |
| 2006/0251658 | A1 | 11/2006 | Ledbetter et al. | |
| 2008/0125328 | A1 | 5/2008 | Wyrick et al. | |
| 2009/0117587 | A1 | 5/2009 | Stanker | |
| 2009/0123481 | A1 | 5/2009 | Marks et al. | |
| 2009/0324606 | A1 | 12/2009 | Marks et al. | |
| 2010/0150934 | A1 | 6/2010 | Pomato | |
| 2010/0166773 | A1 | 7/2010 | Marks et al. | |
| 2010/0222555 | A1 | 9/2010 | Dessain et al. | |
| 2011/0059079 | A1 | 3/2011 | Babuka et al. | |
| 2012/0121581 | A1 | 5/2012 | Babuka et al. | |
| 2012/0177663 | A1 | 7/2012 | Marks et al. | |
| 2012/0225436 | A1 | 9/2012 | Fernandez-Salas et al. | |
| 2012/0269822 | A1 | 10/2012 | Marks et al. | |
| 2013/0040368 | A1 | 2/2013 | Fernandez-Salas et al. | |
| 2014/0105910 | A1 | 4/2014 | Marks | |
| 2015/0030600 | A1 | 1/2015 | Marks | |
| 2015/0197559 | A1 * | 7/2015 | Marks | C07K 16/1282 424/167.1 |
| 2016/0168265 | A1 * | 6/2016 | Marks | C07K 16/1282 424/158.1 |
| 2016/0229921 | A1 | 8/2016 | Marks | |
| 2016/0362501 | A1 | 12/2016 | Shoemaker | |
| 2017/0096474 | A1 * | 4/2017 | Marks | C07K 16/1282 |
| 2018/0208679 | A1 * | 7/2018 | Marks | C07K 16/1282 |
| 2018/0208680 | A1 * | 7/2018 | Marks | G01N 33/573 |

FOREIGN PATENT DOCUMENTS

| | | |
|---|---|---|
| WO | WO 1996025669 | 8/1996 |
| WO | WO 1999056129 | 11/1999 |
| WO | WO 2000069891 | 11/2000 |
| WO | WO 2000069895 | 11/2000 |
| WO | WO 2001019992 | 3/2001 |
| WO | WO 2003057857 | 7/2003 |
| WO | WO 2004106376 | 12/2004 |
| WO | WO 2005084361 | 9/2005 |
| WO | WO 2005118635 | 12/2005 |
| WO | 2006124269 | 11/2006 |
| WO | WO 2007094754 | 8/2007 |
| WO | WO 2008097866 | 8/2008 |
| WO | 2009008916 | 1/2009 |
| WO | WO 2009105150 | 8/2009 |
| WO | WO 2009131605 | 10/2009 |
| WO | 2010004434 | 1/2010 |
| WO | WO 2011028961 | 3/2011 |
| WO | WO 2011028962 | 3/2011 |
| WO | 2012047427 | 4/2012 |

OTHER PUBLICATIONS

Goldman et al. (2008) "Thermostable Llama Single Domain Antibodies for Detection of Botulinum A Neurotoxin Complex" *Anal Chem* 80(22):8583-8591.

Lee et al. (2008) "Production and characterization of monoclonal antibody to botulinum neurotoxin type B light chain by phage display" *Hybridoma* (*Larchmt*) 27(1):18-24.

Liu et al. (2007) "Isolation of Anti-Toxin Single Domain Antibodies from a Semi-Synthetic Spiny Dogfish Shark Display Library" *BMC Biotechnol* 7:78.

Meng et al. (2012) "Engineered domain-based assays to identify individual antibodies in oligoclonal combinations targeting the same protein" *Anal Biochem* 430(2):141-150.

Padlan et al. (1989) "Structure of an antibody-antigen complex: crystal structure of the HyHEL-10 Fab-lysozyme complex" *Proc Natl Acad Sci USA* 86:5938-5942.

Swaminathan & Eswaramoorthy (2000) "Structural Analysis of the Catalytic and Binding Sites of Clostridium Botulinum Neurotoxin B" *Nat Struct Biol* 7(8):693-699.

Thanongsaksrikul et al. (2010) "A V H H That Neutralizes the Zinc Metalloproteinase Activity of Botulinum Neurotoxin Type A" *J Biol Chem* 285(13):9657-9666.

Yang et al. (2004) "Isolation and characterization of a neutralizing antibody specific to internalization domain of Clostridium botulinum neurotoxin type B" *Toxicon* 44(1):19-25.

Amersdorfer & Marks (2000) "Phage libraries for generation of anti-botulinum scFv antibodies" *Meth. Mol. Biol.* 145:219-240.

Arndt, et al. (2005) "The structure of the neurotoxin-associated protein HA33/A from *Clostridium botulinum* suggests a reoccurring beta-trefoil fold in the progenitor toxin complex" *J. Mol. Biol.* 346(4):1083-1093.

Baldwin, et al. (2005) "Characterization of the antibody response to the receptor binding domain of botulinum neurotoxin serotypes A and E" *Infect. Immun.* 73(10): 6998-7005.

Bartels, et al. (1994) "Specific antibodies against the Zn(2+)-binding domain of clostridial neurotoxins restore exocytosis in chromaffin cells treated with tetanus or botulinum A neurotoxin" *J. Biol. Chem.* 269(11): 8122-8127.

Bendig (1995) "Humanization of Rodent Monoclonal Antibodies by CDR Grafting" *METHODS: Companion to Methods in Enzymology* 8:83-93.

Berzofsky, et al. (1993) "Immunogenicity and Antigen Structure" *Fundamental Immunology* 3rd edition, Ed. William E. Paul, Chapter 8, p. 242.

Black & Dolly (1986) "Interaction of 125I-labeled botulinum neurotoxins with nerve terminals. I. Ultrastructural autoradiographic localization and quantitation of distinct membrane acceptors for types A and B on motor nerves" *J. Cell Biol.* 103(2):521-534.

Bowmer (1963) "Preparation and Assay of the International Standards for *Clostridium botulinum* Types A, B, C, D and E Antitoxins" *Bull. World Health Organ.* 29:701-709.

Brown, et al. (1997) "Identification and Characterization of a Neutralizing Monoclonal Antibody against Botulinum Neurotoxin Serotype F, Following Vaccination with Active Toxin" *Hybridoma* 16(5):447-456.

Byrne & Smith (2000) "Development of vaccines for prevention of botulism" *Biochimie* 82(9-10): 955-966.

Casset, et al. (2003) "A peptide mimetic of an anti-CD4 monoclonal antibody by rational design" *Biochem Biophys. Res Comm.* 307(1): 198-205.

Cenci Di Bello, et al. (1994) "Antagonism of the Intracellular Action of Botulinum Neurotoxin Type A with Monoclonal Antibodies That Map to Light-Chain Epitopes" Eur. J. Biochem. 219(1-2):161-169.

Chen, et al. (1998) "Biophysical characterization of the stability of the 150-kilodalton botulinum toxin, the nontoxic component, and the 900-kilodalton botulinum toxin complex species" *Infect. Immun.* 66(6):2420-2425.

Colcher et al. (1990) "In vivo tumor targeting of a recombinant single-chain antigen-binding protein" *J. Natl. Cancer Inst.* 82(14):1191-1197.

(56) References Cited

OTHER PUBLICATIONS

Daniels-Holgate & Dolly (1996) "Productive and non-productive binding of botulinum neurotoxin A to motor nerve endings are distinguished by its heavy chain" *J. Neurosci. Res.* 44(3):263-271.
Dixit et al. (2005) "Characterization of *Clostridium* sp. RKD producing botulinum-like Neurotoxin" *Syst. Appl. Microbiol.* 28(5):405-414.
Dixit et al. (2006) Development of an immunodetection test for a botulinum-like neurotoxin produced by *Clostridium* sp. *Indian J Med Res.* 124(3):355-362.
Doellgast, et al. (1993) "Sensitive enzyme-linked immunosorbent assay for detection of *Clostridium botulinum* neurotoxins A, B, and E using signal amplification via enzyme-linked coagulation assay" *J. Clin. Microbiol.* 31(9):2402-2409.
Doellgast, et al. (1997) "Sensitive assay for measurement of antibodies to *Clostridium botulinum* neurotoxins A, B, and E: use of hapten-labeled-antibody elution to isolate specific complexes" *J. Clin. Microbiol.* 35(3):578-583.
Dolly, et al. (1984) "Acceptors for botulinum neurotoxin reside on motor nerve terminals and mediate its internalization" *Nature* (*London*) 307(5950):457-460.
Emanuel, et al. (1996) "Directing antigen specificity towards botulinum neurotoxin with combinatorial phage display libraries" *J. Immunol. Meth.* 193(2):189-197.
Ferreira, et al. (1987) "Monoclonal Antibody for the Detection of *Clostridium botulinum* Type A toxin" *Mol. Cell Probes* 1(4):337-345.
Ferreira, et al. (1990) "Monoclonal antibody to type F *Clostridium botulinum* toxin" *Appl. Environ Microbiol.* 56(3):808-811.
Fitzsimmons, et al. (2000) "Inhibition of tetanus toxin fragment C binding to ganglioside G(Tlb) by monoclonal antibodies recognizing different epitopes" *Vaccine* 19(1):114-121.
Foote & Milstein (1991) "Kinetic maturation of an immune response" *Nature* 352(6335):530-532.
Fotinou, et al. (2001) "The crystal structure of tetanus toxin Hc fragment complexed with a synthetic GT1b analogue suggests cross-linking between ganglioside receptors and the toxin" *J. Biol. Chem.* 276(34):32274-32281.
Garcia-Rodriguez, et al. (2007) "Molecular evolution of antibody specificity and cross reactivity for type A botulinum neurotoxins" *Nature Biotech.* 25(1):107-116.
Gibson, et al. (1988) "Evaluation of a monoclonal antibody-based immunoassay for detecting type B *Clostridium botulinum* toxin produced in pure culture and an inoculated model cured meat system" *J. Appl. Bacterial.* 64(4):285-291.
Gill (1982) "Bacterial Toxins: A Table of Lethal Amounts" *Mol. Biol. Rev.* 46(1):86-94.
Hallis, et al. (1993) "Characterization of Monoclonal Antibodies to Botulinum" *Botulinum and Tetanus Neurotoxins: Neurotransmission and Biomedical Aspects*, ed. DasGupta, B. R. Plenum, New York., pp. 433-436.
Hathaway, et al. (1984) "Antitoxin levels in botulism patients treated with trivalent equine botulism antitoxin to toxin types A, B, and E" *J. Infect. Dis.* 150(3):407-412.
Hatheway & Dang (1994) "Immunogenicity of the Neurotoxins of *Clostridium botulinum*" *Therapy with Botulinum Toxin* ed. Jankovic & Hallet, Marcel Dekker, New York, pp. 93-107.
Hildebrand & Archer (1961) "Evidence Concerning Liquid Structure" *PNAS USA* 47(12):1881-1882.
Hildebrand, et al. (1961) "Distribution and Particle Size of Type A Botulinum Toxin in Body Fluids of Intravenously Injected Rabbits" *Proc. Soc. Exp. Biol. Med.* 107(2):284-289.
Huston, et al. (1996) "Single-chain Fv radioimmunotargeting" Q. J. Nucl. Med. 40(3):320-333.
Koriazova & Montal (2003) "Translocation of botulinum neurotoxin light chain protease through the heavy chain channel" *Nat. Struct. Biol.* 10(1):13-18.
Kozaki, et al. (1986) "The use of monoclonal antibodies to analyze the structure of *Clostridium botulinum* type E derivative toxin" *Infect Immun.* 52(3):786-791.
Lacy, et al. (1998) "Crystal structure of botulinum neurotoxin type A and implications for toxicity" *Nat. Struct. Biol.* 5(10): 898-902.
Lang, et al. (1993) "Immunotherapy with human monoclonal antibodies. Fragment A specificity of polyclonal and monoclonal antibodies is crucial for full protection against tetanus toxin" *J. Immunol.* 151(13):466-472.
Levy, et al. (2007) "Fine and domain-level epitope mapping of botulinum neurotoxin type A neutralizing antibodies by yeast surface display" *J. Mol. Biol.* 365(1):196-210.
Lipps & Khan (2000) "Antigenic cross reactivity among the venoms and toxins from unrelated diverse sources" *Toxicon.* 38(7):973-980.
MacCallum, et al. (1996) "Antibody-antigen Interactions: Contact Analysis and Binding Site Topography" *J. Mol. Biol.* 262(5):732-45.
Mahant, et al. (2000) "The current use of botulinum toxin" *J. Clin. Neurosci.* 7(5):389-394.
Marchev & Marcheva (1982) "[Production of Mono Specific Type A Botulinum Toxin and Antiserum Using a Column Chromatographic Method]" *Vet. Med. Nauki.* 19(1):57-63.
Middlebrook & Brown (1995) "Immunodiagnosis and immunotherapy of tetanus and botulinum neurotoxins" *Curr. Top. Microbiol. Immunol.* 195:89-122.
Montecucco & Schiavo (1995) "Structure and function of tetanus and botulinum neurotoxins" *Q. Rev. Biophys.* 28(4):423-472.
Montecucco (1986) "How do Tetanus and Botulinum Toxins Bind to Neuronal Membranes?" *Trends Biochem. Sci.* 11(8):314-317.
Montero-Julian, et al. (1995) "Pharmacokinetic study of anti-interleukin-6 (IL-6) therapy with monoclonal antibodies: enhancement of IL-6 clearance by cocktails of anti-IL-6 antibodies" *Blood* 85(4): 917-924.
Noah, et al. (1995) "Production of Monoclonal Antibodies Specific to *Clostridium botulinum* Type B Neurotoxin" *J. AOAC Int.* 78(2):381-385.
O'Connell, et al. (2007) "Production of a recombinant antibody fragment in whole insect larvae" *Mol Biotechnol.* 36(1): 44-51.
Oguma, et al. (1982) "Four different monoclonal antibodies against type C1 toxin of *Clostridium botulinum* " *Infect. Immun.* 38(1):14-20.
Oguma, et al. (1984) "Analysis of antigenicity of *Clostridium botulinum* type C1 and D toxins by polyclonal and monoclonal antibodies" *Infect Immun.* 43(2):584-588.
Palys, et al. (2006) "Conversion of a mouse Fab into a whole humanized IgG antibody for detecting botulinum toxin" *Hum Antibodies* 15(4):125-132.
Park, et al. (2003) "Immunologic characterization of spasmodic dysphonia patients who develop resistance to botulinum toxin" *J. Voice.* 17(2):255-264.
Pless, et al. (2001) "High-affinity, protective antibodies to the binding domain of botulinum neurotoxin type A" *Infect. Immun.* 69(1):570-574.
Reichert (2001) "Monoclonal antibodies in the clinic" *Nat. Biotechnol.* 19(9):819-822.
Schengrund (1999) "What is the Cell Surface Receptor(s) for the Different Serotypes of Botulinum Neurotoxin?" *J Toxicol.—Toxin Rev.* 18(1):35-44.
Schiavo, et al. (1992) "Tetanus and botulinum-B neurotoxins block neurotransmitter release by proteolytic cleavage of synaptobrevin" *Nature* (*London*) 359(6398):832-835.
Schiavo, et al. (1993) "Identification of the nerve terminal targets of botulinum neurotoxin serotypes A, D, and E" *J. Biol. Chem.* 268(32):23784-23787.
Schier, et al. (1995) "In vitro and in vivo characterization of a human anti-c-eibB-2 single-chain Fv isolated from a filementous phage antibody library" *Immunotechnology*, 1(1):73-81.
Schmidt & Stafford (2005) "Botulinum neurotoxin serotype F: identification of substrate recognition requirements and development of inhibitors with low nanomolar affinity" *Biochemistry* 44(10):4067-4073.
Sharma, et al. (2006) "Detection of type A, B, E, and F Clostridium botulinum neurotoxins in foods by using an amplified enzyme-linked immunosorbent assay with digoxigenin-labeled antibodies" Appl Environ. Microbiol. 72(2):1231-1238.

(56) References Cited

OTHER PUBLICATIONS

Simpson (1980) "Kinetic studies on the interaction between botulinum toxin type A and the cholinergic neuromuscular junction" *J. Pharmacol. Exp. Ther.* 212(1):16-21.
Tacket et al. (1984) "Equine antitoxin use and other factors that predict outcome in type A foodborne botulism" *Am. J. Med.* 76(5):794-798.
Tsuzuki, et al. (1988) "Establishment of a monoclonal antibody recognizing an antigenic site common to *Clostridium botulinum* type B, C1, D, and E toxins and tetanus toxin" *Infect Immun.* 56(4):898-902.
Volk, et al. (1984) "Neutralization of tetanus toxin by distinct monoclonal antibodies binding to multiple epitopes on the toxin molecule" *Infect. Immun.* 45(3):604-609.
Williams, et al. (1983) "Radioiodination of botulinum neurotoxin type A with retention of biological activity and its binding to brain synaptosomes" *Eur. J. Biochem.*, 131(2):437-445.
Wu, et al. (2001) "Characterization of neutralizing antibodies and identification of neutralizing epitope mimics on the *Clostridium botulinum* neurotoxin type A" *Appl. Environ. Microbiol.* 67(7):3201-3207.
Zwick, et al. (2001) "Neutralization synergy of human immunodeficiency virus type 1 primary isolates by cocktails of broadly neutralizing antibodies" *J. Virol.* 75(24):12198-12208.
Almquist, et al. (2006) "Expression of an anti-botulinum toxin A neutralizing single-chain Fv recombinant antibody in transgenic tobacco" *Vaccine* 24(12):2079-2086.
Amersdorfer (1997) "Molecular Characterization of Murine Humoral Immune Response to Botulinum Neurotoxin Type A Binding Domain as Assessed by Using Phage Antibody Libraries" *Infect. Immun.* 65(9):3743-3752.
Amersdorfer, et al. (2002) "Genetic and Immunological Comparison of Anti-Botulinum Type A Antibodies from Immune and Non-Immune Human Phage Libraries" *Vaccine* 20(11-12):1640-1648.
Atassi, et al. (1996) "Mapping of the Antibody-Binding Regions on Botulinum Neurotoxin H-Chain Domain 855-1296 with Antitoxin Antibodies from Three Host Species" *J. Protein Chem.* 15(7):691-699.
Bavari, et al. (1998) "Identifying the principal protective antigenic determinants of type A botulinum neurotoxin" *Vaccine* 16(19):1850-1856.
Boder, et al. (2000) "CDR loops can be grafted onto a different scFV framework without loss of affinity" *Proc. Natl. Acad. Sci. USA* 97:10701-10705.
Boles, et al. (2006) "Recombinant C Fragment of Botulinum Neurotoxin B Serotype (rBoNTB (HC)) Immune Response and Protection in the Rhesus Monkey" Toxicon 47(8):877-884.
Caton, et al. (1986) "Structural and functional implications of a restricted antibody response to a defined antigenic region on the influenza virus hemagglutinin" *EMBO J.* 5(7):1577-1587.
Chen, et al. (1997) "Antibody Mapping to Domains of Botulinum Neurotoxin Serotype A in the Complexed and Uncomplexed Forms" *Infect. Immun.* 65(5):1626-1630.
Coleman et al. (2004) *FASEB Journal* 18(8):Suppl. S:C174, Meeting abstract, Abstract Only.
Colman (1994) "Effects of Amino Acid Sequence Changes on Antibody-Antigen Interactions" Res. Immunol. 145(1):33-36.
Dolimbek, et al. (2008) "Immune recognition of botulinum neurotoxin B: Antibody binding regions on the heavy chain of the toxin" *Mol. Immunol.* 45(4):910-924.
Emanuel, et al. (2000) "Recombinant antibodies: a new reagent for biological agent detection" *Biosen. Bioelectron.* 14(10-11):751-759.
Gozales, et al. (2005) "grafting of murine complementarity determining regions (CDRs) onto the variable light and variable heavy frameworks of human immunoglobulin molecules" *Tumour Biol.* 26:31-43.
Hall (2004) "Novel Application of an In Vitro Technique to the Detection and Quantification of Botulinum Neurotoxin Antibodies" *J. Immunol. Methods* 288(1-2):55-60.
Jung & Plückthun (1997) "Improving In Vivo Folding and Stability of a Single-Chain Fv Antibody Fragment by Loop Grafting" *Protein Eng.* 10(8):959-66.
Kozaki, et al. (1995) "Immunological characterization of the neurotoxin produced by *Clostridium botulinum* type A associated with infant botulism in Japan" *Microbiol. Immunol.* 39(10):767-774.
Lebecque & Gearhart (1990) "Boundaries of somatic mutation in rearranged immunoglobulin genes: 5' boundary is near the promoter, and 3' boundary is approximately 1 kb from V(D)J gene" *J. Exp. Med.* 172(6):1717-1727.
Levy, et al. (1989) "Early onset of somatic mutation in immunoglobulin VH genes during the primary immune response" *J. Exp. Med.* 169(6):2007-2019.
Mah, et al. (2003) "Recombinant antibody generated using a phage anti-botulinum neurotoxin A single-chain variable fragment antibody generated using a phage display system" *Hybrid Hybridomics.* 22(5):277-283.
Marks (2004) "Deciphering antibody properties that lead to potent botulinum neurotoxin neutralization" *Mov. Disord.* 19(Suppl. 8):S101-S108.
Mcheyzer-Williams (1993) "B Lymphocyte Biology" Fundamental Immunology, 3rd Edition, Ed. William E. Paul Raven Press: NY, Chapter 9, pp. 292-295.
McKean, et al. (1978) "Mechanisms of antibody diversity: multiple genes encode structurally related mouse κ variable regions" *PNAS USA* 75(8):3913-3917.
Mowry, et al. (2004) "Production and purification of a chimeric monoclonal antibody against botulinum neurotoxin serotype A" *Protein Expr. Purif.* 37(2):399-408.
Mullaney, et al. (2001) "Epitope Mapping of Neutralizing Botulinum Neurotoxin A Antibodies by Ohage Display" *Infect. Immun.* 69(10):6511-6514.
Nowakowski, et al. (2002) "Potent Neutralization of Botulinum Neurotoxin by Recombinant Oligoclonal Antibody" PNAS USA 99(17):11346-11350.
Oshima (1997) "Immune Recognition of Botulinum Neurotoxin Type A: Regions Recognized by T cells and Antibodies against the Protective H(C) Fragment (residues 855-1296) of Toxin" *Mol. Immunol.* 34(14):1031-1040.
Razai, et al. (2005) "Molecular evolution neutralization of antibody affinity for sensitive detection and neutralization of botulinum neurotoxin type A" *J. Mol. Biol.* 351(1):158-169.
Rudikoff, et al. (1982) "Single Amino Acid Substitution Altering Antigen-Binding Specificity" PNAS USA 79(6):1979-1983.
Schier, et al. (1996) "Isolation of picomolar affinity anti-c-erbB-2 single-chain Fv by molecular evolution of the complementarity determining regions in the center of the antibody binding site" *J. Mol. Biol.* 263(4):551-567.
Scotcher, et al. (2009) "Characterization of the Epitope Region of F1-2 and F1-5, Two Monoclonal Antibodies to Botulinum Neurotoxin Type A" Hybridoma 28(5):315-325.
Shone, et al. (1985) "Monoclonal antibody-based immunoassay for type A *Clostridium botulinum* toxin is comparable to the mouse bioassay" *Appl Environ Microbiol.* 50(1):63-67.
Smith, et al. (2005) "Sequence variation within botulinum neurotoxin serotypes impacts antibody binding and neutralization" *Infect. Immun.* 73(9):5450-5457.
Stark & Caton (1991) "Antibodies that are specific for a single amino acid interchange in a protein epitope use structurally distinct variable regions" *J. Exp. Med.* 174(3):613-624.
Weigert, et al. (1978) "Rearrangement of genetic information may produce immunoglobulin diversity" *Nature* 276(5690):785-790.
Arnon (1993) "Clinical Trial of Human Botulism" *Botulinum and Tetanus Neurotoxins: Neurotransmission and Biomedical Aspects*, ed. DasGupta, B. R. Plenum, New York., pp. 477-482.
Arnon et al. (2001) "Botulinum toxin as a biological weapon: medical and public health management" *JAMA* 285(8):1059-1070.
Black & Gunn (1980) "Hypersensitivity reactions associated with botulinal antitoxin" *Am. J. Med.* 69(4): 567-570.
Franz, et al. (1993) "Efficacy of Prophylactic and Therapeutic Administration of Antitoxin for Inhalation Botulism" *Botulinum and Tetanus Neurotoxins: Neurotransmission and Biomedical Aspects*, ed. DasGupta, B. R. Plenum, New York, pp. 473-476.

(56) References Cited

OTHER PUBLICATIONS

Hatheway (1995) "Botulism: the present status of the disease" *Curr Top. Microbiol. Immunol*, 195:55-75.
Hibbs, et al. (1996) "Experience with the use of an investigational F(ab')2 heptavalent botulism immune globulin of equine origin during an outbreak of type E botulism in Egypt" *Clin. Infect. Dis.* 23(2):337-340.
Kozaki, et al. (1998) "Characterization of *Clostridium botulinum* type B neurotoxin associated with infant botulism in japan" *Infect. Immun.* 66(10):4811-4816.
Lacy & Stevens (1999) "Sequence homology and structural analysis of the clostridial neurotoxins" *J. Mol. Biol.* 291(5):1091-1104.
Middlebrook & Franz (1997) "Botulinum Toxins" *Medical Aspects of Chemical and Biological Warfare* Ed. Sidell, et al. TMM publications, Washington, D.C., Chapter 33, pp. 643-654.
Oguma et al. (1990) "Infant botulism due to *Clostridium botulinum* type C toxin" *Lancet* 336(8728):1449-1450.
Siegel (1988) "Human immune response to botulinum pentavalent (ABCDE) toxoid determined by a neutralization test and by an enyme-linked immunoabsorbent assay" *J. Clin. Microbiol.* 26(11):2351-2356.
Sonnabend, et al. (1981) "Isolation of *Clostridium botulinum* type G and identification of type G botulinal toxin in humans: report of five sudden unexpected deaths" *J. Infect. Dis.* 143(1):22-27.
Garcia, et al., (2013), "Human monoclonal antibodies binding botulinum neurotoxin types C, D, and mosaic neurotoxins C-D and D-C", Abstracts Toxins 2011 / Toxicon 68, 86-87, abstract only.
Lou, et al., (2015), "Human antibody engineering for prevention and treatment of botulinum neurotixin (BONT) intoxication", Abstracts / Toxicon 93 S40-S41, Abstract #131.

* cited by examiner

| VH/Clone | Framework1 | CDR1 | Framework2 | CDR2 |
|---|---|---|---|---|
| A12 | EVQLVESGGGVVQPGRSLRLSCAASGFTFS | SYGMH | WVRQAPGKGLEWVA | VIWYDGSNKYYADSVKG |
| 6A12 | QVQLVESGGGVVQPGRSLRLSCAASGFTFS | SYGMH | WVRQAPGKGLEWVS | YISSSGSTIYYADSVKG |
| B1.1 | EVQLVQSGAEVEKPGSSVKVSCKASGGSFS | SYAFT | WVRQAPGQGLEWMG | RIVPFLGVPYYTQKFRG |
| B6 | QVQLVQSGAEVKKPGESLVISCKASGDKDTFT | SFWIA | WVRQMPGKGLEWMG | IIYAGDSDTRYSPSFQG |
| B6.1 | QVQLVQSGAEVKKPGESLVISCKASGDKDTFT | SFWIA | WVRQMPGKGLEWMG | IIYAGDSDTRYSPSFQG |
| B8 | QVQLLESGGGVVQPGRSLRLSCAASGFTFS | SYGMH | WVRQAPGKGLEWVA | VIWYDGSNKYYADSVKG |
| B8.1 | QVQLLESGGGVVQPGRSLRLSCAASGFTFS | SYGMH | WVRQAPGKGLEWVA | VIWYDGSNKYYADSVKG |
| B11 | QVQLLQSAGGVVQPGRSLRLSCAASGFIFR | TYGMH | WVRQAPGKGLEWVA | FVSSDGNNKFYSDSVKG |
| B11C3 | EVQLVESGGGVVQPGRSLRLSCATSGFILR | TYGMH | WVRQAPGKGLEWVA | FVSSDGNNKFYSDSVKG |
| B11E8 | EVQLVQSGGGVVQPGRSLRLSCAASGFIFR | TYGMH | WVRQAPGKGLEWVA | FVSSDGNNKFYSDSVKG |
| B12 | QVNLRESGGGVVQPGRSLRLSCAASGFTFS | SYALH | WVRQTPGKGLEWVA | LISYDGSNKYYADSVKG |
| B12.1 | QVNLRESGGGVVQPGRSLRLSCAASGFTFS | SYALH | WVRQTPGKGLEWVA | LISYDGSNKYYADSVKG |
| B12.2 | QVNLRESGGGVVQPGRSLRLSCAASGFTFS | SYALH | WVRQTPGKGLEWVA | LISYDGSNKYYADSVKG |
| 1B18 | EVQLVQSGGGLVQPGGSRRLSCAASGFYFN | AYWMT | WVRQAPGKGLEWVA | NINLDGTEIYYLDSVKG |
| 2B18.1 | QVQLVQSGGGLVQPGGSRRLSCAASGFYFN | AYWMT | WVRQAPGKGLEWVA | NINLDGTEIYYLDSVKG |
| 4B19 | QVQLVQSGAEVKKPGASVNVSCKASGYTFT | GYYIY | WVRQAPGQGLEWMG | WINPNSGVTKYAQKFQG |
| 1B22 | QVQLQESGSRLVKPSQTLSLTCGVSGGSIS | SSSYSWS | WIRQTPGKGLEWIG | YIYHSGSTYYNPSLKS |
| 1B10 | QVQLVESGGGVVQPGRSLRLSCAASGFTFS | HYGMH | WVRQSPGKGLEWVA | VIWYDGRNPYYAASVKG |
| 1B10.1 | QVQLVESGGGVVQPGRSLRLSCAASGFTFS | HYGMH | WVRQSPGKGLEWVA | VIWYDGRNPYYAASVKG |
| 2B18.2 | QVQLVQSGGGLVQPGGSRRLSCAASGFYFK | AYWMT | WVRQAPGKGLEWVA | NINLDGTEIYYLDSVKG |
| 2B18.3 | EVQLVESGGGLVQPGGSRRLSCAASGFYFN | AYWMT | WVRQAPGKGLEWVA | NINLDGTEIYYLDSVKG |
| 1B22.4 | QVQLQESGSRLVKPSQTLSLTCGVSGGSIS | SSSYSWS | WIRQTPGKGLEWIG | YIYHSGSTYYNPSLKS |
| 2B23 | EVQLLESGGGLVQPGGSLRLSCAASGFTFS | NYPMS | WVRQAPGKGLAWVS | SLTASGDNTFYADSVKG |
| 2B24 | QVQLVESGGGVVQPGRSLRLSCAASGLTFS | VYGMH | WVRQAPGKGLEWVA | VISHTGSEEYYADSVKG |
| 2B25 | QVQLQESGPGLVKPSQTLSLSCSVSGASIT | SGTFYWS | WIRQHPGKDLEWIG | YIYYSGTTYYNPSLKS |
| 2B25.1 | QVQLQESGPGLVKPSQTLSLSCSVSGASIT | SGTFYWS | WIRQHPGKDLEWIG | YIYYSGTTYYNPSLKS |
| 2B26 | QVQLVQSGGTLVQPGGSLRLSCAASGFTFS | NYPMT | WVRQAPGKGLAWVS | SVIASGDNTFYADSVKG |
| 2B27 | EVQLQESGPGLVKPSETLSVTCAVSGGSIS | SSNYSWA | WIRQPPGKGLEWIG | TMYYSGSTHYHPSLKS |
| 2B28 | EVQLVQSGGGVVQPGRSLRLSCAASGFTFR | RNAIH | WVRQAPGKGLEWVA | LISYDGINKYYADSVKG |
| 2B29 | QVQLQESGPGLVKPSETLSLTCSVSGGSIN | SGTYYWT | WIRQHPGKGLEWIG | YIYYSGTTYYNPSLKS |
| 2B30 | EVQLVESGGGVVQPGRSLRLSCAASGFTFR | RNAIH | WVRQAPGKGLEWVA | VISYDGVNKYYAASVKG |
| 4B17.1 | EVQLVRSGGNLVQPGGSLRLSCAATGPIG | SHWMT | WVRQAPGQGLEWVA | NINLDGTEKFYVDSVKG |
| 4B17.1C | EVQLVQSGGNLVQPGGSLRLSCAATGFPIG | SHWMT | WVRQAPGQGLEWVA | NINLDGTEKFYVDSVKG |
| 4B17.1D | EVQLVQSGGNLVQPGGSLRLSCAATGGPIG | SHWMT | WVRQAPGQGLEWVA | NINLDGTEKFYVDSVKG |
| 4B17.1F | EVQLVQSGGNLVQPGGSLRLSCAATGFYIG | SHWMT | WVRQAPGQGLEWVA | NINLDGTEKFYVDSVKG |
| 4B17.1G | EVQLVQSGGNLVQPGGSLRLSCAATGFTIG | SHWMT | WVRQAPGQGLEWVA | NINLDGTEKFYVDSVKG |

FIG. 1

| VH/Clone | Framework3 | CDR3 | Framework4 | Gene Family |
| --- | --- | --- | --- | --- |
| A12 | RFTISRDNSKNTLYLQMNSLRAEDTAVYYCAR | GYSNYDYYYGMDV | WGQGTTVTVSS | VH3 |
| 6A12 | RFTISRDNAKNSLYLQMNSLRAEDTAVYYCAR | VSIVGGPYGMDV | WGQGTTVTVSS | VH3 |
| B1.1 | RVTITADKATSTVYMELSSLTFDDTAVYYCAR | DKRTYEYNWNSLWF | WGRGTTVTVSS | VH1 |
| B6 | HVNISVDRSTNTAYLQWSSLKASDTAMYYCAR | HDSRYKYFYFGMDV | WGQGTTVTVSS | VH5 |
| B6.1 | HVNISVDRSTNTAYLQWSSLKASDTAMYYCAR | HDSRYKYFYFGMDV | WGQGTTVTVSS | VH5 |
| B8 | RFTISRDNSKDTLYLQMNSLRAEDTAVYYCAR | GYSNYDYYYGMDV | WGQGTTVTVSS | VH3 |
| B8.1 | RFTISRDNSKNTLYLQMNSLRAEDTAVYYCAR | GYSNYDYYYGMDV | WGQGTTVTVSS | VH3 |
| B11 | RFTIPRDNAKNTLYLQMNSLETEDTAVYYCAK | DRYPIDCSGGSCFSYGMDV | WGQGTTVTVSS | VH3 |
| B11C3 | RFTIPRDNAKNTLYLQMNSLETEDTAVYYCAK | DRYPIDCSGGSCFSYGMDV | WGQGTLVTVSS | VH3 |
| B11E8 | RFTISRDNAKNTLYLQMNSLETEDTAMYYCAK | DRYPIDCSGGSCFSYGMDV | WGQGTTVTVSS | VH3 |
| B12 | RFTISRDNSKNMLYLQMNSLRAEDTAVYYCAK | DRSHYGDYVGYLDY | WGQGTLVTVSS | VH3 |
| B12.1 | RFTISRDNSKNMLYLQMNSLRAEDTAVYYCAK | DRSHYGDYVGYLDY | WGQGTLVTVSS | VH3 |
| B12.2 | RFTISRDNSKNMLYLQMNSLRAEDTAVYYCAK | DRSHYGDYVGYLDY | WGQGTLVTVSS | VH3 |
| 1B18 | RFTVSRDNVKNSVFLQMSSLRVEDTAVYFCAR | LEWGGRNGWVSP | WGQGTLVTVSS | VH3 |
| 2B18.1 | RFTVSRDNVKNSVFLQMSSLRVEDTAVYFCAR | LEWGGRNGWVSP | WGQGTLVTVSS | VH3 |
| 4B19 | RVTMTIDTSTNTAYMELNRLRADDTAVYYCAR | EWTQLWSPYDY | WGQGTTVTVSS | VH1 |
| 1B22 | RVTMSVDKSRNQFSLNMSSVTAADTAVYYCAR | TAFYYENTGPIRCYLDF | WGQGTLVTVSS | VH4 |
| 1B10 | RFTISRDNDKNTLYLQMNSLRAEDTAVYYCVK | DLTRFHDTTFGVFEM | WGPGTTVTVSS | VH3 |
| 1B10.1 | RFTISRDNDKNTLYLQMNSLRAEDTAVYYCVK | DLTRFHDTTFGVFEM | WGPGTTVTVSS | VH3 |
| 2B18.2 | RFTVSRDNVKNSVFLQMSSLRVEDTAVYFCAR | LEWGGRNGWVSP | WGQGTLVTVSS | VH3 |
| 2B18.3 | RFTVSRDNVKNSVFLQMSSLRVEDTAVYFCAR | LEWGGRNGWLSP | WGQGTLVTVSS | VH3 |
| 1B22.4 | RVTMSVDKSRNQFSLNMSSVTAADTAVYYCAR | TAFYYENTGPIRCYLDF | WGQGTLVTVSS | VH4 |
| 2B23 | RFTISRDNSNNTLYLQMHSLRAEDTAVYYCAK | ALVGRYDISTGYYRPVMDS | WGQGTLVTVSS | VH3 |
| 2B24 | RFSISRDNSNNTLFLQMNSLRPEDTAVYYCVK | DGPMAAIPFYYFDF | WGQGTLVTVSS | VH3 |
| 2B25 | RVTLSVDTSKNQFSLKVTSLTAADTAVYHCAR | GVPIYDSSGTYRGTYFDY | WGQGTLVTVSS | VH4 |
| 2B25.1 | RVTLSVDTSKNQFSLKVTSLTAADTAVYHCAR | GVPIYDSSGTYRGTYFDY | WGQGTLVTVSS | VH4 |
| 2B26 | RFTISRDNSKNTLYLQMDSLRAEDTAVYYCAK | ALVGRYDISTGYYRPVLDY | WGQGTTVTVSS | VH3 |
| 2B27 | RVTISVDTSKSQLSLKLSSVTAADTAVYYCAR | RRLLGPSPYYFDY | WGQGTLVTVSS | VH3 |
| 2B28 | RFAISRDNAKNTLFLQMNSLRAEDTAVYYCAR | DVSEYGDYVGHFDY | WGQGTLVTVSS | VH3 |
| 2B29 | RVSMSVDTSKNLFSLKMNSVTAADTALYYCAR | GNPQYDTSGSYTGLYFDF | WGQGTLVTVSS | VH4 |
| 2B30 | RFAISRDNAKNTLFLQMNSLRPEDSAIYYCAR | DVSEYGDYVGHFDY | WGQGTLVTVSS | VH3 |
| 4B17.1 | RFTVSRDNRKSSVFLQMNNLRVDDTAVYYCAR | LQWGGYNGWLSP | WGQGTLVTVSS | VH3 |
| 4B17.1C | RFTVSRDNRKSSVFLQMNNLRVDDTAVYYCAR | LQWGGYNGWLSP | WGQGTLVTVSS | VH3 |
| 4B17.1D | RFTVSRDNRKSSVFLQMNNLRVDDTAVYYCAR | LQWGGYNGWLSP | WGQGTLVTVSS | VH3 |
| 4B17.1F | RFTVSRDNRKSSVFLQMNNLRVDDTAVYYCAR | LQWGGYNGWLSP | WGQGTLVTVSS | VH3 |
| 4B17.1G | RFTVSRDNRKSSVFLQMNNLRVDDTAVYYCAR | LQWGGYNGWLSP | WGQGTLVTVSS | VH3 |

FIG. 1
(Cont.)

| VL/Clone | Framework1 | CDR1 | Framework2 | CDR2 |
|---|---|---|---|---|
| A12 | DIQMTQSPSSLSASVGDRVTITC | RASQRISNYLN | WYQQKPGKAPKLLIY | AASSLQS |
| 6A12 | DIQMTQSPSSVSASVGNRVTITC | RASQGISSWLA | WYQQKPGKAPKLLIY | AASSLQS |
| B1.1 | DVVMTQSPSSLSASVGDRVTITC | RASQSISSYLN | WYQQKPGKAPKLLIY | AASSLQS |
| B6 | DVVMTQSPSSLSASVGDRITITC | QAGQDISNFLN | WYQQKPGKAPKLLIR | DASNLET |
| B6.1 | DIQMTQSPSSLSASVGDRVTITC | RASQSISSYLN | WYQQEPGKAPKLLIY | SASSLQS |
| B8 | DIQMTQSPSSLSASVGDRVTITC | RASQRISNYLN | WYQQKPGKAPKLLIY | AASSLQS |
| B8.1 | DIQMTQSPSSLSASVGDRVTITC | RASQRISNYLN | WYQQKPGKAPKLLIY | AASSLQS |
| B11 | DIVMTQSPSTLSASVGDRVTVTC | RASQSINSWLA | WYQQKPGKAPKLLIY | EASSLES |
| B11C3 | DIQMTQSPSSVSASVGDRVTITC | RASQGVSRWLA | WYQQRPGEAPKLLIY | GASSLQS |
| B11E8 | EIVLTQSPATLSVSPGERATLSC | RASQSVSKFLA | WYQQKRGQAPRLLIY | GASTRAT |
| B12 | DIVMTQSPSTLSASVGDRVTITC | RASQGISSWLA | WYQQKPGKAPKLLIY | KASSLES |
| B12.1 | AYVLTQPPSVSVAPGKTAAITC | EGNNVGNKNVH | WYQQRPGQAPVLVVH | DDSDRPS |
| B12.2 | ESVLTQPPLVSAAPGQKVTISC | SGSSSNIGNNYVS | WYQQLPGTAPKLLIY | ENSKRSS |
| 1B18 | DVVMTQSPSSVSASVGDRVTITC | RASQSISSYLN | WYQQRPGKAPKLLIF | AASSLQS |
| 2B18.1 | DIVMTQSPSSLSASVGDRVSISC | RASQSISSYLN | WYQQKPGKAPKLLIY | KTSSLES |
| 1B22 | DIQMTQSPSTLSASIGDRVTISC | RASQSIQSWLA | WYQQRPGEAPKLLIY | SASTLQT |
| 4B19 | DIVLTQSPSTLSASVGDRVTISC | RASRSIGWYLN | WYQQRPGKAPKLLIY | AASSLHN |
| 1B10 | EIVLTQSPSSLSASVGDRITITC | RASQSISSWLA | WYQQKPGKAPMVLIY | KASSLEN |
| 1B10.1 | EIVLTQSPSFVSASVGDRVTITC | RASQGISSWLA | WYQQKPGKAPKLLIY | AASSLQS |
| 2B18.2 | DIVMTQSPSSLSASVGDRVSISC | RASQSISSYLN | WYQQKPGKAPKLLIY | KTSSLES |
| 2B18.3 | DIVMTQSPSTLSASVGDRVTITC | RASQSSTYWLS | WYQQKPGKAPKLLIY | KTSSLES |
| 1B22.4 | DVVMTQSPSSVSASVGDRVTITC | RASQGIGYWLA | WYQQKPGKGPKLLIY | DASRLQG |
| 2B23 | DIQMTQSPPSLSASVGDRVTITC | RTSQGFTSALA | WYQQKPGEPPKLLIY | DASKLES |
| 2B24 | QSVVTQPPSVSAAPGQKVTISC | SGSSSNIGNNYVS | WYQQLPGTAPKLLIY | DNNKRPS |
| 2B25 | QPGLTQPPSASGTPGQRVTISC | SGSSSNVGSNTVN | WYQQLPGTAPKLLIY | RNDQRPS |
| 2B25.1 | ESVLTQPPSVSAAPGQKVTISC | SGSSSNIGNNYVS | WYQQLPGTAPKLLIY | DNNRRPS |
| 2B26 | QPGLTQPPSASGTPGQRVTISC | SGSSSNIGSNPVN | WYQHLPGTAPKLLIY | SNNQRPS |
| 2B27 | QSVVTQPPSVSGAPGQRVTISC | SGSSSNIGAGYDVH | WYQQLPGTAPKLLIY | GNNNRPS |
| 2B28 | QSVLTQPPSVSAAPGQKVTISC | SGSSSNIGNNYVS | WYQQLPGTAPKLLIY | DNNKRPS |
| 2B29 | QPVLTQSPSASGTPGQRVTISC | SGSSSNLGSNTVS | WYQQLPGTAPKLLIY | SNNQRPS |
| 2B30 | SYELMQLPSASGTPGQRVSISC | SGSSSNIGSNPVN | WYQQLPGTAPKLLIY | SNNHRPS |
| 4B17.1 | DIVMTQSPSSLSASVGDRVTISC | RASQSIRHYVN | WYQQKPGKAPKLLIY | KASSLAS |
| 4B17.1C | DIVMTQSPSSLSASVGDRVTISC | RASQSIRHYVN | WYQQKPGKAPKLLIY | KASSLAS |
| 4B17.1D | DIVMTQSPSSLSASVGDRVTISC | RASQSIRHYVN | WYQQKPGKAPKLLIY | KASSLAS |
| 4B17.1F | DIVMTQSPSSLSASVGDRVTISC | RASQSIRHYVN | WYQQKPGKAPKLLIY | KASSLAS |
| 4B17.1G | DIVMTQSPSSLSASVGDRVTISC | RASQSIRHYVN | WYQQKPGKAPKLLIY | KASSLAS |

FIG. 1 (Cont.)

| VL/Clone | Framework3 | CDR3 | Framework4 | Gene Family |
|---|---|---|---|---|
| A12 | EVPSRFSGSGSGTDFTLTISSLQPEDFATYYC | QQSYRPPLT | FGGGTKVEIKR | VK1 |
| 6A12 | GVPSRFSGSGSGTDFTLTISSLQPEDFATYYC | QKANSFPLT | FGGGTKMEIKR | VK2 |
| B1.1 | GVPSRFSGSGSGTDFTLTISSLQPEDFATYYC | QQSYSTPLT | FGQGTKLEIKR | VK1 |
| B6 | GVPSRFSGGGSGTHFTFTISSLHPEDIATYFC | QQYDNLPYT | FGQGTKLEIKR | VK1 |
| B6.1 | GVPSRFSGSGSGTDFTLTISSLQPEDFATYYC | QQSYSTPPYT | FGQGTKLEIKR | VK1 |
| B8 | EVPSRFSGSGSGTDFTLTISSLQPEDFATYYC | QQSYRPPLT | FGGGTKVDIKR | VK1 |
| B8.1 | EVPSRFSGSGYGTDFTLTISSLQPEDFATYYC | QQSYRPPLT | FGGGTKVDIKR | VK1 |
| B11 | GVPSRFSGSGSGTEFTLTISSLQPDDFATYYC | QQYDSYWLT | FGGGTKVEIKR | VK1 |
| B11C3 | GVPSRFSGSGSGTDFTLTISSLQPEDFATYYC | QQYDSFPLT | FGGGTKVEIKR | VK1 |
| B11E8 | GIPARFSGSGSGTEFALTISSLQSEDFADYYC | QQYDNWPIT | FGQGTRLEIKR | VK1 |
| B12 | GVPSRFSGSGSGTEFTLTISSLQPEDFATYYC | LQHNSYPRA | FGQGTKLEIKR | VK1 |
| B12.1 | GIPERFSGSNSGNTATLTINRVEAGDEADYYC | QVWDSSSAQWV | FGGGTKLTVLG | VL3 |
| B12.2 | GIPDRFSGSKSGTSATLGITGLQTGDEADYYC | GTWDSSLSAVV | FGGGTKLTVLG | VL1 |
| 1B18 | AVPSRFSGSGSGTDFTLTISSLQPEDFATYYC | QQSYSTPPT | FGQGTKVEIKR | VK1 |
| 2B18.1 | GVPSRFSGRGSGTDFTLTISSLQPEDFATYYC | QQSYSTPLT | FGGGTKVEIKR | VK1 |
| 1B22 | GVPSRFSGSGSGTDFTLTISSLQPEDFATYYC | QQYNSYPLT | FGQGTKLEIKR | VK1 |
| 4B19 | GVPSRFSGSGSGTEFTLTISSLQPDDFATYYC | QQAFGFPRT | FGQGTKVEIKR | VK1 |
| 1B10 | GVPSRFSGSGSGTEFTLTISSLQPDDFATYYC | QQYSTYSRT | FGQGTKVEIKR | VK1 |
| 1B10.1 | GVPSRFSGSGSGTEFTLTISSLQPDDFATYYC | QQYSSLYT | FGQGTKVDIKR | VK1 |
| 2B18.2 | GVPSRFSGRGSGTDFTLTISSLQPEDFATYYC | QQSYSTPLT | FGGGTKVEIKR | VK1 |
| 2B18.3 | GVPSRFSGSGSGTEFTLTISSLQPDDFATYYC | QQSWT | FGQGTKVEIKR | VK1 |
| 1B22.4 | GVPSRFSGSGSGTDFTLTISSLQPEDFATYYC | QQYNSYPLT | FGGGTKLEIKR | VK1 |
| 2B23 | GVPSRFSGSGSGTNFALTISSLQPEDFATYFC | QQSNSYPLT | FGGGTKVEIKR | VK1 |
| 2B24 | GIPDRFSGSKSGTSATLGITGLQTGDEADYYC | GTWDSSLSAGV | FGGGTKLTVLG | VL1 |
| 2B25 | GVPDRFSGSKSGASASLAISGLRSEDEADYYC | AAWDDSLNGLL | FGGGTQLTVLG | VL1 |
| 2B25.1 | GIPDRFSGSKSGTSATLGITGLQTGDEADYYC | GTWDSSLSEVV | FGGGTKVTVLG | VL1 |
| 2B26 | GVPDRFSGSKSGTSASLAISGLQSEDEADYYC | AAWADSLNGVV | FGGGTKVTVLG | VL1 |
| 2B27 | GVPDRFSGSKSGTSASLAITGLQAEDEADYYC | QSYDSSLSAYV | FGTGTKLTVLG | VL1 |
| 2B28 | GIPDRFSGSKSGTSATLGITGLQTGDEADYYC | GTWDSSLSAVV | FGGGTQLTVLG | VL1 |
| 2B29 | GVPDRFSGSKSGTSASLAISGLQSEDEADYYC | ATWDDSLSGGV | FGGGTKLTVLG | VL1 |
| 2B30 | GVPDRFSGSKSGTSASLAISGLQSEDEADYYC | AAWDGSLNGHVV | FGGGTKLTVLG | VL1 |
| 4B17.1 | GAPSRFSGSGSGTDFTLTISSLQPDDFATYYC | QQSYSIPLT | FGGGTKLEIKR | VK1 |
| 4B17.1C | GAPSRFSGSGSGTDFTLTISSLQPDDFATYYC | QQSYSIPLT | FGGGTKLEIKR | VK1 |
| 4B17.1D | GAPSRFSGSGSGTDFTLTISSLQPDDFATYYC | QQSYSIPLT | FGGGTKLEIKR | VK1 |
| 4B17.1F | GAPSRFSGSGSGTDFTLTISSLQPDDFATYYC | QQSYSIPLT | FGGGTKLEIKR | VK1 |
| 4B17.1G | GAPSRFSGSGSGTDFTLTISSLQPDDFATYYC | QQSYSIPLT | FGGGTKLEIKR | VK1 |

FIG. 1 (Cont.)

| VH | Framework1 | CDR1 | Framework2 | CDR2 |
|---|---|---|---|---|
| 2A10 | QVQLQQSGAEVKKPGSSVKVSCKASGGTFT | RYTIT | WVRQAPGQGLEWMG | GIIPIFDKANYAQKFQS |
| 3E1 | QVQLVESGAEVKKPGSSVKVSCKASGGTFS | NSGFT | WVRQVPGQGLEWMG | GIIPMFGPANYAQKFQG |
| 3E2 | QVQLQESGAEVKKPGSSVKVSCKASGGDLN | KYAIT | WLRQAPGQGFEWMG | GITPIFATTNYAQKFQG |
| 3E3 | QVQLVESGGGLVKPGESLRLSCAASGFTFS | NYNMN | WVRQAPGKGLEWVS | SISDGGSYRYYAYSVKG |
| 3E4 | QVQLQESGGGLVQPGGSLRLSCGASGFTFS | SDAMS | WVRQAPGKGLEWVA | AILPSGEATYYADSVKG |
| 3E4.1 | QVQLQESGGGLVQPGGSLRLSCGASGFTFS | SDAMS | WVRQAPGKGLEWVA | AILPSGEATYYADSVKG |
| 3E5 | QVQLVQSGGGVVQPGRPLRLSCAASTFNFR | DFYMS | WIRQAPGKGLEWVS | YIGSSGSALQYADSVKG |
| 3E6 | QVQLVQSGGGVVQPGKSLRLSCAASGFTFS | SYAMH | WVRQAPGKGLEWVA | VISYDGNKKYYADSVKG |
| 3E6.1 | QVQLVQSGGGVVQPGKSLRLSCAASGFTFS | SYAMH | WVRQAPGKGLEWVA | VISYDGNKKYYADSVKG |
| 3E6.2 | QVQLVQSGGGVVQPGKSLRLSCAASGFAFG | GYAMH | WVRQAPGKGLEWVA | VISYDGNKKYYADSVKG |
| 4E11 | QVQLVQSGGGLVQPGGSLRLSCAASGFRFS | GYSFN | WVRQAPGKGLEWVA | YMSSGGSIKNYADSVKG |
| 4E13 | EVQLVQSGGGLVQPGGSLRLSCAASGFTFS | SYAMT | WVRQAPGKGLEWVS | SISVSGDSTYYADSVKG |
| 4E16 | QVQLQESGPGLVKPSETLSLTCSVSGVSIS | DYYWS | WIRQPPGKGLEWIG | YIYYSGSTNYNPSLKS |
| 4E16.1 | QVQLQESGPGLVKPSETLSLTCSVSGVSIS | DYYWS | WIRQPPGKGLEWIG | YIYYSGSTNYNPSLKS |
| 4E17 | EVQLVQSGGNLVQPGGSLRLSCAATGPIG | SHWMT | WVRQAPGQGLEWVA | NINLDGTEKFYVDSVKG |
| 4E17.1 | EVQLVRSGGNLVQPGGSLRLSCAATGPIG | SHWMT | WVRQAPGQGLEWVA | NINLDGTEKFYVDSVKG |
| 4E17.4 | EVQLVRSGGNLVQPGGSLRLSCAATGPIT | QHWMT | WVRQAPGQGLEWVA | NINLDGTEKFYVDSVKG |
| 4E17.6 | EVQLVRSGGNLVQPGGSLRLSCAATGPIT | QHWMT | WVRQAPGQGLEWVA | NINLDGTEKFYVDSVKG |

| VL | Framework1 | CDR1 | Framework2 | CDR2 |
|---|---|---|---|---|
| 2A10 | DIVMTQSPSFLSASVGDRVTITC | WASQGISSYLA | WYQQKPGKAPKLLIY | AASTLQS |
| 3E1 | EIVLTQSPDSLSASVGDRVTITC | RASQGISGYLA | WYQHKAGKAPKLLIY | AASSLQS |
| 3E2 | EIVLTQSPSFLSAFVGDRVTITC | RTSQSINNYLN | WYQQKAGKAPKLLIY | AASTLHT |
| 3E3 | DIVMTQSPDSLSASVGDSVTITC | RASQSFSSSYLA | WYQQKPGQAPRLLIY | AASSRAA |
| 3E4 | DIVMTQSPSFLSAFVGDRVTITC | RASQSISNWLA | WYQQKPGKAPKVLIY | KASSLEN |
| 3E4.1 | EIVLTQSPSTLSASVGDRVAITC | RASQRIGSWLA | WYQQKPGKAPNPLIY | KAFSLES |
| 3E5 | DVVMTQSPSSLSASIGDRVTFTC | QASQDISNRLN | WYQQKPGKVPKLLIS | DASNLET |
| 3E6 | DIQMTQSPSSVSASVGDTVTISC | RASQGISSWLA | WYQQKSGQAPTLLIY | AASSLQS |
| 3E6.1 | DIQMTQSPSSVSASVGDRVSITC | QASQDISNYLN | WYQQKPGKAPKLLIY | AASSLQS |
| 3E6.2 | DIQMTQSPSSVSASVGDRVSITC | QASQDISNYLN | WYQQKPGKAPKLLIY | AASSLQS |
| 4E11 | ASVLTQDPAVSVALGQTVRITC | QGDSLRSYYAS | WYQQKPGQAPVLVIY | GKSNRPS |
| 4E13 | AELTQDPAVSVALGQTVRITC | QGDSLRSYYAS | WYQQKPGQAPVLVIY | GENSRPS |
| 4E16 | EIVLTQSPDSLAVSLGERATINC | KSSQSVLYSSNNKNYLA | WYQQKPGQPPKLLFY | WASTRES |
| 4E16.1 | EIVLTQSPNSLAVSLGERATIRC | KSSQSVLYSGNNKNYIA | WYQQKPGQPPKLLIY | WASTRES |
| 4E17 | DIVMTQSPSSVSASVGDRVTITC | RASQSISSYLN | WYQQKPGKAPKLLIY | GTSNLQS |
| 4E17.1 | DIVMTQSPSSLSASVGDRVTISC | RASQSIRHYVN | WYQQKPGKAPKLLIY | KASSLAS |
| 4E17.4 | DIVMTQSPSSLSASVGDRVTISC | RASQSIRHYVN | WYQQKPGKAPKLLIY | KASSLAS |

FIG. 2

| VH | Framework3 | CDR3 | Framework4 | Gene Family |
|---|---|---|---|---|
| 2A10 | RVTFTADASTSTAYMELGSLRPEDTAVYYCAA | YSRGYVHFDY | WGPGTLVTVSS | VH1 |
| 3E1 | RVTITADESTRMVYMELRSLRSEDTAVYYCAR | DQGEYTVGMLLYYAMDV | WGEGTTVTVSS | VH1 |
| 3E2 | RVMITADEVTSTVYMDLSSLGSEDTAIYFCAK | SPRGGIVGTFDT | WGQGTMVTVSS | VH1 |
| 3E3 | RFTISRDNTKNSLYLQMNSLRAEDTALYYCAR | DEMVHGILVYYGMDV | WGQGTTVTVSS | VH3 |
| 3E4 | RFTISRHSSKNTLYLQMNSLRADDTAVYYCAR | DSYHSRLAAFDI | WGQGTMVTVSS | VH3 |
| 3E4.1 | RFTISRHSSKNTLYLQMNSLRADDTAVYYCAR | DSYHSRLAAFDI | WGQGTMVTVSS | VH3 |
| 3E5 | RFTISRDNDKNVLYLQMTSLRAEDTAVYYCAR | VASRYHDVLTDGFDI | WGQGTMVTVSS | VH3 |
| 3E6 | RFTISRDNSKNTLYLQMNSLRAEDAAVFYCAR | ARLCTSTSCYWTFDP | WGQGTLVTVSS | VH3 |
| 3E6.1 | RFTISRDNSKNTLYLQMNSLRAEDAAVFYCAR | ARLCTSTSCYWTFDP | WGQGTLVTVSS | VH3 |
| 3E6.2 | RFTISRDNSKNTLYLQMNSLRAEDAAVFYCAR | ARLCTSTSCYWTFDP | WGQGTLVTVSS | VH3 |
| 4E11 | RFTISRDNAKNSLYLQVNSLRDEDTALYYCAR | GPPGRPNDAFDI | WGQGTMVTVSS | VH3 |
| 4E13 | RFTISRDNSKNTVSLQMNSLRAEDTALYYCAK | GLSKADLFGMDV | WGQGTMVTVSS | VH3 |
| 4E16 | RVTISVDTSKNQFSLNLSSVTAADTAVYYCAR | HTSGWSGGAFDI | WGQGTMVTVSS | VH4 |
| 4E16.1 | RVTISVDTSKNQFSLNLSSVTAADTAVYYCAR | HTSGWSGGAFDI | WGQGTMVTVSS | VH4 |
| 4E17 | RFTVSRDNRKSSVFLQMNNLRVDDTAVYYCAR | LQWGGYNGWLSP | WGQGTLVTVSS | VH3 |
| 4E17.1 | RFTVSRDNRKSSVFLQMNNLRVDDTAVYYCAR | LQWGGYNGWLSP | WGQGTLVTVSS | VH3 |
| 4E17.4 | RFTVSRDNRKSSVFLQMNNLRVDDTAVYYCAR | LQWGGYNGWLSP | WGQGTLVTVSS | VH3 |
| 4E17.6 | RFTVSRDNRKSSVFLQMNNLRVDDTAVYYCAR | LQWGGYNGWLSP | WGQGTLVTVSS | VH3 |

| VL | Framework3 | CDR3 | Framework4 | Gene Family |
|---|---|---|---|---|
| 2A10 | GVPSRFSGSGSGTEFTLTISSLQPEDFATYYC | QQLNSYPLT | FGGGTKVDIKR | VK1 |
| 3E1 | GVPSRFSGSGYGTEFTLTISSLQPDDFATYYC | QQYNSYPFT | FGGGTKVEIKR | VK1 |
| 3E2 | GVPSRFSGSGSGTEFTLTISSLQPEDFATYYC | QQSYSIPLT | FGGGTKVEIKR | VK1 |
| 3E3 | GVPTGSVADGSGTDFTLTISGLQPEDFAAYYC | QQSYSTPYT | FGGGTKVEIKR | VK3 |
| 3E4 | GVPSRFSGSGSGTDFTLTITSLQPDDFATYYC | QQYNAYPLT | FGGGTKVEIKR | VK1 |
| 3E4.1 | GVPSRFSGSRSGTEFTLTISSLQPDDFATYFC | QQYDSYPYT | FGQGTKLEIKR | VK1 |
| 3E5 | GVPSRFSGSGSGTDFTFTISSLQPEDIATYYC | QQYDPLLT | FGGGTKVEIKR | VK1 |
| 3E6 | GVPSRFSGSGSGTDFTLTISSLQPEDFATYYC | QQAYRTPIT | FGGGTKVEIKR | VK1 |
| 3E6.1 | GVPSRFSGSGSGTDFTLTISSLQPEDFATYYC | QQSYNTPPT | FGQGTKLEIKR | VK1 |
| 3E6.2 | GVPSRFSGSGSGTDFTLTISSLQPEDFATYYC | QQSYDTPPT | FGQGTKLEIKR | VK1 |
| 4E11 | GIPDRFSGSSSGNTASLTITGAQAEDEADYYC | NSRDSTGNQL | FGGGTKVTVLG | VL3 |
| 4E13 | GIPDRFSGSSSGNTASLTIAGAQAEDEADYYC | NSPDSSGIHLV | FGGGTKVTVLG | VL3 |
| 4E16 | GVPDRFSGSGSGTDFTLTISSLQAEDVAVYYC | HQYYSSPLT | FGGGTKLEIKR | VK4 |
| 4E16.1 | GVPDRFSGSGSETDFTLTISSLRAEDVALYYC | QQYYSRWT | FGQGTKLEIKR | VK4 |
| 4E17 | GVPSGFSGSGSGTDFTLTISSLQPEDFATYYC | QETYSTPPT | FGGGTKLEIKR | VK1 |
| 4E17.1 | GAPSRFSGSGSGTDFTLTISSLQPDDFATYYC | QQSYSIPLT | FGGGTKVEIKR | VK1 |
| 4E17.4 | GAPSRFSGSGSGTDFTLTISSLQPDDFATYYC | QQSYSIPLT | FGGGTKVEIKR | VK1 |

FIG. 2 (Cont.)

bivalent BoNT B
    (3.6-4.0% difference) BoNT B1
    (4.6-5.0% difference)         BoNT B2
        (7.6-7.7% difference)              nonproteolytic BoNT B
            (4.3% difference)
                (7.2% difference)
                (7.0% difference)

─── Danish
─── Strain 111
─── Eklund 17B
─── CDC 1436
─── CDC 588
─── CDC 593
─── CDC 3281

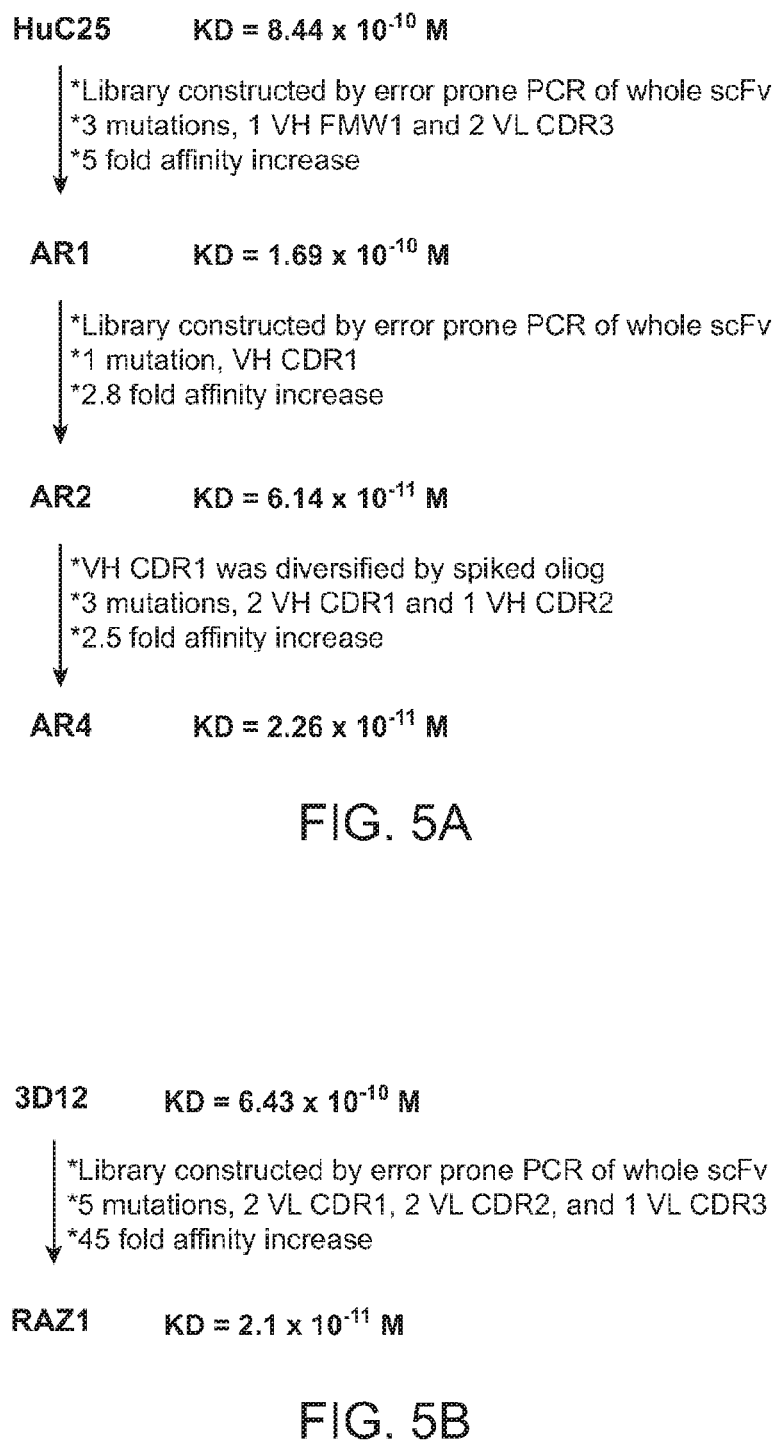

HuC25 KD = $8.44 \times 10^{-10}$ M

*Library constructed by error prone PCR of whole scFv
*3 mutations, 1 VH FMW1 and 2 VL CDR3
*5 fold affinity increase

AR1 KD = $1.69 \times 10^{-10}$ M

*Library constructed by error prone PCR of whole scFv
*1 mutation, VH CDR1
*2.8 fold affinity increase

AR2 KD = $6.14 \times 10^{-11}$ M

*VH CDR1 was diversified by spiked oliog
*3 mutations, 2 VH CDR1 and 1 VH CDR2
*2.5 fold affinity increase

AR4 KD = $2.26 \times 10^{-11}$ M

FIG. 5A

3D12 KD = $6.43 \times 10^{-10}$ M

*Library constructed by error prone PCR of whole scFv
*5 mutations, 2 VL CDR1, 2 VL CDR2, and 1 VL CDR3
*45 fold affinity increase

RAZ1 KD = $2.1 \times 10^{-11}$ M

FIG. 5B

α-BoNT/E:

3E6 → 3E6.1 → 3E6.2

4E17 → 4E17.1 → 4E17.6, 4E17.4

α-BoNT/B:

1B10 → 1B10.1

2B25 → 2B25.1

4B17.1 → 4B17.1C, 4B17.1D, 4B17.1F, 4B17.1G

2B27

A.

| Clone | Framework1 | CDR1 | Framework2 | CDR2 |
|---|---|---|---|---|
| ING1 | QVQLQQSGGGLVQPGGSLRLSCAASGFTFS | NYAMT | WVRQAPGKGLEWVS | SISVGGSDTYYADSVKG |
| ING1.1C1 | QVQLVQSGGGLVQPGGSLRLSCAASGFTFS | NYAMT | WVRQAPGKGLEWVS | SISVGGSDTYYADSVKG |
| ING1.2B10 | QVQLVQSGGGLVQPGGSLRLSCAASGFTFS | NYAMT | WVRQAPGKGLEWVS | SISVGGSDTYYADSVKG |
| ING1.5B1 | QVQLVQSGGGLVQPGGSLRLSCAASGFTFS | NYAMT | WVRQAPGKGLEWVS | SISVGGSDTYYADSVKG |
| ING1.3C2 | QVQLVQSGGGLVQPGGSLRLSCAASGFTFS | NYAMT | WVRQAPGKGLEWVS | SISVGGSDTYYADSVKG |
| 4A1 | QVQLVQSGGGLAQPGGSLRLSCAASGFTFG | SYSMN | WVRQAPGKGLEWVS | SITGNSGLIYYADSVKG |
| 4A1.1 | QVQLVQSGGGLAQPGGSLRLSCAASGFTFG | SYSMN | WVRQAPGKGLEWVS | SITGNSGLIYYADSVKG |
| 5A20 | QVQLVQSGAEVKKPGASVKVSCQASGYTFA | DYYIH | WVRQAPGQGLEWMG | RINSNSGGPNYAQNYQG |

B.

| Clone | Framework1 | CDR1 | Framework2 | CDR2 |
|---|---|---|---|---|
| ING1 | DIVMTQSPSSLSASVGDRVTITC | RASQSISSYLN | WYQQKPGKAPKLLIY | AASSLQS |
| ING1.1C1 | EIVLTQSPSSLSASVGDRVTITC | RASQSISSYLN | WYQQKPGKAPKLLIY | AASSLQS |
| ING1.2B10 | DVVMTQSPSSLSASVGDRVTITC | RASQSISSYLH | WYQQKPGKATKLLIS | DASSSQS |
| ING1.5B1 | DVVMTQSPSSLSASVGDRVTITC | RASQSISSYLH | WYQQKPGKAPTLLIS | DASSSQS |
| ING1.3C2 | EIVLTQSPSSLSASVGDRVTITC | RASQGISNYLA | WYQQKPGKVPKLLIY | AASTLQS |
| 4A1 | DIVMTQSPSSLSASVGDRVTITC | RASQSISSYLN | WYQQKPGKAPKLLIY | AASSLQS |
| 4A1.1 | DVVMTQSPSTLSASVGDRVTITC | RASQTISSYLN | WYQQKPGKAPKLLIY | AASSLQS |
| 5A20 | DIQMTQSPSFLSASVGDRVTITC | RASQGISSALA | WYQQKPGKAPKLLIY | GASSLQS |

| Clone | Framework3 | CDR3 | Framework4 |
|---|---|---|---|
| ING1 | RFTVSRDNSKNTLLLQMNSLRAEDTAVYYCAK | VRTKYCSSLSCFAGFDS | WGQGTRVTVSS |
| ING1.1C1 | RFTVSRDNSKNTLLLQMNSLRAEDTAVYYCAK | VRTKYCSSLSCFAGFDS | WGQGTLVTVSS |
| ING1.2B10 | RFTVSRDNSKNTLLLQMNSLRAEDTAVYYCAK | VRTKYCSSLSCFAGFDS | WGQGTLVTVSS |
| ING1.5B1 | RFTVSRDNSKNTLLLQMNSLRAEDTAVYYCAK | VRTKYCSSLSCFAGFDS | WGQGTLVTVSS |
| ING1.3C2 | RFTVSRDNSKNTLLLQMNSLRAEDTAVYYCAK | VRTKYCSSLSCFAGFDS | WGQGTLVTVSS |
| 4A1 | RFTVSRDNAKNSLFLHMHSLRADDTAVYYCAR | DPGWIYSDTSAAGWFDP | WGHGTLVTVSS |
| 4A1.1 | RFTVSRDNAKNSLFLHMHSLRADDTAVYYCAR | DPGWIYSDTSAAGWFDP | WGHGTLVTVSS |
| 5A20 | RVTMTRDTSISTAYMEVISLRSDDTAVYYCAR | EASFGWSYLGHDDAFDI | WGQGTMVTVSS |

B.

| Clone | Framework3 | CDR3 | Framework4 |
|---|---|---|---|
| ING1 | GVPSRFSGSGSGTDFTLTISSLQPEDFATYYC | QQSYSTPRTT | FGGGTKVDIKR |
| ING1.1C1 | GVPSRFSGSGSGTDFTLTISSLQPEDFATYYC | QQSYSTPPT | FGQGTKVEIKR |
| ING1.2B10 | GVPSRFRFSGSGTDFTLTISSLQPEDFATYYC | QQSYSTRALT | FGGGTKVDIRR |
| ING1.5B1 | GVPSRFSGSRFGTDFTLTISSLQPEDFATYYC | QQSYSTRALT | FGGGTKVEIRR |
| ING1.3C2 | GVPSRFSGSGSGTDFTLTISSLQPEDVATYYC | QQSYSTLMCS | FGQGTKLEIKR |
| 4A1 | GVPSRFSGSGSGTDFTLTISSLQPEDFATYYC | QQSYDTPRT | FGQGTRLEIKR |
| 4A1.1 | GVPSRFSGSGSGTDFTLTISSLQPEDFATYYC | QQSYDTPRT | FGQGTRLEIKR |
| 5A20 | GVPSRFSGSGSGTEFTLTISSLQPDDFATYYC | QQYHTYWT | FGQGTKVEIKR |

| Clone | Framework1 | CDR1 | Framework2 | CDR2 |
|---|---|---|---|---|
| 4B1 | QVQLVQSGAEVEKPGSSVKVSCKASGGSFS | SYAFT | WVRQAPGQGLEWMG | RIVPFLGVPYYTQKFRG |
| 4B3 | QVQLLESGGGLVQPGRSLRLSCAGSGFTFG | DYALS | WFRQAPGKGLEWIG | LIRSRAHGGTIEYAASVKG |
| 4B5 | QVQLVESGGALVKPGGSLRLSCAASGFTFS | DYYMS | WIRQAPGKGLEWVS | YISSSSSYTNYADSVKG |
| 4B6 | QVQLVQSGAEVKKPGESLVISCKASGDKDTFT | SFWIA | WVRQMPGKGLEWMG | IIYAGDSDTRYSPSFQG |
| B6.1 | QVQLVQSGAEVKKPGESLVISCKASGDKDTFT | SFWIA | WVRQMPGKGLEWMG | IIYAGDSDTRYSPSFQG |
| B6.C12 | QVQLVQSGAEVKKPGESLVISCKASGDKDTFT | SFWIA | WVRQMPGKGLEWMG | IIYAGDSDTRYSPSFQG |
| B6.D2 | QVQLVQSGAEVKKPGESLVISCKASGDKDTFT | SFWIA | WVRQMPGKGLEWMG | IIYAGDSDTRYSPSFQG |
| 4B7 | QVQLQQSGPGLVKPSQTLSLTCSVSGGSINSD | GSYWS | WVRQHPGKGLEWIG | YIYYSGTTYFNPSLKS |
| B11 | QVQLLQSAGGVVQPGRSLRLSCAASGFIFR | TYGMH | WVRQAPGKGLEWVA | FVSSDGNNKFYSDSVKG |
| B11.A5 | EVQLVESGGGVVQPGRSLRLSCATSGFILR | TYGMH | WVRQAPGKGLEWVA | FVSSDGNNKFYSDSVKG |
| B11.E9 | EVRLVQSGGGMVQPGRSLRLSCAASGFVFR | TYGMH | WVRQAPGKGLEWVA | FVSSDGNNKFYSDSVKG |
| B11.F7 | EVQLVESGGGVVQPGRSLRLSCAASGFIFR | TYGMH | WVRQAPGKGLEWVA | FVSSDGNNKFYSDSVKG |
| B11.H12 | EVQLVQSGGGVVQPGRSLRLSCAASGFIFR | TYGMH | WVRQAPGKGLEWVA | FVSSDGNNKFYSDSVKG |
| 1B14 | EVQLVESGGGLVQPGGSLRLSCAASGFTFS | SYSMN | WVRQAPGKGLEWVA | VIWYDGSNKYYADSVKG |
| 4B19.1 | QVQLVQSGAEVKKPGASVNVSCKASGYTFT | GYYIY | WVRQAPGQGLEWMG | WINPNSGVTKYAQKFQG |

D.

| Clone | Framework1 | CDR1 | Framework2 | CDR2 |
|---|---|---|---|---|
| 4B1 | EIVLTQSPSSLSASVGDRVTITC | RASQGVSTDLA | WYQQKPGKSPRLLIY | AASTLHS |
| 4B3 | DIQMTQSPSSLSASVGDRVTITC | RASQSISNYLN | WYQKKPGKAPRLLML | AASTLHD |
| 4B5 | DIQMTQSPSSLSASVGDRVTITC | RASQSVTTFLN | WYQQKPGKAPNLLIY | ATSSLQS |
| 4B6 | DVVMTQSPSSLSASVGDRITITC | QAGQDISNFLN | WYQQKPGKAPKLLIR | DASNLET |
| B6.1 | DIQMTQSPSSLSASVGDRVTITC | RASQSISSYLN | WYQQEPGKAPKLLIY | SASSLQS |
| B6.C12 | DIVMTQSPSSLSASVGDRVTITC | RASQSISSYLN | WYQQKPGKAPKLLIY | AASSLQS |
| B6.D2 | DVVMTQSPCLPCLHLIGDRVTITC | RASQSIRDYLS | WYQQEPGKAPKLLIY | SASSLQS |
| 4B7 | DIQMTQSPSSLSASVGDRVTITC | RASQSISSYLN | WYQQKPGTAPKLLIS | DASTLQS |
| B11 | DIVMTQSPSTLSASVGDRVTVTC | RASQSINSWLA | WYQQKPGKAPKLLIY | EASSLES |
| B11.A5 | DIQMTQSPSSVSASVGDRVTITC | RASQGVSRWLA | WYQQRPGEAPKLLIY | GASSLQS |
| B11.E9 | EIVLTQSPATLSVSPGERATLSC | RASQSVSKFLA | WYQQKRGQAPRLLIY | GASTRAT |

| Clone | Framework3 | CDR3 | Framework4 |
|---|---|---|---|
| 4B1 | RVTITADKATSTVYMELSSLTFDDTAVYYCAR | DKRTYEYNWNSLWF | WGRGTLVTVSS |
| 4B3 | RFTISRDDSKSIGYLQMNSLKSEDTAVYYCTR | DILYYHDSSDYWGRGHFYYMDV | WGTGTPVTVSS |
| 4B5 | RFTISRDNAKNSLYLQMNSLRAEDTAVYYCAR | MRGYSSSWHYSYYYVMDV | WGQGTTVTVSS |
| 4B6 | HVNISVDRSTNTAYLQWSSLKASDTAMYYCAR | HDSRYKYFYFGMDV | WGQGTTVTVSS |
| B6.1 | HVNISVDRSTNTAYLQWSSLKASDTAMYYCAR | HDSRYKYFYFGMDV | WGQGTTVTVSS |
| B6.C12 | HVNISVDRSTNTAYLQWSSLKASDTAMYYCAR | HDSRYKYFYFGMDV | WGQGTTVTVSS |
| B6.D2 | HVNISVDRSTNTAYLQWSSLKASDTAMYYCAR | HDSRYKYFYFGMDV | WGQGTTVTVSS |
| 4B7 | RLTMSVDTSKNQFSLKMTSVTAADTAVYYCAR | MSGSRSYSQYYFDS | WGQGTLVTVSS |
| B11 | RFTIPRDNAKNTLYLQMNSLETEDTAVYYCAK | DRYPIDCSGGSCFSYGMDV | WGQGTTVTVSS |
| B11.A5 | RFTIPRDNAKNTLYLQMNSLETEDTAVYYCAK | DRYPIDCSGGSCFSYGMDV | WGQGTLVTVSS |
| B11.E9 | RFTIPRDNAKNTLYLQMNSLETEDTAVYYCAK | DRYPIDCSGGSCFSYGMDV | WGQGTPVTVSS |
| B11.F7 | RFTIPRDNAKNTLYLQMNSLETEDTAVYYCAK | DRYPIDCSGGSCFSYGMDV | WGQGTMVTVSS |
| B11.H12 | RFTIPRDNAKNTLYLQMNSLETEDTAVYYCAK | DRYPIDCSGGSCFSYGMDV | WGQGTLVTVSS |
| 1B14 | RFTISRDNSKNTLYLQMNSLRAEDTAVYYCAR | SSIVGAPYGMDV | WGQGTTVTVSS |
| 4B19.1 | RVTMTIDTSTNTAYMELNRLRADDTAVYYCAR | EWTQLWSPYDY | WGQGTTVTVSS |

D.

| Clone | Framework3 | CDR3 | Framework4 |
|---|---|---|---|
| 4B1 | GVPSRFSGSGSGTDFTLTISSLQPEDVATYFC | QKYYTAPLT | FGGGTKVEIKR |
| 4B3 | GVPSRFSGSGSGQSDFTLTINGLQPEDFATYYC | QESYSVYRT | FGQGTKVEIKR |
| 4B5 | GVPSRFSGSGSGTDFTLTISSLQPEDFATYYC | QQSYSTPLT | FGGGTKLEIKR |
| 4B6 | GVPSRFSGGGSGTHFTFTISSLHPEDIATYFC | QQYDNLPYT | FGQGTKLEIKR |
| B6.1 | GVPSRFSGSGSGTDFTLTISSLQPEDFATYYC | QQSYSTPPYT | FGQGTKLEIKR |
| B6.C12 | GVPSRFSGSGSGTDFTLTISSLQPEAFATYYC | QQSYTAPCT | FGQGTKLEIKR |
| B6.D2 | GVPSRFSGSGSGTDFTLTITNLQPEDFATYYC | LEKYSFPRCT | FGQGTKLDIKR |
| 4B7 | GVPSRFSGSGSGTEFTLTISNLQPEDFATYYC | QQFNSYVWT | FGQGTKLEIKR |
| B11 | GVPSRFSGSGSGTEFTLTISSLQPDDFATYYC | QQYDSYWLT | FGGGTKVEIKR |
| B11.A5 | GVPSRFSGSGSGTDFTLTISSLQPEDFATYYC | QQYDSFPLT | FGGGTKVEIKR |
| B11.E9 | GIPARFSGSGSGTEFALTISSLQSEDFADYYC | QQYDNWPIT | FGQGTRLEIKR |

FIG. 11 (Cont.)

| Clone | Framework1 | CDR1 | Framework2 | CDR2 |
|---|---|---|---|---|
| B11.F7 | ETLTQSPATLSVSPGERATLSC | RASQSVGSTLA | WYQQKPGQAPRLLVY | GASTRAT |
| B11.H12 | EIVLTQSPSSFSASTGDRVTITC | RASQGINNYLA | WYQQKPGKAPKLLIY | AASTLQS |
| 1B14 | EIVLTQSPSSLSAAVGDRVTITC | RASQNIYSYLN | WYQQKLGKAPNLLIY | AVFSLQS |
| 4B19.1 | DIVLTQSPSTLSASVGDRVTISC | RASRSIGWYLN | WYQQRPGKAPKLLIY | AASSLHN |

| Clone | Framework3 | CDR3 | Framework4 |
|---|---|---|---|
| B11.F7 | GIPARFSGSGSGTEFTLTISSLQSEDFAVYYC | QQYNSWPIT | FGQGTRLEIKR |
| B11.H12 | GVPSRFSGGGSGTDFTLTISCLQSEDFATYYC | QQYYSYPLT | FGGGTKVEIKR |
| 1B14 | GVPSRFSGSGYGTDFTLTISSLQPEDFATYYC | QQSSSSPLT | FGGGTKVEIKR |
| 4B19.1 | GVPSRFSGSGSGTEFTLTISSLQPDDFATYYC | QQAFGFPRT | FGQGTKVEIKR |

Heavy Chain

QVQLVESGGGVVQPGRSLRLSCAASGFTFSHYGMHWVRQSPGKGLEWVAVIWYDGRNPYYAASVKGRFTISRDNDKNTLYLQMNSLRAEDTAVYYCVKDLTRFHDT
TFGVFEMWGPGTTVTVSS

Light Chain

EIVLTQSPSFVSASVGDRVTITCRASQGISSWLAWYQQKPGKAPKLLIYAASSLQSGVPSRFSGSGSGTEFTLTISSLQPDDFATYYCQQYSSLYTFGQGTKVDIK
R

FIG. 12

ANTIBODIES THAT NEUTRALIZE BOTULINUM NEUROTOXINS

CROSS-REFERENCE TO RELATED APPLICATIONS

This application claims priority benefit to U.S. provisional application Ser. No. 61/085,328 filed on Jul. 31, 2008, which application is incorporated herein by reference in its entirety.

STATEMENT AS TO FEDERALLY SPONSORED RESEARCH

This invention was made with the support of the United States government under Grant No: UO1AI056493, awarded by the National Institutes of Health and by the Department of Defense Grant DAMD17-98-C-8030. The government has certain rights in the invention.

FIELD OF THE INVENTION

This disclosure relates antibodies that neutralize *botulinum* neurotoxins (e.g., BoNT/A) and their use in the treatment of botulism.

INTRODUCTION

Botulism is caused by *botulinum* neurotoxin secreted by members of the genus *Clostridium* and is characterized by flaccid paralysis, which if not immediately fatal requires prolonged hospitalization in an intensive care unit and mechanical ventilation. Naturally occurring botulism is found in infants or adults whose gastrointestinal tracts become colonized by Clostridial bacteria (infant or intestinal botulism), after ingestion of contaminated food products (food botulism), or in anaerobic wound infections (wound botulism) (Center for Disease Control (1998) Botulism in the United States, 1899-1998. Handbook for epidemiologists, clinicians, and laboratory workers. Atlanta, Ga. U.S. Department of Health and Human Services, Public Health Service: downloadable at "bt.cdc.gov/agent/botulism/index.asp"). Botulism neurotoxins (BoNTs) are also classified by the Centers for Disease Control (CDC) as one of the six highest-risk threat agents for bioterrorism (the "Category A agents"), due to their extreme potency and lethality, ease of production and transport, and need for prolonged intensive care (Arnon et al. (2001) *JAMA* 285: 1059-1070). As a result of these threats, specific pharmaceutical agents are needed for prevention and treatment of intoxication.

No specific small molecule drugs exist for prevention or treatment of botulism, but an investigational pentavalent toxoid vaccine is available from the CDC (Siegel (1988) *J. Clin. Microbiol.* 26: 2351-2356) and a recombinant vaccine is under development (Smith (1998) *Toxicon* 36: 1539-1548). Regardless, mass civilian or military vaccination is unlikely due to the rarity of disease or exposure and the fact that vaccination would prevent subsequent medicinal use of BoNT. Post-exposure vaccination is useless, due to the rapid onset of disease. Toxin neutralizing antibody (Ab) can be used for pre- or post-exposure prophylaxis or for treatment (Franz et al. (1993) Pp. 473-476 In B. R. DasGupta (ed.), *Botulinum* and Tetanus Neurotoxins: Neurotransmission and Biomedical Aspects. Plenum Press, New York). Small quantities of both equine antitoxin and human *botulinum* immune globulin exist and are currently used to treat adult (Black and Gunn. (1980) *Am. J. Med.,* 69: 567-570; Hibbs et al. (1996) *Clin. Infect. Dis.,* 23: 337-340) and infant botulism (Arnon (1993). Clinical trial of human botulism immune globulin, p. 477-482. In B. R. DasGupta (ed.), *Botulinum* and Tetanus Neurotoxins: Neurotransmission and Biomedical Aspects. Plenum Press, New York) respectively.

The development of mAb therapy for botulism is complicated by the fact that there are at least seven BoNT serotypes (A-G) (Hatheway (1995) *Curr. Top. Microbio. Immunol,* 195: 55-75) that show little, if any, antibody cross-reactivity. While only four of the BoNT serotypes routinely cause human disease (A, B, E, and F), there has been one reported case of infant botulism caused by BoNT C (Oguma et al. (1990) *Lancet* 336: 1449-1450), one outbreak of foodborne botulism linked to BoNT D (Demarchi, et al. (1958) *Bull. Acad. Nat. Med,* 142: 580-582), and several cases of suspicious deaths where BoNT G was isolated (Sonnabend et al. (1981) *J. Infect. Dis.,* 143: 22-27). Aerosolized BoNT/C, D, and G have also been shown to produce botulism in primates by the inhalation route (Middlebrook and Franz (1997) *Botulinum* Toxins, chapter 33. In F. R. Sidell, E. T. Takafuji, D. R. Franz (eds.), Medical Aspects of Chemical and Biological Warfare. TMM publications, Washington, D.C.), and would most likely also affect humans. Thus, it is likely that any one of the seven BoNT serotypes can be used as a biothreat agent.

Variability of the BoNT gene and protein sequence within serotypes has also been reported and there is evidence that such variability can affect the binding of monoclonal antibodies to BoNT/A (Kozaki et al. (1998) *Infect. Immun.,* 66: 4811-4816; Kozaki et al. (1995) *Microbiol. Immumol.,* 39: 767-774).

SUMMARY

Antibodies that bind to and neutralize and/or otherwise clear *botulinum* neurotoxin(s) are disclosed herein. Particularly effective neutralization of a Botulism neurotoxin (BoNT) serotype can be achieved by the use of neutralizing antibodies that bind two or more subtypes of the particular neurotoxin serotype with particularly high affinity and/or by combinations of such antibodies. The present disclosure provides antibodies that bind BoNT subtypes BoNT/A, BoNT/B, and BoNT/E. Compositions comprising neutralizing antibodies that bind two or more BoNT subtypes (e.g., BoNT/B1, BoNT/B2, BoNT/B3, etc.) with high affinity are also provided herein.

A neutralizing antibody for *Botulinum* neurotoxin (BoNT) is provided herein. The antibody typically comprises at least one VH complementarity determining region (CDR) selected from the group consisting of a 2A10 VH CDR, a 3E1VH CDR, a 3E2VH CDR, a 3E3VH CDR, a 3E4VH CDR, a 3E4.1VH CDR, a 3E5VH CDR, a 3E6VH CDR, a 3E6.1VH CDR, a 4E1IVH CDR, a 4E13VH CDR, a 4E16VH CDR, a 4E16.1VH CDR, a 4E17VH CDR, a 4E17.1VH CDR, an A12 VH CDR, a 6A12 VH CDR, a B1.1 VH CDR, a B6 VH CDR, a B6.1 VH CDR, a B8 VH CDR, a B8.1 VHCDR, a B11 VH CDR, a B11C3 VH CDR, a B11E8 VH CDR, a B12 VH CDR, a B12.1 VH CDR, a B12.2 VH CDR, a 1B18 VH CDR, a 2B18.1 VH CDR, a 4B19 VH CDR, and a 1B22 VH CDR, a 1B10 VH CDR, a 1B10.1 VH CDR, a 2B18.2 VH CDR, a 5 2B18.3 VH CDR, a 1B22.4 VH CDR, a 2B23 VH CDR, a 2B24 VH CDR, a 2B25 VH CDR, a 2B25.1 VH CDR, a 2B26 VH CDR, a 2B27 VH CDR, a 2B28 VH CDR, a 2B29 VH CDR, a 2B30 VH CDR, a 4B17.1 VH CDR, a 4B17.1C VH CDR, a 4B17.1D VH CDR, a 4B17.1F VH CDR, a 4B17.1G VH CDR, a 3E6.2 VH CDR, a 4E17.4 VH CDR, a 4E17.6 VH CDR, B11.H12 VH CDR, B11.E9 VH CDR, 4B1 VH CDR, 4B3 VH CDR, 4B5 VH CDR, 4B6 VH CDR, 4B7 VH CDR, 1B14 VH CDR, 4A1 VH CDR, 4A1.1 VH CDR, 5A20.4 VH CDR, ING1.1C1 VH CDR, ING1.5B1 VH CDR, ING1.2B10 VH CDR, and ING1.3C2 VH CDR, and/or at least one VL complementarity determining region selected from the group consisting of a 2A10 VL CDR, a 3E1VL CDR, a 3E2 VL CDR, a 3E3 VL CDR, a 3E4 VL CDR, a 3E4.1VL CDR, a 3E5 VL CDR, a 3E6 VL CDR, a 3E6.1 VL CDR, a 4E11 VL CDR, a 4E13 VL CDR, a 4E16 VL CDR, a 4E16.1 VL CDR, a 4E17 VL CDR, a 4E17.1 VL CDR, an A12 VL CDR, a 6A12 VL CDR, a B1.1 VL CDR, a B6 VL CDR, a B6.1 VL CDR, a B8 VL CDR, a B8.1 VL CDR, a B11 VLCDR, a B11C3 VL CDR, a B11E8 VL CDR, a B12 VL CDR, a B12.1 VL CDR, a B12.2 VL CDR, a 1B18 VL CDR, a 2B18.1 VL CDR, a 4B19 VL CDR, and a 1B22 VL CDR, a 1B10 VL CDR, a 1B10.1 VL CDR, a 2B18.2 VL CDR, a 2B18.3 VL CDR, a 1B22.4 VL CDR, a 2B23 VL CDR, a 2B24 VL CDR, a 2B25 VL CDR, a 2B25.1 VL CDR, a 2B26 VL CDR, a 2B27 VL CDR, a 2B28 VL CDR, a 2B29 VL CDR, a 2B30 VL CDR, a 4B17.1 VL CDR, a 4B17.1C VL CDR, a 4B17.1D VL CDR, a 4B17.1F VL CDR, a 4B17.1G VL CDR, a 3E6.2 VL CDR, a 4E17.4 VL CDR, a 4E17.6 VL CDR, B11.H12 VL CDR, B11.E9 VL CDR, 4B1 VL CDR, 4B3 VL CDR, 4B5 VL CDR, 4B6 VL CDR, 4B7 VL CDR, 1B14 VL CDR, 4A1 VL CDR, 4A1.1 VL CDR, 5A20.4 VL CDR, ING1.1C1 VL CDR, ING1.5B1 VL CDR, ING1.2B10 VL CDR, and ING1.3C2 VL CDR.

The antibody may contain the VH CDRs of an antibody selected from the group consisting of 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6 B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2; and/or the VL CDRs of an antibody selected from the group consisting of 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6 B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2.

The antibody may contain the VH and VL CDRs of an antibody selected from the group consisting of 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6 B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2

The antibody may contain the VH and VL domains of an antibody selected from the group consisting of 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6 B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2.

The antibody may be a single chain Fv (scFv), a Fab, a $(Fab')_2$, an $(ScFv)_2$, and the like. The antibody may be an IgG. The antibody may be selected from the group consisting of 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, B6.1, B11E8, 4E17.1, 4E16.1, 3E6.1, B12.1, 4E17.4, 4E17.6 B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2. The antibody may also be in a pharmaceutically acceptable excipient (e.g., in a unit dosage formulation).

Methods of inhibiting the activity of *Botulinum* neurotoxin in a mammal may involve administering to a mammal in need thereof a composition comprising at least one neutralizing anti-BoNT antibody as described herein. The composition may include at least two different antibodies, each of which binds to different BoNT subtypes. The composition may also include at least three, at least four, or more different antibodies, each of which may bind to different BoNT epitopes.

Compositions provided herein may partially or fully neutralize a *Botulinum* neurotoxin (BoNT). The compositions typically include a first antibody that binds a BoNT/B or a BoNT/E serotype, e.g., one or more antibodies as described above, and a second antibody that binds a BoNT serotype selected from the group consisting of BoNT/A, BoNT/B, BoNT/C, BoNT/D, BoNT/E, and BoNT/F.

Nucleic acids provided herein encode one or more antibodies that are described herein. Cells containing such antibodies are also provided herein. Kits provided for neutralizing a *Botulinum* neurotoxin may include a composition containing one or more antibodies as described herein. The kits optionally also include instructional materials teaching the use of the composition to neutralize a *Botulinum* neurotoxin. The composition may be stored in a disposable syringe.

BRIEF DESCRIPTION OF THE DRAWINGS

FIG. 1 shows deduced protein sequences of heavy (VH) and light (VL) chain variable regions of BoNT B binders. VH domains: A12 (SEQ ID NO:1), 6A12 (SEQ ID NO:2), B1.1 (SEQ ID NO:3), B6 (SEQ ID NO:4), B6.1 (SEQ ID NO:5), B8 (SEQ ID NO:6), B8.1 (SEQ ID NO:7), B11 (SEQ ID NO:8), B11C3 (SEQ ID NO:9), B11E8 (SEQ ID NO:10), B12 (SEQ ID NO:11), B12.1 (SEQ ID NO:12), B12.2 (SEQ ID NO:13), 1B18 (SEQ ID NO:14), 2B18.1 (SEQ ID NO:15), 4B19 (SEQ ID NO:16), 1B22 (SEQ ID NO:17), 1B10 (SEQ ID NO:18), 1B10.1 (SEQ ID NO:19), 2B18.2 (SEQ ID NO:20), 2B18.3 (SEQ ID NO:21), 1B22.4 (SEQ ID NO:22), 2B23 (SEQ ID NO:23), 2B24 (SEQ ID NO:24), 2B25 (SEQ ID NO:25), 2B25.1 (SEQ ID NO:26), 2B26 (SEQ ID NO:27), 2B27 (SEQ ID NO:28), 2B28 (SEQ ID NO:29), 2B29 (SEQ ID NO:30), 2B30 (SEQ ID NO:31), 4B17.1 (SEQ ID NO:32), 4B17.1C (SEQ ID NO:33), 4B17.1D (SEQ ID NO:34), 4B17.1F (SEQ ID NO:35), 4B17.1G (SEQ ID NO:36). VL domains: A12 (SEQ ID NO:37), 6A12 (SEQ ID NO:38), B1.1 (SEQ ID NO:39), B6 (SEQ ID NO:40), B6.1 (SEQ ID NO:41), B8 (SEQ ID NO:42), B8.1 (SEQ ID NO:43), B11 (SEQ ID NO:44), B11C3 (SEQ ID NO:45), B11E8 (SEQ ID NO:46), B12 (SEQ ID NO:47), B12.1 (SEQ ID NO:48), B12.2 (SEQ ID NO:49), 1B18 (SEQ ID NO:50), 2B18.1 (SEQ ID NO:51), 4B19 (SEQ ID NO:52), 1B22 (SEQ ID NO:53), 1B10 (SEQ ID NO:54), 1B10.1 (SEQ ID NO:55), 2B18.2 (SEQ ID NO:56), 2B18.3 (SEQ ID NO:57), 1B22.4 (SEQ ID NO:58), 2B23 (SEQ ID NO:59), 2B24 (SEQ ID NO:60), 2B25 (SEQ ID NO:61), 2B25.1 (SEQ ID NO:62), 2B26 (SEQ ID NO:63), 2B27 (SEQ ID NO:64), 2B28 (SEQ ID NO:65), 2B29 (SEQ ID NO:66), 2B30 (SEQ ID NO:67), 4B17.1 (SEQ ID NO:68), 4B17.1C (SEQ ID NO:69), 4B17.1D (SEQ ID NO:70), 4B17.1F (SEQ ID NO:71), 4B17.1G (SEQ ID NO:72).

FIG. 2 shows deduced protein sequences of heavy and light chain variable regions of BoNT/E binders. VH domains: 2A10 (SEQ ID NO:73), 3E1 (SEQ ID NO:74), 3E2 (SEQ ID NO:75), 3E3 (SEQ ID NO:76), 3E4 (SEQ ID NO:77), 3E4.1 (SEQ ID NO:78), 3E5 (SEQ ID NO:79), 3E6 (SEQ ID NO:80), 3E6.1 (SEQ ID NO:81), 4E11 (SEQ ID NO:82), 4E13 (SEQ ID NO:83), 4E16 (SEQ ID NO:84), 4E16.1 (SEQ ID NO:85), 4E17 (SEQ ID NO:86), 4E17.1 (SEQ ID NO:87), 3E6.2 (SEQ ID NO:88), 4E17.4 (SEQ ID NO:89), 4E17.6 (SEQ ID NO:90); VL domains: 2A10 (SEQ ID NO:91), 3E1 (SEQ ID NO:92), 3E2 (SEQ ID NO:93), 3E3 (SEQ ID NO:94), 3E4 (SEQ ID NO:95), 3E4.1 (SEQ ID NO:96), 3E5 (SEQ ID NO:97), 3E6 (SEQ ID NO:98), 3E6.1 (SEQ ID NO:99), 4E11 (SEQ ID NO:100), 4E13 (SEQ ID NO:101), 4E16 (SEQ ID NO:102), 4E16.1 (SEQ ID NO:103), 4E17 (SEQ ID NO:104), 4E17.1 (SEQ ID NO:105), 3E6.2 (SEQ ID NO:106), 4E17.4 (SEQ ID NO:107), 4E17.6 (SEQ ID NO:108).

FIGS. 5A and 5B show a scheme used for affinity maturation of HuC25 (FIG. 5A) and 3D12 (FIG. 5B) scFv using yeast display.

FIG. 11 is a schematic providing the amino acid sequences of the $V_H$ and $V_L$ of certain antibodies disclosed herein. Panels A and B present $V_H$ and $V_L$ amino acid sequences, respectively, for BoNT/A binding antibodies, while panels C and D present $V_H$ and $V_L$ amino acid sequences, respectively, for BoNT/B binding antibodies.

FIG. 11, Panel A, $V_H$ domains: ING1 (SEQ ID NO:939), ING1.1C1 (SEQ ID NO:940), ING1.2B10 (SEQ ID NO:941), ING1.5B1 (SEQ ID NO:942), ING1.3C2 (SEQ ID NO:943), 4A1 (SEQ ID NO:944), 4A1.1 (SEQ ID NO:945), 5A20 (SEQ ID NO:946).

FIG. 11, Panel B, $V_L$ domains: ING1 (SEQ ID NO:947), ING1.1C1 (SEQ ID NO:948), ING1.2B10 (SEQ ID NO:949), ING1.5B1 (SEQ ID NO:950), ING1.3C2 (SEQ ID NO:951), 4A1 (SEQ ID NO:952), 4A1.1 (SEQ ID NO:953), 5A20 (SEQ ID NO:954).

FIG. 11, Panel C, $V_H$ domains: 4B1 (SEQ ID NO:955), 4B3 (SEQ ID NO:956), 4B5 (SEQ ID NO:957), 4B6 (SEQ ID NO:958), B6.1 (SEQ ID NO:959), B6.C12 (SEQ ID NO:960), B6.D2 (SEQ ID NO:961), 4B7 (SEQ ID NO:962), B11(SEQ ID NO:963), B11.A5 (SEQ ID NO:964), B11.B9 (SEQ ID NO:965), B11.F7 (SEQ ID NO:966), B11.H12 (SEQ ID NO:967), 1B14 (SEQ ID NO:968), 4B19.1(SEQ ID NO:969).

FIG. 11, Panel D, $V_L$ domains: 4B1 (SEQ ID NO:970), 4B3 (SEQ ID NO:971), 4B5 (SEQ ID NO:972), 4B6 (SEQ ID NO:973), B6.1 (SEQ ID NO:974), B6.C12 (SEQ ID NO:975), B6.D2 (SEQ ID NO:976), 4B7 (SEQ ID NO:977), B11(SEQ ID NO:978), B11.A5 (SEQ ID NO:979), B11.B9 (SEQ ID NO:980), B11.F7 (SEQ ID NO:981), B11.H12 (SEQ ID NO:982), 1B14 (SEQ ID NO:983), 4B19.1(SEQ ID NO:984).

FIG. 12 depicts the amino acid sequences of the VH (SEQ ID NO:1307) and VL (SEQ ID NO:1308) of 1B10.1, in which the bolded amino acid residues are the CDRs according to the IMGT definition (SEQ ID NOS:1309-1314, respectively) while the underlined residues represent the CDRs according to Kabat et al., supra. (SEQ ID NOS: 484, 486, 488, 742, 744, and 746, respectively).

DEFINITIONS

Figure 3:
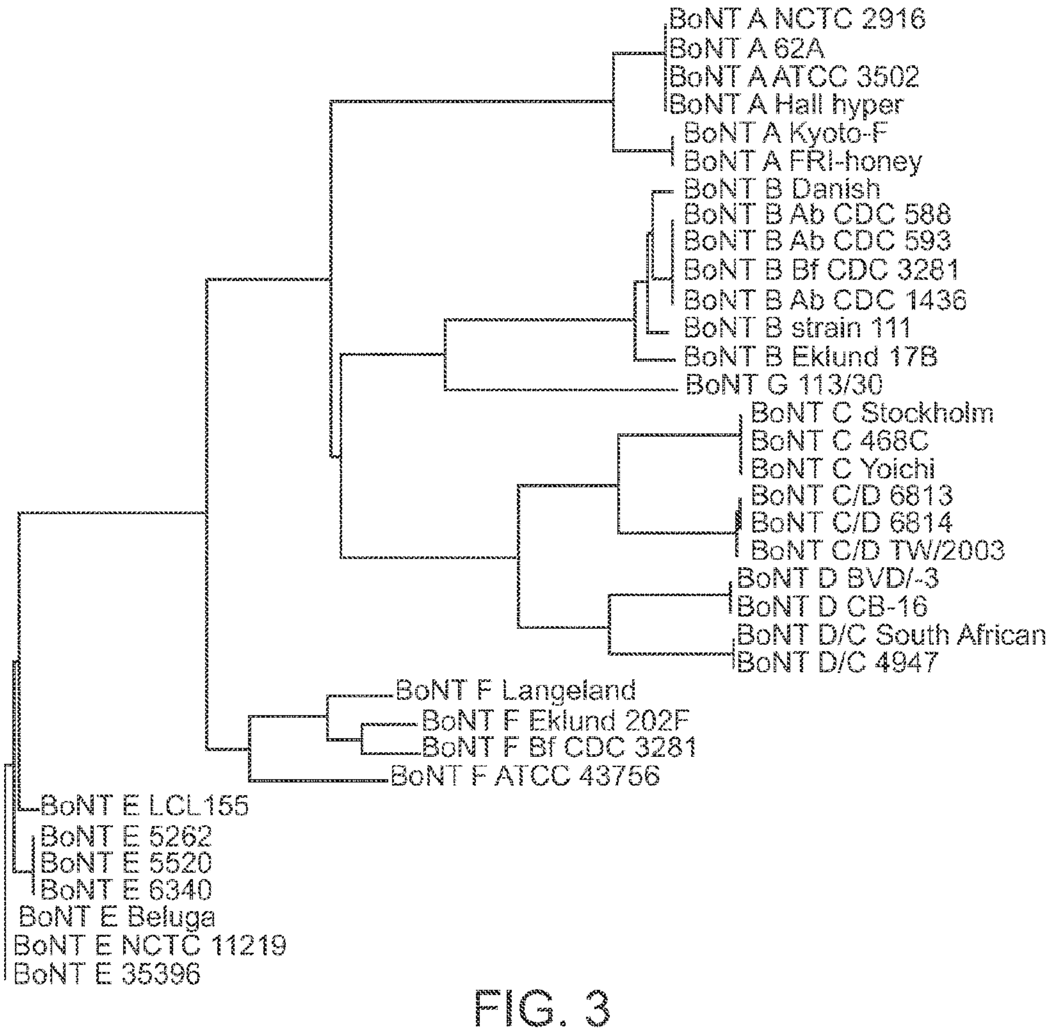
FIG. 3 shows a phylogenetic tree of published *botulinum* neurotoxin genes. The phylogenetic tree was constructed from the DNA sequences of published Clostridial neurotoxin genes using Vector NTI software.
Figure 4:
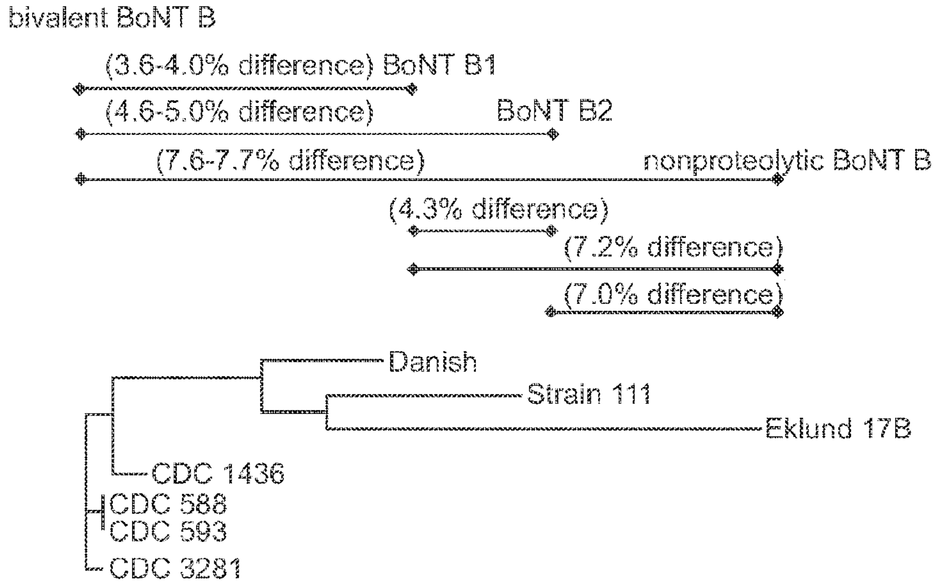
FIG. 4 shows an analysis of BoNT/B gene sequences. A phylogenetic tree of BoNT/B genes reveals four clusters: BoNT/B1, BoNT/B2, nonproteolytic BoNT/B, and bivalent BoNT/B. Percent differences between clusters range from 3.6 to 7.7%. As with BoNT/A, the greatest differences are seen in the heavy chain.

A "BoNT polypeptide" refers to a *Botulinum* neurotoxin polypeptide (e.g., a BoNT/A polypeptide, a BoNT/B polypeptide, a BoNT/C polypeptide, and so forth). The BoNT polypeptide can refer to a full-length polypeptide or to a fragment thereof. Thus, for example, the term "BoNT/A polypeptide" refers to either a full-length BoNT/A (a neurotoxin produced by *Clostridium botulinum* of the type A serotype) or a fragment thereof (e.g. the $H_C$ fragment). The $H_C$ fragment of BoNT/A is an approximately 50 kDa C-terminal fragment (residues 873-1296) of BoNT/A (Lacy and Stevens (1999) *J. Mol. Biol.,* 291: 1091-1104).

A "BoNT" serotype refers one of the standard known BoNT serotypes (e.g. BoNT/A, BoNT/B, BoNT/C, BoNT/D, BoNT/E, BoNT/F, BoNT/G etc.). BoNT serotypes differ from each other by as little as about 35% at the amino acid level (e.g., between BoNT/E and BoNT/F) up to about 66% at the amino acid level, (e.g., for BoNT/A vs BoNT/C or D). Thus, BoNT serotypes differ from each other by about 35-66% at the amino acid level.

The term "BoNT subtype" (e.g., a BoNT/A1 subtype) refers to *botulinum* neurotoxin gene sequences of a particular serotype (e.g., A, B, C, D, E, F, etc.) that differ from each other sufficiently to produce differential antibody binding. The subtypes may differ from each other by at least 2.5%, by at least 5%, by at least 10%, by at least 15% or up to about at least 20% at the amino acid level. The subtypes differ from each other by no more than 35%, by no more than 31.6%, by no more than 30%, or 25%, by less than about 20% or 16% at the amino acid level. BoNT subtypes may differ from each other by at least 2.6%, by at least 3%, and by at least 3.6% at the amino acid level. BoNT subtypes typically differ from each other by less than about 31.6%, by less than about 16%, at the amino acid level, other by less than about 31.6%, by less than about 16%, at the amino acid level.

An "anti-BoNT antibody" refers to an antibody that binds a BoNT polypeptide, specifically binds a BoNT polypeptide with a $K_D$ less than $10^{-7}$, less than $10^{-8}$, less than $10^{-9}$, less than $10^{-10}$, less than $10^{-11}$, or less than $10^{-12}$ or less.

"Neutralization" refers to a measurable decrease in the toxicity and/or circulating level of a *Botulinum* neurotoxin (e.g., BoNT/A).

"Potency" refers to the degree of protection from challenge with BoNT. This can be measured/quantified for example, as an increase in the $LD_{50}$ of a *Botulinum* neurotoxin (BoNT). In toxicology, the median lethal dose, $LD_{50}$ (abbreviation for "Lethal Dose, 50%"), or $LCt_{50}$ (Lethal Concentration & Time) of a toxic substance or radiation is the dose required to kill half the members of a tested population. The $LD_{50}$ usually expressed as the mass of substance administered per unit mass of test subject, such as grams of substance per kilogram of body mass. Stating it this way allows the relative toxicity of different substances to be compared, and normalizes for the variation in the size of the animals exposed (although toxicity does not always scale simply with body mass). Typically, the $LD_{50}$ of a substance is given in milligrams per kilogram of body weight. In the case of some toxins, the $LD_{50}$ may be more conveniently expressed as micrograms per kilogram (μg/kg) of body mass.

The term "high affinity" when used with respect to an antibody refers to an antibody that specifically binds to its target(s) with an affinity ($K_D$) of at least about $10^{-8}$ M, preferably at least about $10^{-9}$ M, at least about $10^{-10}$ M, and at least about $10^{-11}$ M. "High affinity" antibodies may have a $K_D$ that ranges from about 1 nM to about 5 pM.

The following abbreviations are used herein: AMP, ampicillin; BIG, *botulinum* immune globulin; BoNT, *botulinum* neurotoxin; BoNT/A, BoNT type A; BoNT/B: *Botulinum* neurotoxin serotype B, BoNT/A $H_C$: *Botulinum* neurotoxin serotype A binding domain, C-terminal domain of the BoNT/A heavy chain; BoNT/A $H_N$: *Botulinum* neurotoxin serotype A translocation domain, N-terminal domain of the BoNT/A heavy chain; BoNT/A $L_C$: *Botulinum* neurotoxin serotype A catalytic domain; CDR, complementarity determining region; ELISA, enzyme-linked immunosorbent assay; GLU, glucose; HBS, HEPES-buffered saline (10 mM HEPES, 150 mM NaCl [pH 7.4]); IgG, immunoglobulin G; IMAC, immobilized-metal affinity chromatography; IPTG, isopropyl-β-D-thiogalactopyranoside; KAN, kanamycin; $K_D$, equilibrium constant; $k_{off}$, dissociation rate constant; $k_{on}$, association rate constant; MPBS, skim milk powder in PBS; NTA, nitrilotriacetic acid; PBS, phosphate-buffered saline (25 mM $NaH_2PO_4$, 125 mM NaCl [pH 7.0]; RU, resonance units; scFv, single-chain Fv antibody fragment; TPBS, 0.05% (vol/vol) Tween 20 in PBS; TMPBS, 0.05% (vol/vol) Tween 20 in MPBS; TU, transducing units; $V_H$, immunoglobulin heavy-chain variable region; $V_K$, immunoglobulin kappa light-chain variable region; $V_L$ immunoglobulin light-chain variable region; wt, wild type; CDC: Centers for Disease Control, CMV: cytomegalovirus; Fab: antigen binding fragment of immunoglobulin with variable domain and first constant domain, Fc: fragment crystalizable, Fab'$_2$; fragment, antigen binding; mAb; monoclonal antibody, FACS: fluorescence activated cell sorting, $LD_{50}$,; lethal dose 50%; MFI: mean fluorescent intensity, MLA: mouse lethality assay; PCR: polymerase chain reaction, SD-CAA: selective growth dextrose casamino acids media, SG-CAA media: selective growth galactose casamino acids media; AgaII; yeast agglutinin receptor, pM; picomolar, fM; femtomolar, IU; International Unit, CHO; Chinese hamster ovary cells.

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR (§ 1.822(b)(4)). Furthermore, it should be noted that a dash at the beginning or end of an amino acid residue sequence indicates either a peptide bond to a further sequence of one or more amino acid residues or a covalent bond to a carboxyl or hydroxyl end group. However, the absence of a dash should not be taken to mean that such peptide bonds or covalent bond to a carboxyl or hydroxyl end group is not present, as it is conventional in representation of amino acid sequences to omit such.

The term "antibody" (also used interchangeably with "immunoglobulin") encompasses polyclonal and monoclonal antibody preparations where the antibody may be of any class of interest (e.g., IgM, IgG, and subclasses thereof), as well as preparations including hybrid antibodies, altered antibodies, F(ab')$_2$ fragments, F(ab) molecules. Fv fragments, single chain fragment variable displayed on phage (scFv), single chain antibodies, single domain antibodies, chimeric antibodies, humanized antibodies, and functional fragments thereof which exhibit immunological binding properties of the parent antibody molecule. The antibodies may be conjugated to other moieties, and/or may be bound to a support (e.g., a solid support), such as a polystyrene plate or bead, test strip, and the like.

Immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (usually of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 150 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, (1991 and Lefranc et al. IMGT, the international ImMunoGeneTics information System®. Nucl. Acids Res., 2005, 33, D593-D597)). A detailed discussion of the IMGTS system, including how the IMGTS system was formulated and how it compares to other systems, is provided on the World Wide Web at imgt.cines.fr/textes/IMGTScientificChart/Numbering/IMGTnumberingsTable.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. All CDRs and framework provided by the present disclosure are defined according to Kabat et al, supra, unless otherwise indicated.

An "antibody" thus encompasses a protein having one or more polypeptides that can be genetically encodable, e.g., by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies encompass intact immunoglobulins as well as a number of well characterized fragments produced by digestion with various peptidases. Thus, for example, pepsin digests an antibody below the disulfide linkages in the hinge region to produce $F(ab)'_2$, a dimer of Fab which itself is a light chain joined to VH-CHI by a disulfide bond. The $F(ab)'_2$ may be reduced under mild conditions to break the disulfide linkage in the hinge region thereby converting the $(Fab')_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, $Fab'_2$, IgG, IgM, IgA, scFv, dAb, nanobodies, unibodies, and diabodies.

Antibodies and fragments of the present disclosure encompass those that are bispecific. Bispecific antibodies or fragments can be of several configurations. For example, bispecific antibodies may resemble single antibodies (or antibody fragments) but have two different antigen binding sites (variable regions). Bispecific antibodies may be produced by chemical techniques (Kranz et al. (1981) *Proc. Natl. Acad. Sci., USA,* 78: 5807), by "polydoma" techniques (see, e.g., U.S. Pat. No. 4,474,893), or by recombinant DNA techniques. Bispecific antibodies may have binding specificities for at least two different epitopes, at least one of which is an epitope of BoNT. The BoNT binding antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest,* 4th ed. U.S. Dept. Health and Human Services, Public Health Services, Bethesda, Md. (1987).

A 1B10 antibody refers to an antibody expressed by clone 1B10 or to an antibody synthesized in other manners, but having the same CDRs and optionally, the same framework regions as the antibody expressed by clone 1B10. Similarly, antibodies 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.E9, B11.F7, B6.1. B11E8, 4E17.1, 4E16.1, 3E6.1, B12.1, B11.H12 B11.E9, 4B1, 4B3, 4B5, 4B6, 4B7, 1B14, 4A1, 4A1.1, 5A20.4, ING1.1C1, ING1.5B1, ING1.2B10, ING1.3C2, and the like refer to antibodies expressed by the corresponding clone(s) and/or to antibodies synthesized in other manners, but having the same CDRs and optionally, the same framework regions as the referenced antibodies.

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity and is thus equal to the equilibrium dissociation constant $K_D$ (see, generally, Davies et al. *Ann. Rev. Biochem.* 1990, 59: 439-15 473).

A "BoNT-neutralizing antibody" refers to an antibody that binds to one or more *Botulinum* neurotoxin(s) (e.g., BoNT/B1, BoNT/B2, etc.) and that by so-binding reduces the toxicity and/or circulating level of that BoNT neurotoxin. Thus, for example the term "BoNT/B-neutralizing antibody", as used herein refers to an antibody that specifically binds to a BoNT/B polypeptide (e.g. a BoNT/B1 polypeptide). An exemplary antibody may bind to an $H_C$ domain of a BoNT/B polypeptide and reduces the toxicity and/or circulating level of the BoNT/B polypeptide. Reduced toxicity can be measured as an increase in the time that paralysis developed and/or as a lethal dosage (e.g., $LD_{50}$) as described herein. Antibodies derived from BoNT-neutralizing antibodies include, but are not limited to, the antibodies whose sequence is expressly provided herein.

Antibodies derived from BoNT-neutralizing antibodies have a binding affinity of about $1.6\times10^{-8}$ or better and can be derived by screening libraries of single chain Fv fragments displayed on phage or yeast constructed from heavy ($V_H$) and light ($V_L$) chain variable region genes obtained from mammals, including mice and humans, immunized with *botulinum* toxoid, toxin, or BoNT fragments. Antibodies can also be derived by screening phage or yeast display libraries in which a known BoNT-neutralizing variable heavy ($V_H$) chain is expressed in combination with a multiplicity of variable light ($V_L$) chains or conversely a known BoNT-neutralizing variable light chain is expressed in combination with a multiplicity of variable heavy ($V_H$) chains. BoNT-neutralizing antibodies also include those antibodies produced by the introduction of mutations into the variable heavy or variable light complementarity determining regions (CDR1, CDR2 or CDR3) as described herein. Finally BoNT-neutralizing antibodies include those antibodies produced by any combination of these modification methods as applied to the BoNT-neutralizing antibodies described herein and their derivatives.

An "epitope" is a site on an antigen (e.g. BoNT) to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

A neutralizing epitope refers to the epitope specifically bound by a neutralizing antibody.

"Isolated" refers to an entity of interest that is in an environment different from that in which the compound may naturally occur. An "isolated" compound is separated from all or some of the components that accompany it in nature and may be substantially enriched. "Isolated" also refers to the state of a compound separated from all or some of the components that accompany it during manufacture (e.g., chemical synthesis, recombinant expression, culture medium, and the like).

A single chain Fv ("scFv") polypeptide is a covalently linked $V_H$::$V_L$ heterodimer which may be expressed from a nucleic acid including $V_H$- and $V_L$-encoding sequences either joined directly or joined by a peptide-encoding linker (Huston, et al. (1988) *Proc. Nat. Acad. Sci. USA,* 85: 5879-5883). A number of structures are available for converting the light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Recombinant design methods may be used to develop suitable chemical structures (linkers) for converting two heavy and light polypeptide chains from an antibody variable region into a scFv molecule which will fold into a three-dimensional structure that is substantially similar to native antibody structure.

Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and may be free of residues having large side groups which might interfere with proper folding of the $V_H$ and $V_L$ chains. Thus, suitable linkers generally comprise polypeptide chains of alternating sets of glycine and serine residues, and may include glutamic acid and lysine residues inserted to enhance solubility. One particular linker has the amino acid sequence $(Gly_4Ser)_3$ (SEQ ID NO:109). Another particularly preferred linker has the amino acid sequence comprising 2 or 3 repeats of $[(Ser)_4Gly]$ (SEQ ID NO:110), such as $[(Ser)_4Gly]_3$ (SEQ ID NO:111), and the like. Nucleotide sequences encoding such linker moieties can be readily provided using various oligonucleotide synthesis techniques known in the art (see, e.g., Sambrook, supra.).

The phrase "specifically binds to" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, BoNT/B-neutralizing antibodies can be raised to BoNT/B protein(s) that specifically bind to BoNT/B protein(s), and not to other proteins present in a tissue sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The term "conservative substitution" is used in reference to proteins or peptides to reflect amino acid substitutions that do not substantially alter the activity (specificity or binding affinity) of the molecule. Typically conservative amino acid substitutions involve substituting one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (1), Leucine (L), Methionine (M), Valine (V); and 6) Phenylalanine (F), Tyrosine (Y), Tryptophan (W).

DETAILED DESCRIPTION

This disclosure provides antibodies that specifically bind to *botulinum* neurotoxin, with those that bind to *botulinum* neurotoxin serotype B and E being of particular interest, as well as antibodies that bind other *botulinum* neurotoxin serotypes (e.g., A). *Botulinum* neurotoxin is produced by the anaerobic bacterium *Clostridium botulinum*. *Botulinum* neurotoxin poisoning (botulism) arises in a number of contexts including, but not limited to food poisoning (food borne botulism), infected wounds (wound botulism), "infant botulism" from ingestion of spores and production of toxin in the intestine of infants, and as a chemical/biological warfare agent. Botulism is a paralytic disease that typically begins with cranial nerve involvement and progresses causally to involve the extremities. In acute cases, botulism can prove fatal.

There are multiple subtypes of various BoNT serotypes. There are also many antibodies that bind, for example the BoNT/A1 subtype but will not bind the BoNT/A2 subtype, and so forth.

The present disclosure is related to the discovery that particularly efficient neutralization of a botulism neurotoxin (BoNT) subtype is achieved by the use of neutralizing antibodies that bind two, three, or more subtypes of the particular BoNT serotype with high affinity. This may be accomplished by using two, three, four, or more different antibodies directed against each of the subtypes, or alternatively, by the use of antibodies that are cross-reactive for different BoNT subtypes, or by bispecific or polyspecific antibodies with specificities for two, three, or four or more BoNT epitopes, and/or serotypes, and/or subtypes.

It was discovered that combining neutralizing antibodies increases the potency of the antibody composition dramatically. This increase makes it possible to generate a multi-antibody, and/or multi-specific antibodies of the required potency for therapeutic use. The high potency of the antibody combinations can allow vialling of an extremely low dose of total antibody as a therapeutic dose, resulting in lower manufacturing costs. As one combines two, three or four monoclonal antibodies, the particular BoNT epitope that is recognized becomes less important. Thus, compositions containing at least two, or at least three high affinity antibodies that bind overlapping or non-overlapping epitopes on the BoNT are contemplated herein.

Thus, compositions contemplated herein may include two or more, three or more, four or more, five or more different antibodies selected from the antibodies described herein (see, e.g., FIGS. 1, 2, and 11) and/or antibodies comprising one or more CDRs from these antibodies, and/or one or more antibodies comprising mutants or derivatives of these antibodies. The composition may include antibodies selected from the group consisting of 1B10.1, 2B18.1, B11.E8, and optionally B6.1 and B8.1. The compositions may also contain antibodies 4E17.1 together with two of the following: 3E2, 3E6.1, 3E6.2, 4E16.1.

Compositions contemplated herein may include monovalent BoNT/B antitoxins (e.g. comprising B12.1, B11.E8, B6.1, 2B18.1 and 1B10.1). Compositions may also include monovalent BoNT/E antitoxins (e.g. comprising 3E2, 3E6.1, 3E6.2, 4E16.1, and 4E17.1). Compositions containing trivalent BoNT/A, BoNT/B and BoNT/E toxins (e.g. comprising antibodies selected from those described in PCT Pub. Nos. WO 07/094754, WO 05/016232, and 09/008916, and B12.1, B11.E8, B6.1, 2B18.1, 1B10.1, 3E2, 3E6.1, 3E6.2, 4E16.1, and 4E17.1) are also contemplated.

As indicated above, the antibodies provided by the present disclosure bind to one or more *botulinum* neurotoxin type B, E, and in certain instances Bont/A subtypes, and, in some embodiments, can neutralize the neurotoxin. Neutralization, in this context, refers to a measurable decrease in the toxicity and/for circulating level of the target neurotoxin. Such a decrease in toxicity can be measured in vitro by a number of methods well known to those of skill in the art. One such assay involves measuring the time to a given percentage (e.g., 50%) twitch tension reduction in a hemidiaphragm preparation. Toxicity can be determined in vivo, e.g. as an $LD_{50}$ in a test animal (e.g. mouse) *botulinum* neurotoxin type A in the presence of one or more putative neutralizing antibodies. The neutralizing antibody or antibody combination can be combined with the *botulinum* neurotoxin prior to administration, or the animal can be administered the antibody prior to, simultaneous with, or after administration of the neurotoxin. The rate of clearance of BoNT mediated by a test antibody, or combination of test antibodies, can be measured (e.g. in mice) by administering labeled BoNT (e.g. radiolabeled BoNT/A) and measuring the levels of BoNT in the serum and the liver over time in the presence or absence of test antibody or antibodies (see, e.g., Ravichandran et al. (2006) *J Pharmacol Exp Ther* 318: 1343-1351 (2006).

As the antibodies of the present disclosure act to neutralize *botulinum* neurotoxins, they are useful in the treatment of pathologies associated with *botulinum* neurotoxin poisoning. The treatments essentially comprise administering to the poisoned organism (e.g. human or non-human mammal) a quantity of one or more neutralizing antibodies sufficient to neutralize (e.g. mitigate or eliminate) symptoms of BoNT poisoning.

Such treatments are most desired and efficacious in acute cases (e.g. where vital capacity is less than 30-40 percent of predicted and/or paralysis is progressing rapidly and/or hypoxemia with absolute or relative hypercarbia is present. These antibodies can also be used to treat early cases with symptoms milder than indicated (to prevent progression) or even prophylactically (a use the military envisions for soldiers going in harm's way). Treatment with the neutralizing antibody can be provided as an adjunct to other therapies (e.g. antibiotic treatment).

The antibodies provided by this disclosure can also be used for the rapid detection/diagnosis of botulism (type B, E, or A toxin(s)) and thereby supplement and/or replace previous laboratory diagnostics.

This disclosure also provides the epitopes specifically bound by *botulinum* neurotoxin antibodies described herein. These epitopes can be used to isolate, and/or identify and/or screen for other antibodies BoNT neutralizing antibodies as described herein.

I. Potency of *Botulinum* Neurotoxin (BoNT)-Neutralizing Antibodies.

Without being bound to a particular theory, it is believed that the current antitoxins used to treat botulism (horse and human) have a potency of about 5000 mouse $LD_{50}$s/mg (human) and 55.000 mouse $LD_{50}$s/mg (horse).

Based on calculation, a commercially desirable antitoxin may generally have a potency greater than about 10,000 to 100,000 $LD_{50}$s/mg. Combinations of the antibodies described herein (e.g., two or three antibodies) can meet this potency. Thus, this disclosure provides antibodies and/or antibody combinations that neutralize at least about 10,000 mouse $LD_{50}$s/mg of antibody, preferably at least about 15,000 mouse $LD_{50}$s/mg of antibody, more preferably at least about 20,000 mouse $LD_{50}$s/mg of antibody, and most preferably at least about 25,000 mouse $LD_{50}$s/mg of antibody.

II. *Botulinum* Neurotoxin (BoNT)-Neutralizing Antibodies.

BoNT neutralizing antibodies may be selected based on their affinity to one or more BoNT subtypes. A number of subtypes are known for each BoNT serotype. Thus, for example, BoNT/A subtypes include, but are not limited to, BoNT/A1, BoNT/A2, BoNT/A3, and the like (see, e.g., FIG. 3). It is also noted, for example, that the BoNT/A1 subtype includes, but is not limited to 62A, NCTC 2916, ATCC 3502, and Hall hyper (Hall Allergan) and are identical (99.9-100% identity at the amino acid level.) and have been classified as subtype A1. The BoNT/A2 sequences (Kyoto-F and FRI-A2H) (Willems, et al. (1993) Res. *Microbiol.* 144:547-556) are 100% identical at the amino acid level. Another BoNT/A subtype, (that we are calling A3) is produced by a strain called Loch Maree that killed a number of people in an outbreak in Scotland.

Similarly, as shown in FIG. 3, a number of subtypes are also known for serotypes B, C, E, and F. Using, the methods described herein, it was discovered that high affinity antibodies that are cross-reactive with two or more subtypes within a serotype can also be produced (e.g., selected/engineered). Moreover, without being bound to a particular theory, it appears that these cross-reactive antibodies can be more efficient in neutralizing *Botulinum* neurotoxin, particularly when used in combination one or more different neutralizing antibodies.

Figure 10:
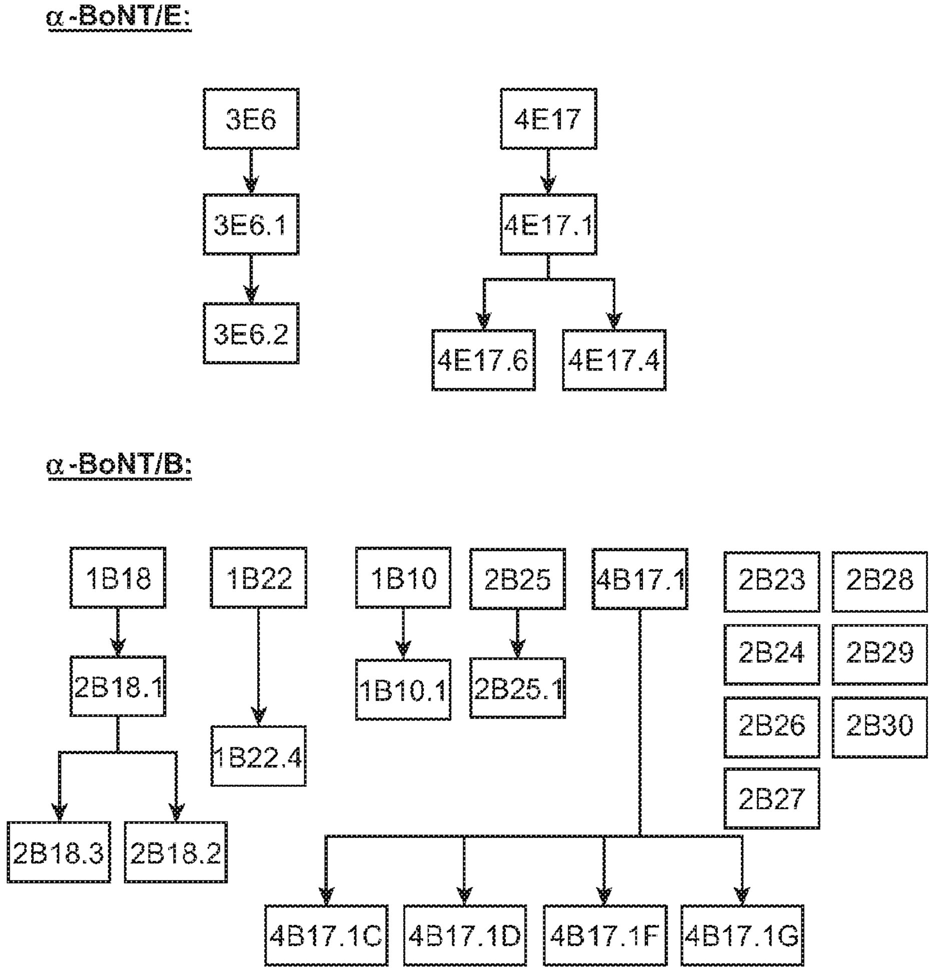
FIG. 10 is a schematic showing the relationship of certain antibodies specific for BoNT/E and BoNT/B disclosed herein with respect to the clonal lineage of the first lead selected.

The sequences of the variable heavy ($V_H$) and variable light ($V_L$) domains for a number of prototypical BoNTB and BoNT/E antibodies are illustrated in Tables 1-5, and in FIGS. 1-2 and 11. The relationship of certain antibodies specific for BoNT/E and BoNT/B disclosed herein with respect to the clonal lineage of the first lead selected is provided in FIG. 10.

The antibodies of the present disclosure can be used individually, and/or in combination with each other, and/or in combination with other known anti-BoNT antibodies (see, e.g., Application Pub. No: 20080124328, filed on Jan. 26, 2006, Application Ser. No. 09/144,886, filed on Aug. 31, 1998, Applicant Pub. No. 20040175385, filed on Aug. 1, 2003, 60/942,173, filed on Jun. 5, 2007 and PCT Pub. Nos. WO 07/094754, WO 05/016232, and WO 09/008916, which are incorporated herein by reference for all purposes). These antibodies can be used individually, and/or in combination with each other, and/or in combination with other known anti-BoNT antibodies to form bispecific or polyspecific antibodies.

TABLE 1

Deduced protein sequences of heavy chain variable regions (VH) of BoNT/E binders. Sequence identification numbers next to each clone name identifies an amino acid sequences for the full length heavy chain variable region.

| VH Clone/ Gene Family | Framework 1 | CDR1 | Framework 2 | CDR2 | Framework 3 | CDR3 | Framework 4 |
|---|---|---|---|---|---|---|---|
| 2A10 VH1 | QVQLQQS GAEVKKP GSSVKVS CKASGGT FT (SEQ ID NO: 112) | RYTIT (SEQ ID NO: 113) | WVRQAPG QGLEWMG (SEQ ID NO: 114) | GIIPIFDKA NYAQKFQS (SEQ ID NO: 115) | RVTFTAD ASTSTAY MELGSLR PEDTAVY YCAA (SEQ ID NO: 116) | YSRGY VHFDY (SEQ ID NO: 117) | WGPGTL VTVSS (SEQ ID NO: 118) |
| 3E1 VH1 | QVQLVES GAEVKKP GSSVKVS CKASGGT FS (SEQ ID NO: 119) | NSGFT (SEQ ID NO: 120) | WVRQVPG QGLEWMG (SEQ ID NO: 121) | GIIPMFGP ANYAQKF QG (SEQ ID NO: 122) | RVTITADE STRMVYM ELRSLRSE DTAVYYC AR (SEQ ID NO: 123) | DQGEY TVGML LYYAM DV (SEQ ID NO: 124) | WGEGTT VTVSS (SEQ ID NO: 125) |
| 3E2 VH1 | QVQLQES GAEVKKP GSSVKVS CKASGGD LN (SEQ ID NO: 126) | KYAIT (SEQ ID NO: 127) | WLRQAPG QGFEWMG (SEQ ID NO: 128) | GITPIFATT NYAQKFQG (SEQ ID NO: 129) | RVMITAD EVTSTVY MDLSSLG SEDTAIYF CAK (SEQ ID NO: 130) | SPRGGI VGTFDT (SEQ ID NO: 131) | WGQGTM VTVSS (SEQ ID NO: 132) |

TABLE 1-continued

Deduced protein sequences of heavy chain variable regions (VH) of BoNT/E binders. Sequence identification numbers next to each clone name identifies an amino acid sequences for the full length heavy chain variable region.

| VH Clone/ Gene Family | Framework 1 | CDR1 | Framework 2 | CDR2 | Framework 3 | CDR3 | Framework 4 |
|---|---|---|---|---|---|---|---|
| 3E3 VH3 | QVQLVES GGGLVKP GESLRLSC AASGFTFS (SEQ ID NO: 133) | NYNMN (SEQ ID NO: 134) | WVRQAPG KGLEWVS (SEQ ID NO: 135) | SISDGGSY RYYAYSV KG (SEQ ID NO: 136) | RETISRDN TKNSLYL QMNSLRA EDTALYY CAR (SEQ ID NO: 137) | DEMVH GILVYY GMDV (SEQ ID NO: 138) | WGQGTT VTVSS (SEQ ID NO: 139) |
| 3E4 VH3 | QVQLQES GGGLVQP GGSLRLSC GASGFTFS (SEQ ID NO: 140) | SDAMS (SEQ ID NO: 141) | WVRQAPG KGLEWVA (SEQ ID NO: 142) | AILPSGEA TYYADSV KG (SEQ ID NO: 143) | RETISRHS SKNTEYL QMNSLRA DDTAVYY CAR (SEQ ID NO: 144) | DSYHS RLAAF DI (SEQ ID NO: 145) | WGQGTM VTVSS (SEQ ID NO: 146) |
| 3E4.1 VH3 | QVQLQES GGGLVQP GGSLRLSC GASGFTFS (SEQ ID NO: 147) | SDAMS (SEQ ID NO: 148) | WVRQAPG KGLEWVA (SEQ ID NO: 149) | AILPSGEA TYYADSV KG (SEQ ID NO: 150) | RFTISRHS SKNTLYL QMNSLRA DDTAVYY CAR (SEQ ID NO: 151) | DSYHS RLAAF DI (SEQ ID NO: 152) | WGQGTM VTVSS (SEQ ID NO: 153) |
| 3E5 VH3 | QVQLVQS GGGVVQE GRPLRLSC AASTFNFR (SEQ ID NO: 154) | DFYMS (SEQ ID NO: 155) | WIRQAPG KGLEWVS (SEQ ID NO: 156) | YIGSSGSA LQYADSV KG (SEQ ID NO: 157) | RFTISRDN DKNVLYL QMTSLRA EDTAVYY CAR (SEQ ID NO: 158) | VASRY HDVLT DGFDI (SEQ ID NO: 159) | WGQGTM VTVSS (SEQ ID NO: 160) |
| 3E6 VH3 | QVQLVQS GGGVVQP GKSLRLSC AASGFTFS (SEQ ID NO: 161) | SYAMH (SEQ ID NO: 162) | WVRQAPG KGLEWVA (SEQ ID NO: 163) | VISYDGN KKYYADS VKG (SEQ ID NO: 164) | RFTISRDN SKNTLYL QMNSLRA EDAAVFY CAR (SEQ ID NO: 165) | ARLCTS TSCYW TFDP (SEQ ID NO: 166) | WGQGTL VTVSS (SEQ ID NO: 167) |
| 3E6.1 VH3 | QVQLVQS GGGVVQP GKSLRLSC AASGFTFS (SEQ ID NO: 168) | SYAMH (SEQ ID NO: 169) | WVRQAPG KGLEWVA (SEQ ID NO: 170) | VISYDGN KKYYADS VKG (SEQ ID NO: 171) | RFTISRDN SKNTLYL QMNSLRA EDAAVFY CAR (SEQ ID NO: 172) | ARLCTS TSCYW TFDP (SEQ ID NO: 173) | WGQGTL VTVSS (SEQ ID NO: 174) |
| 4E11 VH3 | QVQLVQS GGGLVQP GGSLRLSC AASGFRFS (SEQ ID NO: 175) | GYSFN (SEQ ID NO: 176) | WVRQAPG KGLEWVA (SEQ ID NO: 177) | YMSSGGSI KNYADSV KG (SEQ ID NO: 178) | RFTISRDN AKNSLYL QVNSLRD EDTALYY CAR (SEQ ID NO: 179) | GPPGRP NDAFDI (SEQ ID NO: 180) | WGQGTM VTVSS (SEQ ID NO: 181) |
| 4E13 VH3 | EVQLVQS GGGLVQP GGSLRLSC AASGFTFS (SEQ ID NO: 182) | SYAMT (SEQ ID NO: 183) | WVRQAPG KGLEWVS (SEQ ID NO: 184) | SISVSGDS TYYADSV KG (SEQ ID NO: 185) | RFTISRDN SKNTVSL QMNSLRA EDTALYY CAK (SEQ ID NO: 186) | GLSKA DLFGM DV (SEQ ID NO: 187) | WGQGTM VTVSS (SEQ ID NO: 188) |

TABLE 1-continued

Deduced protein sequences of heavy chain variable regions (VH) of BoNT/E binders. Sequence identification numbers next to each clone name identifies an amino acid sequences for the full length heavy chain variable region.

| VH Clone/ Gene Family | Framework 1 | CDR1 | Framework 2 | CDR2 | Framework 3 | CDR3 | Framework 4 |
|---|---|---|---|---|---|---|---|
| 4E16 VH4 | QVQLQESGPGLVKPSETLSLTCSVSGVSIS (SEQ ID NO: 189) | DYYWS (SEQ ID NO: 190) | WIRQPPGKGLEWIG (SEQ ID NO: 191) | YIYYSGSTNYNPSLKS (SEQ ID NO: 192) | RVTISVDTSKNQFSLNLSSVTAADTAVYYCAR (SEQ ID NO: 193) | HTSGWSGGAFDI (SEQ ID NO: 194) | WGQGTMVTVSS (SEQ ID NO: 195) |
| 4E16.1 VH4 | QVQLQESGPGLVKPSETLSLTCSVSGVSIS (SEQ ID NO: 196) | DYYWS (SEQ ID NO: 197) | WIRQPPGKGLEWIG (SEQ ID NO: 198) | YIYYSGSTNYNPSLKS (SEQ ID NO: 199) | RVTISVDTSKNQFSLNLSSVTAADTAVYYCAR (SEQ ID NO: 200) | HTSGWSGGAFDI (SEQ ID NO: 201) | WGQGTMVTVSS (SEQ ID NO: 202) |
| 4E17 VH3 | EVQLVQSGGNLVQPGGSLRLSCAATGPIG (SEQ ID NO: 203) | SHWMT (SEQ ID NO: 204) | WVRQAPGQGLEWVA (SEQ ID NO: 205) | NINLDGTEKFYVDSVKG (SEQ ID NO: 206) | RFTVSRDNRKSSVFLQMNNLRVDDTAVYYCAR (SEQ ID NO: 207) | LQWGGYNGWLSP (SEQ ID NO: 208) | WGQGTLVTVSS (SEQ ID NO: 209) |
| 4E17.1 VH3 | EVQLVRSGGNLVQPGGSLRLSCAATGPIG (SEQ ID NO: 210) | SHWMT (SEQ ID NO: 211) | WVRQAPGQGLEWVA (SEQ ID NO: 212) | NINLDGTEKEYVDSVKG (SEQ ID NO: 213) | RFTVSRDNRKSSVFLQMNNLRVDDTAVYYCAR (SEQ ID NO: 214) | LQWGGYNGWLSP (SEQ ID NO: 215) | WGQGTLVTVSS (SEQ ID NO: 216) |
| 3E6.2 VH3 | QVQLVQSGGGVVQPGKSLRLSCAASGFAFG (SEQ ID NO: 217) | GYAMH (SEQ ID NO: 218) | WVRQAPGKGLEWVA (SEQ ID NO: 219) | VISYDGNKKYYADSVKG (SEQ ID NO: 220) | RFTISRDNSKNTLYLQMNSLRAEDAAVFYCAR (SEQ ID NO: 221) | ARLCTSTSCYWTFDP (SEQ ID NO: 222) | WGQGTLVTVSS (SEQ ID NO: 223) |
| 4E17.4 VH3 | EVQLVRSGGNLVQPGGSLRLSCAATGPIT (SEQ ID NO: 224) | QHWMT (SEQ ID NO: 225) | WVRQAPGQGLEWVA (SEQ ID NO: 226) | NINLDGTEKFYVDSVKG (SEQ ID NO: 227) | RFTVSRDNRKSSVFLQMNNLRVDDTAVYYCAR (SEQ ID NO: 228) | LQWGGYNGWLSP (SEQ ID NO: 229) | WGQGTLVTVSS (SEQ ID NO: 230) |
| 4E17.6 VH3 | EVQLVRSGGNLVQPGGSLRLSCAATGPIT (SEQ ID NO: 231) | QHWMT (SEQ ID NO: 232) | WVRQAPGQGLEWVA (SEQ ID NO: 233) | NINLDGTEKEYVDSVKG (SEQ ID NO: 234) | RFTVSRDNRKSSVFLQMNNLRVDDTAVYYCAR (SEQ ID NO: 235) | LQWGGYNGWLSP (SEQ ID NO: 236) | WGQGTLVTVSS (SEQ ID NO: 237) |

TABLE 2

Deduced protein sequences of light chain variable regions (VL) of BoNT/E binders. Sequence identification numbers next to each clone name identifies an amino acid sequences for the full length light chain variable region.

| VL/Clone/ Gene Family | Framework 1 | CDR1 | Framework 2 | CDR2 | Framework 3 | CDR3 | Framework 4 |
|---|---|---|---|---|---|---|---|
| 2A10 VK1 | DIVMTQSPSFLSASVGDRVTITC (SEQ ID NO: 238) | WASQGISSYLA (SEQ ID NO: 239) | WYQQKPGKAPKLLIY (SEQ ID NO: 240) | AASTLQS (SEQ ID NO: 241) | GVPSRFSGSGSGTEFTLTISSLQPEDFATYYC (SEQ ID NO: 242) | QQLNSYPLT (SEQ ID NO: 243) | FGGGTKVDIKR (SEQ ID NO: 244) |
| 3E1 VK1 | EIVLTQSPDSLSASVGDRVTITC (SEQ ID NO: 245) | RASQGISGYLA (SEQ ID NO: 246) | WYQHKAGKAPKLLIY (SEQ ID NO: 247) | AASSLQS (SEQ ID NO: 248) | GVPSRFSGSGYGTEFTLTISSLQPDDFATYYC (SEQ ID NO: 249) | QQYNSYPFT (SEQ ID NO: 250) | FGGGTKVEIKR (SEQ ID NO: 251) |
| 3E2 VK1 | EIVLTQSPSFLSAFVGDRVTITC (SEQ ID NO: 252) | RTSQSINNYLN (SEQ ID NO: 253) | WYQQKAGKAPKLLIY (SEQ ID NO: 254) | AASTLHT (SEQ ID NO: 255) | GVPSRFSGSGSGTEFTLTISSLQPEDFATYYC (SEQ ID NO: 256) | QQSYSIPLT (SEQ ID NO: 257) | FGGGTKVEIKR (SEQ ID NO: 258) |
| 3E3 VK3 | DIVMTQSPDSLSASVGDSVTITC (SEQ ID NO: 259) | RASQSFSSSYLA (SEQ ID NO: 260) | WYQQKPGQAPRLLIY (SEQ ID NO: 261) | AASSRAA (SEQ ID NO: 262) | GVPTGSVADGSGTDFTLTISGLQPEDFAAYYC (SEQ ID NO: 263) | QQSYSTPYT (SEQ ID NO: 264) | FGGGTKVEIKR (SEQ ID NO: 265) |
| 3E4 VK1 | DIVMTQSPSFLSAFVGDRVTITC (SEQ ID NO: 266) | RASQSISNWLA (SEQ ID NO: 267) | WYQQKPGKAPKVLIY (SEQ ID NO: 268) | KASSLEN (SEQ ID NO: 269) | GVPSRFSGSGSGTDFTLTITSLQPDDFATYYC (SEQ ID NO: 270) | QQYNAYPLT (SEQ ID NO: 271) | FGGGTKVEIKR (SEQ ID NO: 272) |
| 3E4.1 VK1 | EIVLTQSPSTLSASVGDRVAITC (SEQ ID NO: 273) | RASQRIGSWLA (SEQ ID NO: 274) | WYQQKPGKAPNPLIY (SEQ ID NO: 275) | KAFSLES (SEQ ID NO: 276) | GVPSRFSGSRSGTEFTLTISSLQPDDFATYFC (SEQ ID NO: 277) | QQYDSYPYT (SEQ ID NO: 278) | FGQGTKLEIKR (SEQ ID NO: 279) |
| 3E5 VK1 | DVVMTQSPSSLSASIGDRVTFTC (SEQ ID NO: 280) | QASQDISNRLN (SEQ ID NO: 281) | WYQQKPGKVPKLLIS (SEQ ID NO: 282) | DASNLET (SEQ ID NO: 283) | GVPSRFSGSGSGTDFTFTISSLQPEDIATYYC (SEQ ID NO: 284) | QQYDPLLT (SEQ ID NO: 285) | FGGGTKVEIKR (SEQ ID NO: 286) |
| 3E6 VK1 | DIQMTQSPSSVSASVGDTVTISC (SEQ ID NO: 287) | RASQGISSWLA (SEQ ID NO: 288) | WYQQKSGQAPTLLIY (SEQ ID NO: 289) | AASSLQS (SEQ ID NO: 290) | GVPSRFSGSGSGTDFTLIISSLQPEDFATYYC (SEQ ID NO: 291) | QQAYRTPIT (SEQ ID NO: 292) | FGGGTKVEIKR (SEQ ID NO: 293) |
| 3E6.1 VK1 | DIQMTQSPSSVSASVGDRVSITC (SEQ ID NO: 294) | QASQDISNYLN (SEQ ID NO: 295) | WYQQKPGKAPKLLIY (SEQ ID NO: 296) | AASSLQS (SEQ ID NO: 297) | GVPSRFSGSGSGTDFTLTISSLQPEDFATYYC (SEQ ID NO: 298) | QQSYNTPPT (SEQ ID NO: 299) | FGQGTKLEIKR (SEQ ID NO: 300) |
| 4E11 VL3 | ASVLTQDPAVSVALGQTVRITC (SEQ ID NO: 301) | QGDSLRSYYAS (SEQ ID NO: 302) | WYQQKPGQAPVLVIY (SEQ ID NO: 303) | GKSNRPS (SEQ ID NO: 304) | GIPDRFSGSSSGNTASLTITGAQAEDEADYYC (SEQ ID NO: 305) | NSRDSTGNQL (SEQ ID NO: 306) | FGGGTKVTVLG (SEQ ID NO: 307) |
| 4E13 VL3 | AELTQDPAVSVALGQTVRITC (SEQ ID NO: 308) | QGDSLRSYYAS (SEQ ID NO: 309) | WYQQKPGQAPVLVIY (SEQ ID NO: 310) | GENSRPS (SEQ ID NO: 311) | GIPDRFSGSSSGNTASLTIAGAQAEDEADYYC (SEQ ID NO: 312) | NSPDSSGIHLV (SEQ ID NO: 313) | FGGGTKVTVLG (SEQ ID NO: 314) |

TABLE 2-continued

Deduced protein sequences of light chain variable regions (VL) of BoNT/E binders. Sequence identification numbers next to each clone name identifies an amino acid sequences for the full length light chain variable region.

| VL/Clone/ Gene Family | Framework 1 | CDR1 | Framework 2 | CDR2 | Framework 3 | CDR3 | Framework 4 |
|---|---|---|---|---|---|---|---|
| 4E16 VK4 | EIVLTQSP DSLAVSL GERATINC (SEQ ID NO: 315) | KSSQSV LYSSN NKNYL A (SEQ ID NO: 316) | WYQQKPG QPPKLLFY (SEQ ID NO: 317) | WASTRE S (SEQ ID NO: 318) | GVPDRFSGS GSGTDFTLTI SSLQAEDVA VYYC (SEQ ID NO: 319) | HQYYSS PLT (SEQ ID NO: 320) | FGGGTKL EIKR (SEQ ID NO: 321) |
| 4E16.1 VK4 | EIVLTQSP NSLAVSL GERATIRC (SEQ ID NO: 322) | KSSQSV LYSGN NKNYI A (SEQ ID NO: 323) | WYQQKPG QPPKLLIY (SEQ ID NO: 324) | WASTRE S (SEQ ID NO: 325) | GVPDRFSGS GSETDFTLTI SSLRAEDVA LYYC (SEQ ID NO: 326) | QQYYSR WT (SEQ ID NO: 327) | FGQGTKL EIKR (SEQ ID NO: 328) |
| 4E17 VK1 | DIVMTQSP SSVSASVG DRVTITC (SEQ ID NO: 329) | RASQSI SSYLN (SEQ ID NO: 330) | WYQQKPG KAPKLLIY (SEQ ID NO: 331) | GTSNLQ S (SEQ ID NO: 332) | GVPSGFSGS GSGTDFTLTI SSLQPEDFA TYYC (SEQ ID NO: 333) | QETYST PPT (SEQ ID NO: 334) | FGGGTKL EIKR (SEQ ID NO: 335) |
| 4E17.1 VK1 | DIVMTQSP SSLSASVG DRVTISC (SEQ ID NO: 336) | RASQSI RHYVN (SEQ ID NO: 337) | WYQQKPG KAPKLLIY (SEQ ID NO: 338) | KASSLA S (SEQ ID NO: 339) | GAPSRFSGS GSGTDFTLTI SSLQPDDFA TYYC (SEQ ID NO: 340) | QQSYSIP LT (SEQ ID NO: 341) | FGGGTK VEIKR (SEQ ID NO: 342) |
| 3E6.2 VK1 | DIQMTQSP SSVSASVG DRVSITC (SEQ ID NO: 343) | QASQDI SNYLN (SEQ ID NO: 344) | WYQQKPG KAPKLLIY (SEQ ID NO: 345) | AASSLQ S (SEQ ID NO: 346) | GVPSRFSGS GSGTDFTLTI SSLQPEDFA TYYC (SEQ ID NO: 347) | QQSYDT PPT (SEQ ID NO: 348) | FGQGTKL EIKR (SEQ ID NO: 349) |
| 4E17.4 VK1 | DIVMTQSP SSLSASVG DRVTISC (SEQ ID NO: 350) | RASQSI RHYVN (SEQ ID NO: 351) | WYQQKPG KAPKLLIY (SEQ ID NO: 352) | KASSLA S (SEQ ID NO: 353) | GAPSRFSGS GSGTDFTLTI SSLQPDDFA TYYC (SEQ ID NO: 354) | QQSYSIP LT (SEQ ID NO: 355) | FGGGTK VEIKR (SEQ ID NO: 356) |
| 4E17.6 VK1 | DIQMTQSP SFLSASVG DRVTITC (SEQ ID NO: 357) | RASQGI SSYLA (SEQ ID NO: 358) | WYQQKPG KAPKLLIY (SEQ ID NO: 359) | KASSLE S (SEQ ID NO: 360) | GVPSRFSGS GSGTDFALT ISSLQPEDFA TYYC (SEQ ID NO: 361) | QQLNTY PQT (SEQ ID NO: 362) | FGQGTK VEIKR (SEQ ID NO: 363) |

TABLE 3

Deduced protein sequences of heavy chain variable regions (VH) of BoNT/B binders. Sequence identification numbers next to each clone name identifies an amino acid sequences for the full length heavy chain variable region.

| VH/Clone/ Gene Family | Framework 1 | CDR1 | Framework 2 | CDR2 | Framework 3 | CDR3 | Framework 4 |
|---|---|---|---|---|---|---|---|
| A12 VH3 | EVQLVES GGGVVQP GRSLRLSC AASGFTFS (SEQ ID NO: 364) | SYGMH (SEQ ID NO: 365) | WVRQAP GKGLEW VA (SEQ ID NO: 366) | VIWYD GSNKY YADSV KG (SEQ ID NO: 367) | RFTISRDNSK NTLYLQMN SLRAEDTAV YYCAR (SEQ ID NO: 368) | GYSNYD YYYGM DV (SEQ ID NO: 369) | WGQGTT VTVSS (SEQ ID NO: 370) |
| 6A12 VH3 | QVQLVES GGGVVQP GRSLRLSC AASGFTFS (SEQ ID NO: 371) | SYGMH (SEQ ID NO: 372) | WVRQAP GKGLEW VS (SEQ ID NO: 373) | YISSSG STIYYA DSVKG (SEQ ID NO: 374) | RFTISRDNA KNSLYLQM NSLRAEDTA VYYCAR (SEQ ID NO: 375) | VSIVGG PYGMD V (SEQ ID NO: 376) | WGQGTT VTVSS (SEQ ID NO: 377) |

TABLE 3-continued

Deduced protein sequences of heavy chain variable regions (VH) of BoNT/B binders. Sequence identification numbers next to each clone name identifies an amino acid sequences for the full length heavy chain variable region.

| VH/Clone/ Gene Family | Framework 1 | CDR1 | Framework 2 | CDR2 | Framework 3 | CDR3 | Framework 4 |
|---|---|---|---|---|---|---|---|
| B1.1 VH1 | QVQLVQSGAEVEKPGSSVKVSCKASGGSFS (SEQ ID NO: 378) | SYAFT (SEQ ID NO: 379) | WVRQAPGQGLEWMG (SEQ ID NO: 380) | RIVPFLGVPYYTQKFRG (SEQ ID NO: 381) | RVTITADKATSTVYMELSSLTFDDTAVYYCAR (SEQ ID NO: 382) | DKRTYEYNWNSLWF (SEQ ID NO: 383) | WGRGTLVTVSS (SEQ ID NO: 384) |
| B6 VH5 | QVQLVQSGAEVKKPGESLVISCKASGDKDTFT (SEQ ID NO: 385) | SFWIA (SEQ ID NO: 386) | WVRQMPGKGLEWMG (SEQ ID NO: 387) | IIYAGDSDTRYSPSFQG (SEQ ID NO: 388) | HVNISVDRSTNTAYLQWSSLKASDTAMYYCAR (SEQ ID NO: 389) | HDSRYKYFYFGMDV (SEQ ID NO: 390) | WGQGTTVTVSS (SEQ ID NO: 391) |
| B6.1 VH5 | QVQLVQSGAEVKKPGESLVISCKASGDKDTFT (SEQ ID NO: 392) | SFWIA (SEQ ID NO: 393) | WVRQMPGKGLEWMG (SEQ ID NO: 394) | IIYAGDSDTRYSPSFQG (SEQ ID NO: 395) | HVNISVDRSTNTAYLQWSSLKASDTAMYYCAR (SEQ ID NO: 396) | HDSRYKYFYFGMDV (SEQ ID NO: 397) | WGQGTTVTVSS (SEQ ID NO: 398) |
| B8 VH3 | QVQLLESGGGVVQPGRSLRLSCAASGFTFS (SEQ ID NO: 399) | SYGMH (SEQ ID NO: 400) | WVRQAPGKGLEWVA (SEQ ID NO: 401) | VIWYDGSNKYYADSVKG (SEQ ID NO: 402) | RFTISRDNSKDTLYLQMNSLRAEDTAVYYCAR (SEQ ID NO: 403) | GYSNYDYYYGMDV (SEQ ID NO: 404) | WGQGTTVTVSS (SEQ ID NO: 405) |
| B8.1 VH3 | QVQLLESGGGVVQPGRSLRLSCAASGFTFS (SEQ ID NO: 406) | SYGMH (SEQ ID NO: 407) | WVRQAPGKGLEWVA (SEQ ID NO: 408) | VIWYDGSNKYYADSVKG (SEQ ID NO: 409) | RFTISRDNSKNTLYLQMNSLRAEDTAVYYCAR (SEQ ID NO: 410) | GYSNYDYYYGMDV (SEQ ID NO: 411) | WGQGTTVTVSS (SEQ ID NO: 412) |
| B11 VH3 | QVQLLQSAGGVVQPGRSLRLSCAASGFIFR (SEQ ID NO: 413) | TYGMH (SEQ ID NO: 414) | WVRQAPGKGLEWVA (SEQ ID NO: 415) | FVSSDGNNKFYSDSVKG (SEQ ID NO: 416) | RFTIPRDNAKNTLYLQMNSLETEDTAVYYCAK (SEQ ID NO: 417) | DRYPIDCSGGSCFSYGMDV (SEQ ID NO: 418) | WGQGTTVTVSS (SEQ ID NO: 419) |
| B11C3 VH3 | EVQLVESGGGVVQPGRSLRLSCATSGFILR (SEQ ID NO: 420) | TYGMH (SEQ ID NO: 421) | WVRQAPGKGLEWVA(SEQ ID NO: 422) | FVSSDGNNKFYSDSVKG (SEQ ID NO: 423) | RFTIPRDNAKNTLYLQMNSLETEDTAVYYCAK (SEQ ID NO: 424) | DRYPIDCSGGSCFSYGMDV(SEQ ID NO: 425) | WGQGTLVTVSS (SEQ ID NO: 426) |
| B11E8 VH3 | EVQLVQSGGGVVQPGRSLRLSCAASGFIFR (SEQ ID NO: 427) | TYGMH (SEQ ID NO: 428) | WVRQAPGKGLEWVA (SEQ ID NO: 429) | FVSSDGNNKFYSDSVKG (SEQ ID NO: 430) | RFTISRDNAKNTLYLQMNSLETEDTAMYYCAK (SEQ ID NO: 431) | DRYPIDCSGGSCFSYGMDV (SEQ ID NO: 432) | WGQGTTVTVSS (SEQ ID NO: 433) |
| B12 VH3 | QVNLRESGGGVVQPGRSLRLSCAASGFTFS (SEQ ID NO: 434) | SYALH (SEQ ID NO: 435) | WVRQTPGKGLEWVA (SEQ ID NO: 436) | LISYDGSNKYYADSVKG (SEQ ID NO: 437) | RFTISRDNSKNMLYLQMNSLRAEDTAVYYCAK (SEQ ID NO: 438) | DRSHYGDYVGYLDY (SEQ ID NO: 439) | WGQGTLVTVSS (SEQ ID NO: 440) |
| B12.1 VH3 | QVNLRESGGGVVQPGRSLRLSCAASGFTFS (SEQ ID NO: 441) | SYALH (SEQ ID NO: 442) | WVRQTPGKGLEWVA (SEQ ID NO: 443) | LISYDGSNKYYADSVKG (SEQ ID NO: 444) | RFTISRDNSKNMLYLQMNSLRAEDTAVYYCAK (SEQ ID NO: 445) | DRSHYGDYVGYLDY (SEQ ID NO: 446) | WGQGTLVTVSS (SEQ ID NO: 447) |
| B12.2 VH3 | QVNLRESGGGVVQP | SYALH (SEQ ID | WVRQTPGKGLEW | LISYDGSNKYY | RFTISRDNSKNMLYLQMN | DRSHYGDYVGYL | WGQGTLVTVSS |

TABLE 3-continued

Deduced protein sequences of heavy chain variable regions (VH) of BoNT/B binders. Sequence identification numbers next to each clone name identifies an amino acid sequences for the full length heavy chain variable region.

| VH/Clone/ Gene Family | Framework 1 | CDR1 | Framework 2 | CDR2 | Framework 3 | CDR3 | Framework 4 |
|---|---|---|---|---|---|---|---|
| | GRSLRLSC AASGFTFS (SEQ ID NO: 448) | NO: 449) | VA (SEQ ID NO: 450) | ADSVK G (SEQ ID NO: 451) | SLRAEDTAV YYCAK (SEQ ID NO: 452) | DY (SEQ ID NO: 453) | (SEQ ID NO: 454) |
| 1B18 VH3 | EVQLVQS GGGLVQP GGSRRLSC AASGFYF N (SEQ ID NO: 455) | AYWM T (SEQ ID NO: 456) | WVRQAP GKGLEW VA (SEQ ID NO: 457) | NINLDG TEIYYL DSVKG (SEQ ID NO: 458) | RFTVSRDNV KNSVFLQMS SLRVEDTAV YFCAR (SEQ ID NO: 459) | LEWGGR NGWVSP (SEQ ID NO: 460) | WGQGTL VTVSS (SEQ ID NO: 461) |
| 2B18.1 VH3 | QVQLVQS GGGLVQP GGSRRLSC AASGFYF N (SEQ ID NO: 462) | AYWM T (SEQ ID NO: 463) | WVRQAP GKGLEW VA (SEQ ID NO: 464) | NINLDG TEIYYL DSVKG (SEQ ID NO: 465) | RFTVSRDNV KNSVFLQMS SLRVEDTAV YFCAR (SEQ ID NO: 466) | LEWGGR NGWVSP (SEQ ID NO: 467) | WGQGTL VTVSS (SEQ ID NO: 468) |
| 4B19 VH1 | QVQLVQS GAEVKKP GASVNVS CKASGYT FT (SEQ ID NO: 469) | GYYIY (SEQ ID NO: 470) | WVRQAP GQGLEW MG (SEQ ID NO: 471) | WINPNS GVTKY AQKFQ G (SEQ ID NO: 472) | RVTMTIDTS TNTAYMEL NRLRADDT AVYYCAR (SEQ ID NO: 473) | EWTQL WSPYDY (SEQ ID NO: 474) | WGQGTT VTVSS (SEQ ID NO: 475) |
| 1B22 VH4 | QVQLQES GSRLVKPS QTLSLTCG VSGGSISS S (SEQ ID NO: 476) | SYSWS (SEQ ID NO: 477) | WIRQTPG KGLEWIG (SEQ ID NO: 478) | YIYHSG STYYN PSLKS (SEQ ID NO: 479) | RVTMSVDK SRNQFSLNM SSVTAADTA VYYCAR (SEQ ID NO: 480) | TAFYYE NTGPIRC YLDF (SEQ ID NO: 481) | WGQGTL VTVSS (SEQ ID NO: 482) |
| 1B10 VH3 | QVQLVES GGGVVQP GRSLRLSC AASGFTFS (SEQ ID NO: 483) | HYGMH (SEQ ID NO: 484) | WVRQSP GKGLEW VA (SEQ ID NO: 485) | VIWYD GRNPY YAASV KG (SEQ ID NO: 486) | RFTISRDND KNTLYLQM NSLRAEDTA VYYCVK (SEQ ID NO: 487) | DLTRFH DTTFGV FEM (SEQ ID NO: 488) | WGPGTT VTVSS (SEQ ID NO: 489) |
| 1B10.1 VH3 | QVQLVES GGGVVQP GRSLRLSC AASGFTFS (SEQ ID NO: 491) | HYGMH (SEQ ID NO: 492) | WVRQSP GKGLEW VA (SEQ ID NO: 493) | VIWYD GRNPY YAASV KG (SEQ ID NO: 494) | RFTISRDND KNTLYLQM NSLRAEDTA VYYCVK (SEQ ID NO: 495) | DLTRFH DTTFGV FEM (SEQ ID NO: 496) | WGPGTT VTVSS (SEQ ID NO: 497) |
| 2B18.2 VH3 | QVQLVQS GGGLVQP GGSRRLSC AASGFYF K (SEQ ID NO: 498) | AYWM T (SEQ ID NO: 499) | WVRQAP GKGLEW VA (SEQ ID NO: 500) | NINLDG TEIYYL DSVKG (SEQ ID NO: 501) | RFTVSRDNV KNSVFLQMS SLRVEDTAV YFCAR (SEQ ID NO: 502) | LEWGGR NGWVSP (SEQ ID NO: 503) | WGQGTL VTVSS (SEQ ID NO: 504) |
| 2B18.3 VH3 | EVQLVES GGGLVQP GGSRRLSC AASGFYF N (SEQ ID NO: 505) | AYWM T (SEQ ID NO: 506) | WVRQAP GKGLEW VA (SEQ ID NO: 507) | NINLDG TEIYYL DSVKG (SEQ ID NO: 508) | RFTVSRDNV KNSVFLQMS SLRVEDTAV YFCAR (SEQ ID NO: 509) | LEWGGR NGWLSP (SEQ ID NO: 510) | WGQGTL VTVSS (SEQ ID NO: 511) |
| 1B22.4 VH4 | QVQLQES GSRLVKPS QTLSLTCG VSGGSISS S (SEQ ID NO: 512) | SYSWS (SEQ ID NO: 513) | WIRQTPG KGLEWIG (SEQ ID NO: 514) | YIYHSG STYYN PSLKS (SEQ ID NO: 515) | RVTMSVDK SRNQFSLNM SSVTAADTA VYYCAR (SEQ ID NO: 516) | TAFYYE NTGPIRC YLDF (SEQ ID NO: 517) | WGQGTL VTVSS (SEQ ID NO: 518) |
| 2B23 VH3 | EVQLLESG GGLVQPG | NYPMS (SEQ ID | WVRQAP GKGLAW | SLTASG DNTFY | RFTISRDNSN NTLYLQMH | ALVGRY DISTGY | WGQGTL VTVSS |

TABLE 3-continued

Deduced protein sequences of heavy chain variable regions (VH) of BoNT/B binders. Sequence identification numbers next to each clone name identifies an amino acid sequences for the full length heavy chain variable region.

| VH/Clone/ Gene Family | Framework 1 | CDR1 | Framework 2 | CDR2 | Framework 3 | CDR3 | Framework 4 |
|---|---|---|---|---|---|---|---|
| | GSLRLSCA ASGFTFS (SEQ ID NO: 519) | NO: 520) | VS (SEQ ID NO: 521) | ADSVK G (SEQ ID NO: 522) | SLRAEDTAV YYCAK (SEQ ID NO: 523) | YRPVMD S (SEQ ID NO: 524) | (SEQ ID NO: 525) |
| 2B24 VH3 | QVQLVES GGGVVQP GRSLRLSC AASGLTFS (SEQ ID NO: 526) | VYGMH (SEQ ID NO: 527) | WVRQAP GKGLEW VA (SEQ ID NO: 528) | VISHTG SEEYY ADSVK G (SEQ ID NO: 529) | RFSISRDNSN NTLFLQMNS LRPEDTAVY YCVK (SEQ ID NO: 530) | DGPMA AIPFYYF DF (SEQ ID NO: 531) | WGQGTL VTVSS (SEQ ID NO: 532) |
| 2B25 VH4 | QVQLQES GPGLVKPS QTLSLSCS VSGASIT (SEQ ID NO: 533) | SGTFY WS (SEQ ID NO: 534) | WIRQHPG KDLEWIG (SEQ ID NO: 535) | YIYYSG TTYYN PSLKS (SEQ ID NO: 536) | RVTLSVDTS KNQFSLKVT SLTAADTAV YHCAR (SEQ ID NO: 537) | GVPIYD SSGTYR GTYFDY (SEQ ID NO: 538) | WGQGTL VTVSS (SEQ ID NO: 539) |
| 2B25.1 VH4 | QVQLQES GPGLVKPS QTLSLSCS VSGASIT (SEQ ID NO: 540) | SGTFY WS (SEQ ID NO: 541) | WIRQHPG KDLEWIG (SEQ ID NO: 542) | YIYYSG TTYYN PSLKS (SEQ ID NO: 543) | RVTLSVDTS KNQFSLKVT SLTAADTAV YHCAR (SEQ ID NO: 544) | GVPIYD SSGTYR GTYFDY (SEQ ID NO: 538) | WGQGTL VTVSS (SEQ ID NO: 545) |
| 2B26 VH3 | QVQLVQS GGTLVQP GGSLRLSC AASGFTFS (SEQ ID NO: 546) | NYPMT (SEQ ID NO: 547) | WVRQAP GKGLAW VS (SEQ ID NO: 548) | SVIASG DNTFY ADSVK G (SEQ ID NO: 549) | RFTISRDNSK NTLYLQMD SLRAEDTAV YYCAK (SEQ ID NO: 550) | ALVGRY DISTGY YRPVLD Y (SEQ ID NO: 551) | WGQGTT VTVSS (SEQ ID NO: 552) |
| 2B27 VH3 | EVQLQES GPGLVKPS ETLSVTCA VSGGSISS (SEQ ID NO: 553) | SNYSW A (SEQ ID NO: 554) | WIRQPPG KGLEWIG (SEQ ID NO: 555) | TMYYS GSTHY HPSLKS (SEQ ID NO: 556) | RVTISVDTS KSQLSLKLS SVTAADTAV YYCAR (SEQ ID NO: 557) | RRLLGP SPYYFD Y (SEQ ID NO: 558) | WGQGTL VTVSS (SEQ ID NO: 559) |
| 2B28 VH3 | EVQLVQS GGGVVQP GRSLRLSC AASGFTFR (SEQ ID NO: 560) | RNAIH (SEQ ID NO: 561) | WVRQAP GKGLEW VA (SEQ ID NO: 562) | LISYDG INKYY ADSVK G (SEQ ID NO: 563) | RFAISRDNA KNTLFLQM NSLRAEDTA VYYCAR (SEQ ID NO: 564) | DVSEYG DYVGHF DY (SEQ ID NO: 565) | WGQGTL VTVSS (SEQ ID NO: 566) |
| 2B29 VH4 | QVQLQES GPGLVKPS ETLSLTCS VSGGSIN (SEQ ID NO: 567) | SGTYY WT (SEQ ID NO: 568) | WIRQHPG KGLEWIG (SEQ ID NO: 569) | YIYYSG TTYYN PSLKS (SEQ ID NO: 570) | RVSMSVDTS KNLFSLKMN SVTAADTAL YYCAR (SEQ ID NO: 571) | GNPQYD TSGSYT GLYFDF (SEQ ID NO: 572) | WGQGTL VTVSS (SEQ ID NO: 573) |
| 2B30 VH3 | EVQLVES GGGVVQP GRSLRLSC AASGFTFR (SEQ ID NO: 574) | RNAIH (SEQ ID NO: 575) | WVRQAP GKGLEW VA (SEQ ID NO: 576) | VISYDG VNKYY AASVK G (SEQ ID NO: 577) | RFAISRDNA KNTLFLQM NSLRPEDSAI YYCAR (SEQ ID NO: 578) | DVSEYG DYVGHF DY (SEQ ID NO: 579) | WGQGTL VTVSS (SEQ ID NO: 580) |
| 4B17.1 VH3 | EVQLVRS GGNLVQP GGSLRLSC AATGPIG (SEQ ID NO: 581) | SHWMT (SEQ ID NO: 582) | WVRQAP GQGLEW VA (SEQ ID NO: 583) | NINLDG TEKFY VDSVK G (SEQ ID NO: 584) | RFTVSRDNR KSSVFLQMN NLRVDDTA VYYCAR (SEQ ID NO: 207) | LQWGG YNGWLS P (SEQ ID NO: 585) | WGQGTL VTVSS (SEQ ID NO: 586) |
| 4B17.1C VH3 | EVQLVRS GGNLVQP | SHWMT (SEQ ID | WVRQAP GQGLEW | NINLDG TEKFY | RFTVSRDNR KSSVFLQMN | LQWGG YNGWLS | WGQGTL VTVSS |

TABLE 3-continued

Deduced protein sequences of heavy chain variable regions (VH) of BoNT/B binders. Sequence identification numbers next to each clone name identifies an amino acid sequences for the full length heavy chain variable region.

| VH/Clone/ Gene Family | Framework 1 | CDR1 | Framework 2 | CDR2 | Framework 3 | CDR3 | Framework 4 |
|---|---|---|---|---|---|---|---|
| | GGSLRLSC AATGFPIG (SEQ ID NO: 587) | NO: 588) | VA (SEQ ID NO: 589) | VDSVK G (SEQ ID NO: 590) | NLRVDDTA VYYCAR (SEQ ID NO: 591) | P (SEQ ID NO: 592) | (SEQ ID NO: 593) |
| 4B17.1D VH3 | EVQLVRS GGNLVQP GGSLRLSC AATGGPIG (SEQ ID NO: 594) | SHWMT (SEQ ID NO: 595) | WVRQAP GQGLEW VA (SEQ ID NO: 596) | NINLDG TEKFY VDSVK G (SEQ ID NO: 597) | RFTVSRDNR KSSVFLQMN NLRVDDTA VYYCAR (SEQ ID NO: 598) | LQWGG YNGWLS P (SEQ ID NO: 599) | WGQGTL VTVSS (SEQ ID NO: 600) |
| 4B17.1F VH3 | EVQLVRS GGNLVQP GGSLRLSC AATGFYIG (SEQ ID NO: 601) | SHWMT (SEQ ID NO: 602) | WVRQAP GQGLEW VA (SEQ ID NO: 603) | NINLDG TEKFY VDSVK G (SEQ ID NO: 604) | RFTVSRDNR KSSVFLQMN NLRVDDTA VYYCAR (SEQ ID NO: 605) | LQWGG YNGWLS P (SEQ ID NO: 606) | WGQGTL VTVSS (SEQ ID NO: 607) |
| 4B17.1G VH3 | EVQLVRS GGNLVQP GGSLRLSC AATGFTIG (SEQ ID NO: 608) | SHWMT (SEQ ID NO: 609) | WVRQAP GQGLEW VA (SEQ ID NO: 610) | NINLDG TEKFY VDSVK G (SEQ ID NO: 611) | RFTVSRDNR KSSVFLQMN NLRVDDTA VYYCAR (SEQ ID NO: 612) | LQWGG YNGWLS P (SEQ ID NO: 613) | WGQGTL VTVSS (SEQ ID NO: 614) |

TABLE 4

Deduced protein sequences of light chain variable regions (VL) of BoNT/B binders. Sequence identification numbers next to each clone name identifies an amino acid sequences for the full length light chain variable region.

| VL/Clone/ Gene Family | Framework 1 | CDR1 | Framework 2 | CDR2 | Framework 3 | CDR3 | Framework 4 |
|---|---|---|---|---|---|---|---|
| A12 VK1 | DIQMTQSP SSLSASVG DRVTITC (SEQ ID NO: 615) | RASQRI SNYLN (SEQ ID NO: 616) | WYQQKP GKAPKLL IY (SEQ ID NO: 617) | AASSL QS (SEQ ID NO: 618) | EVPSRFSGS GSGTDFTLTI SSLQPEDFA TYYC (SEQ ID NO: 619) | QQSYRP PLT (SEQ ID NO: 620) | FGGGTK VEIKR (SEQ ID NO: 621) |
| 6A12 VK2 | DIQMTQSP SSVSASVG NRVTITC (SEQ ID NO: 622) | RASQGI SSWLA (SEQ ID NO: 623) | WYQQKP GKAPKLL IY (SEQ ID NO: 624) | AASSL QS (SEQ ID NO: 625) | GVPSRFSGS GSGTDFTLTI SSLQPEDFA TYYC (SEQ ID NO: 626) | QKANSF PLT (SEQ ID NO: 627) | FGGGTK VEIKR (SEQ ID NO: 628) |
| B1.1 VK1 | DVVMTQS PSSLSASV GDRVTITC (SEQ ID NO: 629) | RASQSI SSYLN (SEQ ID NO: 630) | WYQQKP GKAPKLL IY (SEQ ID NO: 631) | AASSL QS (SEQ ID NO: 632) | GVPSRFSGS GSGTDFTLTI SSLQPEDFA TYYC (SEQ ID NO: 633) | QQSYST PLT (SEQ ID NO: 634) | FGQGTKL EIKR (SEQ ID NO: 635) |
| B6 VK1 | DVVMTQS PSSLSASV GDRITITC (SEQ ID NO: 636) | QAGQD ISNFLN (SEQ ID NO: 637) | WYQQKP GKAPKLL IR (SEQ ID NO: 638) | DASNL ET (SEQ ID NO: 639) | GVPSRFSGG GSGTHFTFTI SSLHPEDIAT YFC (SEQ ID NO: 640) | QQYDNL PYT (SEQ ID NO: 641) | FGQGTKL EIKR (SEQ ID NO: 642) |
| B6.1 VK1 | DIQMTQSP SSLSASVG DRVTITC (SEQ ID NO: 643) | RASQSI SSYLN (SEQ ID NO: 644) | WYQQEP GKAPKLL IY (SEQ ID NO: 645) | SASSLQ S (SEQ ID NO: 646) | GVPSRFSGS GSGTDFTLTI SSLQPEDFA TYYC (SEQ ID NO: 647) | QQSYST PPYT (SEQ ID NO: 648) | FGQGTKL EIKR (SEQ ID NO: 649) |
| B8 VK1 | DIQMTQSP SSLSASVG DRVTITC (SEQ ID NO: 650) | RASQRI SNYLN (SEQ ID NO: 651) | WYQQKP GKAPKLL IY (SEQ ID NO: 652) | AASSL QS (SEQ ID NO: 653) | EVPSRFSGS GSGTDFTLTI SSLQPEDFA TYYC (SEQ ID NO: 654) | QQSYRP PLT (SEQ ID NO: 655) | FGGGTK VDIKR (SEQ ID NO: 656) |

TABLE 4-continued

Deduced protein sequences of light chain variable regions (VL) of BoNT/B binders. Sequence identification numbers next to each clone name identifies an amino acid sequences for the full length light chain variable region.

| VL/Clone/ Gene Family | Framework 1 | CDR1 | Framework 2 | CDR2 | Framework 3 | CDR3 | Framework 4 |
|---|---|---|---|---|---|---|---|
| B8.1 VK1 | DIQMTQSPSSLSASVGDRVTITC (SEQ ID NO: 657) | RASQRISNYLN (SEQ ID NO: 658) | WYQQKPGKAPKLLIY (SEQ ID NO: 659) | AASSLQS (SEQ ID NO: 660) | EVPSRFSGSGYGTDFTLTISSLQPEDFATYYC (SEQ ID NO: 661) | QQSYRPPLT (SEQ ID NO: 662) | FGGGTKVDIKR (SEQ ID NO: 663) |
| B11 VK1 | DIVMTQSPSTLSASVGDRVTVTC (SEQ ID NO: 664) | RASQSINSWLA (SEQ ID NO: 665) | WYQQKPGKAPKLLIY (SEQ ID NO: 666) | EASSLES(SEQ ID NO: 667) | GVPSRFSGSGSGTEFTLTISSLQPDDFATYYC(SEQ ID NO: 668) | QQYDSYWLT(SEQ ID NO: 669) | FGGGTKVEIKR(SEQ ID NO: 670) |
| B11C3 VK1 | DIQMTQSPSSVSASVGDRVTITC (SEQ ID NO: 671) | RASQGVSRWLA (SEQ ID NO: 672) | WYQQRPEKAPKLLIY (SEQ ID NO: 673) | GASSLQS (SEQ ID NO: 674) | GVPSRFSGSGSGTDFTLTISSLQPEDFATYYC (SEQ ID NO: 675) | QQYDSFPLT (SEQ ID NO: 676) | FGGGTKVEIKR (SEQ ID NO: 677) |
| B11E8 VK1 | EIVLTQSPATLSVSPGERATLSC (SEQ ID NO: 678) | RASQSVSKFLA (SEQ ID NO: 679) | WYQQKRGQAPRLLIY (SEQ ID NO: 680) | GASTRAT (SEQ ID NO: 681) | GIPARFSGSGSGTEFALTISSLQSEDFADYYC (SEQ ID NO: 682) | QQYDNWPIT (SEQ ID NO: 683) | FGQGTRLEIKR (SEQ ID NO: 684) |
| B12 VK1 | DIVMTQSPSTLSASVGDRVTITC (SEQ ID NO: 685) | RASQGISSWLA (SEQ ID NO: 686) | WYQQKPGKAPKLLIY (SEQ ID NO: 687) | KASSLES (SEQ ID NO: 688) | GVPSRFSGSGSGTEFTLTISSLQPEDFATYYC (SEQ ID NO: 689) | LQHNSYPRA (SEQ ID NO: 690) | FGQGTKLEIKR (SEQ ID NO: 691) |
| B12.1 VL3 | AYVLTQPPSVSVAPGKTAAITC (SEQ ID NO: 692) | EGNNVGNKNVH (SEQ ID NO: 693) | WYQQRPGQAPVLVVH (SEQ ID NO: 694) | DDSDRPS (SEQ ID NO: 695) | GIPERFSGSNSGNTATLTINRVEAGDEADYYC (SEQ ID NO: 696) | QVWDSSSAQWV (SEQ ID NO: 697) | FGGGTKLTVLG (SEQ ID NO: 698) |
| B12.2 VL1 | ESVLTQPPLVSAAPGQKVTISC (SEQ ID NO: 699) | SGSSSNIGNNYVS (SEQ ID NO: 700) | WYQQLPGTAPKLLIY (SEQ ID NO: 701) | ENSKRSS (SEQ ID NO: 702) | GIPDRFSGSKSGTSATLGITGLQTGDEADYYC (SEQ ID NO: 703) | GTWDSSLSAVV (SEQ ID NO: 704) | FGGGTKLTVLG (SEQ ID NO: 705) |
| 1B18 VK1 | DVVMTQSPSSVSASVGDRVTITC (SEQ ID NO: 706) | RASQSISSYLN (SEQ ID NO: 707) | WYQQRPGKAPKLLIF (SEQ ID NO: 708) | AASSLQS (SEQ ID NO: 709) | AVPSRFSGSGSGTDFTLTISSLQPEDFATYYC (SEQ ID NO: 710) | QQSYSTPPT (SEQ ID NO: 711) | FGQGTKVEIKR (SEQ ID NO: 712) |
| 2B18.1 VK1 | DIVMTQSPSSLSASVGDRVSISC (SEQ ID NO: 713) | RASQSISSYLN (SEQ ID NO: 714) | WYQQKPGKAPKLLIY (SEQ ID NO: 715) | KTSSLES (SEQ ID NO: 716) | GVPSRFSGRGSGTDFTLTISSLQPEDFATYYC (SEQ ID NO: 717) | QQSYSTPLT (SEQ ID NO: 718) | FGGGTKVEIKR (SEQ ID NO: 719) |
| 1B22 VK1 | DIQMTQSPSTLSASIGDRVTISC (SEQ ID NO: 720) | RASQSIQSWLA (SEQ ID NO: 721) | WYQQRPGEAPKLLIY (SEQ ID NO: 722) | SASTLQT (SEQ ID NO: 723) | GVPSRFSGSGSGTDFTLTISSLQPEDFATYYC (SEQ ID NO: 724) | QQYNSYPLT (SEQ ID NO: 725) | FGQGTKLEIKR (SEQ ID NO: 726) |
| 4B19 VK1 | DIVLTQSPSTLSASVGDRVTISC (SEQ ID NO: 727) | RASRSIGWYLN (SEQ ID NO: 728) | WYQQRPGKAPKLLIY (SEQ ID NO: 729) | AASSLHN (SEQ ID NO: 730) | GVPSRFSGSGSGTEFTLTISSLQPDDFATYYC (SEQ ID NO: 731) | QQAFGFPRT (SEQ ID NO: 732) | FGQGTKVEIKR (SEQ ID NO: 733) |
| 1B10 VK1 | EIVLTQSPSSLSASVGDRITITC (SEQ ID NO: 734) | RASQSISSWLA (SEQ ID NO: 735) | WYQQKPGKAPMVLIY (SEQ ID NO: 736) | KASSLEN (SEQ ID NO: 737) | GVPSRFSGSGSGTEFTLTISSLQPDDFATYYC (SEQ ID NO: 738) | QQYSTYSRT (SEQ ID NO: 739) | FGQGTKVEIKR (SEQ ID NO: 740) |

TABLE 4-continued

Deduced protein sequences of light chain variable regions (VL) of BoNT/B binders. Sequence identification numbers next to each clone name identifies an amino acid sequences for the full length light chain variable region.

| VL/Clone/ Gene Family | Framework 1 | CDR1 | Framework 2 | CDR2 | Framework 3 | CDR3 | Framework 4 |
|---|---|---|---|---|---|---|---|
| 1B10.1 VK1 | EIVLTQSPSFVSASVGDRVTITC (SEQ ID NO: 741) | RASQGISSWLA (SEQ ID NO: 742) | WYQQKPGKAPKLLIY (SEQ ID NO: 743) | AASSLQS (SEQ ID NO: 744) | GVPSRFSGSGSGTEFTLTISSLQPDDFATYYC (SEQ ID NO: 745) | QQYSSLYT (SEQ ID NO: 746) | FGQGTKVDIKR (SEQ ID NO: 747) |
| 2B18.2 VK1 | DIVMTQSPSSLSASVGDRVSISC (SEQ ID NO: 748) | RASQSISSYLN (SEQ ID NO: 749) | WYQQKPGKAPKLLIY (SEQ ID NO: 750) | KTSSLES (SEQ ID NO: 751) | GVPSRFSGRGSGTDFTLTISSLQPEDFATYYC (SEQ ID NO: 752) | QQSYSTPLT (SEQ ID NO: 753) | FGGGTKVEIKR (SEQ ID NO: 754) |
| 2B18.3 VK1 | DIVMTQSPSTLSASVGDRVTITC (SEQ ID NO: 755) | RASQSSTYWLS (SEQ ID NO: 756) | WYQQKPGKAPKLLIY (SEQ ID NO: 757) | KTSSLES (SEQ ID NO: 758) | GVPSRFSGSGSGTEFTLTISSLQPDDFATYYC (SEQ ID NO: 759) | QQSWT (SEQ ID NO: 760) | FGQGTKVEIKR (SEQ ID NO: 761) |
| 1B22.4 VK1 | DVVMTQSPSSVSASVGDRVTITC (SEQ ID NO: 762) | RASQGIGYWLA (SEQ ID NO: 763) | WYQQKPGKGPKLLIY (SEQ ID NO: 764) | DASRLQG (SEQ ID NO: 765) | GVPSRFSGSGSGTDFTLTISSLQPEDFATYYC (SEQ ID NO: 766) | QQYNSYPLT (SEQ ID NO: 767) | FGGGTKLEIKR (SEQ ID NO: 768) |
| 2B23 VK1 | DIQMTQSPPSLSASVGDRVTITC (SEQ ID NO: 769) | RTSQGFTSALA (SEQ ID NO: 770) | WYQQKPGEPPKLLIY (SEQ ID NO: 771) | DASKLES (SEQ ID NO: 772) | GVPSRFSGSGSGTNFALTISSLQPEDFATYFC (SEQ ID NO: 773) | QQSNSYPLT (SEQ ID NO: 774) | FGGGTKVEIKR (SEQ ID NO: 775) |
| 2B24 VL1 | QSVVTQPPSVSAAPGQKVTISC (SEQ ID NO: 776) | SGSSSNIGNNYVS (SEQ ID NO: 777) | WYQQLPGTAPKLLIY (SEQ ID NO: 778) | DNNKRPS (SEQ ID NO: 779) | GIPDRFSGSKSGTSATLGITGLQTGDEADYYC (SEQ ID NO: 780) | GTWDSSLSAGV (SEQ ID NO: 781) | FGGGTKLTVLG (SEQ ID NO: 782) |
| 2B25 VL1 | QPGLTQPPSASGTPGQRVTISC (SEQ ID NO: 783) | SGSSSNVGSNTVN (SEQ ID NO: 784) | WYQQLPGTAPKLLIY (SEQ ID NO: 785) | RNDQRPS (SEQ ID NO: 786) | GVPDRFSGSKSGASASLAISGLRSEDEADYYC (SEQ ID NO: 787) | AAWDDSLNGLL (SEQ ID NO: 788) | FGGGTQLTVLG (SEQ ID NO: 789) |
| 2B25.1 VL1 | ESVLTQPPSVSAAPGQKVTISC (SEQ ID NO: 790) | SGSSSNIGNNYVS (SEQ ID NO: 791) | WYQQLPGTAPKLLIY (SEQ ID NO: 792) | DNNRRPS (SEQ ID NO: 793) | GIPDRFSGSKSGTSATLGITGLQTGDEADYYC (SEQ ID NO: 794) | GTWDSSLSEVV (SEQ ID NO: 795) | FGGGTKVTVLG (SEQ ID NO: 796) |
| 2B26 VL1 | QPGLTQPPSASGTPGQRVTISC (SEQ ID NO: 797) | SGSSSNIGSNPVN (SEQ ID NO: 798) | WYQHLPGTAPKLLIY (SEQ ID NO: 799) | SNNQRPS (SEQ ID NO: 800) | GVPDRFSGSKSGTSASLAISGLQSEDEADYYC (SEQ ID NO: 801) | AAWADSLNGVV (SEQ ID NO: 802) | FGGGTKVTVLG (SEQ ID NO: 803) |
| 2B27 VL1 | QSVVTQPPSVSGAPGQRVTISC (SEQ ID NO: 804) | SGSSSNIGAGYDVH (SEQ ID NO: 805) | WYQQLPGTAPKLLIY (SEQ ID NO: 806) | GNNNRPS (SEQ ID NO: 807) | GVPDRFSGSKSGTSASLAITGLQAEDEADYYC (SEQ ID NO: 808) | QSYDSSLSAYV (SEQ ID NO: 809) | FGTGTKLTVLG (SEQ ID NO: 810) |
| 2B28 VL1 | QSVLTQPPSVSAAPGQKVTISC (SEQ ID NO: 811) | SGSSSNIGNNYVS (SEQ ID NO: 812) | WYQQLPGTAPKLLIY (SEQ ID NO: 813) | DNNKRPS (SEQ ID NO: 814) | GIPDRFSGSKSGTSATLGITGLQTGDEADYYC (SEQ ID NO: 815) | GTWDSSLSAVV (SEQ ID NO: 816) | FGGGTQLTVLG (SEQ ID NO: 817) |
| 2B29 VL1 | QPVLTQSPSASGTPGQRVTISC (SEQ ID NO: 818) | SGSSSNLGSNTVS (SEQ ID NO: 819) | WYQQLPGTAPKLLIY (SEQ ID NO: 820) | SNNQRPS (SEQ ID NO: 821) | GVPDRFSGSKSGTSASLAISGLQSEDEADYYC (SEQ ID NO: 822) | ATWDDSLSGGV (SEQ ID NO: 823) | FGGGTKLTVLG (SEQ ID NO: 824) |

TABLE 4-continued

Deduced protein sequences of light chain variable regions (VL) of BoNT/B binders. Sequence identification numbers next to each clone name identifies an amino acid sequences for the full length light chain variable region.

| VL/Clone/ Gene Family | Framework 1 | CDR1 | Framework 2 | CDR2 | Framework 3 | CDR3 | Framework 4 |
|---|---|---|---|---|---|---|---|
| 2B30 VL1 | SYELMQLPSASGTPGQRVSISC (SEQ ID NO: 825) | SGSSSNIGSNPVN (SEQ ID NO: 826) | WYQQLPGTAPKLLIY (SEQ ID NO: 827) | SNNHRPS (SEQ ID NO: 828) | GVPDRFSGSKSGTSASLAISGLQSEDEADYYC (SEQ ID NO: 829) | AAWDGSLNGHVV (SEQ ID NO: 830) | FGGGTKLTVLG (SEQ ID NO: 831) |
| 4B17.1 VK1 | DIVMTQSPSSLSASVGDRVTISC (SEQ ID NO: 832) | RASQSIRHYVN (SEQ ID NO: 833) | WYQQKPGKAPKLLIY (SEQ ID NO: 834) | KASSLAS (SEQ ID NO: 835) | GAPSRFSGSGSGTDFTLTISSLQPDDFATYYC (SEQ ID NO: 836) | QQSYSIPLT (SEQ ID NO: 837) | FGGGTKVEIKR (SEQ ID NO: 838) |
| 4B17.1C VK1 | DIVMTQSPSSLSASVGDRVTISC (SEQ ID NO: 839) | RASQSIRHYVN (SEQ ID NO: 840) | WYQQKPGKAPKLLIY (SEQ ID NO: 841) | KASSLAS (SEQ ID NO: 842) | GAPSRFSGSGSGTDFTLTISSLQPDDFATYYC (SEQ ID NO: 843) | QQSYSIPLT (SEQ ID NO: 844) | FGGGTKVEIKR (SEQ ID NO: 845) |
| 4B17.1D VK1 | DIVMTQSPSSLSASVGDRVTISC (SEQ ID NO: 846) | RASQSIRHYVN (SEQ ID NO: 847) | WYQQKPGKAPKLLIY (SEQ ID NO: 848) | KASSLAS (SEQ ID NO: 849) | GAPSRFSGSGSGTDFTLTISSLQPDDFATYYC (SEQ ID NO: 850) | QQSYSIPLT (SEQ ID NO: 851) | FGGGTKVEIKR (SEQ ID NO: 852) |
| 4B17.1F VK1 | DIVMTQSPSSLSASVGDRVTISC (SEQ ID NO: 853) | RASQSIRHYVN (SEQ ID NO: 854) | WYQQKPGKAPKLLIY (SEQ ID NO: 855) | KASSLAS (SEQ ID NO: 856) | GAPSRFSGSGSGTDFTLTISSLQPDDFATYYC (SEQ ID NO: 857) | QQSYSIPLT (SEQ ID NO: 858) | FGGGTKVEIKR (SEQ ID NO: 859) |
| 4B17.1G VK1 | DIVMTQSPSSLSASVGDRVTISC (SEQ ID NO: 860) | RASQSIRHYVN (SEQ ID NO: 861) | WYQQKPGKAPKLLIY (SEQ ID NO: 862) | KASSLAS (SEQ ID NO: 863) | GAPSRFSGSGSGTDFTLTISSLQPDDFATYYC (SEQ ID NO: 864) | QQSYSIPLT (SEQ ID NO: 865) | FGGGTKVEIKR (SEQ ID NO: 866) |

TABLE 5

BoNT/A light chain antibodies. Shown are the clone name, VH CDR3, VL CDR3, $K_D$ for BoNT/A light chain, and epitope recognized. Epitopes are assigned sequential numbers, if the epitope does not overlap with other light chain antibodies. Affinities are for BoNT/A1 as determined using yeast displayed scFv and soluble BoNT/A1.

| Clone | VH CDR3 | VL CDR3 | KD (nM) | Epitope |
|---|---|---|---|---|
| ING2 | DPYYYSYMDV (SEQ ID NO: 867) | QQYYSTPFT (SEQ ID NO: 868) | 0.25 | 1 |
| 5A20.4 | EASFGWSYLGHDDAFDI (SEQ ID NO: 869) | QQYGSSLWT (SEQ ID NO: 870) | 0.34 | 2 |
| CON1 (4A1.1) | DPGWIYSDTSAAGWFDP (SEQ ID NO: 871) | QQSYDTPRT (SEQ ID NO: 872) | 10 | 3 |

It will be appreciated that the amino acid sequence of a CDR can also be defined using alternative systems, which will be readily apparent to and applied by the ordinarily skilled artisan (see, "Sequences of Proteins of Immunological Interest," E. Kabat et al., U.S. Department of Health and Human Services, (1991 and Lefranc et al. IMGT, the international ImMunoGeneTics information system. Nucl. Acids Res., 2005, 33, D593-D597)). A detailed discussion of the IMGTS system, including how the IMGTS system was formulated and how it compares to other systems, is provided on the World Wide Web at imgt.cines.fr/textes/IMGT-ScientificChart/Numbering/IMGTnumberingsTable.html. An example of a definition of CDRs of an exemplary antibody, 1B10.1, is provided in FIG. 12. Amino acids indicated in bold are CDR regions according to IMGT boundary definitions, with underlined residues defined according to The Kabat system that resulted in the CDRs described above. All amino acid sequences of CDR in the present disclosure are defined according to Kabat et al., supra, unless otherwise indicated.

Using the teachings and the sequence information provided herein, the variable light and variable heavy chains can be joined directly or through a linker (e.g., $(Gly_4Ser)_3$, SEQ ID NO:1) to form a single-chain Fv antibody. The various CDRs and/or framework regions can be used to form human antibodies, chimeric antibodies, antibody fragments, polyvalent antibodies, and the like.

Anti-BoNT antibodies of the present disclosure have a binding affinity ($K_D$) for a BoNT protein of at least $10^{-8}$, at least $10^{-9}$, at least $10^{-10}$, and most preferably at least $10^{-11}$, $10^{-12}$M or less. Some exemplary $K_D$s ($M^{-1}$) for BoNT/B or BoNT/E fall in the following ranges: between $5\times10^{-11}$ to $3\times10^{-10}$, between $4\times10^{-10}$ to $2\times10^{-10}$, between $7\times10^{-10}$ to $1\times10^{-9}$, between $8\times10^{-10}$ to $5\times10^{-9}$, between $1\times10^{-9}$ to $3\times10^{-9}$, between $4\times10^{-9}$ to $2\times10^{-8}$.

The antibody of the present disclosure may be defined by the epitope of BoNT bound by the antibody. The antibodies provided here may encompass those that bind to one or more epitopes of BoNT to which an antibody containing one or more of the CDRs set forth in Tables 1-5 bind. Epitopes bound by an antibody may be described by a specific BoNT domain and/or the residues therein that contribute to the interaction between the antibody and a BoNT protein. Certain residues of the epitopes bound by the exemplary antibodies are provided in the table below.

TABLE 6

| Epitope Data | | |
|---|---|---|
| IgG | Toxin/Domain | Residues Defining Epitope |
| 4E17.1 | A1/$H_N$ | Y753, E756, **E757** |
| 1B18 | A1/$H_N$ | Y750, N751, **T754** |
| HuC25 | A1/$H_C$ | E920, F953, **H1064** |
| AR2/CR1 | A1/$H_C$ | B918, L919, E920, F953, D1062, T1063, **H1064** |
| 3D12/RAZ1 | A1/$H_C$ | G1129, I1130, **R1131** |
| 1B11 | B1/$H_N$ | **I549**, **S565** |
| 4E17.1 | B1/$H_N$ | K747, **R749**, Y750, N751 |
| 1B18 | B1/$H_N$ | N751, Y750, Y753 |
| 3E1 | E1/$L_C$ | **N14**, **D15**, R16, Q29, E30, **Y32**, **E135**, **K137**, **F138**, **N140**, S142, **Q143**, **D144**, **I145** |
| 3E3 | E1/$L_C$ | **N14**, Y32, **E135**, **K137**, **F138**, N140, S142, **Q143**, **D144**, **I145** |
| 3E5 | E1/$L_C$ | **N14**, D15, **Y30**, D144 |
| 3E6.1 | E1/$L_C$ | **S604**, **Q607**, **Q608** |
| 4E11 | E1/$L_C$ | **N14**, D15, E30, **Y32** |
| 4E16.1 | E1/$L_C$ | **N14**, **D15**, E30, **Y32**, D144 |
| 4E17.1 | E1/$L_C$ | **E754b**, **E755** |

Numbering system used for the toxin in the table above is based on Lacy et al. (1999) *J. Mol. Biol.* 291:1091-1104. Residues that are bolded and underlined have important contributions energetically and eliminations of these residues often lead to total loss of detectable binding by the corresponding antibodies to a particular BoNT. Based on the table above, an antibody such as 4E17.1, may be described by its affinity to the $H_N$ domain of BoNT/A. The antibody having the same epitope as 4E17.1 may also be characterized as an antibody with an epitope(s) containing one or more of the residues: Y753, E756, E757 in BoNT/A. In another example, an antibody such as 3E6.1, may be described by its affinity to the $L_C$ domain of BoNT/E. The antibody having the same epitope as 3E6.1 may be characterized as an antibody with an epitope(s) containing one or more of the residues: S604, Q607, Q608 in BoNT/E The ability of a particular antibody to recognize the same epitope as another antibody can be determined by the ability of one antibody to competitively inhibit binding of the second antibody to the antigen. Competitive inhibition of binding may also be referred to as cross-reactivity of antibodies. Any of a number of competitive binding assays can be used to measure competition between two antibodies to the same antigen. For example, a sandwich ELISA assay can be used for this purpose. Additional methods for assaying for cross-reactivity are described later below.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays used to assess competitive binding.

Accordingly, antibodies provided by the present disclosure encompass those that compete for binding to a BoNT/E with an antibody that includes one or more of the $V_H$ CDRs set forth in Table 1 and/or one or more of the $V_L$ CDRs set forth in Table 2. Antibodies provided by the present disclosure also encompass those that compete for binding to a BoNT/B with an antibody that includes one or more of the $V_H$ CDRs set forth in Table 3 and/or one or more of the $V_L$ CDRs set forth in Table 4. Additional antibodies may encompass those that compete for binding to a BoNT/A with an antibody with one or more CDRs set forth in Table 5.

For example, an antibody may have the binding specificity (i.e., in this context, the same CDRs, or substantially the same CDRs) of an antibody having $V_H$ and $V_L$ CDRs or full length $V_H$ and $V_L$ as set forth in Tables 1-5. An antibody of the present disclosure may therefore contain a CDR as set forth in a $V_H$ or $V_L$ sequence shown in Tables 1-5 and, additionally, may have at least 80% identity, preferably, 85%, 90%, or 95% identity to a full-length $V_H$ or $V_L$ sequence. For example, an antibody may contain the CDRs of a $V_H$ and a $V_L$ sequence and human framework sequences set forth in Tables 1-5.

III. Preparation of BoNT Neutralizing Antibodies.

A) Recombinant Expression of BoNT-Neutralizing Antibodies.

Using the information provided herein, the *botulinum* neurotoxin-neutralizing antibodies of the present disclosure are prepared using standard techniques well known to those of skill in the art.

For example, the polypeptide sequences provided herein (see, e.g., Tables 1-5, and/or FIGS. 1-2 and 11) can be used to determine appropriate nucleic acid sequences encoding the BoNT-neutralizing antibodies and the nucleic acids sequences then used to express one or more BoNT-neutralizing antibodies. The nucleic acid sequence(s) can be optimized to reflect particular codon "preferences" for various expression systems according to standard methods well known to those of skill in the art.

Using the sequence information provided, the nucleic acids may be synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12:6159-6168) or manually synthesized using, for example, the solid phase phosphoramidite triester method described by Beaucage et. al. (1981) *Tetrahedron Letts.* 22(20): 1859-1862.

Once a nucleic acid encoding an anti-BoNT antibody is synthesized it can be amplified and/or cloned according to standard methods. Molecular cloning techniques to achieve these ends are known in the art. A wide variety of cloning and in vitro amplification methods suitable for the construction of recombinant nucleic acids are known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc, and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Nat'l Acad. Sci. USA* 86: 10029-10033.

Examples of techniques sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94: (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080: Van Brunt (1990) *Biotechnology* 8, 291-294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

Once the nucleic acid for an anti-BoNT antibody is isolated and cloned, one can express the gene in a variety of recombinantly engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of antibodies.

In brief summary, the expression of natural or synthetic nucleic acids encoding anti-BoNT antibodies will typically be achieved by operably linking a nucleic acid encoding the antibody to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the anti-BoNT antibody. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook et al (1989) supra.

To obtain high levels of expression of a cloned nucleic acid it is common to construct expression plasmids which typically contain a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018-1024, and the leftward promoter of phage lambda ($P_L$) as described by Herskowitz and Hagen (1980) *Ann. Rev. Genet.*, 14:399-445 and the L-arabinose (araBAD) operon (Better (1999) *Gene Exp Systems* pp 95-107 Academic Press, Inc., San Diego, Calif.). The inclusion of selection markers in DNA vectors transformed in *E. coli* is also useful. Examples of such markers include genes specifying resistance to ampicillin, tetracycline, or chloramphenicol. See Sambrook et al (1989) supra for details concerning selection markers, e.g., for use in *E. coli.*

Expression systems for expressing anti-BoNT antibodies are available using, for example, *E. coli, Bacillus* sp. (see, e.g., Palva, et al. (1983) *Gene* 22:229-235; Mosbach et al. (1983) *Nature,* 302: 543-545), and *Salmonella. E. coli* systems may also be used.

The anti-BoNT antibodies produced by prokaryotic cells may require exposure to chaotropic agents for proper folding. During purification from, e.g., *E. coli*, the expressed protein is optionally denatured and then renatured. This can be accomplished, e.g., by solubilizing the bacterially produced antibodies in a chaotropic agent such as guanidine HCl. The antibody is then renatured, either by slow dialysis or by gel filtration (see, e.g., U.S. Pat. No. 4,511,503). Alternatively, nucleic acid encoding the anti-BoNT antibodies may be operably linked to a secretion signal sequence such as pelB so that the anti-BoNT antibodies are secreted into the medium in correctly-folded form (Better et al (1988) *Science* 240: 1041-1043).

Methods of transfecting and expressing genes in mammalian cells are known in the art (see e.g. Birch and Racher *Adv. Drug Deliv. Rev.* 2006, 58: 671-685). Transducing cells with nucleic acids can involve, for example, incubating viral vectors containing anti-BoNT nucleic acids with cells within the host range of the vector (see, e.g., Goeddel (1990) *Methods in Enzymology*, vol. 185, Academic Press, Inc., San Diego, Calif. or Krieger (1990) *Gene Transfer and Erpression—A laboratory Manual*, Stockton Press, New York, N.Y. and the references cited therein).

The culture of cells used in the present disclosure, including cell lines and cultured cells from tissue or blood samples is well known in the art (see, e.g., Freshney (1994) *Culture of Animal Cells, a Manual of Basic Technique, third edition*, Wiley-Liss, N. Y, and the references cited therein).

Techniques for using and manipulating antibodies are found in Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

The BoNT-neutralizing antibody gene(s) (e.g. BoNT-neutralizing scFv gene) may be subcloned into the expression vector pUC119mycHis (Tomlinson et al. (1996) *J. Mol. Biol.,* 256: 813-817) or pSYN3, resulting in the addition of a hexahistidine tag at the C-terminal end of the scFv to facilitate purification. Detailed protocols for the cloning and purification of certain BoNT-neutralizing antibodies are found, for example, in Amersdorfer et al. (1997) *Infect. Immunity,* 65(9): 3743-3752, and the like.

B) Preparation of Whole Polyclonal or Monoclonal Antibodies.

The anti-BoNT antibodies of the present disclosure include individual, allelic, strain, or species variants, and fragments thereof, both in their naturally occurring (full-length) forms and in recombinant forms. Certain antibodies may be selected to bind one or more epitopes bound by the antibodies described herein (e.g., 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B111.E9, 4B1, 4B3, 4B5, 4B6, 4B7, 1B14, 4A1, 4A1.1, 5A20.4, ING1.1C1, ING1.5B1, ING1.2B10, and ING1.3C2). The antibodies can be raised in their native configurations or in non-native configurations. Anti-idiotypic antibodies can also be generated. Many methods of making antibodies that specifically bind to a particular epitope are known to persons of skill. The following discussion is presented as a general overview of the techniques available; however, one of skill will recognize that many variations upon the following methods are known.

1) Polyclonal Antibody Production.

Methods of producing polyclonal antibodies are known to those of skill in the art. In brief, an immunogen (e.g., BoNT/A, BoNT/B, BoNT/E, etc.), subsequences including, but not limited to subsequences comprising epitopes specifically bound by antibodies expressed by clones 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B117.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2 disclosed herein, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the BoNT polypeptide is performed where desired (see, e.g., Coligan (1991) *Current Protocols in Immunology* Wiley/Greene, NY; and Harlow and Lane (1989) *Antibodies: A Laboratory Manual* Cold Spring Harbor Press, NY).

Antibodies that specifically bind to the neutralizing epitopes described herein can be selected from polyclonal sera using the selection techniques described herein.

2) Monoclonal Antibody Production.

In some instances, it is desirable to prepare monoclonal antibodies from various mammalian hosts, such as mice, rodents, primates, humans, etc. Descriptions of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495-497.

Summarized briefly, monoclonal antibody production using hybridomas may proceed by injecting an animal with an (e.g., BoNT/A, BoNT/B, BoNT/E, etc.) subsequences including, but not limited to subsequences comprising epitopes specifically bound by antibodies expressed by clones 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.C1, ING1.5B1, ING1.2B10, and ING1.3C2 disclosed herein. The animal is then sacrificed and cells taken from its spleen, which are fused with myeloma cells. The result is a hybrid cell or "hybridoma" that is capable of reproducing antibodies in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the BoNT antigen, and yield of the monoclonal antibodies produced by such cells is enhanced by various techniques, including injection into the peritoneal cavity of a vertebrate (preferably mammalian) host. The antibodies of the present disclosure are used with or without modification, and include chimeric antibodies such as humanized murine antibodies.

Techniques for creating recombinant DNA versions of the antigen-binding regions of antibody molecules which bypass the generation of hybridomas are contemplated for the present BoNT (e.g., BoNT/B) binding antibodies and fragments. DNA is cloned into a bacterial expression system. One example of a suitable technique uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind BoNT. Such BoNT binding agents (Fab fragments with specificity for a BoNT polypeptide) are specifically encompassed within the BoNT binding antibodies and fragments of the present disclosure. Other methods for screening and production of antibodies may employ one or more of display systems such as phage display, yeast display, ribosome, etc., and an antibody production system such as that derived from transgenic mice.

IV. Modification of BoNT Neutralizing Antibodies.

A) Display Techniques can be Used to Increase Antibody Affinity.

To create higher affinity antibodies, mutant scFv gene repertories, based on the sequence of a binding scFv (see, e.g., Tables 1-5, and/or FIGS. 1, 2, and/or 11), can be created and expressed on the surface of phage. Display of antibody fragments on the surface of viruses which infect bacteria (bacteriophage or phage) makes it possible to produce human or other mammalian antibodies (e.g., scFvs) with a wide range of affinities and kinetic characteristics. To display antibody fragments on the surface of phage (phage display), an antibody fragment gene is inserted into the gene encoding a phage surface protein (e.g., pIII) and the antibody fragment-pill fusion protein is expressed on the phage surface (McCafferty et al. (1990) *Nature,* 348: 552-554; Hoogenboom et al. (1991) *Nucleic Acids Res.,* 19: 4133-4137).

Since the antibody fragments on the surface of the phage are functional, those phage bearing antigen binding antibody fragments can be separated from non-binding or lower affinity phage by antigen affinity chromatography (McCafferty et al. (1990) *Nature,* 348: 552-554). Mixtures of phage are allowed to bind to the affinity matrix, non-binding or lower affinity phage are removed by washing, and bound phage are eluted by treatment with acid or alkali.

By infecting bacteria with the eluted phage or modified variants of the eluted phage as described below, more phage can be grown and subjected to another round of selection. In this way, an enrichment of 1000 fold in one round may become 1,000,000 fold in two rounds of selection (see, e.g., McCafferty et al. (1990) *Nature,* 348: 552-554). Thus, even when enrichments in each round are low, multiple rounds of affinity selection leads to the isolation of rare phage and the genetic material contained within which encodes the sequence of the binding antibody (see, e.g., Marks et al. (1991) *J. Mol. Biol.,* 222: 581-597). The physical link between genotype and phenotype provided by phage display makes it possible to test every member of an antibody fragment library for binding to antigen, even with libraries as large as 100,000,000 clones. For example, after multiple rounds of selection on antigen, a binding scFv that occurred with a frequency of only 1/30,000,000 clones was recovered (Marks et al. (1991) *J. Mol. Biol.,* 222: 581-597.).

Yeast display may also be utilized to increase antibody affinity and has the ability to finely discriminate between mutants of close affinity. Antibody variable region genes (V-genes) may be diversified either randomly or using spiked oligonucleotides, and higher affinity mutants selected using various types of affinity chromatography or flow cytometry.

1) Chain Shuffling.

One approach for creating mutant scFv gene repertoires involves replacing either the $V_H$ or $V_L$ gene from a binding scFv with a repertoire of $V_H$ or $V_L$ genes (chain shuffling) (see, e.g., Clackson et al. (1991) *Nature,* 352: 624-628). Such gene repertoires contain numerous variable genes derived from the same germline gene as the binding scFv, but with point mutations (see. e.g., Marks et al. (1992) *Bio/Technology,* 10: 779-783). Using light or heavy chain shuffling and phage display, the binding avidities of, e.g., BoNT/E or BoNT/B-neutralizing antibody fragment can be dramatically increased (see, e.g., Marks et al. (1992) *Bio/Technology,* 10: 779-785 in which the affinity of a human scFv antibody fragment which bound the hapten phenyloxazolone (phox) was increased from 300 nM to 15 nM (20 fold)).

Thus, to alter the affinity of BoNT-neutralizing antibody a mutant scFv gene repertoire may be created containing the $V_H$ gene of a known BoNT-neutralizing antibody (e.g., 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A, 4A1.1, 5A20.4, ING1.1C1, ING1.5B1, ING1.2B10, and ING1.3C2) and a $V_L$ gene repertoire (light chain shuffling). Alternatively, an scFv gene repertoire is created containing the $V_L$ gene of a known BoNT-neutralizing antibody (e.g 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2) and a $V_H$ gene repertoire (heavy chain shuffling). The scFv gene repertoire may be cloned into a phage display vector (e.g., pHEN-1, Hoogenboom et al. (1991) *Nucleic Acids Res.,* 19: 4133-4137) and after transformation a library of transformants is obtained. Phage are prepared and concentrated and selections are performed. In addition to chain shuffling, it is also possible to shuffle individual complementarity determining regions (CDRs).

The antigen concentration may be decreased in each round of selection, reaching a concentration less than the desired $K_d$ by the final rounds of selection. This results in the selection of phage on the basis of affinity (Hawkins et al. (1992) *J. Mol. Biol.* 226: 889-896).

Chain shuffling may be combined with the stringent selections made possible by yeast display and flow cytometry. This novel approach was found to be particularly powerful for increasing antibody affinity (see example 1).

2) Increasing the Affinity of Anti-BoNT Antibodies by Site Directed Mutagenesis.

The majority of antigen contacting amino acid side chains are located in the complementarity determining regions (CDRs), three in the $V_H$ (CDR1, CDR2, and CDR3) and three in the $V_L$ (CDR1, CDR2, and CDR3) (see. e.g., Chothia et al. (1987) *J. Mol. Biol.,* 196: 901-917: Chothia et al. (1986) *Science,* 233: 755-8; Nhan et al. (1991) *J. Mol. Biol.,* 217: 133-151). Without being bound to a theory, it is believed that these residues contribute the majority of binding energetics responsible for antibody affinity for antigen. In other molecules, mutating amino acids that contact ligand has been shown to be an effective means of increasing the affinity of one protein molecule for its binding partner (Lowman et al. (1993) *J. Mol. Biol.,* 234: 564-578; Wells (1990) *Biochemistry,* 29: 8509-8516). Thus mutation (randomization) of the CDRs and screening against, for example, BoNT/A, BoNT/E, BoNT/B, or the epitopes thereof, can be used to generate anti-BoNT antibodies having improved binding affinity.

Each CDR is randomized in a separate library, using, for example, A12 as a template. To simplify affinity measurement, A12, or other lower affinity anti-BoNT antibodies, are used as a template, rather than a higher affinity scFv. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4\times10^{-10}$ to $9.0\times10^{-13}$ M (see, e.g., Lowman et al. (1993) *J. Mol. Biol.,* 234: 564-578).

To increase the affinity of BoNT-neutralizing antibodies, amino acid residues located in one or more CDRs (e.g., 9 amino acid residues located in $V_L$ CDR3) are partially randomized by synthesizing a "doped" oligonucleotide in which the wild type nucleotide occurred with a frequency of, e.g. 49%. The oligonucleotide is used to amplify the remainder of the BoNT-neutralizing scFv gene(s) using PCR.

For example, to create a library in which $V_H$ CDR3 is randomized, an oligonucleotide is synthesized which anneals to the BoNT-neutralizing antibody $V_H$ framework 3 and encodes $V_H$ CDR3 and a portion of framework 4. At the four positions to be randomized, the sequence NNS can be used, where N is any of the 4 nucleotides, and S is "C" or "T". The oligonucleotide is used to amplify the BoNT-neutralizing antibody $V_H$ gene using PCR, creating a mutant BoNT-neutralizing antibody $V_H$ gene repertoire. PCR is used to splice the $V_H$ gene repertoire with the BoNT-neutralizing antibody light chain gene, and the resulting scFv gene repertoire cloned into a phage display vector (e.g., pHEN-1 or pCANTAB5E). Ligated vector DNA is used to transform electrocompetent *E. coli* to produce a phage antibody library.

To select higher affinity mutant scFv, each round of selection of the phage antibody libraries is conducted on decreasing amounts of one or more BoNT subtypes. Clones from the third and fourth round of selection can screened for binding to the desired antigen(s) (e.g., BoNT/B BoNT/E, etc.) by ELISA on 96 well plates. scFv from, e.g., twenty to forty ELISA positive clones can be expressed, e.g. in 10 ml cultures, the periplasm harvested, and the scFv $k_{off}$ determined by BIAcore. Clones with the slowest $k_{off}$ are sequenced, and each unique scFv subcloned into an appropriate vector (e.g., pUC119 mycHis). The scFv are expressed in culture, and purified. Affinities of purified scFv can be determined by BIAcore.

By way of illustration, FIG. 5 shows a scheme used for affinity maturation of HuC25 (FIG. 5A) and 3D12 (FIG. 5B) scFv using yeast display (see, e.g., Ser. No. 11/342,271, filed on Jan. 26, 2006, Ser. No. 09/144,886, filed on Aug. 31, 1998, Ser. No. 10/632,706, filed on Aug. 1, 2003, U.S. Ser. No. 60/942,173 filed on Jun. 5, 2008, and PCT application Nos: PCT/US2006/003070 and PCT/US03/24371, which are incorporated herein by reference for all purposes).

3) Creation of Anti-BoNT (scFv')2 Homodimers.

To create anti-BoNT (e.g., BoNT-neutralizing) $(scFv')_2$ antibodies, two anti-BoNT scFvs are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis between a myc tag and a hexahistidine tag at the carboxy-terminus of an anti-BoNT/B. Introduction of the correct sequence can be verified by DNA sequencing. The construct may be in pUC119, so that the pelB leader directs expressed scFv to the periplasm and cloning sites (Nco1 and Not1) exist to introduce anti-BoNT mutant scFv. Expressed scFv has the myc tag at the C-terminus, followed by two glycines, a cysteine, and then 6 histidines to facilitate purification by IMAC. After disulfide bond formation between the two cysteine residues, the two scFv can be separated from each other by 26 amino acids (two 11 amino acid myc tags and 4 glycines). An scFv expressed from this construct, purified by IMAC may predominantly comprise monomeric scFv. To produce $(scFv')_2$ dimers, the cysteine can be reduced by incubation with 1 MM beta-mercaptoethanol, and half of the scFv blocked by the addition of DTNB. Blocked and unblocked scFvs can be incubated together to form $(scFv')_2$ and the resulting material can optionally be analyzed by gel filtration. The affinity of the anti-BoNT scFv' monomer and $(scFv')_2$ dimer can optionally be determined by BIAcore.

The $(scFv')_2$ dimer may be created by joining the scFv fragments through a linker, more preferably through a peptide linker. This can be accomplished by a wide variety of means well known to those of skill in the art. For example, one preferred approach is described by Holliger et al. (1993) *Proc. Natl. Acad. Sci. USA,* 90: 6444-6448 (see also WO 94/13804).

Typically, linkers are introduced by PCR cloning. For example, synthetic oligonucleotides encoding the 5 amino acid linker ($Gly_4Ser$, SEQ ID NO:938) can be used to PCR amplify the BoNT-neutralizing antibody $V_H$ and $V_L$ genes which are then spliced together to create the BoNT-neutralizing diabody gene. The gene can then be cloned into an appropriate vector, expressed, and purified according to standard methods well known to those of skill in the art.

4) Preparation of Anti-BoNT $(scFv)_2$, Fab, and $(Fab')_2$ Molecules.

Anti-BoNT antibodies such as anti-BoNT/E or anti-BoNT/B scFv, or variant(s) with higher affinity, are suitable templates for creating size and valency variants. For example, an anti-BoNT $(scFv')_2$ can be created from the parent scFv (e.g., 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2, etc.) as described above. An scFv gene can be excised using appropriate restriction enzymes and cloned into another vector as described herein.

Expressed scFv may include a myc tag at the C-terminus, followed by two glycines, a cysteine, and six histidines to facilitate purification. After disulfide bond formation between the two cystine residues, the two scFv may be separated from each other by 26 amino acids (e.g., two eleven amino acid myc tags and four glycines). Single-chain Fv (scFv) can be expressed from this construct and purified.

To produce $(scFv')_2$ dimers, the cysteine is reduced by incubation with 1 mM 3-mercaptoethanol, and half of the scFv blocked by the addition of DTNB. Blocked and unblocked scFv are incubated together to form $(scFv')_2$, which is purified. As higher affinity scFv are isolated, their genes are similarly used to construct $(scFv')_2$.

Anti-BoNT Fab may also be expressed in *E. coli* using an expression vector similar to the one described by Better et. al. (1988) *Science,* 240: 1041-1043. For example, to create a BoNT/B or BoNT/E-neutralizing Fab, the $V_H$ and $V_L$ genes are amplified from the scFv using PCR. The $V_H$ gene is cloned into an expression vector (e.g., a pUC119 based bacterial expression vector) that provides an IgG $C_H1$ domain downstream from, and in frame with, the $V_H$ gene. The vector also contains the lac promoter, a pelB leader sequence to direct expressed $V_H$-$C_H1$ domain into the periplasm, a gene 3 leader sequence to direct expressed light chain into the periplasm, and cloning sites for the light chain gene. Clones containing the correct $V_H$ gene are identified, e.g., by PCR fingerprinting. The $V_L$ gene is spliced to the $C_L$ gene using PCR and cloned into the vector containing the $V_H$ $C_H1$ gene.

B) Selection of Neutralizing Antibodies.

Selection of anti-BoNT antibodies (whether produced by phage display, yeast display, immunization methods, hybridoma technology, etc.) involves screening the resulting antibodies for specific binding to an appropriate antigen(s). In the instant case, suitable antigens can include, but are not limited to BoNT/E1, BoNT/E2, BoNT/E3, BoNT/B, BoNT/B2, BoNT/B3, BoNT/B4, BoNT/A1, BoNT/A2, BoNT/A3, a C-terminal domain of BoNT heavy chain (binding domain), BoNT holotoxins, recombinant BoNT domains such as $H_C$ (binding domain), $H_N$ (translocation domain), or $L_C$ (light chain), and the like. The neutralizing antibodies may be selected for specific binding of an epitope recognized by one or more of the antibodies described herein.

Selection can be by any of a number of methods well known to those of skill in the art. In one example, selection is by immunochromatography (e.g., using immunotubes, Maxisorp, Nunc) against the desired target, e.g., BoNT/E, BoNT/B, etc. In a related example, selection is against a BoNT protein in a surface plasmon resonance system (e.g., BIAcore, Pharmacia) either alone or in combination with an antibody that binds to an epitope specifically bound by one or more of the antibodies described herein. Selection can also be done using flow cytometry for yeast display libraries. Yeast display libraries are sequentially selected, first on BoNT/B1, then on other BoNT/B subtypes (BoNT/B2, B3 and B4) to obtain antibodies that bind with high affinity to all subtypes of BoNT/B. This can be repeated for other subtypes.

For phage display, analysis of binding can be simplified by including an amber codon between the antibody fragment gene and gene III. This makes it possible to easily switch between displayed and soluble antibody fragments simply by changing the host bacterial strain. When phage are grown in a supE suppresser strain of *E. coli*, the amber stop codon between the antibody gene and gene III is read as glutamine and the antibody fragment is displayed on the surface of the phage. When eluted phage are used to infect a non-suppressor strain, the amber codon is read as a stop codon and soluble antibody is secreted from the bacteria into the periplasm and culture media (Hoogenboom et al. (1991) *Nucleic Acids Res.,* 19: 4133-4137). Binding of soluble scFv to antigen can be detected, e.g., by ELISA using a murine IgG monoclonal antibody (e.g., 9E10) which recognizes a C-terminal myc peptide tag on the scFv (Evan et al. (1985) *Mol. Cell Biol.,* 5: 3610-3616; Munro et al. (1986) *Cell,* 46: 291-300), e.g., followed by incubation with polyclonal anti-mouse Fc conjugated to a detectable label (e.g., horseradish peroxidase).

As indicated above, purification of the anti-BoNT antibody can be facilitated by cloning of the scFv gene into an expression vector (e.g., expression vector pUC119mycHIS) that results in the addition of the myc peptide tag followed by a hexahistidine tag at the C-terminal end of the scFv. The vector also preferably encodes the pectate lyase leader sequence that directs expression of the scFv into the bacterial periplasm where the leader sequence is cleaved. This makes it possible to harvest native properly folded scFv directly from the bacterial periplasm. The BoNT-neutralizing antibody is then expressed and purified from the bacterial supernatant using immobilized metal affinity chromatography.

C) Measurement of Anti-BoNT Antibody Affinity for One or More BoNT Subtypes.

As explained above, selection for increased avidity involves measuring the affinity of an anti-BoNT (e.g., a BoNT-neutralizing) antibody (or a modified BoNT-neutralizing antibody) for one or more targets of interest (e.g. BoNT/E subtype(s) or domains thereof. For example, the $K_D$ of a BoNT/E-neutralizing antibody and the kinetics of binding to BoNT/E are determined in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0\times10^2$ to $5.0\times10^6$ M and $k_{off}$ in the range $1.0\times10^{-1}$ to $1.0\times10^{-6}$M. The equilibrium constant $K_d$ is then calculated as $k_{off}/k_{on}$ and thus is typically measured in the range $10^{-5}$ to $10^{-12}$ M. Affinities measured in this manner correlate well with affinities measured in solution by fluorescence quench titration.

Phage display and selection generally results in the selection of higher affinity mutant scFvs (Marks et al. (1992) *Bio/Technology.* 10: 779-783; Hawkins et al. (1992) *J. Mol. Biol.* 226: 889-896; Riechmann et al. (1993) *Biochemistry,* 32: 8848-8855; Clackson et al. (1991) *Nature,* 352: 624-628), but probably does not result in the separation of mutants with less than a 6 fold difference in affinity (Riechmann et al. (1993) *Biochemistry,* 32: 8848-8855). Thus a rapid method is needed to estimate the relative affinities of mutant scFvs isolated after selection. Since increased affinity results primarily from a reduction in the $k_{off}$, measurement of $k_{off}$ should identify higher affinity scFv. $k_{off}$ can be measured in the BIAcore on unpurified scFv in bacterial periplasm, since expression levels are high enough to give an adequate binding signal and $k_{off}$ is independent of concentration. The value of $k_{off}$ for periplasmic and purified scFv is typically in close agreement.

V. Humanized, Human Engineered or Human Antibody Production.

The present BoNT (e.g., BoNT/B) binding antibodies and fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment may be derived from a human or non-human (e.g., mouse) source that has been engineered by modifying (e.g., deleting, inserting, or substituting) amino acids at specific positions so as to alter certain biophysical properties or to reduce any detectable immunogenicity of the modified antibody in a human.

Humanized antibodies also encompass chimeric antibodies and CDR-grafted antibodies in which various regions may be derived from different species. Chimeric antibodies may be antibodies that include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad. Sci. USA,* 81: 6841-6855 (1984), Boulianne, et al., *Nature,* 312: 643-646 (1984), and PCT Application Publication WO 86/01533. Although, they can be less immunogenic than a mouse monoclonal antibody, administrations of chimeric antibodies have been associated with human anti-mouse antibody responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), *Proc. Natl. Acad. Sci.,* 81: 6851; Neuberger et al. (1984), *Nature,* 312: 604. One example is the replacement of an Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody may comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., *Nature,* 321: 522-525 (1986), Riechmann et al., *Nature,* 332: 323-327 (1988), and Verhoeyen et al., *Science,* 239: 1534-1536 (1988)). Methods that can be used to produce humanized antibodies also are described in U.S. Pat. Nos. 4,816,567, 5,721,367, 5,837,243, and 6,180,377, CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., *Nature,* 332: 323-327 (1988), and Verhoeyen et al., *Science,* 239: 1534-1536 (1988).

Human engineered antibodies include for example "veneered" antibodies and antibodies prepared using HUMAN ENGINEERING™ technology (U.S. Pat. No. 5,869,619). HUMAN ENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Techniques for making human engineered proteins are described in Studnicka et al., *Protein Engineering,* 7: 805-814 (1994), U.S. Pat. Nos. 5,766,886, 5,770,196, 5,821,123, and 5,869,619, and PCT Application Publication WO 93/11794.

"Veneered" antibodies are non-human or humanized (e.g., chimeric or CDR-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody and replacing at least one of them with the corresponding surface residues from a human framework region. Veneering can be accomplished by any suitable engineering technique, including the use of the above-described HUMAN ENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (ii) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., *Antibody Engineering*, Springer, New York, N.Y., 2001.

The present antibodies and fragments encompass human antibodies, such as antibodies which bind BoNT polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598, 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851, 1996), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102, 2002) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TC MOUSE™ with various human antigens produces antibody responses comprising human antibodies. See also Jakobovits et al., *Proc. Natl. Acad. Sci. USA,* 90:2551 (1993); Jakobovits et al., *Nature,* 362:255-258

(1993); Bruggermann et al., *Year in Immunol.,* 7:33 (1993); and U.S. Pat. Nos. 5,591,669; 5,589,369; 5,545,807; and U.S Patent Publication Nos. 20020199213 and 20030092125, which describe methods for biasing the immune response of an animal to the desired epitope. Human antibodies may also be generated by in vitro activated B cells (see U.S. Pat. Nos. 5,567,610 and 5,229,275).

Human antibodies can also be generated through the in vitro screening of antibody display libraries. See Hoogenboom et al. (1991), *J. Mol. Biol.* 227: 381; and Marks et al. (1991), *J. Mol. Biol.* 222: 581. Various antibody-containing phage display libraries have been described and may be readily prepared. Libraries may contain a diversity of human antibody sequences, such as human Fab, Fv, and scFv fragments that may be screened against an appropriate target. Phage display libraries may comprise peptides or proteins other than antibodies which may be screened to identify selective binding agents of BoNT.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Methods for display of peptides on the surface of yeast and microbial cells have also been used to identify antigen specific antibodies. See, for example, U.S. Pat. No. 6,699, 658. Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial cell display methods. Selection of polypeptide using ribosome display is described in Hanes et al., (*Proc. Natl. Acad. Sci. USA,* 94:4937-4942, 1997) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Human BoNT-neutralizing antibodies of the present disclosure are may be produced in trioma cells. Genes encoding the antibodies are then cloned and expressed in other cells, particularly, nonhuman mammalian cells.

The general approach for producing human antibodies by trioma technology has been described by Ostberg et al. (1983) *Hybridoman* 2: 361-367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Other approaches to antibody production include in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produce human BoNT-neutralizing antibodies are prepared (see, e.g., U.S. Pat. No. 5,506,132). Other approaches include immunization of murines transformed to express human immunoglobulin genes, and phage display screening (Vaughan et al. supra.).

VI. Other Antibody Forms.

Sequence provided herein can be used to generate other antibody forms, including but not limited to nanobodies, UniBodies, and/or affibodies.

VHH and/or Nanobodies.

The Camelidae heavy chain antibodies are found as homodimers of a single heavy chain, dimerized via their constant regions. The variable domains of these camelidae heavy chain antibodies are referred to as $V_{HH}$ domains or $V_{HH}$, and can be either used per se as nanobodies and/or as a starting point for obtaining nanobodies. Isolated $V_{HH}$ retain the ability to bind antigen with high specificity (see, e.g., Hamers-Casterman et al. (1993) *Nature* 363: 446-448). $V_{HH}$ domains, or nucleotide sequences encoding them, can be derived from antibodies raised in Camelidae species, for example in camel, dromedary, llama, alpaca and guanaco. Other species besides Camelidae (e.g. shark, pufferfish) can produce functional antigen-binding heavy chain antibodies, from which (nucleotide sequences encoding) such naturally occurring $V_{HH}$ can be obtained, e.g. using the methods described in U.S. Patent Publication US 2006/0211088.

Human proteins may be used in therapy primarily because they are not as likely to provoke an immune response when administered to a patient. Comparisons of camelid $V_{HH}$ with the $V_H$ domains of human antibodies reveals several key differences in the framework regions of the camelid $V_{HH}$ domain corresponding to the $V_H/V_L$ interface of the human $V_H$ domains. Mutation of these human residues to $V_{HH}$ resembling residues has been performed to produce "camelized" human $V_H$ domains that retain antigen binding activity, yet have improved expression and solubility.

Libraries of single $V_H$ domains have also been derived for example from $V_H$ genes amplified from genomic DNA or from mRNA from the spleens of immunized mice and expressed in *E. coli* (Ward et al. (1989) *Nature* 341: 544-546) and similar approaches can be performed using the $V_H$ domains and/or the $V_L$ domains described herein. The isolated single $V_H$ domains are called "dAbs" or domain antibodies. A "dAb" is an antibody single variable domain ($V_H$ or $V_L$) polypeptide that specifically binds antigen. A "dAbV binds antigen independently of other V domains; however, as the term is used herein, a "dAbU can be present in a homo- or heteromultimer with other $V_H$ or $V_L$ domains where the other domains are not required for antigen binding by the dAb, i.e., where the dAb binds antigen independently of the additional $V_H$ or $V_L$ domains.

As described in U.S. Patent Publication No. 2006/0211088 methods are known for the cloning and direct screening of immunoglobulin sequences (including but not limited to multivalent polypeptides comprising: two or more variable domains—or antigen binding domains—and in particular $V_H$ domains or $V_{HH}$ domains; fragments of $V_L$, $V_H$ or $V_{HH}$ domains, such as CDR regions, for example CDR3 regions; antigen-binding fragments of conventional 4-chain antibodies such as Fab fragments and scFv's, heavy chain antibodies and domain antibodies; and in particular of VH sequences, and more in particular of $V_{HH}$ sequences) that can be used as part of and/or to construct such nanobodies.

Methods and procedures for the production of $V_{HH}$/nanobodies can also be found for example in WO 94/04678, WO 96/34103, WO 97/49805, WO 97/49805 WO 94/25591, WO 00/43507 WO 01/90190, WO 03/025020, WO 04/062551, WO 04/041863, WO 04/041865, WO 04/041862, WO 04/041867. PCT/BE2004/000159, Hamers-Casterman et al. (1993) *Nature* 363: 446; Riechmann and Muyldermans (1999) *J. Immunological Meth.,* 231: 25-38; Vu et al. (1997) *Molecular Immunology,* 34(16-17): 1121-1131; Nguyen et al. (2000) *EMBO J.,* 19(5): 921-930; Arbabi Ghahroudi et al. (19997) *FEBS Letters* 414: 521-526; van der Linden et al. (2000) *J. Immunological Meth.,* 240: 185-195; Muyldermans (2001) *Rev. Molecular Biotechnology* 74: 277-302; Nguyen et al. (2001) *Adv. Immunol.* 79:261, and the like, which are all incorporated herein by reference.

UniBodies.

UniBodies are generated by an antibody technology that produces a stable, smaller antibody format with an anticipated longer therapeutic window than certain small antibody formats. UniBodies may be produced from IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to a target. Methods of producing UniBodies are described in detail in PCT Publication WO2007/059782, which is incorporated herein by reference in its entirety (see, also, Kolfschoten et al. (2007) *Science* 317: 1554-1557).

Affibodies.

Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.,* 269: 2647-2655.). Details of affibodies and methods of production are known to those of skill (see, e.g., U.S. Pat. No. 5,831,012 which is incorporated herein by reference in its entirety).

VI. Assaying for Cross-Reactivity at a Neutralizing Epitope.

The antibodies of the present disclosure encompass those that specifically bind to one or more epitopes recognized by antibodies described herein (e.g., 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2, etc.). In other words, antibodies are cross-reactive with one of more of these antibodies. Means of assaying for cross-reactivity are well known to those of skill in the art (see, e.g., Dowbenko et al. (1988) *J. Virol.* 62: 4703-4711).

This can be ascertained by providing one or more isolated target BoNT polypeptide(s) (e.g. BoNT/B1 and/or BoNT/B2, or recombinant domains of said toxin, such as $H_C$) attached to a solid support and assaying the ability of a test antibody to compete with, an antibody described herein for binding to the target BoNT peptide. Thus, immunoassays in a competitive binding format are preferably used for cross-reactivity determinations. For example, a BoNT/E and/or BoNT/B polypeptide may be immobilized to a solid support. Antibodies to be tested (e.g. generated by selection from a phage-display library) added to the assay compete with 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2, etc antibodies binding to the immobilized BoNT polypeptide(s). The ability of test antibodies to compete with the binding of the 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, A12, 6A12, B1.1, B6, B6.1, B8, B8.1, B11, B11C3, B11E8, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2, etc antibodies to the immobilized protein(s) are compared. The percent cross-reactivity above proteins is then calculated, using standard calculations.

If the test antibody competes with one or more of the 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, n A12, 6A12, B1.1, B6, B6.1, B8, B8.1, B11, B11C3, B11E8, B12. B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B11.H12, B11.E9, 4B1, 4B3, 4B5, 4B6, 4B7, 1B14, 4A1, 4A1.1, 5A20.4, ING1.1C1, ING1.5B1, ING1.2B10, and ING1.3C2, etc antibodies and has a binding affinity comparable to or greater than about $1\times10^{-8}$ M with the same target then the test antibody is expected to be a BoNT-neutralizing antibody.

Cross-reactivity may performed by using surface plasmon resonance in a BIAcore. In a BIAcore flow cell, the BoNT polypeptide(s) (e.g., BoNT/B and/or BoNT/E) are coupled to a sensor chip (e.g. CM5) as described in copending application No. 60/942,173, disclosure of which is incorporated herein by reference. With a flow rate of 5 μl/min, a titration of 100 nM to 1 μM antibody is injected over the flow cell surface for about 5 minutes to determine an antibody concentration that results in near saturation of the surface. Epitope mapping or cross-reactivity is then evaluated using pairs of antibodies at concentrations resulting in near saturation and at least 100 RU of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU. Antibodies may be said to be cross-reactive if, when "injected" together they show an essentially additive increase (preferably an increase by at least a factor of about 1.4, more preferably an increase by at least a factor of about 1.6, and most preferably an increase by at least a factor of about 1.8 or 2.

Cross-reactivity may also be determined by incubating a yeast displayed scFv with a BoNT domain polypeptide followed by incubation with an epitope-tagged scFv. Bound scFv is detected with an antibody recognizing the epitope tag and the level of BoNT domain display quantitated by incubation with anti-SV5 (see example 1).

Cross-reactivity at the desired epitopes can ascertained by a number of other standard techniques (see, e.g., Geysen et al (1987) *J. Immunol. Meth.* 102, 259-274). This technique involves the synthesis of large numbers of overlapping BoNT peptides. The synthesized peptides are then screened against one or more of the prototypical antibodies (e.g., 1B10, 3E6.2, etc.) and the characteristic epitopes specifically bound by these antibodies can be identified by binding specificity and affinity. The epitopes thus identified can be conveniently used for competitive assays as described herein to identify cross-reacting antibodies.

The peptides for epitope mapping can be conveniently prepared using "Multipin" peptide synthesis techniques (see, e.g., Geysen et al (1987) *Science,* 235: 1184-1190). Using the known sequence of one or more BoNT subtypes (see, e.g., Atassi et al. (1996) *J. Prot. Chem.,* 7: 691-700 and references cited therein), overlapping BoNT polypeptide sequences can be synthesized individually in a sequential manner on plastic pins in an array of one or more 96-well microtest plate(s).

The procedure for epitope mapping using this multipin peptide system is described in U.S. Pat. No. 5,739,306. Briefly, the pins are first treated with a pre-coat buffer containing 2% bovine serum albumin and 0.1% Tween 20 in PBS for 1 hour at room temperature. Then the pins are then inserted into the individual wells of 96-well microtest plate containing the antibodies in the pre-coat buffer, e.g. at 2 μg/ml. The incubation is preferably for about 1 hour at room temperature. The pins are washed in PBST (e.g., 3 rinses for every 10 minutes), and then incubated in the wells of a 96-well microtest plate containing 100 mu 1 of HRP-conjugated goat anti-mouse IgG (Fc) (Jackson ImmunoResearch Laboratories) at a 1:4,000 dilution for 1 hour at room temperature. After the pins are washed as before, the pins are put into wells containing peroxidase substrate solution of diammonium 2,2'-azino-bis [3-ethylbenzthiazoline-b-sulfonate] (ABTS) and $H_2O_2$ (Kirkegaard & Perry Laboratories Inc., Gaithersburg, Md.) for 30 minutes at room temperature for color reaction. The plate is read at 405 nm by a plate reader (e.g., BioTek ELISA plate reader) against a background absorption wavelength of 492 nm. Wells showing color development indicate reactivity of the BoNT peptides in such wells with the test antibodies.

VII. Assaying for Neutralizing Activity of Anti-BoNT Antibodies

Preferred antibodies of the present disclosure act, individually or in combination, to neutralize (reduce or eliminate) the toxicity of *botulinum* neurotoxin type. Neutralization can be evaluated in vivo or in vitro. In vivo neutralization measurements simply involve measuring changes in the lethality (e.g., $LD_{50}$ or other standard metric) due to a BoNT neurotoxin administration due to the presence of one or more antibodies being tested for neutralizing activity. The neurotoxin can be directly administered to the test organism (e.g. mouse) or the organism can harbor a botulism infection (e.g., be infected with *Clostridium botulinum*). The antibody can be administered before, during, or after the injection of BoNT neurotoxin or infection of the test animal. A decrease in the rate of progression, or mortality rate indicates that the antibody(s) have neutralizing activity.

One suitable in vitro assay for neutralizing activity uses a hemidiaphragm preparation (Deshpande et al. (1995) *Toxicon,* 33: 551-557). Briefly, left and right phrenic nerve hemidiaphragm preparations are suspended in physiological solution and maintained at a constant temperature (e.g. 36° C.). The phrenic nerves are stimulated supramaximally (e.g. at 0.05 Hz with square waves of 0.2 ms duration). Isometric twitch tension is measured with a force displacement transducer (e.g., GrassModel FT03) connected to a chart recorder.

Purified antibodies are incubated with purified BoNT (e.g. BoNT/A1, BoNT/A2, BoNT/B1, etc.) for 30 min at room temperature and then added to the tissue bath, resulting in a final antibody concentration of about $2.0\times10^{-8}$ M and a final BoNT concentration of about $2.0\times10^{-11}$ M. For each antibody studied, time to 50% twitch tension reduction is determined (e.g., three times for BoNT alone and three times for antibody plus BoNT). Differences between times to a given (arbitrary) percentage (e.g. 50%) twitch reduction are determined by standard statistical analyses (e.g. two-tailed t test) at standard levels of significance (e.g., a P value of <0.05 considered significant).

VIII. Diagnostic Assays.

As explained above, the anti-BoNT antibodies of the present disclosure can be used for the in vivo or in vitro detection of BoNT toxin (e.g. BoNT/E toxin) and thus, are useful in the diagnosis (e.g. confirmatory diagnosis) of botulism. The detection and/or quantification of BoNT in a biological sample obtained from an organism is indicative of a *Clostridium botulinum* infection of that organism.

The BoNT antigen can be quantified in a biological sample derived from a patient such as a cell, or a tissue sample derived from a patient. As used herein, a biological sample is a sample of biological tissue or fluid that contains a BoNT concentration that may be correlated with and indicative of a *Clostridium botulinum* infection. Preferred biological samples include blood, urine, saliva, and tissue biopsies.

Although the sample is typically taken from a human patient, the assays can be used to detect BoNT antigen in samples from mammals in general, such as dogs, cats, sheep, cattle and pigs, and most particularly primates such as humans, chimpanzees, gorillas, macaques, and baboons, and rodents such as mice, rats, and guinea pigs.

Tissue or fluid samples are isolated from a patient according to standard methods well known to those of skill in the art, most typically by biopsy or venipuncture. The sample is optionally pretreated as necessary by dilution in an appropriate buffer solution or concentrated, if desired. Any of a number of standard aqueous buffer solutions, employing one of a variety of buffers, such as phosphate. Tris, or the like, at physiological pH can be used.

A) Immunological Binding Assays

The BoNT polypeptide (e.g., BoNT/E, BoNT/B, etc.) can be detected in an immunoassay utilizing one or more of the anti-BoNT antibodies of the present disclosure as a capture agent that specifically binds to the BoNT polypeptide.

As used herein, an immunoassay is an assay that utilizes an antibody (e.g. a anti-BoNT/E antibody) to specifically bind an analyte (e.g., BoNT/E). The immunoassay is characterized by the binding of one or more anti-BoNT antibodies to a target (e.g. one or more BoNT/E subtypes) as opposed to other physical or chemical properties to isolate, target, and quantify the BoNT analyte.

The BoNT marker can be detected and quantified using any of a number of well recognized immunological binding assays (see, e.g., U.S. Pat. Nos. 4,366,241; 4,376,110; 4,517,288; and 4,837,168, and the like). For a review of the general immunoassays, see also *Methods in Cell Biology Volume* 37*: Antibodies in Cell Biology*, Asai, ed. Academic Press, Inc. New York (1993); *Basic and Clinical Immunology* 7th Edition, Stites & Terr, eds. (1991)).

The immunoassays of the present disclosure can be performed in any of a number of configurations (see, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, NY).

Immunoassays often utilize a labeling agent to specifically bind to and label the binding complex formed by the capture agent and the analyte (e.g., an anti-BoNT/E antibody/BoNT/E complex). The labeling agent can itself be one of the moieties comprising the antibody/analyte complex. Thus, for example, the labeling agent can be a labeled BoNT/E polypeptide or a labeled anti-BoNT/E antibody. Alternatively, the labeling agent is optionally a third moiety, such as another antibody, that specifically binds to the BoNT antibody, the BoNT peptide(s), the antibody/polypeptide complex, or to a modified capture group (e.g., biotin) which is covalently linked to BoNT polypeptide or to the anti-BoNT antibody.

The labeling agent encompasses an antibody that specifically binds to the anti-BoNT antibody. Such agents are well known to those of skill in the art, and most typically comprise labeled antibodies that specifically bind antibodies of the particular animal species from which the anti-BoNT antibody is derived (e.g., an anti-species antibody). Thus, for example, where the capture agent is a human derived BoNT/E antibody, the label agent may be a mouse anti-human IgG, i.e., an antibody specific to the constant region of the human antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species (see generally Kronval, et al., (1973) *J. Immunol.,* 111:1401-1406, and Akerstrom, et al., (1985) *J. Immunol.,* 135:2589-2542, and the like).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

1) Non Competitive Assay Formats.

Immunoassays for detecting BoNT neurotoxins (e.g. BoNT serotypes and/or subtypes) may be either competitive or noncompetitive. Noncompetitive immunoassays are assays in which the amount of captured analyte (in this case, BoNT polypeptide) is directly measured. In one preferred "sandwich" assay, for example, the capture agent (e.g., an anti-BoNT antibody) is bound directly or indirectly to a solid substrate where it is immobilized. These immobilized anti-BoNT antibodies capture BoNT polypeptide(s) present in a test sample (e.g., a blood sample). The BoNT polypeptide(s) thus immobilized are then bound by a labeling agent, e.g., an anti-BoNT/E antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive).

2) Competitive Assay Formats.

In competitive assays, the amount of analyte (e.g., BoNT/E) present in the sample is measured indirectly by measuring the amount of an added (exogenous) analyte displaced (or competed away) from a capture agent (e.g., anti-BoNT/E antibody) by the analyte present in the sample. For example, in one competitive assay, a known amount of BoNT/E is added to a test sample with an unquantified amount of BoNT/E, and the sample is contacted with a capture agent, e.g., an anti-BoNT/E antibody that specifically binds BoNT/E. The amount of added BoNT/E that binds to the anti-BoNT/E-neutralizing antibody is inversely proportional to the concentration of BoNT/E present in the test sample.

The anti-BoNT/E antibody can be immobilized on a solid substrate. The amount of BoNT/E bound to the anti-BoNT/E antibody is determined either by measuring the amount of BoNT/E present in a BoNT/E-anti-BoNT/E antibody complex, or alternatively by measuring the amount of remaining uncomplexed BoNT/E.

B) Reduction of Non Specific Binding.

One of skill will appreciate that it is often desirable to reduce non specific binding in immunoassays and during analyte purification. Where the assay involves, for example BoNT/E polypeptide(s), BoNT/E-neutralizing antibody, or other capture agent(s) immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

C) Substrates.

As mentioned above, depending upon the assay, various components, including the BoNT polypeptide(s), anti-BoNT antibodies, etc., are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, (1970) *J. Biol. Chem.* 245 3059.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

D) Other Assay Formats

BoNT polypeptides or anti-BoNT antibodies (e.g. BoNT/E neutralizing antibodies) can also be detected and quantified by any of a number of other means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Western blot analysis and related methods can also be used to detect and quantify the presence of BoNT polypeptides in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind either the BoNT polypeptide. The antibodies specifically bind to the biological agent of interest on the solid support. These antibodies are directly labeled or alternatively are subsequently detected using labeled antibodies (e.g., labeled sheep anti-human antibodies where the antibody to a marker gene is a human antibody) which specifically bind to the antibody which binds the BoNT polypeptide.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34-41).

E) Labeling of Anti-BoNT (e.g., Anti-BoNT/E) Antibodies.

Anti-BoNT antibodies can be labeled by any of a number of methods known to those of skill in the art. Thus, for example, the labeling agent can be, e.g., a monoclonal antibody, a polyclonal antibody, a protein or complex such as those described herein, or a polymer such as an affinity matrix, carbohydrate or lipid. Detection proceeds by any known method, including immunoblotting, western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The detectable group can be any material having a detectable physical or chemical property. Such detectable labels have been well-developed in the field of immunoassays and, in general, any label useful in such methods can be applied in the various embodiments of the present disclosure. Thus, a label is any composition detectable by spectroscopic, photochemical, biochemical, immunochemical, electrical, optical or chemical means. Useful labels in the present disclosure include magnetic beads (e.g. Dynabeads™), fluorescent dyes (e.g., fluorescein isothiocyanate, Texas red, rhodamine, ALEXA FLUOR dyes and the like), radiolabels (e.g., $^{3}H$, $^{125}I$,$^{35}S$, $^{14}C$ or $^{32}P$), enzymes (e.g., LacZ, CAT, horse radish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of BoNT peptides. In this case, antigen-coated particles are agglutinated by samples comprising the target antibodies. In this format, none of the components need be labeled and the presence of the target antibody is detected by simple visual inspection.

IX. Compositions.

The BoNT-neutralizing antibodies of this disclosure are useful in mitigating the progression of botulism produced, e.g., by endogenous disease processes or by chemical/biological warfare agents. Typically compositions comprising one, two, or more different antibodies can be provided as a pharmaceutical composition and administered to a mammal (e.g., to a human) in need thereof.

As disclosed herein, particularly efficient neutralization of a botulism neurotoxin (BoNT) subtype is achieved by the use of neutralizing antibodies that bind two or more subtypes of the particular BoNT serotype with high affinity. This can be accomplished by using two or more different antibodies directed against each of the subtypes and/or neutralizing antibodies that bind two or more BoNT subtypes (e.g., BoNT/B1, BoNT/B2, BoNT/B3, etc.) with high affinity.

Different neutralizing antibodies when combined, exhibit a potency that is increased dramatically. This increase makes it possible to generate a *botulinum* antibody composition of the required potency for therapeutic use. It was also surprising that as one begins combining two and three monoclonal antibodies, the particular BoNT epitope that is recognized becomes less important. Compositions comprising at least two, at least three, or more high affinity antibodies that bind overlapping or non-overlapping epitopes on the BoNT are contemplated herein.

Compositions contemplated herein may contain two, three, or more different antibodies selected from the following: 2A10, 3E1, 3E2, 3E3, 3E4, 3E4.1, 3E5, 3E6, 3E6.1, 3E6.2, 4E11, 4E13, 4E16, 4E16.1, 4E17, 4E17.1, A12, 6A12, B1.1, B6, B6.1, B6.C12, B6.D2, B8, B8.1, B11, B11C3, B11E8, B11.A5, B11.F7, B11.H12, B12, B12.1, B12.2, 1B18, 2B18.1, 4B19, 4B19.1, 1B22, 1B10, 1B10.1, 2B18.2, 2B18.3, 1B22.4, 2B23, 2B24, 2B25, 2B25.1, 2B26, 2B27, 2B28, 2B29, 2B30, 4B17.1, 4B17.1C, 4B17.1D, 4B17.1F, 4B17.1G, 3E6.2, 4E17.4, 4E17.6, 4B19.1, B6.C12, B6.D2, B11.A5, B11.F7, B.H12, 4B1, 4B3, 4B5, 4B6, 4B7, 1B14, 4A1, 4A1.1, 5A20.4, 1C1, 5B1, 2B10, B11.E9, and 3C2. The composition may optionally further include antibodies comprising one or more CDRs from these antibodies, and/or one or more antibodies comprising mutants or derivatives of these antibodies. Exemplary compositions of the present disclosure contains at least 2, at least 3, or at least 4 of the antibodies B10.1, 2B18.1 B11E8, B6.1, B12.1 or of the antibodies 3E6.2, 4E17.1, 4E16.1, 3E2, which antibodies can be provided in combination with a pharmaceutical carrier.

An exemplary composition for binding BoNT/B includes 1B10.1, 2B18.1, and B11E8, 2B18.3 may be optionally included in addition to this exemplary composition. 2B18.1 may also be optionally substituted with 2B18.3 and vice versa. B11E8 may also be substituted with B12.1, 4B19.1, 2B23, or 1B22. This composition may further include B6.1 and/or B8.1. Such compositions can find use in neutralizing BoNT/B.

An exemplary composition for binding BoNT/E includes 4E17.1 and two or more antibodies from the following: 4E16.1, 3E2, 3E6.2, and 3E6.1, 3E6.1 may optionally be substituted with 3E6.2 and vice versa. Such compositions can find use in neutralizing BoNT/E.

The subject composition encompasses compositions that specifically neutralize one serotype, such as serotype BoNT/A, BoNT/B, or BoNT/E. The composition may also contain any first combination of antibodies described above that specifically neutralizes one serotype together with a second combination of antibodies that specifically neutralizes a different serotype. The subject composition may contain multiple combinations such that that composition may neutralize two, three, or more serotypes (e.g. BoNT/A, BoNT/B, and/or BoNT/E).

An exemplary composition that neutralizes multiple serotypes may include any of the combinations described above or one or more of the antibodies disclosed in Tables 1-5, together with one or more of the antibodies that bind to BoNT/A. Antibodies that bind to BoNT/A that may be included in the subject composition encompass those that have one or more CDRs or full-length $V_H$ or $V_L$ from clone 3D12, RAZ1, CR2, or 2G11, listed in the table below.

TABLE 7

Amino acid sequences for $V_H$ or $V_L$ CDRs of antibodies of BoNT/A

| clone | $V_H$ CDR1 | $V_H$ CDR2 | $V_H$ CDR3 |
|---|---|---|---|
| 3D12 | DYDMH (SEQ ID NO: 873) | VMWFDGTEKYSAESVKG (SEQ ID NO: 874) | EPDWLLWGDRGALDV (SEQ ID NO: 875) |
| RAZ1 | DYDMH (SEQ ID NO: 876) | VMWFDGTEKYSAESVKG (SEQ ID NO: 877) | EPDWLLWGDRGALDV (SEQ ID NO: 878) |
| CR2 | YDYMY (SEQ ID NO: 879) | TISDGGSYTYYSDSVEG (SEQ ID NO: 880) | YRYDDAMDY (SEQ ID NO: 881) |

TABLE 7-continued

| Amino acid sequences for $V_H$ or $V_L$ CDRs of antibodies of BoNT/A | | | |
|---|---|---|---|
| 2G11 | NYAMT (SEQ ID NO: 882) | SISVGGSDTYYADSVKG (SEQ ID NO: 883) | VRTKYCSSLSCFAGFDS (SEQ ID NO: 884) |
| | $V_L$ CDR1 | $V_L$ CDR2 | $V_L$ CDR3 |
| 3D12 | RASQSISSWLA (SEQ ID NO: 885) | EASSLES (SEQ ID NO: 886) | QHYNTYPYT (SEQ ID NO: 887) |
| RAZ1 | WASQSISSRLA (SEQ ID NO: 888) | EATSLGS (SEQ ID NO: 889) | QHYDTYPYT (SEQ ID NO: 890) |
| CR2 | RASESVDSYGHSFMQ (SEQ ID NO: 891) | RASNLEP (SEQ ID NO: 892) | QQGNEVPFT (SEQ ID NO: 893) |
| 2G11 | RASQSISSYLH (SEQ ID NO: 894) | DASSSQS (SEQ ID NO: 895) | QQSYSTRALT (SEQ ID NO: 896) |

For example, a combination of antibodies that neutralize BoNT/A that may be in the subject composition may include RAZ1, CR2, and 2G11. Such a combination that neutralizes BoNT/A may be included in a composition containing the various exemplary combinations described above to neutralize BoNT/B or BoNT/E. As an example of a composition that neutralizes both BoNT/A and BoNT/B, the composition may include RAZ1, CR2, and 2G11 together with 1B10.1, 2B18.1, and B11E8, with any optional addition or substitutions mentioned above. One optional substitution of any of RAZ1, CR2, and 2G11 may be 4E17.1, 4E17.1 may also be added to a composition used to neutralize BoNT/A. Where a composition neutralizes all BoNT/A, BoNT/B, and BoNT/E, the composition may contain RAZ1, CR2, 2G11, 1B10.1, 2B18.1, B11E8, 4E17.1, together with two or more of 4E16.1, 3E2, 3E6.2 and/or 3E6.1. Similarly, any composition described herein may modified to include additional antibodies or to have an antibody substituted with another (e.g. derivative thereof).

Where combinations of antibodies are disclosed herein, such combinations can be provided in a single formulation or can be provided as separate formulations in a kit, where the separate formulations may contain a single antibody or two antibodies. Such separate formulations of a kit may be combined prior to administration or administered by separate injection.

The BoNT-neutralizing antibodies provided by the present disclosure are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. The antibodies comprising the pharmaceutical compositions of the present disclosure, when administered orally, are preferably protected from digestion. This is typically accomplished either by complexing the antibodies with a composition to render them resistant to acidic and enzymatic hydrolysis or by packaging the antibodies in an appropriately resistant carrier such as a liposome. Means of protecting proteins from digestion are well known in the art.

The pharmaceutical compositions of the present disclosure are particularly useful for parenteral administration, such as intravenous administration or administration into a body cavity or lumen of an organ. The compositions for administration will commonly comprise a solution of one or more BoNT-neutralizing antibody dissolved in a pharmaceutically acceptable carrier, which may be an aqueous carrier. A variety of aqueous carriers can be used, e.g., buffered saline and the like.

Non-aqueous pharmaceutically acceptable carriers (excipients) are known to those of skill in the art. Such excipients, can comprise any substance that is biocompatible and liquid or soft enough at the subject's body temperature to release the active agent(s) (e.g., antibodies) somatotropin into the subject's bloodstream at a desired rate. Non-aqueous carriers are usually hydrophobic and commonly organic, e. g., an oil or fat of vegetable, animal, mineral or synthetic origin or derivation. The carrier may include at least one chemical moiety of the kind that typifies "fatty" compounds, e. g., fatty acids, alcohols, esters, etc., i. e., a hydrocarbon chain, an ester linkage, or both. "Fatty" acids in this context include, but are not limited to, acetic, propionic and butyric acids through straight- or branched-chain organic acids containing up to 30 or more carbon atoms. The non-aqueous carrier may be immiscible in water and/or soluble in the substances commonly known as fat solvents. The non-aqueous carrier can correspond to a reaction product of a "fatty" compound or compounds with a hydroxy compound, e, g., a mono-hydric, di-hydric, trihydric or other polyhydric alcohol, e.g., glycerol, propanediol, lauryl alcohol, polyethylene or -propylene glycol, etc. These compounds include, but are not limited to, the fat-soluble vitamins, e.g., tocopherols and their esters, e. g., acetates sometimes produced to stabilize tocopherols. Sometimes, for economic reasons, the carrier can comprise a natural, unmodified vegetable oil such as sesame oil, soybean oil, peanut oil, palm oil, or an unmodified fat. Alternatively the vegetable oil or fat may be modified by hydrogenation or other chemical means which is compatible with the present disclosure. The appropriate use of hydrophobic substances prepared by synthetic means is also envisioned. Non-aqueous excipient compositions can also comprise, in addition to a biocompatible oil, an "anti-hydration agent" which term as used herein means a substance that retards hydration of the active agent(s) and/or the biocompatible oil or fat and thereby further decreases and/or stabilizes the rate of release of the active agent(s) from that composition following administration to an animal. A great variety of non-toxic antihydration agents are known. By way of example there are "gelling" agents that, when dispersed, and in some cases heated to dissolve them in the oil, give the body of oil greater visco-elasticity (and therefore greater structural stability) and thereby slow down penetration of the oil by body fluids.

Illustrative antihydration agents include various polyvalent metal salts or complexes of organic acids, for instance fatty acids having from about 8 or 10 to about 20 or 22 carbon atoms, e. g. aluminum, zinc, magnesium or calcium salts of lauric acid, palmitic acid, stearic acid and the like. Such salts can be mono-, di- or tri-substituted, depending on the valence of the metal and the degree of oxidation of the metal by the acid. Of common usage are the aluminum salts of such fatty acids. Aluminum monostearate and distearate are frequently used anti-hydration agents. Others that are useful include aluminum tristearate, calcium mono- and distearate, magnesium mono- and distearate and the corresponding palmitates, laurates and the like. The concentration of such an antihydration agent, based on the weight of the oil plus that agent, may be between about 1% and about 10% (most typically between about 2% and about 5%), although other concentrations may be suitable in some cases.

The various solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of BoNT-neutralizing antibody in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from about 1 mg up to about 200 mg per patient per day can be used. Methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the BoNT-neutralizing antibodies of the present disclosure or a cocktail thereof are generally administered for therapeutic treatments. Preferred pharmaceutical compositions are administered in a dosage sufficient to neutralize (mitigate or eliminate) the BoNT toxin(s) (i.e., reduce or eliminate a symptom of BoNT poisoning (botulism)). An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the antibodies of the present disclosure to effectively treat the patient.

X. Kits for Diagnosis or Treatment.

Kits for the treatment of botulism or for the detection/confirmation of a *Clostridium botulinum* infection are also provided. Kits will typically comprise one or more anti-BoNT antibodies (e.g., BoNT-neutralizing antibodies for pharmaceutical use). For diagnostic purposes, the antibody(s) can optionally be labeled. In addition the kits will typically include instructional materials disclosing means of use BoNT-neutralizing antibodies in the treatment of symptoms of botulism. The kits may also include additional components to facilitate the particular application for which the kit is designed. Thus, for example, where a kit contains one or more anti-BoNT antibodies for detection of diagnosis of BoNT subtype, the antibody can be labeled, and the kit can additionally contain means of detecting the label (e.g. enzyme substrates for enzymatic labels, filter sets to detect fluorescent labels, appropriate secondary labels such as a sheep anti-human antibodies, or the like). The kits may additionally include buffers and other reagents routinely used for the practice of a particular method. Such kits and appropriate contents are well known to those of skill in the art.

Kits provided for the treatment of botulism may contain one or more BoNT neutralizing antibodies. The antibodies can be provided separately or mixed together. Typically the antibodies will be provided in a sterile pharmacologically acceptable excipient. The antibodies can also be provided pre-loaded into a delivery device (e.g., a disposable syringe).

The kits can optionally include instructional materials teaching the use of the antibodies, recommended dosages, contraindications, and the like.

EXAMPLES

The following examples are offered to illustrate, but not to limit any embodiments provided by the present disclosure.

Example 1

Human Monoclonal Antibodies to *Botulinum* Neurotoxin Types A and B from Immune Yeast Displayed Antibody Libraries The following methods and materials were used in the present example.

Methods and Materials

```
Oligonucleotide primers
Primary library construction
HuVH2bBACK:
                                        (SEQ ID NO: 897)
5'-CAGGTCACCTTGAAGGAGTCTGG-3'

HuVH5bBACK:
                                        (SEQ ID NO: 898)
5'-GAGGTGCAGCTGGTGCAGTCTGG-3'

HuVH7aBACK:
                                        (SEQ ID NO: 899)
5'-CAGGTGCAGCTGGTGCAATCTGG-3'

HuVK2aBACK:
                                        (SEQ ID NO: 900)
5'-GATATTGTGATGACTCAGTCTCC-3'

HuVK2bBACK:
                                        (SEQ ID NO: 901)
5'-GATATTGTGATGACCCAGATCCC-3'

Light chain shuffled library construction
GAP5-HuRJH1-2BACK:
                                        (SEQ ID NO: 902)
5'-GTG GTG GTG GTT CTG CTA GCG GGG CCA TGG CCA
CCC TGG TCA CCG TCT CCT CA-3'

GAP5-HuRJH3BACK:
                                        (SEQ ID NO: 903)
5'-GGT GGT GGT TCT GCT AGC GGG GCC ATG GCG ACA ATG
GTC ACC GTC TCT TCA-3'
```

-continued

GAP5-HuRJH4-5 BACK:

(SEQ ID NO: 904)

5'-GGT GGT GGT TCT GCT AGC GGG GCC ATG GCA ACC CTG GTC ACC GTC TCC TCA-3

GAP5-HuRJH6 BACK:

(SEQ ID NO: 905)

5'-GGT GGT GGT TCT GCT AGC GGG GCC ATG GCG ACC ACG GTC ACC GTC TCC TCA-3

PYDFOR1:

(SEQ ID NO: 906)

5'-GTCGATTTTGTTACATCTACAC-3'

$V_H$ gene amplification from pYD2
pYD BACK1:

(SEQ ID NO: 907)

5'-AGTAACGTTTGTCAGTAATTGC-3'

The underlined segment is the reverse complement of the JHF or primers

Other Primers

Other primers include the family of primers that used to create the VL-rep library (should anneal to the different Vk and Vl genes are add the scFv linker, VHFR4, Nco1-Xho1 site. Also used is a family of primers to amplify the VH gene to clone into this vector, with 5' overhang and 3' overhang for gap repair into VL-rep library.

Strains, Media Antibodies, and Toxins

Yeast strain Saccharomyces cerevisiae EBY100 (GAL1-AGA1TURA3 ura3-52 trpl leu2Δ1his3Δ200 pep4::HIS3 prbl Δ1.6R can1) was maintained in YPD medium (1% yeast extract, 2% peptone, 2% dextrose) (Current Protocols in Molecular Biology, John Wiley and Sons, Chapter 13.1.2). EBY100 transformed with expression vector pYD2 (Razai et al., *JMol Biol.* 2005, 351:158-69) was selected on SD-CAA medium (0.7% yeast nitrogen base, 0.1M Sodium phosphate, 0.5% casamino acids, 2% dextrose, 0.006% Leucine). ScFv yeast surface display was induced by transferring yeast cultures from SD-CAA to SG-CAA medium (identical to SD-CAA medium except the glucose was replaced by galactose) and growing at 18° C. for 24 ~ 48 hr as described previously (Feldhaus et al. Nat Biotechnol. 2003, 21:163-70). Bacteria strain *E. coli* DH5 α, (K12, Δ(lac-pro), supE, thi, hsdD5/F' traD36, proA+B+, laclq, lacZΔM15) was used for cloning and preparation of plasmid DNA. Pure BoNT/A1 (Hall hyper), BoNT/A2 (FRI-H1A2), BoNT/B1, BoNT/B2, BoNT/B3, and BoNT/B4 were purified from their respective strains or purchased from Metabiologics (Madison, WI). Complex BoNT/A3was expressed and purified from strains A254 and Ba207 (Hill et al. *J Bacteriol.* 2007, 189:818-32). Mouse anti-SV5 and anti-myc 9E10 antibody and BoNT/A antibodies 7C1 and 9D8 were purified from hybridoma supernatant using Protein G and directly labeled with ALEXA FLUOR 488dye or ALEXA FLUOR 647 dye using a kit provided by the manufacturer (MOLECULAR PROBES). Recombinant human BoNT/A antibodies 3D12 and AR2 and BoNT/B antibodies A12 and 6A12 were purified from Chinese hamster ovary cells (CHO) supernatants (Nowakowski et al. *Proc Natl Acad Sci* USA. 2002, 99:11346-50; Razai et al., *J Mol Biol.* 2005, 351:158-69). For flow cytometry (FACS), purified human or mouse IgGs were directly labeled with either ALEXA FLUOR 647 dye or ALEXA FLUOR 488 dye using a kit provided by the manufacturer (MOLECULAR PROBES).

Immune scFv Yeast Antibody Library Generation scFv yeast libraries were constructed from human volunteers immunized with pentavalent toxoid. Briefly approximately 25ml of blood was drawn 7 days after immunization and PBLs isolated using LYMPHOPREP tubes (Axis-Shield PoC AS, Norway). Blood was drawn after obtaining informed consent and under a protocol reviewed and approved by the USAMRIID and UCSF IRBs. Total RNA was isolated from PBLs using an RNAgents® kit (Promega). cDNA was synthesized from total RNA by using AMV reverse transcriptase (Invitrogen) and HuIgG1-4-C1FOR, HuCK1FOR primers (Amersdorfer et al. *Vaccine* 2002, 20:1640-8; Marks et al. *Eur J Immunol.* 1991, 21:985-91). $V_H$ and $V_K$ gene fragments were amplified by PCR from cDNA by using Pfu polymerase (Stratagene) and a mixture of HuVH1-6BACK, HuVH2bBACK, HuVH5bBACK, HuVH7aBACK and HuJH1-5FOR mix primers for the $V_H$ gene and HuVK1-6BACK, HuVK2aBACK, HuVK2bBACK and HuJK1-5FOR primers or the $V_k$ gene (Marks et al. 1991, supra). scFv linker DNA template was prepared as previously described (Marks et al. 1991, supra). PCR fragments were gel purified, isolated from the gel using GENECLEAN® Turbo (Q.BIOgene). scFv gene repertoires were constructed by using PCR to splice together the $V_H$ and $V_K$ gene repertoires with scFv linker DNA (Marks et al.1991, supra). The scFv genes were gel purified, isolated from the gel and reamplified using HuVHBACK and HuJk-FOR primer mixes which appended Arcol and Notl site restriction sites (Marks et al. 1991, supra). scFv genes were digested with Arcol an Notl and ligated into Ncol-Notl digested pYD2vector (Razai et al. 2005, supra). scFv gene repertoires were amplified from the ligation mixtures using primers GAPS and GAPS (Razai et al. 2005, supra) to append homologous overlaps with pYD vector DNA. Appended scFv PCR products were ethanol precipitated, combined with NcoI-NotI digested pYD2 and used to transform EBY100. Transformed yeast were cultured and subcultured in SDCAA and library size calculated by serially diluting and plating the transformed culture on SDCAA plates. Final library size was calculated as the product of the number of transformants and the percentage of clones with full length scFv insert as determined by PCR (Razai et al., 2005, supra).

Selection and Characterization of Lead BoNT/B and BoNT/A scFv Antibodies

For antibody selection, forty times the library size was grown and scFv display induced. For sorting, libraries were incubated with BoNT/A or BoNT/B in five times excess antigen, assuming each yeast expresses $1 \times 10^5$ scFv on the surface, at room temperature (RT) for 1 hr. For BoNT/B sorting, the first two rounds were done by staining with 50-100 nM BoNT/B1and the third and fourth round of staining were done by staining with 1-10nM BoNT/B1. Libraries were washed once with ice cold FACS buffer (PBS (1.9mM $NaH_2PO_4$, 8.1mM $Na_2HPO_4$, 154mM $NaC1_2$, pH7.4), 0.5% BSA, 1mM $MgC1_2$, 0.5mM $CaC1_2$). BoNT/B binding was detected by staining with using 2.5 μml of an equimolar mixture of mAbs A12 and 6A12 labeled with ALEXA FLUOR 647 dye for 1 hr. at 4° C. Simultaneously, scFv display level was quantitated by staining with 2.5 μml anti-SV5 mAb labeled with ALEXA FLUOR 488 dye. Yeast libraries were washed as described above, resuspended in 200 to 700 μl FACS buffer and were sorted on a FACSARIA cell sorter (Becton-Dickinson) with sort gates set to collect all SV5 positive BoNT/B binding yeast. After the last round of sorting yeast were plated on SD-CAA plates and individual clones grown and induced. Individual clones were screened to identify BoNT/B binding scFv and unique clones identified by PCR fingerprinting and DNA sequencing (Amersdorfer et al. 2002 , supra). For each unique clone, the affinity of the yeast displayed scFv for BoNT/B1, B2,B3, and B4 was determined exactly as previously described (Razai et al. 2005,supra).

For one set of BoNT/A sortings, the first two rounds of sorting were done by staining with 100nM BoNT/A1 and 20nM BoNT/A2 respectively. Libraries were washed once with ice cold FACS buffer (PBS (1.9mM $NaH_2PO_4$, 8.1mM $Na_2HPO_4$, 154mM $NaCl_2$, pH7.4), 0.5% BSA, 1mM $MgCl_2$, 0.5mM $CaCl_2$). BoNT/A binding was detected by staining with using 2.5 μml of an equimolar mixture of mAbs 7C1 and 9D8 labeled with ALEXA FLUOR 647 dye for 1 hr. at 4° C. Simultaneously, scFv display level was quantitated by staining with 2.5 μml anti-SV5 mAb labeled with ALEXA FLUOR 488 dye. Yeast libraries were washed as described above, resuspended in 200 to 700μl FACS buffer and were sorted on a FACSARIA cell sorter (Becton-Dickinson) with sort gates set as in FIG. 8. For the last two rounds of sorting, yeast libraries were incubated with either 20 nM BoNT/A1 or 20 nM BoNT/A2 (see FIG. 8), washed, then stained with a combination of 2.5 μml of AR1-ALEXA FLUOR 647 dye and 3D12-ALEXA FLUOR 488 dye. Sort gates were set to capture only yeast binding BoNT/A which was bound by both 3D12 and AR1, thus ensuring that any resulting scFv would bind BoNT/A epitopes that did not overlap with these two mAbs. For a second set of BoNT/A sortings, the first three rounds of sorting were done by staining with 100 nM BoNT/A1, the third and fourth round of sorting were done by staining with 50 nM BoNT/A1, and the final round of sorting was done by staining with 50 nM recombinant BoNT/A1 $L_c$ or BoNT/A1 $H_N$. For the first four rounds of sorting, BoNT/A binding was detected by staining with using 2.5 μml of an equimolar mixture of mAbs 7C1 and 9D8 labeled with ALEXA FLUOR 647 dye for 1 hr at 4° C. For the final round of sorting, BoNT/A binding was detected by staining with 2.5 μml of either mAbs 7C1 (for $L_c$ incubation) or 9D8 (for $H_N$ incubation) labeled with ALEXA FLUOR 647 dye for 1 hr. at 4° C.

After the last round of sorting, yeast were plated on SD-CAA plates and individual clones grown and induced. Individual clones were screened to identify BoNT/A binding scFv and unique clones identified by PCR fingerprinting and DNA sequencing (Amersdorfer et al. 2002, supra). For each unique clone, the affinity of the yeast displayed scFv for BoNT/A1 and BoNT/A2 was determined exactly as previously described (Razai et al. 2005, supra).

Construction and Expression of Yeast Displayed BoNT/B Domains and Mapping of Antibody Binding Primers HCFor, HCRev, HNFor, HNRev, and LCFor and LCRev were designed to PCR amplify the BoNT/B $H_c$, $H_N$ , or $L_c$ gene fragment respectively from the vectors, adding the restriction sites Ncol and Notl. Following digestion of both pYD2 and the resulting PCR amplification product with Ncol and Notl, the BoNT/B gene fragments were gel-purified and ligated into pYD2. Ligation mixtures were used to transform *E. coli* DH5α and correct clones identified by DNA sequencing. Plasmid DNA was used to transform LiAc-treated EBY100 cells. Yeast cultures were then grown and induced, as described above. For mapping scFv binding to yeast displayed BoNT/B domains, scFv genes in pYD2were excised by digestion with Nco1 and Not1, ligated into pSYN1, and the ligation mixture used to transform *E. coli* TG1. scFv expression was induced and the periplasmic fraction containing the scFv prepared as previously described. Periplasmic fractions containing scFv were incubated for 1 hour at RT with yeast displaying BoNT/B domains. After washing with PBS, yeast were incubated with 1 ug/ml of mAb 9E10 which recognizes an epitope tag at the scFv C-terminus. After washing, 9E10 binding was detected using 1 ug/ml anti-mouse gammal specific antibody and the level of BoNT domain display quantitated by incubation with 1μml of anti-SV5-ALEXA FLUOR 488 dye. For some antibodies, mapping was performed by staining with 1μml of the respective IgG conjugated to ALEXA FLUOR 647 dye.

Mapping the Overlap of BoNT Antibodies

Each yeast displayed scFv was grown and induced and incubated with 100 nM BoNT/B for 1 hour at RT followed by washing with PBS. After resuspension, yeast were incubated with scFv containing periplasmic preparations (see above), followed by washing and then incubation with 1μg/ml 9E10. After washing, 9E10 binding was detected using 1 ug/ml anti-mouse gammal specific antibody and the level of BoNT domain display quantitated by incubation with 1μg/ml of anti-SV5-ALEXA FLUOR 488 dye. For some antibodies, mapping was performed by staining with 1μg/ml of the respective IgG conjugated to ALEXA FLUOR 647 dye.

Construction and Sorting of Chain Shuffled Yeast Antibody Libraries

To facilitate light chain shuffling, a light chain library was created in the yeast display vector pYD2 by cloning in $V_L$ gene repertoires from donors six, nine, and ten. cDNA was synthesized from total RNA prepared from donor PBLs by using AMV reverse transcriptase (Invitrogen) and HuCK1FOR primers (Amersdorfer et al. 2002, supra; Marks et al. 1991, supra). $V_K$ gene fragments were amplified by PCR from cDNA by using Pfu polymerase (Stratagene) and a mixture of HuVK1-6BACK, HuVK2aBACK, HuVK2bBACK and HuJK1-5FOR primers (Marks et al. 1991, supra). To further increase light chain diversity, the light chain repertoire from a large non-immune scFv phage antibody library was also utilized (Sheets et al. *Proc Natl Acad Sci USA*. 1998, 95:6157-62). Phage antibody library plasmid DNA was prepared and the VL genes PCR amplified using primers HuVK1-6BACK, HuVK2aBACK, HuVK2bBACK and HuJK1-5FOR for Vk genes and primers Vl genes. PCR fragments were gel purified and isolated from the gel using GENECLEAN® Turbo (Q.BIOgene). $V_L$ genes were reamplified by using PCR primers to append the 3' end of the $V_H$ framework 4, containing a Xho1 restriction site, and the $(Gly_4Ser)_3$ scFv linker to the 5' end of the $V_L$ genes (see FIG. 9). VL repertoire DNA was gel purified, digested with Nco1 and NotI and ligated into NcoI-NotI digested pYD2 DNA. The ligation mixture was used to transform *E. coli* DH5α, creating a library that was determined to be diverse by PCR fingerprinting and DNA sequencing. To create light chain shuffled scFv libraries, light chain library DNA was prepared and digested with either NcoI or HindIII and XhoI. It was determined that when cutting with Nco1-Not1, recombination could occur between the scFv linker DNA and the Gly-Ser linker after the AgaII protein, resulting in approximately 25% of transformants having no light chain. Digesting with HindIII cuts in AgaII, eliminating this problem. The $V_H$ gene was amplified from its respective scFv gene in pYD2 using primers that had 25 nucleotide sequences complementary to the 5' and 3' ends of the digested library vector DNA depending on whether the vector was digested with Nco1 or HindIII, respectively. Gel purified $V_H$ gene was mixed with digested vector DNA and used to transform LiAc-treated EBY100 cells. Chain shuffled libraries were created for scFv 4A1.1, 5A20.4, B12.1, 2B18.1, 1B10.1, 4B19.1, and 2B25.1.

To select higher affinity scFv, light chain shuffled libraries were grown and scFv display induced. Yeast were stained with BoNT/A1 or BoNT/B1 at a concentration 10 times greater then the Ku and equal to the $K_D$ for the first two rounds of sorting respectively with the majority of BoNT binding yeast collected. Subsequent rounds of sorting were increasingly stringent with the antigen concentration decreased and less than 1% of the yeast collected. A total of four to six rounds of sorting were performed for each chain shuffled library, after which the sort output was plated to allow for characterization of individual yeast displayed scFv. Twelve individual clones were characterized by DNA sequencing of the scFv gene and the affinity for BoNT determined as previously described.

Construction and Purification of IgG

The $V_H$ and $V_K$ genes of scFv ING1, ING2 were amplified with primers annealing to the 5' and 3' ends of the full length $V_H$ and $V_K$ genes and containing in frame Mlu1 and NheI or DraIII and BsiWI restriction sites respectively for cloning into N5KG1Val-Lark or N5LG1Val-Lark (see Nowakowski et al. 2002, supra and Razai et al. 2005, supra for details of primer design). These vector results in expression of IgG of the γ1/kappa or γ1/lambda isotype. Amplified $V_H$ DNA was digested with Mlu1 and Nhel, and ligated into N5KG1Val-Lark or N5LG1Val-Lark. Clones containing the correct $V_H$ were identified by DNA sequencing. Amplified $V_K$ genes were cloned into pCR-TOPO vector (Invitrogen) and clones containing the correct $V_K$ identified by DNA sequencing. $V_K$ genes were excised from pCR-TOPO vector by digestion with DraIII and BsiWI and ligated into DraIII-and BsiWI-digested N5KG1Val-Lark or N5LG1Val-Lark DNA containing the appropriate $V_H$ gene. Clones containing the correct $V_H$ and $V_K$ genes were identified by DNA sequencing, and vector DNA was used to transfect CHO DG44 cells by electroporation. Stable cell lines were established by selection in G418and expanded into 1L spinner flasks. Supernatant containing IgG were collected, concentrated by ultra filtration, and purified on Protein G (Pharmacia) column.

Measurement of Solution Phase Affinity at Equilibrium

Equilibrium binding studies were conducted at room temperature (~25° C.) using a KinExA 3000 flow fluorimeter to quantify the free BoNT/A or BoNT/B at equilibrium using varying concentrations of antibody as previously described (Razai et al. 2005, supra). Studies of reaction mixtures were performed in PBS (pH 7.4), with 1 mg/ml BSA and 0.02% (w/v) sodium azide as a preservative. Antibody was serially diluted into a constant concentration of pure BoNT/A or BoNT/B sufficient to produce a reasonable signal, where the antibody concentration was varied from less than 0.1to greater than 10-fold above the value of the apparent $K_D$. The BoNT/A and BoNT/B concentrations were no more than 4-fold above the $K_D$ to ensure a $K_D$ controlled experiment. Samples were allowed to reach equilibrium for as long as two days, then each of the 12 dilutions were passed over a flow cell with a 4 mm column of Azlactone beads (Sapidyne Instruments) covalently coated with the corresponding antibody to capture the free BoNT/A or free BoNT/B. Passing an ALEXA FLUOR 647dye labeled BoNT/A or BoNT/B antibody binding a non-overlapping epitope over the beads produced a signal relative to the amount of free BoNT/A or BoNT/B bound to the beads. All data points were run in duplicate and sample volume varied from 4 to 25 ml depending on antibody affinity. The equilibrium titration data were fit to a 1:1 reversible binding model using KinExA Pro Software (version 1.0.2; Sapidyne Instruments) to determine the $K_D$ (Drake et al. 2004 *Anal. Biochem.* 325:35-43).

Results

Generation of Human Yeast Displayed scFv Antibody Libraries

Immune yeast displayed scFv antibody libraries were constructed from human volunteers immunized with pentavalent *botulinum* toxoid (serotypes BoNT/A1, BoNT/B1, BoNT/C, BoNT/D, and BoNT/E). RNA was prepared from the peripheral blood lymphocytes of six different donors and the immunoglobulin heavy ($V_H$) and kappa light ($V_K$) chain variable regions amplified by using the polymerase chain reaction (PCR) as previously described (Marks 1991, supra; Marks et al. *J Mol Biol.* 1991, 222:581-97). $V_H$ and $V_K$ gene repertoires from each donor were spliced together to create scFv gene repertoires which were cloned for display as N-terminal fusions to the agglutinin receptor (AgaII) protein on the surface of yeast. A total of six yeast displayed scFv libraries was generated, ranging in size from 4.1 to $25.7\times10^6$ members. Each library was diverse as determined by PCR fingerprinting and DNA sequencing of 10 randomly selected clones. After induction of scFv display, the percentage of yeast displaying scFv ranged from 45-55% as determined by staining with SV5 antibody binding the C-terminal SV5 tag fused to each scFv.

Generation of High Affinity Human Antibodies to Type B *Botulinum* Neurotoxins

To generate a panel of human antibodies to type B *botulinum* neurotoxins, six different yeast displayed scFv libraries were sorted separately on BoNT/B1. Sorts were performed using relatively high concentrations of BoNT/B1 holotoxin in the initial rounds ($50\text{-}100\times10^{-9}$ M, nM) to ensure collection of all antigen binding scFv. In later rounds, the antigen concentration was decreased to between 1-10 nM to select for the higher affinity antibodies and sorts were performed on other BoNT/B subtypes (BoNT/B2, B3, and B4). Libraries were sorted a total of three to six rounds and yeast displayed scFv from individual colonies were screened for binding to BoNT/B1. Antigen binding clones were further characterized with respect to the diversity of scFv present using colony PCR, BstN1 fingerprinting (Marks et al. 1991, supra), and DNA sequencing. In this manner, 18 scFv were isolated, each with a different $V_H$ CDR3 (Table 8). The equilibrium binding constant for BoNT/B1 was measured for each of the yeast displayed scFv (Table 8). Affinities ranged from 60 to $0.08\times10^{-9}$ M, with a mean $K_D$ of $8.6\times10^{-9}$ M. For many of these scFv, a number of additional clonally related scFv were also isolated that were of lower affinity.

TABLE 8

Characteristics of lead yeast displayed scFv BoNT/B antibodies. Clone name, epitope, $V_H$ CDR3 sequence, $V_H$ and $V_\kappa$ germline gene family and equilibrium dissociation constant ($K_D$) for BoNT/B subtypes are shown. scFv $K_D$ measured on yeast displayed scFv. $L_C$ = toxin light chain; $H_N$ = toxin translocation domain; $H_C$ = toxin binding domain; NB = no binding.

| Clone | Epitope | $V_H$ CDR3 Sequence | $V_H/V_k$ Gene Family | BoNT/B $K_D$ by FACS ($\times 10^{-9}$ $M^{-1}$) B1 | B2 | B3 | B4 |
|---|---|---|---|---|---|---|---|
| 4B6 | $L_C$ | HDSRYKYFYFGMDV (SEQ ID NO: 390) | VH5/VKI | 2.7 | 1.77 | 1.08 | 1.61 |
| 4B7 | $L_C$ | MSGSRSYSQYYFDS (SEQ ID NO: 911) | VH4/VK1 | 29.4 | 34.8 | 25.1 | 10.0 |
| 1B10 | $L_C$ | DLTRFHDTTFGVFEM (SEQ ID NO: 488) | VH3/VKI | 11.2 | 9.4 | >5000 | 4.69 |
| 4B19 | $L_C$ | EWTQLWSPYDY (SEQ ID NO: 474) | VH1/VKI | 6.45 | 7.03 | 3.9 | 3.3 |
| 1B22 | $L_C$ | TAFYYENTGPIRCYLDF (SEQ ID NO: 481) | VH4/VKI | 0.52 | 0.46 | 0.39 | 0.48 |
| 2B23 | $L_C$ | ALVGRYDISTGYYRPVMDS (SEQ ID NO: 524) | VH3/VKI | 0.08 | 0.13 | 0.25 | 0.19 |
| 2B24 | $L_C$ | DGPMAAIPFYYFDF (SEQ ID NO: 531) | VH3/VLI | 0.79 | 4.0 | 4.0 | 0.72 |
| 2B25 | $L_C$ | GVPIYDSSGTYRGTYFDY (SEQ ID NO: 538) | VH4/VLI | 0.95 | 0.63 | 0.93 | 0.68 |
| 2B27 | $L_C$ | RRLLGPSPYYFDY (SEQ ID NO: 558) | VH3/VLI | 1.9 | 0.56 | 2.32 | 0.77 |
| 2B29 | $L_C$ | GNPQYDTSGSYTGLYFDF (SEQ ID NO: 572) | VH4/VL1 | 1.11 | 1.02 | 1.61 | 1.29 |
| 4B3 | $H_N$ | DILYYHDSSDYWGRGHFY YMDV (SEQ ID NO: 920) | VH3/VKI | 26.7 | 43.0 | 1265 | NB |
| 1B11 | $H_N$ | DRYPIDCSGGSCFSYGMDV (SEQ ID NO: 418) | VH3/VK1 | 2.6 | 2.1 | 4.43 | NB |
| 1B18 | $H_N$ | LEWGGRNGWVSP (SEQ ID NO: 460) | VH3/VKI | 7.3 | 3.8 | 3.04 | 1.7 |
| 4B1 | $H_C$ | DKRTYEYNWNSLWF (SEQ ID NO: 383) | VH1/VK1 | 1.08 | 14.9 | NB | 0.85 |
| 4B5 | $H_C$ | MRGYSSWHYSYYYVMDV (SEQ ID NO: 924) | VH3/VKI | 59.6 | NB | NB | NB |
| 1B12 | $H_C$ | DRSHYGDYVGYLDY (SEQ ID NO: 439) | VH3/VKI | 1.17 | 1.08 | NB | 6.01 |
| 1B14 | $H_C$ | SSIVGAPYGMDV (SEQ ID NO: 926) | VH3/VKI | 0.98 | >5000 | NB | 2.12 |
| 2B30 | $H_C$ | DVSEYGDYVGHFDY (SEQ ID NO: 579) | VH3/VL1 | 0.37 | 0.19 | NB | NB |

Figure 6:
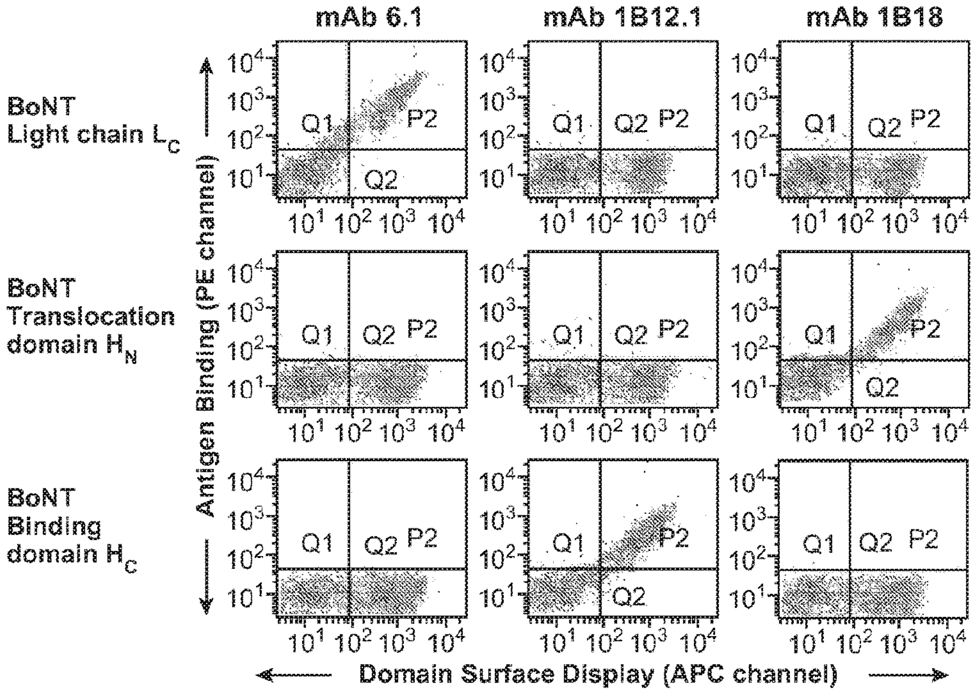
FIG. 6 illustrates mapping toxin domains recognized by mAbs by using yeast displayed BoNT domains. BoNT/B binding domain Hc), translocation domain ($H_N$), and light chain ($L_c$) were well displayed on the yeast surface as evidenced by staining with anti-SV5-ALEXA FLUOR 647 (APC channel). Each domain was only bound by a mAb specific for 20 that domain, but not by other BoNT/B mAbs as evidenced by staining with mAb 6.1 ($L_c$ specific), mAb 1B12.1 ($H_c$ specific), and mAb 1B18 ($H_N$ specific) detected with anti-human phycoerythrin (PE channel).
Figure 7:
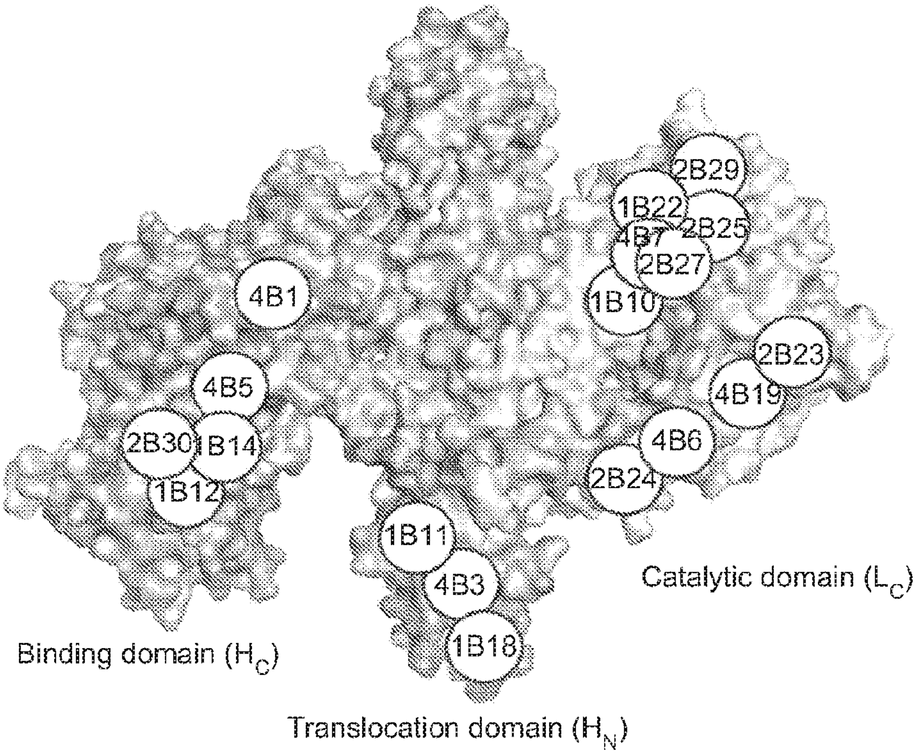
FIG. 7 shows a model of the epitopes of BoNT/B mAbs. The data generated by the studies described in FIG. 6 were used to map each scFv to the BoNT/B domain that it bound. scFv binding overlapping epitopes are indicated by overlap of the circle representing the scFv. Non-overlapping circles indicate that the scFv epitopes do not overlap. Otherwise, the scFv epitopes have been randomly placed on each of the BoNT/B domains. Modeling was done on the X-ray crystal structure of BoNT/B.

To determine the BoNT/B subtype specificity, the $K_D$ of the yeast displayed scFv were measured for BoNT/B2, B3, and B4 (Table 8). A number of scFv only bound the immunizing BoNT/B1 subtypes, e.g. mAb 4B1. To determine which BoNT/B functional domain the scFv bound, the BoNT/B $H_C$, $H_N$, and $L_C$ genes were cloned into pYD2 and displayed on the surface of *Saccharomyces cerevisiae* (FIG. 6), as previously reported for BoNT/A domains (Levy et al. *J Mol Biol.* 2007, 365:196-210). Each domain was well displayed on the yeast surface, as quantitated using a C-terminal SV5 tag fused to each domain (FIG. 6). The domain recognized by each of the scFv was determined by incubating yeast displayed BoNT/B domains with either native scFv expressed in *E. coli* or IgG constructed from scFv genes (see below). Native scFv was generated by subcloning the scFv genes into the bacterial secretion vector pSYN1. To determine how many non-overlapping BoNT/B epitopes were recognized by the lead antibodies, yeast displayed scFv were incubated with BoNT/B holotoxin, followed by incubation with purified native scFv. scFv recognizing overlapping epitopes showed no yeast staining while scFv binding non-overlapping epitopes stained the yeast surface. For some of these assays, purified IgG constructed from the scFv V-genes was used for yeast staining instead of the scFv. Using these assays, it was determined that of the 18 scFv, five bound the BoNT/B $H_C$, three bound the $H_N$, and ten bound the $L_C$ (FIG. 7). A total of nine non-overlapping epitopes were recognized by the scFv antibodies, three on the $H_C$, two on the $H_N$, and four on the $L_C$. Seven of the ten $L_C$ antibodies clustered within one antibody footprint of each other (FIG. 7). Of note, of the 10 scFv that bound to all four BoNT/B subtypes, 9 bound to $L_C$, 1 bound to $H_N$, and none bound to $H_C$. This is consistent with the relative percent homology of the three domains between the four BoNT/B subtypes, the $L_C$ is the most conserved and the $H_C$ is the least conserved.

Figure 8:
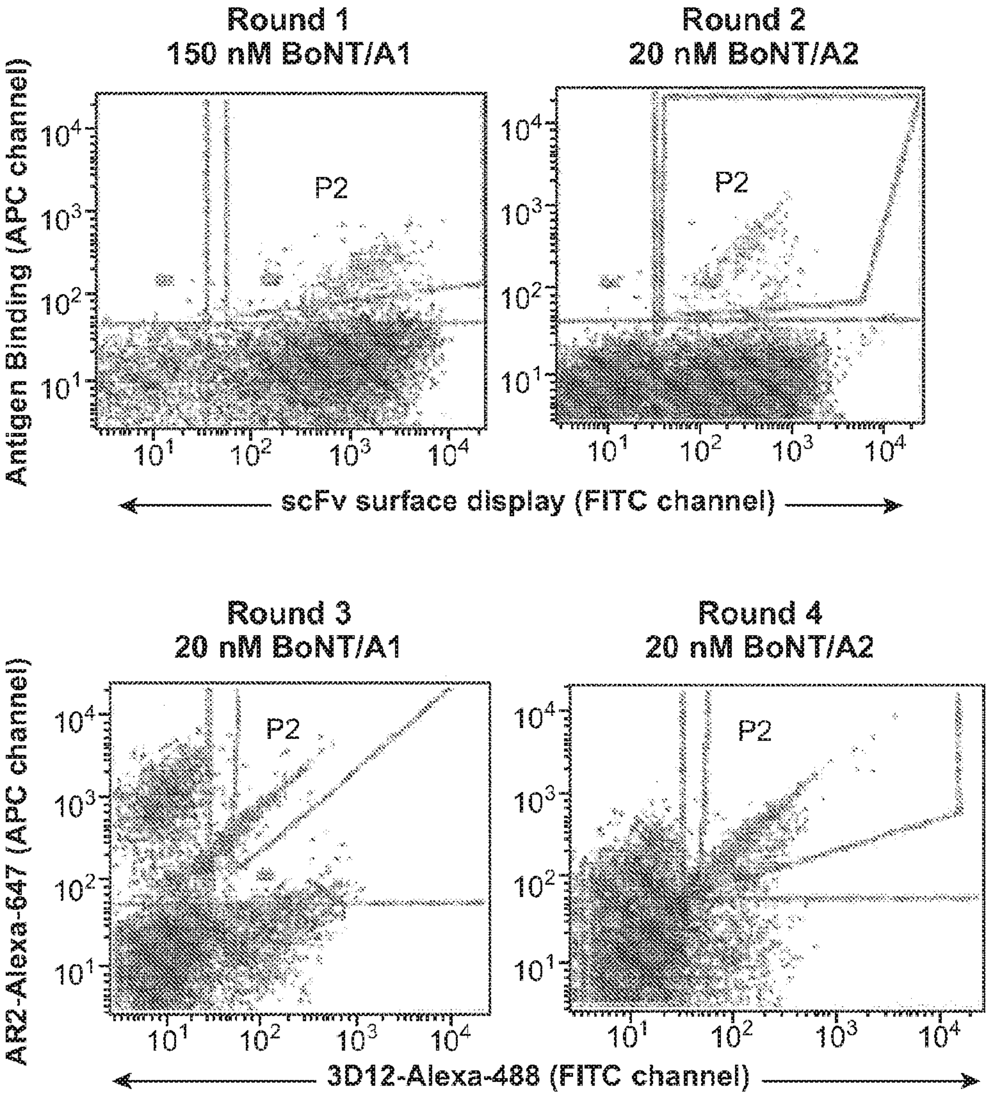
FIG. 8 illustrates the selection of yeast displayed antibodies cross reactive with BoNT/A subtypes. Dot-plots of flow cytometry sorting of scFv displaying yeast labeled with BoNT/A are shown. For each of the four rounds of sorting, the concentration of BoNT/A1 or BoNT/A2 used to stain yeast is indicated. For the first two rounds of sorting, BoNT/A binding is indicated on the Y-axis and the scFv display level on the X-axis. For the last two rounds of sorting, scFv displaying yeast which bound toxin epitopes that did not overlap with mAb AR1 or mAb 3D12 are indicated on the Y and X axes respectively (see methods section for staining details). The sort gates used for yeast collection are indicated and the yeast in these gates are colored green.

Generation and Characterization of High Affinity Human Antibodies to Type A *Botulinum* Neurotoxins The sortings of yeast displayed scFv libraries were designed to generate antibodies that bound multiple BoNT/A subtypes and/or bound to epitopes not recognized by previously generated antibodies. To generate antibodies binding multiple BoNT/A subtypes, a library constructed from donor six was sequentially sorted on BoNT/A1 and BoNT/A2 (FIG. 8). To generate antibodies binding epitopes not recognized by existing mAbs, yeast libraries were incubated with BoNT/A then simultaneously stained with mAbs 3D12 and AR2 labeled with different fluorophores and sorted (FIG. 8). Using this approach, two yeast displayed scFv were identified, ING1 and ING2. A number of additional scFv were also isolated that were of lower affinity but which were clonally related to ING1 or ING2, having the same $V_H$ CDR3 but point mutations in the $V_H$ gene and/or different light chain genes. ING1 and ING2 both bound BoNT/A1 and A2 with high affinity as yeast displayed scFv, but only ING1 bound BoNT/A3 (Table 9). Additional mAbs to BoNT/A epitopes were generated by sorting a yeast displayed library constructed from donor ten on BoNT/A1. From these sorts, two new yeast displayed scFv were identified, 4A1 and 5A20. Both of these yeast displayed scFv only bound BoNT/A1. A number of additional scFv were also isolated that were of lower affinity but which were clonally related to 4A1 or 5A20, having the same $V_H$ CDR3 but point mutations in the $V_H$ gene and/or different light chain genes.

TABLE 9

Characteristics of lead yeast displayed BoNT/A antibodies. Clone name, epitope, VH CDR3 sequence, $V_H$ and $V_\kappa$ germline gene family and equilibrium dissociation constant ($K_D$) for three BoNT/A subtypes are shown. scFv $K_D$ measured on yeast displayed scFv. $L_C$ = light chain; $H_N$ = translocation domain; $L_C$-$H_N$ = epitope requiring presence of both $L_C$ and $H_N$ for binding; NB = no binding; ND = not determined due to absence of purified BoNT/A3.

| Clone | Epitope | $V_H$ CDR3 Sequence | $V_H/V_k$ Gene Family | BoNT/A $K_D$ by FACS ($\times10^{-9}M^{-1}$) A1 | A2 | A3 |
|---|---|---|---|---|---|---|
| ING2 | $L_C$ | DPYYYSYMDV (SEQ ID NO: 867) | VH1/VK4 | 0.24 | 0.25 | NB |
| 5A20 | $L_C$ | EASFGWSYLGHDDAFDI (SEQ ID NO: 869) | VH1/VK1 | 0.40 | NB | NB |
| 4A1 | $H_N$ | DPGWIYSDTSAAGWFDP (SEQ ID NO: 871) | VH3/VK1 | 7.4 | >5000 | NB |
| ING1 | $L_C$-$H_N$ | VRTKYCSSLSCFAGFDS (SEQ ID NO: 884) | VH3/VK1 | 5.28 | 3.83 | ND |

Yeast displayed BoNT/A scFv were further characterized to determine which BoNT domain they bound by staining with recombinant BoNT/A $H_C$, $H_N$, or $L_C$. 4A1 was determined to bind the $H_N$ domain and both ING2 and 5A20 bound the $L_C$ (Table 9). We previously determined using yeast displayed BoNT/A domains that ING1 recognized a complex epitope requiring the presence of both the N-terminal domain of the BoNT/A heavy chain translocation domain ($H_N$) and the BoNT/A light chain by ($L_C$) (Levy et al. 2007, supra). To determine whether the epitopes recognized by the antibodies overlapped, yeast displayed ING1, ING2, 4A1, or 5A20 scFv was incubated with BoNT/A and then stained with IgG constructed from each of these scFv. Each of these mAbs was found to recognize non-overlapping epitopes.

Affinity Maturation of Antibodies to Type a and Type B *Botulinum* Neurotoxins

Figure 9:
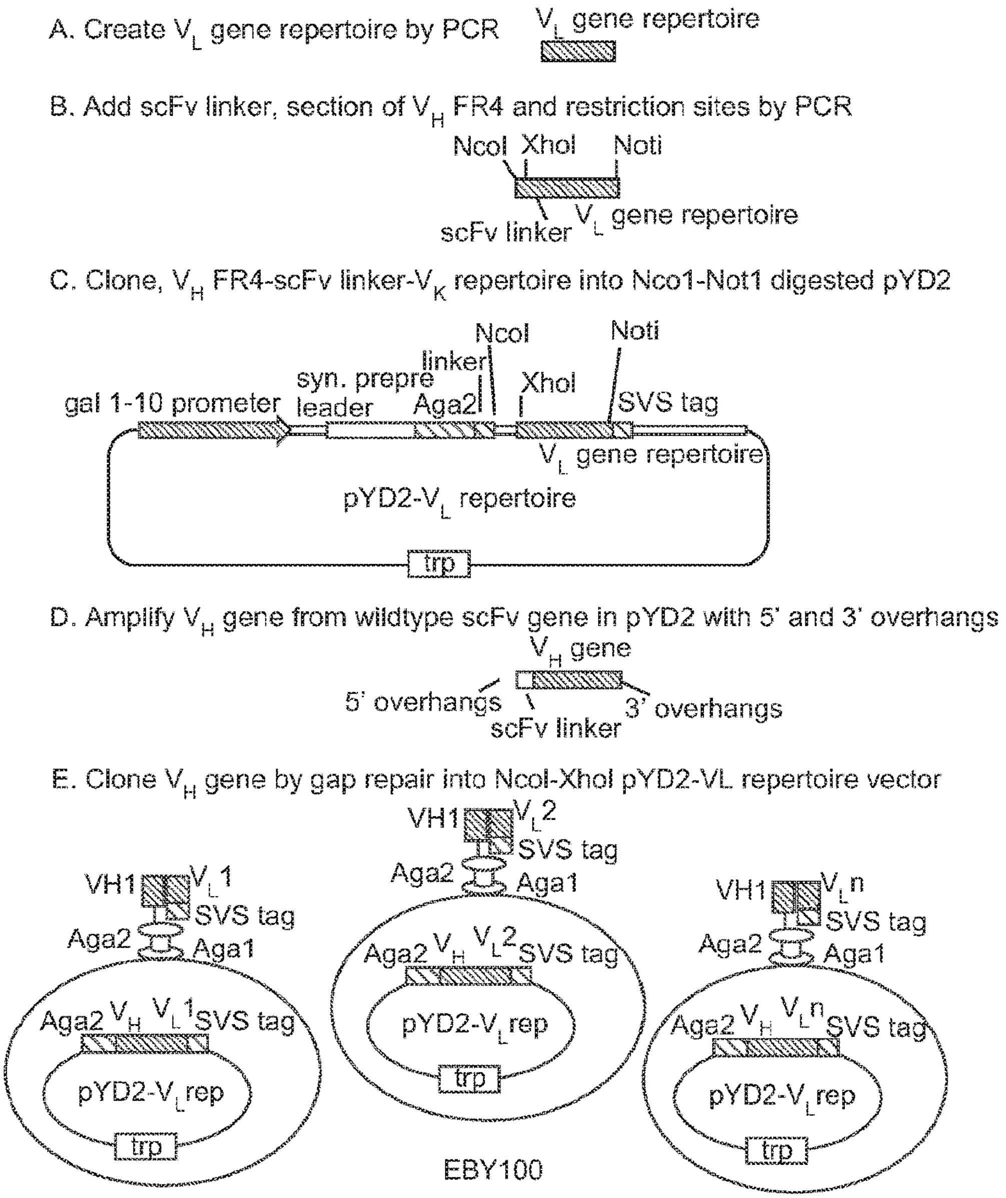
FIG. 9 shows a schematic of one method used to construct yeast displayed light chain shuffled scFv antibody libraries. A. $V_L$ gene repertoires were amplified by using PCR from donor cDNA or cloned scFv gene repertoires. B. $V_L$ gene repertoires are reamplified to append the $V_H$ framework 4, scFv linker, and cloning sites at the 5' and 3' end of the genes. C. The $V_L$ gene repertoire is cloned into the yeast display vector pYD2. D. The $V_H$ gene of a binding scFv is PCR amplified using primers that append overhangs complementary to Nco1-NotI or HindIII-NotI digested pYD2-$V_L$ gene repertoire vector DNA. E. The $V_H$ gene is cloned into the pYD-$V_L$ repertoire vector to create a light chain shuffled library. Gal1-10 promoter=galactose promoter; syn prepro leader=synthetic leader sequence; Aga1=Aga1 surface protein; Aga2=Aga2 surface protein gene; trp=tryptophan selectable marker.

Since it is statistically improbable that the original immune cognate $V_H$-$V_L$ pair is recreated in the primary library, scFv affinity maturation was performed by recombining the scFv $V_H$ gene with a library of $V_L$ genes, so called light chain shuffling (Clackson et al. *Nature* 1991, 352:624-8; Marks et al. *Biotechnology* (*NY*). 1992, 10:779-83; Schier et al. *J Mol Biol.* 1996, 263:551-67). To facilitate light chain shuffling, a light chain library was created in the yeast display vector pYD2 by subcloning the $V_L$ genes from the donor six, nine, and ten scFv gene repertoires in pYD2. To further increase light chain diversity, especially since lambda light chain V-genes had not been amplified from the immune donors, the light chain repertoire from a large non-immune scFv phage antibody library (Sheets et al. 1998, supra) that had been subcloned into pYD2 was also utilized. $V_L$ genes were amplified from the scFv gene repertoires in pYD2 by using PCR and then reamplified to append the 3' end of the $V_H$ framework 4 (FR4), containing a Xho1 restriction site, and the (Gly4Ser)3 scFv linker to the 5' end of the $V_L$ genes (FIG. 9). After cloning into pYD2, a library of size $4.2\times10^7$ was created that was determined to be diverse by PCR fingerprinting and DNA sequencing.

To create light chain shuffled scFv libraries, the light chain library was digested with NcoI or HindIII and XhoI. The $V_H$ gene was amplified from its respective scFv gene in pYD2 using primers that had 25 nucleotide sequences complementary to the 5' and 3' ends of the digested library vector DNA and was cloned into *Saccharomyces cerevisiae* by gap repair. Alternatively, scFv chain shuffled libraries were created by amplifying the $V_H$ FR4-scFv linker-$V_L$ gene repertoire from pYD2 and splicing it to a specific $V_H$ gene by overlap extension. The chain shuffled scFv gene repertoire was then cloned into pYD2. A total of seven chain shuffled libraries were created from the $V_H$ genes of scFv 4A1, 5A20, 1B18, 1B10, 1B22, 2B25, and 4B19. Their sizes ranged from $2.0\times10^7$ to $4.0\times10^7$. An additional chain shuffled library was created from the $V_H$ genes of scFv B12 (see table 3) using splicing by overlap extension as previously described (Marks et al. 1992, supra). Each of these libraries was sorted separately using BoNT/A1 or BoNT/B1 at decreasing concentrations for four to six rounds until a single clone became dominant. The highest affinity clone was identified by DNA sequencing and measuring the $K_D$ of yeast displayed scFv. The $K_D$ of the light chain shuffled scFv increased 2.2 to 74 fold from the $K_D$ of the parental scFv to a $K_D$ between 1.0 and $6.38\times10^{-10}$ M. In general, the largest increase in affinities was observed for the lowest affinity parental scFv. The average $K_D$ increased 16 fold from $4.98\times10^{-9}$ M to $0.31\times10^{-9}$ M (Table 10).

TABLE 10

Affinities of affinity matured scFv and IgG for BoNT/A and BoNT/B subtypes. scFv $K_D$ measured on yeast displayed scFv. IgG $K_D$ measured in solution using a flow fluorimeter (KinExA).

| Clone | ScFv Affinity $K_D$ ($\times10^{-12}M^{-1}$) | Fold increase in affinity scFv | $K_D$ of affinity matured IgG for BoNT by KinExA ($\times10^{-12}M^{-1}$) | | | |
|---|---|---|---|---|---|---|
| Initial Isolate/Affinity matured | BoNT/A1 | $K_D$ wild type/$K_D$ matured | A1 | A2 | | A3 |
| 4A1/4A1.1 | 100 | 74 | 11.34 | >1000 | | NB |
| 5A20/5A20.4 | 182 | 2.2 | 13.6 | NB | | NB |
| | BoNT/B1 | | B1 | B2 | B3 | B4 |
| B12/B12.1 | 300 | 30 | 33.0 | 16.2 | 46.2 | 625 |
| 1B18/2B18.1 | 638 | 11.4 | 72.4 | 181 | 98.4 | 382 |
| 1B10/1B10.1 | 235 | 47.7 | 0.33 | 0.31 | 1200 | 0.47 |
| 2B25/2B25.1 | 349 | 2.7 | 16.7 | 53.2 | 17.7 | 30.0 |
| 4B19/4B19.1 | 396 | 25 | 176 | 138 | 156 | 194 |

Impact of Conversion of Yeast Displayed scFv to IgG on Affinity

For many applications, such as diagnostic ELISA based assays as well as in vivo BoNT neutralization studies, it is desirable to utilize IgG. To determine the success rate of converting scFv to IgG, we converted twelve yeast displayed scFv, including five lead antibodies and seven affinity matured chain shuffled scFv, to full length IgG consisting of the human gamma 1 constant region and the human kappa or lambda constant region (Nowakowski et al. 2002, supra). Stable CHO DG44 cell lines were established for each of the twelve antibodies and IgG was purified from cell culture supernatant. The monovalent $K_D$ was determined for each IgG using kinetic exclusion analysis (KinExA).

Each of the twelve scFv was successfully cloned, stable cell lines established, and IgG purified at yields of 5 to 50 mg/L of cell culture supernatant. The solution $K_D$ of each of these IgG was lower (higher affinity) than the parental scFv (Tables 10, and 11). The affinity of the five IgG constructed from the lead scFv increased 1.5 to 25 fold from the affinity of the parental scFv, with the average $K_D$ decreasing 8.8 fold from $2.68\times10^{-9}$ M to $0.31\times10^{-9}$ M (Table 11). Similarly, the affinity of the seven IgG constructed from the affinity matured scFv increased 2.25 to 712 fold from the affinity of the parental scFv, with the average $K_D$ decreasing 6.43 fold from $3.14\times10^{-10}$ M to $0.49\times10^{-10}$ M (Table 10). Six of the seven IgG constructed from the affinity matured scFv had $K_D$'s less than $1.0\times10^{-10}$ M.

TABLE 11

Affinities of lead scFv and IgG for BoNT/A and BoNT/B subtypes. scFv $K_D$ measured on yeast displayed scFv. IgG $K_D$ measured in solution using a flow fluorimeter (KinExA).

| | scFv Affinity $K_D$ ($\times10^{-12}M^{-1}$) | IgG Affinity for BoNT by KinExA $K_D$ ($\times10^{-12}M^{-1}$) | | |
|---|---|---|---|---|
| Clone | BoNT/A1 | A1 | A2 | A3 |
| ING1 | 5280 | 314.3 | 719.1 | 400 |
| ING2 | 238 | 9.57 | 7.42 | NB |

TABLE 11-continued

Affinities of lead scFv and IgG for BoNT/A and BoNT/B subtypes. scFv $K_D$ measured on yeast displayed scFv. IgG $K_D$ measured in solution using a flow fluorimeter (KinExA).

| | BoNT/B1 | B1 | B2 | B3 | B4 |
|---|---|---|---|---|---|
| 1B18 | 7300 | 816 | 817 | 972 | 21 |
| 1B22 | 515 | 335 | 319 | 221 | 129 |
| 2B23 | 79 | 38.2 | 45.3 | 48.0 | 55.2 |

NB = no binding.

Discussion

These studies indicated that the scFv were diverse with respect to epitope recognized and were of an affinity (average $K_D$=9.2×10$^{-9}$ M) expected from an immune library. On average, three lead scFv were generated from each library constructed from a human donor, a relatively small number.

The magnitude of the increase in affinity from chain shuffling did not appear to be dependent on whether the source of the $V_L$ genes was from the same donor as the initial $V_H$-$V_L$ gene pairing or not. Presumably, light chain diversity across donors was similar enough that shuffling recapitulated the high affinity scFv binding site. The average affinity of the seven IgG constructed from the chain shuffled scFv V-genes was 45 pM, a value that would be at the very high end of antibodies generated by the humoral immune system. Three of these antibodies had $K_D$<15 pM. The very high average affinity suggests that these scFv do not represent the cognate $V_H$-$V_L$ pairing, which should not have such a high affinity. Rather it is likely that a $V_L$ pair was found for the $V_H$ that generated an antibody of higher affinity than that of the cognate $V_H$-$V_L$ pairing.

Example 2

Affinity Maturation of Human *Botulinum* Neurotoxin Antibodies by Light Chain Shuffling Via Yeast Mating The following methods and materials were used in the present example.

Methods and Materials

```
Oligonucleotide primers
Primers for VL library construction
For: 5P-AAGGCTCTTTGGACAAGAGAAACTCTGGATCC
                                   (SEQ ID NO: 908)
VH specific forward oligo

Rev: 5P-GTGCCAGGGGGAAGACCGATGGGCCCTTGGTGCTAGC
                                   (SEQ ID NO: 909)
VH specific reverse oligo
```

Strains, Media Antibodies, and Toxins:

Yeast strains *Saccharomyces cerevisiae* JAR300 ((GAL1-AGAlTURA3 ura3-52 trpl leu2Δ1 his3Δ200 pep4::HIS3 prb1Δ1.6R canl MATa) and YVH10 (BJ5464 Ura-Trp-MAT alpha) were maintained in synthetic dextrose plus casein amino acids (SD-CAA, 0.7% yeast nitrogen base, 0.1M Sodium phosphate, 0.5% casamino acids, 2% dextrose, 0.006% leucine) media with tryptophan and uracil added. After transformation with pPNL20s, JAR300 transformants were selected in SD-CAA media with uracil. After transformation with pPNL30s, YVH10 transformants were selected in SDCAA media with tryptophan. Yeast mating was performed on YPD plates (Current Protocols in Molecular Biology, John Wiley and Sons, Chapter 13.1.2). After mating, diploid yeast were selected on SD-CAA media. Fab surface display was induced by transferring yeast cultures from SD-CAA to SG-CAA medium (identical to SD-CAA medium except the glucose was replaced by galactose) and growing at 18° C. for 24-48 hours. Bacteria strain *E. coli* DH5α, (K12, Δ(lac-pro), supE, thi, hsdD5/F' traD36, proA+ B+, laclq, lacZΔM15) was used for all cloning and preparation of plasmid DNA. Chinese Hamster Ovary cell line CHO DG44 was maintained in CHO-SFM-II media (Invitrogen). Pure BoNT/A1 (Hall hyper), BoNT/A2 (FRI-H1A2), BoNT/B1, BoNT/B2, BoNT/B3, and BoNT/B4 were purified from their respective strains or purchased from Metabiologics (Madison, WI). Complex BoNT/A3 was expressed and purified from strains A254 and Ba207. Mouse anti-SV5 antibody was purified from hybridoma supernatant using Protein G and directly labeled with ALEXA FLUOR 488dye or ALEXA FLUOR 647 dye using a kit provided by the manufacturer (MOLECULAR PROBES). Chinese ovary cells (CHO) supernatants (Nowakowski et al. 2002, supra; Razai et al. 2005, supra). For flow cytometry (FACS), purified human or mouse IgGs were directly labeled with either ALEXA FLUOR 647 dye or ALEXA FLUOR 488 dye using a kit provided by the manufacturer (MOLECULAR PROBES).

Construction of a Light Chain Repertoire in YVH10 for Light Chain Shuffling (Donor 9)

A single light chain repertoire in YVH10 was constructed containing kappa and lambda light chains. First, vector pPNL30 was modified to insert a 90 base pair stuffer between the Xho1 and BsiWI sites.

Two different methods were used to construct the three Fab libraries for affinity and specificity maturation of three scFv lead clones: ING1, B6 and B11. For ING1 and B6 Fab library construction before yeast mating, a single VH gene from the lead scFv was PCR amplified using the specific primers mentioned above. But for B11Fab library construction, error-prone PCR was applied when preparing a mutated VH repertoire from the lead scFv B11 VH gene. The single VH gene of ING1 or B6, or the whole repertoire of randomly mutated B11 VH gene were then cloned into pPNL20S vector. Cloning was achieved by co-transforming JAR300 yeast (by the method of Gietz and Schiestl) with BamH I/Nhe I linearized vector and gap-tailed amplicon utilizing yeast gap repair. The transformants were selected on SD-CAA+uracil before mating with VL library yeast.

The VL libraries were constructed using conventional methods. Briefly, the light chain vector pPNL30S was digested with XhoI/BsiWI and gel-purified. YVH10 yeast was used for pPNL30S+VL transformation, and the transformants selected on SD-CAA+tryptophan.

For yeast mating, fresh cultures of VL library in YVH10/pPNL30-LC (MAT α strain) after selection were grown in the selective media at 30° C. with shaking, and a single VH clone or a repertoire of VH (for B11) library in JAR300/pPNL20-HC (MAT "a" strain) were grown in another selectable media similarly. 1 $OD_{600}$/ml (2×10$^7$ yeast) of each culture were mixed together, pelleted, and resuspended in 200 μl YPD media before placing in the center of a pre-warmed 30° C. YPD plate without spreading. The plates were incubated at 30° C. for 6 h for yeast mating and the yeast were resuspended in SD-CAA medium from the plate after mating. To check the mating efficiency and the final Fab library size, appropriate dilutions of mated yeast were plated on SD-CAA agar plates and the Fab library was selectively grown in SD-CAA media without tryptophan or uracil. The $OD_{600}$ reading at the start of growth was 0.025 to allow growth of the diploids to outcompete the non-growing haploids.

For diversity analysis, ten randomly picked clones from each library were checked by BstNI fingerprinting and/or sequencing for both VH and VL genes.

For Fab expression induction, freshly saturated SD-CAA cultures of the yeast libraries were induced in SG-CAA liquid media at 18° C. for 24-48 h with shaking. Anti-SV5/ALEXA FLUOR 647 dye were used to check the Fab expression after induction.

Selection of Mutant Clones from Fab Libraries by FACS

The optimally expressed diploid yeast were FACS sorted two rounds with one of the subtypes of BoNT/A or B, then using different subtypes of BoNT/A or B for the following rounds of sorting. An amount of diploid yeast at least ten times larger than the library size or the sort output from the previous round were washed and resuspended in FACS buffer, and a desired concentration of one subtype of pure BoNT/A or B was added. Sorting and selections were generally performed after allowing the reaction mixture to come to equilibrium. The volume for incubation of yeast with toxin was chosen to ensure that toxin was in at least a five fold excess over the number of expressed Fab (assuming $5\times10^5$ Fab/yeast). Incubation times were chosen to ensure that the reaction had come to at least 90% of equilibrium, using the formula shown in the Discussion section below. BoNT/A1concentration for the first round of sorting of the ING1 Fab library was 10nM. The 1$^{st}$ round sort output were divided into two parts after yeast growth and induction for the second round sorting: one with 10nM BoNT/A2, the other using 5nM BoNT/A1. Since both BoNT/A1 and A2 binders are clearly enriched after two rounds of sorting, for better cross reactive and higher affinity clone selection, decreased concentrations of BoNT/A2 were used for the following 3 rounds of sorting: 5 ,1 and 0.5nM before individual clones were picked out for sequencing and affinity measurement. BoNT/B1concentrations used for the 5 rounds of sorting of the B6 Fab library were: 100, 25, 10, 5, or 2nM separately, while those for the B11 Fab library were: 25, 10, 2, 1, or 1nM. After incubation, cells were washed with ice-cold FACS buffer and resuspended in a 1:400 dilution of Alexa 488 labeled anti-SV5antibody and one of the following: ALEXA FLUOR 647 dye labeled 7C1 or 3D12 antibody (for the ING1 Fab library), or two ALEXA FLUOR 647 dye labeled anti-BoNT/B mAb (A12 and 6A12), which bound the catalytic domain of the toxin, an epitope that did not overlap with B6or B11 (for the B6 Fab library and B11 Fab library). Cells were incubated for 30 minutes with secondary antibodies at 4-8 ° C., washed once with FACS buffer, resuspended in 0.5-1 ml of FACS buffer and sorted on a FACSAria. Typically 0.5~5% of the expressing and toxin binding population was gated for collection in the first 2 round sorting, and 0.1~0.5% of those populations was gated in the following rounds sorting. Collected cells were grown in SD-CAA media and used for the next round of sorting after induction in SG-CAA as described above.

Over a period of 2-3 weeks, each library was sorted 4-6 rounds with sequentially diluted different subtypes of BoNT A or B. Ninety-six individual clones were picked out after the last round of sorting, and 500 pM ALEXA FLUOR 647 dye or ALEXA FLUOR 488 dye labeled toxin were used to screen the best candidates in terms of expression and binding by FACS analysis. Using MFI as a single criterion after fixed concentration toxin staining, six to twelve clones were chosen from the screened ones for further $K_D$ measurement and sequence analysis.

Quantitative equilibrium binding was determined using flow cytometry. In general, six different concentrations of one subtype of pure BoNT/A or B were utilized spanning a range of concentrations from ten times above to ten times below the $K_D$. Incubation volumes and number of yeast stained were chosen to keep the number of antigen molecules in tenfold excess above the number of expressed Fab, assuming $5.0\times10^5$ Fab/yeast. Incubation times were chosen based on anticipated times to equilibrium calculated using approximations of the anticipated $k_{on}$ and $k_{off}$ (see above). This was usually performed by overnight incubation. Binding of either subtype of BoNT/A to yeast-displayed Fab was detected using a 1:200 dilution of 1 mg/ml monoclonal antibody binding a non-overlapping BoNT/A epitope (3D12 for the ING1 Fab library)labeled with ALEXA FLUOR 647 dye. To quantify the protein-ligand affinity constant ($K_D$) within the surface display context, only the Fab displaying yeast (SV5 binding positive) were included in the analysis by co-staining with SV5-ALEXA FLUOR 488. Each $K_D$ was determined in triplicate, three separate inductions and measurements. The best Fab clone from the ING1 Fab library was designated as 2G11, the highest affinity clone from B6Fab library was named as B6.1, and that from the B11 Fab library was called B11E8 (Table 13).

Generation of IgG from Fab

IgG were generated from Fab genes. Briefly, the VH genes were amplified using PCR from their respective pPNL20 vectors with the primer pairs. DNA was digested with MluI and NheI, ligated into N5KG1Val-Lark (a gift from Mitch Reff. IDEC Pharmaceuticals, San Diego) and clones containing the correct VH identified by DNA sequencing. Vk genes were amplified from the same diploid yeast containing pPNL30 vectors and cloned into pCR-2.1 vector (Invitrogen) and clones containing the correct Vk identified by DNA sequencing. Vk genes were excised from pCR-2.1 vector with DraIII and BsiWI and ligated into DraIII and BsiWI-digested N5KG1Val-Lark DNA containing the appropriate VH gene. Clones containing the correct VH and Vk gene were identified by DNA sequencing, and vector DNA was used to transfect CHO DG44 cells by electroporation. Stable cell lines were established by selection inG418 and expanded into one liter spinner flasks. Supernatant containing IgG was collected and purified on Protein G (Pharmacia). IgG purity was assessed by native and denaturing SDS PAGE and concentration determined by $A_{280}$ nm.

Measurement of IgG Solution Equilibrium Binding Constants by Flow Fluorimetry

Equilibrium binding studies were conducted at room temperature (~25° C.) using a KinExA 3000 flow fluorimeter to quantify the free BoNT/A or B at equilibrium using varying concentrations of antibody. Studies of sensitive detection of BoNT/A or B reaction mixtures were performed in PBS (pH 7.4), with 1 mg/ml BSA and 0.02% (w/v) sodium azide as a preservative. Antibody was serially diluted into a constant concentration of BoNT/A or B sufficient to produce a reasonable signal, where the antibody concentration was varied from less than 0.1 to greater than tenfold above the value of the apparent $K_D$. The BoNT/A or B concentrations were no more than fourfold above the $K_D$ to ensure a $K_D$ controlled experiment. Samples were allowed to reach equilibrium for as long as two days, then each of the 12 dilutions were passed over a flow cell with a 4 mm column of Azlactone beads (Sapidyne Instruments) covalently coated with the corresponding antibody to capture the free BoNT/A or B. Passing an Alexa-647 labeled BoNT/A or B antibody binding a non-overlapping epitope over the beads produced a signal relative to the amount of free BoNT/A or B bound to the beads. All data points were run in duplicate and sample volume varied from 4 to 25 ml depending on antibody affinity. The equilibrium titration data were fitted to a 1:1 reversible binding model using KinExA Pro Software (version 1.0.2; Sapidyne Instruments) to determine the $K_D$.

Antibodies Selected for Affinity Maturation by Light Chain Shuffling

One BoNT/A and two BoNT/B scFv antibodies were chosen for affinity maturation. The BoNT/A scFv antibody ING1 was selected from an immune scFv yeast display library constructed from a human donor (donor 6) immunized with pentavalent *botulinum* toxoid. ING1 binds the BoNT/A1 translocation domain ($H_N$) with an equilibrium dissociation constant ($K_D$) of $5.28\times10^{-9}$ M as a yeast displayed scFv (Table 12). Two BoNT/B scFv antibodies (B6 and B11) were also selected from an immune scFv yeast display library constructed from a human donor immunized with pentavalent *botulinum* toxoid. B6 binds the BoNT/B light chain ($L_C$) with a $K_D$ of $2.71\times10^{-9}$ M and B11 binds the BoNT/B $H_N$ with a $K_D$ of $2.62\times10^{-9}$ M (Table 12).

TABLE 12

Equilibrium dissociation constants for wild-type and affinity matured BoNT antibodies. Equilibrium dissociation constants ($K_D$) for wild type and affinity matured yeast displayed BoNT antibodies in both the scFv and Fab format were measured by flow cytometry.

| Clone | | BoNT KD by FACS ($\times10^{-12}M^{-1}$) | | | |
|---|---|---|---|---|---|
| Initial Isolate | Affinity matured | | | | |
| scFv | Fab | scFv | Fab | scFv | Fab |
| | | BoNT/A1 | | BoNT/A2 | |
| ING1 | | 5284 | 20630 | 3834 | 14297 |
| | 2G11 | 369 | 205 | 205 | 193 |
| | | BoNT/B1 | | BoNT/B2 | |
| B6 | | 2714 | NM | 1767 | NM |
| | B6.1 | 291 | 286 | 394 | 246 |
| B11 | | 2620 | NM | 2114 | NM |
| | B11E8 | 193 | 81 | 189 | 166 |

Generation of BoNT Fab from the V-Genes of scFv by Yeast Mating

To determine the feasibility of affinity maturing ING1, B6, and B11 by yeast mating, yeast displayed Fab were constructed and the display level and $K_D$ for BoNT determined. The $V_H$ gene from each of the three scFv was PCR amplified and cloned directly into *S. cerevisiae* strain JAR300 by gap repair into BamH I and Nhe I digested pPNL20s. This fuses the $V_H$ gene to the $C_H1$ gene which is fused to the N-terminus of the Aga2 yeast surface protein, resulting in display of the $V_H$-$C_H1$ on the yeast surface. The $V_k$ gene from each of the three scFv was PCR amplified and cloned directly into *S. cerevisiae* strain YVH10 by gap repair into Xho1 and BsiWII digested pPNL30s. This fuses the $V_k$ gene to the $C_k$ and results in secretion of the light chain. To create Fab, *S. cervisiae* JAR300 (a-mating type) containing the relevant $V_H$-$C_H1$ in pPNL20s was mixed with *S. cervisiae* YVH10 (a-mating type) containing the relevant light chain in pPNL30s and the resulting diploid yeast selected on uracil$^-$, tryptophan$^-$ plates. Fab display was induced and the display level and affinity for BoNT measured by flow cytometry. All three Fab were well displayed on the yeast surface (data not shown). The affinity of the ING1 Fab was 3.9 and 4.4 fold lower than the scFv for BoNT/A1 and BoNT/A2 respectively, while the affinity of the B6 Fab was essentially identical to the affinity of the scFv for BoNT/B1 and BoNT/B2 (Table 12). Interestingly, the affinity of the B11 Fab was 2.5 lower than the scFv for BoNT/B1 but 1.46 higher than the scFv for BoNT/B2 (Table 12). The results indicate that Fab can be constructed from the V-genes of scFv using yeast mating and that the $K_D$ of yeast displayed Fab and scFv are comparable.

Generation and Sorting of Fab Chain Shuffled Libraries

The following strategy was used to create ING1, B6, and B11 light chain shuffled libraries. A library of human kappa and lambda light chains from donor 10 was cloned directly into vector pPNL30s in *S. cerevisiae* strain YVH10 by gap repair. The resulting light chain library contained transformants containing a light chain insert and was diverse as determined by DNA sequencing. To create Fab light chain shuffled libraries, *S. cervisiae* JAR300 (a-mating type) containing the relevant $V_H$-$C_H1$ (ING1, B6, or B11) in pPNL20s was mixed with *S. cervisiae* YVH10 (a-mating type) containing the light chain library in pPNL30s and the resulting diploid yeast selected on uracil$^-$, tryptophan$^-$ plates. The number of diploid yeast colonies was at least 100 times greater than the size of the light chain shuffled library, suggesting that the light chain library diversity was captured in the chain shuffled library. Analysis of 10 colonies from each mating indicated that each had the expected wild-type $V_H$ gene and a different $V_L$ gene. Each of the 10 colonies also expressed a Fab on the yeast surface, as determined by staining with anti-SV5 antibody.

Higher affinity chain shuffled Fab were isolated by FACS. For each of the three chain shuffled libraries, Fab expression was induced and yeast stained with $1\sim10\times10^{-8}$ M (10 nM-100 nM) BoNT/A1 or BoNT/B1 for the first two rounds of sorting with the majority of BoNT binding yeast collected. Subsequent rounds of sorting were increasingly stringent with the antigen concentration decreased and less than 1% of the yeast collected. A total of six rounds of sorting were performed for each Fab library, after which the sort output was plated to allow for characterization of individual yeast displayed Fab. Ninety-six clones were randomly picked into 96 well microtiter plates from each of the three Fab sortings and Fab expression and BoNT binding quantitated using a single antigen concentration ($5.0\times10^{-10}$ M, 500 pM). While almost 100% of the picked clones showed a positive BoNT binding signal, the mean fluorescence intensity (MFI) varied significantly among them. Twelve individual clones with the highest MFI were chosen for further analysis.

Characterization of Chain Shuffled Fab

The $V_H$ and $V_L$ genes were PCR amplified from the three sets of twelve yeast colonies and the $V_H$ and $V_L$ genes sequenced. For each of the three chain shuffled libraries, sequence analysis revealed a single $V_H$ gene (the same as the original $V_H$ gene) paired with different $V_L$ genes (Table 13). Affinities ($K_D$) of the yeast displayed Fab were measured by flow cytometry for BoNT/A1 or BoNT/B1 and compared to the affinities of the parental scFv (Table 13). Overall the affinities of the best ING1, B6, and B11 chain shuffled Fab increased 3 to 43 fold compared to their parental scFv, with yeast displayed $K_D$ ranging from 32 to 1645 pM (Table 13). The complete amino acid sequences of the $V_H$ and $V_L$ of the antibodies described in Table 13 are provided in FIG. 11.

TABLE 13

Characteristics of affinity matured BoNT antibodies. Clone name, location of mutations in the Vκ complementarity determining regions (CDRs), number of mutations between the wild type and affinity matured Vκ and the germline gene family and germline gene of origin are indicated. Equilibrium dissociation constant ($K_D$) was measured by flow cytometry.

| Clone Name | Amino acid sequence of Vk CDRs CDR1 | CDR2 | CDR3 | Number of mutations from wild-type Vk gene | Germline family gene | BoNT $K_D$ by FACS ($\times 10^{-12}M^{-1}$) | $K_D$ wild type/$K_D$ matured |
|---|---|---|---|---|---|---|---|
| | | | | | | BoNT/A1 | |
| ING1 | RASQSISSYLN (SEQ ID NO: 1042) | AASSLQS (SEQ ID NO: 1044) | QQSYSTPRTT (SEQ ID NO: 1046) | 0 | IGKV1-39*01 | 5284 | |
| 2G11 | ----------H (SEQ ID NO: 1056) | D---S-- (SEQ ID NO: 1058) | ------RAL- (SEQ ID NO: 1060) | 12 | IGKV1-39*01 | 205 | 25 |
| 1D11 | ----------H (SEQ ID NO: 1056) | D------ (SEQ ID NO: 1051) | ------RAL- (SEQ ID NO: 1060) | 12 | IGKV1-39*01 | 420 | 12 |
| ING1.1C1 | ----------- (SEQ ID NO: 1049) | ------- (SEQ ID NO: 1044) | -------P-- (SEQ ID NO: 711) | 6 | IGKV1-39*01 | 890 | 6 |
| ING1.2B10 | ----------H (SEQ ID NO: 1056) | D---S-- (SEQ ID NO: 1058) | ------RAL- (SEQ ID NO: 1060) | 13 | IGKV1-39*01 | 1645 | 3 |
| ING1.5B1 | ----------H (SEQ ID NO: 1063) | D---S-- (SEQ ID NO: 1065) | ------RAL- (SEQ ID NO: 1060) | 12 | IGKV1-39*01 | 290 | 18 |
| ING1.3C2 | ------G-SNA (SEQ ID NO: 1070) | ----T-- (SEQ ID NO: 1072) | ------LMCS (SEQ ID NO: 1074) | 16 | IGKV1-27*01 | 710 | 7 |
| 5G4 | ----G--N--A (SEQ ID NO: 1070) | ---T--- (SEQ ID NO: 1072) | ------LMCS (SEQ ID NO: 1074) | 14 | IGKV1-27*01 | 430 | 12 |
| | | | | | | BoNT/B1 | |
| B6 | QAGQDISNFLN (SEQ ID NO: 637) | DASNLET (SEQ ID NO: 639) | QQYDNLPYT (SEQ ID NO: 641) | 0 | IGKV1-33*01 | 2714 | |
| B6.1 | R-S-S--SY-- (SEQ ID NO: 644) | S--S-QS (SEQ ID NO: 646) | --SYST-PYT (SEQ ID NO: 648) | 26 | IGKV1-39*01 | 286 | 9 |
| B6.C12 | R-S-S--SY-- (SEQ ID NO: 1238) | A--S-QS (SEQ ID NO: 1240) | --SYTA-C- (SEQ ID NO: 1242) | 24 | IGKV1-39*01 | 405 | 7 |
| B6.D2 | R-S-S-RDY-S (SEQ ID NO: 1245) | S--S-QS (SEQ ID NO: 1247) | LEKYSF-RCT (SEQ ID NO: 1249) | 39 | IGKV1-6*01 | 254 | 11 |
| B11 | RASQSINSWLA (SEQ ID NO: 665) | EASSLES (SEQ ID NO: 667) | QQYDSYWLT (SEQ ID NO: 669) | 0 | IGKV1-5*03 | 2620 | |
| B11.A5 | ----GVSR--- (SEQ ID NO: 1266) | G----Q- (SEQ ID NO: 1268) | -----FP-- (SEQ ID NO: 1270) | 16 | IGKV1-12*01 | 61 | 43 |
| B11.E8 | -----VSKF-- (SEQ ID NO: 679) | G--TRAT (SEQ ID NO: 681) | ----NWPI- (SEQ ID NO: 683) | 32 | IGKV3D-15*01 | 32 | 32 |
| B11.E9 | -----VSKF-- (SEQ ID NO: 1273) | G--TRAT (SEQ ID NO: 1275) | ----NWPI- (SEQ ID NO: 1277) | 32 | IGKV3D-15*01 | 69 | 38 |

TABLE 13-continued

Characteristics of affinity matured BoNT antibodies. Clone name, location of mutations in the Vκ complementarity determining regions (CDRs), number of mutations between the wild type and affinity matured Vκ and the germline gene family and germline gene of origin are indicated. Equilibrium dissociation constant ($K_D$) was measured by flow cytometry.

| Clone Name | Amino acid sequence of Vk CDRs CDR1 | CDR2 | CDR3 | Number of mutations from wild-type Vk gene | Germline family gene | BoNT $K_D$ by FACS ($\times10^{-12}M^{-1}$) | $K_D$ wild type/$K_D$ matured |
|---|---|---|---|---|---|---|---|
| B11.F7 | -----VG-T-- (SEQ ID NO: 1280) | G--TRAT (SEQ ID NO: 1282) | ---N-WPI- (SEQ ID NO: 1284) | 33 | IGKV3D?-15*01 | 177 | 15 |
| B11.H12 | ----G--NY-- (SEQ ID NO: 1287) | A--T-Q- (SEQ ID NO: 1289) | ---Y-P-- (SEQ ID NO: 1291) | 19 | IGKV1-8*01 | 175 | 15 |

In the case of the BoNT/A antibody ING1, seven Fab were identified which had affinities 3 to 25 fold higher than the parental ING1 scFv (Table 13). All seven had $V_L$ genes derived from the same Vk1 germline gene family and 5 of the 7 were derived from the same IGKV1-39*01 germline gene. Compared to the parental Vk gene, the Vk genes from the affinity matured Fab had 6 to 16 amino acid substitutions (Table 13). In the case of the BoNT/B antibody B6, three different Fab were identified which had affinities higher than the parental B6 scFv (Table 13). All three had $V_L$ genes derived from exactly the same Vk1 germline gene family as the parental Vk gene. The Vk genes from the affinity matured B6 Fab were more mutated than those of the ING1 affinity matured Fab, having 26 to 39 amino acid substitutions compared to the parental Vk gene (Table 13). In the case of the BoNT/B antibody B11, different Fab were identified which had affinities 61 to 177 fold higher than the parental B11 scFv (Table 13). Two had $V_L$ genes derived from the same Vk1 germline gene family as the parental Vk gene, however three had Vk genes derived from the Vk3 family. The Vk genes from the affinity matured Fab had 16 to 33 amino acid substitutions compared to the parental Vk gene (Table 13).

Generation and Characterization of IgG Constructed from the V-Genes of Fab

To determine whether the affinities observed for the Fab were recapitulated in IgG, and to generate antibodies for the diagnosis and treatment of botulism, we converted 2G11, B6.1 and B11E8 to human IgG1/kappa antibodies. IgG were expressed from stable CHO cell lines, purified using protein G and solution $K_D$ for BoNT/A or BoNT/B subtypes measured by flow fluorimetry. The affinities of the three IgG ranged from 25.1 to 6.59 pM for BoNT/A1 or BoNT/B1 and were increased from 4.85 fold to 42 fold compared to the affinities measured for the yeast displayed Fab (Table 14). We have previously observed comparable increases in affinities for yeast displayed scFv converted to IgG. 2G11 bound three BoNT/A subtypes (Bont/A1, A2, and A3 with comparable and high affinity. B6.1 bound four BoNT/B subtypes (BoNT/B1, B2, B3, and B4) with comparable and high affinity. In contrast, B11E8 only bound BoNT/B1, B2, and B3 (Table 14).

TABLE 14

Solution equilibrium binding constants for Ig6 constructed from affinity matured BoNT Fab. Equilibrium dissociation constants ($K_D$) for affinity matured BoNT IgG were measured for the different BoNT subtypes by flow fluorimetry in a KinExA.

| Clone | IgG Affinity by KinExA $K_D$ ($\times10^{-12}M^{-1}$) | | | |
|---|---|---|---|---|
| | BoNT/A1 | BoNT/A2 | BoNT/A3 | |
| 2G11 | 25.1 | 40.4 | 18 | |
| | BoNT/B1 | BoNT/B2 | BoNT/B3 | BoNT/B4 |
| B6.1 | 6.82 | 9.18 | 28.5 | 9.41 |
| B11E8 | 6.59 | 18.1 | 15.6 | NB |

Example 3

Neutralization of BoNT/B In Vivo by BoNT/B Antibody Combinations

In vivo, as found for BoNT/A, single mAbs protected mice against only relatively low BoNT/B challenge doses (up to 100 mouse LD50s per 50 μg of mAb). But for BoNT/A and BoNT/E, mAb combinations showed much more potent neutralization than for BoNT/B neutralization. The most potent three mAb combination (2B18.1:1B10.1:B12.1), however, only protected mice up to a challenge dose of 40,000 $LD_{50}$s/50 μg of antibody, about 10 fold less than seen for three mAb combinations against BoNT/A and BoNT/E (Table 15). Addition of a fourth mAb (B11E8) increased potency of about 50 fold, such that all mice receiving 2 μg total of antibody were completely protected against challenge with 40,000 mouse $LD_{50}$s of BoNT/B1. Since 1 IU for BoNT/B is the amount of antibody neutralizing 10,000 $LD_{50}$s of BoNT/B (50% of mice survive), this would translate into a potency of about 2000-4000 IU/mg. Thus a total human therapeutic dose equivalent to the 5500 IU of licensed equine antitoxin used to treat type B botulism would be less than about 2.5 mg. Other combinations of four mAbs had comparable potency against BoNT/B1. Protection against challenge by BoNT/B2 by mAbs 2B18.1:1B10.1:B12.1:B11E8 was about 4 to 5 fold less than the protection seen for BoNT/B1, similar to the reduced potency seen against this subtype for the equine antitoxin. The reason for the reduced potency is not clear, since the mAbs bind BoNT/B2 with affinities comparable to the affinities for BoNT/B1. Regardless, the four mAb combination is still highly potent against BoNT/B2. Based on the significantly higher potency observed for the four mAb combinations, a combination of four mAbs rather than three may be preferable for BoNT/B antitoxin compositions.

TABLE 15

In vivo potency of BoNT/B neutralization by BoNT/B antibody combinations

| | Mice surviving per 10 dosed | | | | | | |
|---|---|---|---|---|---|---|---|
| | 10,000 $LD_{50}$ | 20,000 $LD_{50}$ | 40,000 $LD_{50}$ | 40,000 $LD_{50}$ | 40,000 $LD_{50}$ | 40,000 $LD_{50}$ | 40,000 $LD_{50}$ |
| | BoNT/B1 | | | | | | |
| Antibody mixture/amount | 50 µg | 50 µg | 50 µg | 10 µg | 5 µg | 2 µg | 1 µg |
| 2B18.1:1B10.1:B12.1 | 10 | 10 | 6 | 0 | | | |
| 2B18.1:1B10.1:B12.1:B11E8 | | | | 10 | 10 | 10 | 3 |
| 2B18.1:B10.1:B12.1:B6.1 | | | | 10 | 10 | 9 | 1 |
| 2B18.1:B6.1:B11E8:B12.1 | | | | 10 | 10 | 7 | |
| | BoNT/B2 | | | | | | |
| Antibody mixture/amount | 50 µg | 50 µg | 50 µg | 10 µg | 5 µg | 2 µg | 1 µg |
| 2B18.1:1B10.1:B12.1 | 4 | 0 | | | | | |
| 2B18.1:1B10.1:B12.1:B11E8 | 10 | 10 | 10 | 6 | 0 | | |

An equimolar combination of the indicated amount of mAb was mixed with the indicated BoNT/B subtype and injected into mice. The amount of mAb given is the total dose of the four mAb combination. The number of mice surviving of 10 studied is reported.

Example 4

Neutralization of BoNT/E In Vivo by BoNT/E Antibody Combinations

In vivo, as found for BoNT/A, single mAbs protected mice against only relatively low BoNT/E challenge doses (up to 200 mouse $LD_{50}$s per 50 µg of mAb). Similar as for BoNT/A, mAb combinations showed highly potent BoNT/E neutralization. In vivo, 5-10 ug of the most potent combination of three mAbs (3E2, 3E6.1, and 4E16.1) protected mice challenged with 40,000 mouse $LD_{50}$s of BoNT/E1 and BoNT/E3 (Table 16). Since 1 IU of BoNT/E antibody neutralizes 1,000 mouse $LD_{50}$s, about 1 mg of this mAb combination would be the equivalent of 8,000 IU of antitoxin for BoNT/E1 or E3. This is equivalent to the human therapeutic dose of investigational BoNT/E equine antitoxin given to treat type E botulism. The potency of some of the different three mAb combinations of the four different BoNT/E mAbs was also studied, and found to be approximately equipotent in the three mAb combination.

TABLE 16

In vivo potency of BoNT/E neutralization by BoNT/E antibody combinations

| | Mice surviving per 10 dosed | | | | | | |
|---|---|---|---|---|---|---|---|
| | 10,000 $LD_{50}$ | 20,000 $LD_{50}$ | 40,000 $LD_{50}$ | 40,000 $LD_{50}$ | 40,000 $LD_{50}$ | 40,000 $LD_{50}$ | 40,000 $LD_{50}$ |
| | BoNT/E1 | | | | | | |
| Antibody mixture/amount | 50 µg | 50 µg | 50 µg | 10 µg | 5 µg | 2 µg | 1 µg |
| 3E2:3E6.1:4E16.1 | 10 | | 10 | 10 | 8 | 10 | 0 |
| 3E2:3E6.1:4E17.1 | | | | 10 | 10 | 0 | |
| | BoNT/E3 | | | | | | |
| Antibody mixture/amount | 50 µg | 50 µg | 50 µg | 10 µg | 5 µg | 2 µg | 1 µg |
| 3E2:3E6.1:4E16.1 | | | 10 | 9 | 9 | 0 | |
| 3E2:3E6.1:4E17.1 | | | 10 | 10 | 2 | | |
| 3E2:3E16.1:4E17.1 | | | 10 | 10 | 9 | 1 | |

An equimolar combination of the indicated amount of three mAbs was mixed with the indicated BoNT/E subtype and injected into mice. The amount of mAb given is the total dose of the three mAb combination. The number of mice surviving of 10 dosed is reported.

Example 5

Residues Involved in the Binding of Various IgG to BoNT Methods and Materials

Oligonucleotide Primers

Standard PYD2 primers: pair Gap 5 and Gap 3 or pair PYDFor and PYDRev are used for per for sequencing and/or cloning. Gap 5 and Gap3-1 are used for DNA sequencing.

```
Gap repair 5' (Gap5):
                                    (SEQ ID NO: 932)
5'-TTAAGCTTCTGCAGGCTAGTG-3'
```

-continued

```
Gap repair 3' (Gap3):
                                    (SEQ ID NO: 933)
5'-GAGACCGAGGAGAGGGTTAGG-3'

Gap repair 3'-1 (Gap 3-1):
                                    (SEQ ID NO: 934)
5'-GAGAGGGTTAGGGATAGG-3'

pYDFor:
                                    (SEQ ID NO: 935)
5'-AGTAACGTTTGTCAGTAATTGC-3'

PYDRev:
                                    (SEQ ID NO: 936)
5'-GTCGATTTTGTTACATCTACAC-3'
```

Primers for amplifying and cloning the target antigen gene by gap repair:

```
                                    (SEQ ID NO: 937)
Ag-Gap5 primer 5'GTTGTTCTGCTAGCGGGGCCAATG
G-------------------------3'

                                    (SEQ ID NO: 490)
Ag-Gap3 primer 5'-TTCGAAGGGCCCGCCTGCGGCCG
C-------------------------3'
```

The 5' sequence indicated anneals to NcoI-NotI digested pYD2 DNA for cloning by gap repair, the bolded sequences are the NcoI and NotI sites. The dashed sequence should include approximately 24nucleotides that anneal to the 5' and 3' ends of the target antigen DNA. Primers for amplifying and introducing alanine on the target antigen gene: These primers are designed specifically for each toxin domain and mutation to construct.

Strains, Media, and Reagents

Pfu DNA Polymerase (Stratagene); Taq Polymerase (New England Biolabs (NEB)); GENECLEAN TURBO kit (MP Biomedicals, LLC, Cat. 1102-600); Custom DNA primers (many vendors); deoxynucleotide triphosphates (NEB); Nco I, Not I restriction enzymes (NEB); SV5 Antibody (Invitrogen); APC conjugated Fab-specific goat-anti-human $(Fab)_2$ (Jackson Immuno Research); Fab preparation kit (Pierce product number 44985); *saccharomyces cerevisiae* EBY100(Invitrogen); 1 M lithium acetate (LiAc); 0.1 M LiAc; 2 mg/mL single stranded DNA (ssDNA); polyethylene glycol (PEG) 3350 (50%); plasmid vector pYD2 as describe above; YPD medium (recipe: to 900 mL deionized $H_2O$ add: 10 g Yeast extract and 20 g Peptone. Optional: Add 17 g agar/L for plates. autoclave, cool to 55-60° C. Add 100 ml of 20% dextrose (filter sterilized). For liquid media preparation filter sterilize (0.22 μm filter) after all components have been added and dissolved.) SD-CAA medium (recipe: to 900 mL deionized $H_2O$ add: 7 g Yeast Nitrogen base w/o amino acid, 10.19 g $Na_2HPO_4.7H_2O$ or 5.4 g $Na_2HPO_4$, 8.56 g $NaH_2PO_4.H_2O$ or 7.4 g $NaH_2PO_4$, and 5 g CAA (DIFCO) w/o Tryptophan or Ura. After all components dissolve, add 100 ml of 20% dextrose and 10 ml of 0.6% (100X) Leucine. Sterilize by filtering through 0.22 μm filter; SG-CAA medium (recipe: to 900 mL deionized $H_2O$ add: 7 g Yeast Nitrogen base w/o amino acid, 10.19 g $Na_2HPO_4.7H_2O$ or 5.4 g $Na_2HPO_4$, 8.56 g $NaH_2PO_4.H_2O$ or 7.4 g $NaH_2PO_4$, and 5 g CAA (DIFCO) w/o Tryptophan or Ura. After all components dissolve, add 100 ml of 20% galactose and 10 ml of 0.6% (100X) Leucine. Sterilize by filtering through 0.22 μm filter; ALEXA FLUOR 647 dye labeling kit (MOLECULAR PROBES); ALEXA FLUOR 488 dye labeling kit (MOLECULAR PROBES); PE conjugated anti-human Fc specific antibody (Jackson Immunoresearch); FACS Buffer: to 1L 1x PBS add 5 g BSA (final 0.5%), 1 mL 1M $MgCl_2$(final 1 mM) and 0.5 mL 1 M $CaCl_2$ (final 0.5 mM), sterile filter; FACS-ARIA Cell Sorter (BD Biosciences); Pure BoNToxins (USAMIIRID, Metabiologics); recombinant BoNToxins Fragments (UASAMIIRID).

Specificity and Crossreactivity Test $5.0\times10^5$ scFv/yeast of an induced culture, from the scFv to test, were incubated with 100uL of a 10 nM solution of the toxin to test. After 2 hours of incubation at 4° C., cells were washed with 500 uL of cold FACS buffer and resuspended in 200 uL of the detecting antibodies. Binding of BoNToxins to yeast-displayed scFv was detected using a 1:500 dilution of 1 mg/ml mAb binding a non-overlapping epitope labeled with ALEXA FLUOR 647 dye. Expression of yeast cells was detected using and anti-SV5 tag IgG labeled with ALEXA FLUOR 488 dye, 1:300 dilution.

This test was repeated for each available subtype of the corresponding BoNToxin. To test for nonspecific binding, cells were also incubated with the detection antibodies only. No toxin was used for this test. Recognition of each toxin was estimated by measuring yeast fluorescence in a FACS ARIA cell sorter, using the FITC and APC channels.

Measurement of Yeast-Displayed scFv Affinity for the Corresponding BoNToxin

Quantitative equilibrium binding was determined using yeast-displayed scFv and flow cytometry as described previously (Boder et al. *Proc. Natl. Acad. Sci. USA* 2000, 97:10701-10705) In general, six to eight different concentrations of pure BoNT/A were used spanning a range of concentrations from ten times above to ten times below the KD. Incubation volumes and number of yeast stained were chosen to keep the number of antigen molecules in fivefold excess above the number of scFv, assuming $5.0\times10^5$ scFv/yeast. Incubation times were chosen based on anticipated times to equilibrium calculated using approximations of the anticipated association rate constant (kon) and dissociation rate constant ($k_{off}$). For the higher affinity scFv, this was as long as 18-24 h. Binding of BoNToxins to yeast-displayed scFv was detected as for specificity test. Each KD was determined in triplicate, three separate inductions and measurements. To measure the antibody-toxin affinity constant ($K_D$) within the surface display context, only the scFv displaying yeast (SV5 binding) were included in the analysis by co-staining with SV5-Alexa-488. Affinity determination was performed for each one of the toxin subtypes recognized by the scFv being analyzed.

Binding Domain Test

Binding to recombinant purified toxin domains was performed using the same protocol as for the whole toxin, on the yeast-displayed scFv. When recombinant toxin was not available the desired toxin domains were cloned and displayed in EBY 100 yeast cells (Levy et al, supra). Only the IgG format, or free scFv can be used in this test. Binding to the yeast displayed toxin domain was performed by incubating $5.0\times10^5$ induced cells with 100 uL of the IgG-ALEXA FLUOR 647 dye to test. 1:500 dilution of the labeled IgG plus 1:300 dilution of SV5-488 were used. Cells were incubated at 4° C. for 30 min and after washing with cold FACS buffer, fluorescence was measured.

Construction of Yeast-Displayed BoNToxins Fragments, Wild Type or Alanine Mutants.

Genes encoding the desired *botulinum* neurotoxin fragments (Lc, Hn or HC) in pYD2, wt fragments or alanine mutated, were constructed by using PCR and gap repair. Primers For and Rev were designed to amplify the synthetic gene fragment, adding the restriction sites NcoI and NotI to the 5' and 3' ends, respectively. The pYD2 vector was digested with NcoI and NotI, and together with the gel purified per fragment used to transform EBY100 by gap repair (Orr-Weaver et al. *Proc Natl Acad Sci USA* 1983, 80: 4417-21; Gietz et al. *Yeast* 1983, 7: 253-63). Clones containing the correct insert were confirmed by DNA sequencing to yield pYD2/Toxin fragment.

For each Alanine mutant constructed a pair of specific oligos were designed and used in combination with the pYD2 standard oligos pYDFor and pYDRev to construct the mutated fragment by per. Transformation was performed, by gap repair, using the double digested plasmid and the two per products, all gel purified. After induction, mutated fragments had display levels resulting in at least a 1.5 log shift when stained with SV5-ALEXA FLUOR 488 dye, comparable to the levels of wild-type fragment.

Generation of IgG from scFv

Each scFv of interest was converted into full length IgG. Briefly, genes encoding scFv VH and VL were amplified using PCR from their respective pYD2 vectors with a designed primer pair and cloned into plasmid N5KG1. Clones containing the correct genes were identified by DNA sequencing and vector DNA was used to transfect CHO DG44 cells by electroporation. Stable cell lines were established by selection in G418 and expanded into 1-liter spinner flasks. Supernatant containing IgG was collected, concentrated by ultrafiltration and purified on Protein G (Pharmacia). IgG purity was assessed by native and denaturing SDS-PAGE and concentration determined by absorbance at 280 nm.

Epitope Sharing Test

Each scFv to test was stained with the corresponding toxin, as described above for the specificity test. Detection was done, separately, by each existing IgGs that binds to the toxin used. Fluorescence measurements were used as indicator of the spatial proximity of both epitopes, for the scFv and for the IgG. No signal meant that epitopes were too close and both antibodies could not bind simultaneously. The contrary was assumed for a strong signal, epitopes were well separated permitting binding of both antibodies.

After full characterization of each scFv an analysis of the toxin sequences was performed but only for the determined binding fragment. For an antibody that had been shown to bind the Hn domain, or translocation domain, toxin alignment was done only for the sequences regions corresponding to the Hn domains of the toxin subtypes.

Protein Sequence Alignment

The protein analysis and multiple sequence alignment were performed using the ClustalW application from the Mac Vector Software (Mac Vector, INC.). All known sequences for the different subtypes of the BoNT serotype were used to find the areas that presented antigen differences. The differential binding to each subtype was used as an indicator of a probable binding site, normally several regions were found. Each region was located in the 3D structure of the whole toxin assessing the level of exposure and conservation of the amino acids in the area.

The aim was to locate areas that could explain the binding pattern of the antibody and then test by alanine scanning the energetic importance of each site. Mutated amino acids that led to loss of binding were considered as energetically favorable contacts. Further single yeast displayed alanine mutants of the putative epitope site are constructed and antibody binding determined in order to identify the epitope.

Measurement of the Affinity of Fab Fragments for Yeast Displayed Wild Type and Alanine Mutants Toxin Domains.

By measuring the affinity of antibody for the alanine mutants compared to the wild type yeast displayed antigen, it is possible to determine the energetic contribution of the amino acid side chain to antibody binding.

The dissociation equilibrium constants ($K_D$) of the Fab fragment of the antibody to test for wild type and alanine mutants of yeast displayed toxin fragments were measured by flow cytometry on a FACS ARIA cell sorter. First, EBY100 yeast cultures harboring the pYD2/toxin domain, wild type or the pYD2/alanine mutant plasmids were grown and induced as described above for yeast-displayed scFv. Aliquots of $1\times10^5$ induced yeast cells (0.005 OD600 ml $^{1}$) were washed in FACS buffer and incubated with dilutions (according to the IgG $K_D$) of the Fab fragments such that the $K_D$ would be spanned by at least fivefold, where possible. Incubation volumes were chosen to ensure that a tenfold molar excess of the antibody (ligand) over the displayed moiety ($H_c$, $H_N$ or $L_c$) would be maintained. For this purpose, it was assumed that $10^5$ copies of the toxin domain were displayed on the yeast surface. Incubation with the Fab was allowed to proceed for 4 h at 23° C. Cells were then washed in FACS buffer and resuspended in allophycocyanin-conjugated Fab-specific goat-anti-human F(ab)¢2 at 1:1000 dilution in FACS buffer. To accurately determine the $K_D$ of the Fab fragments within the surface display context, we included only protein displaying yeast in the analysis by staining with SV5 (ALEXA FLUOR 488 dye) mAb (VanAntwerp et al. *Biotechnol. Prog.* 2000, 16:31-37).

Calculation of the Change in Free Energy of Binding to the Wild Type and Alanine Mutants.

For each alanine mutation, the change of free energy (DDGmut-wt) between the alanine (Ala) mutant relative to that of the wild type (wt) was calculated using the following standard formula and using the previously measured KD constants:

$$\Delta\Delta G_{mut-wt}=RT\ \ln(K_{Dmut}/K_{Dwt})$$

These calculations provide a measure of the energetic contribution of each one of the alanine substituted amino acid residues, for the mAb, therefore indicating the position of its functional epitope. Fab was used as it is monovalent, compared to the bivalent IgG. This eliminates the avidity effect that can occur with bivalent binding which can lead to falsely high (and inaccurate) affinities (Levy et al, supra).

TABLE 17

Epitope Data

| IgG | Toxin/Domain | Residues Involved |
|---|---|---|
| 4E17.1 | A1/Hn | Y753, E756, **E757** |
| 1B18 | A1/Hn | Y750, N751, **T754** |
| HuC25 | A1/Hc | E920, F953, **H1064** |
| AR2/CR1 | A1/Hc | B918, L919, E920, F953, D1062, T1063, **H1064** |
| 3D12/RAZ1 | Al/Hc | G1129, I1130, **R1131** |
| 1B11 | B1/Hn | **I549**, **S565** |
| 4E17.1 | B1/Hn | K747, **R749**, Y750, N751 |
| 1B18 | B1/Hn | N751, Y750, Y753 |
| 3E1 | E1/Lc | **N14**, **D15**, R16, Q29, E30, **Y32**, **E135**, **K137**, **F138**, **N140**, S142, **Q143**, **D144**, **I145** |
| 3E3 | E1/Lc | **N14**, Y32, **E135**, **K137**, **F138**, N140, S142, **Q143**, **D144**, **I145** |
| 3E5 | E1/Lc | **N14**, D15, **Y30**, D144 |
| 3E6.1 | E1/Lc | **S604**, **Q607**, **Q608** |
| 4E11 | E1/Lc | **N14**, D15, E30, **Y32** |
| 4E16.1 | E1/Lc | **N14**, **D15**, E30, **Y32**, D144 |
| 4E17.1 | E1/Hc | **E754b**, **E755** |

The numbering system used for the residues of toxin in the table above is based on Lacy et al. (1999) *J. Mol. Biol.*

291:1091-1104. Residues that are bolded and underlined were found to have important contributions energetically and eliminations of the residues often lead to total loss of binding the corresponding antibodies.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

While the subject antibody, method, and composition have been particularly shown and described with references to preferred embodiments thereof, it will be understood by those skilled in the art that various changes in form and details may be made therein without departing from the scope of the invention encompassed by the appended claims.

What is claimed is:

1. A composition comprising:

a first nucleic acid comprising the isolated nucleic acid comprising a nucleotide sequence encoding a variable heavy chain ($V_H$) polypeptide comprising a $V_H$ CDR1 comprising the amino acid sequence of HYGMH (SEQ ID NO:492);

a $V_H$ CDR2 comprising the amino acid sequence of VIWYDGRNPYYAASVKG (SEQ ID NO:494); and a $V_H$ CDR3 comprising the amino acid sequence of DLTRFHDTTFGVFEM (SEQ ID NO:496); and a second nucleic acid comprising the isolated nucleic acid comprising a nucleotide sequence encoding a variable light chain ($V_L$) polypeptide comprising a $V_L$ CDR1 comprising the amino acid sequence of RASQGISSWLA (SEQ ID NO:742);

a $V_L$ CDR2 comprising the amino acid sequence of AASSLQS (SEQ ID NO:744); and a $V_L$ CDR3 comprising the amino acid sequence of QQYSSLYT (SEQ ID NO:746);

wherein the first and second isolated nucleic acids are on the same or different nucleic acid constructs.

2. A composition comprising:

a first nucleic acid comprising the isolated nucleic acid comprising a nucleotide sequence encoding a variable heavy chain ($V_H$) polypeptide comprising a $V_H$ CDR1 comprising the amino acid sequence of GFTFSHYG (SEQ ID NO:1309);

a $V_H$ CDR2 comprising the amino acid sequence of IWYDGRNP (SEQ ID NO:1310);

and a $V_H$ CDR3 comprising the amino acid sequence of VKDLTRFHDTTFGVFEM (SEQ ID NO:1311); and a second nucleic acid comprising the isolated nucleic acid comprising a nucleotide sequence encoding a variable light chain ($V_L$) polypeptide comprising a $V_L$ CDR1 comprising the amino acid sequence of QGISSW (SEQ ID NO:1312);

a $V_L$ CDR2 comprising the amino acid sequence of AAS (SEQ ID NO:1313); and a $V_L$ CDR3 comprising the amino acid sequence of QQYSSL (SEQ ID NO:1314);

wherein the first and second isolated nucleic acids are on the same or different nucleic acid constructs.

3. A composition comprising:

a first nucleic acid comprising the isolated nucleic acid comprising a nucleotide sequence encoding a variable heavy chain ($V_H$) polypeptide comprising a $V_H$ CDR1 comprising the amino acid sequence of HYGMH (SEQ ID NO:492);

a $V_H$ CDR2 comprising the amino acid sequence of VIWYDGRNPYYAASVKG (SEQ ID NO:494); and a $V_H$ CDR3 comprising the amino acid sequence of DLTRFHDTTFGVFEM (SEQ ID NO:496); and a second nucleic acid comprising the isolated nucleic acid comprising a nucleotide sequence encoding a variable light chain ($V_L$) polypeptide comprising a $V_L$ CDR1 comprising the amino acid sequence of RASQSISSWLA (SEQ ID NO:735);

a $V_L$ CDR2 comprising the amino acid sequence of KASSLEN (SEQ ID NO:737); and a $V_L$ CDR3 comprising the amino acid sequence of QQYSTYSRT (SEQ ID NO:739);

wherein the first and second isolated nucleic acids are on the same or different nucleic acid constructs.

4. A composition comprising:

a first isolated nucleic acid comprising a nucleotide sequence encoding a variable heavy chain ($V_H$) polypeptide comprising the amino acid sequence of SEQ ID NO:19; and a second isolated nucleic acid comprising a nucleotide sequence encoding a variable light chain ($V_L$) polypeptide comprising:

a $V_L$ CDR1 comprising the amino acid sequence of RASQGISSWLA (SEQ ID NO:742);

a $V_L$ CDR2 comprising the amino acid sequence of AASSLQS (SEQ ID NO:744); and a $V_L$ CDR3 comprising the amino acid sequence of QQYSSLYT (SEQ ID NO:746); or a $V_L$ CDR1 comprising the amino acid sequence of QGISSW (SEQ ID NO:1312);

a $V_L$ CDR2 comprising the amino acid sequence of AAS (SEQ ID NO:1313); and a $V_L$ CDR3 comprising the amino acid sequence of QQYSSL (SEQ ID NO:1314); or a $V_L$ CDR1 comprising the amino acid sequence of RASQSISSWLA (SEQ ID NO:735);

a $V_L$ CDR2 comprising the amino acid sequence of KASSLEN (SEQ ID NO:737); and a $V_L$ CDR3 comprising the amino acid sequence of QQYSTYSRT (SEQ ID NO:739); or the amino acid sequence of SEQ ID NO: 55; or the amino acid sequence of SEQ ID NO: 54 wherein the first and second isolated nucleic acids are on the same or different nucleic acid constructs.

5. The composition of claim 4, wherein the second isolated nucleic acid comprises a nucleotide sequence encoding a $V_L$ polypeptide comprising:

a $V_L$ CDR1 comprising the amino acid sequence of RASQGISSWLA (SEQ ID NO:742);

a $V_L$ CDR2 comprising the amino acid sequence of AASSLQS (SEQ ID NO:744); and a $V_L$ CDR3 comprising the amino acid sequence of QQYSSLYT (SEQ ID NO:746).

6. The composition of claim 4, wherein the second isolated nucleic acid comprises a nucleotide sequence encoding a $V_L$ polypeptide comprising:

a $V_L$ CDR1 comprising the amino acid sequence of QGISSW (SEQ ID NO:1312);

a $V_L$ CDR2 comprising the amino acid sequence of AAS (SEQ ID NO:1313); and a $V_L$ CDR3 comprising the amino acid sequence of QQYSSL (SEQ ID NO:1314).

7. The composition of claim 4, wherein the second isolated nucleic acid comprises a nucleotide sequence encoding a $V_L$ polypeptide comprising the amino acid sequence of SEQ ID NO: 55.

8. The composition of claim 4, wherein the second isolated nucleic acid comprises a nucleotide sequence encoding a $V_L$ polypeptide comprising:

a $V_L$ CDR1 comprising the amino acid sequence of RASQSISSWLA (SEQ ID NO:735);

a $V_L$ CDR2 comprising the amino acid sequence of KASSLEN (SEQ ID NO:737); and a $V_L$ CDR3 comprising the amino acid sequence of QQYSTYSRT (SEQ ID NO:739).

9. The composition of claim 4, wherein the second isolated nucleic acid comprises a nucleotide sequence encoding a $V_L$ polypeptide comprising the amino acid sequence of SEQ ID NO: 54.

10. A composition comprising:

a first isolated nucleic acid comprising a nucleotide sequence encoding a $V_L$ polypeptide comprising the amino acid sequence of SEQ ID NO:55; and a second isolated nucleic acid comprising a nucleotide sequence encoding a $V_H$ polypeptide comprising:

a $V_H$ CDR1 comprising the amino acid sequence of HYGMH (SEQ ID NO:492);

a $V_H$ CDR2 comprising the amino acid sequence of VIWYDGRNPYYAASVKG (SEQ ID NO:494);

a $V_H$ CDR3 comprising the amino acid sequence of DLTRFHDTTFGVFEM (SEQ ID NO:496); or a second isolated nucleic acid present on a nucleic acid construct, the second isolated nucleic acid comprising a nucleotide sequence encoding a $V_H$ polypeptide comprising:

a $V_H$ CDR1 comprising the amino acid sequence of GFTFSHYG (SEQ ID NO:1309);

a $V_H$ CDR2 comprising the amino acid sequence of IWYDGRNP (SEQ ID NO:1310);

a $V_H$ CDR3 comprising the amino acid sequence of VKDLTRFHDTTFGVFEM (SEQ ID NO:1311);

wherein the first and second isolated nucleic acids are on the same or different constructs.

11. The composition of claim 10, wherein the second isolated nucleic acid comprises a nucleotide sequence encoding an amino acid sequence of a $V_H$ polypeptide comprising:

a $V_H$ CDR1 comprising the amino acid sequence of HYGMH (SEQ ID NO:492);

a $V_H$ CDR2 comprising the amino acid sequence of VIWYDGRNPYYAASVKG (SEQ ID NO:494); and a $V_H$ CDR3 comprising the amino acid sequence of DLTRFHDTTFGVFEM (SEQ ID NO:496).

12. The composition of claim 10, wherein the second isolated nucleic acid comprises a nucleotide sequence encoding an amino acid sequence of a $V_H$ polypeptide comprising:

a $V_H$ CDR1 comprising the amino acid sequence of GFTFSHYG (SEQ ID NO:1309);

a $V_H$ CDR2 comprising the amino acid sequence of IWYDGRNP (SEQ ID NO:1310); and a $V_H$ CDR3 comprising the amino acid sequence of VKDLTRFHDTTFGVFEM (SEQ ID NO:1311).

13. A nucleic acid construct comprising:

i) a first nucleic acid comprising a nucleotide sequence encoding an amino acid sequence of a variable heavy chain ($V_H$ ) polypeptide comprising a $V_H$ CDR1 comprising the amino acid sequence of HYGMH (SEQ ID NO:492);

a $V_H$ CDR2 comprising the amino acid sequence of VIWYDGRNPYYAASVKG (SEQ ID NO:494); and a $V_H$ CDR3 comprising the amino acid sequence of DLTRFHDTTFGVFEM (SEQ ID NO:496); or a $V_H$ CDR1 comprising the amino acid sequence of GFTFSHYG (SEQ ID NO:1309);

a $V_H$ CDR2 comprising the amino acid sequence of IWYDGRNP (SEQ ID NO:1310); and a $V_H$ CDR3 comprising the amino acid sequence of VKDLTRFHDTTFGVFEM (SEQ ID NO:1311); and ii) a second nucleic acid comprising a nucleotide sequence encoding a variable light chain ($V_L$ ) polypeptide comprising:

a $V_L$ CDR1 comprising the amino acid sequence of RASQGISSWLA (SEQ ID NO:742);

a $V_L$ CDR2 comprising the amino acid sequence of AASSLQS (SEQ ID NO:744); and a $V_L$ CDR3 comprising the amino acid sequence of QQYSSLYT (SEQ ID NO:746); or a $V_L$ CDR1 comprising the amino acid sequence of QGISSW (SEQ ID NO:1312);

a $V_L$ CDR2 comprising the amino acid sequence of AAS (SEQ ID NO:1313); and a $V_L$ CDR3 comprising the amino acid sequence of QQYSSL (SEQ ID NO:1314) or a $V_L$ CDR1 comprising the amino acid sequence of RASQSISSWLA (SEQ ID NO:735);

a $V_L$ CDR2 comprising the amino acid sequence of KASSLEN (SEQ ID NO:737); and a $V_L$ CDR3 comprising the amino acid sequence of QQYSTYSRT (SEQ ID NO:739).

14. A cell comprising the first and second isolated nucleic acids of claim 1.

15. A cell comprising the first and second isolated nucleic acids of claim 2.

16. A cell comprising the first and second isolated nucleic acids of claim 3.

17. A method of making a polypeptide, the method comprising culturing the cell of claim 14 under conditions suitable for the cell to express the polypeptide, wherein the polypeptide is produced.

18. A method of making a polypeptide, the method comprising culturing the cell of claim 15 under conditions suitable for the cell to express the polypeptide, wherein the polypeptide is produced.

19. A method of making a polypeptide, the method comprising culturing the cell of claim 16 under conditions suitable for the cell to express the polypeptide, wherein the polypeptide is produced.

* * * * *

SEQUENCE LISTING

```
<160> NUMBER OF SEQ ID NOS: 1314

<210> SEQ ID NO 1
<211> LENGTH: 122
<212> TYPE: PRT
<213> ORGANISM: Homo sapiens

<400> SEQUENCE: 1

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asn Tyr Asp Tyr Tyr Tyr Gly Met Asp Val Trp
            100                 105                 110

Gly Gln Gly Thr Thr Val Thr Val Ser Ser
        115                 120


<210> SEQ ID NO 2
<211> LENGTH: 121
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Ile Val Gly Gly Pro Tyr Gly Met Asp Val Trp Gly
            100                 105                 110

Gln Gly Thr Thr Val Thr Val Ser Ser
        115                 120
```

-continued

<210> SEQ ID NO 3
<211> LENGTH: 123
<212> TYPE: PRT
<213> ORGANISM: Homo sapiens

<400> SEQUENCE: 3

Glu Val Gln Leu Val Gln Ser Gly Ala Glu Val Glu Lys Pro Gly Ser
1               5                   10                  15

Ser Val Lys Val Ser Cys Lys Ala Ser Gly Gly Ser Phe Ser Ser Tyr
            20                  25                  30

Ala Phe Thr Trp Val Arg Gln Ala Pro Gly Gln Gly Leu Glu Trp Met
        35                  40                  45

Gly Arg Ile Val Pro Phe Leu Gly Val Pro Tyr Tyr Thr Gln Lys Phe
    50                  55                  60

Arg Gly Arg Val Thr Ile Thr Ala Asp Lys Ala Thr Ser Thr Val Tyr
65                  70                  75                  80

Met Glu Leu Ser Ser Leu Thr Phe Asp Asp Thr Ala Val Tyr Tyr Cys
                85                  90                  95

Ala Arg Asp Lys Arg Thr Tyr Glu Tyr Asn Trp Asn Ser Leu Trp Phe
            100                 105                 110

Trp Gly Arg Gly Thr Thr Val Thr Val Ser Ser
        115                 120

<210> SEQ ID NO 4
<211> LENGTH: 125
<212> TYPE: PRT
<213> ORGANISM: Homo sapiens

<400> SEQUENCE: 4

Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

Ser Phe Trp Ile Ala Trp Val Arg Gln Met Pro Gly Lys Gly Leu Glu
        35                  40                  45

Trp Met Gly Ile Ile Tyr Ala Gly Asp Ser Asp Thr Arg Tyr Ser Pro
    50                  55                  60

Ser Phe Gln Gly His Val Asn Ile Ser Val Asp Arg Ser Thr Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
        115                 120                 125

<210> SEQ ID NO 5
<211> LENGTH: 125
<212> TYPE: PRT
<213> ORGANISM: Homo sapiens

<400> SEQUENCE: 5

Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

Ser Phe Trp Ile Ala Trp Val Arg Gln Met Pro Gly Lys Gly Leu Glu
        35                  40                  45

```
Trp Met Gly Ile Ile Tyr Ala Gly Asp Ser Asp Thr Arg Tyr Ser Pro
    50                  55                  60

Ser Phe Gln Gly His Val Asn Ile Ser Val Asp Arg Ser Thr Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
        115                 120                 125


<210> SEQ ID NO 6
<211> LENGTH: 122
<212> TYPE: PRT
<213> ORGANISM: Homo sapiens

<400> SEQUENCE: 6

Gln Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asn Tyr Asp Tyr Tyr Tyr Gly Met Asp Val Trp
            100                 105                 110

Gly Gln Gly Thr Thr Val Thr Val Ser Ser
        115                 120


<210> SEQ ID NO 7
<211> LENGTH: 122
<212> TYPE: PRT
<213> ORGANISM: Homo sapiens

<400> SEQUENCE: 7

Gln Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asn Tyr Asp Tyr Tyr Tyr Gly Met Asp Val Trp
            100                 105                 110

Gly Gln Gly Thr Thr Val Thr Val Ser Ser
        115                 120
```

<210> SEQ ID NO 8
<211> LENGTH: 128
<212> TYPE: PRT
<213> ORGANISM: Homo sapiens

<400> SEQUENCE: 8

```
Gln Val Gln Leu Leu Gln Ser Ala Gly Gly Val Val Gln Pro Gly Arg
1               5                   10                  15

Ser Leu Arg Leu Ser Cys Ala Ala Ser Gly Phe Ile Phe Arg Thr Tyr
            20                  25                  30

Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Pro Arg Asp Asn Ala Lys Asn Thr Leu Tyr
65                  70                  75                  80

Leu Gln Met Asn Ser Leu Glu Thr Glu Asp Thr Ala Val Tyr Tyr Cys
                85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Thr Val Thr Val Ser Ser
        115                 120                 125
```

<210> SEQ ID NO 9
<211> LENGTH: 128
<212> TYPE: PRT
<213> ORGANISM: Homo sapiens

<400> SEQUENCE: 9

```
Glu Val Gln Leu Val Glu Ser Gly Gly Gly Val Val Gln Pro Gly Arg
1               5                   10                  15

Ser Leu Arg Leu Ser Cys Ala Thr Ser Gly Phe Ile Leu Arg Thr Tyr
            20                  25                  30

Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Pro Arg Asp Asn Ala Lys Asn Thr Leu Tyr
65                  70                  75                  80

Leu Gln Met Asn Ser Leu Glu Thr Glu Asp Thr Ala Val Tyr Tyr Cys
                85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Leu Val Thr Val Ser Ser
        115                 120                 125
```

<210> SEQ ID NO 10
<211> LENGTH: 128
<212> TYPE: PRT
<213> ORGANISM: Homo sapiens

<400> SEQUENCE: 10

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Ile Phe Arg Thr Tyr
            20                  25                  30
```

```
Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Glu Thr Glu Asp Thr Ala Met Tyr Tyr Cys
                85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Thr Val Thr Val Ser Ser
        115                 120                 125


<210> SEQ ID NO 11
<211> LENGTH: 123
<212> TYPE: PRT
<213> ORGANISM: Homo sapiens

<400> SEQUENCE: 11

Gln Val Asn Leu Arg Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110

Trp Gly Gln Gly Thr Leu Val Thr Val Ser Ser
        115                 120


<210> SEQ ID NO 12
<211> LENGTH: 123
<212> TYPE: PRT
<213> ORGANISM: Homo sapiens

<400> SEQUENCE: 12

Gln Val Asn Leu Arg Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110
```

Trp Gly Gln Gly Thr Leu Val Thr Val Ser Ser
115 120

<210> SEQ ID NO 13
<211> LENGTH: 123
<212> TYPE: PRT
<213> ORGANISM: Homo sapiens

<400> SEQUENCE: 13

Gln Val Asn Leu Arg Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Leu His Trp Val Arg Gln Thr Pro Gly Lys Gly Leu Glu Trp Val
35 40 45

Ala Leu Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Met Leu Tyr
65 70 75 80

Leu Gln Met Asn Ser Leu Arg Ala Glu Asp Thr Ala Val Tyr Tyr Cys
85 90 95

Ala Lys Asp Arg Ser His Tyr Gly Asp Tyr Val Gly Tyr Leu Asp Tyr
100 105 110

Trp Gly Gln Gly Thr Leu Val Thr Val Ser Ser
115 120

<210> SEQ ID NO 14
<211> LENGTH: 121
<212> TYPE: PRT
<213> ORGANISM: Homo sapiens

<400> SEQUENCE: 14

Glu Val Gln Leu Val Gln Ser Gly Gly Gly Leu Val Gln Pro Gly Gly
1 5 10 15

Ser Arg Arg Leu Ser Cys Ala Ala Ser Gly Phe Tyr Phe Asn Ala Tyr
20 25 30

Trp Met Thr Trp Val Arg Gln Ala Pro Gly Lys Gly Leu Glu Trp Val
35 40 45

Ala Asn Ile Asn Leu Asp Gly Thr Glu Ile Tyr Tyr Leu Asp Ser Val
50 55 60

Lys Gly Arg Phe Thr Val Ser Arg Asp Asn Val Lys Asn Ser Val Phe
65 70 75 80

Leu Gln Met Ser Ser Leu Arg Val Glu Asp Thr Ala Val Tyr Phe Cys
85 90 95

Ala Arg Leu Glu Trp Gly Gly Arg Asn Gly Trp Val Ser Pro Trp Gly
100 105 110

Gln Gly Thr Leu Val Thr Val Ser Ser
115 120

<210> SEQ ID NO 15
<211> LENGTH: 121
<212> TYPE: PRT
<213> ORGANISM: Homo sapiens

<400> SEQUENCE: 15

Gln Val Gln Leu Val Gln Ser Gly Gly Gly Leu Val Gln Pro Gly Gly
1 5 10 15

Ser Arg Arg Leu Ser Cys Ala Ala Ser Gly Phe Tyr Phe Asn Ala Tyr

```
            20                  25                  30

Trp Met Thr Trp Val Arg Gln Ala Pro Gly Lys Gly Leu Glu Trp Val
        35                  40                  45

Ala Asn Ile Asn Leu Asp Gly Thr Glu Ile Tyr Tyr Leu Asp Ser Val
    50                  55                  60

Lys Gly Arg Phe Thr Val Ser Arg Asp Asn Val Lys Asn Ser Val Phe
65                  70                  75                  80

Leu Gln Met Ser Ser Leu Arg Val Glu Asp Thr Ala Val Tyr Phe Cys
                85                  90                  95

Ala Arg Leu Glu Trp Gly Gly Arg Asn Gly Trp Val Ser Pro Trp Gly
            100                 105                 110

Gln Gly Thr Leu Val Thr Val Ser Ser
        115                 120


<210> SEQ ID NO 16
<211> LENGTH: 120
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Asn Val Ser Cys Lys Ala Ser Gly Tyr Thr Phe Thr Gly Tyr
            20                  25                  30

Tyr Ile Tyr Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Ile Asp Thr Ser Thr Asn Thr Ala Tyr
65                  70                  75                  80

Met Glu Leu Asn Arg Leu Arg Ala Asp Asp Thr Ala Val Tyr Tyr Cys
                85                  90                  95

Ala Arg Glu Trp Thr Gln Leu Trp Ser Pro Tyr Asp Tyr Trp Gly Gln
            100                 105                 110

Gly Thr Thr Val Thr Val Ser Ser
        115                 120


<210> SEQ ID NO 17
<211> LENGTH: 127
<212> TYPE: PRT
<213> ORGANISM: Homo sapiens

<400> SEQUENCE: 17

Gln Val Gln Leu Gln Glu Ser Gly Ser Arg Leu Val Lys Pro Ser Gln
1               5                   10                  15

Thr Leu Ser Leu Thr Cys Gly Val Ser Gly Gly Ser Ile Ser Ser Ser
            20                  25                  30

Ser Tyr Ser Trp Ser Trp Ile Arg Gln Thr Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Met Ser Val Asp Lys Ser Arg Asn Gln Phe
65                  70                  75                  80

Ser Leu Asn Met Ser Ser Val Thr Ala Ala Asp Thr Ala Val Tyr Tyr
                85                  90                  95

Cys Ala Arg Thr Ala Phe Tyr Tyr Glu Asn Thr Gly Pro Ile Arg Cys
```

```
            100                 105                 110

Tyr Leu Asp Phe Trp Gly Gln Gly Thr Leu Val Thr Val Ser Ser
        115                 120                 125


<210> SEQ ID NO 18
<211> LENGTH: 124
<212> TYPE: PRT
<213> ORGANISM: Homo sapiens

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Gly Met His Trp Val Arg Gln Ser Pro Gly Lys Gly Leu Glu Trp Val
        35                  40                  45

Ala Val Ile Trp Tyr Asp Gly Arg Asn Pro Tyr Tyr Ala Ala Ser Val
    50                  55                  60

Lys Gly Arg Phe Thr Ile Ser Arg Asp Asn Asp Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Leu Thr Arg Phe His Asp Thr Thr Phe Gly Val Phe Glu
            100                 105                 110

Met Trp Gly Pro Gly Thr Thr Val Thr Val Ser Ser
        115                 120


<210> SEQ ID NO 19
<211> LENGTH: 124
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Gly Met His Trp Val Arg Gln Ser Pro Gly Lys Gly Leu Glu Trp Val
        35                  40                  45

Ala Val Ile Trp Tyr Asp Gly Arg Asn Pro Tyr Tyr Ala Ala Ser Val
    50                  55                  60

Lys Gly Arg Phe Thr Ile Ser Arg Asp Asn Asp Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Leu Thr Arg Phe His Asp Thr Thr Phe Gly Val Phe Glu
            100                 105                 110

Met Trp Gly Pro Gly Thr Thr Val Thr Val Ser Ser
        115                 120


<210> SEQ ID NO 20
<211> LENGTH: 121
<212> TYPE: PRT
<213> ORGANISM: Homo sapiens

<400> SEQUENCE: 20

Gln Val Gln Leu Val Gln Ser Gly Gly Gly Leu Val Gln Pro Gly Gly
1               5                   10                  15
```

```
Ser Arg Arg Leu Ser Cys Ala Ala Ser Gly Phe Tyr Phe Lys Ala Tyr
            20                  25                  30

Trp Met Thr Trp Val Arg Gln Ala Pro Gly Lys Gly Leu Glu Trp Val
        35                  40                  45

Ala Asn Ile Asn Leu Asp Gly Thr Glu Ile Tyr Tyr Leu Asp Ser Val
    50                  55                  60

Lys Gly Arg Phe Thr Val Ser Arg Asp Asn Val Lys Asn Ser Val Phe
65                  70                  75                  80

Leu Gln Met Ser Ser Leu Arg Val Glu Asp Thr Ala Val Tyr Phe Cys
                85                  90                  95

Ala Arg Leu Glu Trp Gly Gly Arg Asn Gly Trp Val Ser Pro Trp Gly
            100                 105                 110

Gln Gly Thr Leu Val Thr Val Ser Ser
        115                 120


<210> SEQ ID NO 21
<211> LENGTH: 121
<212> TYPE: PRT
<213> ORGANISM: Homo sapiens

<400> SEQUENCE: 21

Glu Val Gln Leu Val Glu Ser Gly Gly Gly Leu Val Gln Pro Gly Gly
1               5                   10                  15

Ser Arg Arg Leu Ser Cys Ala Ala Ser Gly Phe Tyr Phe Asn Ala Tyr
            20                  25                  30

Trp Met Thr Trp Val Arg Gln Ala Pro Gly Lys Gly Leu Glu Trp Val
        35                  40                  45

Ala Asn Ile Asn Leu Asp Gly Thr Glu Ile Tyr Tyr Leu Asp Ser Val
    50                  55                  60

Lys Gly Arg Phe Thr Val Ser Arg Asp Asn Val Lys Asn Ser Val Phe
65                  70                  75                  80

Leu Gln Met Ser Ser Leu Arg Val Glu Asp Thr Ala Val Tyr Phe Cys
                85                  90                  95

Ala Arg Leu Glu Trp Gly Gly Arg Asn Gly Trp Leu Ser Pro Trp Gly
            100                 105                 110

Gln Gly Thr Leu Val Thr Val Ser Ser
        115                 120


<210> SEQ ID NO 22
<211> LENGTH: 127
<212> TYPE: PRT
<213> ORGANISM: Homo sapiens

<400> SEQUENCE: 22

Gln Val Gln Leu Gln Glu Ser Gly Ser Arg Leu Val Lys Pro Ser Gln
1               5                   10                  15

Thr Leu Ser Leu Thr Cys Gly Val Ser Gly Gly Ser Ile Ser Ser Ser
            20                  25                  30

Ser Tyr Ser Trp Ser Trp Ile Arg Gln Thr Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Met Ser Val Asp Lys Ser Arg Asn Gln Phe
65                  70                  75                  80

Ser Leu Asn Met Ser Ser Val Thr Ala Ala Asp Thr Ala Val Tyr Tyr
                85                  90                  95
```

Cys Ala Arg Thr Ala Phe Tyr Tyr Glu Asn Thr Gly Pro Ile Arg Cys
100 105 110

Tyr Leu Asp Phe Trp Gly Gln Gly Thr Leu Val Thr Val Ser Ser
115 120 125

<210> SEQ ID NO 23
<211> LENGTH: 128
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Pro Met Ser Trp Val Arg Gln Ala Pro Gly Lys Gly Leu Ala Trp Val
35 40 45

Ser Ser Leu Thr Ala Ser Gly Asp Asn Thr Phe Tyr Ala Asp Ser Val
50 55 60

Lys Gly Arg Phe Thr Ile Ser Arg Asp Asn Ser Asn Asn Thr Leu Tyr
65 70 75 80

Leu Gln Met His Ser Leu Arg Ala Glu Asp Thr Ala Val Tyr Tyr Cys
85 90 95

Ala Lys Ala Leu Val Gly Arg Tyr Asp Ile Ser Thr Gly Tyr Tyr Arg
100 105 110

Pro Val Met Asp Ser Trp Gly Gln Gly Thr Leu Val Thr Val Ser Ser
115 120 125

<210> SEQ ID NO 24
<211> LENGTH: 123
<212> TYPE: PRT
<213> ORGANISM: Homo sapiens

<400> SEQUENCE: 24

Gln Val Gln Leu Val Glu Ser Gly Gly Gly Val Val Gln Pro Gly Arg
1 5 10 15

Ser Leu Arg Leu Ser Cys Ala Ala Ser Gly Leu Thr Phe Ser Val Tyr
20 25 30

Gly Met His Trp Val Arg Gln Ala Pro Gly Lys Gly Leu Glu Trp Val
35 40 45

Ala Val Ile Ser His Thr Gly Ser Glu Glu Tyr Tyr Ala Asp Ser Val
50 55 60

Lys Gly Arg Phe Ser Ile Ser Arg Asp Asn Ser Asn Asn Thr Leu Phe
65 70 75 80

Leu Gln Met Asn Ser Leu Arg Pro Glu Asp Thr Ala Val Tyr Tyr Cys
85 90 95

Val Lys Asp Gly Pro Met Ala Ala Ile Pro Phe Tyr Tyr Phe Asp Phe
100 105 110

Trp Gly Gln Gly Thr Leu Val Thr Val Ser Ser
115 120

<210> SEQ ID NO 25
<211> LENGTH: 128
<212> TYPE: PRT
<213> ORGANISM: Homo sapiens

<400> SEQUENCE: 25

-continued

```
Gln Val Gln Leu Gln Glu Ser Gly Pro Gly Leu Val Lys Pro Ser Gln
1               5                   10                  15

Thr Leu Ser Leu Ser Cys Ser Val Ser Gly Ala Ser Ile Thr Ser Gly
            20                  25                  30

Thr Phe Tyr Trp Ser Trp Ile Arg Gln His Pro Gly Lys Asp Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Leu Ser Val Asp Thr Ser Lys Asn Gln Phe
65                  70                  75                  80

Ser Leu Lys Val Thr Ser Leu Thr Ala Ala Asp Thr Ala Val Tyr His
                85                  90                  95

Cys Ala Arg Gly Val Pro Ile Tyr Asp Ser Ser Gly Thr Tyr Arg Gly
            100                 105                 110

Thr Tyr Phe Asp Tyr Trp Gly Gln Gly Thr Leu Val Thr Val Ser Ser
        115                 120                 125


<210> SEQ ID NO 26
<211> LENGTH: 128
<212> TYPE: PRT
<213> ORGANISM: Homo sapiens

<400> SEQUENCE: 26

Gln Val Gln Leu Gln Glu Ser Gly Pro Gly Leu Val Lys Pro Ser Gln
1               5                   10                  15

Thr Leu Ser Leu Ser Cys Ser Val Ser Gly Ala Ser Ile Thr Ser Gly
            20                  25                  30

Thr Phe Tyr Trp Ser Trp Ile Arg Gln His Pro Gly Lys Asp Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Leu Ser Val Asp Thr Ser Lys Asn Gln Phe
65                  70                  75                  80

Ser Leu Lys Val Thr Ser Leu Thr Ala Ala Asp Thr Ala Val Tyr His
                85                  90                  95

Cys Ala Arg Gly Val Pro Ile Tyr Asp Ser Ser Gly Thr Tyr Arg Gly
            100                 105                 110

Thr Tyr Phe Asp Tyr Trp Gly Gln Gly Thr Leu Val Thr Val Ser Ser
        115                 120                 125


<210> SEQ ID NO 27
<211> LENGTH: 128
<212> TYPE: PRT
<213> ORGANISM: Homo sapiens

<400> SEQUENCE: 27

Gln Val Gln Leu Val Gln Ser Gly Gly Thr Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Thr Trp Val Arg Gln Ala Pro Gly Lys Gly Leu Ala Trp Val
        35                  40                  45

Ser Ser Val Ile Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asp Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Leu Asp Tyr Trp Gly Gln Gly Thr Thr Val Thr Val Ser Ser
        115                 120                 125


<210> SEQ ID NO 28
<211> LENGTH: 123
<212> TYPE: PRT
<213> ORGANISM: Homo sapiens

<400> SEQUENCE: 28

Glu Val Gln Leu Gln Glu Ser Gly Pro Gly Leu Val Lys Pro Ser Glu
1               5                   10                  15

Thr Leu Ser Val Thr Cys Ala Val Ser Gly Gly Ser Ile Ser Ser Ser
            20                  25                  30

Asn Tyr Ser Trp Ala Trp Ile Arg Gln Pro Pro Gly Lys Gly Leu Glu
        35                  40                  45

Trp Ile Gly Thr Met Tyr Tyr Ser Gly Ser Thr His Tyr His Pro Ser
    50                  55                  60

Leu Lys Ser Arg Val Thr Ile Ser Val Asp Thr Ser Lys Ser Gln Leu
65                  70                  75                  80

Ser Leu Lys Leu Ser Ser Val Thr Ala Ala Asp Thr Ala Val Tyr Tyr
                85                  90                  95

Cys Ala Arg Arg Arg Leu Leu Gly Pro Ser Pro Tyr Tyr Phe Asp Tyr
            100                 105                 110

Trp Gly Gln Gly Thr Leu Val Thr Val Ser Ser
        115                 120


<210> SEQ ID NO 29
<211> LENGTH: 123
<212> TYPE: PRT
<213> ORGANISM: Homo sapiens

<400> SEQUENCE: 29

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Arg Arg Asn
            20                  25                  30

Ala Ile His Trp Val Arg Gln Ala Pro Gly Lys Gly Leu Glu Trp Val
        35                  40                  45

Ala Leu Ile Ser Tyr Asp Gly Ile Asn Lys Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Val Ser Glu Tyr Gly Asp Tyr Val Gly His Phe Asp Tyr
            100                 105                 110

Trp Gly Gln Gly Thr Leu Val Thr Val Ser Ser
        115                 120


<210> SEQ ID NO 30
<211> LENGTH: 128
<212> TYPE: PRT
<213> ORGANISM: Homo sapiens
```

<400> SEQUENCE: 30

Gln Val Gln Leu Gln Glu Ser Gly Pro Gly Leu Val Lys Pro Ser Glu
1 5 10 15

Thr Leu Ser Leu Thr Cys Ser Val Ser Gly Gly Ser Ile Asn Ser Gly
20 25 30

Thr Tyr Tyr Trp Thr Trp Ile Arg Gln His Pro Gly Lys Gly Leu Glu
35 40 45

Trp Ile Gly Tyr Ile Tyr Tyr Ser Gly Thr Thr Tyr Tyr Asn Pro Ser
50 55 60

Leu Lys Ser Arg Val Ser Met Ser Val Asp Thr Ser Lys Asn Leu Phe
65 70 75 80

Ser Leu Lys Met Asn Ser Val Thr Ala Ala Asp Thr Ala Leu Tyr Tyr
85 90 95

Cys Ala Arg Gly Asn Pro Gln Tyr Asp Thr Ser Gly Ser Tyr Thr Gly
100 105 110

Leu Tyr Phe Asp Phe Trp Gly Gln Gly Thr Leu Val Thr Val Ser Ser
115 120 125

<210> SEQ ID NO 31
<211> LENGTH: 123
<212> TYPE: PRT
<213> ORGANISM: Homo sapiens

<400> SEQUENCE: 31

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Arg Arg Asn
20 25 30

Ala Ile His Trp Val Arg Gln Ala Pro Gly Lys Gly Leu Glu Trp Val
35 40 45

Ala Val Ile Ser Tyr Asp Gly Val Asn Lys Tyr Tyr Ala Ala Ser Val
50 55 60

Lys Gly Arg Phe Ala Ile Ser Arg Asp Asn Ala Lys Asn Thr Leu Phe
65 70 75 80

Leu Gln Met Asn Ser Leu Arg Pro Glu Asp Ser Ala Ile Tyr Tyr Cys
85 90 95

Ala Arg Asp Val Ser Glu Tyr Gly Asp Tyr Val Gly His Phe Asp Tyr
100 105 110

Trp Gly Gln Gly Thr Leu Val Thr Val Ser Ser
115 120

<210> SEQ ID NO 32
<211> LENGTH: 120
<212> TYPE: PRT
<213> ORGANISM: Homo sapiens

<400> SEQUENCE: 32

Glu Val Gln Leu Val Arg Ser Gly Gly Asn Leu Val Gln Pro Gly Gly
1 5 10 15

Ser Leu Arg Leu Ser Cys Ala Ala Thr Gly Pro Ile Gly Ser His Trp
20 25 30

Met Thr Trp Val Arg Gln Ala Pro Gly Gln Gly Leu Glu Trp Val Ala
35 40 45

Asn Ile Asn Leu Asp Gly Thr Glu Lys Phe Tyr Val Asp Ser Val Lys
50 55 60

Gly Arg Phe Thr Val Ser Arg Asp Asn Arg Lys Ser Ser Val Phe Leu

```
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120


<210> SEQ ID NO 33
<211> LENGTH: 121
<212> TYPE: PRT
<213> ORGANISM: Homo sapiens

<400> SEQUENCE: 33

Glu Val Gln Leu Val Gln Ser Gly Gly Asn Leu Val Gln Pro Gly Gly
1               5                   10                  15

Ser Leu Arg Leu Ser Cys Ala Ala Thr Gly Phe Pro Ile Gly Ser His
            20                  25                  30

Trp Met Thr Trp Val Arg Gln Ala Pro Gly Gln Gly Leu Glu Trp Val
        35                  40                  45

Ala Asn Ile Asn Leu Asp Gly Thr Glu Lys Phe Tyr Val Asp Ser Val
    50                  55                  60

Lys Gly Arg Phe Thr Val Ser Arg Asp Asn Arg Lys Ser Ser Val Phe
65                  70                  75                  80

Leu Gln Met Asn Asn Leu Arg Val Asp Asp Thr Ala Val Tyr Tyr Cys
                85                  90                  95

Ala Arg Leu Gln Trp Gly Gly Tyr Asn Gly Trp Leu Ser Pro Trp Gly
            100                 105                 110

Gln Gly Thr Leu Val Thr Val Ser Ser
        115                 120


<210> SEQ ID NO 34
<211> LENGTH: 121
<212> TYPE: PRT
<213> ORGANISM: Homo sapiens

<400> SEQUENCE: 34

Glu Val Gln Leu Val Gln Ser Gly Gly Asn Leu Val Gln Pro Gly Gly
1               5                   10                  15

Ser Leu Arg Leu Ser Cys Ala Ala Thr Gly Gly Pro Ile Gly Ser His
            20                  25                  30

Trp Met Thr Trp Val Arg Gln Ala Pro Gly Gln Gly Leu Glu Trp Val
        35                  40                  45

Ala Asn Ile Asn Leu Asp Gly Thr Glu Lys Phe Tyr Val Asp Ser Val
    50                  55                  60

Lys Gly Arg Phe Thr Val Ser Arg Asp Asn Arg Lys Ser Ser Val Phe
65                  70                  75                  80

Leu Gln Met Asn Asn Leu Arg Val Asp Asp Thr Ala Val Tyr Tyr Cys
                85                  90                  95

Ala Arg Leu Gln Trp Gly Gly Tyr Asn Gly Trp Leu Ser Pro Trp Gly
            100                 105                 110

Gln Gly Thr Leu Val Thr Val Ser Ser
        115                 120


<210> SEQ ID NO 35
<211> LENGTH: 121
<212> TYPE: PRT
```

<213> ORGANISM: Homo sapiens

<400> SEQUENCE: 35

Glu Val Gln Leu Val Gln Ser Gly Gly Asn Leu Val Gln Pro Gly Gly
1               5                   10                  15

Ser Leu Arg Leu Ser Cys Ala Ala Thr Gly Phe Tyr Ile Gly Ser His
            20                  25                  30

Trp Met Thr Trp Val Arg Gln Ala Pro Gly Gln Gly Leu Glu Trp Val
        35                  40                  45

Ala Asn Ile Asn Leu Asp Gly Thr Glu Lys Phe Tyr Val Asp Ser Val
    50                  55                  60

Lys Gly Arg Phe Thr Val Ser Arg Asp Asn Arg Lys Ser Ser Val Phe
65                  70                  75                  80

Leu Gln Met Asn Asn Leu Arg Val Asp Asp Thr Ala Val Tyr Tyr Cys
                85                  90                  95

Ala Arg Leu Gln Trp Gly Gly Tyr Asn Gly Trp Leu Ser Pro Trp Gly
            100                 105                 110

Gln Gly Thr Leu Val Thr Val Ser Ser
        115                 120

<210> SEQ ID NO 36
<211> LENGTH: 121
<212> TYPE: PRT
<213> ORGANISM: Homo sapiens

<400> SEQUENCE: 36

Glu Val Gln Leu Val Gln Ser Gly Gly Asn Leu Val Gln Pro Gly Gly
1               5                   10                  15

Ser Leu Arg Leu Ser Cys Ala Ala Thr Gly Phe Thr Ile Gly Ser His
            20                  25                  30

Trp Met Thr Trp Val Arg Gln Ala Pro Gly Gln Gly Leu Glu Trp Val
        35                  40                  45

Ala Asn Ile Asn Leu Asp Gly Thr Glu Lys Phe Tyr Val Asp Ser Val
    50                  55                  60

Lys Gly Arg Phe Thr Val Ser Arg Asp Asn Arg Lys Ser Ser Val Phe
65                  70                  75                  80

Leu Gln Met Asn Asn Leu Arg Val Asp Asp Thr Ala Val Tyr Tyr Cys
                85                  90                  95

Ala Arg Leu Gln Trp Gly Gly Tyr Asn Gly Trp Leu Ser Pro Trp Gly
            100                 105                 110

Gln Gly Thr Leu Val Thr Val Ser Ser
        115                 120

<210> SEQ ID NO 37
<211> LENGTH: 108
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Glu Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Pro Pro Leu
                85                  90                  95

Thr Phe Gly Gly Gly Thr Lys Val Glu Ile Lys Arg
            100                 105
```

<210> SEQ ID NO 38
<211> LENGTH: 108
<212> TYPE: PRT
<213> ORGANISM: Homo sapiens

<400> SEQUENCE: 38

```
Asp Ile Gln Met Thr Gln Ser Pro Ser Ser Val Ser Ala Ser Val Gly
1               5                   10                  15

Asn Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala Asn Ser Phe Pro Leu
                85                  90                  95

Thr Phe Gly Gly Gly Thr Lys Met Glu Ile Lys Arg
            100                 105
```

<210> SEQ ID NO 39
<211> LENGTH: 108
<212> TYPE: PRT
<213> ORGANISM: Homo sapiens

<400> SEQUENCE: 39

```
Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Leu Glu Ile Lys Arg
            100                 105
```

<210> SEQ ID NO 40
<211> LENGTH: 108
<212> TYPE: PRT
<213> ORGANISM: Homo sapiens

<400> SEQUENCE: 40

```
Asp Val Val Met Thr Gln Ser Pro Ser Ser Leu Ser Ala Ser Val Gly
1               5                   10                  15
```

```
Asp Arg Ile Thr Ile Thr Cys Gln Ala Gly Gln Asp Ile Ser Asn Phe
            20                  25                  30

Leu Asn Trp Tyr Gln Gln Lys Pro Gly Lys Ala Pro Lys Leu Leu Ile
        35                  40                  45

Arg Asp Ala Ser Asn Leu Glu Thr Gly Val Pro Ser Arg Phe Ser Gly
    50                  55                  60

Gly Gly Ser Gly Thr His Phe Thr Phe Thr Ile Ser Ser Leu His Pro
65                  70                  75                  80

Glu Asp Ile Ala Thr Tyr Phe Cys Gln Gln Tyr Asp Asn Leu Pro Tyr
                85                  90                  95

Thr Phe Gly Gln Gly Thr Lys Leu Glu Ile Lys Arg
            100                 105


<210> SEQ ID NO 41
<211> LENGTH: 109
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Glu Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Tyr Thr Phe Gly Gln Gly Thr Lys Leu Glu Ile Lys Arg
            100                 105


<210> SEQ ID NO 42
<211> LENGTH: 108
<212> TYPE: PRT
<213> ORGANISM: Homo sapiens

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Glu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Pro Pro Leu
                85                  90                  95

Thr Phe Gly Gly Gly Thr Lys Val Asp Ile Lys Arg
            100                 105


<210> SEQ ID NO 43
<211> LENGTH: 108
```

<212> TYPE: PRT
<213> ORGANISM: Homo sapiens

<400> SEQUENCE: 43

Asp Ile Gln Met Thr Gln Ser Pro Ser Ser Leu Ser Ala Ser Val Gly
1 5 10 15

Asp Arg Val Thr Ile Thr Cys Arg Ala Ser Gln Arg Ile Ser Asn Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Glu Val Pro Ser Arg Phe Ser Gly
50 55 60

Ser Gly Tyr Gly Thr Asp Phe Thr Leu Thr Ile Ser Ser Leu Gln Pro
65 70 75 80

Glu Asp Phe Ala Thr Tyr Tyr Cys Gln Gln Ser Tyr Arg Pro Pro Leu
85 90 95

Thr Phe Gly Gly Gly Thr Lys Val Asp Ile Lys Arg
100 105

<210> SEQ ID NO 44
<211> LENGTH: 108
<212> TYPE: PRT
<213> ORGANISM: Homo sapiens

<400> SEQUENCE: 44

Asp Ile Val Met Thr Gln Ser Pro Ser Thr Leu Ser Ala Ser Val Gly
1 5 10 15

Asp Arg Val Thr Val Thr Cys Arg Ala Ser Gln Ser Ile Asn Ser Trp
20 25 30

Leu Ala Trp Tyr Gln Gln Lys Pro Gly Lys Ala Pro Lys Leu Leu Ile
35 40 45

Tyr Glu Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asp Ser Tyr Trp Leu
85 90 95

Thr Phe Gly Gly Gly Thr Lys Val Glu Ile Lys Arg
100 105

<210> SEQ ID NO 45
<211> LENGTH: 108
<212> TYPE: PRT
<213> ORGANISM: Homo sapiens

<400> SEQUENCE: 45

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Val Ser Arg Trp
20 25 30

Leu Ala Trp Tyr Gln Gln Arg Pro Gly Glu Ala Pro Lys Leu Leu Ile
35 40 45

Tyr Gly Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asp Ser Phe Pro Leu

```
                85                  90                  95

Thr Phe Gly Gly Gly Thr Lys Val Glu Ile Lys Arg
            100                 105


<210> SEQ ID NO 46
<211> LENGTH: 108
<212> TYPE: PRT
<213> ORGANISM: Homo sapiens

<400> SEQUENCE: 46

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Lys Phe
            20                  25                  30

Leu Ala Trp Tyr Gln Gln Lys Arg Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Ala Leu Thr Ile Ser Ser Leu Gln Ser
65                  70                  75                  80

Glu Asp Phe Ala Asp Tyr Tyr Cys Gln Gln Tyr Asp Asn Trp Pro Ile
                85                  90                  95

Thr Phe Gly Gln Gly Thr Arg Leu Glu Ile Lys Arg
            100                 105


<210> SEQ ID NO 47
<211> LENGTH: 108
<212> TYPE: PRT
<213> ORGANISM: Homo sapiens

<400> SEQUENCE: 47

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Ala Phe Gly Gln Gly Thr Lys Leu Glu Ile Lys Arg
            100                 105


<210> SEQ ID NO 48
<211> LENGTH: 109
<212> TYPE: PRT
<213> ORGANISM: Homo sapiens

<400> SEQUENCE: 48

Ala Tyr Val Leu Thr Gln Pro Pro Ser Val Ser Val Ala Pro Gly Lys
1               5                   10                  15

Thr Ala Ala Ile Thr Cys Glu Gly Asn Asn Val Gly Asn Lys Asn Val
            20                  25                  30

His Trp Tyr Gln Gln Arg Pro Gly Gln Ala Pro Val Leu Val Val His
        35                  40                  45
```

```
Asp Asp Ser Asp Arg Pro Ser Gly Ile Pro Glu Arg Phe Ser Gly Ser
    50                  55                  60

Asn Ser Gly Asn Thr Ala Thr Leu Thr Ile Asn Arg Val Glu Ala Gly
65                  70                  75                  80

Asp Glu Ala Asp Tyr Tyr Cys Gln Val Trp Asp Ser Ser Ser Ala Gln
                85                  90                  95

Trp Val Phe Gly Gly Gly Thr Lys Leu Thr Val Leu Gly
            100                 105


<210> SEQ ID NO 49
<211> LENGTH: 111
<212> TYPE: PRT
<213> ORGANISM: Homo sapiens

<400> SEQUENCE: 49

Glu Ser Val Leu Thr Gln Pro Pro Leu Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Glu Asn Ser Lys Arg Ser Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly
            100                 105                 110


<210> SEQ ID NO 50
<211> LENGTH: 108
<212> TYPE: PRT
<213> ORGANISM: Homo sapiens

<400> SEQUENCE: 50

Asp Val Val Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Arg Pro Gly Lys Ala Pro Lys Leu Leu Ile
        35                  40                  45

Phe Ala Ala Ser Ser Leu Gln Ser Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105


<210> SEQ ID NO 51
<211> LENGTH: 108
<212> TYPE: PRT
<213> ORGANISM: Homo sapiens

<400> SEQUENCE: 51
```

```
Asp Ile Val Met Thr Gln Ser Pro Ser Ser Leu Ser Ala Ser Val Gly
1               5                   10                  15

Asp Arg Val Ser Ile Ser Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Thr Ser Ser Leu Glu Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105


<210> SEQ ID NO 52
<211> LENGTH: 108
<212> TYPE: PRT
<213> ORGANISM: Homo sapiens

<400> SEQUENCE: 52

Asp Ile Gln Met Thr Gln Ser Pro Ser Thr Leu Ser Ala Ser Ile Gly
1               5                   10                  15

Asp Arg Val Thr Ile Ser Cys Arg Ala Ser Gln Ser Ile Gln Ser Trp
            20                  25                  30

Leu Ala Trp Tyr Gln Gln Arg Pro Gly Glu Ala Pro Lys Leu Leu Ile
        35                  40                  45

Tyr Ser Ala Ser Thr Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Lys Leu Glu Ile Lys Arg
            100                 105


<210> SEQ ID NO 53
<211> LENGTH: 108
<212> TYPE: PRT
<213> ORGANISM: Homo sapiens

<400> SEQUENCE: 53

Asp Ile Val Leu Thr Gln Ser Pro Ser Thr Leu Ser Ala Ser Val Gly
1               5                   10                  15

Asp Arg Val Thr Ile Ser Cys Arg Ala Ser Arg Ser Ile Gly Trp Tyr
            20                  25                  30

Leu Asn Trp Tyr Gln Gln Arg Pro Gly Lys Ala Pro Lys Leu Leu Ile
        35                  40                  45

Tyr Ala Ala Ser Ser Leu His Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ala Phe Gly Phe Pro Arg
                85                  90                  95

Thr Phe Gly Gln Gly Thr Lys Val Glu Ile Lys Arg
            100                 105
```

-continued

<210> SEQ ID NO 54
<211> LENGTH: 108
<212> TYPE: PRT
<213> ORGANISM: Homo sapiens

<400> SEQUENCE: 54

```
Glu Ile Val Leu Thr Gln Ser Pro Ser Ser Leu Ser Ala Ser Val Gly
1               5                   10                  15

Asp Arg Ile Thr Ile Thr Cys Arg Ala Ser Gln Ser Ile Ser Ser Trp
            20                  25                  30

Leu Ala Trp Tyr Gln Gln Lys Pro Gly Lys Ala Pro Met Val Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Ser Arg
                85                  90                  95

Thr Phe Gly Gln Gly Thr Lys Val Glu Ile Lys Arg
            100                 105
```

<210> SEQ ID NO 55
<211> LENGTH: 107
<212> TYPE: PRT
<213> ORGANISM: Homo sapiens

<400> SEQUENCE: 55

```
Glu Ile Val Leu Thr Gln Ser Pro Ser Phe Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Leu Tyr Thr
                85                  90                  95

Phe Gly Gln Gly Thr Lys Val Asp Ile Lys Arg
            100                 105
```

<210> SEQ ID NO 56
<211> LENGTH: 108
<212> TYPE: PRT
<213> ORGANISM: Homo sapiens

<400> SEQUENCE: 56

```
Asp Ile Val Met Thr Gln Ser Pro Ser Ser Leu Ser Ala Ser Val Gly
1               5                   10                  15

Asp Arg Val Ser Ile Ser Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Thr Ser Ser Leu Glu Ser Gly Val Pro Ser Arg Phe Ser Gly
    50                  55                  60

Arg Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105


<210> SEQ ID NO 57
<211> LENGTH: 104
<212> TYPE: PRT
<213> ORGANISM: Homo sapiens

<400> SEQUENCE: 57

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ser Thr Tyr Trp
            20                  25                  30

Leu Ser Trp Tyr Gln Gln Lys Pro Gly Lys Ala Pro Lys Leu Leu Ile
        35                  40                  45

Tyr Lys Thr Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Trp Thr Phe Gly Gln
                85                  90                  95

Gly Thr Lys Val Glu Ile Lys Arg
            100


<210> SEQ ID NO 58
<211> LENGTH: 108
<212> TYPE: PRT
<213> ORGANISM: Homo sapiens

<400> SEQUENCE: 58

Asp Val Val Met Thr Gln Ser Pro Ser Ser Val Ser Ala Ser Val Gly
1               5                   10                  15

Asp Arg Val Thr Ile Thr Cys Arg Ala Ser Gln Gly Ile Gly Tyr Trp
            20                  25                  30

Leu Ala Trp Tyr Gln Gln Lys Pro Gly Lys Gly Pro Lys Leu Leu Ile
        35                  40                  45

Tyr Asp Ala Ser Arg Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Leu Glu Ile Lys Arg
            100                 105


<210> SEQ ID NO 59
<211> LENGTH: 108
<212> TYPE: PRT
<213> ORGANISM: Homo sapiens

<400> SEQUENCE: 59

Asp Ile Gln Met Thr Gln Ser Pro Pro Ser Leu Ser Ala Ser Val Gly
1               5                   10                  15

Asp Arg Val Thr Ile Thr Cys Arg Thr Ser Gln Gly Phe Thr Ser Ala
            20                  25                  30
```

```
Leu Ala Trp Tyr Gln Gln Lys Pro Gly Glu Pro Pro Lys Leu Leu Ile
        35                  40                  45

Tyr Asp Ala Ser Lys Leu Glu Ser Gly Val Pro Ser Arg Phe Ser Gly
    50                  55                  60

Ser Gly Ser Gly Thr Asn Phe Ala Leu Thr Ile Ser Ser Leu Gln Pro
65                  70                  75                  80

Glu Asp Phe Ala Thr Tyr Phe Cys Gln Gln Ser Asn Ser Tyr Pro Leu
                85                  90                  95

Thr Phe Gly Gly Gly Thr Lys Val Glu Ile Lys Arg
            100                 105


<210> SEQ ID NO 60
<211> LENGTH: 111
<212> TYPE: PRT
<213> ORGANISM: Homo sapiens

<400> SEQUENCE: 60

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu Gly
            100                 105                 110


<210> SEQ ID NO 61
<211> LENGTH: 111
<212> TYPE: PRT
<213> ORGANISM: Homo sapiens

<400> SEQUENCE: 61

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Ser Asn Val Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asp Gln Arg Pro Ser Gly Val Pro Asp Arg Phe Ser
    50                  55                  60

Gly Ser Lys Ser Gly Ala Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Leu Leu Phe Gly Gly Gly Thr Gln Leu Thr Val Leu Gly
            100                 105                 110


<210> SEQ ID NO 62
<211> LENGTH: 111
<212> TYPE: PRT
<213> ORGANISM: Homo sapiens
```

<400> SEQUENCE: 62

Glu Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Asn Asn Arg Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Ser Ser Leu
85 90 95

Ser Glu Val Val Phe Gly Gly Gly Thr Lys Val Thr Val Leu Gly
100 105 110

<210> SEQ ID NO 63
<211> LENGTH: 111
<212> TYPE: PRT
<213> ORGANISM: Homo sapiens

<400> SEQUENCE: 63

Gln Pro Gly Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Pro Val Asn Trp Tyr Gln His Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Ala Asp Ser Leu
85 90 95

Asn Gly Val Val Phe Gly Gly Gly Thr Lys Val Thr Val Leu Gly
100 105 110

<210> SEQ ID NO 64
<211> LENGTH: 112
<212> TYPE: PRT
<213> ORGANISM: Homo sapiens

<400> SEQUENCE: 64

Gln Ser Val Val Thr Gln Pro Pro Ser Val Ser Gly Ala Pro Gly Gln
1 5 10 15

Arg Val Thr Ile Ser Cys Ser Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Asn Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

```
Leu Ser Ala Tyr Val Phe Gly Thr Gly Thr Lys Leu Thr Val Leu Gly
            100                 105                 110


<210> SEQ ID NO 65
<211> LENGTH: 111
<212> TYPE: PRT
<213> ORGANISM: Homo sapiens

<400> SEQUENCE: 65

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Gln Leu Thr Val Leu Gly
            100                 105                 110


<210> SEQ ID NO 66
<211> LENGTH: 111
<212> TYPE: PRT
<213> ORGANISM: Homo sapiens

<400> SEQUENCE: 66

Gln Pro Val Leu Thr Gln Ser Pro Ser Ala Ser Gly Thr Pro Gly Gln
1               5                   10                  15

Arg Val Thr Ile Ser Cys Ser Gly Ser Ser Ser Asn Leu Gly Ser Asn
            20                  25                  30

Thr Val Ser Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ser Gly Gly Val Phe Gly Gly Gly Thr Lys Leu Thr Val Leu Gly
            100                 105                 110


<210> SEQ ID NO 67
<211> LENGTH: 112
<212> TYPE: PRT
<213> ORGANISM: Homo sapiens

<400> SEQUENCE: 67

Ser Tyr Glu Leu Met Gln Leu Pro Ser Ala Ser Gly Thr Pro Gly Gln
1               5                   10                  15

Arg Val Ser Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Ser Asn Asn His Arg Pro Ser Gly Val Pro Asp Arg Phe Ser
```

```
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly His Val Val Phe Gly Gly Gly Thr Lys Leu Thr Val Leu Gly
            100                 105                 110


<210> SEQ ID NO 68
<211> LENGTH: 108
<212> TYPE: PRT
<213> ORGANISM: Homo sapiens

<400> SEQUENCE: 68

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Leu Glu Ile Lys Arg
            100                 105


<210> SEQ ID NO 69
<211> LENGTH: 108
<212> TYPE: PRT
<213> ORGANISM: Homo sapiens

<400> SEQUENCE: 69

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Leu Glu Ile Lys Arg
            100                 105


<210> SEQ ID NO 70
<211> LENGTH: 108
<212> TYPE: PRT
<213> ORGANISM: Homo sapiens

<400> SEQUENCE: 70

Asp Ile Val Met Thr Gln Ser Pro Ser Ser Leu Ser Ala Ser Val Gly
1               5                   10                  15
```

```
Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Leu Glu Ile Lys Arg
            100                 105


<210> SEQ ID NO 71
<211> LENGTH: 108
<212> TYPE: PRT
<213> ORGANISM: Homo sapiens

<400> SEQUENCE: 71

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Leu Glu Ile Lys Arg
            100                 105


<210> SEQ ID NO 72
<211> LENGTH: 108
<212> TYPE: PRT
<213> ORGANISM: Homo sapiens

<400> SEQUENCE: 72

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Leu Glu Ile Lys Arg
            100                 105


<210> SEQ ID NO 73
```

<211> LENGTH: 119
<212> TYPE: PRT
<213> ORGANISM: Homo sapiens

<400> SEQUENCE: 73

Gln Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Thr Arg Tyr
20 25 30

Thr Ile Thr Trp Val Arg Gln Ala Pro Gly Gln Gly Leu Glu Trp Met
35 40 45

Gly Gly Ile Ile Pro Ile Phe Asp Lys Ala Asn Tyr Ala Gln Lys Phe
50 55 60

Gln Ser Arg Val Thr Phe Thr Ala Asp Ala Ser Thr Ser Thr Ala Tyr
65 70 75 80

Met Glu Leu Gly Ser Leu Arg Pro Glu Asp Thr Ala Val Tyr Tyr Cys
85 90 95

Ala Ala Tyr Ser Arg Gly Tyr Val His Phe Asp Tyr Trp Gly Pro Gly
100 105 110

Thr Leu Val Thr Val Ser Ser
115

<210> SEQ ID NO 74
<211> LENGTH: 126
<212> TYPE: PRT
<213> ORGANISM: Homo sapiens

<400> SEQUENCE: 74

Gln Val Gln Leu Val Glu Ser Gly Ala Glu Val Lys Lys Pro Gly Ser
1 5 10 15

Ser Val Lys Val Ser Cys Lys Ala Ser Gly Gly Thr Phe Ser Asn Ser
20 25 30

Gly Phe Thr Trp Val Arg Gln Val Pro Gly Gln Gly Leu Glu Trp Met
35 40 45

Gly Gly Ile Ile Pro Met Phe Gly Pro Ala Asn Tyr Ala Gln Lys Phe
50 55 60

Gln Gly Arg Val Thr Ile Thr Ala Asp Glu Ser Thr Arg Met Val Tyr
65 70 75 80

Met Glu Leu Arg Ser Leu Arg Ser Glu Asp Thr Ala Val Tyr Tyr Cys
85 90 95

Ala Arg Asp Gln Gly Glu Tyr Thr Val Gly Met Leu Leu Tyr Tyr Ala
100 105 110

Met Asp Val Trp Gly Glu Gly Thr Thr Val Thr Val Ser Ser
115 120 125

<210> SEQ ID NO 75
<211> LENGTH: 121
<212> TYPE: PRT
<213> ORGANISM: Homo sapiens

<400> SEQUENCE: 75

Gln Val Gln Leu Gln Glu Ser Gly Ala Glu Val Lys Lys Pro Gly Ser
1 5 10 15

Ser Val Lys Val Ser Cys Lys Ala Ser Gly Gly Asp Leu Asn Lys Tyr
20 25 30

Ala Ile Thr Trp Leu Arg Gln Ala Pro Gly Gln Gly Phe Glu Trp Met
35 40 45

```
Gly Gly Ile Thr Pro Ile Phe Ala Thr Thr Asn Tyr Ala Gln Lys Phe
    50                  55                  60

Gln Gly Arg Val Met Ile Thr Ala Asp Glu Val Thr Ser Thr Val Tyr
65                  70                  75                  80

Met Asp Leu Ser Ser Leu Gly Ser Glu Asp Thr Ala Ile Tyr Phe Cys
                85                  90                  95

Ala Lys Ser Pro Arg Gly Gly Ile Val Gly Thr Phe Asp Thr Trp Gly
            100                 105                 110

Gln Gly Thr Met Val Thr Val Ser Ser
        115                 120


<210> SEQ ID NO 76
<211> LENGTH: 124
<212> TYPE: PRT
<213> ORGANISM: Homo sapiens

<400> SEQUENCE: 76

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asn Tyr
            20                  25                  30

Asn Met Asn Trp Val Arg Gln Ala Pro Gly Lys Gly Leu Glu Trp Val
        35                  40                  45

Ser Ser Ile Ser Asp Gly Gly Ser Tyr Arg Tyr Tyr Ala Tyr Ser Val
    50                  55                  60

Lys Gly Arg Phe Thr Ile Ser Arg Asp Asn Thr Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Met Val His Gly Ile Leu Val Tyr Tyr Gly Met Asp
            100                 105                 110

Val Trp Gly Gln Gly Thr Thr Val Thr Val Ser Ser
        115                 120


<210> SEQ ID NO 77
<211> LENGTH: 121
<212> TYPE: PRT
<213> ORGANISM: Homo sapiens

<400> SEQUENCE: 77

Gln Val Gln Leu Gln Glu Ser Gly Gly Gly Leu Val Gln Pro Gly Gly
1               5                   10                  15

Ser Leu Arg Leu Ser Cys Gly Ala Ser Gly Phe Thr Phe Ser Ser Asp
            20                  25                  30

Ala Met Ser Trp Val Arg Gln Ala Pro Gly Lys Gly Leu Glu Trp Val
        35                  40                  45

Ala Ala Ile Leu Pro Ser Gly Glu Ala Thr Tyr Tyr Ala Asp Ser Val
    50                  55                  60

Lys Gly Arg Phe Thr Ile Ser Arg His Ser Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Ser Tyr His Ser Arg Leu Ala Ala Phe Asp Ile Trp Gly
            100                 105                 110

Gln Gly Thr Met Val Thr Val Ser Ser
        115                 120
```

<210> SEQ ID NO 78
<211> LENGTH: 121
<212> TYPE: PRT
<213> ORGANISM: Homo sapiens

<400> SEQUENCE: 78

Gln Val Gln Leu Gln Glu Ser Gly Gly Gly Leu Val Gln Pro Gly Gly
1 5 10 15

Ser Leu Arg Leu Ser Cys Gly Ala Ser Gly Phe Thr Phe Ser Ser Asp
20 25 30

Ala Met Ser Trp Val Arg Gln Ala Pro Gly Lys Gly Leu Glu Trp Val
35 40 45

Ala Ala Ile Leu Pro Ser Gly Glu Ala Thr Tyr Tyr Ala Asp Ser Val
50 55 60

Lys Gly Arg Phe Thr Ile Ser Arg His Ser Ser Lys Asn Thr Leu Tyr
65 70 75 80

Leu Gln Met Asn Ser Leu Arg Ala Asp Asp Thr Ala Val Tyr Tyr Cys
85 90 95

Ala Arg Asp Ser Tyr His Ser Arg Leu Ala Ala Phe Asp Ile Trp Gly
100 105 110

Gln Gly Thr Met Val Thr Val Ser Ser
115 120

<210> SEQ ID NO 79
<211> LENGTH: 124
<212> TYPE: PRT
<213> ORGANISM: Homo sapiens

<400> SEQUENCE: 79

Gln Val Gln Leu Val Gln Ser Gly Gly Gly Val Val Gln Pro Gly Arg
1 5 10 15

Pro Leu Arg Leu Ser Cys Ala Ala Ser Thr Phe Asn Phe Arg Asp Phe
20 25 30

Tyr Met Ser Trp Ile Arg Gln Ala Pro Gly Lys Gly Leu Glu Trp Val
35 40 45

Ser Tyr Ile Gly Ser Ser Gly Ser Ala Leu Gln Tyr Ala Asp Ser Val
50 55 60

Lys Gly Arg Phe Thr Ile Ser Arg Asp Asn Asp Lys Asn Val Leu Tyr
65 70 75 80

Leu Gln Met Thr Ser Leu Arg Ala Glu Asp Thr Ala Val Tyr Tyr Cys
85 90 95

Ala Arg Val Ala Ser Arg Tyr His Asp Val Leu Thr Asp Gly Phe Asp
100 105 110

Ile Trp Gly Gln Gly Thr Met Val Thr Val Ser Ser
115 120

<210> SEQ ID NO 80
<211> LENGTH: 124
<212> TYPE: PRT
<213> ORGANISM: Homo sapiens

<400> SEQUENCE: 80

Gln Val Gln Leu Val Gln Ser Gly Gly Gly Val Val Gln Pro Gly Lys
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val

```
        35                  40                  45

Ala Val Ile Ser Tyr Asp Gly Asn Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Phe Tyr Cys
                85                  90                  95

Ala Arg Ala Arg Leu Cys Thr Ser Thr Ser Cys Tyr Trp Thr Phe Asp
            100                 105                 110

Pro Trp Gly Gln Gly Thr Leu Val Thr Val Ser Ser
        115                 120


<210> SEQ ID NO 81
<211> LENGTH: 124
<212> TYPE: PRT
<213> ORGANISM: Homo sapiens

<400> SEQUENCE: 81

Gln Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Phe Tyr Cys
                85                  90                  95

Ala Arg Ala Arg Leu Cys Thr Ser Thr Ser Cys Tyr Trp Thr Phe Asp
            100                 105                 110

Pro Trp Gly Gln Gly Thr Leu Val Thr Val Ser Ser
        115                 120


<210> SEQ ID NO 82
<211> LENGTH: 121
<212> TYPE: PRT
<213> ORGANISM: Homo sapiens

<400> SEQUENCE: 82

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Arg Phe Ser Gly Tyr
            20                  25                  30

Ser Phe Asn Trp Val Arg Gln Ala Pro Gly Lys Gly Leu Glu Trp Val
        35                  40                  45

Ala Tyr Met Ser Ser Gly Gly Ser Ile Lys Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Val Asn Ser Leu Arg Asp Glu Asp Thr Ala Leu Tyr Tyr Cys
                85                  90                  95

Ala Arg Gly Pro Pro Gly Arg Pro Asn Asp Ala Phe Asp Ile Trp Gly
            100                 105                 110

Gln Gly Thr Met Val Thr Val Ser Ser
```

115 120

<210> SEQ ID NO 83
<211> LENGTH: 121
<212> TYPE: PRT
<213> ORGANISM: Homo sapiens

<400> SEQUENCE: 83

Glu Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Thr Trp Val Arg Gln Ala Pro Gly Lys Gly Leu Glu Trp Val
35 40 45

Ser Ser Ile Ser Val Ser Gly Asp Ser Thr Tyr Tyr Ala Asp Ser Val
50 55 60

Lys Gly Arg Phe Thr Ile Ser Arg Asp Asn Ser Lys Asn Thr Val Ser
65 70 75 80

Leu Gln Met Asn Ser Leu Arg Ala Glu Asp Thr Ala Leu Tyr Tyr Cys
85 90 95

Ala Lys Gly Leu Ser Lys Ala Asp Leu Phe Gly Met Asp Val Trp Gly
100 105 110

Gln Gly Thr Met Val Thr Val Ser Ser
115 120

<210> SEQ ID NO 84
<211> LENGTH: 120
<212> TYPE: PRT
<213> ORGANISM: Homo sapiens

<400> SEQUENCE: 84

Gln Val Gln Leu Gln Glu Ser Gly Pro Gly Leu Val Lys Pro Ser Glu
1 5 10 15

Thr Leu Ser Leu Thr Cys Ser Val Ser Gly Val Ser Ile Ser Asp Tyr
20 25 30

Tyr Trp Ser Trp Ile Arg Gln Pro Pro Gly Lys Gly Leu Glu Trp Ile
35 40 45

Gly Tyr Ile Tyr Tyr Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Asn Leu Ser Ser Val Thr Ala Ala Asp Thr Ala Val Tyr Tyr Cys Ala
85 90 95

Arg His Thr Ser Gly Trp Ser Gly Gly Ala Phe Asp Ile Trp Gly Gln
100 105 110

Gly Thr Met Val Thr Val Ser Ser
115 120

<210> SEQ ID NO 85
<211> LENGTH: 120
<212> TYPE: PRT
<213> ORGANISM: Homo sapiens

<400> SEQUENCE: 85

Gln Val Gln Leu Gln Glu Ser Gly Pro Gly Leu Val Lys Pro Ser Glu
1 5 10 15

Thr Leu Ser Leu Thr Cys Ser Val Ser Gly Val Ser Ile Ser Asp Tyr
20 25 30

Tyr Trp Ser Trp Ile Arg Gln Pro Pro Gly Lys Gly Leu Glu Trp Ile
35 40 45

Gly Tyr Ile Tyr Tyr Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Asn Leu Ser Ser Val Thr Ala Ala Asp Thr Ala Val Tyr Tyr Cys Ala
85 90 95

Arg His Thr Ser Gly Trp Ser Gly Gly Ala Phe Asp Ile Trp Gly Gln
100 105 110

Gly Thr Met Val Thr Val Ser Ser
115 120

<210> SEQ ID NO 86
<211> LENGTH: 120
<212> TYPE: PRT
<213> ORGANISM: Homo sapiens

<400> SEQUENCE: 86

Glu Val Gln Leu Val Gln Ser Gly Gly Asn Leu Val Gln Pro Gly Gly
1 5 10 15

Ser Leu Arg Leu Ser Cys Ala Ala Thr Gly Pro Ile Gly Ser His Trp
20 25 30

Met Thr Trp Val Arg Gln Ala Pro Gly Gln Gly Leu Glu Trp Val Ala
35 40 45

Asn Ile Asn Leu Asp Gly Thr Glu Lys Phe Tyr Val Asp Ser Val Lys
50 55 60

Gly Arg Phe Thr Val Ser Arg Asp Asn Arg Lys Ser Ser Val Phe Leu
65 70 75 80

Gln Met Asn Asn Leu Arg Val Asp Asp Thr Ala Val Tyr Tyr Cys Ala
85 90 95

Arg Leu Gln Trp Gly Gly Tyr Asn Gly Trp Leu Ser Pro Trp Gly Gln
100 105 110

Gly Thr Leu Val Thr Val Ser Ser
115 120

<210> SEQ ID NO 87
<211> LENGTH: 120
<212> TYPE: PRT
<213> ORGANISM: Homo sapiens

<400> SEQUENCE: 87

Glu Val Gln Leu Val Arg Ser Gly Gly Asn Leu Val Gln Pro Gly Gly
1 5 10 15

Ser Leu Arg Leu Ser Cys Ala Ala Thr Gly Pro Ile Gly Ser His Trp
20 25 30

Met Thr Trp Val Arg Gln Ala Pro Gly Gln Gly Leu Glu Trp Val Ala
35 40 45

Asn Ile Asn Leu Asp Gly Thr Glu Lys Phe Tyr Val Asp Ser Val Lys
50 55 60

Gly Arg Phe Thr Val Ser Arg Asp Asn Arg Lys Ser Ser Val Phe Leu
65 70 75 80

Gln Met Asn Asn Leu Arg Val Asp Asp Thr Ala Val Tyr Tyr Cys Ala
85 90 95

Arg Leu Gln Trp Gly Gly Tyr Asn Gly Trp Leu Ser Pro Trp Gly Gln
100 105 110

```
Gly Thr Leu Val Thr Val Ser Ser
        115                 120


<210> SEQ ID NO 88
<211> LENGTH: 124
<212> TYPE: PRT
<213> ORGANISM: Homo sapiens

<400> SEQUENCE: 88

Gln Val Gln Leu Val Gln Ser Gly Gly Gly Val Val Gln Pro Gly Lys
1               5                   10                  15

Ser Leu Arg Leu Ser Cys Ala Ala Ser Gly Phe Ala Phe Gly Gly Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Phe Tyr Cys
                85                  90                  95

Ala Arg Ala Arg Leu Cys Thr Ser Thr Ser Cys Tyr Trp Thr Phe Asp
            100                 105                 110

Pro Trp Gly Gln Gly Thr Leu Val Thr Val Ser Ser
        115                 120


<210> SEQ ID NO 89
<211> LENGTH: 120
<212> TYPE: PRT
<213> ORGANISM: Homo sapiens

<400> SEQUENCE: 89

Glu Val Gln Leu Val Arg Ser Gly Gly Asn Leu Val Gln Pro Gly Gly
1               5                   10                  15

Ser Leu Arg Leu Ser Cys Ala Ala Thr Gly Pro Ile Thr Gln His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120


<210> SEQ ID NO 90
<211> LENGTH: 120
<212> TYPE: PRT
<213> ORGANISM: Homo sapiens

<400> SEQUENCE: 90

Glu Val Gln Leu Val Arg Ser Gly Gly Asn Leu Val Gln Pro Gly Gly
1               5                   10                  15
```

```
Ser Leu Arg Leu Ser Cys Ala Ala Thr Gly Pro Ile Thr Gln His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120


<210> SEQ ID NO 91
<211> LENGTH: 108
<212> TYPE: PRT
<213> ORGANISM: Homo sapiens

<400> SEQUENCE: 91

Asp Ile Val Met Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Asp Ile Lys Arg
            100                 105


<210> SEQ ID NO 92
<211> LENGTH: 108
<212> TYPE: PRT
<213> ORGANISM: Homo sapiens

<400> SEQUENCE: 92

Glu Ile Val Leu Thr Gln Ser Pro Asp Ser Leu Ser Ala Ser Val Gly
1               5                   10                  15

Asp Arg Val Thr Ile Thr Cys Arg Ala Ser Gln Gly Ile Ser Gly Tyr
            20                  25                  30

Leu Ala Trp Tyr Gln His Lys Ala Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Tyr Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Phe
                85                  90                  95

Thr Phe Gly Gly Gly Thr Lys Val Glu Ile Lys Arg
            100                 105
```

<210> SEQ ID NO 93
<211> LENGTH: 108
<212> TYPE: PRT
<213> ORGANISM: Homo sapiens

<400> SEQUENCE: 93

```
Glu Ile Val Leu Thr Gln Ser Pro Ser Phe Leu Ser Ala Phe Val Gly
1               5                   10                  15

Asp Arg Val Thr Ile Thr Cys Arg Thr Ser Gln Ser Ile Asn Asn Tyr
            20                  25                  30

Leu Asn Trp Tyr Gln Gln Lys Ala Gly Lys Ala Pro Lys Leu Leu Ile
        35                  40                  45

Tyr Ala Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys Arg
            100                 105
```

<210> SEQ ID NO 94
<211> LENGTH: 109
<212> TYPE: PRT
<213> ORGANISM: Homo sapiens

<400> SEQUENCE: 94

```
Asp Ile Val Met Thr Gln Ser Pro Asp Ser Leu Ser Ala Ser Val Gly
1               5                   10                  15

Asp Ser Val Thr Ile Thr Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Ala Ala Ser Ser Arg Ala Ala Gly Val Pro Thr Gly Ser Val
    50                  55                  60

Ala Asp Gly Ser Gly Thr Asp Phe Thr Leu Thr Ile Ser Gly Leu Gln
65                  70                  75                  80

Pro Glu Asp Phe Ala Ala Tyr Tyr Cys Gln Gln Ser Tyr Ser Thr Pro
                85                  90                  95

Tyr Thr Phe Gly Gly Gly Thr Lys Val Glu Ile Lys Arg
            100                 105
```

<210> SEQ ID NO 95
<211> LENGTH: 108
<212> TYPE: PRT
<213> ORGANISM: Homo sapiens

<400> SEQUENCE: 95

```
Asp Ile Val Met Thr Gln Ser Pro Ser Phe Leu Ser Ala Phe Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Asp Phe Thr Leu Thr Ile Thr Ser Leu Gln Pro
```

```
65                  70                  75                  80

Asp Asp Phe Ala Thr Tyr Tyr Cys Gln Gln Tyr Asn Ala Tyr Pro Leu
                85                  90                  95

Thr Phe Gly Gly Gly Thr Lys Val Glu Ile Lys Arg
            100                 105


<210> SEQ ID NO 96
<211> LENGTH: 108
<212> TYPE: PRT
<213> ORGANISM: Homo sapiens

<400> SEQUENCE: 96

Glu Ile Val Leu Thr Gln Ser Pro Ser Thr Leu Ser Ala Ser Val Gly
1               5                   10                  15

Asp Arg Val Ala Ile Thr Cys Arg Ala Ser Gln Arg Ile Gly Ser Trp
            20                  25                  30

Leu Ala Trp Tyr Gln Gln Lys Pro Gly Lys Ala Pro Asn Pro Leu Ile
        35                  40                  45

Tyr Lys Ala Phe Ser Leu Glu Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Asp Ser Tyr Pro Tyr
                85                  90                  95

Thr Phe Gly Gln Gly Thr Lys Leu Glu Ile Lys Arg
            100                 105


<210> SEQ ID NO 97
<211> LENGTH: 107
<212> TYPE: PRT
<213> ORGANISM: Homo sapiens

<400> SEQUENCE: 97

Asp Val Val Met Thr Gln Ser Pro Ser Ser Leu Ser Ala Ser Ile Gly
1               5                   10                  15

Asp Arg Val Thr Phe Thr Cys Gln Ala Ser Gln Asp Ile Ser Asn Arg
            20                  25                  30

Leu Asn Trp Tyr Gln Gln Lys Pro Gly Lys Val Pro Lys Leu Leu Ile
        35                  40                  45

Ser Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Pro Leu Leu Thr
                85                  90                  95

Phe Gly Gly Gly Thr Lys Val Glu Ile Lys Arg
            100                 105


<210> SEQ ID NO 98
<211> LENGTH: 108
<212> TYPE: PRT
<213> ORGANISM: Homo sapiens

<400> SEQUENCE: 98

Asp Ile Gln Met Thr Gln Ser Pro Ser Ser Val Ser Ala Ser Val Gly
1               5                   10                  15

Asp Thr Val Thr Ile Ser Cys Arg Ala Ser Gln Gly Ile Ser Ser Trp
            20                  25                  30
```

-continued

```
Leu Ala Trp Tyr Gln Gln Lys Ser Gly Gln Ala Pro Thr Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Ile Ile Ser Ser Leu Gln Pro
65                  70                  75                  80

Glu Asp Phe Ala Thr Tyr Tyr Cys Gln Gln Ala Tyr Arg Thr Pro Ile
                85                  90                  95

Thr Phe Gly Gly Gly Thr Lys Val Glu Ile Lys Arg
            100                 105


<210> SEQ ID NO 99
<211> LENGTH: 108
<212> TYPE: PRT
<213> ORGANISM: Homo sapiens

<400> SEQUENCE: 99

Asp Ile Gln Met Thr Gln Ser Pro Ser Ser Val Ser Ala Ser Val Gly
1               5                   10                  15

Asp Arg Val Ser Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Pro
                85                  90                  95

Thr Phe Gly Gln Gly Thr Lys Leu Glu Ile Lys Arg
            100                 105


<210> SEQ ID NO 100
<211> LENGTH: 108
<212> TYPE: PRT
<213> ORGANISM: Homo sapiens

<400> SEQUENCE: 100

Ala Ser Val Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Ser Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Thr Gly Asn Gln
                85                  90                  95

Leu Phe Gly Gly Gly Thr Lys Val Thr Val Leu Gly
            100                 105


<210> SEQ ID NO 101
<211> LENGTH: 108
<212> TYPE: PRT
<213> ORGANISM: Homo sapiens
```

<400> SEQUENCE: 101

Ala Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Glu Asn Ser Arg Pro Ser Gly Ile Pro Asp Arg Phe Ser Gly Ser Ser
    50                  55                  60

Ser Gly Asn Thr Ala Ser Leu Thr Ile Ala Gly Ala Gln Ala Glu Asp
65                  70                  75                  80

Glu Ala Asp Tyr Tyr Cys Asn Ser Pro Asp Ser Ser Gly Ile His Leu
                85                  90                  95

Val Phe Gly Gly Gly Thr Lys Val Thr Val Leu Gly
            100                 105

<210> SEQ ID NO 102
<211> LENGTH: 114
<212> TYPE: PRT
<213> ORGANISM: Homo sapiens

<400> SEQUENCE: 102

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Pro Leu Thr Phe Gly Gly Gly Thr Lys Leu Glu Ile
            100                 105                 110

Lys Arg

<210> SEQ ID NO 103
<211> LENGTH: 113
<212> TYPE: PRT
<213> ORGANISM: Homo sapiens

<400> SEQUENCE: 103

Glu Ile Val Leu Thr Gln Ser Pro Asn Ser Leu Ala Val Ser Leu Gly
1               5                   10                  15

Glu Arg Ala Thr Ile Arg Cys Lys Ser Ser Gln Ser Val Leu Tyr Ser
            20                  25                  30

Gly Asn Asn Lys Asn Tyr Ile Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Glu Thr Asp Phe Thr Leu Thr
65                  70                  75                  80

Ile Ser Ser Leu Arg Ala Glu Asp Val Ala Leu Tyr Tyr Cys Gln Gln

```
                85                  90                  95

Tyr Tyr Ser Arg Trp Thr Phe Gly Gln Gly Thr Lys Leu Glu Ile Lys
            100                 105                 110

Arg


<210> SEQ ID NO 104
<211> LENGTH: 108
<212> TYPE: PRT
<213> ORGANISM: Homo sapiens

<400> SEQUENCE: 104

Asp Ile Val Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Thr Ser Asn Leu Gln Ser Gly Val Pro Ser Gly Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Thr Tyr Ser Thr Pro Pro
                85                  90                  95

Thr Phe Gly Gly Gly Thr Lys Leu Glu Ile Lys Arg
            100                 105


<210> SEQ ID NO 105
<211> LENGTH: 108
<212> TYPE: PRT
<213> ORGANISM: Homo sapiens

<400> SEQUENCE: 105

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys Arg
            100                 105


<210> SEQ ID NO 106
<211> LENGTH: 108
<212> TYPE: PRT
<213> ORGANISM: Homo sapiens

<400> SEQUENCE: 106

Asp Ile Gln Met Thr Gln Ser Pro Ser Ser Val Ser Ala Ser Val Gly
1               5                   10                  15

Asp Arg Val Ser Ile Thr Cys Gln Ala Ser Gln Asp Ile Ser Asn Tyr
            20                  25                  30
```

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Thr Pro Pro
                85                  90                  95

Thr Phe Gly Gln Gly Thr Lys Leu Glu Ile Lys Arg
            100                 105


<210> SEQ ID NO 107
<211> LENGTH: 108
<212> TYPE: PRT
<213> ORGANISM: Homo sapiens

<400> SEQUENCE: 107

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys Arg
            100                 105


<210> SEQ ID NO 108
<211> LENGTH: 108
<212> TYPE: PRT
<213> ORGANISM: Homo sapiens

<400> SEQUENCE: 108

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Leu Asn Thr Tyr Pro Gln
                85                  90                  95

Thr Phe Gly Gln Gly Thr Lys Val Glu Ile Lys Arg
            100                 105


<210> SEQ ID NO 109
<211> LENGTH: 15
<212> TYPE: PRT
<213> ORGANISM: Artificial Sequence
<220> FEATURE:
```

<223> OTHER INFORMATION: Polypeptide Linker

<400> SEQUENCE: 109

Gly Gly Gly Gly Ser Gly Gly Gly Gly Ser Gly Gly Gly Gly Ser
1 5 10 15

<210> SEQ ID NO 110
<211> LENGTH: 5
<212> TYPE: PRT
<213> ORGANISM: Artificial Sequence
<220> FEATURE:
<223> OTHER INFORMATION: Polypeptide Linker

<400> SEQUENCE: 110

Ser Ser Ser Ser Gly
1 5

<210> SEQ ID NO 111
<211> LENGTH: 15
<212> TYPE: PRT
<213> ORGANISM: Artificial Sequence
<220> FEATURE:
<223> OTHER INFORMATION: Polypeptide Linker

<400> SEQUENCE: 111

Ser Ser Ser Ser Gly Ser Ser Ser Ser Gly Ser Ser Ser Ser Gly
1 5 10 15

<210> SEQ ID NO 112
<211> LENGTH: 30
<212> TYPE: PRT
<213> ORGANISM: Homo sapiens

<400> SEQUENCE: 112

Gln Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Thr
20 25 30

<210> SEQ ID NO 113
<211> LENGTH: 5
<212> TYPE: PRT
<213> ORGANISM: Homo sapiens

<400> SEQUENCE: 113

Arg Tyr Thr Ile Thr
1 5

<210> SEQ ID NO 114
<211> LENGTH: 14
<212> TYPE: PRT
<213> ORGANISM: Homo sapiens

<400> SEQUENCE: 114

Trp Val Arg Gln Ala Pro Gly Gln Gly Leu Glu Trp Met Gly
1 5 10

<210> SEQ ID NO 115
<211> LENGTH: 17
<212> TYPE: PRT
<213> ORGANISM: Homo sapiens

<400> SEQUENCE: 115

Gly Ile Ile Pro Ile Phe Asp Lys Ala Asn Tyr Ala Gln Lys Phe Gln
1 5 10 15

Ser

<210> SEQ ID NO 116
<211> LENGTH: 32
<212> TYPE: PRT
<213> ORGANISM: Homo sapiens

<400> SEQUENCE: 116

Arg Val Thr Phe Thr Ala Asp Ala Ser Thr Ser Thr Ala Tyr Met Glu
1 5 10 15

Leu Gly Ser Leu Arg Pro Glu Asp Thr Ala Val Tyr Tyr Cys Ala Ala
20 25 30

<210> SEQ ID NO 117
<211> LENGTH: 10
<212> TYPE: PRT
<213> ORGANISM: Homo sapiens

<400> SEQUENCE: 117

Tyr Ser Arg Gly Tyr Val His Phe Asp Tyr
1 5 10

<210> SEQ ID NO 118
<211> LENGTH: 11
<212> TYPE: PRT
<213> ORGANISM: Homo sapiens

<400> SEQUENCE: 118

Trp Gly Pro Gly Thr Leu Val Thr Val Ser Ser
1 5 10

<210> SEQ ID NO 119
<211> LENGTH: 30
<212> TYPE: PRT
<213> ORGANISM: Homo sapiens

<400> SEQUENCE: 119

Gln Val Gln Leu Val Glu Ser Gly Ala Glu Val Lys Lys Pro Gly Ser
1 5 10 15

Ser Val Lys Val Ser Cys Lys Ala Ser Gly Gly Thr Phe Ser
20 25 30

<210> SEQ ID NO 120
<211> LENGTH: 5
<212> TYPE: PRT
<213> ORGANISM: Homo sapiens

<400> SEQUENCE: 120

Asn Ser Gly Phe Thr
1 5

<210> SEQ ID NO 121
<211> LENGTH: 14
<212> TYPE: PRT
<213> ORGANISM: Homo sapiens

<400> SEQUENCE: 121

Trp Val Arg Gln Val Pro Gly Gln Gly Leu Glu Trp Met Gly
1 5 10

<210> SEQ ID NO 122
<211> LENGTH: 17
<212> TYPE: PRT

<213> ORGANISM: Homo sapiens

<400> SEQUENCE: 122

Gly Ile Ile Pro Met Phe Gly Pro Ala Asn Tyr Ala Gln Lys Phe Gln
1 5 10 15

Gly

<210> SEQ ID NO 123
<211> LENGTH: 32
<212> TYPE: PRT
<213> ORGANISM: Homo sapiens

<400> SEQUENCE: 123

Arg Val Thr Ile Thr Ala Asp Glu Ser Thr Arg Met Val Tyr Met Glu
1 5 10 15

Leu Arg Ser Leu Arg Ser Glu Asp Thr Ala Val Tyr Tyr Cys Ala Arg
20 25 30

<210> SEQ ID NO 124
<211> LENGTH: 17
<212> TYPE: PRT
<213> ORGANISM: Homo sapiens

<400> SEQUENCE: 124

Asp Gln Gly Glu Tyr Thr Val Gly Met Leu Leu Tyr Tyr Ala Met Asp
1 5 10 15

Val

<210> SEQ ID NO 125
<211> LENGTH: 11
<212> TYPE: PRT
<213> ORGANISM: Homo sapiens

<400> SEQUENCE: 125

Trp Gly Glu Gly Thr Thr Val Thr Val Ser Ser
1 5 10

<210> SEQ ID NO 126
<211> LENGTH: 30
<212> TYPE: PRT
<213> ORGANISM: Homo sapiens

<400> SEQUENCE: 126

Gln Val Gln Leu Gln Glu Ser Gly Ala Glu Val Lys Lys Pro Gly Ser
1 5 10 15

Ser Val Lys Val Ser Cys Lys Ala Ser Gly Gly Asp Leu Asn
20 25 30

<210> SEQ ID NO 127
<211> LENGTH: 5
<212> TYPE: PRT
<213> ORGANISM: Homo sapiens

<400> SEQUENCE: 127

Lys Tyr Ala Ile Thr
1 5

<210> SEQ ID NO 128
<211> LENGTH: 14
<212> TYPE: PRT
<213> ORGANISM: Homo sapiens

<400> SEQUENCE: 128

Trp Leu Arg Gln Ala Pro Gly Gln Gly Phe Glu Trp Met Gly
1 5 10

<210> SEQ ID NO 129
<211> LENGTH: 17
<212> TYPE: PRT
<213> ORGANISM: Homo sapiens

<400> SEQUENCE: 129

Gly Ile Thr Pro Ile Phe Ala Thr Thr Asn Tyr Ala Gln Lys Phe Gln
1 5 10 15

Gly

<210> SEQ ID NO 130
<211> LENGTH: 32
<212> TYPE: PRT
<213> ORGANISM: Homo sapiens

<400> SEQUENCE: 130

Arg Val Met Ile Thr Ala Asp Glu Val Thr Ser Thr Val Tyr Met Asp
1 5 10 15

Leu Ser Ser Leu Gly Ser Glu Asp Thr Ala Ile Tyr Phe Cys Ala Lys
20 25 30

<210> SEQ ID NO 131
<211> LENGTH: 12
<212> TYPE: PRT
<213> ORGANISM: Homo sapiens

<400> SEQUENCE: 131

Ser Pro Arg Gly Gly Ile Val Gly Thr Phe Asp Thr
1 5 10

<210> SEQ ID NO 132
<211> LENGTH: 11
<212> TYPE: PRT
<213> ORGANISM: Homo sapiens

<400> SEQUENCE: 132

Trp Gly Gln Gly Thr Met Val Thr Val Ser Ser
1 5 10

<210> SEQ ID NO 133
<211> LENGTH: 30
<212> TYPE: PRT
<213> ORGANISM: Homo sapiens

<400> SEQUENCE: 133

Gln Val Gln Leu Val Glu Ser Gly Gly Gly Leu Val Lys Pro Gly Glu
1 5 10 15

Ser Leu Arg Leu Ser Cys Ala Ala Ser Gly Phe Thr Phe Ser
20 25 30

<210> SEQ ID NO 134
<211> LENGTH: 5
<212> TYPE: PRT
<213> ORGANISM: Homo sapiens

<400> SEQUENCE: 134

Asn Tyr Asn Met Asn
1 5

<210> SEQ ID NO 135
<211> LENGTH: 14
<212> TYPE: PRT
<213> ORGANISM: Homo sapiens

<400> SEQUENCE: 135

Trp Val Arg Gln Ala Pro Gly Lys Gly Leu Glu Trp Val Ser
1 5 10

<210> SEQ ID NO 136
<211> LENGTH: 17
<212> TYPE: PRT
<213> ORGANISM: Homo sapiens

<400> SEQUENCE: 136

Ser Ile Ser Asp Gly Gly Ser Tyr Arg Tyr Tyr Ala Tyr Ser Val Lys
1 5 10 15

Gly

<210> SEQ ID NO 137
<211> LENGTH: 32
<212> TYPE: PRT
<213> ORGANISM: Homo sapiens

<400> SEQUENCE: 137

Arg Phe Thr Ile Ser Arg Asp Asn Thr Lys Asn Ser Leu Tyr Leu Gln
1 5 10 15

Met Asn Ser Leu Arg Ala Glu Asp Thr Ala Leu Tyr Tyr Cys Ala Arg
20 25 30

<210> SEQ ID NO 138
<211> LENGTH: 15
<212> TYPE: PRT
<213> ORGANISM: Homo sapiens

<400> SEQUENCE: 138

Asp Glu Met Val His Gly Ile Leu Val Tyr Tyr Gly Met Asp Val
1 5 10 15

<210> SEQ ID NO 139
<211> LENGTH: 11
<212> TYPE: PRT
<213> ORGANISM: Homo sapiens

<400> SEQUENCE: 139

Trp Gly Gln Gly Thr Thr Val Thr Val Ser Ser
1 5 10

<210> SEQ ID NO 140
<211> LENGTH: 30
<212> TYPE: PRT
<213> ORGANISM: Homo sapiens

<400> SEQUENCE: 140

Gln Val Gln Leu Gln Glu Ser Gly Gly Gly Leu Val Gln Pro Gly Gly
1 5 10 15

Ser Leu Arg Leu Ser Cys Gly Ala Ser Gly Phe Thr Phe Ser
20 25 30

<210> SEQ ID NO 141
<211> LENGTH: 5
<212> TYPE: PRT
<213> ORGANISM: Homo sapiens

<400> SEQUENCE: 141

Ser Asp Ala Met Ser
1               5

<210> SEQ ID NO 142
<211> LENGTH: 14
<212> TYPE: PRT
<213> ORGANISM: Homo sapiens

<400> SEQUENCE: 142

Trp Val Arg Gln Ala Pro Gly Lys Gly Leu Glu Trp Val Ala
1               5                   10

<210> SEQ ID NO 143
<211> LENGTH: 17
<212> TYPE: PRT
<213> ORGANISM: Homo sapiens

<400> SEQUENCE: 143

Ala Ile Leu Pro Ser Gly Glu Ala Thr Tyr Tyr Ala Asp Ser Val Lys
1               5                   10                  15

Gly

<210> SEQ ID NO 144
<211> LENGTH: 32
<212> TYPE: PRT
<213> ORGANISM: Homo sapiens

<400> SEQUENCE: 144

Arg Phe Thr Ile Ser Arg His Ser Ser Lys Asn Thr Leu Tyr Leu Gln
1               5                   10                  15

Met Asn Ser Leu Arg Ala Asp Asp Thr Ala Val Tyr Tyr Cys Ala Arg
            20                  25                  30

<210> SEQ ID NO 145
<211> LENGTH: 12
<212> TYPE: PRT
<213> ORGANISM: Homo sapiens

<400> SEQUENCE: 145

Asp Ser Tyr His Ser Arg Leu Ala Ala Phe Asp Ile
1               5                   10

<210> SEQ ID NO 146
<211> LENGTH: 11
<212> TYPE: PRT
<213> ORGANISM: Homo sapiens

<400> SEQUENCE: 146

Trp Gly Gln Gly Thr Met Val Thr Val Ser Ser
1               5                   10

<210> SEQ ID NO 147
<211> LENGTH: 30
<212> TYPE: PRT
<213> ORGANISM: Homo sapiens

<400> SEQUENCE: 147

Gln Val Gln Leu Gln Glu Ser Gly Gly Gly Leu Val Gln Pro Gly Gly
1               5                   10                  15

Ser Leu Arg Leu Ser Cys Gly Ala Ser Gly Phe Thr Phe Ser
            20                  25                  30

-continued

<210> SEQ ID NO 148
<211> LENGTH: 5
<212> TYPE: PRT
<213> ORGANISM: Homo sapiens

<400> SEQUENCE: 148

Ser Asp Ala Met Ser
1 5

<210> SEQ ID NO 149
<211> LENGTH: 14
<212> TYPE: PRT
<213> ORGANISM: Homo sapiens

<400> SEQUENCE: 149

Trp Val Arg Gln Ala Pro Gly Lys Gly Leu Glu Trp Val Ala
1 5 10

<210> SEQ ID NO 150
<211> LENGTH: 17
<212> TYPE: PRT
<213> ORGANISM: Homo sapiens

<400> SEQUENCE: 150

Ala Ile Leu Pro Ser Gly Glu Ala Thr Tyr Tyr Ala Asp Ser Val Lys
1 5 10 15

Gly

<210> SEQ ID NO 151
<211> LENGTH: 32
<212> TYPE: PRT
<213> ORGANISM: Homo sapiens

<400> SEQUENCE: 151

Arg Phe Thr Ile Ser Arg His Ser Ser Lys Asn Thr Leu Tyr Leu Gln
1 5 10 15

Met Asn Ser Leu Arg Ala Asp Asp Thr Ala Val Tyr Tyr Cys Ala Arg
20 25 30

<210> SEQ ID NO 152
<211> LENGTH: 12
<212> TYPE: PRT
<213> ORGANISM: Homo sapiens

<400> SEQUENCE: 152

Asp Ser Tyr His Ser Arg Leu Ala Ala Phe Asp Ile
1 5 10

<210> SEQ ID NO 153
<211> LENGTH: 11
<212> TYPE: PRT
<213> ORGANISM: Homo sapiens

<400> SEQUENCE: 153

Trp Gly Gln Gly Thr Met Val Thr Val Ser Ser
1 5 10

<210> SEQ ID NO 154
<211> LENGTH: 30
<212> TYPE: PRT
<213> ORGANISM: Homo sapiens

<400> SEQUENCE: 154

```
Gln Val Gln Leu Val Gln Ser Gly Gly Gly Val Val Gln Pro Gly Arg
1               5                   10                  15

Pro Leu Arg Leu Ser Cys Ala Ala Ser Thr Phe Asn Phe Arg
            20                  25                  30


<210> SEQ ID NO 155
<211> LENGTH: 5
<212> TYPE: PRT
<213> ORGANISM: Homo sapiens

<400> SEQUENCE: 155

Asp Phe Tyr Met Ser
1               5


<210> SEQ ID NO 156
<211> LENGTH: 14
<212> TYPE: PRT
<213> ORGANISM: Homo sapiens

<400> SEQUENCE: 156

Trp Ile Arg Gln Ala Pro Gly Lys Gly Leu Glu Trp Val Ser
1               5                   10


<210> SEQ ID NO 157
<211> LENGTH: 17
<212> TYPE: PRT
<213> ORGANISM: Homo sapiens

<400> SEQUENCE: 157

Tyr Ile Gly Ser Ser Gly Ser Ala Leu Gln Tyr Ala Asp Ser Val Lys
1               5                   10                  15

Gly


<210> SEQ ID NO 158
<211> LENGTH: 32
<212> TYPE: PRT
<213> ORGANISM: Homo sapiens

<400> SEQUENCE: 158

Arg Phe Thr Ile Ser Arg Asp Asn Asp Lys Asn Val Leu Tyr Leu Gln
1               5                   10                  15

Met Thr Ser Leu Arg Ala Glu Asp Thr Ala Val Tyr Tyr Cys Ala Arg
            20                  25                  30


<210> SEQ ID NO 159
<211> LENGTH: 15
<212> TYPE: PRT
<213> ORGANISM: Homo sapiens

<400> SEQUENCE: 159

Val Ala Ser Arg Tyr His Asp Val Leu Thr Asp Gly Phe Asp Ile
1               5                   10                  15


<210> SEQ ID NO 160
<211> LENGTH: 11
<212> TYPE: PRT
<213> ORGANISM: Homo sapiens

<400> SEQUENCE: 160

Trp Gly Gln Gly Thr Met Val Thr Val Ser Ser
1               5                   10


<210> SEQ ID NO 161
```

<211> LENGTH: 30
<212> TYPE: PRT
<213> ORGANISM: Homo sapiens

<400> SEQUENCE: 161

Gln Val Gln Leu Val Gln Ser Gly Gly Gly Val Val Gln Pro Gly Lys
1 5 10 15

Ser Leu Arg Leu Ser Cys Ala Ala Ser Gly Phe Thr Phe Ser
20 25 30

<210> SEQ ID NO 162
<211> LENGTH: 5
<212> TYPE: PRT
<213> ORGANISM: Homo sapiens

<400> SEQUENCE: 162

Ser Tyr Ala Met His
1 5

<210> SEQ ID NO 163
<211> LENGTH: 14
<212> TYPE: PRT
<213> ORGANISM: Homo sapiens

<400> SEQUENCE: 163

Trp Val Arg Gln Ala Pro Gly Lys Gly Leu Glu Trp Val Ala
1 5 10

<210> SEQ ID NO 164
<211> LENGTH: 17
<212> TYPE: PRT
<213> ORGANISM: Homo sapiens

<400> SEQUENCE: 164

Val Ile Ser Tyr Asp Gly Asn Lys Lys Tyr Tyr Ala Asp Ser Val Lys
1 5 10 15

Gly

<210> SEQ ID NO 165
<211> LENGTH: 32
<212> TYPE: PRT
<213> ORGANISM: Homo sapiens

<400> SEQUENCE: 165

Arg Phe Thr Ile Ser Arg Asp Asn Ser Lys Asn Thr Leu Tyr Leu Gln
1 5 10 15

Met Asn Ser Leu Arg Ala Glu Asp Ala Ala Val Phe Tyr Cys Ala Arg
20 25 30

<210> SEQ ID NO 166
<211> LENGTH: 15
<212> TYPE: PRT
<213> ORGANISM: Homo sapiens

<400> SEQUENCE: 166

Ala Arg Leu Cys Thr Ser Thr Ser Cys Tyr Trp Thr Phe Asp Pro
1 5 10 15

<210> SEQ ID NO 167
<211> LENGTH: 11
<212> TYPE: PRT
<213> ORGANISM: Homo sapiens

<400> SEQUENCE: 167

Trp Gly Gln Gly Thr Leu Val Thr Val Ser Ser
1 5 10

<210> SEQ ID NO 168
<211> LENGTH: 30
<212> TYPE: PRT
<213> ORGANISM: Homo sapiens

<400> SEQUENCE: 168

Gln Val Gln Leu Val Gln Ser Gly Gly Gly Val Val Gln Pro Gly Lys
1 5 10 15

Ser Leu Arg Leu Ser Cys Ala Ala Ser Gly Phe Thr Phe Ser
20 25 30

<210> SEQ ID NO 169
<211> LENGTH: 5
<212> TYPE: PRT
<213> ORGANISM: Homo sapiens

<400> SEQUENCE: 169

Ser Tyr Ala Met His
1 5

<210> SEQ ID NO 170
<211> LENGTH: 14
<212> TYPE: PRT
<213> ORGANISM: Homo sapiens

<400> SEQUENCE: 170

Trp Val Arg Gln Ala Pro Gly Lys Gly Leu Glu Trp Val Ala
1 5 10

<210> SEQ ID NO 171
<211> LENGTH: 17
<212> TYPE: PRT
<213> ORGANISM: Homo sapiens

<400> SEQUENCE: 171

Val Ile Ser Tyr Asp Gly Asn Lys Lys Tyr Tyr Ala Asp Ser Val Lys
1 5 10 15

Gly

<210> SEQ ID NO 172
<211> LENGTH: 32
<212> TYPE: PRT
<213> ORGANISM: Homo sapiens

<400> SEQUENCE: 172

Arg Phe Thr Ile Ser Arg Asp Asn Ser Lys Asn Thr Leu Tyr Leu Gln
1 5 10 15

Met Asn Ser Leu Arg Ala Glu Asp Ala Ala Val Phe Tyr Cys Ala Arg
20 25 30

<210> SEQ ID NO 173
<211> LENGTH: 15
<212> TYPE: PRT
<213> ORGANISM: Homo sapiens

<400> SEQUENCE: 173

Ala Arg Leu Cys Thr Ser Thr Ser Cys Tyr Trp Thr Phe Asp Pro
1 5 10 15

<210> SEQ ID NO 174
<211> LENGTH: 11
<212> TYPE: PRT
<213> ORGANISM: Homo sapiens

<400> SEQUENCE: 174

Trp Gly Gln Gly Thr Leu Val Thr Val Ser Ser
1               5                   10

<210> SEQ ID NO 175
<211> LENGTH: 30
<212> TYPE: PRT
<213> ORGANISM: Homo sapiens

<400> SEQUENCE: 175

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Arg Phe Ser
            20                  25                  30

<210> SEQ ID NO 176
<211> LENGTH: 5
<212> TYPE: PRT
<213> ORGANISM: Homo sapiens

<400> SEQUENCE: 176

Gly Tyr Ser Phe Asn
1               5

<210> SEQ ID NO 177
<211> LENGTH: 14
<212> TYPE: PRT
<213> ORGANISM: Homo sapiens

<400> SEQUENCE: 177

Trp Val Arg Gln Ala Pro Gly Lys Gly Leu Glu Trp Val Ala
1               5                   10

<210> SEQ ID NO 178
<211> LENGTH: 17
<212> TYPE: PRT
<213> ORGANISM: Homo sapiens

<400> SEQUENCE: 178

Tyr Met Ser Ser Gly Gly Ser Ile Lys Asn Tyr Ala Asp Ser Val Lys
1               5                   10                  15

Gly

<210> SEQ ID NO 179
<211> LENGTH: 32
<212> TYPE: PRT
<213> ORGANISM: Homo sapiens

<400> SEQUENCE: 179

Arg Phe Thr Ile Ser Arg Asp Asn Ala Lys Asn Ser Leu Tyr Leu Gln
1               5                   10                  15

Val Asn Ser Leu Arg Asp Glu Asp Thr Ala Leu Tyr Tyr Cys Ala Arg
            20                  25                  30

<210> SEQ ID NO 180
<211> LENGTH: 12
<212> TYPE: PRT
<213> ORGANISM: Homo sapiens

<400> SEQUENCE: 180

Gly Pro Pro Gly Arg Pro Asn Asp Ala Phe Asp Ile
1 5 10

<210> SEQ ID NO 181
<211> LENGTH: 11
<212> TYPE: PRT
<213> ORGANISM: Homo sapiens

<400> SEQUENCE: 181

Trp Gly Gln Gly Thr Met Val Thr Val Ser Ser
1 5 10

<210> SEQ ID NO 182
<211> LENGTH: 30
<212> TYPE: PRT
<213> ORGANISM: Homo sapiens

<400> SEQUENCE: 182

Glu Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 183
<211> LENGTH: 5
<212> TYPE: PRT
<213> ORGANISM: Homo sapiens

<400> SEQUENCE: 183

Ser Tyr Ala Met Thr
1 5

<210> SEQ ID NO 184
<211> LENGTH: 14
<212> TYPE: PRT
<213> ORGANISM: Homo sapiens

<400> SEQUENCE: 184

Trp Val Arg Gln Ala Pro Gly Lys Gly Leu Glu Trp Val Ser
1 5 10

<210> SEQ ID NO 185
<211> LENGTH: 17
<212> TYPE: PRT
<213> ORGANISM: Homo sapiens

<400> SEQUENCE: 185

Ser Ile Ser Val Ser Gly Asp Ser Thr Tyr Tyr Ala Asp Ser Val Lys
1 5 10 15

Gly

<210> SEQ ID NO 186
<211> LENGTH: 32
<212> TYPE: PRT
<213> ORGANISM: Homo sapiens

<400> SEQUENCE: 186

Arg Phe Thr Ile Ser Arg Asp Asn Ser Lys Asn Thr Val Ser Leu Gln
1 5 10 15

Met Asn Ser Leu Arg Ala Glu Asp Thr Ala Leu Tyr Tyr Cys Ala Lys
20 25 30

```
<210> SEQ ID NO 187
<211> LENGTH: 12
<212> TYPE: PRT
<213> ORGANISM: Homo sapiens

<400> SEQUENCE: 187

Gly Leu Ser Lys Ala Asp Leu Phe Gly Met Asp Val
1               5                   10


<210> SEQ ID NO 188
<211> LENGTH: 11
<212> TYPE: PRT
<213> ORGANISM: Homo sapiens

<400> SEQUENCE: 188

Trp Gly Gln Gly Thr Met Val Thr Val Ser Ser
1               5                   10


<210> SEQ ID NO 189
<211> LENGTH: 30
<212> TYPE: PRT
<213> ORGANISM: Homo sapiens

<400> SEQUENCE: 189

Gln Val Gln Leu Gln Glu Ser Gly Pro Gly Leu Val Lys Pro Ser Glu
1               5                   10                  15

Thr Leu Ser Leu Thr Cys Ser Val Ser Gly Val Ser Ile Ser
            20                  25                  30


<210> SEQ ID NO 190
<211> LENGTH: 5
<212> TYPE: PRT
<213> ORGANISM: Homo sapiens

<400> SEQUENCE: 190

Asp Tyr Tyr Trp Ser
1               5


<210> SEQ ID NO 191
<211> LENGTH: 14
<212> TYPE: PRT
<213> ORGANISM: Homo sapiens

<400> SEQUENCE: 191

Trp Ile Arg Gln Pro Pro Gly Lys Gly Leu Glu Trp Ile Gly
1               5                   10


<210> SEQ ID NO 192
<211> LENGTH: 16
<212> TYPE: PRT
<213> ORGANISM: Homo sapiens

<400> SEQUENCE: 192

Tyr Ile Tyr Tyr Ser Gly Ser Thr Asn Tyr Asn Pro Ser Leu Lys Ser
1               5                   10                  15


<210> SEQ ID NO 193
<211> LENGTH: 32
<212> TYPE: PRT
<213> ORGANISM: Homo sapiens

<400> SEQUENCE: 193

Arg Val Thr Ile Ser Val Asp Thr Ser Lys Asn Gln Phe Ser Leu Asn
1               5                   10                  15
```

```
Leu Ser Ser Val Thr Ala Ala Asp Thr Ala Val Tyr Tyr Cys Ala Arg
            20                  25                  30


<210> SEQ ID NO 194
<211> LENGTH: 12
<212> TYPE: PRT
<213> ORGANISM: Homo sapiens

<400> SEQUENCE: 194

His Thr Ser Gly Trp Ser Gly Gly Ala Phe Asp Ile
1               5                   10


<210> SEQ ID NO 195
<211> LENGTH: 11
<212> TYPE: PRT
<213> ORGANISM: Homo sapiens

<400> SEQUENCE: 195

Trp Gly Gln Gly Thr Met Val Thr Val Ser Ser
1               5                   10


<210> SEQ ID NO 196
<211> LENGTH: 30
<212> TYPE: PRT
<213> ORGANISM: Homo sapiens

<400> SEQUENCE: 196

Gln Val Gln Leu Gln Glu Ser Gly Pro Gly Leu Val Lys Pro Ser Glu
1               5                   10                  15

Thr Leu Ser Leu Thr Cys Ser Val Ser Gly Val Ser Ile Ser
            20                  25                  30


<210> SEQ ID NO 197
<211> LENGTH: 5
<212> TYPE: PRT
<213> ORGANISM: Homo sapiens

<400> SEQUENCE: 197

Asp Tyr Tyr Trp Ser
1               5


<210> SEQ ID NO 198
<211> LENGTH: 14
<212> TYPE: PRT
<213> ORGANISM: Homo sapiens

<400> SEQUENCE: 198

Trp Ile Arg Gln Pro Pro Gly Lys Gly Leu Glu Trp Ile Gly
1               5                   10


<210> SEQ ID NO 199
<211> LENGTH: 16
<212> TYPE: PRT
<213> ORGANISM: Homo sapiens

<400> SEQUENCE: 199

Tyr Ile Tyr Tyr Ser Gly Ser Thr Asn Tyr Asn Pro Ser Leu Lys Ser
1               5                   10                  15


<210> SEQ ID NO 200
<211> LENGTH: 32
<212> TYPE: PRT
<213> ORGANISM: Homo sapiens
```

<400> SEQUENCE: 200

Arg Val Thr Ile Ser Val Asp Thr Ser Lys Asn Gln Phe Ser Leu Asn
1 5 10 15

Leu Ser Ser Val Thr Ala Ala Asp Thr Ala Val Tyr Tyr Cys Ala Arg
20 25 30

<210> SEQ ID NO 201
<211> LENGTH: 12
<212> TYPE: PRT
<213> ORGANISM: Homo sapiens

<400> SEQUENCE: 201

His Thr Ser Gly Trp Ser Gly Gly Ala Phe Asp Ile
1 5 10

<210> SEQ ID NO 202
<211> LENGTH: 11
<212> TYPE: PRT
<213> ORGANISM: Homo sapiens

<400> SEQUENCE: 202

Trp Gly Gln Gly Thr Met Val Thr Val Ser Ser
1 5 10

<210> SEQ ID NO 203
<211> LENGTH: 29
<212> TYPE: PRT
<213> ORGANISM: Homo sapiens

<400> SEQUENCE: 203

Glu Val Gln Leu Val Gln Ser Gly Gly Asn Leu Val Gln Pro Gly Gly
1 5 10 15

Ser Leu Arg Leu Ser Cys Ala Ala Thr Gly Pro Ile Gly
20 25

<210> SEQ ID NO 204
<211> LENGTH: 5
<212> TYPE: PRT
<213> ORGANISM: Homo sapiens

<400> SEQUENCE: 204

Ser His Trp Met Thr
1 5

<210> SEQ ID NO 205
<211> LENGTH: 14
<212> TYPE: PRT
<213> ORGANISM: Homo sapiens

<400> SEQUENCE: 205

Trp Val Arg Gln Ala Pro Gly Gln Gly Leu Glu Trp Val Ala
1 5 10

<210> SEQ ID NO 206
<211> LENGTH: 17
<212> TYPE: PRT
<213> ORGANISM: Homo sapiens

<400> SEQUENCE: 206

Asn Ile Asn Leu Asp Gly Thr Glu Lys Phe Tyr Val Asp Ser Val Lys
1 5 10 15

Gly

<210> SEQ ID NO 207
<211> LENGTH: 32
<212> TYPE: PRT
<213> ORGANISM: Homo sapiens

<400> SEQUENCE: 207

Arg Phe Thr Val Ser Arg Asp Asn Arg Lys Ser Ser Val Phe Leu Gln
1 5 10 15

Met Asn Asn Leu Arg Val Asp Asp Thr Ala Val Tyr Tyr Cys Ala Arg
20 25 30

<210> SEQ ID NO 208
<211> LENGTH: 12
<212> TYPE: PRT
<213> ORGANISM: Homo sapiens

<400> SEQUENCE: 208

Leu Gln Trp Gly Gly Tyr Asn Gly Trp Leu Ser Pro
1 5 10

<210> SEQ ID NO 209
<211> LENGTH: 11
<212> TYPE: PRT
<213> ORGANISM: Homo sapiens

<400> SEQUENCE: 209

Trp Gly Gln Gly Thr Leu Val Thr Val Ser Ser
1 5 10

<210> SEQ ID NO 210
<211> LENGTH: 29
<212> TYPE: PRT
<213> ORGANISM: Homo sapiens

<400> SEQUENCE: 210

Glu Val Gln Leu Val Arg Ser Gly Gly Asn Leu Val Gln Pro Gly Gly
1 5 10 15

Ser Leu Arg Leu Ser Cys Ala Ala Thr Gly Pro Ile Gly
20 25

<210> SEQ ID NO 211
<211> LENGTH: 5
<212> TYPE: PRT
<213> ORGANISM: Homo sapiens

<400> SEQUENCE: 211

Ser His Trp Met Thr
1 5

<210> SEQ ID NO 212
<211> LENGTH: 14
<212> TYPE: PRT
<213> ORGANISM: Homo sapiens

<400> SEQUENCE: 212

Trp Val Arg Gln Ala Pro Gly Gln Gly Leu Glu Trp Val Ala
1 5 10

<210> SEQ ID NO 213
<211> LENGTH: 17
<212> TYPE: PRT
<213> ORGANISM: Homo sapiens

<400> SEQUENCE: 213

Asn Ile Asn Leu Asp Gly Thr Glu Lys Phe Tyr Val Asp Ser Val Lys
1 5 10 15

Gly

<210> SEQ ID NO 214
<211> LENGTH: 32
<212> TYPE: PRT
<213> ORGANISM: Homo sapiens

<400> SEQUENCE: 214

Arg Phe Thr Val Ser Arg Asp Asn Arg Lys Ser Ser Val Phe Leu Gln
1 5 10 15

Met Asn Asn Leu Arg Val Asp Asp Thr Ala Val Tyr Tyr Cys Ala Arg
20 25 30

<210> SEQ ID NO 215
<211> LENGTH: 12
<212> TYPE: PRT
<213> ORGANISM: Homo sapiens

<400> SEQUENCE: 215

Leu Gln Trp Gly Gly Tyr Asn Gly Trp Leu Ser Pro
1 5 10

<210> SEQ ID NO 216
<211> LENGTH: 11
<212> TYPE: PRT
<213> ORGANISM: Homo sapiens

<400> SEQUENCE: 216

Trp Gly Gln Gly Thr Leu Val Thr Val Ser Ser
1 5 10

<210> SEQ ID NO 217
<211> LENGTH: 30
<212> TYPE: PRT
<213> ORGANISM: Homo sapiens

<400> SEQUENCE: 217

Gln Val Gln Leu Val Gln Ser Gly Gly Gly Val Val Gln Pro Gly Lys
1 5 10 15

Ser Leu Arg Leu Ser Cys Ala Ala Ser Gly Phe Ala Phe Gly
20 25 30

<210> SEQ ID NO 218
<211> LENGTH: 5
<212> TYPE: PRT
<213> ORGANISM: Homo sapiens

<400> SEQUENCE: 218

Gly Tyr Ala Met His
1 5

<210> SEQ ID NO 219
<211> LENGTH: 14
<212> TYPE: PRT
<213> ORGANISM: Homo sapiens

<400> SEQUENCE: 219

Trp Val Arg Gln Ala Pro Gly Lys Gly Leu Glu Trp Val Ala
1 5 10

<210> SEQ ID NO 220
<211> LENGTH: 17
<212> TYPE: PRT
<213> ORGANISM: Homo sapiens

<400> SEQUENCE: 220

Val Ile Ser Tyr Asp Gly Asn Lys Lys Tyr Tyr Ala Asp Ser Val Lys
1 5 10 15

Gly

<210> SEQ ID NO 221
<211> LENGTH: 32
<212> TYPE: PRT
<213> ORGANISM: Homo sapiens

<400> SEQUENCE: 221

Arg Phe Thr Ile Ser Arg Asp Asn Ser Lys Asn Thr Leu Tyr Leu Gln
1 5 10 15

Met Asn Ser Leu Arg Ala Glu Asp Ala Ala Val Phe Tyr Cys Ala Arg
20 25 30

<210> SEQ ID NO 222
<211> LENGTH: 15
<212> TYPE: PRT
<213> ORGANISM: Homo sapiens

<400> SEQUENCE: 222

Ala Arg Leu Cys Thr Ser Thr Ser Cys Tyr Trp Thr Phe Asp Pro
1 5 10 15

<210> SEQ ID NO 223
<211> LENGTH: 11
<212> TYPE: PRT
<213> ORGANISM: Homo sapiens

<400> SEQUENCE: 223

Trp Gly Gln Gly Thr Leu Val Thr Val Ser Ser
1 5 10

<210> SEQ ID NO 224
<211> LENGTH: 29
<212> TYPE: PRT
<213> ORGANISM: Homo sapiens

<400> SEQUENCE: 224

Glu Val Gln Leu Val Arg Ser Gly Gly Asn Leu Val Gln Pro Gly Gly
1 5 10 15

Ser Leu Arg Leu Ser Cys Ala Ala Thr Gly Pro Ile Thr
20 25

<210> SEQ ID NO 225
<211> LENGTH: 5
<212> TYPE: PRT
<213> ORGANISM: Homo sapiens

<400> SEQUENCE: 225

Gln His Trp Met Thr
1 5

<210> SEQ ID NO 226
<211> LENGTH: 14
<212> TYPE: PRT
<213> ORGANISM: Homo sapiens

<400> SEQUENCE: 226

Trp Val Arg Gln Ala Pro Gly Gln Gly Leu Glu Trp Val Ala
1 5 10

<210> SEQ ID NO 227
<211> LENGTH: 17
<212> TYPE: PRT
<213> ORGANISM: Homo sapiens

<400> SEQUENCE: 227

Asn Ile Asn Leu Asp Gly Thr Glu Lys Phe Tyr Val Asp Ser Val Lys
1 5 10 15

Gly

<210> SEQ ID NO 228
<211> LENGTH: 32
<212> TYPE: PRT
<213> ORGANISM: Homo sapiens

<400> SEQUENCE: 228

Arg Phe Thr Val Ser Arg Asp Asn Arg Lys Ser Ser Val Phe Leu Gln
1 5 10 15

Met Asn Asn Leu Arg Val Asp Asp Thr Ala Val Tyr Tyr Cys Ala Arg
20 25 30

<210> SEQ ID NO 229
<211> LENGTH: 12
<212> TYPE: PRT
<213> ORGANISM: Homo sapiens

<400> SEQUENCE: 229

Leu Gln Trp Gly Gly Tyr Asn Gly Trp Leu Ser Pro
1 5 10

<210> SEQ ID NO 230
<211> LENGTH: 11
<212> TYPE: PRT
<213> ORGANISM: Homo sapiens

<400> SEQUENCE: 230

Trp Gly Gln Gly Thr Leu Val Thr Val Ser Ser
1 5 10

<210> SEQ ID NO 231
<211> LENGTH: 29
<212> TYPE: PRT
<213> ORGANISM: Homo sapiens

<400> SEQUENCE: 231

Glu Val Gln Leu Val Arg Ser Gly Gly Asn Leu Val Gln Pro Gly Gly
1 5 10 15

Ser Leu Arg Leu Ser Cys Ala Ala Thr Gly Pro Ile Thr
20 25

<210> SEQ ID NO 232
<211> LENGTH: 5
<212> TYPE: PRT
<213> ORGANISM: Homo sapiens

<400> SEQUENCE: 232

Gln His Trp Met Thr
1 5

<210> SEQ ID NO 233
<211> LENGTH: 14
<212> TYPE: PRT
<213> ORGANISM: Homo sapiens

<400> SEQUENCE: 233

Trp Val Arg Gln Ala Pro Gly Gln Gly Leu Glu Trp Val Ala
1 5 10

<210> SEQ ID NO 234
<211> LENGTH: 17
<212> TYPE: PRT
<213> ORGANISM: Homo sapiens

<400> SEQUENCE: 234

Asn Ile Asn Leu Asp Gly Thr Glu Lys Phe Tyr Val Asp Ser Val Lys
1 5 10 15

Gly

<210> SEQ ID NO 235
<211> LENGTH: 32
<212> TYPE: PRT
<213> ORGANISM: Homo sapiens

<400> SEQUENCE: 235

Arg Phe Thr Val Ser Arg Asp Asn Arg Lys Ser Ser Val Phe Leu Gln
1 5 10 15

Met Asn Asn Leu Arg Val Asp Asp Thr Ala Val Tyr Tyr Cys Ala Arg
20 25 30

<210> SEQ ID NO 236
<211> LENGTH: 12
<212> TYPE: PRT
<213> ORGANISM: Homo sapiens

<400> SEQUENCE: 236

Leu Gln Trp Gly Gly Tyr Asn Gly Trp Leu Ser Pro
1 5 10

<210> SEQ ID NO 237
<211> LENGTH: 11
<212> TYPE: PRT
<213> ORGANISM: Homo sapiens

<400> SEQUENCE: 237

Trp Gly Gln Gly Thr Leu Val Thr Val Ser Ser
1 5 10

<210> SEQ ID NO 238
<211> LENGTH: 23
<212> TYPE: PRT
<213> ORGANISM: Homo sapiens

<400> SEQUENCE: 238

Asp Ile Val Met Thr Gln Ser Pro Ser Phe Leu Ser Ala Ser Val Gly
1 5 10 15

Asp Arg Val Thr Ile Thr Cys
20

<210> SEQ ID NO 239
<211> LENGTH: 11
<212> TYPE: PRT
<213> ORGANISM: Homo sapiens

<400> SEQUENCE: 239

Trp Ala Ser Gln Gly Ile Ser Ser Tyr Leu Ala
1 5 10

<210> SEQ ID NO 240
<211> LENGTH: 15
<212> TYPE: PRT
<213> ORGANISM: Homo sapiens

<400> SEQUENCE: 240

Trp Tyr Gln Gln Lys Pro Gly Lys Ala Pro Lys Leu Leu Ile Tyr
1 5 10 15

<210> SEQ ID NO 241
<211> LENGTH: 7
<212> TYPE: PRT
<213> ORGANISM: Homo sapiens

<400> SEQUENCE: 241

Ala Ala Ser Thr Leu Gln Ser
1 5

<210> SEQ ID NO 242
<211> LENGTH: 32
<212> TYPE: PRT
<213> ORGANISM: Homo sapiens

<400> SEQUENCE: 242

Gly Val Pro Ser Arg Phe Ser Gly Ser Gly Ser Gly Thr Glu Phe Thr
1 5 10 15

Leu Thr Ile Ser Ser Leu Gln Pro Glu Asp Phe Ala Thr Tyr Tyr Cys
20 25 30

<210> SEQ ID NO 243
<211> LENGTH: 9
<212> TYPE: PRT
<213> ORGANISM: Homo sapiens

<400> SEQUENCE: 243

Gln Gln Leu Asn Ser Tyr Pro Leu Thr
1 5

<210> SEQ ID NO 244
<211> LENGTH: 11
<212> TYPE: PRT
<213> ORGANISM: Homo sapiens

<400> SEQUENCE: 244

Phe Gly Gly Gly Thr Lys Val Asp Ile Lys Arg
1 5 10

<210> SEQ ID NO 245
<211> LENGTH: 23
<212> TYPE: PRT
<213> ORGANISM: Homo sapiens

<400> SEQUENCE: 245

Glu Ile Val Leu Thr Gln Ser Pro Asp Ser Leu Ser Ala Ser Val Gly
1 5 10 15

Asp Arg Val Thr Ile Thr Cys
20

<210> SEQ ID NO 246
<211> LENGTH: 11
<212> TYPE: PRT
<213> ORGANISM: Homo sapiens

<400> SEQUENCE: 246

Arg Ala Ser Gln Gly Ile Ser Gly Tyr Leu Ala
1 5 10

<210> SEQ ID NO 247
<211> LENGTH: 15
<212> TYPE: PRT
<213> ORGANISM: Homo sapiens

<400> SEQUENCE: 247

Trp Tyr Gln His Lys Ala Gly Lys Ala Pro Lys Leu Leu Ile Tyr
1 5 10 15

<210> SEQ ID NO 248
<211> LENGTH: 7
<212> TYPE: PRT
<213> ORGANISM: Homo sapiens

<400> SEQUENCE: 248

Ala Ala Ser Ser Leu Gln Ser
1 5

<210> SEQ ID NO 249
<211> LENGTH: 32
<212> TYPE: PRT
<213> ORGANISM: Homo sapiens

<400> SEQUENCE: 249

Gly Val Pro Ser Arg Phe Ser Gly Ser Gly Tyr Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 250
<211> LENGTH: 9
<212> TYPE: PRT
<213> ORGANISM: Homo sapiens

<400> SEQUENCE: 250

Gln Gln Tyr Asn Ser Tyr Pro Phe Thr
1 5

<210> SEQ ID NO 251
<211> LENGTH: 11
<212> TYPE: PRT
<213> ORGANISM: Homo sapiens

<400> SEQUENCE: 251

Phe Gly Gly Gly Thr Lys Val Glu Ile Lys Arg
1 5 10

<210> SEQ ID NO 252
<211> LENGTH: 23
<212> TYPE: PRT
<213> ORGANISM: Homo sapiens

<400> SEQUENCE: 252

Glu Ile Val Leu Thr Gln Ser Pro Ser Phe Leu Ser Ala Phe Val Gly
1 5 10 15

```
Asp Arg Val Thr Ile Thr Cys
            20


<210> SEQ ID NO 253
<211> LENGTH: 11
<212> TYPE: PRT
<213> ORGANISM: Homo sapiens

<400> SEQUENCE: 253

Arg Thr Ser Gln Ser Ile Asn Asn Tyr Leu Asn
1               5                   10


<210> SEQ ID NO 254
<211> LENGTH: 15
<212> TYPE: PRT
<213> ORGANISM: Homo sapiens

<400> SEQUENCE: 254

Trp Tyr Gln Gln Lys Ala Gly Lys Ala Pro Lys Leu Leu Ile Tyr
1               5                   10                  15


<210> SEQ ID NO 255
<211> LENGTH: 7
<212> TYPE: PRT
<213> ORGANISM: Homo sapiens

<400> SEQUENCE: 255

Ala Ala Ser Thr Leu His Thr
1               5


<210> SEQ ID NO 256
<211> LENGTH: 32
<212> TYPE: PRT
<213> ORGANISM: Homo sapiens

<400> SEQUENCE: 256

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30


<210> SEQ ID NO 257
<211> LENGTH: 9
<212> TYPE: PRT
<213> ORGANISM: Homo sapiens

<400> SEQUENCE: 257

Gln Gln Ser Tyr Ser Ile Pro Leu Thr
1               5


<210> SEQ ID NO 258
<211> LENGTH: 11
<212> TYPE: PRT
<213> ORGANISM: Homo sapiens

<400> SEQUENCE: 258

Phe Gly Gly Gly Thr Lys Val Glu Ile Lys Arg
1               5                   10


<210> SEQ ID NO 259
<211> LENGTH: 23
<212> TYPE: PRT
<213> ORGANISM: Homo sapiens

<400> SEQUENCE: 259
```

```
Asp Ile Val Met Thr Gln Ser Pro Asp Ser Leu Ser Ala Ser Val Gly
1               5                   10                  15

Asp Ser Val Thr Ile Thr Cys
            20


<210> SEQ ID NO 260
<211> LENGTH: 12
<212> TYPE: PRT
<213> ORGANISM: Homo sapiens

<400> SEQUENCE: 260

Arg Ala Ser Gln Ser Phe Ser Ser Ser Tyr Leu Ala
1               5                   10


<210> SEQ ID NO 261
<211> LENGTH: 15
<212> TYPE: PRT
<213> ORGANISM: Homo sapiens

<400> SEQUENCE: 261

Trp Tyr Gln Gln Lys Pro Gly Gln Ala Pro Arg Leu Leu Ile Tyr
1               5                   10                  15


<210> SEQ ID NO 262
<211> LENGTH: 7
<212> TYPE: PRT
<213> ORGANISM: Homo sapiens

<400> SEQUENCE: 262

Ala Ala Ser Ser Arg Ala Ala
1               5


<210> SEQ ID NO 263
<211> LENGTH: 32
<212> TYPE: PRT
<213> ORGANISM: Homo sapiens

<400> SEQUENCE: 263

Gly Val Pro Thr Gly Ser Val Ala Asp Gly Ser Gly Thr Asp Phe Thr
1               5                   10                  15

Leu Thr Ile Ser Gly Leu Gln Pro Glu Asp Phe Ala Ala Tyr Tyr Cys
            20                  25                  30


<210> SEQ ID NO 264
<211> LENGTH: 9
<212> TYPE: PRT
<213> ORGANISM: Homo sapiens

<400> SEQUENCE: 264

Gln Gln Ser Tyr Ser Thr Pro Tyr Thr
1               5


<210> SEQ ID NO 265
<211> LENGTH: 11
<212> TYPE: PRT
<213> ORGANISM: Homo sapiens

<400> SEQUENCE: 265

Phe Gly Gly Gly Thr Lys Val Glu Ile Lys Arg
1               5                   10


<210> SEQ ID NO 266
<211> LENGTH: 23
```

<212> TYPE: PRT
<213> ORGANISM: Homo sapiens

<400> SEQUENCE: 266

Asp Ile Val Met Thr Gln Ser Pro Ser Phe Leu Ser Ala Phe Val Gly
1 5 10 15

Asp Arg Val Thr Ile Thr Cys
20

<210> SEQ ID NO 267
<211> LENGTH: 11
<212> TYPE: PRT
<213> ORGANISM: Homo sapiens

<400> SEQUENCE: 267

Arg Ala Ser Gln Ser Ile Ser Asn Trp Leu Ala
1 5 10

<210> SEQ ID NO 268
<211> LENGTH: 15
<212> TYPE: PRT
<213> ORGANISM: Homo sapiens

<400> SEQUENCE: 268

Trp Tyr Gln Gln Lys Pro Gly Lys Ala Pro Lys Val Leu Ile Tyr
1 5 10 15

<210> SEQ ID NO 269
<211> LENGTH: 7
<212> TYPE: PRT
<213> ORGANISM: Homo sapiens

<400> SEQUENCE: 269

Lys Ala Ser Ser Leu Glu Asn
1 5

<210> SEQ ID NO 270
<211> LENGTH: 32
<212> TYPE: PRT
<213> ORGANISM: Homo sapiens

<400> SEQUENCE: 270

Gly Val Pro Ser Arg Phe Ser Gly Ser Gly Ser Gly Thr Asp Phe Thr
1 5 10 15

Leu Thr Ile Thr Ser Leu Gln Pro Asp Asp Phe Ala Thr Tyr Tyr Cys
20 25 30

<210> SEQ ID NO 271
<211> LENGTH: 9
<212> TYPE: PRT
<213> ORGANISM: Homo sapiens

<400> SEQUENCE: 271

Gln Gln Tyr Asn Ala Tyr Pro Leu Thr
1 5

<210> SEQ ID NO 272
<211> LENGTH: 11
<212> TYPE: PRT
<213> ORGANISM: Homo sapiens

<400> SEQUENCE: 272

Phe Gly Gly Gly Thr Lys Val Glu Ile Lys Arg
1 5 10

<210> SEQ ID NO 273
<211> LENGTH: 23
<212> TYPE: PRT
<213> ORGANISM: Homo sapiens

<400> SEQUENCE: 273

Glu Ile Val Leu Thr Gln Ser Pro Ser Thr Leu Ser Ala Ser Val Gly
1 5 10 15

Asp Arg Val Ala Ile Thr Cys
20

<210> SEQ ID NO 274
<211> LENGTH: 11
<212> TYPE: PRT
<213> ORGANISM: Homo sapiens

<400> SEQUENCE: 274

Arg Ala Ser Gln Arg Ile Gly Ser Trp Leu Ala
1 5 10

<210> SEQ ID NO 275
<211> LENGTH: 15
<212> TYPE: PRT
<213> ORGANISM: Homo sapiens

<400> SEQUENCE: 275

Trp Tyr Gln Gln Lys Pro Gly Lys Ala Pro Asn Pro Leu Ile Tyr
1 5 10 15

<210> SEQ ID NO 276
<211> LENGTH: 7
<212> TYPE: PRT
<213> ORGANISM: Homo sapiens

<400> SEQUENCE: 276

Lys Ala Phe Ser Leu Glu Ser
1 5

<210> SEQ ID NO 277
<211> LENGTH: 32
<212> TYPE: PRT
<213> ORGANISM: Homo sapiens

<400> SEQUENCE: 277

Gly Val Pro Ser Arg Phe Ser Gly Ser Arg Ser Gly Thr Glu Phe Thr
1 5 10 15

Leu Thr Ile Ser Ser Leu Gln Pro Asp Asp Phe Ala Thr Tyr Phe Cys
20 25 30

<210> SEQ ID NO 278
<211> LENGTH: 9
<212> TYPE: PRT
<213> ORGANISM: Homo sapiens

<400> SEQUENCE: 278

Gln Gln Tyr Asp Ser Tyr Pro Tyr Thr
1 5

<210> SEQ ID NO 279
<211> LENGTH: 11
<212> TYPE: PRT
<213> ORGANISM: Homo sapiens

<400> SEQUENCE: 279

Phe Gly Gln Gly Thr Lys Leu Glu Ile Lys Arg
1 5 10

<210> SEQ ID NO 280
<211> LENGTH: 23
<212> TYPE: PRT
<213> ORGANISM: Homo sapiens

<400> SEQUENCE: 280

Asp Val Val Met Thr Gln Ser Pro Ser Ser Leu Ser Ala Ser Ile Gly
1 5 10 15

Asp Arg Val Thr Phe Thr Cys
20

<210> SEQ ID NO 281
<211> LENGTH: 11
<212> TYPE: PRT
<213> ORGANISM: Homo sapiens

<400> SEQUENCE: 281

Gln Ala Ser Gln Asp Ile Ser Asn Arg Leu Asn
1 5 10

<210> SEQ ID NO 282
<211> LENGTH: 15
<212> TYPE: PRT
<213> ORGANISM: Homo sapiens

<400> SEQUENCE: 282

Trp Tyr Gln Gln Lys Pro Gly Lys Val Pro Lys Leu Leu Ile Ser
1 5 10 15

<210> SEQ ID NO 283
<211> LENGTH: 7
<212> TYPE: PRT
<213> ORGANISM: Homo sapiens

<400> SEQUENCE: 283

Asp Ala Ser Asn Leu Glu Thr
1 5

<210> SEQ ID NO 284
<211> LENGTH: 32
<212> TYPE: PRT
<213> ORGANISM: Homo sapiens

<400> SEQUENCE: 284

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys
20 25 30

<210> SEQ ID NO 285
<211> LENGTH: 8
<212> TYPE: PRT
<213> ORGANISM: Homo sapiens

<400> SEQUENCE: 285

Gln Gln Tyr Asp Pro Leu Leu Thr
1 5

<210> SEQ ID NO 286

<211> LENGTH: 11
<212> TYPE: PRT
<213> ORGANISM: Homo sapiens

<400> SEQUENCE: 286

Phe Gly Gly Gly Thr Lys Val Glu Ile Lys Arg
1               5                   10

<210> SEQ ID NO 287
<211> LENGTH: 23
<212> TYPE: PRT
<213> ORGANISM: Homo sapiens

<400> SEQUENCE: 287

Asp Ile Gln Met Thr Gln Ser Pro Ser Ser Val Ser Ala Ser Val Gly
1               5                   10                  15

Asp Thr Val Thr Ile Ser Cys
            20

<210> SEQ ID NO 288
<211> LENGTH: 11
<212> TYPE: PRT
<213> ORGANISM: Homo sapiens

<400> SEQUENCE: 288

Arg Ala Ser Gln Gly Ile Ser Ser Trp Leu Ala
1               5                   10

<210> SEQ ID NO 289
<211> LENGTH: 15
<212> TYPE: PRT
<213> ORGANISM: Homo sapiens

<400> SEQUENCE: 289

Trp Tyr Gln Gln Lys Ser Gly Gln Ala Pro Thr Leu Leu Ile Tyr
1               5                   10                  15

<210> SEQ ID NO 290
<211> LENGTH: 7
<212> TYPE: PRT
<213> ORGANISM: Homo sapiens

<400> SEQUENCE: 290

Ala Ala Ser Ser Leu Gln Ser
1               5

<210> SEQ ID NO 291
<211> LENGTH: 32
<212> TYPE: PRT
<213> ORGANISM: Homo sapiens

<400> SEQUENCE: 291

Gly Val Pro Ser Arg Phe Ser Gly Ser Gly Ser Gly Thr Asp Phe Thr
1               5                   10                  15

Leu Ile Ile Ser Ser Leu Gln Pro Glu Asp Phe Ala Thr Tyr Tyr Cys
            20                  25                  30

<210> SEQ ID NO 292
<211> LENGTH: 9
<212> TYPE: PRT
<213> ORGANISM: Homo sapiens

<400> SEQUENCE: 292

Gln Gln Ala Tyr Arg Thr Pro Ile Thr 1 5

<210> SEQ ID NO 293
<211> LENGTH: 11
<212> TYPE: PRT
<213> ORGANISM: Homo sapiens

<400> SEQUENCE: 293

Phe Gly Gly Gly Thr Lys Val Glu Ile Lys Arg
1 5 10

<210> SEQ ID NO 294
<211> LENGTH: 23
<212> TYPE: PRT
<213> ORGANISM: Homo sapiens

<400> SEQUENCE: 294

Asp Ile Gln Met Thr Gln Ser Pro Ser Ser Val Ser Ala Ser Val Gly
1 5 10 15

Asp Arg Val Ser Ile Thr Cys
20

<210> SEQ ID NO 295
<211> LENGTH: 11
<212> TYPE: PRT
<213> ORGANISM: Homo sapiens

<400> SEQUENCE: 295

Gln Ala Ser Gln Asp Ile Ser Asn Tyr Leu Asn
1 5 10

<210> SEQ ID NO 296
<211> LENGTH: 15
<212> TYPE: PRT
<213> ORGANISM: Homo sapiens

<400> SEQUENCE: 296

Trp Tyr Gln Gln Lys Pro Gly Lys Ala Pro Lys Leu Leu Ile Tyr
1 5 10 15

<210> SEQ ID NO 297
<211> LENGTH: 7
<212> TYPE: PRT
<213> ORGANISM: Homo sapiens

<400> SEQUENCE: 297

Ala Ala Ser Ser Leu Gln Ser
1 5

<210> SEQ ID NO 298
<211> LENGTH: 32
<212> TYPE: PRT
<213> ORGANISM: Homo sapiens

<400> SEQUENCE: 298

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 299
<211> LENGTH: 9
<212> TYPE: PRT
<213> ORGANISM: Homo sapiens

<400> SEQUENCE: 299

Gln Gln Ser Tyr Asn Thr Pro Pro Thr
1 5

<210> SEQ ID NO 300
<211> LENGTH: 11
<212> TYPE: PRT
<213> ORGANISM: Homo sapiens

<400> SEQUENCE: 300

Phe Gly Gln Gly Thr Lys Leu Glu Ile Lys Arg
1 5 10

<210> SEQ ID NO 301
<211> LENGTH: 22
<212> TYPE: PRT
<213> ORGANISM: Homo sapiens

<400> SEQUENCE: 301

Ala Ser Val Leu Thr Gln Asp Pro Ala Val Ser Val Ala Leu Gly Gln
1 5 10 15

Thr Val Arg Ile Thr Cys
20

<210> SEQ ID NO 302
<211> LENGTH: 11
<212> TYPE: PRT
<213> ORGANISM: Homo sapiens

<400> SEQUENCE: 302

Gln Gly Asp Ser Leu Arg Ser Tyr Tyr Ala Ser
1 5 10

<210> SEQ ID NO 303
<211> LENGTH: 15
<212> TYPE: PRT
<213> ORGANISM: Homo sapiens

<400> SEQUENCE: 303

Trp Tyr Gln Gln Lys Pro Gly Gln Ala Pro Val Leu Val Ile Tyr
1 5 10 15

<210> SEQ ID NO 304
<211> LENGTH: 7
<212> TYPE: PRT
<213> ORGANISM: Homo sapiens

<400> SEQUENCE: 304

Gly Lys Ser Asn Arg Pro Ser
1 5

<210> SEQ ID NO 305
<211> LENGTH: 32
<212> TYPE: PRT
<213> ORGANISM: Homo sapiens

<400> SEQUENCE: 305

Gly Ile Pro Asp Arg Phe Ser Gly Ser Ser Ser Gly Asn Thr Ala Ser
1 5 10 15

Leu Thr Ile Thr Gly Ala Gln Ala Glu Asp Glu Ala Asp Tyr Tyr Cys
20 25 30

<210> SEQ ID NO 306
<211> LENGTH: 10
<212> TYPE: PRT
<213> ORGANISM: Homo sapiens

<400> SEQUENCE: 306

```
Asn Ser Arg Asp Ser Thr Gly Asn Gln Leu
1               5                   10
```

<210> SEQ ID NO 307
<211> LENGTH: 11
<212> TYPE: PRT
<213> ORGANISM: Homo sapiens

<400> SEQUENCE: 307

```
Phe Gly Gly Gly Thr Lys Val Thr Val Leu Gly
1               5                   10
```

<210> SEQ ID NO 308
<211> LENGTH: 21
<212> TYPE: PRT
<213> ORGANISM: Homo sapiens

<400> SEQUENCE: 308

```
Ala Glu Leu Thr Gln Asp Pro Ala Val Ser Val Ala Leu Gly Gln Thr
1               5                   10                  15

Val Arg Ile Thr Cys
            20
```

<210> SEQ ID NO 309
<211> LENGTH: 11
<212> TYPE: PRT
<213> ORGANISM: Homo sapiens

<400> SEQUENCE: 309

```
Gln Gly Asp Ser Leu Arg Ser Tyr Tyr Ala Ser
1               5                   10
```

<210> SEQ ID NO 310
<211> LENGTH: 15
<212> TYPE: PRT
<213> ORGANISM: Homo sapiens

<400> SEQUENCE: 310

```
Trp Tyr Gln Gln Lys Pro Gly Gln Ala Pro Val Leu Val Ile Tyr
1               5                   10                  15
```

<210> SEQ ID NO 311
<211> LENGTH: 7
<212> TYPE: PRT
<213> ORGANISM: Homo sapiens

<400> SEQUENCE: 311

```
Gly Glu Asn Ser Arg Pro Ser
1               5
```

<210> SEQ ID NO 312
<211> LENGTH: 32
<212> TYPE: PRT
<213> ORGANISM: Homo sapiens

<400> SEQUENCE: 312

```
Gly Ile Pro Asp Arg Phe Ser Gly Ser Ser Ser Gly Asn Thr Ala Ser
1               5                   10                  15
```

Leu Thr Ile Ala Gly Ala Gln Ala Glu Asp Glu Ala Asp Tyr Tyr Cys
20 25 30

<210> SEQ ID NO 313
<211> LENGTH: 11
<212> TYPE: PRT
<213> ORGANISM: Homo sapiens

<400> SEQUENCE: 313

Asn Ser Pro Asp Ser Ser Gly Ile His Leu Val
1 5 10

<210> SEQ ID NO 314
<211> LENGTH: 11
<212> TYPE: PRT
<213> ORGANISM: Homo sapiens

<400> SEQUENCE: 314

Phe Gly Gly Gly Thr Lys Val Thr Val Leu Gly
1 5 10

<210> SEQ ID NO 315
<211> LENGTH: 23
<212> TYPE: PRT
<213> ORGANISM: Homo sapiens

<400> SEQUENCE: 315

Glu Ile Val Leu Thr Gln Ser Pro Asp Ser Leu Ala Val Ser Leu Gly
1 5 10 15

Glu Arg Ala Thr Ile Asn Cys
20

<210> SEQ ID NO 316
<211> LENGTH: 17
<212> TYPE: PRT
<213> ORGANISM: Homo sapiens

<400> SEQUENCE: 316

Lys Ser Ser Gln Ser Val Leu Tyr Ser Ser Asn Asn Lys Asn Tyr Leu
1 5 10 15

Ala

<210> SEQ ID NO 317
<211> LENGTH: 15
<212> TYPE: PRT
<213> ORGANISM: Homo sapiens

<400> SEQUENCE: 317

Trp Tyr Gln Gln Lys Pro Gly Gln Pro Pro Lys Leu Leu Phe Tyr
1 5 10 15

<210> SEQ ID NO 318
<211> LENGTH: 7
<212> TYPE: PRT
<213> ORGANISM: Homo sapiens

<400> SEQUENCE: 318

Trp Ala Ser Thr Arg Glu Ser
1 5

<210> SEQ ID NO 319
<211> LENGTH: 32
<212> TYPE: PRT
<213> ORGANISM: Homo sapiens

<400> SEQUENCE: 319

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 320
<211> LENGTH: 9
<212> TYPE: PRT
<213> ORGANISM: Homo sapiens

<400> SEQUENCE: 320

His Gln Tyr Tyr Ser Ser Pro Leu Thr
1               5

<210> SEQ ID NO 321
<211> LENGTH: 11
<212> TYPE: PRT
<213> ORGANISM: Homo sapiens

<400> SEQUENCE: 321

Phe Gly Gly Gly Thr Lys Leu Glu Ile Lys Arg
1               5                   10

<210> SEQ ID NO 322
<211> LENGTH: 23
<212> TYPE: PRT
<213> ORGANISM: Homo sapiens

<400> SEQUENCE: 322

Glu Ile Val Leu Thr Gln Ser Pro Asn Ser Leu Ala Val Ser Leu Gly
1               5                   10                  15

Glu Arg Ala Thr Ile Arg Cys
            20

<210> SEQ ID NO 323
<211> LENGTH: 17
<212> TYPE: PRT
<213> ORGANISM: Homo sapiens

<400> SEQUENCE: 323

Lys Ser Ser Gln Ser Val Leu Tyr Ser Gly Asn Asn Lys Asn Tyr Ile
1               5                   10                  15

Ala

<210> SEQ ID NO 324
<211> LENGTH: 15
<212> TYPE: PRT
<213> ORGANISM: Homo sapiens

<400> SEQUENCE: 324

Trp Tyr Gln Gln Lys Pro Gly Gln Pro Pro Lys Leu Leu Ile Tyr
1               5                   10                  15

<210> SEQ ID NO 325
<211> LENGTH: 7
<212> TYPE: PRT
<213> ORGANISM: Homo sapiens

<400> SEQUENCE: 325

Trp Ala Ser Thr Arg Glu Ser
1               5

<210> SEQ ID NO 326
<211> LENGTH: 32
<212> TYPE: PRT
<213> ORGANISM: Homo sapiens

<400> SEQUENCE: 326

Gly Val Pro Asp Arg Phe Ser Gly Ser Gly Ser Glu Thr Asp Phe Thr
1 5 10 15

Leu Thr Ile Ser Ser Leu Arg Ala Glu Asp Val Ala Leu Tyr Tyr Cys
20 25 30

<210> SEQ ID NO 327
<211> LENGTH: 8
<212> TYPE: PRT
<213> ORGANISM: Homo sapiens

<400> SEQUENCE: 327

Gln Gln Tyr Tyr Ser Arg Trp Thr
1 5

<210> SEQ ID NO 328
<211> LENGTH: 11
<212> TYPE: PRT
<213> ORGANISM: Homo sapiens

<400> SEQUENCE: 328

Phe Gly Gln Gly Thr Lys Leu Glu Ile Lys Arg
1 5 10

<210> SEQ ID NO 329
<211> LENGTH: 23
<212> TYPE: PRT
<213> ORGANISM: Homo sapiens

<400> SEQUENCE: 329

Asp Ile Val Met Thr Gln Ser Pro Ser Ser Val Ser Ala Ser Val Gly
1 5 10 15

Asp Arg Val Thr Ile Thr Cys
20

<210> SEQ ID NO 330
<211> LENGTH: 11
<212> TYPE: PRT
<213> ORGANISM: Homo sapiens

<400> SEQUENCE: 330

Arg Ala Ser Gln Ser Ile Ser Ser Tyr Leu Asn
1 5 10

<210> SEQ ID NO 331
<211> LENGTH: 15
<212> TYPE: PRT
<213> ORGANISM: Homo sapiens

<400> SEQUENCE: 331

Trp Tyr Gln Gln Lys Pro Gly Lys Ala Pro Lys Leu Leu Ile Tyr
1 5 10 15

<210> SEQ ID NO 332
<211> LENGTH: 7
<212> TYPE: PRT
<213> ORGANISM: Homo sapiens

<400> SEQUENCE: 332

Gly Thr Ser Asn Leu Gln Ser
1 5

<210> SEQ ID NO 333
<211> LENGTH: 32
<212> TYPE: PRT
<213> ORGANISM: Homo sapiens

<400> SEQUENCE: 333

Gly Val Pro Ser Gly Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 334
<211> LENGTH: 9
<212> TYPE: PRT
<213> ORGANISM: Homo sapiens

<400> SEQUENCE: 334

Gln Glu Thr Tyr Ser Thr Pro Pro Thr
1 5

<210> SEQ ID NO 335
<211> LENGTH: 11
<212> TYPE: PRT
<213> ORGANISM: Homo sapiens

<400> SEQUENCE: 335

Phe Gly Gly Gly Thr Lys Leu Glu Ile Lys Arg
1 5 10

<210> SEQ ID NO 336
<211> LENGTH: 23
<212> TYPE: PRT
<213> ORGANISM: Homo sapiens

<400> SEQUENCE: 336

Asp Ile Val Met Thr Gln Ser Pro Ser Ser Leu Ser Ala Ser Val Gly
1 5 10 15

Asp Arg Val Thr Ile Ser Cys
20

<210> SEQ ID NO 337
<211> LENGTH: 11
<212> TYPE: PRT
<213> ORGANISM: Homo sapiens

<400> SEQUENCE: 337

Arg Ala Ser Gln Ser Ile Arg His Tyr Val Asn
1 5 10

<210> SEQ ID NO 338
<211> LENGTH: 15
<212> TYPE: PRT
<213> ORGANISM: Homo sapiens

<400> SEQUENCE: 338

Trp Tyr Gln Gln Lys Pro Gly Lys Ala Pro Lys Leu Leu Ile Tyr
1 5 10 15

<210> SEQ ID NO 339

<211> LENGTH: 7
<212> TYPE: PRT
<213> ORGANISM: Homo sapiens

<400> SEQUENCE: 339

Lys Ala Ser Ser Leu Ala Ser
1               5

<210> SEQ ID NO 340
<211> LENGTH: 32
<212> TYPE: PRT
<213> ORGANISM: Homo sapiens

<400> SEQUENCE: 340

Gly Ala Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr Cys
            20                  25                  30

<210> SEQ ID NO 341
<211> LENGTH: 9
<212> TYPE: PRT
<213> ORGANISM: Homo sapiens

<400> SEQUENCE: 341

Gln Gln Ser Tyr Ser Ile Pro Leu Thr
1               5

<210> SEQ ID NO 342
<211> LENGTH: 11
<212> TYPE: PRT
<213> ORGANISM: Homo sapiens

<400> SEQUENCE: 342

Phe Gly Gly Gly Thr Lys Val Glu Ile Lys Arg
1               5                   10

<210> SEQ ID NO 343
<211> LENGTH: 23
<212> TYPE: PRT
<213> ORGANISM: Homo sapiens

<400> SEQUENCE: 343

Asp Ile Gln Met Thr Gln Ser Pro Ser Ser Val Ser Ala Ser Val Gly
1               5                   10                  15

Asp Arg Val Ser Ile Thr Cys
            20

<210> SEQ ID NO 344
<211> LENGTH: 11
<212> TYPE: PRT
<213> ORGANISM: Homo sapiens

<400> SEQUENCE: 344

Gln Ala Ser Gln Asp Ile Ser Asn Tyr Leu Asn
1               5                   10

<210> SEQ ID NO 345
<211> LENGTH: 15
<212> TYPE: PRT
<213> ORGANISM: Homo sapiens

<400> SEQUENCE: 345

Trp Tyr Gln Gln Lys Pro Gly Lys Ala Pro Lys Leu Leu Ile Tyr 1 5 10 15

<210> SEQ ID NO 346
<211> LENGTH: 7
<212> TYPE: PRT
<213> ORGANISM: Homo sapiens

<400> SEQUENCE: 346

Ala Ala Ser Ser Leu Gln Ser
1 5

<210> SEQ ID NO 347
<211> LENGTH: 32
<212> TYPE: PRT
<213> ORGANISM: Homo sapiens

<400> SEQUENCE: 347

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 348
<211> LENGTH: 9
<212> TYPE: PRT
<213> ORGANISM: Homo sapiens

<400> SEQUENCE: 348

Gln Gln Ser Tyr Asp Thr Pro Pro Thr
1 5

<210> SEQ ID NO 349
<211> LENGTH: 11
<212> TYPE: PRT
<213> ORGANISM: Homo sapiens

<400> SEQUENCE: 349

Phe Gly Gln Gly Thr Lys Leu Glu Ile Lys Arg
1 5 10

<210> SEQ ID NO 350
<211> LENGTH: 23
<212> TYPE: PRT
<213> ORGANISM: Homo sapiens

<400> SEQUENCE: 350

Asp Ile Val Met Thr Gln Ser Pro Ser Ser Leu Ser Ala Ser Val Gly
1 5 10 15

Asp Arg Val Thr Ile Ser Cys
20

<210> SEQ ID NO 351
<211> LENGTH: 11
<212> TYPE: PRT
<213> ORGANISM: Homo sapiens

<400> SEQUENCE: 351

Arg Ala Ser Gln Ser Ile Arg His Tyr Val Asn
1 5 10

<210> SEQ ID NO 352
<211> LENGTH: 15
<212> TYPE: PRT
<213> ORGANISM: Homo sapiens

<400> SEQUENCE: 352

Trp Tyr Gln Gln Lys Pro Gly Lys Ala Pro Lys Leu Leu Ile Tyr
1 5 10 15

<210> SEQ ID NO 353
<211> LENGTH: 7
<212> TYPE: PRT
<213> ORGANISM: Homo sapiens

<400> SEQUENCE: 353

Lys Ala Ser Ser Leu Ala Ser
1 5

<210> SEQ ID NO 354
<211> LENGTH: 32
<212> TYPE: PRT
<213> ORGANISM: Homo sapiens

<400> SEQUENCE: 354

Gly Ala Pro Ser Arg Phe Ser Gly Ser Gly Ser Gly Thr Asp Phe Thr
1 5 10 15

Leu Thr Ile Ser Ser Leu Gln Pro Asp Asp Phe Ala Thr Tyr Tyr Cys
20 25 30

<210> SEQ ID NO 355
<211> LENGTH: 9
<212> TYPE: PRT
<213> ORGANISM: Homo sapiens

<400> SEQUENCE: 355

Gln Gln Ser Tyr Ser Ile Pro Leu Thr
1 5

<210> SEQ ID NO 356
<211> LENGTH: 11
<212> TYPE: PRT
<213> ORGANISM: Homo sapiens

<400> SEQUENCE: 356

Phe Gly Gly Gly Thr Lys Val Glu Ile Lys Arg
1 5 10

<210> SEQ ID NO 357
<211> LENGTH: 23
<212> TYPE: PRT
<213> ORGANISM: Homo sapiens

<400> SEQUENCE: 357

Asp Ile Gln Met Thr Gln Ser Pro Ser Phe Leu Ser Ala Ser Val Gly
1 5 10 15

Asp Arg Val Thr Ile Thr Cys
20

<210> SEQ ID NO 358
<211> LENGTH: 11
<212> TYPE: PRT
<213> ORGANISM: Homo sapiens

<400> SEQUENCE: 358

Arg Ala Ser Gln Gly Ile Ser Ser Tyr Leu Ala
1 5 10

<210> SEQ ID NO 359
<211> LENGTH: 15
<212> TYPE: PRT
<213> ORGANISM: Homo sapiens

<400> SEQUENCE: 359

```
Trp Tyr Gln Gln Lys Pro Gly Lys Ala Pro Lys Leu Leu Ile Tyr
1               5                   10                  15
```

<210> SEQ ID NO 360
<211> LENGTH: 7
<212> TYPE: PRT
<213> ORGANISM: Homo sapiens

<400> SEQUENCE: 360

```
Lys Ala Ser Ser Leu Glu Ser
1               5
```

<210> SEQ ID NO 361
<211> LENGTH: 32
<212> TYPE: PRT
<213> ORGANISM: Homo sapiens

<400> SEQUENCE: 361

```
Gly Val Pro Ser Arg Phe Ser Gly Ser Gly Ser Gly Thr Asp Phe Ala
1               5                   10                  15

Leu Thr Ile Ser Ser Leu Gln Pro Glu Asp Phe Ala Thr Tyr Tyr Cys
            20                  25                  30
```

<210> SEQ ID NO 362
<211> LENGTH: 9
<212> TYPE: PRT
<213> ORGANISM: Homo sapiens

<400> SEQUENCE: 362

```
Gln Gln Leu Asn Thr Tyr Pro Gln Thr
1               5
```

<210> SEQ ID NO 363
<211> LENGTH: 11
<212> TYPE: PRT
<213> ORGANISM: Homo sapiens

<400> SEQUENCE: 363

```
Phe Gly Gln Gly Thr Lys Val Glu Ile Lys Arg
1               5                   10
```

<210> SEQ ID NO 364
<211> LENGTH: 30
<212> TYPE: PRT
<213> ORGANISM: Homo sapiens

<400> SEQUENCE: 364

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30
```

<210> SEQ ID NO 365
<211> LENGTH: 5
<212> TYPE: PRT
<213> ORGANISM: Homo sapiens

<400> SEQUENCE: 365

Ser Tyr Gly Met His
1 5

<210> SEQ ID NO 366
<211> LENGTH: 14
<212> TYPE: PRT
<213> ORGANISM: Homo sapiens

<400> SEQUENCE: 366

Trp Val Arg Gln Ala Pro Gly Lys Gly Leu Glu Trp Val Ala
1 5 10

<210> SEQ ID NO 367
<211> LENGTH: 17
<212> TYPE: PRT
<213> ORGANISM: Homo sapiens

<400> SEQUENCE: 367

Val Ile Trp Tyr Asp Gly Ser Asn Lys Tyr Tyr Ala Asp Ser Val Lys
1 5 10 15

Gly

<210> SEQ ID NO 368
<211> LENGTH: 32
<212> TYPE: PRT
<213> ORGANISM: Homo sapiens

<400> SEQUENCE: 368

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 369
<211> LENGTH: 13
<212> TYPE: PRT
<213> ORGANISM: Homo sapiens

<400> SEQUENCE: 369

Gly Tyr Ser Asn Tyr Asp Tyr Tyr Tyr Gly Met Asp Val
1 5 10

<210> SEQ ID NO 370
<211> LENGTH: 11
<212> TYPE: PRT
<213> ORGANISM: Homo sapiens

<400> SEQUENCE: 370

Trp Gly Gln Gly Thr Thr Val Thr Val Ser Ser
1 5 10

<210> SEQ ID NO 371
<211> LENGTH: 30
<212> TYPE: PRT
<213> ORGANISM: Homo sapiens

<400> SEQUENCE: 371

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 372

<211> LENGTH: 5
<212> TYPE: PRT
<213> ORGANISM: Homo sapiens

<400> SEQUENCE: 372

Ser Tyr Gly Met His
1 5

<210> SEQ ID NO 373
<211> LENGTH: 14
<212> TYPE: PRT
<213> ORGANISM: Homo sapiens

<400> SEQUENCE: 373

Trp Val Arg Gln Ala Pro Gly Lys Gly Leu Glu Trp Val Ser
1 5 10

<210> SEQ ID NO 374
<211> LENGTH: 17
<212> TYPE: PRT
<213> ORGANISM: Homo sapiens

<400> SEQUENCE: 374

Tyr Ile Ser Ser Ser Gly Ser Thr Ile Tyr Tyr Ala Asp Ser Val Lys
1 5 10 15

Gly

<210> SEQ ID NO 375
<211> LENGTH: 32
<212> TYPE: PRT
<213> ORGANISM: Homo sapiens

<400> SEQUENCE: 375

Arg Phe Thr Ile Ser Arg Asp Asn Ala Lys Asn Ser Leu Tyr Leu Gln
1 5 10 15

Met Asn Ser Leu Arg Ala Glu Asp Thr Ala Val Tyr Tyr Cys Ala Arg
20 25 30

<210> SEQ ID NO 376
<211> LENGTH: 12
<212> TYPE: PRT
<213> ORGANISM: Homo sapiens

<400> SEQUENCE: 376

Val Ser Ile Val Gly Gly Pro Tyr Gly Met Asp Val
1 5 10

<210> SEQ ID NO 377
<211> LENGTH: 11
<212> TYPE: PRT
<213> ORGANISM: Homo sapiens

<400> SEQUENCE: 377

Trp Gly Gln Gly Thr Thr Val Thr Val Ser Ser
1 5 10

<210> SEQ ID NO 378
<211> LENGTH: 30
<212> TYPE: PRT
<213> ORGANISM: Homo sapiens

<400> SEQUENCE: 378

Gln Val Gln Leu Val Gln Ser Gly Ala Glu Val Glu Lys Pro Gly Ser
1 5 10 15

```
Ser Val Lys Val Ser Cys Lys Ala Ser Gly Gly Ser Phe Ser
            20                  25                  30


<210> SEQ ID NO 379
<211> LENGTH: 5
<212> TYPE: PRT
<213> ORGANISM: Homo sapiens

<400> SEQUENCE: 379

Ser Tyr Ala Phe Thr
1               5


<210> SEQ ID NO 380
<211> LENGTH: 14
<212> TYPE: PRT
<213> ORGANISM: Homo sapiens

<400> SEQUENCE: 380

Trp Val Arg Gln Ala Pro Gly Gln Gly Leu Glu Trp Met Gly
1               5                   10


<210> SEQ ID NO 381
<211> LENGTH: 17
<212> TYPE: PRT
<213> ORGANISM: Homo sapiens

<400> SEQUENCE: 381

Arg Ile Val Pro Phe Leu Gly Val Pro Tyr Tyr Thr Gln Lys Phe Arg
1               5                   10                  15

Gly


<210> SEQ ID NO 382
<211> LENGTH: 32
<212> TYPE: PRT
<213> ORGANISM: Homo sapiens

<400> SEQUENCE: 382

Arg Val Thr Ile Thr Ala Asp Lys Ala Thr Ser Thr Val Tyr Met Glu
1               5                   10                  15

Leu Ser Ser Leu Thr Phe Asp Asp Thr Ala Val Tyr Tyr Cys Ala Arg
            20                  25                  30


<210> SEQ ID NO 383
<211> LENGTH: 14
<212> TYPE: PRT
<213> ORGANISM: Homo sapiens

<400> SEQUENCE: 383

Asp Lys Arg Thr Tyr Glu Tyr Asn Trp Asn Ser Leu Trp Phe
1               5                   10


<210> SEQ ID NO 384
<211> LENGTH: 11
<212> TYPE: PRT
<213> ORGANISM: Homo sapiens

<400> SEQUENCE: 384

Trp Gly Arg Gly Thr Leu Val Thr Val Ser Ser
1               5                   10


<210> SEQ ID NO 385
<211> LENGTH: 32
<212> TYPE: PRT
```

<213> ORGANISM: Homo sapiens

<400> SEQUENCE: 385

Gln Val Gln Leu Val Gln Ser Gly Ala Glu Val Lys Lys Pro Gly Glu
1 5 10 15

Ser Leu Val Ile Ser Cys Lys Ala Ser Gly Asp Lys Asp Thr Phe Thr
20 25 30

<210> SEQ ID NO 386
<211> LENGTH: 5
<212> TYPE: PRT
<213> ORGANISM: Homo sapiens

<400> SEQUENCE: 386

Ser Phe Trp Ile Ala
1 5

<210> SEQ ID NO 387
<211> LENGTH: 14
<212> TYPE: PRT
<213> ORGANISM: Homo sapiens

<400> SEQUENCE: 387

Trp Val Arg Gln Met Pro Gly Lys Gly Leu Glu Trp Met Gly
1 5 10

<210> SEQ ID NO 388
<211> LENGTH: 17
<212> TYPE: PRT
<213> ORGANISM: Homo sapiens

<400> SEQUENCE: 388

Ile Ile Tyr Ala Gly Asp Ser Asp Thr Arg Tyr Ser Pro Ser Phe Gln
1 5 10 15

Gly

<210> SEQ ID NO 389
<211> LENGTH: 32
<212> TYPE: PRT
<213> ORGANISM: Homo sapiens

<400> SEQUENCE: 389

His Val Asn Ile Ser Val Asp Arg Ser Thr Asn Thr Ala Tyr Leu Gln
1 5 10 15

Trp Ser Ser Leu Lys Ala Ser Asp Thr Ala Met Tyr Tyr Cys Ala Arg
20 25 30

<210> SEQ ID NO 390
<211> LENGTH: 14
<212> TYPE: PRT
<213> ORGANISM: Homo sapiens

<400> SEQUENCE: 390

His Asp Ser Arg Tyr Lys Tyr Phe Tyr Phe Gly Met Asp Val
1 5 10

<210> SEQ ID NO 391
<211> LENGTH: 11
<212> TYPE: PRT
<213> ORGANISM: Homo sapiens

<400> SEQUENCE: 391

Trp Gly Gln Gly Thr Thr Val Thr Val Ser Ser 1 5 10

<210> SEQ ID NO 392
<211> LENGTH: 32
<212> TYPE: PRT
<213> ORGANISM: Homo sapiens

<400> SEQUENCE: 392

Gln Val Gln Leu Val Gln Ser Gly Ala Glu Val Lys Lys Pro Gly Glu
1 5 10 15

Ser Leu Val Ile Ser Cys Lys Ala Ser Gly Asp Lys Asp Thr Phe Thr
20 25 30

<210> SEQ ID NO 393
<211> LENGTH: 5
<212> TYPE: PRT
<213> ORGANISM: Homo sapiens

<400> SEQUENCE: 393

Ser Phe Trp Ile Ala
1 5

<210> SEQ ID NO 394
<211> LENGTH: 14
<212> TYPE: PRT
<213> ORGANISM: Homo sapiens

<400> SEQUENCE: 394

Trp Val Arg Gln Met Pro Gly Lys Gly Leu Glu Trp Met Gly
1 5 10

<210> SEQ ID NO 395
<211> LENGTH: 17
<212> TYPE: PRT
<213> ORGANISM: Homo sapiens

<400> SEQUENCE: 395

Ile Ile Tyr Ala Gly Asp Ser Asp Thr Arg Tyr Ser Pro Ser Phe Gln
1 5 10 15

Gly

<210> SEQ ID NO 396
<211> LENGTH: 32
<212> TYPE: PRT
<213> ORGANISM: Homo sapiens

<400> SEQUENCE: 396

His Val Asn Ile Ser Val Asp Arg Ser Thr Asn Thr Ala Tyr Leu Gln
1 5 10 15

Trp Ser Ser Leu Lys Ala Ser Asp Thr Ala Met Tyr Tyr Cys Ala Arg
20 25 30

<210> SEQ ID NO 397
<211> LENGTH: 14
<212> TYPE: PRT
<213> ORGANISM: Homo sapiens

<400> SEQUENCE: 397

His Asp Ser Arg Tyr Lys Tyr Phe Tyr Phe Gly Met Asp Val
1 5 10

<210> SEQ ID NO 398
<211> LENGTH: 11

<212> TYPE: PRT
<213> ORGANISM: Homo sapiens

<400> SEQUENCE: 398

Trp Gly Gln Gly Thr Thr Val Thr Val Ser Ser
1               5                   10

<210> SEQ ID NO 399
<211> LENGTH: 30
<212> TYPE: PRT
<213> ORGANISM: Homo sapiens

<400> SEQUENCE: 399

Gln Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 400
<211> LENGTH: 5
<212> TYPE: PRT
<213> ORGANISM: Homo sapiens

<400> SEQUENCE: 400

Ser Tyr Gly Met His
1               5

<210> SEQ ID NO 401
<211> LENGTH: 14
<212> TYPE: PRT
<213> ORGANISM: Homo sapiens

<400> SEQUENCE: 401

Trp Val Arg Gln Ala Pro Gly Lys Gly Leu Glu Trp Val Ala
1               5                   10

<210> SEQ ID NO 402
<211> LENGTH: 17
<212> TYPE: PRT
<213> ORGANISM: Homo sapiens

<400> SEQUENCE: 402

Val Ile Trp Tyr Asp Gly Ser Asn Lys Tyr Tyr Ala Asp Ser Val Lys
1               5                   10                  15

Gly

<210> SEQ ID NO 403
<211> LENGTH: 32
<212> TYPE: PRT
<213> ORGANISM: Homo sapiens

<400> SEQUENCE: 403

Arg Phe Thr Ile Ser Arg Asp Asn Ser Lys Asp Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 404
<211> LENGTH: 13
<212> TYPE: PRT
<213> ORGANISM: Homo sapiens

<400> SEQUENCE: 404

Gly Tyr Ser Asn Tyr Asp Tyr Tyr Tyr Gly Met Asp Val
1 5 10

<210> SEQ ID NO 405
<211> LENGTH: 11
<212> TYPE: PRT
<213> ORGANISM: Homo sapiens

<400> SEQUENCE: 405

Trp Gly Gln Gly Thr Thr Val Thr Val Ser Ser
1 5 10

<210> SEQ ID NO 406
<211> LENGTH: 30
<212> TYPE: PRT
<213> ORGANISM: Homo sapiens

<400> SEQUENCE: 406

Gln Val Gln Leu Leu Glu Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 407
<211> LENGTH: 5
<212> TYPE: PRT
<213> ORGANISM: Homo sapiens

<400> SEQUENCE: 407

Ser Tyr Gly Met His
1 5

<210> SEQ ID NO 408
<211> LENGTH: 14
<212> TYPE: PRT
<213> ORGANISM: Homo sapiens

<400> SEQUENCE: 408

Trp Val Arg Gln Ala Pro Gly Lys Gly Leu Glu Trp Val Ala
1 5 10

<210> SEQ ID NO 409
<211> LENGTH: 17
<212> TYPE: PRT
<213> ORGANISM: Homo sapiens

<400> SEQUENCE: 409

Val Ile Trp Tyr Asp Gly Ser Asn Lys Tyr Tyr Ala Asp Ser Val Lys
1 5 10 15

Gly

<210> SEQ ID NO 410
<211> LENGTH: 32
<212> TYPE: PRT
<213> ORGANISM: Homo sapiens

<400> SEQUENCE: 410

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 411

<211> LENGTH: 13
<212> TYPE: PRT
<213> ORGANISM: Homo sapiens

<400> SEQUENCE: 411

Gly Tyr Ser Asn Tyr Asp Tyr Tyr Tyr Gly Met Asp Val
1 5 10

<210> SEQ ID NO 412
<211> LENGTH: 11
<212> TYPE: PRT
<213> ORGANISM: Homo sapiens

<400> SEQUENCE: 412

Trp Gly Gln Gly Thr Thr Val Thr Val Ser Ser
1 5 10

<210> SEQ ID NO 413
<211> LENGTH: 30
<212> TYPE: PRT
<213> ORGANISM: Homo sapiens

<400> SEQUENCE: 413

Gln Val Gln Leu Leu Gln Ser Ala Gly Gly Val Val Gln Pro Gly Arg
1 5 10 15

Ser Leu Arg Leu Ser Cys Ala Ala Ser Gly Phe Ile Phe Arg
20 25 30

<210> SEQ ID NO 414
<211> LENGTH: 5
<212> TYPE: PRT
<213> ORGANISM: Homo sapiens

<400> SEQUENCE: 414

Thr Tyr Gly Met His
1 5

<210> SEQ ID NO 415
<211> LENGTH: 14
<212> TYPE: PRT
<213> ORGANISM: Homo sapiens

<400> SEQUENCE: 415

Trp Val Arg Gln Ala Pro Gly Lys Gly Leu Glu Trp Val Ala
1 5 10

<210> SEQ ID NO 416
<211> LENGTH: 17
<212> TYPE: PRT
<213> ORGANISM: Homo sapiens

<400> SEQUENCE: 416

Phe Val Ser Ser Asp Gly Asn Asn Lys Phe Tyr Ser Asp Ser Val Lys
1 5 10 15

Gly

<210> SEQ ID NO 417
<211> LENGTH: 32
<212> TYPE: PRT
<213> ORGANISM: Homo sapiens

<400> SEQUENCE: 417

Arg Phe Thr Ile Pro Arg Asp Asn Ala Lys Asn Thr Leu Tyr Leu Gln
1 5 10 15

```
Met Asn Ser Leu Glu Thr Glu Asp Thr Ala Val Tyr Tyr Cys Ala Lys
            20                  25                  30


<210> SEQ ID NO 418
<211> LENGTH: 19
<212> TYPE: PRT
<213> ORGANISM: Homo sapiens

<400> SEQUENCE: 418

Asp Arg Tyr Pro Ile Asp Cys Ser Gly Gly Ser Cys Phe Ser Tyr Gly
1               5                   10                  15

Met Asp Val


<210> SEQ ID NO 419
<211> LENGTH: 11
<212> TYPE: PRT
<213> ORGANISM: Homo sapiens

<400> SEQUENCE: 419

Trp Gly Gln Gly Thr Thr Val Thr Val Ser Ser
1               5                   10


<210> SEQ ID NO 420
<211> LENGTH: 30
<212> TYPE: PRT
<213> ORGANISM: Homo sapiens

<400> SEQUENCE: 420

Glu Val Gln Leu Val Glu Ser Gly Gly Gly Val Val Gln Pro Gly Arg
1               5                   10                  15

Ser Leu Arg Leu Ser Cys Ala Thr Ser Gly Phe Ile Leu Arg
            20                  25                  30


<210> SEQ ID NO 421
<211> LENGTH: 5
<212> TYPE: PRT
<213> ORGANISM: Homo sapiens

<400> SEQUENCE: 421

Thr Tyr Gly Met His
1               5


<210> SEQ ID NO 422
<211> LENGTH: 14
<212> TYPE: PRT
<213> ORGANISM: Homo sapiens

<400> SEQUENCE: 422

Trp Val Arg Gln Ala Pro Gly Lys Gly Leu Glu Trp Val Ala
1               5                   10


<210> SEQ ID NO 423
<211> LENGTH: 17
<212> TYPE: PRT
<213> ORGANISM: Homo sapiens

<400> SEQUENCE: 423

Phe Val Ser Ser Asp Gly Asn Asn Lys Phe Tyr Ser Asp Ser Val Lys
1               5                   10                  15

Gly


<210> SEQ ID NO 424
```

<211> LENGTH: 32
<212> TYPE: PRT
<213> ORGANISM: Homo sapiens

<400> SEQUENCE: 424

Arg Phe Thr Ile Pro Arg Asp Asn Ala Lys Asn Thr Leu Tyr Leu Gln
1 5 10 15

Met Asn Ser Leu Glu Thr Glu Asp Thr Ala Val Tyr Tyr Cys Ala Lys
20 25 30

<210> SEQ ID NO 425
<211> LENGTH: 19
<212> TYPE: PRT
<213> ORGANISM: Homo sapiens

<400> SEQUENCE: 425

Asp Arg Tyr Pro Ile Asp Cys Ser Gly Gly Ser Cys Phe Ser Tyr Gly
1 5 10 15

Met Asp Val

<210> SEQ ID NO 426
<211> LENGTH: 11
<212> TYPE: PRT
<213> ORGANISM: Homo sapiens

<400> SEQUENCE: 426

Trp Gly Gln Gly Thr Leu Val Thr Val Ser Ser
1 5 10

<210> SEQ ID NO 427
<211> LENGTH: 30
<212> TYPE: PRT
<213> ORGANISM: Homo sapiens

<400> SEQUENCE: 427

Glu Val Gln Leu Val Gln Ser Gly Gly Gly Val Val Gln Pro Gly Arg
1 5 10 15

Ser Leu Arg Leu Ser Cys Ala Ala Ser Gly Phe Ile Phe Arg
20 25 30

<210> SEQ ID NO 428
<211> LENGTH: 5
<212> TYPE: PRT
<213> ORGANISM: Homo sapiens

<400> SEQUENCE: 428

Thr Tyr Gly Met His
1 5

<210> SEQ ID NO 429
<211> LENGTH: 14
<212> TYPE: PRT
<213> ORGANISM: Homo sapiens

<400> SEQUENCE: 429

Trp Val Arg Gln Ala Pro Gly Lys Gly Leu Glu Trp Val Ala
1 5 10

<210> SEQ ID NO 430
<211> LENGTH: 17
<212> TYPE: PRT
<213> ORGANISM: Homo sapiens

<400> SEQUENCE: 430

Phe Val Ser Ser Asp Gly Asn Asn Lys Phe Tyr Ser Asp Ser Val Lys
1 5 10 15

Gly

<210> SEQ ID NO 431
<211> LENGTH: 32
<212> TYPE: PRT
<213> ORGANISM: Homo sapiens

<400> SEQUENCE: 431

Arg Phe Thr Ile Ser Arg Asp Asn Ala Lys Asn Thr Leu Tyr Leu Gln
1 5 10 15

Met Asn Ser Leu Glu Thr Glu Asp Thr Ala Met Tyr Tyr Cys Ala Lys
20 25 30

<210> SEQ ID NO 432
<211> LENGTH: 19
<212> TYPE: PRT
<213> ORGANISM: Homo sapiens

<400> SEQUENCE: 432

Asp Arg Tyr Pro Ile Asp Cys Ser Gly Gly Ser Cys Phe Ser Tyr Gly
1 5 10 15

Met Asp Val

<210> SEQ ID NO 433
<211> LENGTH: 11
<212> TYPE: PRT
<213> ORGANISM: Homo sapiens

<400> SEQUENCE: 433

Trp Gly Gln Gly Thr Thr Val Thr Val Ser Ser
1 5 10

<210> SEQ ID NO 434
<211> LENGTH: 30
<212> TYPE: PRT
<213> ORGANISM: Homo sapiens

<400> SEQUENCE: 434

Gln Val Asn Leu Arg Glu Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 435
<211> LENGTH: 5
<212> TYPE: PRT
<213> ORGANISM: Homo sapiens

<400> SEQUENCE: 435

Ser Tyr Ala Leu His
1 5

<210> SEQ ID NO 436
<211> LENGTH: 14
<212> TYPE: PRT
<213> ORGANISM: Homo sapiens

<400> SEQUENCE: 436

Trp Val Arg Gln Thr Pro Gly Lys Gly Leu Glu Trp Val Ala
1 5 10

<210> SEQ ID NO 437
<211> LENGTH: 17
<212> TYPE: PRT
<213> ORGANISM: Homo sapiens

<400> SEQUENCE: 437

Leu Ile Ser Tyr Asp Gly Ser Asn Lys Tyr Tyr Ala Asp Ser Val Lys
1 5 10 15

Gly

<210> SEQ ID NO 438
<211> LENGTH: 32
<212> TYPE: PRT
<213> ORGANISM: Homo sapiens

<400> SEQUENCE: 438

Arg Phe Thr Ile Ser Arg Asp Asn Ser Lys Asn Met Leu Tyr Leu Gln
1 5 10 15

Met Asn Ser Leu Arg Ala Glu Asp Thr Ala Val Tyr Tyr Cys Ala Lys
20 25 30

<210> SEQ ID NO 439
<211> LENGTH: 14
<212> TYPE: PRT
<213> ORGANISM: Homo sapiens

<400> SEQUENCE: 439

Asp Arg Ser His Tyr Gly Asp Tyr Val Gly Tyr Leu Asp Tyr
1 5 10

<210> SEQ ID NO 440
<211> LENGTH: 11
<212> TYPE: PRT
<213> ORGANISM: Homo sapiens

<400> SEQUENCE: 440

Trp Gly Gln Gly Thr Leu Val Thr Val Ser Ser
1 5 10

<210> SEQ ID NO 441
<211> LENGTH: 30
<212> TYPE: PRT
<213> ORGANISM: Homo sapiens

<400> SEQUENCE: 441

Gln Val Asn Leu Arg Glu Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 442
<211> LENGTH: 5
<212> TYPE: PRT
<213> ORGANISM: Homo sapiens

<400> SEQUENCE: 442

Ser Tyr Ala Leu His
1 5

<210> SEQ ID NO 443
<211> LENGTH: 14
<212> TYPE: PRT

<213> ORGANISM: Homo sapiens

<400> SEQUENCE: 443

Trp Val Arg Gln Thr Pro Gly Lys Gly Leu Glu Trp Val Ala
1               5                   10

<210> SEQ ID NO 444
<211> LENGTH: 17
<212> TYPE: PRT
<213> ORGANISM: Homo sapiens

<400> SEQUENCE: 444

Leu Ile Ser Tyr Asp Gly Ser Asn Lys Tyr Tyr Ala Asp Ser Val Lys
1               5                   10                  15

Gly

<210> SEQ ID NO 445
<211> LENGTH: 32
<212> TYPE: PRT
<213> ORGANISM: Homo sapiens

<400> SEQUENCE: 445

Arg Phe Thr Ile Ser Arg Asp Asn Ser Lys Asn Met Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 446
<211> LENGTH: 14
<212> TYPE: PRT
<213> ORGANISM: Homo sapiens

<400> SEQUENCE: 446

Asp Arg Ser His Tyr Gly Asp Tyr Val Gly Tyr Leu Asp Tyr
1               5                   10

<210> SEQ ID NO 447
<211> LENGTH: 11
<212> TYPE: PRT
<213> ORGANISM: Homo sapiens

<400> SEQUENCE: 447

Trp Gly Gln Gly Thr Leu Val Thr Val Ser Ser
1               5                   10

<210> SEQ ID NO 448
<211> LENGTH: 30
<212> TYPE: PRT
<213> ORGANISM: Homo sapiens

<400> SEQUENCE: 448

Gln Val Asn Leu Arg Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 449
<211> LENGTH: 5
<212> TYPE: PRT
<213> ORGANISM: Homo sapiens

<400> SEQUENCE: 449

Ser Tyr Ala Leu His 1 5

<210> SEQ ID NO 450
<211> LENGTH: 14
<212> TYPE: PRT
<213> ORGANISM: Homo sapiens

<400> SEQUENCE: 450

Trp Val Arg Gln Thr Pro Gly Lys Gly Leu Glu Trp Val Ala
1 5 10

<210> SEQ ID NO 451
<211> LENGTH: 17
<212> TYPE: PRT
<213> ORGANISM: Homo sapiens

<400> SEQUENCE: 451

Leu Ile Ser Tyr Asp Gly Ser Asn Lys Tyr Tyr Ala Asp Ser Val Lys
1 5 10 15

Gly

<210> SEQ ID NO 452
<211> LENGTH: 32
<212> TYPE: PRT
<213> ORGANISM: Homo sapiens

<400> SEQUENCE: 452

Arg Phe Thr Ile Ser Arg Asp Asn Ser Lys Asn Met Leu Tyr Leu Gln
1 5 10 15

Met Asn Ser Leu Arg Ala Glu Asp Thr Ala Val Tyr Tyr Cys Ala Lys
20 25 30

<210> SEQ ID NO 453
<211> LENGTH: 14
<212> TYPE: PRT
<213> ORGANISM: Homo sapiens

<400> SEQUENCE: 453

Asp Arg Ser His Tyr Gly Asp Tyr Val Gly Tyr Leu Asp Tyr
1 5 10

<210> SEQ ID NO 454
<211> LENGTH: 11
<212> TYPE: PRT
<213> ORGANISM: Homo sapiens

<400> SEQUENCE: 454

Trp Gly Gln Gly Thr Leu Val Thr Val Ser Ser
1 5 10

<210> SEQ ID NO 455
<211> LENGTH: 30
<212> TYPE: PRT
<213> ORGANISM: Homo sapiens

<400> SEQUENCE: 455

Glu Val Gln Leu Val Gln Ser Gly Gly Gly Leu Val Gln Pro Gly Gly
1 5 10 15

Ser Arg Arg Leu Ser Cys Ala Ala Ser Gly Phe Tyr Phe Asn
20 25 30

<210> SEQ ID NO 456
<211> LENGTH: 5

<212> TYPE: PRT
<213> ORGANISM: Homo sapiens

<400> SEQUENCE: 456

Ala Tyr Trp Met Thr
1 5

<210> SEQ ID NO 457
<211> LENGTH: 14
<212> TYPE: PRT
<213> ORGANISM: Homo sapiens

<400> SEQUENCE: 457

Trp Val Arg Gln Ala Pro Gly Lys Gly Leu Glu Trp Val Ala
1 5 10

<210> SEQ ID NO 458
<211> LENGTH: 17
<212> TYPE: PRT
<213> ORGANISM: Homo sapiens

<400> SEQUENCE: 458

Asn Ile Asn Leu Asp Gly Thr Glu Ile Tyr Tyr Leu Asp Ser Val Lys
1 5 10 15

Gly

<210> SEQ ID NO 459
<211> LENGTH: 32
<212> TYPE: PRT
<213> ORGANISM: Homo sapiens

<400> SEQUENCE: 459

Arg Phe Thr Val Ser Arg Asp Asn Val Lys Asn Ser Val Phe Leu Gln
1 5 10 15

Met Ser Ser Leu Arg Val Glu Asp Thr Ala Val Tyr Phe Cys Ala Arg
20 25 30

<210> SEQ ID NO 460
<211> LENGTH: 12
<212> TYPE: PRT
<213> ORGANISM: Homo sapiens

<400> SEQUENCE: 460

Leu Glu Trp Gly Gly Arg Asn Gly Trp Val Ser Pro
1 5 10

<210> SEQ ID NO 461
<211> LENGTH: 11
<212> TYPE: PRT
<213> ORGANISM: Homo sapiens

<400> SEQUENCE: 461

Trp Gly Gln Gly Thr Leu Val Thr Val Ser Ser
1 5 10

<210> SEQ ID NO 462
<211> LENGTH: 30
<212> TYPE: PRT
<213> ORGANISM: Homo sapiens

<400> SEQUENCE: 462

Gln Val Gln Leu Val Gln Ser Gly Gly Gly Leu Val Gln Pro Gly Gly
1 5 10 15

```
Ser Arg Arg Leu Ser Cys Ala Ala Ser Gly Phe Tyr Phe Asn
            20                  25                  30


<210> SEQ ID NO 463
<211> LENGTH: 5
<212> TYPE: PRT
<213> ORGANISM: Homo sapiens

<400> SEQUENCE: 463

Ala Tyr Trp Met Thr
1               5


<210> SEQ ID NO 464
<211> LENGTH: 14
<212> TYPE: PRT
<213> ORGANISM: Homo sapiens

<400> SEQUENCE: 464

Trp Val Arg Gln Ala Pro Gly Lys Gly Leu Glu Trp Val Ala
1               5                   10


<210> SEQ ID NO 465
<211> LENGTH: 17
<212> TYPE: PRT
<213> ORGANISM: Homo sapiens

<400> SEQUENCE: 465

Asn Ile Asn Leu Asp Gly Thr Glu Ile Tyr Tyr Leu Asp Ser Val Lys
1               5                   10                  15

Gly


<210> SEQ ID NO 466
<211> LENGTH: 32
<212> TYPE: PRT
<213> ORGANISM: Homo sapiens

<400> SEQUENCE: 466

Arg Phe Thr Val Ser Arg Asp Asn Val Lys Asn Ser Val Phe Leu Gln
1               5                   10                  15

Met Ser Ser Leu Arg Val Glu Asp Thr Ala Val Tyr Phe Cys Ala Arg
            20                  25                  30


<210> SEQ ID NO 467
<211> LENGTH: 12
<212> TYPE: PRT
<213> ORGANISM: Homo sapiens

<400> SEQUENCE: 467

Leu Glu Trp Gly Gly Arg Asn Gly Trp Val Ser Pro
1               5                   10


<210> SEQ ID NO 468
<211> LENGTH: 11
<212> TYPE: PRT
<213> ORGANISM: Homo sapiens

<400> SEQUENCE: 468

Trp Gly Gln Gly Thr Leu Val Thr Val Ser Ser
1               5                   10


<210> SEQ ID NO 469
<211> LENGTH: 30
<212> TYPE: PRT
<213> ORGANISM: Homo sapiens
```

<400> SEQUENCE: 469

Gln Val Gln Leu Val Gln Ser Gly Ala Glu Val Lys Lys Pro Gly Ala
1               5                   10                  15

Ser Val Asn Val Ser Cys Lys Ala Ser Gly Tyr Thr Phe Thr
            20                  25                  30

<210> SEQ ID NO 470
<211> LENGTH: 5
<212> TYPE: PRT
<213> ORGANISM: Homo sapiens

<400> SEQUENCE: 470

Gly Tyr Tyr Ile Tyr
1               5

<210> SEQ ID NO 471
<211> LENGTH: 14
<212> TYPE: PRT
<213> ORGANISM: Homo sapiens

<400> SEQUENCE: 471

Trp Val Arg Gln Ala Pro Gly Gln Gly Leu Glu Trp Met Gly
1               5                   10

<210> SEQ ID NO 472
<211> LENGTH: 17
<212> TYPE: PRT
<213> ORGANISM: Homo sapiens

<400> SEQUENCE: 472

Trp Ile Asn Pro Asn Ser Gly Val Thr Lys Tyr Ala Gln Lys Phe Gln
1               5                   10                  15

Gly

<210> SEQ ID NO 473
<211> LENGTH: 32
<212> TYPE: PRT
<213> ORGANISM: Homo sapiens

<400> SEQUENCE: 473

Arg Val Thr Met Thr Ile Asp Thr Ser Thr Asn Thr Ala Tyr Met Glu
1               5                   10                  15

Leu Asn Arg Leu Arg Ala Asp Asp Thr Ala Val Tyr Tyr Cys Ala Arg
            20                  25                  30

<210> SEQ ID NO 474
<211> LENGTH: 11
<212> TYPE: PRT
<213> ORGANISM: Homo sapiens

<400> SEQUENCE: 474

Glu Trp Thr Gln Leu Trp Ser Pro Tyr Asp Tyr
1               5                   10

<210> SEQ ID NO 475
<211> LENGTH: 11
<212> TYPE: PRT
<213> ORGANISM: Homo sapiens

<400> SEQUENCE: 475

Trp Gly Gln Gly Thr Thr Val Thr Val Ser Ser
1               5                   10

<210> SEQ ID NO 476
<211> LENGTH: 32
<212> TYPE: PRT
<213> ORGANISM: Homo sapiens

<400> SEQUENCE: 476

Gln Val Gln Leu Gln Glu Ser Gly Ser Arg Leu Val Lys Pro Ser Gln
1 5 10 15

Thr Leu Ser Leu Thr Cys Gly Val Ser Gly Gly Ser Ile Ser Ser Ser
20 25 30

<210> SEQ ID NO 477
<211> LENGTH: 5
<212> TYPE: PRT
<213> ORGANISM: Homo sapiens

<400> SEQUENCE: 477

Ser Tyr Ser Trp Ser
1 5

<210> SEQ ID NO 478
<211> LENGTH: 14
<212> TYPE: PRT
<213> ORGANISM: Homo sapiens

<400> SEQUENCE: 478

Trp Ile Arg Gln Thr Pro Gly Lys Gly Leu Glu Trp Ile Gly
1 5 10

<210> SEQ ID NO 479
<211> LENGTH: 16
<212> TYPE: PRT
<213> ORGANISM: Homo sapiens

<400> SEQUENCE: 479

Tyr Ile Tyr His Ser Gly Ser Thr Tyr Tyr Asn Pro Ser Leu Lys Ser
1 5 10 15

<210> SEQ ID NO 480
<211> LENGTH: 32
<212> TYPE: PRT
<213> ORGANISM: Homo sapiens

<400> SEQUENCE: 480

Arg Val Thr Met Ser Val Asp Lys Ser Arg Asn Gln Phe Ser Leu Asn
1 5 10 15

Met Ser Ser Val Thr Ala Ala Asp Thr Ala Val Tyr Tyr Cys Ala Arg
20 25 30

<210> SEQ ID NO 481
<211> LENGTH: 17
<212> TYPE: PRT
<213> ORGANISM: Homo sapiens

<400> SEQUENCE: 481

Thr Ala Phe Tyr Tyr Glu Asn Thr Gly Pro Ile Arg Cys Tyr Leu Asp
1 5 10 15

Phe

<210> SEQ ID NO 482
<211> LENGTH: 11
<212> TYPE: PRT

<213> ORGANISM: Homo sapiens

<400> SEQUENCE: 482

Trp Gly Gln Gly Thr Leu Val Thr Val Ser Ser
1               5                   10

<210> SEQ ID NO 483
<211> LENGTH: 30
<212> TYPE: PRT
<213> ORGANISM: Homo sapiens

<400> SEQUENCE: 483

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 484
<211> LENGTH: 5
<212> TYPE: PRT
<213> ORGANISM: Homo sapiens

<400> SEQUENCE: 484

His Tyr Gly Met His
1               5

<210> SEQ ID NO 485
<211> LENGTH: 14
<212> TYPE: PRT
<213> ORGANISM: Homo sapiens

<400> SEQUENCE: 485

Trp Val Arg Gln Ser Pro Gly Lys Gly Leu Glu Trp Val Ala
1               5                   10

<210> SEQ ID NO 486
<211> LENGTH: 17
<212> TYPE: PRT
<213> ORGANISM: Homo sapiens

<400> SEQUENCE: 486

Val Ile Trp Tyr Asp Gly Arg Asn Pro Tyr Tyr Ala Ala Ser Val Lys
1               5                   10                  15

Gly

<210> SEQ ID NO 487
<211> LENGTH: 32
<212> TYPE: PRT
<213> ORGANISM: Homo sapiens

<400> SEQUENCE: 487

Arg Phe Thr Ile Ser Arg Asp Asn Asp Lys Asn Thr Leu Tyr Leu Gln
1               5                   10                  15

Met Asn Ser Leu Arg Ala Glu Asp Thr Ala Val Tyr Tyr Cys Val Lys
            20                  25                  30

<210> SEQ ID NO 488
<211> LENGTH: 15
<212> TYPE: PRT
<213> ORGANISM: Homo sapiens

<400> SEQUENCE: 488

Asp Leu Thr Arg Phe His Asp Thr Thr Phe Gly Val Phe Glu Met 1 5 10 15

<210> SEQ ID NO 489
<211> LENGTH: 11
<212> TYPE: PRT
<213> ORGANISM: Homo sapiens

<400> SEQUENCE: 489

Trp Gly Pro Gly Thr Thr Val Thr Val Ser Ser
1 5 10

<210> SEQ ID NO 490
<211> LENGTH: 24
<212> TYPE: DNA
<213> ORGANISM: Artificial Sequence
<220> FEATURE:
<223> OTHER INFORMATION: Primer

<400> SEQUENCE: 490
ttcgaagggc ccgcctgcgg ccgc 24

<210> SEQ ID NO 491
<211> LENGTH: 30
<212> TYPE: PRT
<213> ORGANISM: Homo sapiens

<400> SEQUENCE: 491

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 492
<211> LENGTH: 5
<212> TYPE: PRT
<213> ORGANISM: Homo sapiens

<400> SEQUENCE: 492

His Tyr Gly Met His
1 5

<210> SEQ ID NO 493
<211> LENGTH: 14
<212> TYPE: PRT
<213> ORGANISM: Homo sapiens

<400> SEQUENCE: 493

Trp Val Arg Gln Ser Pro Gly Lys Gly Leu Glu Trp Val Ala
1 5 10

<210> SEQ ID NO 494
<211> LENGTH: 17
<212> TYPE: PRT
<213> ORGANISM: Homo sapiens

<400> SEQUENCE: 494

Val Ile Trp Tyr Asp Gly Arg Asn Pro Tyr Tyr Ala Ala Ser Val Lys
1 5 10 15

Gly

<210> SEQ ID NO 495
<211> LENGTH: 32
<212> TYPE: PRT
<213> ORGANISM: Homo sapiens

<400> SEQUENCE: 495

Arg Phe Thr Ile Ser Arg Asp Asn Asp Lys Asn Thr Leu Tyr Leu Gln
1 5 10 15

Met Asn Ser Leu Arg Ala Glu Asp Thr Ala Val Tyr Tyr Cys Val Lys
20 25 30

<210> SEQ ID NO 496
<211> LENGTH: 15
<212> TYPE: PRT
<213> ORGANISM: Homo sapiens

<400> SEQUENCE: 496

Asp Leu Thr Arg Phe His Asp Thr Thr Phe Gly Val Phe Glu Met
1 5 10 15

<210> SEQ ID NO 497
<211> LENGTH: 11
<212> TYPE: PRT
<213> ORGANISM: Homo sapiens

<400> SEQUENCE: 497

Trp Gly Pro Gly Thr Thr Val Thr Val Ser Ser
1 5 10

<210> SEQ ID NO 498
<211> LENGTH: 30
<212> TYPE: PRT
<213> ORGANISM: Homo sapiens

<400> SEQUENCE: 498

Gln Val Gln Leu Val Gln Ser Gly Gly Gly Leu Val Gln Pro Gly Gly
1 5 10 15

Ser Arg Arg Leu Ser Cys Ala Ala Ser Gly Phe Tyr Phe Lys
20 25 30

<210> SEQ ID NO 499
<211> LENGTH: 5
<212> TYPE: PRT
<213> ORGANISM: Homo sapiens

<400> SEQUENCE: 499

Ala Tyr Trp Met Thr
1 5

<210> SEQ ID NO 500
<211> LENGTH: 14
<212> TYPE: PRT
<213> ORGANISM: Homo sapiens

<400> SEQUENCE: 500

Trp Val Arg Gln Ala Pro Gly Lys Gly Leu Glu Trp Val Ala
1 5 10

<210> SEQ ID NO 501
<211> LENGTH: 17
<212> TYPE: PRT
<213> ORGANISM: Homo sapiens

<400> SEQUENCE: 501

Asn Ile Asn Leu Asp Gly Thr Glu Ile Tyr Tyr Leu Asp Ser Val Lys
1 5 10 15

Gly

<210> SEQ ID NO 502
<211> LENGTH: 32
<212> TYPE: PRT
<213> ORGANISM: Homo sapiens

<400> SEQUENCE: 502

```
Arg Phe Thr Val Ser Arg Asp Asn Val Lys Asn Ser Val Phe Leu Gln
1               5                   10                  15

Met Ser Ser Leu Arg Val Glu Asp Thr Ala Val Tyr Phe Cys Ala Arg
            20                  25                  30
```

<210> SEQ ID NO 503
<211> LENGTH: 12
<212> TYPE: PRT
<213> ORGANISM: Homo sapiens

<400> SEQUENCE: 503

```
Leu Glu Trp Gly Gly Arg Asn Gly Trp Val Ser Pro
1               5                   10
```

<210> SEQ ID NO 504
<211> LENGTH: 11
<212> TYPE: PRT
<213> ORGANISM: Homo sapiens

<400> SEQUENCE: 504

```
Trp Gly Gln Gly Thr Leu Val Thr Val Ser Ser
1               5                   10
```

<210> SEQ ID NO 505
<211> LENGTH: 30
<212> TYPE: PRT
<213> ORGANISM: Homo sapiens

<400> SEQUENCE: 505

```
Glu Val Gln Leu Val Glu Ser Gly Gly Gly Leu Val Gln Pro Gly Gly
1               5                   10                  15

Ser Arg Arg Leu Ser Cys Ala Ala Ser Gly Phe Tyr Phe Asn
            20                  25                  30
```

<210> SEQ ID NO 506
<211> LENGTH: 5
<212> TYPE: PRT
<213> ORGANISM: Homo sapiens

<400> SEQUENCE: 506

```
Ala Tyr Trp Met Thr
1               5
```

<210> SEQ ID NO 507
<211> LENGTH: 14
<212> TYPE: PRT
<213> ORGANISM: Homo sapiens

<400> SEQUENCE: 507

```
Trp Val Arg Gln Ala Pro Gly Lys Gly Leu Glu Trp Val Ala
1               5                   10
```

<210> SEQ ID NO 508
<211> LENGTH: 17
<212> TYPE: PRT
<213> ORGANISM: Homo sapiens

<400> SEQUENCE: 508

Asn Ile Asn Leu Asp Gly Thr Glu Ile Tyr Tyr Leu Asp Ser Val Lys
1 5 10 15

Gly

<210> SEQ ID NO 509
<211> LENGTH: 32
<212> TYPE: PRT
<213> ORGANISM: Homo sapiens

<400> SEQUENCE: 509

Arg Phe Thr Val Ser Arg Asp Asn Val Lys Asn Ser Val Phe Leu Gln
1 5 10 15

Met Ser Ser Leu Arg Val Glu Asp Thr Ala Val Tyr Phe Cys Ala Arg
20 25 30

<210> SEQ ID NO 510
<211> LENGTH: 12
<212> TYPE: PRT
<213> ORGANISM: Homo sapiens

<400> SEQUENCE: 510

Leu Glu Trp Gly Gly Arg Asn Gly Trp Leu Ser Pro
1 5 10

<210> SEQ ID NO 511
<211> LENGTH: 11
<212> TYPE: PRT
<213> ORGANISM: Homo sapiens

<400> SEQUENCE: 511

Trp Gly Gln Gly Thr Leu Val Thr Val Ser Ser
1 5 10

<210> SEQ ID NO 512
<211> LENGTH: 32
<212> TYPE: PRT
<213> ORGANISM: Homo sapiens

<400> SEQUENCE: 512

Gln Val Gln Leu Gln Glu Ser Gly Ser Arg Leu Val Lys Pro Ser Gln
1 5 10 15

Thr Leu Ser Leu Thr Cys Gly Val Ser Gly Gly Ser Ile Ser Ser Ser
20 25 30

<210> SEQ ID NO 513
<211> LENGTH: 5
<212> TYPE: PRT
<213> ORGANISM: Homo sapiens

<400> SEQUENCE: 513

Ser Tyr Ser Trp Ser
1 5

<210> SEQ ID NO 514
<211> LENGTH: 14
<212> TYPE: PRT
<213> ORGANISM: Homo sapiens

<400> SEQUENCE: 514

Trp Ile Arg Gln Thr Pro Gly Lys Gly Leu Glu Trp Ile Gly
1 5 10

<210> SEQ ID NO 515
<211> LENGTH: 16
<212> TYPE: PRT
<213> ORGANISM: Homo sapiens

<400> SEQUENCE: 515

Tyr Ile Tyr His Ser Gly Ser Thr Tyr Tyr Asn Pro Ser Leu Lys Ser
1               5                   10                  15

<210> SEQ ID NO 516
<211> LENGTH: 32
<212> TYPE: PRT
<213> ORGANISM: Homo sapiens

<400> SEQUENCE: 516

Arg Val Thr Met Ser Val Asp Lys Ser Arg Asn Gln Phe Ser Leu Asn
1               5                   10                  15

Met Ser Ser Val Thr Ala Ala Asp Thr Ala Val Tyr Tyr Cys Ala Arg
            20                  25                  30

<210> SEQ ID NO 517
<211> LENGTH: 17
<212> TYPE: PRT
<213> ORGANISM: Homo sapiens

<400> SEQUENCE: 517

Thr Ala Phe Tyr Tyr Glu Asn Thr Gly Pro Ile Arg Cys Tyr Leu Asp
1               5                   10                  15

Phe

<210> SEQ ID NO 518
<211> LENGTH: 11
<212> TYPE: PRT
<213> ORGANISM: Homo sapiens

<400> SEQUENCE: 518

Trp Gly Gln Gly Thr Leu Val Thr Val Ser Ser
1               5                   10

<210> SEQ ID NO 519
<211> LENGTH: 30
<212> TYPE: PRT
<213> ORGANISM: Homo sapiens

<400> SEQUENCE: 519

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 520
<211> LENGTH: 5
<212> TYPE: PRT
<213> ORGANISM: Homo sapiens

<400> SEQUENCE: 520

Asn Tyr Pro Met Ser
1               5

<210> SEQ ID NO 521
<211> LENGTH: 14
<212> TYPE: PRT
<213> ORGANISM: Homo sapiens

<400> SEQUENCE: 521

Trp Val Arg Gln Ala Pro Gly Lys Gly Leu Ala Trp Val Ser
1 5 10

<210> SEQ ID NO 522
<211> LENGTH: 17
<212> TYPE: PRT
<213> ORGANISM: Homo sapiens

<400> SEQUENCE: 522

Ser Leu Thr Ala Ser Gly Asp Asn Thr Phe Tyr Ala Asp Ser Val Lys
1 5 10 15

Gly

<210> SEQ ID NO 523
<211> LENGTH: 32
<212> TYPE: PRT
<213> ORGANISM: Homo sapiens

<400> SEQUENCE: 523

Arg Phe Thr Ile Ser Arg Asp Asn Ser Asn Asn Thr Leu Tyr Leu Gln
1 5 10 15

Met His Ser Leu Arg Ala Glu Asp Thr Ala Val Tyr Tyr Cys Ala Lys
20 25 30

<210> SEQ ID NO 524
<211> LENGTH: 19
<212> TYPE: PRT
<213> ORGANISM: Homo sapiens

<400> SEQUENCE: 524

Ala Leu Val Gly Arg Tyr Asp Ile Ser Thr Gly Tyr Tyr Arg Pro Val
1 5 10 15

Met Asp Ser

<210> SEQ ID NO 525
<211> LENGTH: 11
<212> TYPE: PRT
<213> ORGANISM: Homo sapiens

<400> SEQUENCE: 525

Trp Gly Gln Gly Thr Leu Val Thr Val Ser Ser
1 5 10

<210> SEQ ID NO 526
<211> LENGTH: 30
<212> TYPE: PRT
<213> ORGANISM: Homo sapiens

<400> SEQUENCE: 526

Gln Val Gln Leu Val Glu Ser Gly Gly Gly Val Val Gln Pro Gly Arg
1 5 10 15

Ser Leu Arg Leu Ser Cys Ala Ala Ser Gly Leu Thr Phe Ser
20 25 30

<210> SEQ ID NO 527
<211> LENGTH: 5
<212> TYPE: PRT
<213> ORGANISM: Homo sapiens

<400> SEQUENCE: 527

Val Tyr Gly Met His
1 5

<210> SEQ ID NO 528
<211> LENGTH: 14
<212> TYPE: PRT
<213> ORGANISM: Homo sapiens

<400> SEQUENCE: 528

Trp Val Arg Gln Ala Pro Gly Lys Gly Leu Glu Trp Val Ala
1 5 10

<210> SEQ ID NO 529
<211> LENGTH: 17
<212> TYPE: PRT
<213> ORGANISM: Homo sapiens

<400> SEQUENCE: 529

Val Ile Ser His Thr Gly Ser Glu Glu Tyr Tyr Ala Asp Ser Val Lys
1 5 10 15

Gly

<210> SEQ ID NO 530
<211> LENGTH: 32
<212> TYPE: PRT
<213> ORGANISM: Homo sapiens

<400> SEQUENCE: 530

Arg Phe Ser Ile Ser Arg Asp Asn Ser Asn Asn Thr Leu Phe Leu Gln
1 5 10 15

Met Asn Ser Leu Arg Pro Glu Asp Thr Ala Val Tyr Tyr Cys Val Lys
20 25 30

<210> SEQ ID NO 531
<211> LENGTH: 14
<212> TYPE: PRT
<213> ORGANISM: Homo sapiens

<400> SEQUENCE: 531

Asp Gly Pro Met Ala Ala Ile Pro Phe Tyr Tyr Phe Asp Phe
1 5 10

<210> SEQ ID NO 532
<211> LENGTH: 11
<212> TYPE: PRT
<213> ORGANISM: Homo sapiens

<400> SEQUENCE: 532

Trp Gly Gln Gly Thr Leu Val Thr Val Ser Ser
1 5 10

<210> SEQ ID NO 533
<211> LENGTH: 30
<212> TYPE: PRT
<213> ORGANISM: Homo sapiens

<400> SEQUENCE: 533

Gln Val Gln Leu Gln Glu Ser Gly Pro Gly Leu Val Lys Pro Ser Gln
1 5 10 15

Thr Leu Ser Leu Ser Cys Ser Val Ser Gly Ala Ser Ile Thr
20 25 30

<210> SEQ ID NO 534

<211> LENGTH: 7
<212> TYPE: PRT
<213> ORGANISM: Homo sapiens

<400> SEQUENCE: 534

Ser Gly Thr Phe Tyr Trp Ser
1 5

<210> SEQ ID NO 535
<211> LENGTH: 14
<212> TYPE: PRT
<213> ORGANISM: Homo sapiens

<400> SEQUENCE: 535

Trp Ile Arg Gln His Pro Gly Lys Asp Leu Glu Trp Ile Gly
1 5 10

<210> SEQ ID NO 536
<211> LENGTH: 16
<212> TYPE: PRT
<213> ORGANISM: Homo sapiens

<400> SEQUENCE: 536

Tyr Ile Tyr Tyr Ser Gly Thr Thr Tyr Tyr Asn Pro Ser Leu Lys Ser
1 5 10 15

<210> SEQ ID NO 537
<211> LENGTH: 32
<212> TYPE: PRT
<213> ORGANISM: Homo sapiens

<400> SEQUENCE: 537

Arg Val Thr Leu Ser Val Asp Thr Ser Lys Asn Gln Phe Ser Leu Lys
1 5 10 15

Val Thr Ser Leu Thr Ala Ala Asp Thr Ala Val Tyr His Cys Ala Arg
20 25 30

<210> SEQ ID NO 538
<211> LENGTH: 18
<212> TYPE: PRT
<213> ORGANISM: Homo sapiens

<400> SEQUENCE: 538

Gly Val Pro Ile Tyr Asp Ser Ser Gly Thr Tyr Arg Gly Thr Tyr Phe
1 5 10 15

Asp Tyr

<210> SEQ ID NO 539
<211> LENGTH: 11
<212> TYPE: PRT
<213> ORGANISM: Homo sapiens

<400> SEQUENCE: 539

Trp Gly Gln Gly Thr Leu Val Thr Val Ser Ser
1 5 10

<210> SEQ ID NO 540
<211> LENGTH: 30
<212> TYPE: PRT
<213> ORGANISM: Homo sapiens

<400> SEQUENCE: 540

Gln Val Gln Leu Gln Glu Ser Gly Pro Gly Leu Val Lys Pro Ser Gln
1 5 10 15

```
Thr Leu Ser Leu Ser Cys Ser Val Ser Gly Ala Ser Ile Thr
            20                  25                  30


<210> SEQ ID NO 541
<211> LENGTH: 7
<212> TYPE: PRT
<213> ORGANISM: Homo sapiens

<400> SEQUENCE: 541

Ser Gly Thr Phe Tyr Trp Ser
1               5


<210> SEQ ID NO 542
<211> LENGTH: 14
<212> TYPE: PRT
<213> ORGANISM: Homo sapiens

<400> SEQUENCE: 542

Trp Ile Arg Gln His Pro Gly Lys Asp Leu Glu Trp Ile Gly
1               5                   10


<210> SEQ ID NO 543
<211> LENGTH: 16
<212> TYPE: PRT
<213> ORGANISM: Homo sapiens

<400> SEQUENCE: 543

Tyr Ile Tyr Tyr Ser Gly Thr Thr Tyr Tyr Asn Pro Ser Leu Lys Ser
1               5                   10                  15


<210> SEQ ID NO 544
<211> LENGTH: 32
<212> TYPE: PRT
<213> ORGANISM: Homo sapiens

<400> SEQUENCE: 544

Arg Val Thr Leu Ser Val Asp Thr Ser Lys Asn Gln Phe Ser Leu Lys
1               5                   10                  15

Val Thr Ser Leu Thr Ala Ala Asp Thr Ala Val Tyr His Cys Ala Arg
            20                  25                  30


<210> SEQ ID NO 545
<211> LENGTH: 11
<212> TYPE: PRT
<213> ORGANISM: Homo sapiens

<400> SEQUENCE: 545

Trp Gly Gln Gly Thr Leu Val Thr Val Ser Ser
1               5                   10


<210> SEQ ID NO 546
<211> LENGTH: 30
<212> TYPE: PRT
<213> ORGANISM: Homo sapiens

<400> SEQUENCE: 546

Gln Val Gln Leu Val Gln Ser Gly Gly Thr Leu Val Gln Pro Gly Gly
1               5                   10                  15

Ser Leu Arg Leu Ser Cys Ala Ala Ser Gly Phe Thr Phe Ser
            20                  25                  30


<210> SEQ ID NO 547
<211> LENGTH: 5
```

<212> TYPE: PRT
<213> ORGANISM: Homo sapiens

<400> SEQUENCE: 547

Asn Tyr Pro Met Thr
1 5

<210> SEQ ID NO 548
<211> LENGTH: 14
<212> TYPE: PRT
<213> ORGANISM: Homo sapiens

<400> SEQUENCE: 548

Trp Val Arg Gln Ala Pro Gly Lys Gly Leu Ala Trp Val Ser
1 5 10

<210> SEQ ID NO 549
<211> LENGTH: 17
<212> TYPE: PRT
<213> ORGANISM: Homo sapiens

<400> SEQUENCE: 549

Ser Val Ile Ala Ser Gly Asp Asn Thr Phe Tyr Ala Asp Ser Val Lys
1 5 10 15

Gly

<210> SEQ ID NO 550
<211> LENGTH: 32
<212> TYPE: PRT
<213> ORGANISM: Homo sapiens

<400> SEQUENCE: 550

Arg Phe Thr Ile Ser Arg Asp Asn Ser Lys Asn Thr Leu Tyr Leu Gln
1 5 10 15

Met Asp Ser Leu Arg Ala Glu Asp Thr Ala Val Tyr Tyr Cys Ala Lys
20 25 30

<210> SEQ ID NO 551
<211> LENGTH: 19
<212> TYPE: PRT
<213> ORGANISM: Homo sapiens

<400> SEQUENCE: 551

Ala Leu Val Gly Arg Tyr Asp Ile Ser Thr Gly Tyr Tyr Arg Pro Val
1 5 10 15

Leu Asp Tyr

<210> SEQ ID NO 552
<211> LENGTH: 11
<212> TYPE: PRT
<213> ORGANISM: Homo sapiens

<400> SEQUENCE: 552

Trp Gly Gln Gly Thr Thr Val Thr Val Ser Ser
1 5 10

<210> SEQ ID NO 553
<211> LENGTH: 31
<212> TYPE: PRT
<213> ORGANISM: Homo sapiens

<400> SEQUENCE: 553

Glu Val Gln Leu Gln Glu Ser Gly Pro Gly Leu Val Lys Pro Ser Glu 1 5 10 15

Thr Leu Ser Val Thr Cys Ala Val Ser Gly Gly Ser Ile Ser Ser
20 25 30

<210> SEQ ID NO 554
<211> LENGTH: 6
<212> TYPE: PRT
<213> ORGANISM: Homo sapiens

<400> SEQUENCE: 554

Ser Asn Tyr Ser Trp Ala
1 5

<210> SEQ ID NO 555
<211> LENGTH: 14
<212> TYPE: PRT
<213> ORGANISM: Homo sapiens

<400> SEQUENCE: 555

Trp Ile Arg Gln Pro Pro Gly Lys Gly Leu Glu Trp Ile Gly
1 5 10

<210> SEQ ID NO 556
<211> LENGTH: 16
<212> TYPE: PRT
<213> ORGANISM: Homo sapiens

<400> SEQUENCE: 556

Thr Met Tyr Tyr Ser Gly Ser Thr His Tyr His Pro Ser Leu Lys Ser
1 5 10 15

<210> SEQ ID NO 557
<211> LENGTH: 32
<212> TYPE: PRT
<213> ORGANISM: Homo sapiens

<400> SEQUENCE: 557

Arg Val Thr Ile Ser Val Asp Thr Ser Lys Ser Gln Leu Ser Leu Lys
1 5 10 15

Leu Ser Ser Val Thr Ala Ala Asp Thr Ala Val Tyr Tyr Cys Ala Arg
20 25 30

<210> SEQ ID NO 558
<211> LENGTH: 13
<212> TYPE: PRT
<213> ORGANISM: Homo sapiens

<400> SEQUENCE: 558

Arg Arg Leu Leu Gly Pro Ser Pro Tyr Tyr Phe Asp Tyr
1 5 10

<210> SEQ ID NO 559
<211> LENGTH: 11
<212> TYPE: PRT
<213> ORGANISM: Homo sapiens

<400> SEQUENCE: 559

Trp Gly Gln Gly Thr Leu Val Thr Val Ser Ser
1 5 10

<210> SEQ ID NO 560
<211> LENGTH: 30
<212> TYPE: PRT
<213> ORGANISM: Homo sapiens

<400> SEQUENCE: 560

Glu Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Arg
20 25 30

<210> SEQ ID NO 561
<211> LENGTH: 5
<212> TYPE: PRT
<213> ORGANISM: Homo sapiens

<400> SEQUENCE: 561

Arg Asn Ala Ile His
1 5

<210> SEQ ID NO 562
<211> LENGTH: 14
<212> TYPE: PRT
<213> ORGANISM: Homo sapiens

<400> SEQUENCE: 562

Trp Val Arg Gln Ala Pro Gly Lys Gly Leu Glu Trp Val Ala
1 5 10

<210> SEQ ID NO 563
<211> LENGTH: 17
<212> TYPE: PRT
<213> ORGANISM: Homo sapiens

<400> SEQUENCE: 563

Leu Ile Ser Tyr Asp Gly Ile Asn Lys Tyr Tyr Ala Asp Ser Val Lys
1 5 10 15

Gly

<210> SEQ ID NO 564
<211> LENGTH: 32
<212> TYPE: PRT
<213> ORGANISM: Homo sapiens

<400> SEQUENCE: 564

Arg Phe Ala Ile Ser Arg Asp Asn Ala Lys Asn Thr Leu Phe Leu Gln
1 5 10 15

Met Asn Ser Leu Arg Ala Glu Asp Thr Ala Val Tyr Tyr Cys Ala Arg
20 25 30

<210> SEQ ID NO 565
<211> LENGTH: 14
<212> TYPE: PRT
<213> ORGANISM: Homo sapiens

<400> SEQUENCE: 565

Asp Val Ser Glu Tyr Gly Asp Tyr Val Gly His Phe Asp Tyr
1 5 10

<210> SEQ ID NO 566
<211> LENGTH: 11
<212> TYPE: PRT
<213> ORGANISM: Homo sapiens

<400> SEQUENCE: 566

Trp Gly Gln Gly Thr Leu Val Thr Val Ser Ser
1 5 10

<210> SEQ ID NO 567
<211> LENGTH: 30
<212> TYPE: PRT
<213> ORGANISM: Homo sapiens

<400> SEQUENCE: 567

Gln Val Gln Leu Gln Glu Ser Gly Pro Gly Leu Val Lys Pro Ser Glu
1 5 10 15

Thr Leu Ser Leu Thr Cys Ser Val Ser Gly Gly Ser Ile Asn
20 25 30

<210> SEQ ID NO 568
<211> LENGTH: 7
<212> TYPE: PRT
<213> ORGANISM: Homo sapiens

<400> SEQUENCE: 568

Ser Gly Thr Tyr Tyr Trp Thr
1 5

<210> SEQ ID NO 569
<211> LENGTH: 14
<212> TYPE: PRT
<213> ORGANISM: Homo sapiens

<400> SEQUENCE: 569

Trp Ile Arg Gln His Pro Gly Lys Gly Leu Glu Trp Ile Gly
1 5 10

<210> SEQ ID NO 570
<211> LENGTH: 16
<212> TYPE: PRT
<213> ORGANISM: Homo sapiens

<400> SEQUENCE: 570

Tyr Ile Tyr Tyr Ser Gly Thr Thr Tyr Tyr Asn Pro Ser Leu Lys Ser
1 5 10 15

<210> SEQ ID NO 571
<211> LENGTH: 32
<212> TYPE: PRT
<213> ORGANISM: Homo sapiens

<400> SEQUENCE: 571

Arg Val Ser Met Ser Val Asp Thr Ser Lys Asn Leu Phe Ser Leu Lys
1 5 10 15

Met Asn Ser Val Thr Ala Ala Asp Thr Ala Leu Tyr Tyr Cys Ala Arg
20 25 30

<210> SEQ ID NO 572
<211> LENGTH: 18
<212> TYPE: PRT
<213> ORGANISM: Homo sapiens

<400> SEQUENCE: 572

Gly Asn Pro Gln Tyr Asp Thr Ser Gly Ser Tyr Thr Gly Leu Tyr Phe
1 5 10 15

Asp Phe

<210> SEQ ID NO 573
<211> LENGTH: 11
<212> TYPE: PRT

<213> ORGANISM: Homo sapiens

<400> SEQUENCE: 573

Trp Gly Gln Gly Thr Leu Val Thr Val Ser Ser
1 5 10

<210> SEQ ID NO 574
<211> LENGTH: 30
<212> TYPE: PRT
<213> ORGANISM: Homo sapiens

<400> SEQUENCE: 574

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Arg
20 25 30

<210> SEQ ID NO 575
<211> LENGTH: 5
<212> TYPE: PRT
<213> ORGANISM: Homo sapiens

<400> SEQUENCE: 575

Arg Asn Ala Ile His
1 5

<210> SEQ ID NO 576
<211> LENGTH: 14
<212> TYPE: PRT
<213> ORGANISM: Homo sapiens

<400> SEQUENCE: 576

Trp Val Arg Gln Ala Pro Gly Lys Gly Leu Glu Trp Val Ala
1 5 10

<210> SEQ ID NO 577
<211> LENGTH: 17
<212> TYPE: PRT
<213> ORGANISM: Homo sapiens

<400> SEQUENCE: 577

Val Ile Ser Tyr Asp Gly Val Asn Lys Tyr Tyr Ala Ala Ser Val Lys
1 5 10 15

Gly

<210> SEQ ID NO 578
<211> LENGTH: 32
<212> TYPE: PRT
<213> ORGANISM: Homo sapiens

<400> SEQUENCE: 578

Arg Phe Ala Ile Ser Arg Asp Asn Ala Lys Asn Thr Leu Phe Leu Gln
1 5 10 15

Met Asn Ser Leu Arg Pro Glu Asp Ser Ala Ile Tyr Tyr Cys Ala Arg
20 25 30

<210> SEQ ID NO 579
<211> LENGTH: 14
<212> TYPE: PRT
<213> ORGANISM: Homo sapiens

<400> SEQUENCE: 579

Asp Val Ser Glu Tyr Gly Asp Tyr Val Gly His Phe Asp Tyr 1 5 10

<210> SEQ ID NO 580
<211> LENGTH: 11
<212> TYPE: PRT
<213> ORGANISM: Homo sapiens

<400> SEQUENCE: 580

Trp Gly Gln Gly Thr Leu Val Thr Val Ser Ser
1 5 10

<210> SEQ ID NO 581
<211> LENGTH: 29
<212> TYPE: PRT
<213> ORGANISM: Homo sapiens

<400> SEQUENCE: 581

Glu Val Gln Leu Val Arg Ser Gly Gly Asn Leu Val Gln Pro Gly Gly
1 5 10 15

Ser Leu Arg Leu Ser Cys Ala Ala Thr Gly Pro Ile Gly
20 25

<210> SEQ ID NO 582
<211> LENGTH: 5
<212> TYPE: PRT
<213> ORGANISM: Homo sapiens

<400> SEQUENCE: 582

Ser His Trp Met Thr
1 5

<210> SEQ ID NO 583
<211> LENGTH: 14
<212> TYPE: PRT
<213> ORGANISM: Homo sapiens

<400> SEQUENCE: 583

Trp Val Arg Gln Ala Pro Gly Gln Gly Leu Glu Trp Val Ala
1 5 10

<210> SEQ ID NO 584
<211> LENGTH: 17
<212> TYPE: PRT
<213> ORGANISM: Homo sapiens

<400> SEQUENCE: 584

Asn Ile Asn Leu Asp Gly Thr Glu Lys Phe Tyr Val Asp Ser Val Lys
1 5 10 15

Gly

<210> SEQ ID NO 585
<211> LENGTH: 12
<212> TYPE: PRT
<213> ORGANISM: Homo sapiens

<400> SEQUENCE: 585

Leu Gln Trp Gly Gly Tyr Asn Gly Trp Leu Ser Pro
1 5 10

<210> SEQ ID NO 586
<211> LENGTH: 11
<212> TYPE: PRT
<213> ORGANISM: Homo sapiens

<400> SEQUENCE: 586

Trp Gly Gln Gly Thr Leu Val Thr Val Ser Ser
1 5 10

<210> SEQ ID NO 587
<211> LENGTH: 30
<212> TYPE: PRT
<213> ORGANISM: Homo sapiens

<400> SEQUENCE: 587

Glu Val Gln Leu Val Arg Ser Gly Gly Asn Leu Val Gln Pro Gly Gly
1 5 10 15

Ser Leu Arg Leu Ser Cys Ala Ala Thr Gly Phe Pro Ile Gly
20 25 30

<210> SEQ ID NO 588
<211> LENGTH: 5
<212> TYPE: PRT
<213> ORGANISM: Homo sapiens

<400> SEQUENCE: 588

Ser His Trp Met Thr
1 5

<210> SEQ ID NO 589
<211> LENGTH: 14
<212> TYPE: PRT
<213> ORGANISM: Homo sapiens

<400> SEQUENCE: 589

Trp Val Arg Gln Ala Pro Gly Gln Gly Leu Glu Trp Val Ala
1 5 10

<210> SEQ ID NO 590
<211> LENGTH: 17
<212> TYPE: PRT
<213> ORGANISM: Homo sapiens

<400> SEQUENCE: 590

Asn Ile Asn Leu Asp Gly Thr Glu Lys Phe Tyr Val Asp Ser Val Lys
1 5 10 15

Gly

<210> SEQ ID NO 591
<211> LENGTH: 32
<212> TYPE: PRT
<213> ORGANISM: Homo sapiens

<400> SEQUENCE: 591

Arg Phe Thr Val Ser Arg Asp Asn Arg Lys Ser Ser Val Phe Leu Gln
1 5 10 15

Met Asn Asn Leu Arg Val Asp Asp Thr Ala Val Tyr Tyr Cys Ala Arg
20 25 30

<210> SEQ ID NO 592
<211> LENGTH: 12
<212> TYPE: PRT
<213> ORGANISM: Homo sapiens

<400> SEQUENCE: 592

Leu Gln Trp Gly Gly Tyr Asn Gly Trp Leu Ser Pro
1 5 10

<210> SEQ ID NO 593
<211> LENGTH: 11
<212> TYPE: PRT
<213> ORGANISM: Homo sapiens

<400> SEQUENCE: 593

Trp Gly Gln Gly Thr Leu Val Thr Val Ser Ser
1               5                   10

<210> SEQ ID NO 594
<211> LENGTH: 30
<212> TYPE: PRT
<213> ORGANISM: Homo sapiens

<400> SEQUENCE: 594

Glu Val Gln Leu Val Arg Ser Gly Gly Asn Leu Val Gln Pro Gly Gly
1               5                   10                  15

Ser Leu Arg Leu Ser Cys Ala Ala Thr Gly Gly Pro Ile Gly
            20                  25                  30

<210> SEQ ID NO 595
<211> LENGTH: 5
<212> TYPE: PRT
<213> ORGANISM: Homo sapiens

<400> SEQUENCE: 595

Ser His Trp Met Thr
1               5

<210> SEQ ID NO 596
<211> LENGTH: 14
<212> TYPE: PRT
<213> ORGANISM: Homo sapiens

<400> SEQUENCE: 596

Trp Val Arg Gln Ala Pro Gly Gln Gly Leu Glu Trp Val Ala
1               5                   10

<210> SEQ ID NO 597
<211> LENGTH: 17
<212> TYPE: PRT
<213> ORGANISM: Homo sapiens

<400> SEQUENCE: 597

Asn Ile Asn Leu Asp Gly Thr Glu Lys Phe Tyr Val Asp Ser Val Lys
1               5                   10                  15

Gly

<210> SEQ ID NO 598
<211> LENGTH: 32
<212> TYPE: PRT
<213> ORGANISM: Homo sapiens

<400> SEQUENCE: 598

Arg Phe Thr Val Ser Arg Asp Asn Arg Lys Ser Ser Val Phe Leu Gln
1               5                   10                  15

Met Asn Asn Leu Arg Val Asp Asp Thr Ala Val Tyr Tyr Cys Ala Arg
            20                  25                  30

<210> SEQ ID NO 599
<211> LENGTH: 12
<212> TYPE: PRT
<213> ORGANISM: Homo sapiens

<400> SEQUENCE: 599

Leu Gln Trp Gly Gly Tyr Asn Gly Trp Leu Ser Pro
1 5 10

<210> SEQ ID NO 600
<211> LENGTH: 11
<212> TYPE: PRT
<213> ORGANISM: Homo sapiens

<400> SEQUENCE: 600

Trp Gly Gln Gly Thr Leu Val Thr Val Ser Ser
1 5 10

<210> SEQ ID NO 601
<211> LENGTH: 30
<212> TYPE: PRT
<213> ORGANISM: Homo sapiens

<400> SEQUENCE: 601

Glu Val Gln Leu Val Arg Ser Gly Gly Asn Leu Val Gln Pro Gly Gly
1 5 10 15

Ser Leu Arg Leu Ser Cys Ala Ala Thr Gly Phe Tyr Ile Gly
20 25 30

<210> SEQ ID NO 602
<211> LENGTH: 5
<212> TYPE: PRT
<213> ORGANISM: Homo sapiens

<400> SEQUENCE: 602

Ser His Trp Met Thr
1 5

<210> SEQ ID NO 603
<211> LENGTH: 14
<212> TYPE: PRT
<213> ORGANISM: Homo sapiens

<400> SEQUENCE: 603

Trp Val Arg Gln Ala Pro Gly Gln Gly Leu Glu Trp Val Ala
1 5 10

<210> SEQ ID NO 604
<211> LENGTH: 17
<212> TYPE: PRT
<213> ORGANISM: Homo sapiens

<400> SEQUENCE: 604

Asn Ile Asn Leu Asp Gly Thr Glu Lys Phe Tyr Val Asp Ser Val Lys
1 5 10 15

Gly

<210> SEQ ID NO 605
<211> LENGTH: 32
<212> TYPE: PRT
<213> ORGANISM: Homo sapiens

<400> SEQUENCE: 605

Arg Phe Thr Val Ser Arg Asp Asn Arg Lys Ser Ser Val Phe Leu Gln
1 5 10 15

Met Asn Asn Leu Arg Val Asp Asp Thr Ala Val Tyr Tyr Cys Ala Arg
20 25 30

<210> SEQ ID NO 606
<211> LENGTH: 12
<212> TYPE: PRT
<213> ORGANISM: Homo sapiens

<400> SEQUENCE: 606

Leu Gln Trp Gly Gly Tyr Asn Gly Trp Leu Ser Pro
1 5 10

<210> SEQ ID NO 607
<211> LENGTH: 11
<212> TYPE: PRT
<213> ORGANISM: Homo sapiens

<400> SEQUENCE: 607

Trp Gly Gln Gly Thr Leu Val Thr Val Ser Ser
1 5 10

<210> SEQ ID NO 608
<211> LENGTH: 30
<212> TYPE: PRT
<213> ORGANISM: Homo sapiens

<400> SEQUENCE: 608

Glu Val Gln Leu Val Arg Ser Gly Gly Asn Leu Val Gln Pro Gly Gly
1 5 10 15

Ser Leu Arg Leu Ser Cys Ala Ala Thr Gly Phe Thr Ile Gly
20 25 30

<210> SEQ ID NO 609
<211> LENGTH: 5
<212> TYPE: PRT
<213> ORGANISM: Homo sapiens

<400> SEQUENCE: 609

Ser His Trp Met Thr
1 5

<210> SEQ ID NO 610
<211> LENGTH: 14
<212> TYPE: PRT
<213> ORGANISM: Homo sapiens

<400> SEQUENCE: 610

Trp Val Arg Gln Ala Pro Gly Gln Gly Leu Glu Trp Val Ala
1 5 10

<210> SEQ ID NO 611
<211> LENGTH: 17
<212> TYPE: PRT
<213> ORGANISM: Homo sapiens

<400> SEQUENCE: 611

Asn Ile Asn Leu Asp Gly Thr Glu Lys Phe Tyr Val Asp Ser Val Lys
1 5 10 15

Gly

<210> SEQ ID NO 612
<211> LENGTH: 32
<212> TYPE: PRT
<213> ORGANISM: Homo sapiens

<400> SEQUENCE: 612

```
Arg Phe Thr Val Ser Arg Asp Asn Arg Lys Ser Ser Val Phe Leu Gln
1               5                   10                  15

Met Asn Asn Leu Arg Val Asp Asp Thr Ala Val Tyr Tyr Cys Ala Arg
            20                  25                  30


<210> SEQ ID NO 613
<211> LENGTH: 12
<212> TYPE: PRT
<213> ORGANISM: Homo sapiens

<400> SEQUENCE: 613

Leu Gln Trp Gly Gly Tyr Asn Gly Trp Leu Ser Pro
1               5                   10


<210> SEQ ID NO 614
<211> LENGTH: 11
<212> TYPE: PRT
<213> ORGANISM: Homo sapiens

<400> SEQUENCE: 614

Trp Gly Gln Gly Thr Leu Val Thr Val Ser Ser
1               5                   10


<210> SEQ ID NO 615
<211> LENGTH: 23
<212> TYPE: PRT
<213> ORGANISM: Homo sapiens

<400> SEQUENCE: 615

Asp Ile Gln Met Thr Gln Ser Pro Ser Ser Leu Ser Ala Ser Val Gly
1               5                   10                  15

Asp Arg Val Thr Ile Thr Cys
            20


<210> SEQ ID NO 616
<211> LENGTH: 11
<212> TYPE: PRT
<213> ORGANISM: Homo sapiens

<400> SEQUENCE: 616

Arg Ala Ser Gln Arg Ile Ser Asn Tyr Leu Asn
1               5                   10


<210> SEQ ID NO 617
<211> LENGTH: 15
<212> TYPE: PRT
<213> ORGANISM: Homo sapiens

<400> SEQUENCE: 617

Trp Tyr Gln Gln Lys Pro Gly Lys Ala Pro Lys Leu Leu Ile Tyr
1               5                   10                  15


<210> SEQ ID NO 618
<211> LENGTH: 7
<212> TYPE: PRT
<213> ORGANISM: Homo sapiens

<400> SEQUENCE: 618

Ala Ala Ser Ser Leu Gln Ser
1               5


<210> SEQ ID NO 619
<211> LENGTH: 32
```

<212> TYPE: PRT
<213> ORGANISM: Homo sapiens

<400> SEQUENCE: 619

Glu Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 620
<211> LENGTH: 9
<212> TYPE: PRT
<213> ORGANISM: Homo sapiens

<400> SEQUENCE: 620

Gln Gln Ser Tyr Arg Pro Pro Leu Thr
1 5

<210> SEQ ID NO 621
<211> LENGTH: 11
<212> TYPE: PRT
<213> ORGANISM: Homo sapiens

<400> SEQUENCE: 621

Phe Gly Gly Gly Thr Lys Val Glu Ile Lys Arg
1 5 10

<210> SEQ ID NO 622
<211> LENGTH: 23
<212> TYPE: PRT
<213> ORGANISM: Homo sapiens

<400> SEQUENCE: 622

Asp Ile Gln Met Thr Gln Ser Pro Ser Ser Val Ser Ala Ser Val Gly
1 5 10 15

Asn Arg Val Thr Ile Thr Cys
20

<210> SEQ ID NO 623
<211> LENGTH: 11
<212> TYPE: PRT
<213> ORGANISM: Homo sapiens

<400> SEQUENCE: 623

Arg Ala Ser Gln Gly Ile Ser Ser Trp Leu Ala
1 5 10

<210> SEQ ID NO 624
<211> LENGTH: 15
<212> TYPE: PRT
<213> ORGANISM: Homo sapiens

<400> SEQUENCE: 624

Trp Tyr Gln Gln Lys Pro Gly Lys Ala Pro Lys Leu Leu Ile Tyr
1 5 10 15

<210> SEQ ID NO 625
<211> LENGTH: 7
<212> TYPE: PRT
<213> ORGANISM: Homo sapiens

<400> SEQUENCE: 625

Ala Ala Ser Ser Leu Gln Ser
1 5

<210> SEQ ID NO 626
<211> LENGTH: 32
<212> TYPE: PRT
<213> ORGANISM: Homo sapiens

<400> SEQUENCE: 626

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 627
<211> LENGTH: 9
<212> TYPE: PRT
<213> ORGANISM: Homo sapiens

<400> SEQUENCE: 627

Gln Lys Ala Asn Ser Phe Pro Leu Thr
1 5

<210> SEQ ID NO 628
<211> LENGTH: 11
<212> TYPE: PRT
<213> ORGANISM: Homo sapiens

<400> SEQUENCE: 628

Phe Gly Gly Gly Thr Lys Val Glu Ile Lys Arg
1 5 10

<210> SEQ ID NO 629
<211> LENGTH: 23
<212> TYPE: PRT
<213> ORGANISM: Homo sapiens

<400> SEQUENCE: 629

Asp Val Val Met Thr Gln Ser Pro Ser Ser Leu Ser Ala Ser Val Gly
1 5 10 15

Asp Arg Val Thr Ile Thr Cys
20

<210> SEQ ID NO 630
<211> LENGTH: 11
<212> TYPE: PRT
<213> ORGANISM: Homo sapiens

<400> SEQUENCE: 630

Arg Ala Ser Gln Ser Ile Ser Ser Tyr Leu Asn
1 5 10

<210> SEQ ID NO 631
<211> LENGTH: 15
<212> TYPE: PRT
<213> ORGANISM: Homo sapiens

<400> SEQUENCE: 631

Trp Tyr Gln Gln Lys Pro Gly Lys Ala Pro Lys Leu Leu Ile Tyr
1 5 10 15

<210> SEQ ID NO 632
<211> LENGTH: 7
<212> TYPE: PRT
<213> ORGANISM: Homo sapiens

<400> SEQUENCE: 632

Ala Ala Ser Ser Leu Gln Ser
1               5

<210> SEQ ID NO 633
<211> LENGTH: 32
<212> TYPE: PRT
<213> ORGANISM: Homo sapiens

<400> SEQUENCE: 633

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 634
<211> LENGTH: 9
<212> TYPE: PRT
<213> ORGANISM: Homo sapiens

<400> SEQUENCE: 634

Gln Gln Ser Tyr Ser Thr Pro Leu Thr
1               5

<210> SEQ ID NO 635
<211> LENGTH: 11
<212> TYPE: PRT
<213> ORGANISM: Homo sapiens

<400> SEQUENCE: 635

Phe Gly Gln Gly Thr Lys Leu Glu Ile Lys Arg
1               5                   10

<210> SEQ ID NO 636
<211> LENGTH: 23
<212> TYPE: PRT
<213> ORGANISM: Homo sapiens

<400> SEQUENCE: 636

Asp Val Val Met Thr Gln Ser Pro Ser Ser Leu Ser Ala Ser Val Gly
1               5                   10                  15

Asp Arg Ile Thr Ile Thr Cys
            20

<210> SEQ ID NO 637
<211> LENGTH: 11
<212> TYPE: PRT
<213> ORGANISM: Homo sapiens

<400> SEQUENCE: 637

Gln Ala Gly Gln Asp Ile Ser Asn Phe Leu Asn
1               5                   10

<210> SEQ ID NO 638
<211> LENGTH: 15
<212> TYPE: PRT
<213> ORGANISM: Homo sapiens

<400> SEQUENCE: 638

Trp Tyr Gln Gln Lys Pro Gly Lys Ala Pro Lys Leu Leu Ile Arg
1               5                   10                  15

<210> SEQ ID NO 639

<211> LENGTH: 7
<212> TYPE: PRT
<213> ORGANISM: Homo sapiens

<400> SEQUENCE: 639

Asp Ala Ser Asn Leu Glu Thr
1               5

<210> SEQ ID NO 640
<211> LENGTH: 32
<212> TYPE: PRT
<213> ORGANISM: Homo sapiens

<400> SEQUENCE: 640

Gly Val Pro Ser Arg Phe Ser Gly Gly Gly Ser Gly Thr His Phe Thr
1               5                   10                  15

Phe Thr Ile Ser Ser Leu His Pro Glu Asp Ile Ala Thr Tyr Phe Cys
            20                  25                  30

<210> SEQ ID NO 641
<211> LENGTH: 9
<212> TYPE: PRT
<213> ORGANISM: Homo sapiens

<400> SEQUENCE: 641

Gln Gln Tyr Asp Asn Leu Pro Tyr Thr
1               5

<210> SEQ ID NO 642
<211> LENGTH: 11
<212> TYPE: PRT
<213> ORGANISM: Homo sapiens

<400> SEQUENCE: 642

Phe Gly Gln Gly Thr Lys Leu Glu Ile Lys Arg
1               5                   10

<210> SEQ ID NO 643
<211> LENGTH: 23
<212> TYPE: PRT
<213> ORGANISM: Homo sapiens

<400> SEQUENCE: 643

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 644
<211> LENGTH: 11
<212> TYPE: PRT
<213> ORGANISM: Homo sapiens

<400> SEQUENCE: 644

Arg Ala Ser Gln Ser Ile Ser Ser Tyr Leu Asn
1               5                   10

<210> SEQ ID NO 645
<211> LENGTH: 15
<212> TYPE: PRT
<213> ORGANISM: Homo sapiens

<400> SEQUENCE: 645

Trp Tyr Gln Gln Glu Pro Gly Lys Ala Pro Lys Leu Leu Ile Tyr 1 5 10 15

<210> SEQ ID NO 646
<211> LENGTH: 7
<212> TYPE: PRT
<213> ORGANISM: Homo sapiens

<400> SEQUENCE: 646

Ser Ala Ser Ser Leu Gln Ser
1 5

<210> SEQ ID NO 647
<211> LENGTH: 32
<212> TYPE: PRT
<213> ORGANISM: Homo sapiens

<400> SEQUENCE: 647

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 648
<211> LENGTH: 10
<212> TYPE: PRT
<213> ORGANISM: Homo sapiens

<400> SEQUENCE: 648

Gln Gln Ser Tyr Ser Thr Pro Pro Tyr Thr
1 5 10

<210> SEQ ID NO 649
<211> LENGTH: 11
<212> TYPE: PRT
<213> ORGANISM: Homo sapiens

<400> SEQUENCE: 649

Phe Gly Gln Gly Thr Lys Leu Glu Ile Lys Arg
1 5 10

<210> SEQ ID NO 650
<211> LENGTH: 23
<212> TYPE: PRT
<213> ORGANISM: Homo sapiens

<400> SEQUENCE: 650

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 651
<211> LENGTH: 11
<212> TYPE: PRT
<213> ORGANISM: Homo sapiens

<400> SEQUENCE: 651

Arg Ala Ser Gln Arg Ile Ser Asn Tyr Leu Asn
1 5 10

<210> SEQ ID NO 652
<211> LENGTH: 15
<212> TYPE: PRT
<213> ORGANISM: Homo sapiens

<400> SEQUENCE: 652

Trp Tyr Gln Gln Lys Pro Gly Lys Ala Pro Lys Leu Leu Ile Tyr
1 5 10 15

<210> SEQ ID NO 653
<211> LENGTH: 7
<212> TYPE: PRT
<213> ORGANISM: Homo sapiens

<400> SEQUENCE: 653

Ala Ala Ser Ser Leu Gln Ser
1 5

<210> SEQ ID NO 654
<211> LENGTH: 32
<212> TYPE: PRT
<213> ORGANISM: Homo sapiens

<400> SEQUENCE: 654

Glu Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 655
<211> LENGTH: 9
<212> TYPE: PRT
<213> ORGANISM: Homo sapiens

<400> SEQUENCE: 655

Gln Gln Ser Tyr Arg Pro Pro Leu Thr
1 5

<210> SEQ ID NO 656
<211> LENGTH: 11
<212> TYPE: PRT
<213> ORGANISM: Homo sapiens

<400> SEQUENCE: 656

Phe Gly Gly Gly Thr Lys Val Asp Ile Lys Arg
1 5 10

<210> SEQ ID NO 657
<211> LENGTH: 23
<212> TYPE: PRT
<213> ORGANISM: Homo sapiens

<400> SEQUENCE: 657

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 658
<211> LENGTH: 11
<212> TYPE: PRT
<213> ORGANISM: Homo sapiens

<400> SEQUENCE: 658

Arg Ala Ser Gln Arg Ile Ser Asn Tyr Leu Asn
1 5 10

<210> SEQ ID NO 659
<211> LENGTH: 15
<212> TYPE: PRT
<213> ORGANISM: Homo sapiens

<400> SEQUENCE: 659

Trp Tyr Gln Gln Lys Pro Gly Lys Ala Pro Lys Leu Leu Ile Tyr
1               5                   10                  15

<210> SEQ ID NO 660
<211> LENGTH: 7
<212> TYPE: PRT
<213> ORGANISM: Homo sapiens

<400> SEQUENCE: 660

Ala Ala Ser Ser Leu Gln Ser
1               5

<210> SEQ ID NO 661
<211> LENGTH: 32
<212> TYPE: PRT
<213> ORGANISM: Homo sapiens

<400> SEQUENCE: 661

Glu Val Pro Ser Arg Phe Ser Gly Ser Gly Tyr Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 662
<211> LENGTH: 9
<212> TYPE: PRT
<213> ORGANISM: Homo sapiens

<400> SEQUENCE: 662

Gln Gln Ser Tyr Arg Pro Pro Leu Thr
1               5

<210> SEQ ID NO 663
<211> LENGTH: 11
<212> TYPE: PRT
<213> ORGANISM: Homo sapiens

<400> SEQUENCE: 663

Phe Gly Gly Gly Thr Lys Val Asp Ile Lys Arg
1               5                   10

<210> SEQ ID NO 664
<211> LENGTH: 23
<212> TYPE: PRT
<213> ORGANISM: Homo sapiens

<400> SEQUENCE: 664

Asp Ile Val Met Thr Gln Ser Pro Ser Thr Leu Ser Ala Ser Val Gly
1               5                   10                  15

Asp Arg Val Thr Val Thr Cys
            20

<210> SEQ ID NO 665
<211> LENGTH: 11
<212> TYPE: PRT
<213> ORGANISM: Homo sapiens

<400> SEQUENCE: 665

```
Arg Ala Ser Gln Ser Ile Asn Ser Trp Leu Ala
1               5                   10


<210> SEQ ID NO 666
<211> LENGTH: 15
<212> TYPE: PRT
<213> ORGANISM: Homo sapiens

<400> SEQUENCE: 666

Trp Tyr Gln Gln Lys Pro Gly Lys Ala Pro Lys Leu Leu Ile Tyr
1               5                   10                  15


<210> SEQ ID NO 667
<211> LENGTH: 7
<212> TYPE: PRT
<213> ORGANISM: Homo sapiens

<400> SEQUENCE: 667

Glu Ala Ser Ser Leu Glu Ser
1               5


<210> SEQ ID NO 668
<211> LENGTH: 32
<212> TYPE: PRT
<213> ORGANISM: Homo sapiens

<400> SEQUENCE: 668

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30


<210> SEQ ID NO 669
<211> LENGTH: 9
<212> TYPE: PRT
<213> ORGANISM: Homo sapiens

<400> SEQUENCE: 669

Gln Gln Tyr Asp Ser Tyr Trp Leu Thr
1               5


<210> SEQ ID NO 670
<211> LENGTH: 11
<212> TYPE: PRT
<213> ORGANISM: Homo sapiens

<400> SEQUENCE: 670

Phe Gly Gly Gly Thr Lys Val Glu Ile Lys Arg
1               5                   10


<210> SEQ ID NO 671
<211> LENGTH: 23
<212> TYPE: PRT
<213> ORGANISM: Homo sapiens

<400> SEQUENCE: 671

Asp Ile Gln Met Thr Gln Ser Pro Ser Ser Val Ser Ala Ser Val Gly
1               5                   10                  15

Asp Arg Val Thr Ile Thr Cys
            20


<210> SEQ ID NO 672
<211> LENGTH: 11
<212> TYPE: PRT
```

```
<213> ORGANISM: Homo sapiens

<400> SEQUENCE: 672

Arg Ala Ser Gln Gly Val Ser Arg Trp Leu Ala
1               5                   10


<210> SEQ ID NO 673
<211> LENGTH: 15
<212> TYPE: PRT
<213> ORGANISM: Homo sapiens

<400> SEQUENCE: 673

Trp Tyr Gln Gln Arg Pro Glu Lys Ala Pro Lys Leu Leu Ile Tyr
1               5                   10                  15


<210> SEQ ID NO 674
<211> LENGTH: 7
<212> TYPE: PRT
<213> ORGANISM: Homo sapiens

<400> SEQUENCE: 674

Gly Ala Ser Ser Leu Gln Ser
1               5


<210> SEQ ID NO 675
<211> LENGTH: 32
<212> TYPE: PRT
<213> ORGANISM: Homo sapiens

<400> SEQUENCE: 675

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 676
<211> LENGTH: 9
<212> TYPE: PRT
<213> ORGANISM: Homo sapiens

<400> SEQUENCE: 676

Gln Gln Tyr Asp Ser Phe Pro Leu Thr
1               5


<210> SEQ ID NO 677
<211> LENGTH: 11
<212> TYPE: PRT
<213> ORGANISM: Homo sapiens

<400> SEQUENCE: 677

Phe Gly Gly Gly Thr Lys Val Glu Ile Lys Arg
1               5                   10


<210> SEQ ID NO 678
<211> LENGTH: 23
<212> TYPE: PRT
<213> ORGANISM: Homo sapiens

<400> SEQUENCE: 678

Glu Ile Val Leu Thr Gln Ser Pro Ala Thr Leu Ser Val Ser Pro Gly
1               5                   10                  15

Glu Arg Ala Thr Leu Ser Cys
            20
```

<210> SEQ ID NO 679
<211> LENGTH: 11
<212> TYPE: PRT
<213> ORGANISM: Homo sapiens

<400> SEQUENCE: 679

Arg Ala Ser Gln Ser Val Ser Lys Phe Leu Ala
1 5 10

<210> SEQ ID NO 680
<211> LENGTH: 15
<212> TYPE: PRT
<213> ORGANISM: Homo sapiens

<400> SEQUENCE: 680

Trp Tyr Gln Gln Lys Arg Gly Gln Ala Pro Arg Leu Leu Ile Tyr
1 5 10 15

<210> SEQ ID NO 681
<211> LENGTH: 7
<212> TYPE: PRT
<213> ORGANISM: Homo sapiens

<400> SEQUENCE: 681

Gly Ala Ser Thr Arg Ala Thr
1 5

<210> SEQ ID NO 682
<211> LENGTH: 32
<212> TYPE: PRT
<213> ORGANISM: Homo sapiens

<400> SEQUENCE: 682

Gly Ile Pro Ala Arg Phe Ser Gly Ser Gly Ser Gly Thr Glu Phe Ala
1 5 10 15

Leu Thr Ile Ser Ser Leu Gln Ser Glu Asp Phe Ala Asp Tyr Tyr Cys
20 25 30

<210> SEQ ID NO 683
<211> LENGTH: 9
<212> TYPE: PRT
<213> ORGANISM: Homo sapiens

<400> SEQUENCE: 683

Gln Gln Tyr Asp Asn Trp Pro Ile Thr
1 5

<210> SEQ ID NO 684
<211> LENGTH: 11
<212> TYPE: PRT
<213> ORGANISM: Homo sapiens

<400> SEQUENCE: 684

Phe Gly Gln Gly Thr Arg Leu Glu Ile Lys Arg
1 5 10

<210> SEQ ID NO 685
<211> LENGTH: 23
<212> TYPE: PRT
<213> ORGANISM: Homo sapiens

<400> SEQUENCE: 685

Asp Ile Val Met Thr Gln Ser Pro Ser Thr Leu Ser Ala Ser Val Gly
1 5 10 15

Asp Arg Val Thr Ile Thr Cys
20

<210> SEQ ID NO 686
<211> LENGTH: 11
<212> TYPE: PRT
<213> ORGANISM: Homo sapiens

<400> SEQUENCE: 686

Arg Ala Ser Gln Gly Ile Ser Ser Trp Leu Ala
1 5 10

<210> SEQ ID NO 687
<211> LENGTH: 15
<212> TYPE: PRT
<213> ORGANISM: Homo sapiens

<400> SEQUENCE: 687

Trp Tyr Gln Gln Lys Pro Gly Lys Ala Pro Lys Leu Leu Ile Tyr
1 5 10 15

<210> SEQ ID NO 688
<211> LENGTH: 7
<212> TYPE: PRT
<213> ORGANISM: Homo sapiens

<400> SEQUENCE: 688

Lys Ala Ser Ser Leu Glu Ser
1 5

<210> SEQ ID NO 689
<211> LENGTH: 32
<212> TYPE: PRT
<213> ORGANISM: Homo sapiens

<400> SEQUENCE: 689

Gly Val Pro Ser Arg Phe Ser Gly Ser Gly Ser Gly Thr Glu Phe Thr
1 5 10 15

Leu Thr Ile Ser Ser Leu Gln Pro Glu Asp Phe Ala Thr Tyr Tyr Cys
20 25 30

<210> SEQ ID NO 690
<211> LENGTH: 9
<212> TYPE: PRT
<213> ORGANISM: Homo sapiens

<400> SEQUENCE: 690

Leu Gln His Asn Ser Tyr Pro Arg Ala
1 5

<210> SEQ ID NO 691
<211> LENGTH: 11
<212> TYPE: PRT
<213> ORGANISM: Homo sapiens

<400> SEQUENCE: 691

Phe Gly Gln Gly Thr Lys Leu Glu Ile Lys Arg
1 5 10

<210> SEQ ID NO 692
<211> LENGTH: 22
<212> TYPE: PRT
<213> ORGANISM: Homo sapiens -continued

<400> SEQUENCE: 692

Ala Tyr Val Leu Thr Gln Pro Pro Ser Val Ser Val Ala Pro Gly Lys
1 5 10 15

Thr Ala Ala Ile Thr Cys
20

<210> SEQ ID NO 693
<211> LENGTH: 11
<212> TYPE: PRT
<213> ORGANISM: Homo sapiens

<400> SEQUENCE: 693

Glu Gly Asn Asn Val Gly Asn Lys Asn Val His
1 5 10

<210> SEQ ID NO 694
<211> LENGTH: 15
<212> TYPE: PRT
<213> ORGANISM: Homo sapiens

<400> SEQUENCE: 694

Trp Tyr Gln Gln Arg Pro Gly Gln Ala Pro Val Leu Val Val His
1 5 10 15

<210> SEQ ID NO 695
<211> LENGTH: 7
<212> TYPE: PRT
<213> ORGANISM: Homo sapiens

<400> SEQUENCE: 695

Asp Asp Ser Asp Arg Pro Ser
1 5

<210> SEQ ID NO 696
<211> LENGTH: 32
<212> TYPE: PRT
<213> ORGANISM: Homo sapiens

<400> SEQUENCE: 696

Gly Ile Pro Glu Arg Phe Ser Gly Ser Asn Ser Gly Asn Thr Ala Thr
1 5 10 15

Leu Thr Ile Asn Arg Val Glu Ala Gly Asp Glu Ala Asp Tyr Tyr Cys
20 25 30

<210> SEQ ID NO 697
<211> LENGTH: 11
<212> TYPE: PRT
<213> ORGANISM: Homo sapiens

<400> SEQUENCE: 697

Gln Val Trp Asp Ser Ser Ser Ala Gln Trp Val
1 5 10

<210> SEQ ID NO 698
<211> LENGTH: 11
<212> TYPE: PRT
<213> ORGANISM: Homo sapiens

<400> SEQUENCE: 698

Phe Gly Gly Gly Thr Lys Leu Thr Val Leu Gly
1 5 10

<210> SEQ ID NO 699

<211> LENGTH: 22
<212> TYPE: PRT
<213> ORGANISM: Homo sapiens

<400> SEQUENCE: 699

Glu Ser Val Leu Thr Gln Pro Pro Leu Val Ser Ala Ala Pro Gly Gln
1 5 10 15

Lys Val Thr Ile Ser Cys
20

<210> SEQ ID NO 700
<211> LENGTH: 13
<212> TYPE: PRT
<213> ORGANISM: Homo sapiens

<400> SEQUENCE: 700

Ser Gly Ser Ser Ser Asn Ile Gly Asn Asn Tyr Val Ser
1 5 10

<210> SEQ ID NO 701
<211> LENGTH: 15
<212> TYPE: PRT
<213> ORGANISM: Homo sapiens

<400> SEQUENCE: 701

Trp Tyr Gln Gln Leu Pro Gly Thr Ala Pro Lys Leu Leu Ile Tyr
1 5 10 15

<210> SEQ ID NO 702
<211> LENGTH: 7
<212> TYPE: PRT
<213> ORGANISM: Homo sapiens

<400> SEQUENCE: 702

Glu Asn Ser Lys Arg Ser Ser
1 5

<210> SEQ ID NO 703
<211> LENGTH: 32
<212> TYPE: PRT
<213> ORGANISM: Homo sapiens

<400> SEQUENCE: 703

Gly Ile Pro Asp Arg Phe Ser Gly Ser Lys Ser Gly Thr Ser Ala Thr
1 5 10 15

Leu Gly Ile Thr Gly Leu Gln Thr Gly Asp Glu Ala Asp Tyr Tyr Cys
20 25 30

<210> SEQ ID NO 704
<211> LENGTH: 11
<212> TYPE: PRT
<213> ORGANISM: Homo sapiens

<400> SEQUENCE: 704

Gly Thr Trp Asp Ser Ser Leu Ser Ala Val Val
1 5 10

<210> SEQ ID NO 705
<211> LENGTH: 11
<212> TYPE: PRT
<213> ORGANISM: Homo sapiens

<400> SEQUENCE: 705

Phe Gly Gly Gly Thr Lys Leu Thr Val Leu Gly

```
1               5                   10


<210> SEQ ID NO 706
<211> LENGTH: 23
<212> TYPE: PRT
<213> ORGANISM: Homo sapiens

<400> SEQUENCE: 706

Asp Val Val Met Thr Gln Ser Pro Ser Ser Val Ser Ala Ser Val Gly
1               5                   10                  15

Asp Arg Val Thr Ile Thr Cys
            20


<210> SEQ ID NO 707
<211> LENGTH: 11
<212> TYPE: PRT
<213> ORGANISM: Homo sapiens

<400> SEQUENCE: 707

Arg Ala Ser Gln Ser Ile Ser Ser Tyr Leu Asn
1               5                   10


<210> SEQ ID NO 708
<211> LENGTH: 15
<212> TYPE: PRT
<213> ORGANISM: Homo sapiens

<400> SEQUENCE: 708

Trp Tyr Gln Gln Arg Pro Gly Lys Ala Pro Lys Leu Leu Ile Phe
1               5                   10                  15


<210> SEQ ID NO 709
<211> LENGTH: 7
<212> TYPE: PRT
<213> ORGANISM: Homo sapiens

<400> SEQUENCE: 709

Ala Ala Ser Ser Leu Gln Ser
1               5


<210> SEQ ID NO 710
<211> LENGTH: 32
<212> TYPE: PRT
<213> ORGANISM: Homo sapiens

<400> SEQUENCE: 710

Ala Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 711
<211> LENGTH: 9
<212> TYPE: PRT
<213> ORGANISM: Homo sapiens

<400> SEQUENCE: 711

Gln Gln Ser Tyr Ser Thr Pro Pro Thr
1               5


<210> SEQ ID NO 712
<211> LENGTH: 11
<212> TYPE: PRT
<213> ORGANISM: Homo sapiens
```

<400> SEQUENCE: 712

Phe Gly Gln Gly Thr Lys Val Glu Ile Lys Arg
1               5                   10

<210> SEQ ID NO 713
<211> LENGTH: 23
<212> TYPE: PRT
<213> ORGANISM: Homo sapiens

<400> SEQUENCE: 713

Asp Ile Val Met Thr Gln Ser Pro Ser Ser Leu Ser Ala Ser Val Gly
1               5                   10                  15

Asp Arg Val Ser Ile Ser Cys
            20

<210> SEQ ID NO 714
<211> LENGTH: 11
<212> TYPE: PRT
<213> ORGANISM: Homo sapiens

<400> SEQUENCE: 714

Arg Ala Ser Gln Ser Ile Ser Ser Tyr Leu Asn
1               5                   10

<210> SEQ ID NO 715
<211> LENGTH: 15
<212> TYPE: PRT
<213> ORGANISM: Homo sapiens

<400> SEQUENCE: 715

Trp Tyr Gln Gln Lys Pro Gly Lys Ala Pro Lys Leu Leu Ile Tyr
1               5                   10                  15

<210> SEQ ID NO 716
<211> LENGTH: 7
<212> TYPE: PRT
<213> ORGANISM: Homo sapiens

<400> SEQUENCE: 716

Lys Thr Ser Ser Leu Glu Ser
1               5

<210> SEQ ID NO 717
<211> LENGTH: 32
<212> TYPE: PRT
<213> ORGANISM: Homo sapiens

<400> SEQUENCE: 717

Gly Val Pro Ser Arg Phe Ser Gly Arg Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 718
<211> LENGTH: 9
<212> TYPE: PRT
<213> ORGANISM: Homo sapiens

<400> SEQUENCE: 718

Gln Gln Ser Tyr Ser Thr Pro Leu Thr
1               5

<210> SEQ ID NO 719
<211> LENGTH: 11
<212> TYPE: PRT
<213> ORGANISM: Homo sapiens

<400> SEQUENCE: 719

Phe Gly Gly Gly Thr Lys Val Glu Ile Lys Arg
1 5 10

<210> SEQ ID NO 720
<211> LENGTH: 23
<212> TYPE: PRT
<213> ORGANISM: Homo sapiens

<400> SEQUENCE: 720

Asp Ile Gln Met Thr Gln Ser Pro Ser Thr Leu Ser Ala Ser Ile Gly
1 5 10 15

Asp Arg Val Thr Ile Ser Cys
20

<210> SEQ ID NO 721
<211> LENGTH: 11
<212> TYPE: PRT
<213> ORGANISM: Homo sapiens

<400> SEQUENCE: 721

Arg Ala Ser Gln Ser Ile Gln Ser Trp Leu Ala
1 5 10

<210> SEQ ID NO 722
<211> LENGTH: 15
<212> TYPE: PRT
<213> ORGANISM: Homo sapiens

<400> SEQUENCE: 722

Trp Tyr Gln Gln Arg Pro Gly Glu Ala Pro Lys Leu Leu Ile Tyr
1 5 10 15

<210> SEQ ID NO 723
<211> LENGTH: 7
<212> TYPE: PRT
<213> ORGANISM: Homo sapiens

<400> SEQUENCE: 723

Ser Ala Ser Thr Leu Gln Thr
1 5

<210> SEQ ID NO 724
<211> LENGTH: 32
<212> TYPE: PRT
<213> ORGANISM: Homo sapiens

<400> SEQUENCE: 724

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 725
<211> LENGTH: 9
<212> TYPE: PRT
<213> ORGANISM: Homo sapiens

<400> SEQUENCE: 725

Gln Gln Tyr Asn Ser Tyr Pro Leu Thr
1 5

<210> SEQ ID NO 726
<211> LENGTH: 11
<212> TYPE: PRT
<213> ORGANISM: Homo sapiens

<400> SEQUENCE: 726

Phe Gly Gln Gly Thr Lys Leu Glu Ile Lys Arg
1 5 10

<210> SEQ ID NO 727
<211> LENGTH: 23
<212> TYPE: PRT
<213> ORGANISM: Homo sapiens

<400> SEQUENCE: 727

Asp Ile Val Leu Thr Gln Ser Pro Ser Thr Leu Ser Ala Ser Val Gly
1 5 10 15

Asp Arg Val Thr Ile Ser Cys
20

<210> SEQ ID NO 728
<211> LENGTH: 11
<212> TYPE: PRT
<213> ORGANISM: Homo sapiens

<400> SEQUENCE: 728

Arg Ala Ser Arg Ser Ile Gly Trp Tyr Leu Asn
1 5 10

<210> SEQ ID NO 729
<211> LENGTH: 15
<212> TYPE: PRT
<213> ORGANISM: Homo sapiens

<400> SEQUENCE: 729

Trp Tyr Gln Gln Arg Pro Gly Lys Ala Pro Lys Leu Leu Ile Tyr
1 5 10 15

<210> SEQ ID NO 730
<211> LENGTH: 7
<212> TYPE: PRT
<213> ORGANISM: Homo sapiens

<400> SEQUENCE: 730

Ala Ala Ser Ser Leu His Asn
1 5

<210> SEQ ID NO 731
<211> LENGTH: 32
<212> TYPE: PRT
<213> ORGANISM: Homo sapiens

<400> SEQUENCE: 731

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 732
<211> LENGTH: 9
<212> TYPE: PRT

<213> ORGANISM: Homo sapiens

<400> SEQUENCE: 732

Gln Gln Ala Phe Gly Phe Pro Arg Thr
1 5

<210> SEQ ID NO 733
<211> LENGTH: 11
<212> TYPE: PRT
<213> ORGANISM: Homo sapiens

<400> SEQUENCE: 733

Phe Gly Gln Gly Thr Lys Val Glu Ile Lys Arg
1 5 10

<210> SEQ ID NO 734
<211> LENGTH: 23
<212> TYPE: PRT
<213> ORGANISM: Homo sapiens

<400> SEQUENCE: 734

Glu Ile Val Leu Thr Gln Ser Pro Ser Ser Leu Ser Ala Ser Val Gly
1 5 10 15

Asp Arg Ile Thr Ile Thr Cys
20

<210> SEQ ID NO 735
<211> LENGTH: 11
<212> TYPE: PRT
<213> ORGANISM: Homo sapiens

<400> SEQUENCE: 735

Arg Ala Ser Gln Ser Ile Ser Ser Trp Leu Ala
1 5 10

<210> SEQ ID NO 736
<211> LENGTH: 15
<212> TYPE: PRT
<213> ORGANISM: Homo sapiens

<400> SEQUENCE: 736

Trp Tyr Gln Gln Lys Pro Gly Lys Ala Pro Met Val Leu Ile Tyr
1 5 10 15

<210> SEQ ID NO 737
<211> LENGTH: 7
<212> TYPE: PRT
<213> ORGANISM: Homo sapiens

<400> SEQUENCE: 737

Lys Ala Ser Ser Leu Glu Asn
1 5

<210> SEQ ID NO 738
<211> LENGTH: 32
<212> TYPE: PRT
<213> ORGANISM: Homo sapiens

<400> SEQUENCE: 738

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 739
<211> LENGTH: 9
<212> TYPE: PRT
<213> ORGANISM: Homo sapiens

<400> SEQUENCE: 739

Gln Gln Tyr Ser Thr Tyr Ser Arg Thr
1 5

<210> SEQ ID NO 740
<211> LENGTH: 11
<212> TYPE: PRT
<213> ORGANISM: Homo sapiens

<400> SEQUENCE: 740

Phe Gly Gln Gly Thr Lys Val Glu Ile Lys Arg
1 5 10

<210> SEQ ID NO 741
<211> LENGTH: 23
<212> TYPE: PRT
<213> ORGANISM: Homo sapiens

<400> SEQUENCE: 741

Glu Ile Val Leu Thr Gln Ser Pro Ser Phe Val Ser Ala Ser Val Gly
1 5 10 15

Asp Arg Val Thr Ile Thr Cys
20

<210> SEQ ID NO 742
<211> LENGTH: 11
<212> TYPE: PRT
<213> ORGANISM: Homo sapiens

<400> SEQUENCE: 742

Arg Ala Ser Gln Gly Ile Ser Ser Trp Leu Ala
1 5 10

<210> SEQ ID NO 743
<211> LENGTH: 15
<212> TYPE: PRT
<213> ORGANISM: Homo sapiens

<400> SEQUENCE: 743

Trp Tyr Gln Gln Lys Pro Gly Lys Ala Pro Lys Leu Leu Ile Tyr
1 5 10 15

<210> SEQ ID NO 744
<211> LENGTH: 7
<212> TYPE: PRT
<213> ORGANISM: Homo sapiens

<400> SEQUENCE: 744

Ala Ala Ser Ser Leu Gln Ser
1 5

<210> SEQ ID NO 745
<211> LENGTH: 32
<212> TYPE: PRT
<213> ORGANISM: Homo sapiens

<400> SEQUENCE: 745

Gly Val Pro Ser Arg Phe Ser Gly Ser Gly Ser Gly Thr Glu Phe Thr
1 5 10 15

```
Leu Thr Ile Ser Ser Leu Gln Pro Asp Asp Phe Ala Thr Tyr Tyr Cys
            20                  25                  30


<210> SEQ ID NO 746
<211> LENGTH: 8
<212> TYPE: PRT
<213> ORGANISM: Homo sapiens

<400> SEQUENCE: 746

Gln Gln Tyr Ser Ser Leu Tyr Thr
1               5


<210> SEQ ID NO 747
<211> LENGTH: 11
<212> TYPE: PRT
<213> ORGANISM: Homo sapiens

<400> SEQUENCE: 747

Phe Gly Gln Gly Thr Lys Val Asp Ile Lys Arg
1               5                   10


<210> SEQ ID NO 748
<211> LENGTH: 23
<212> TYPE: PRT
<213> ORGANISM: Homo sapiens

<400> SEQUENCE: 748

Asp Ile Val Met Thr Gln Ser Pro Ser Ser Leu Ser Ala Ser Val Gly
1               5                   10                  15

Asp Arg Val Ser Ile Ser Cys
            20


<210> SEQ ID NO 749
<211> LENGTH: 11
<212> TYPE: PRT
<213> ORGANISM: Homo sapiens

<400> SEQUENCE: 749

Arg Ala Ser Gln Ser Ile Ser Ser Tyr Leu Asn
1               5                   10


<210> SEQ ID NO 750
<211> LENGTH: 15
<212> TYPE: PRT
<213> ORGANISM: Homo sapiens

<400> SEQUENCE: 750

Trp Tyr Gln Gln Lys Pro Gly Lys Ala Pro Lys Leu Leu Ile Tyr
1               5                   10                  15


<210> SEQ ID NO 751
<211> LENGTH: 7
<212> TYPE: PRT
<213> ORGANISM: Homo sapiens

<400> SEQUENCE: 751

Lys Thr Ser Ser Leu Glu Ser
1               5


<210> SEQ ID NO 752
<211> LENGTH: 32
<212> TYPE: PRT
<213> ORGANISM: Homo sapiens
```

<400> SEQUENCE: 752

Gly Val Pro Ser Arg Phe Ser Gly Arg Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 753
<211> LENGTH: 9
<212> TYPE: PRT
<213> ORGANISM: Homo sapiens

<400> SEQUENCE: 753

Gln Gln Ser Tyr Ser Thr Pro Leu Thr
1 5

<210> SEQ ID NO 754
<211> LENGTH: 11
<212> TYPE: PRT
<213> ORGANISM: Homo sapiens

<400> SEQUENCE: 754

Phe Gly Gly Gly Thr Lys Val Glu Ile Lys Arg
1 5 10

<210> SEQ ID NO 755
<211> LENGTH: 23
<212> TYPE: PRT
<213> ORGANISM: Homo sapiens

<400> SEQUENCE: 755

Asp Ile Val Met Thr Gln Ser Pro Ser Thr Leu Ser Ala Ser Val Gly
1 5 10 15

Asp Arg Val Thr Ile Thr Cys
20

<210> SEQ ID NO 756
<211> LENGTH: 11
<212> TYPE: PRT
<213> ORGANISM: Homo sapiens

<400> SEQUENCE: 756

Arg Ala Ser Gln Ser Ser Thr Tyr Trp Leu Ser
1 5 10

<210> SEQ ID NO 757
<211> LENGTH: 15
<212> TYPE: PRT
<213> ORGANISM: Homo sapiens

<400> SEQUENCE: 757

Trp Tyr Gln Gln Lys Pro Gly Lys Ala Pro Lys Leu Leu Ile Tyr
1 5 10 15

<210> SEQ ID NO 758
<211> LENGTH: 7
<212> TYPE: PRT
<213> ORGANISM: Homo sapiens

<400> SEQUENCE: 758

Lys Thr Ser Ser Leu Glu Ser
1 5

<210> SEQ ID NO 759

<211> LENGTH: 32
<212> TYPE: PRT
<213> ORGANISM: Homo sapiens

<400> SEQUENCE: 759

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 760
<211> LENGTH: 5
<212> TYPE: PRT
<213> ORGANISM: Homo sapiens

<400> SEQUENCE: 760

Gln Gln Ser Trp Thr
1 5

<210> SEQ ID NO 761
<211> LENGTH: 11
<212> TYPE: PRT
<213> ORGANISM: Homo sapiens

<400> SEQUENCE: 761

Phe Gly Gln Gly Thr Lys Val Glu Ile Lys Arg
1 5 10

<210> SEQ ID NO 762
<211> LENGTH: 23
<212> TYPE: PRT
<213> ORGANISM: Homo sapiens

<400> SEQUENCE: 762

Asp Val Val Met Thr Gln Ser Pro Ser Ser Val Ser Ala Ser Val Gly
1 5 10 15

Asp Arg Val Thr Ile Thr Cys
20

<210> SEQ ID NO 763
<211> LENGTH: 11
<212> TYPE: PRT
<213> ORGANISM: Homo sapiens

<400> SEQUENCE: 763

Arg Ala Ser Gln Gly Ile Gly Tyr Trp Leu Ala
1 5 10

<210> SEQ ID NO 764
<211> LENGTH: 15
<212> TYPE: PRT
<213> ORGANISM: Homo sapiens

<400> SEQUENCE: 764

Trp Tyr Gln Gln Lys Pro Gly Lys Gly Pro Lys Leu Leu Ile Tyr
1 5 10 15

<210> SEQ ID NO 765
<211> LENGTH: 7
<212> TYPE: PRT
<213> ORGANISM: Homo sapiens

<400> SEQUENCE: 765

Asp Ala Ser Arg Leu Gln Gly 1 5

<210> SEQ ID NO 766
<211> LENGTH: 32
<212> TYPE: PRT
<213> ORGANISM: Homo sapiens

<400> SEQUENCE: 766

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 767
<211> LENGTH: 9
<212> TYPE: PRT
<213> ORGANISM: Homo sapiens

<400> SEQUENCE: 767

Gln Gln Tyr Asn Ser Tyr Pro Leu Thr
1 5

<210> SEQ ID NO 768
<211> LENGTH: 11
<212> TYPE: PRT
<213> ORGANISM: Homo sapiens

<400> SEQUENCE: 768

Phe Gly Gly Gly Thr Lys Leu Glu Ile Lys Arg
1 5 10

<210> SEQ ID NO 769
<211> LENGTH: 23
<212> TYPE: PRT
<213> ORGANISM: Homo sapiens

<400> SEQUENCE: 769

Asp Ile Gln Met Thr Gln Ser Pro Pro Ser Leu Ser Ala Ser Val Gly
1 5 10 15

Asp Arg Val Thr Ile Thr Cys
20

<210> SEQ ID NO 770
<211> LENGTH: 11
<212> TYPE: PRT
<213> ORGANISM: Homo sapiens

<400> SEQUENCE: 770

Arg Thr Ser Gln Gly Phe Thr Ser Ala Leu Ala
1 5 10

<210> SEQ ID NO 771
<211> LENGTH: 15
<212> TYPE: PRT
<213> ORGANISM: Homo sapiens

<400> SEQUENCE: 771

Trp Tyr Gln Gln Lys Pro Gly Glu Pro Pro Lys Leu Leu Ile Tyr
1 5 10 15

<210> SEQ ID NO 772
<211> LENGTH: 7
<212> TYPE: PRT
<213> ORGANISM: Homo sapiens

<400> SEQUENCE: 772

Asp Ala Ser Lys Leu Glu Ser
1 5

<210> SEQ ID NO 773
<211> LENGTH: 32
<212> TYPE: PRT
<213> ORGANISM: Homo sapiens

<400> SEQUENCE: 773

Gly Val Pro Ser Arg Phe Ser Gly Ser Gly Ser Gly Thr Asn Phe Ala
1 5 10 15

Leu Thr Ile Ser Ser Leu Gln Pro Glu Asp Phe Ala Thr Tyr Phe Cys
20 25 30

<210> SEQ ID NO 774
<211> LENGTH: 9
<212> TYPE: PRT
<213> ORGANISM: Homo sapiens

<400> SEQUENCE: 774

Gln Gln Ser Asn Ser Tyr Pro Leu Thr
1 5

<210> SEQ ID NO 775
<211> LENGTH: 11
<212> TYPE: PRT
<213> ORGANISM: Homo sapiens

<400> SEQUENCE: 775

Phe Gly Gly Gly Thr Lys Val Glu Ile Lys Arg
1 5 10

<210> SEQ ID NO 776
<211> LENGTH: 22
<212> TYPE: PRT
<213> ORGANISM: Homo sapiens

<400> SEQUENCE: 776

Gln Ser Val Val Thr Gln Pro Pro Ser Val Ser Ala Ala Pro Gly Gln
1 5 10 15

Lys Val Thr Ile Ser Cys
20

<210> SEQ ID NO 777
<211> LENGTH: 13
<212> TYPE: PRT
<213> ORGANISM: Homo sapiens

<400> SEQUENCE: 777

Ser Gly Ser Ser Ser Asn Ile Gly Asn Asn Tyr Val Ser
1 5 10

<210> SEQ ID NO 778
<211> LENGTH: 15
<212> TYPE: PRT
<213> ORGANISM: Homo sapiens

<400> SEQUENCE: 778

Trp Tyr Gln Gln Leu Pro Gly Thr Ala Pro Lys Leu Leu Ile Tyr
1 5 10 15

<210> SEQ ID NO 779
<211> LENGTH: 7
<212> TYPE: PRT
<213> ORGANISM: Homo sapiens

<400> SEQUENCE: 779

Asp Asn Asn Lys Arg Pro Ser
1               5

<210> SEQ ID NO 780
<211> LENGTH: 32
<212> TYPE: PRT
<213> ORGANISM: Homo sapiens

<400> SEQUENCE: 780

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 781
<211> LENGTH: 11
<212> TYPE: PRT
<213> ORGANISM: Homo sapiens

<400> SEQUENCE: 781

Gly Thr Trp Asp Ser Ser Leu Ser Ala Gly Val
1               5                   10

<210> SEQ ID NO 782
<211> LENGTH: 11
<212> TYPE: PRT
<213> ORGANISM: Homo sapiens

<400> SEQUENCE: 782

Phe Gly Gly Gly Thr Lys Leu Thr Val Leu Gly
1               5                   10

<210> SEQ ID NO 783
<211> LENGTH: 22
<212> TYPE: PRT
<213> ORGANISM: Homo sapiens

<400> SEQUENCE: 783

Gln Pro Gly Leu Thr Gln Pro Pro Ser Ala Ser Gly Thr Pro Gly Gln
1               5                   10                  15

Arg Val Thr Ile Ser Cys
            20

<210> SEQ ID NO 784
<211> LENGTH: 13
<212> TYPE: PRT
<213> ORGANISM: Homo sapiens

<400> SEQUENCE: 784

Ser Gly Ser Ser Ser Asn Val Gly Ser Asn Thr Val Asn
1               5                   10

<210> SEQ ID NO 785
<211> LENGTH: 15
<212> TYPE: PRT
<213> ORGANISM: Homo sapiens

<400> SEQUENCE: 785

-continued

Trp Tyr Gln Gln Leu Pro Gly Thr Ala Pro Lys Leu Leu Ile Tyr
1               5                   10                  15

<210> SEQ ID NO 786
<211> LENGTH: 7
<212> TYPE: PRT
<213> ORGANISM: Homo sapiens

<400> SEQUENCE: 786

Arg Asn Asp Gln Arg Pro Ser
1               5

<210> SEQ ID NO 787
<211> LENGTH: 32
<212> TYPE: PRT
<213> ORGANISM: Homo sapiens

<400> SEQUENCE: 787

Gly Val Pro Asp Arg Phe Ser Gly Ser Lys Ser Gly Ala Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 788
<211> LENGTH: 11
<212> TYPE: PRT
<213> ORGANISM: Homo sapiens

<400> SEQUENCE: 788

Ala Ala Trp Asp Asp Ser Leu Asn Gly Leu Leu
1               5                   10

<210> SEQ ID NO 789
<211> LENGTH: 11
<212> TYPE: PRT
<213> ORGANISM: Homo sapiens

<400> SEQUENCE: 789

Phe Gly Gly Gly Thr Gln Leu Thr Val Leu Gly
1               5                   10

<210> SEQ ID NO 790
<211> LENGTH: 22
<212> TYPE: PRT
<213> ORGANISM: Homo sapiens

<400> SEQUENCE: 790

Glu Ser Val Leu Thr Gln Pro Pro Ser Val Ser Ala Ala Pro Gly Gln
1               5                   10                  15

Lys Val Thr Ile Ser Cys
            20

<210> SEQ ID NO 791
<211> LENGTH: 13
<212> TYPE: PRT
<213> ORGANISM: Homo sapiens

<400> SEQUENCE: 791

Ser Gly Ser Ser Ser Asn Ile Gly Asn Asn Tyr Val Ser
1               5                   10

<210> SEQ ID NO 792
<211> LENGTH: 15
<212> TYPE: PRT

<213> ORGANISM: Homo sapiens

<400> SEQUENCE: 792

Trp Tyr Gln Gln Leu Pro Gly Thr Ala Pro Lys Leu Leu Ile Tyr
1 5 10 15

<210> SEQ ID NO 793
<211> LENGTH: 7
<212> TYPE: PRT
<213> ORGANISM: Homo sapiens

<400> SEQUENCE: 793

Asp Asn Asn Arg Arg Pro Ser
1 5

<210> SEQ ID NO 794
<211> LENGTH: 32
<212> TYPE: PRT
<213> ORGANISM: Homo sapiens

<400> SEQUENCE: 794

Gly Ile Pro Asp Arg Phe Ser Gly Ser Lys Ser Gly Thr Ser Ala Thr
1 5 10 15

Leu Gly Ile Thr Gly Leu Gln Thr Gly Asp Glu Ala Asp Tyr Tyr Cys
20 25 30

<210> SEQ ID NO 795
<211> LENGTH: 11
<212> TYPE: PRT
<213> ORGANISM: Homo sapiens

<400> SEQUENCE: 795

Gly Thr Trp Asp Ser Ser Leu Ser Glu Val Val
1 5 10

<210> SEQ ID NO 796
<211> LENGTH: 11
<212> TYPE: PRT
<213> ORGANISM: Homo sapiens

<400> SEQUENCE: 796

Phe Gly Gly Gly Thr Lys Val Thr Val Leu Gly
1 5 10

<210> SEQ ID NO 797
<211> LENGTH: 22
<212> TYPE: PRT
<213> ORGANISM: Homo sapiens

<400> SEQUENCE: 797

Gln Pro Gly Leu Thr Gln Pro Pro Ser Ala Ser Gly Thr Pro Gly Gln
1 5 10 15

Arg Val Thr Ile Ser Cys
20

<210> SEQ ID NO 798
<211> LENGTH: 13
<212> TYPE: PRT
<213> ORGANISM: Homo sapiens

<400> SEQUENCE: 798

Ser Gly Ser Ser Ser Asn Ile Gly Ser Asn Pro Val Asn
1 5 10

<210> SEQ ID NO 799
<211> LENGTH: 15
<212> TYPE: PRT
<213> ORGANISM: Homo sapiens

<400> SEQUENCE: 799

Trp Tyr Gln His Leu Pro Gly Thr Ala Pro Lys Leu Leu Ile Tyr
1               5                   10                  15

<210> SEQ ID NO 800
<211> LENGTH: 7
<212> TYPE: PRT
<213> ORGANISM: Homo sapiens

<400> SEQUENCE: 800

Ser Asn Asn Gln Arg Pro Ser
1               5

<210> SEQ ID NO 801
<211> LENGTH: 32
<212> TYPE: PRT
<213> ORGANISM: Homo sapiens

<400> SEQUENCE: 801

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 802
<211> LENGTH: 11
<212> TYPE: PRT
<213> ORGANISM: Homo sapiens

<400> SEQUENCE: 802

Ala Ala Trp Ala Asp Ser Leu Asn Gly Val Val
1               5                   10

<210> SEQ ID NO 803
<211> LENGTH: 11
<212> TYPE: PRT
<213> ORGANISM: Homo sapiens

<400> SEQUENCE: 803

Phe Gly Gly Gly Thr Lys Val Thr Val Leu Gly
1               5                   10

<210> SEQ ID NO 804
<211> LENGTH: 22
<212> TYPE: PRT
<213> ORGANISM: Homo sapiens

<400> SEQUENCE: 804

Gln Ser Val Val Thr Gln Pro Pro Ser Val Ser Gly Ala Pro Gly Gln
1               5                   10                  15

Arg Val Thr Ile Ser Cys
            20

<210> SEQ ID NO 805
<211> LENGTH: 14
<212> TYPE: PRT
<213> ORGANISM: Homo sapiens

<400> SEQUENCE: 805

Ser Gly Ser Ser Ser Asn Ile Gly Ala Gly Tyr Asp Val His
1 5 10

<210> SEQ ID NO 806
<211> LENGTH: 15
<212> TYPE: PRT
<213> ORGANISM: Homo sapiens

<400> SEQUENCE: 806

Trp Tyr Gln Gln Leu Pro Gly Thr Ala Pro Lys Leu Leu Ile Tyr
1 5 10 15

<210> SEQ ID NO 807
<211> LENGTH: 7
<212> TYPE: PRT
<213> ORGANISM: Homo sapiens

<400> SEQUENCE: 807

Gly Asn Asn Asn Arg Pro Ser
1 5

<210> SEQ ID NO 808
<211> LENGTH: 32
<212> TYPE: PRT
<213> ORGANISM: Homo sapiens

<400> SEQUENCE: 808

Gly Val Pro Asp Arg Phe Ser Gly Ser Lys Ser Gly Thr Ser Ala Ser
1 5 10 15

Leu Ala Ile Thr Gly Leu Gln Ala Glu Asp Glu Ala Asp Tyr Tyr Cys
20 25 30

<210> SEQ ID NO 809
<211> LENGTH: 11
<212> TYPE: PRT
<213> ORGANISM: Homo sapiens

<400> SEQUENCE: 809

Gln Ser Tyr Asp Ser Ser Leu Ser Ala Tyr Val
1 5 10

<210> SEQ ID NO 810
<211> LENGTH: 11
<212> TYPE: PRT
<213> ORGANISM: Homo sapiens

<400> SEQUENCE: 810

Phe Gly Thr Gly Thr Lys Leu Thr Val Leu Gly
1 5 10

<210> SEQ ID NO 811
<211> LENGTH: 22
<212> TYPE: PRT
<213> ORGANISM: Homo sapiens

<400> SEQUENCE: 811

Gln Ser Val Leu Thr Gln Pro Pro Ser Val Ser Ala Ala Pro Gly Gln
1 5 10 15

Lys Val Thr Ile Ser Cys
20

<210> SEQ ID NO 812
<211> LENGTH: 13

<212> TYPE: PRT
<213> ORGANISM: Homo sapiens

<400> SEQUENCE: 812

Ser Gly Ser Ser Ser Asn Ile Gly Asn Asn Tyr Val Ser
1               5                   10

<210> SEQ ID NO 813
<211> LENGTH: 15
<212> TYPE: PRT
<213> ORGANISM: Homo sapiens

<400> SEQUENCE: 813

Trp Tyr Gln Gln Leu Pro Gly Thr Ala Pro Lys Leu Leu Ile Tyr
1               5                   10                  15

<210> SEQ ID NO 814
<211> LENGTH: 7
<212> TYPE: PRT
<213> ORGANISM: Homo sapiens

<400> SEQUENCE: 814

Asp Asn Asn Lys Arg Pro Ser
1               5

<210> SEQ ID NO 815
<211> LENGTH: 32
<212> TYPE: PRT
<213> ORGANISM: Homo sapiens

<400> SEQUENCE: 815

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 816
<211> LENGTH: 11
<212> TYPE: PRT
<213> ORGANISM: Homo sapiens

<400> SEQUENCE: 816

Gly Thr Trp Asp Ser Ser Leu Ser Ala Val Val
1               5                   10

<210> SEQ ID NO 817
<211> LENGTH: 11
<212> TYPE: PRT
<213> ORGANISM: Homo sapiens

<400> SEQUENCE: 817

Phe Gly Gly Gly Thr Gln Leu Thr Val Leu Gly
1               5                   10

<210> SEQ ID NO 818
<211> LENGTH: 22
<212> TYPE: PRT
<213> ORGANISM: Homo sapiens

<400> SEQUENCE: 818

Gln Pro Val Leu Thr Gln Ser Pro Ser Ala Ser Gly Thr Pro Gly Gln
1               5                   10                  15

Arg Val Thr Ile Ser Cys
            20

<210> SEQ ID NO 819
<211> LENGTH: 13
<212> TYPE: PRT
<213> ORGANISM: Homo sapiens

<400> SEQUENCE: 819

```
Ser Gly Ser Ser Ser Asn Leu Gly Ser Asn Thr Val Ser
1               5                   10
```

<210> SEQ ID NO 820
<211> LENGTH: 15
<212> TYPE: PRT
<213> ORGANISM: Homo sapiens

<400> SEQUENCE: 820

```
Trp Tyr Gln Gln Leu Pro Gly Thr Ala Pro Lys Leu Leu Ile Tyr
1               5                   10                  15
```

<210> SEQ ID NO 821
<211> LENGTH: 7
<212> TYPE: PRT
<213> ORGANISM: Homo sapiens

<400> SEQUENCE: 821

```
Ser Asn Asn Gln Arg Pro Ser
1               5
```

<210> SEQ ID NO 822
<211> LENGTH: 32
<212> TYPE: PRT
<213> ORGANISM: Homo sapiens

<400> SEQUENCE: 822

```
Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30
```

<210> SEQ ID NO 823
<211> LENGTH: 11
<212> TYPE: PRT
<213> ORGANISM: Homo sapiens

<400> SEQUENCE: 823

```
Ala Thr Trp Asp Asp Ser Leu Ser Gly Gly Val
1               5                   10
```

<210> SEQ ID NO 824
<211> LENGTH: 11
<212> TYPE: PRT
<213> ORGANISM: Homo sapiens

<400> SEQUENCE: 824

```
Phe Gly Gly Gly Thr Lys Leu Thr Val Leu Gly
1               5                   10
```

<210> SEQ ID NO 825
<211> LENGTH: 22
<212> TYPE: PRT
<213> ORGANISM: Homo sapiens

<400> SEQUENCE: 825

```
Ser Tyr Glu Leu Met Gln Leu Pro Ser Ala Ser Gly Thr Pro Gly Gln
```

1 5 10 15

Arg Val Ser Ile Ser Cys
20

<210> SEQ ID NO 826
<211> LENGTH: 13
<212> TYPE: PRT
<213> ORGANISM: Homo sapiens

<400> SEQUENCE: 826

Ser Gly Ser Ser Ser Asn Ile Gly Ser Asn Pro Val Asn
1 5 10

<210> SEQ ID NO 827
<211> LENGTH: 15
<212> TYPE: PRT
<213> ORGANISM: Homo sapiens

<400> SEQUENCE: 827

Trp Tyr Gln Gln Leu Pro Gly Thr Ala Pro Lys Leu Leu Ile Tyr
1 5 10 15

<210> SEQ ID NO 828
<211> LENGTH: 7
<212> TYPE: PRT
<213> ORGANISM: Homo sapiens

<400> SEQUENCE: 828

Ser Asn Asn His Arg Pro Ser
1 5

<210> SEQ ID NO 829
<211> LENGTH: 32
<212> TYPE: PRT
<213> ORGANISM: Homo sapiens

<400> SEQUENCE: 829

Gly Val Pro Asp Arg Phe Ser Gly Ser Lys Ser Gly Thr Ser Ala Ser
1 5 10 15

Leu Ala Ile Ser Gly Leu Gln Ser Glu Asp Glu Ala Asp Tyr Tyr Cys
20 25 30

<210> SEQ ID NO 830
<211> LENGTH: 12
<212> TYPE: PRT
<213> ORGANISM: Homo sapiens

<400> SEQUENCE: 830

Ala Ala Trp Asp Gly Ser Leu Asn Gly His Val Val
1 5 10

<210> SEQ ID NO 831
<211> LENGTH: 11
<212> TYPE: PRT
<213> ORGANISM: Homo sapiens

<400> SEQUENCE: 831

Phe Gly Gly Gly Thr Lys Leu Thr Val Leu Gly
1 5 10

<210> SEQ ID NO 832
<211> LENGTH: 23
<212> TYPE: PRT
<213> ORGANISM: Homo sapiens

<400> SEQUENCE: 832

Asp Ile Val Met Thr Gln Ser Pro Ser Ser Leu Ser Ala Ser Val Gly
1 5 10 15

Asp Arg Val Thr Ile Ser Cys
20

<210> SEQ ID NO 833
<211> LENGTH: 11
<212> TYPE: PRT
<213> ORGANISM: Homo sapiens

<400> SEQUENCE: 833

Arg Ala Ser Gln Ser Ile Arg His Tyr Val Asn
1 5 10

<210> SEQ ID NO 834
<211> LENGTH: 15
<212> TYPE: PRT
<213> ORGANISM: Homo sapiens

<400> SEQUENCE: 834

Trp Tyr Gln Gln Lys Pro Gly Lys Ala Pro Lys Leu Leu Ile Tyr
1 5 10 15

<210> SEQ ID NO 835
<211> LENGTH: 7
<212> TYPE: PRT
<213> ORGANISM: Homo sapiens

<400> SEQUENCE: 835

Lys Ala Ser Ser Leu Ala Ser
1 5

<210> SEQ ID NO 836
<211> LENGTH: 32
<212> TYPE: PRT
<213> ORGANISM: Homo sapiens

<400> SEQUENCE: 836

Gly Ala Pro Ser Arg Phe Ser Gly Ser Gly Ser Gly Thr Asp Phe Thr
1 5 10 15

Leu Thr Ile Ser Ser Leu Gln Pro Asp Asp Phe Ala Thr Tyr Tyr Cys
20 25 30

<210> SEQ ID NO 837
<211> LENGTH: 9
<212> TYPE: PRT
<213> ORGANISM: Homo sapiens

<400> SEQUENCE: 837

Gln Gln Ser Tyr Ser Ile Pro Leu Thr
1 5

<210> SEQ ID NO 838
<211> LENGTH: 11
<212> TYPE: PRT
<213> ORGANISM: Homo sapiens

<400> SEQUENCE: 838

Phe Gly Gly Gly Thr Lys Val Glu Ile Lys Arg
1 5 10

<210> SEQ ID NO 839
<211> LENGTH: 23
<212> TYPE: PRT
<213> ORGANISM: Homo sapiens

<400> SEQUENCE: 839

Asp Ile Val Met Thr Gln Ser Pro Ser Ser Leu Ser Ala Ser Val Gly
1               5                   10                  15

Asp Arg Val Thr Ile Ser Cys
            20

<210> SEQ ID NO 840
<211> LENGTH: 11
<212> TYPE: PRT
<213> ORGANISM: Homo sapiens

<400> SEQUENCE: 840

Arg Ala Ser Gln Ser Ile Arg His Tyr Val Asn
1               5                   10

<210> SEQ ID NO 841
<211> LENGTH: 15
<212> TYPE: PRT
<213> ORGANISM: Homo sapiens

<400> SEQUENCE: 841

Trp Tyr Gln Gln Lys Pro Gly Lys Ala Pro Lys Leu Leu Ile Tyr
1               5                   10                  15

<210> SEQ ID NO 842
<211> LENGTH: 7
<212> TYPE: PRT
<213> ORGANISM: Homo sapiens

<400> SEQUENCE: 842

Lys Ala Ser Ser Leu Ala Ser
1               5

<210> SEQ ID NO 843
<211> LENGTH: 32
<212> TYPE: PRT
<213> ORGANISM: Homo sapiens

<400> SEQUENCE: 843

Gly Ala Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr Cys
            20                  25                  30

<210> SEQ ID NO 844
<211> LENGTH: 9
<212> TYPE: PRT
<213> ORGANISM: Homo sapiens

<400> SEQUENCE: 844

Gln Gln Ser Tyr Ser Ile Pro Leu Thr
1               5

<210> SEQ ID NO 845
<211> LENGTH: 11
<212> TYPE: PRT
<213> ORGANISM: Homo sapiens

<400> SEQUENCE: 845

```
Phe Gly Gly Gly Thr Lys Val Glu Ile Lys Arg
1               5                   10


<210> SEQ ID NO 846
<211> LENGTH: 23
<212> TYPE: PRT
<213> ORGANISM: Homo sapiens

<400> SEQUENCE: 846

Asp Ile Val Met Thr Gln Ser Pro Ser Ser Leu Ser Ala Ser Val Gly
1               5                   10                  15

Asp Arg Val Thr Ile Ser Cys
            20


<210> SEQ ID NO 847
<211> LENGTH: 11
<212> TYPE: PRT
<213> ORGANISM: Homo sapiens

<400> SEQUENCE: 847

Arg Ala Ser Gln Ser Ile Arg His Tyr Val Asn
1               5                   10


<210> SEQ ID NO 848
<211> LENGTH: 15
<212> TYPE: PRT
<213> ORGANISM: Homo sapiens

<400> SEQUENCE: 848

Trp Tyr Gln Gln Lys Pro Gly Lys Ala Pro Lys Leu Leu Ile Tyr
1               5                   10                  15


<210> SEQ ID NO 849
<211> LENGTH: 7
<212> TYPE: PRT
<213> ORGANISM: Homo sapiens

<400> SEQUENCE: 849

Lys Ala Ser Ser Leu Ala Ser
1               5


<210> SEQ ID NO 850
<211> LENGTH: 32
<212> TYPE: PRT
<213> ORGANISM: Homo sapiens

<400> SEQUENCE: 850

Gly Ala Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr Cys
            20                  25                  30


<210> SEQ ID NO 851
<211> LENGTH: 9
<212> TYPE: PRT
<213> ORGANISM: Homo sapiens

<400> SEQUENCE: 851

Gln Gln Ser Tyr Ser Ile Pro Leu Thr
1               5


<210> SEQ ID NO 852
<211> LENGTH: 11
<212> TYPE: PRT
```

<213> ORGANISM: Homo sapiens

<400> SEQUENCE: 852

Phe Gly Gly Gly Thr Lys Val Glu Ile Lys Arg
1               5                   10

<210> SEQ ID NO 853
<211> LENGTH: 23
<212> TYPE: PRT
<213> ORGANISM: Homo sapiens

<400> SEQUENCE: 853

Asp Ile Val Met Thr Gln Ser Pro Ser Ser Leu Ser Ala Ser Val Gly
1               5                   10                  15

Asp Arg Val Thr Ile Ser Cys
            20

<210> SEQ ID NO 854
<211> LENGTH: 11
<212> TYPE: PRT
<213> ORGANISM: Homo sapiens

<400> SEQUENCE: 854

Arg Ala Ser Gln Ser Ile Arg His Tyr Val Asn
1               5                   10

<210> SEQ ID NO 855
<211> LENGTH: 15
<212> TYPE: PRT
<213> ORGANISM: Homo sapiens

<400> SEQUENCE: 855

Trp Tyr Gln Gln Lys Pro Gly Lys Ala Pro Lys Leu Leu Ile Tyr
1               5                   10                  15

<210> SEQ ID NO 856
<211> LENGTH: 7
<212> TYPE: PRT
<213> ORGANISM: Homo sapiens

<400> SEQUENCE: 856

Lys Ala Ser Ser Leu Ala Ser
1               5

<210> SEQ ID NO 857
<211> LENGTH: 32
<212> TYPE: PRT
<213> ORGANISM: Homo sapiens

<400> SEQUENCE: 857

Gly Ala Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr Cys
            20                  25                  30

<210> SEQ ID NO 858
<211> LENGTH: 9
<212> TYPE: PRT
<213> ORGANISM: Homo sapiens

<400> SEQUENCE: 858

Gln Gln Ser Tyr Ser Ile Pro Leu Thr
1               5

<210> SEQ ID NO 859
<211> LENGTH: 11
<212> TYPE: PRT
<213> ORGANISM: Homo sapiens

<400> SEQUENCE: 859

```
Phe Gly Gly Gly Thr Lys Val Glu Ile Lys Arg
1               5                   10
```

<210> SEQ ID NO 860
<211> LENGTH: 23
<212> TYPE: PRT
<213> ORGANISM: Homo sapiens

<400> SEQUENCE: 860

```
Asp Ile Val Met Thr Gln Ser Pro Ser Ser Leu Ser Ala Ser Val Gly
1               5                   10                  15

Asp Arg Val Thr Ile Ser Cys
            20
```

<210> SEQ ID NO 861
<211> LENGTH: 11
<212> TYPE: PRT
<213> ORGANISM: Homo sapiens

<400> SEQUENCE: 861

```
Arg Ala Ser Gln Ser Ile Arg His Tyr Val Asn
1               5                   10
```

<210> SEQ ID NO 862
<211> LENGTH: 15
<212> TYPE: PRT
<213> ORGANISM: Homo sapiens

<400> SEQUENCE: 862

```
Trp Tyr Gln Gln Lys Pro Gly Lys Ala Pro Lys Leu Leu Ile Tyr
1               5                   10                  15
```

<210> SEQ ID NO 863
<211> LENGTH: 7
<212> TYPE: PRT
<213> ORGANISM: Homo sapiens

<400> SEQUENCE: 863

```
Lys Ala Ser Ser Leu Ala Ser
1               5
```

<210> SEQ ID NO 864
<211> LENGTH: 32
<212> TYPE: PRT
<213> ORGANISM: Homo sapiens

<400> SEQUENCE: 864

```
Gly Ala Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr Cys
            20                  25                  30
```

<210> SEQ ID NO 865
<211> LENGTH: 9
<212> TYPE: PRT
<213> ORGANISM: Homo sapiens

<400> SEQUENCE: 865

Gln Gln Ser Tyr Ser Ile Pro Leu Thr
1               5

<210> SEQ ID NO 866
<211> LENGTH: 11
<212> TYPE: PRT
<213> ORGANISM: Homo sapiens

<400> SEQUENCE: 866

Phe Gly Gly Gly Thr Lys Val Glu Ile Lys Arg
1               5                   10

<210> SEQ ID NO 867
<211> LENGTH: 10
<212> TYPE: PRT
<213> ORGANISM: Homo sapiens

<400> SEQUENCE: 867

Asp Pro Tyr Tyr Tyr Ser Tyr Met Asp Val
1               5                   10

<210> SEQ ID NO 868
<211> LENGTH: 9
<212> TYPE: PRT
<213> ORGANISM: Homo sapiens

<400> SEQUENCE: 868

Gln Gln Tyr Tyr Ser Thr Pro Phe Thr
1               5

<210> SEQ ID NO 869
<211> LENGTH: 17
<212> TYPE: PRT
<213> ORGANISM: Homo sapiens

<400> SEQUENCE: 869

Glu Ala Ser Phe Gly Trp Ser Tyr Leu Gly His Asp Asp Ala Phe Asp
1               5                   10                  15

Ile

<210> SEQ ID NO 870
<211> LENGTH: 9
<212> TYPE: PRT
<213> ORGANISM: Homo sapiens

<400> SEQUENCE: 870

Gln Gln Tyr Gly Ser Ser Leu Trp Thr
1               5

<210> SEQ ID NO 871
<211> LENGTH: 17
<212> TYPE: PRT
<213> ORGANISM: Homo sapiens

<400> SEQUENCE: 871

Asp Pro Gly Trp Ile Tyr Ser Asp Thr Ser Ala Ala Gly Trp Phe Asp
1               5                   10                  15

Pro

<210> SEQ ID NO 872
<211> LENGTH: 9
<212> TYPE: PRT
<213> ORGANISM: Homo sapiens

<400> SEQUENCE: 872

Gln Gln Ser Tyr Asp Thr Pro Arg Thr
1 5

<210> SEQ ID NO 873
<211> LENGTH: 5
<212> TYPE: PRT
<213> ORGANISM: Homo sapiens

<400> SEQUENCE: 873

Asp Tyr Asp Met His
1 5

<210> SEQ ID NO 874
<211> LENGTH: 17
<212> TYPE: PRT
<213> ORGANISM: Homo sapiens

<400> SEQUENCE: 874

Val Met Trp Phe Asp Gly Thr Glu Lys Tyr Ser Ala Glu Ser Val Lys
1 5 10 15

Gly

<210> SEQ ID NO 875
<211> LENGTH: 15
<212> TYPE: PRT
<213> ORGANISM: Homo sapiens

<400> SEQUENCE: 875

Glu Pro Asp Trp Leu Leu Trp Gly Asp Arg Gly Ala Leu Asp Val
1 5 10 15

<210> SEQ ID NO 876
<211> LENGTH: 5
<212> TYPE: PRT
<213> ORGANISM: Homo sapiens

<400> SEQUENCE: 876

Asp Tyr Asp Met His
1 5

<210> SEQ ID NO 877
<211> LENGTH: 17
<212> TYPE: PRT
<213> ORGANISM: Homo sapiens

<400> SEQUENCE: 877

Val Met Trp Phe Asp Gly Thr Glu Lys Tyr Ser Ala Glu Ser Val Lys
1 5 10 15

Gly

<210> SEQ ID NO 878
<211> LENGTH: 15
<212> TYPE: PRT
<213> ORGANISM: Homo sapiens

<400> SEQUENCE: 878

Glu Pro Asp Trp Leu Leu Trp Gly Asp Arg Gly Ala Leu Asp Val
1 5 10 15

<210> SEQ ID NO 879
<211> LENGTH: 5

<212> TYPE: PRT
<213> ORGANISM: Homo sapiens

<400> SEQUENCE: 879

Tyr Asp Tyr Met Tyr
1               5

<210> SEQ ID NO 880
<211> LENGTH: 17
<212> TYPE: PRT
<213> ORGANISM: Homo sapiens

<400> SEQUENCE: 880

Thr Ile Ser Asp Gly Gly Ser Tyr Thr Tyr Tyr Ser Asp Ser Val Glu
1               5                   10                  15

Gly

<210> SEQ ID NO 881
<211> LENGTH: 9
<212> TYPE: PRT
<213> ORGANISM: Homo sapiens

<400> SEQUENCE: 881

Tyr Arg Tyr Asp Asp Ala Met Asp Tyr
1               5

<210> SEQ ID NO 882
<211> LENGTH: 5
<212> TYPE: PRT
<213> ORGANISM: Homo sapiens

<400> SEQUENCE: 882

Asn Tyr Ala Met Thr
1               5

<210> SEQ ID NO 883
<211> LENGTH: 17
<212> TYPE: PRT
<213> ORGANISM: Homo sapiens

<400> SEQUENCE: 883

Ser Ile Ser Val Gly Gly Ser Asp Thr Tyr Tyr Ala Asp Ser Val Lys
1               5                   10                  15

Gly

<210> SEQ ID NO 884
<211> LENGTH: 17
<212> TYPE: PRT
<213> ORGANISM: Homo sapiens

<400> SEQUENCE: 884

Val Arg Thr Lys Tyr Cys Ser Ser Leu Ser Cys Phe Ala Gly Phe Asp
1               5                   10                  15

Ser

<210> SEQ ID NO 885
<211> LENGTH: 11
<212> TYPE: PRT
<213> ORGANISM: Homo sapiens

<400> SEQUENCE: 885

Arg Ala Ser Gln Ser Ile Ser Ser Trp Leu Ala
1               5                   10

<210> SEQ ID NO 886
<211> LENGTH: 7
<212> TYPE: PRT
<213> ORGANISM: Homo sapiens

<400> SEQUENCE: 886

Glu Ala Ser Ser Leu Glu Ser
1               5

<210> SEQ ID NO 887
<211> LENGTH: 9
<212> TYPE: PRT
<213> ORGANISM: Homo sapiens

<400> SEQUENCE: 887

Gln His Tyr Asn Thr Tyr Pro Tyr Thr
1               5

<210> SEQ ID NO 888
<211> LENGTH: 11
<212> TYPE: PRT
<213> ORGANISM: Homo sapiens

<400> SEQUENCE: 888

Trp Ala Ser Gln Ser Ile Ser Ser Arg Leu Ala
1               5                   10

<210> SEQ ID NO 889
<211> LENGTH: 7
<212> TYPE: PRT
<213> ORGANISM: Homo sapiens

<400> SEQUENCE: 889

Glu Ala Thr Ser Leu Gly Ser
1               5

<210> SEQ ID NO 890
<211> LENGTH: 9
<212> TYPE: PRT
<213> ORGANISM: Homo sapiens

<400> SEQUENCE: 890

Gln His Tyr Asp Thr Tyr Pro Tyr Thr
1               5

<210> SEQ ID NO 891
<211> LENGTH: 15
<212> TYPE: PRT
<213> ORGANISM: Homo sapiens

<400> SEQUENCE: 891

Arg Ala Ser Glu Ser Val Asp Ser Tyr Gly His Ser Phe Met Gln
1               5                   10                  15

<210> SEQ ID NO 892
<211> LENGTH: 7
<212> TYPE: PRT
<213> ORGANISM: Homo sapiens

<400> SEQUENCE: 892

Arg Ala Ser Asn Leu Glu Pro
1               5

<210> SEQ ID NO 893
<211> LENGTH: 9
<212> TYPE: PRT
<213> ORGANISM: Homo sapiens

<400> SEQUENCE: 893

Gln Gln Gly Asn Glu Val Pro Phe Thr
1 5

<210> SEQ ID NO 894
<211> LENGTH: 11
<212> TYPE: PRT
<213> ORGANISM: Homo sapiens

<400> SEQUENCE: 894

Arg Ala Ser Gln Ser Ile Ser Ser Tyr Leu His
1 5 10

<210> SEQ ID NO 895
<211> LENGTH: 7
<212> TYPE: PRT
<213> ORGANISM: Homo sapiens

<400> SEQUENCE: 895

Asp Ala Ser Ser Ser Gln Ser
1 5

<210> SEQ ID NO 896
<211> LENGTH: 10
<212> TYPE: PRT
<213> ORGANISM: Homo sapiens

<400> SEQUENCE: 896

Gln Gln Ser Tyr Ser Thr Arg Ala Leu Thr
1 5 10

<210> SEQ ID NO 897
<211> LENGTH: 23
<212> TYPE: DNA
<213> ORGANISM: Artificial Sequence
<220> FEATURE:
<223> OTHER INFORMATION: Primer

<400> SEQUENCE: 897
caggtcacct tgaaggagtc tgg 23

<210> SEQ ID NO 898
<211> LENGTH: 23
<212> TYPE: DNA
<213> ORGANISM: Artificial Sequence
<220> FEATURE:
<223> OTHER INFORMATION: Primer

<400> SEQUENCE: 898
gaggtgcagc tggtgcagtc tgg 23

<210> SEQ ID NO 899
<211> LENGTH: 23
<212> TYPE: PRT
<213> ORGANISM: Artificial Sequence
<220> FEATURE:
<223> OTHER INFORMATION: Primer

<400> SEQUENCE: 899

Cys Ala Gly Gly Thr Gly Cys Ala Gly Cys Thr Gly Gly Thr Gly Cys
1 5 10 15

```
Ala Ala Thr Cys Thr Gly Gly
            20


<210> SEQ ID NO 900
<211> LENGTH: 23
<212> TYPE: DNA
<213> ORGANISM: Artificial Sequence
<220> FEATURE:
<223> OTHER INFORMATION: Primer

<400> SEQUENCE: 900

gatattgtga tgactcagtc tcc                                              23


<210> SEQ ID NO 901
<211> LENGTH: 23
<212> TYPE: DNA
<213> ORGANISM: Artificial Sequence
<220> FEATURE:
<223> OTHER INFORMATION: Primer

<400> SEQUENCE: 901

gatattgtga tgacccagat ccc                                              23


<210> SEQ ID NO 902
<211> LENGTH: 53
<212> TYPE: DNA
<213> ORGANISM: Artificial Sequence
<220> FEATURE:
<223> OTHER INFORMATION: Primer

<400> SEQUENCE: 902

gtggtggtgg ttctgctagc ggggccatgg ccaccctggt caccgtctcc tca             53


<210> SEQ ID NO 903
<211> LENGTH: 51
<212> TYPE: DNA
<213> ORGANISM: Artificial Sequence
<220> FEATURE:
<223> OTHER INFORMATION: Primer

<400> SEQUENCE: 903

ggtggtggtt ctgctagcgg ggccatggcg acaatggtca ccgtctcttc a               51


<210> SEQ ID NO 904
<211> LENGTH: 51
<212> TYPE: DNA
<213> ORGANISM: Artificial Sequence
<220> FEATURE:
<223> OTHER INFORMATION: Primer

<400> SEQUENCE: 904

ggtggtggtt ctgctagcgg ggccatggca accctggtca ccgtctcctc a               51


<210> SEQ ID NO 905
<211> LENGTH: 51
<212> TYPE: DNA
<213> ORGANISM: Artificial Sequence
<220> FEATURE:
<223> OTHER INFORMATION: Primer

<400> SEQUENCE: 905

ggtggtggtt ctgctagcgg ggccatggcg accacggtca ccgtctcctc a               51


<210> SEQ ID NO 906
<211> LENGTH: 22
```

<212> TYPE: DNA
<213> ORGANISM: Artificial Sequence
<220> FEATURE:
<223> OTHER INFORMATION: Primer

<400> SEQUENCE: 906
gtcgattttg ttacatctac ac 22

<210> SEQ ID NO 907
<211> LENGTH: 22
<212> TYPE: DNA
<213> ORGANISM: Artificial Sequence
<220> FEATURE:
<223> OTHER INFORMATION: Primer

<400> SEQUENCE: 907
agtaacgttt gtcagtaatt gc 22

<210> SEQ ID NO 908
<211> LENGTH: 32
<212> TYPE: DNA
<213> ORGANISM: Artificial Sequence
<220> FEATURE:
<223> OTHER INFORMATION: Primer

<400> SEQUENCE: 908
aaggctcttt ggacaagaga aactctggat cc 32

<210> SEQ ID NO 909
<211> LENGTH: 37
<212> TYPE: DNA
<213> ORGANISM: Artificial Sequence
<220> FEATURE:
<223> OTHER INFORMATION: Primer

<400> SEQUENCE: 909
gtgccagggg gaagaccgat gggcccttgg tgctagc 37

<210> SEQ ID NO 910
<211> LENGTH: 14
<212> TYPE: PRT
<213> ORGANISM: Homo sapiens

<400> SEQUENCE: 910

His Asp Ser Arg Tyr Lys Tyr Phe Tyr Phe Gly Met Asp Val
1 5 10

<210> SEQ ID NO 911
<211> LENGTH: 14
<212> TYPE: PRT
<213> ORGANISM: Homo sapiens

<400> SEQUENCE: 911

Met Ser Gly Ser Arg Ser Tyr Ser Gln Tyr Tyr Phe Asp Ser
1 5 10

<210> SEQ ID NO 912
<211> LENGTH: 15
<212> TYPE: PRT
<213> ORGANISM: Homo sapiens

<400> SEQUENCE: 912

Asp Leu Thr Arg Phe His Asp Thr Thr Phe Gly Val Phe Glu Met
1 5 10 15

<210> SEQ ID NO 913
<211> LENGTH: 11
<212> TYPE: PRT
<213> ORGANISM: Homo sapiens

<400> SEQUENCE: 913

Glu Trp Thr Gln Leu Trp Ser Pro Tyr Asp Tyr
1 5 10

<210> SEQ ID NO 914
<211> LENGTH: 17
<212> TYPE: PRT
<213> ORGANISM: Homo sapiens

<400> SEQUENCE: 914

Thr Ala Phe Tyr Tyr Glu Asn Thr Gly Pro Ile Arg Cys Tyr Leu Asp
1 5 10 15

Phe

<210> SEQ ID NO 915
<211> LENGTH: 19
<212> TYPE: PRT
<213> ORGANISM: Homo sapiens

<400> SEQUENCE: 915

Ala Leu Val Gly Arg Tyr Asp Ile Ser Thr Gly Tyr Tyr Arg Pro Val
1 5 10 15

Met Asp Ser

<210> SEQ ID NO 916
<211> LENGTH: 14
<212> TYPE: PRT
<213> ORGANISM: Homo sapiens

<400> SEQUENCE: 916

Asp Gly Pro Met Ala Ala Ile Pro Phe Tyr Tyr Phe Asp Phe
1 5 10

<210> SEQ ID NO 917
<211> LENGTH: 18
<212> TYPE: PRT
<213> ORGANISM: Homo sapiens

<400> SEQUENCE: 917

Gly Val Pro Ile Tyr Asp Ser Ser Gly Thr Tyr Arg Gly Thr Tyr Phe
1 5 10 15

Asp Tyr

<210> SEQ ID NO 918
<211> LENGTH: 13
<212> TYPE: PRT
<213> ORGANISM: Homo sapiens

<400> SEQUENCE: 918

Arg Arg Leu Leu Gly Pro Ser Pro Tyr Tyr Phe Asp Tyr
1 5 10

<210> SEQ ID NO 919
<211> LENGTH: 18
<212> TYPE: PRT
<213> ORGANISM: Homo sapiens

<400> SEQUENCE: 919

```
Gly Asn Pro Gln Tyr Asp Thr Ser Gly Ser Tyr Thr Gly Leu Tyr Phe
1               5                   10                  15

Asp Phe


<210> SEQ ID NO 920
<211> LENGTH: 22
<212> TYPE: PRT
<213> ORGANISM: Homo sapiens

<400> SEQUENCE: 920

Asp Ile Leu Tyr Tyr His Asp Ser Ser Asp Tyr Trp Gly Arg Gly His
1               5                   10                  15

Phe Tyr Tyr Met Asp Val
            20


<210> SEQ ID NO 921
<211> LENGTH: 19
<212> TYPE: PRT
<213> ORGANISM: Homo sapiens

<400> SEQUENCE: 921

Asp Arg Tyr Pro Ile Asp Cys Ser Gly Gly Ser Cys Phe Ser Tyr Gly
1               5                   10                  15

Met Asp Val


<210> SEQ ID NO 922
<211> LENGTH: 12
<212> TYPE: PRT
<213> ORGANISM: Homo sapiens

<400> SEQUENCE: 922

Leu Glu Trp Gly Gly Arg Asn Gly Trp Val Ser Pro
1               5                   10


<210> SEQ ID NO 923
<211> LENGTH: 14
<212> TYPE: PRT
<213> ORGANISM: Homo sapiens

<400> SEQUENCE: 923

Asp Lys Arg Thr Tyr Glu Tyr Asn Trp Asn Ser Leu Trp Phe
1               5                   10


<210> SEQ ID NO 924
<211> LENGTH: 17
<212> TYPE: PRT
<213> ORGANISM: Homo sapiens

<400> SEQUENCE: 924

Met Arg Gly Tyr Ser Ser Trp His Tyr Ser Tyr Tyr Tyr Val Met Asp
1               5                   10                  15

Val


<210> SEQ ID NO 925
<211> LENGTH: 14
<212> TYPE: PRT
<213> ORGANISM: Homo sapiens

<400> SEQUENCE: 925

Asp Arg Ser His Tyr Gly Asp Tyr Val Gly Tyr Leu Asp Tyr
1               5                   10
```

<210> SEQ ID NO 926
<211> LENGTH: 12
<212> TYPE: PRT
<213> ORGANISM: Homo sapiens

<400> SEQUENCE: 926

Ser Ser Ile Val Gly Ala Pro Tyr Gly Met Asp Val
1 5 10

<210> SEQ ID NO 927
<211> LENGTH: 14
<212> TYPE: PRT
<213> ORGANISM: Homo sapiens

<400> SEQUENCE: 927

Asp Val Ser Glu Tyr Gly Asp Tyr Val Gly His Phe Asp Tyr
1 5 10

<210> SEQ ID NO 928
<211> LENGTH: 10
<212> TYPE: PRT
<213> ORGANISM: Homo sapiens

<400> SEQUENCE: 928

Asp Pro Tyr Tyr Tyr Ser Tyr Met Asp Val
1 5 10

<210> SEQ ID NO 929
<211> LENGTH: 17
<212> TYPE: PRT
<213> ORGANISM: Homo sapiens

<400> SEQUENCE: 929

Glu Ala Ser Phe Gly Trp Ser Tyr Leu Gly His Asp Asp Ala Phe Asp
1 5 10 15

Ile

<210> SEQ ID NO 930
<211> LENGTH: 17
<212> TYPE: PRT
<213> ORGANISM: Homo sapiens

<400> SEQUENCE: 930

Asp Pro Gly Trp Ile Tyr Ser Asp Thr Ser Ala Ala Gly Trp Phe Asp
1 5 10 15

Pro

<210> SEQ ID NO 931
<211> LENGTH: 17
<212> TYPE: PRT
<213> ORGANISM: Homo sapiens

<400> SEQUENCE: 931

Val Arg Thr Lys Tyr Cys Ser Ser Leu Ser Cys Phe Ala Gly Phe Asp
1 5 10 15

Ser

<210> SEQ ID NO 932
<211> LENGTH: 21
<212> TYPE: DNA
<213> ORGANISM: Artificial Sequence
<220> FEATURE:
<223> OTHER INFORMATION: Primer

<400> SEQUENCE: 932
ttaagcttct gcaggctagt g 21

<210> SEQ ID NO 933
<211> LENGTH: 21
<212> TYPE: DNA
<213> ORGANISM: Artificial Sequence
<220> FEATURE:
<223> OTHER INFORMATION: Primer

<400> SEQUENCE: 933
ttaagcttct gcaggctagt g 21

<210> SEQ ID NO 934
<211> LENGTH: 21
<212> TYPE: DNA
<213> ORGANISM: Artificial Sequence
<220> FEATURE:
<223> OTHER INFORMATION: Primer

<400> SEQUENCE: 934
gagaccgagg agagggttag g 21

<210> SEQ ID NO 935
<211> LENGTH: 22
<212> TYPE: DNA
<213> ORGANISM: Artificial Sequence
<220> FEATURE:
<223> OTHER INFORMATION: Primer

<400> SEQUENCE: 935
agtaacgttt gtcagtaatt gc 22

<210> SEQ ID NO 936
<211> LENGTH: 22
<212> TYPE: DNA
<213> ORGANISM: Artificial Sequence
<220> FEATURE:
<223> OTHER INFORMATION: Primer

<400> SEQUENCE: 936
gtcgattttg ttacatctac ac 22

<210> SEQ ID NO 937
<211> LENGTH: 25
<212> TYPE: DNA
<213> ORGANISM: Artificial Sequence
<220> FEATURE:
<223> OTHER INFORMATION: Primer

<400> SEQUENCE: 937
gttgttctgc tagcggggcc aatgg 25

<210> SEQ ID NO 938
<211> LENGTH: 5
<212> TYPE: PRT
<213> ORGANISM: Artificial Sequence
<220> FEATURE:
<223> OTHER INFORMATION: Polypeptide Linker

<400> SEQUENCE: 938

Gly Gly Gly Gly Ser
1 5

<210> SEQ ID NO 939

<211> LENGTH: 126
<212> TYPE: PRT
<213> ORGANISM: Homo sapiens

<400> SEQUENCE: 939

Gln Val Gln Leu Gln Gln Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Thr Trp Val Arg Gln Ala Pro Gly Lys Gly Leu Glu Trp Val
35 40 45

Ser Ser Ile Ser Val Gly Gly Ser Asp Thr Tyr Tyr Ala Asp Ser Val
50 55 60

Lys Gly Arg Phe Thr Val Ser Arg Asp Asn Ser Lys Asn Thr Leu Leu
65 70 75 80

Leu Gln Met Asn Ser Leu Arg Ala Glu Asp Thr Ala Val Tyr Tyr Cys
85 90 95

Ala Lys Val Arg Thr Lys Tyr Cys Ser Ser Leu Ser Cys Phe Ala Gly
100 105 110

Phe Asp Ser Trp Gly Gln Gly Thr Arg Val Thr Val Ser Ser
115 120 125

<210> SEQ ID NO 940
<211> LENGTH: 126
<212> TYPE: PRT
<213> ORGANISM: Homo sapiens

<400> SEQUENCE: 940

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Thr Trp Val Arg Gln Ala Pro Gly Lys Gly Leu Glu Trp Val
35 40 45

Ser Ser Ile Ser Val Gly Gly Ser Asp Thr Tyr Tyr Ala Asp Ser Val
50 55 60

Lys Gly Arg Phe Thr Val Ser Arg Asp Asn Ser Lys Asn Thr Leu Leu
65 70 75 80

Leu Gln Met Asn Ser Leu Arg Ala Glu Asp Thr Ala Val Tyr Tyr Cys
85 90 95

Ala Lys Val Arg Thr Lys Tyr Cys Ser Ser Leu Ser Cys Phe Ala Gly
100 105 110

Phe Asp Ser Trp Gly Gln Gly Thr Leu Val Thr Val Ser Ser
115 120 125

<210> SEQ ID NO 941
<211> LENGTH: 126
<212> TYPE: PRT
<213> ORGANISM: Homo sapiens

<400> SEQUENCE: 941

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Thr Trp Val Arg Gln Ala Pro Gly Lys Gly Leu Glu Trp Val
35 40 45

```
Ser Ser Ile Ser Val Gly Gly Ser Asp Thr Tyr Tyr Ala Asp Ser Val
    50                  55                  60

Lys Gly Arg Phe Thr Val Ser Arg Asp Asn Ser Lys Asn Thr Leu Leu
65                  70                  75                  80

Leu Gln Met Asn Ser Leu Arg Ala Glu Asp Thr Ala Val Tyr Tyr Cys
                85                  90                  95

Ala Lys Val Arg Thr Lys Tyr Cys Ser Ser Leu Ser Cys Phe Ala Gly
            100                 105                 110

Phe Asp Ser Trp Gly Gln Gly Thr Leu Val Thr Val Ser Ser
        115                 120                 125


<210> SEQ ID NO 942
<211> LENGTH: 126
<212> TYPE: PRT
<213> ORGANISM: Homo sapiens

<400> SEQUENCE: 942

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ser Ile Ser Val Gly Gly Ser Asp Thr Tyr Tyr Ala Asp Ser Val
    50                  55                  60

Lys Gly Arg Phe Thr Val Ser Arg Asp Asn Ser Lys Asn Thr Leu Leu
65                  70                  75                  80

Leu Gln Met Asn Ser Leu Arg Ala Glu Asp Thr Ala Val Tyr Tyr Cys
                85                  90                  95

Ala Lys Val Arg Thr Lys Tyr Cys Ser Ser Leu Ser Cys Phe Ala Gly
            100                 105                 110

Phe Asp Ser Trp Gly Gln Gly Thr Leu Val Thr Val Ser Ser
        115                 120                 125


<210> SEQ ID NO 943
<211> LENGTH: 126
<212> TYPE: PRT
<213> ORGANISM: Homo sapiens

<400> SEQUENCE: 943

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ser Ile Ser Val Gly Gly Ser Asp Thr Tyr Tyr Ala Asp Ser Val
    50                  55                  60

Lys Gly Arg Phe Thr Val Ser Arg Asp Asn Ser Lys Asn Thr Leu Leu
65                  70                  75                  80

Leu Gln Met Asn Ser Leu Arg Ala Glu Asp Thr Ala Val Tyr Tyr Cys
                85                  90                  95

Ala Lys Val Arg Thr Lys Tyr Cys Ser Ser Leu Ser Cys Phe Ala Gly
            100                 105                 110

Phe Asp Ser Trp Gly Gln Gly Thr Leu Val Thr Val Ser Ser
        115                 120                 125
```

<210> SEQ ID NO 944
<211> LENGTH: 126
<212> TYPE: PRT
<213> ORGANISM: Homo sapiens

<400> SEQUENCE: 944

```
Gln Val Gln Leu Val Gln Ser Gly Gly Gly Leu Ala Gln Pro Gly Gly
1               5                   10                  15

Ser Leu Arg Leu Ser Cys Ala Ala Ser Gly Phe Thr Phe Gly Ser Tyr
            20                  25                  30

Ser Met Asn Trp Val Arg Gln Ala Pro Gly Lys Gly Leu Glu Trp Val
        35                  40                  45

Ser Ser Ile Thr Gly Asn Ser Gly Leu Ile Tyr Tyr Ala Asp Ser Val
    50                  55                  60

Lys Gly Arg Phe Thr Val Ser Arg Asp Asn Ala Lys Asn Ser Leu Phe
65                  70                  75                  80

Leu His Met His Ser Leu Arg Ala Asp Asp Thr Ala Val Tyr Tyr Cys
                85                  90                  95

Ala Arg Asp Pro Gly Trp Ile Tyr Ser Asp Thr Ser Ala Ala Gly Trp
            100                 105                 110

Phe Asp Pro Trp Gly His Gly Thr Leu Val Thr Val Ser Ser
        115                 120                 125
```

<210> SEQ ID NO 945
<211> LENGTH: 126
<212> TYPE: PRT
<213> ORGANISM: Homo sapiens

<400> SEQUENCE: 945

```
Gln Val Gln Leu Val Gln Ser Gly Gly Gly Leu Ala Gln Pro Gly Gly
1               5                   10                  15

Ser Leu Arg Leu Ser Cys Ala Ala Ser Gly Phe Thr Phe Gly Ser Tyr
            20                  25                  30

Ser Met Asn Trp Val Arg Gln Ala Pro Gly Lys Gly Leu Glu Trp Val
        35                  40                  45

Ser Ser Ile Thr Gly Asn Ser Gly Leu Ile Tyr Tyr Ala Asp Ser Val
    50                  55                  60

Lys Gly Arg Phe Thr Val Ser Arg Asp Asn Ala Lys Asn Ser Leu Phe
65                  70                  75                  80

Leu His Met His Ser Leu Arg Ala Asp Asp Thr Ala Val Tyr Tyr Cys
                85                  90                  95

Ala Arg Asp Pro Gly Trp Ile Tyr Ser Asp Thr Ser Ala Ala Gly Trp
            100                 105                 110

Phe Asp Pro Trp Gly His Gly Thr Leu Val Thr Val Ser Ser
        115                 120                 125
```

<210> SEQ ID NO 946
<211> LENGTH: 126
<212> TYPE: PRT
<213> ORGANISM: Homo sapiens

<400> SEQUENCE: 946

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ala Asp Tyr
            20                  25                  30

Tyr Ile His Trp Val Arg Gln Ala Pro Gly Gln Gly Leu Glu Trp Met
```

```
        35                  40                  45

Gly Arg Ile Asn Ser Asn Ser Gly Gly Pro Asn Tyr Ala Gln Asn Tyr
    50                  55                  60

Gln Gly Arg Val Thr Met Thr Arg Asp Thr Ser Ile Ser Thr Ala Tyr
65                  70                  75                  80

Met Glu Val Ile Ser Leu Arg Ser Asp Asp Thr Ala Val Tyr Tyr Cys
                85                  90                  95

Ala Arg Glu Ala Ser Phe Gly Trp Ser Tyr Leu Gly His Asp Asp Ala
            100                 105                 110

Phe Asp Ile Trp Gly Gln Gly Thr Met Val Thr Val Ser Ser
        115                 120                 125


<210> SEQ ID NO 947
<211> LENGTH: 109
<212> TYPE: PRT
<213> ORGANISM: Homo sapiens

<400> SEQUENCE: 947

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Thr Phe Gly Gly Gly Thr Lys Val Asp Ile Lys Arg
            100                 105


<210> SEQ ID NO 948
<211> LENGTH: 108
<212> TYPE: PRT
<213> ORGANISM: Homo sapiens

<400> SEQUENCE: 948

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105


<210> SEQ ID NO 949
<211> LENGTH: 109
<212> TYPE: PRT
```

<213> ORGANISM: Homo sapiens

<400> SEQUENCE: 949

Asp Val Val Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu His Trp Tyr Gln Gln Lys Pro Gly Lys Ala Thr Lys Leu Leu Ile
35 40 45

Ser Asp Ala Ser Ser Ser Gln Ser Gly Val Pro Ser Arg Phe Arg Phe
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Arg Ala
85 90 95

Leu Thr Phe Gly Gly Gly Thr Lys Val Asp Ile Arg Arg
100 105

<210> SEQ ID NO 950
<211> LENGTH: 109
<212> TYPE: PRT
<213> ORGANISM: Homo sapiens

<400> SEQUENCE: 950

Asp Val Val Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu His Trp Tyr Gln Gln Lys Pro Gly Lys Ala Pro Thr Leu Leu Ile
35 40 45

Ser Asp Ala Ser Ser Ser Gln Ser Gly Val Pro Ser Arg Phe Ser Gly
50 55 60

Ser Arg Phe Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Arg Ala
85 90 95

Leu Thr Phe Gly Gly Gly Thr Lys Val Glu Ile Arg Arg
100 105

<210> SEQ ID NO 951
<211> LENGTH: 109
<212> TYPE: PRT
<213> ORGANISM: Homo sapiens

<400> SEQUENCE: 951

Glu Ile Val Leu Thr Gln Ser Pro Ser Ser Leu Ser Ala Ser Val Gly
1 5 10 15

Asp Arg Val Thr Ile Thr Cys Arg Ala Ser Gln Gly Ile Ser Asn Tyr
20 25 30

Leu Ala Trp Tyr Gln Gln Lys Pro Gly Lys Val Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Gln Ser Tyr Ser Thr Leu Met
85 90 95

Cys Ser Phe Gly Gln Gly Thr Lys Leu Glu Ile Lys Arg
100 105

<210> SEQ ID NO 952
<211> LENGTH: 108
<212> TYPE: PRT
<213> ORGANISM: Homo sapiens

<400> SEQUENCE: 952

Asp Ile Val Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Asp Thr Pro Arg
85 90 95

Thr Phe Gly Gln Gly Thr Arg Leu Glu Ile Lys Arg
100 105

<210> SEQ ID NO 953
<211> LENGTH: 108
<212> TYPE: PRT
<213> ORGANISM: Homo sapiens

<400> SEQUENCE: 953

Asp Val Val Met Thr Gln Ser Pro Ser Thr Leu Ser Ala Ser Val Gly
1 5 10 15

Asp Arg Val Thr Ile Thr Cys Arg Ala Ser Gln Thr Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Asp Thr Pro Arg
85 90 95

Thr Phe Gly Gln Gly Thr Arg Leu Glu Ile Lys Arg
100 105

<210> SEQ ID NO 954
<211> LENGTH: 107
<212> TYPE: PRT
<213> ORGANISM: Homo sapiens

<400> SEQUENCE: 954

Asp Ile Gln Met Thr Gln Ser Pro Ser Phe Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

```
Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Thr Tyr Trp Thr
                85                  90                  95

Phe Gly Gln Gly Thr Lys Val Glu Ile Lys Arg
            100                 105


<210> SEQ ID NO 955
<211> LENGTH: 123
<212> TYPE: PRT
<213> ORGANISM: Homo sapiens

<400> SEQUENCE: 955

Gln Val Gln Leu Val Gln Ser Gly Ala Glu Val Glu Lys Pro Gly Ser
1               5                   10                  15

Ser Val Lys Val Ser Cys Lys Ala Ser Gly Gly Ser Phe Ser Ser Tyr
            20                  25                  30

Ala Phe Thr Trp Val Arg Gln Ala Pro Gly Gln Gly Leu Glu Trp Met
        35                  40                  45

Gly Arg Ile Val Pro Phe Leu Gly Val Pro Tyr Tyr Thr Gln Lys Phe
    50                  55                  60

Arg Gly Arg Val Thr Ile Thr Ala Asp Lys Ala Thr Ser Thr Val Tyr
65                  70                  75                  80

Met Glu Leu Ser Ser Leu Thr Phe Asp Asp Thr Ala Val Tyr Tyr Cys
                85                  90                  95

Ala Arg Asp Lys Arg Thr Tyr Glu Tyr Asn Trp Asn Ser Leu Trp Phe
            100                 105                 110

Trp Gly Arg Gly Thr Leu Val Thr Val Ser Ser
        115                 120


<210> SEQ ID NO 956
<211> LENGTH: 133
<212> TYPE: PRT
<213> ORGANISM: Homo sapiens

<400> SEQUENCE: 956

Gln Val Gln Leu Leu Glu Ser Gly Gly Gly Leu Val Gln Pro Gly Arg
1               5                   10                  15

Ser Leu Arg Leu Ser Cys Ala Gly Ser Gly Phe Thr Phe Gly Asp Tyr
            20                  25                  30

Ala Leu Ser Trp Phe Arg Gln Ala Pro Gly Lys Gly Leu Glu Trp Ile
        35                  40                  45

Gly Leu Ile Arg Ser Arg Ala His Gly Gly Thr Ile Glu Tyr Ala Ala
    50                  55                  60

Ser Val Lys Gly Arg Phe Thr Ile Ser Arg Asp Asp Ser Lys Ser Ile
65                  70                  75                  80

Gly Tyr Leu Gln Met Asn Ser Leu Lys Ser Glu Asp Thr Ala Val Tyr
                85                  90                  95

Tyr Cys Thr Arg Asp Ile Leu Tyr Tyr His Asp Ser Ser Asp Tyr Trp
            100                 105                 110

Gly Arg Gly His Phe Tyr Tyr Met Asp Val Trp Gly Thr Gly Thr Pro
        115                 120                 125

Val Thr Val Ser Ser
    130
```

<210> SEQ ID NO 957
<211> LENGTH: 127
<212> TYPE: PRT
<213> ORGANISM: Homo sapiens

<400> SEQUENCE: 957

```
Gln Val Gln Leu Val Glu Ser Gly Gly Ala Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Met Arg Gly Tyr Ser Ser Ser Trp His Tyr Ser Tyr Tyr Tyr
            100                 105                 110

Val Met Asp Val Trp Gly Gln Gly Thr Thr Val Thr Val Ser Ser
        115                 120                 125
```

<210> SEQ ID NO 958
<211> LENGTH: 125
<212> TYPE: PRT
<213> ORGANISM: Homo sapiens

<400> SEQUENCE: 958

```
Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

Ser Phe Trp Ile Ala Trp Val Arg Gln Met Pro Gly Lys Gly Leu Glu
        35                  40                  45

Trp Met Gly Ile Ile Tyr Ala Gly Asp Ser Asp Thr Arg Tyr Ser Pro
    50                  55                  60

Ser Phe Gln Gly His Val Asn Ile Ser Val Asp Arg Ser Thr Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
        115                 120                 125
```

<210> SEQ ID NO 959
<211> LENGTH: 125
<212> TYPE: PRT
<213> ORGANISM: Homo sapiens

<400> SEQUENCE: 959

```
Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

Ser Phe Trp Ile Ala Trp Val Arg Gln Met Pro Gly Lys Gly Leu Glu
```

```
        35                  40                  45

Trp Met Gly Ile Ile Tyr Ala Gly Asp Ser Asp Thr Arg Tyr Ser Pro
    50                  55                  60

Ser Phe Gln Gly His Val Asn Ile Ser Val Asp Arg Ser Thr Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
        115                 120                 125


<210> SEQ ID NO 960
<211> LENGTH: 125
<212> TYPE: PRT
<213> ORGANISM: Homo sapiens

<400> SEQUENCE: 960

Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

Ser Phe Trp Ile Ala Trp Val Arg Gln Met Pro Gly Lys Gly Leu Glu
        35                  40                  45

Trp Met Gly Ile Ile Tyr Ala Gly Asp Ser Asp Thr Arg Tyr Ser Pro
    50                  55                  60

Ser Phe Gln Gly His Val Asn Ile Ser Val Asp Arg Ser Thr Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
        115                 120                 125


<210> SEQ ID NO 961
<211> LENGTH: 125
<212> TYPE: PRT
<213> ORGANISM: Homo sapiens

<400> SEQUENCE: 961

Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

Ser Phe Trp Ile Ala Trp Val Arg Gln Met Pro Gly Lys Gly Leu Glu
        35                  40                  45

Trp Met Gly Ile Ile Tyr Ala Gly Asp Ser Asp Thr Arg Tyr Ser Pro
    50                  55                  60

Ser Phe Gln Gly His Val Asn Ile Ser Val Asp Arg Ser Thr Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
```

115 120 125

<210> SEQ ID NO 962
<211> LENGTH: 124
<212> TYPE: PRT
<213> ORGANISM: Homo sapiens

<400> SEQUENCE: 962

Gln Val Gln Leu Gln Gln Ser Gly Pro Gly Leu Val Lys Pro Ser Gln
1 5 10 15

Thr Leu Ser Leu Thr Cys Ser Val Ser Gly Gly Ser Ile Asn Ser Asp
20 25 30

Gly Ser Tyr Trp Ser Trp Val Arg Gln His Pro Gly Lys Gly Leu Glu
35 40 45

Trp Ile Gly Tyr Ile Tyr Tyr Ser Gly Thr Thr Tyr Phe Asn Pro Ser
50 55 60

Leu Lys Ser Arg Leu Thr Met Ser Val Asp Thr Ser Lys Asn Gln Phe
65 70 75 80

Ser Leu Lys Met Thr Ser Val Thr Ala Ala Asp Thr Ala Val Tyr Tyr
85 90 95

Cys Ala Arg Met Ser Gly Ser Arg Ser Tyr Ser Gln Tyr Tyr Phe Asp
100 105 110

Ser Trp Gly Gln Gly Thr Leu Val Thr Val Ser Ser
115 120

<210> SEQ ID NO 963
<211> LENGTH: 128
<212> TYPE: PRT
<213> ORGANISM: Homo sapiens

<400> SEQUENCE: 963

Gln Val Gln Leu Leu Gln Ser Ala Gly Gly Val Val Gln Pro Gly Arg
1 5 10 15

Ser Leu Arg Leu Ser Cys Ala Ala Ser Gly Phe Ile Phe Arg Thr Tyr
20 25 30

Gly Met His Trp Val Arg Gln Ala Pro Gly Lys Gly Leu Glu Trp Val
35 40 45

Ala Phe Val Ser Ser Asp Gly Asn Asn Lys Phe Tyr Ser Asp Ser Val
50 55 60

Lys Gly Arg Phe Thr Ile Pro Arg Asp Asn Ala Lys Asn Thr Leu Tyr
65 70 75 80

Leu Gln Met Asn Ser Leu Glu Thr Glu Asp Thr Ala Val Tyr Tyr Cys
85 90 95

Ala Lys Asp Arg Tyr Pro Ile Asp Cys Ser Gly Gly Ser Cys Phe Ser
100 105 110

Tyr Gly Met Asp Val Trp Gly Gln Gly Thr Thr Val Thr Val Ser Ser
115 120 125

<210> SEQ ID NO 964
<211> LENGTH: 128
<212> TYPE: PRT
<213> ORGANISM: Homo sapiens

<400> SEQUENCE: 964

Glu Val Gln Leu Val Glu Ser Gly Gly Gly Val Val Gln Pro Gly Arg
1 5 10 15

Ser Leu Arg Leu Ser Cys Ala Thr Ser Gly Phe Ile Leu Arg Thr Tyr
20 25 30

```
Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Pro Arg Asp Asn Ala Lys Asn Thr Leu Tyr
65                  70                  75                  80

Leu Gln Met Asn Ser Leu Glu Thr Glu Asp Thr Ala Val Tyr Tyr Cys
                85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Leu Val Thr Val Ser Ser
        115                 120                 125


<210> SEQ ID NO 965
<211> LENGTH: 128
<212> TYPE: PRT
<213> ORGANISM: Homo sapiens

<400> SEQUENCE: 965

Glu Val Arg Leu Val Gln Ser Gly Gly Gly Met Val Gln Pro Gly Arg
1               5                   10                  15

Ser Leu Arg Leu Ser Cys Ala Ala Ser Gly Phe Val Phe Arg Thr Tyr
            20                  25                  30

Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Pro Arg Asp Asn Ala Lys Asn Thr Leu Tyr
65                  70                  75                  80

Leu Gln Met Asn Ser Leu Glu Thr Glu Asp Thr Ala Val Tyr Tyr Cys
                85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Pro Val Thr Val Ser Ser
        115                 120                 125


<210> SEQ ID NO 966
<211> LENGTH: 128
<212> TYPE: PRT
<213> ORGANISM: Homo sapiens

<400> SEQUENCE: 966

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Thr Tyr
            20                  25                  30

Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Pro Arg Asp Asn Ala Lys Asn Thr Leu Tyr
65                  70                  75                  80

Leu Gln Met Asn Ser Leu Glu Thr Glu Asp Thr Ala Val Tyr Tyr Cys
                85                  90                  95

Ala Lys Asp Arg Tyr Pro Ile Asp Cys Ser Gly Gly Ser Cys Phe Ser
            100                 105                 110
```

```
Tyr Gly Met Asp Val Trp Gly Gln Gly Thr Met Val Thr Val Ser Ser
        115                 120                 125


<210> SEQ ID NO 967
<211> LENGTH: 128
<212> TYPE: PRT
<213> ORGANISM: Homo sapiens

<400> SEQUENCE: 967

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Ile Phe Arg Thr Tyr
            20                  25                  30

Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Pro Arg Asp Asn Ala Lys Asn Thr Leu Tyr
65                  70                  75                  80

Leu Gln Met Asn Ser Leu Glu Thr Glu Asp Thr Ala Val Tyr Tyr Cys
                85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Leu Val Thr Val Ser Ser
        115                 120                 125


<210> SEQ ID NO 968
<211> LENGTH: 121
<212> TYPE: PRT
<213> ORGANISM: Homo sapiens

<400> SEQUENCE: 968

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Ile Val Gly Ala Pro Tyr Gly Met Asp Val Trp Gly
            100                 105                 110

Gln Gly Thr Thr Val Thr Val Ser Ser
        115                 120


<210> SEQ ID NO 969
<211> LENGTH: 120
<212> TYPE: PRT
<213> ORGANISM: Homo sapiens

<400> SEQUENCE: 969

Gln Val Gln Leu Val Gln Ser Gly Ala Glu Val Lys Lys Pro Gly Ala
1               5                   10                  15
```

```
Ser Val Asn Val Ser Cys Lys Ala Ser Gly Tyr Thr Phe Thr Gly Tyr
            20                  25                  30

Tyr Ile Tyr Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Ile Asp Thr Ser Thr Asn Thr Ala Tyr
65                  70                  75                  80

Met Glu Leu Asn Arg Leu Arg Ala Asp Asp Thr Ala Val Tyr Tyr Cys
                85                  90                  95

Ala Arg Glu Trp Thr Gln Leu Trp Ser Pro Tyr Asp Tyr Trp Gly Gln
            100                 105                 110

Gly Thr Thr Val Thr Val Ser Ser
        115                 120


<210> SEQ ID NO 970
<211> LENGTH: 108
<212> TYPE: PRT
<213> ORGANISM: Homo sapiens

<400> SEQUENCE: 970

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Thr Asp
            20                  25                  30

Leu Ala Trp Tyr Gln Gln Lys Pro Gly Lys Ser Pro Arg Leu Leu Ile
        35                  40                  45

Tyr Ala Ala Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Lys Tyr Tyr Thr Ala Pro Leu
                85                  90                  95

Thr Phe Gly Gly Gly Thr Lys Val Glu Ile Lys Arg
            100                 105


<210> SEQ ID NO 971
<211> LENGTH: 109
<212> TYPE: PRT
<213> ORGANISM: Homo sapiens

<400> SEQUENCE: 971

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Lys Lys Pro Gly Lys Ala Pro Arg Leu Leu Met
        35                  40                  45

Leu Ala Ala Ser Thr Leu His Asp Gly Val Pro Ser Arg Phe Ser Gly
    50                  55                  60

Ser Gly Ser Gly Gln Ser Asp Phe Thr Leu Thr Ile Asn Gly Leu Gln
65                  70                  75                  80

Pro Glu Asp Phe Ala Thr Tyr Tyr Cys Gln Glu Ser Tyr Ser Val Tyr
                85                  90                  95

Arg Thr Phe Gly Gln Gly Thr Lys Val Glu Ile Lys Arg
            100                 105
```

<210> SEQ ID NO 972
<211> LENGTH: 108
<212> TYPE: PRT
<213> ORGANISM: Homo sapiens

<400> SEQUENCE: 972

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Thr Thr Phe
            20                  25                  30

Leu Asn Trp Tyr Gln Gln Lys Pro Gly Lys Ala Pro Asn Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys Arg
            100                 105

<210> SEQ ID NO 973
<211> LENGTH: 108
<212> TYPE: PRT
<213> ORGANISM: Homo sapiens

<400> SEQUENCE: 973

Asp Val Val Met Thr Gln Ser Pro Ser Ser Leu Ser Ala Ser Val Gly
1               5                   10                  15

Asp Arg Ile Thr Ile Thr Cys Gln Ala Gly Gln Asp Ile Ser Asn Phe
            20                  25                  30

Leu Asn Trp Tyr Gln Gln Lys Pro Gly Lys Ala Pro Lys Leu Leu Ile
        35                  40                  45

Arg Asp Ala Ser Asn Leu Glu Thr Gly Val Pro Ser Arg Phe Ser Gly
    50                  55                  60

Gly Gly Ser Gly Thr His Phe Thr Phe Thr Ile Ser Ser Leu His Pro
65                  70                  75                  80

Glu Asp Ile Ala Thr Tyr Phe Cys Gln Gln Tyr Asp Asn Leu Pro Tyr
                85                  90                  95

Thr Phe Gly Gln Gly Thr Lys Leu Glu Ile Lys Arg
            100                 105

<210> SEQ ID NO 974
<211> LENGTH: 109
<212> TYPE: PRT
<213> ORGANISM: Homo sapiens

<400> SEQUENCE: 974

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Glu Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro 65 70 75 80

Glu Asp Phe Ala Thr Tyr Tyr Cys Gln Gln Ser Tyr Ser Thr Pro Pro
85 90 95

Tyr Thr Phe Gly Gln Gly Thr Lys Leu Glu Ile Lys Arg
100 105

<210> SEQ ID NO 975
<211> LENGTH: 108
<212> TYPE: PRT
<213> ORGANISM: Homo sapiens

<400> SEQUENCE: 975

Asp Ile Val Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Ala Phe Ala Thr Tyr Tyr Cys Gln Gln Ser Tyr Thr Ala Pro Cys
85 90 95

Thr Phe Gly Gln Gly Thr Lys Leu Glu Ile Lys Arg
100 105

<210> SEQ ID NO 976
<211> LENGTH: 110
<212> TYPE: PRT
<213> ORGANISM: Homo sapiens

<400> SEQUENCE: 976

Asp Val Val Met Thr Gln Ser Pro Cys Leu Pro Cys Leu His Leu Ile
1 5 10 15

Gly Asp Arg Val Thr Ile Thr Cys Arg Ala Ser Gln Ser Ile Arg Asp
20 25 30

Tyr Leu Ser Trp Tyr Gln Gln Glu Pro Gly Lys Ala Pro Lys Leu Leu
35 40 45

Ile Tyr Ser Ala Ser Ser Leu Gln Ser Gly Val Pro Ser Arg Phe Ser
50 55 60

Gly Ser Gly Ser Gly Thr Asp Phe Thr Leu Thr Ile Thr Asn Leu Gln
65 70 75 80

Pro Glu Asp Phe Ala Thr Tyr Tyr Cys Leu Glu Lys Tyr Ser Phe Pro
85 90 95

Arg Cys Thr Phe Gly Gln Gly Thr Lys Leu Asp Ile Lys Arg
100 105 110

<210> SEQ ID NO 977
<211> LENGTH: 108
<212> TYPE: PRT
<213> ORGANISM: Homo sapiens

<400> SEQUENCE: 977

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

```
Leu Asn Trp Tyr Gln Gln Lys Pro Gly Thr Ala Pro Lys Leu Leu Ile
        35                  40                  45

Ser Asp Ala Ser Thr Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Phe Asn Ser Tyr Val Trp
                85                  90                  95

Thr Phe Gly Gln Gly Thr Lys Leu Glu Ile Lys Arg
            100                 105


<210> SEQ ID NO 978
<211> LENGTH: 108
<212> TYPE: PRT
<213> ORGANISM: Homo sapiens

<400> SEQUENCE: 978

Asp Ile Val Met Thr Gln Ser Pro Ser Thr Leu Ser Ala Ser Val Gly
1               5                   10                  15

Asp Arg Val Thr Val Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Trp Leu
                85                  90                  95

Thr Phe Gly Gly Gly Thr Lys Val Glu Ile Lys Arg
            100                 105


<210> SEQ ID NO 979
<211> LENGTH: 108
<212> TYPE: PRT
<213> ORGANISM: Homo sapiens

<400> SEQUENCE: 979

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Arg Trp
            20                  25                  30

Leu Ala Trp Tyr Gln Gln Arg Pro Gly Glu Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Phe Pro Leu
                85                  90                  95

Thr Phe Gly Gly Gly Thr Lys Val Glu Ile Lys Arg
            100                 105


<210> SEQ ID NO 980
<211> LENGTH: 108
<212> TYPE: PRT
<213> ORGANISM: Homo sapiens
```

<400> SEQUENCE: 980

Glu Ile Val Leu Thr Gln Ser Pro Ala Thr Leu Ser Val Ser Pro Gly
1 5 10 15

Glu Arg Ala Thr Leu Ser Cys Arg Ala Ser Gln Ser Val Ser Lys Phe
20 25 30

Leu Ala Trp Tyr Gln Gln Lys Arg Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Ala Leu Thr Ile Ser Ser Leu Gln Ser
65 70 75 80

Glu Asp Phe Ala Asp Tyr Tyr Cys Gln Gln Tyr Asp Asn Trp Pro Ile
85 90 95

Thr Phe Gly Gln Gly Thr Arg Leu Glu Ile Lys Arg
100 105

<210> SEQ ID NO 981
<211> LENGTH: 107
<212> TYPE: PRT
<213> ORGANISM: Homo sapiens

<400> SEQUENCE: 981

Glu Thr Leu Thr Gln Ser Pro Ala Thr Leu Ser Val Ser Pro Gly Glu
1 5 10 15

Arg Ala Thr Leu Ser Cys Arg Ala Ser Gln Ser Val Gly Ser Thr Leu
20 25 30

Ala Trp Tyr Gln Gln Lys Pro Gly Gln Ala Pro Arg Leu Leu Val Tyr
35 40 45

Gly Ala Ser Thr Arg Ala Thr Gly Ile Pro Ala Arg Phe Ser Gly Ser
50 55 60

Gly Ser Gly Thr Glu Phe Thr Leu Thr Ile Ser Ser Leu Gln Ser Glu
65 70 75 80

Asp Phe Ala Val Tyr Tyr Cys Gln Gln Tyr Asn Ser Trp Pro Ile Thr
85 90 95

Phe Gly Gln Gly Thr Arg Leu Glu Ile Lys Arg
100 105

<210> SEQ ID NO 982
<211> LENGTH: 108
<212> TYPE: PRT
<213> ORGANISM: Homo sapiens

<400> SEQUENCE: 982

Glu Ile Val Leu Thr Gln Ser Pro Ser Ser Phe Ser Ala Ser Thr Gly
1 5 10 15

Asp Arg Val Thr Ile Thr Cys Arg Ala Ser Gln Gly Ile Asn Asn Tyr
20 25 30

Leu Ala Trp Tyr Gln Gln Lys Pro Gly Lys Ala Pro Lys Leu Leu Ile
35 40 45

Tyr Ala Ala Ser Thr Leu Gln Ser Gly Val Pro Ser Arg Phe Ser Gly
50 55 60

Gly Gly Ser Gly Thr Asp Phe Thr Leu Thr Ile Ser Cys Leu Gln Ser
65 70 75 80

Glu Asp Phe Ala Thr Tyr Tyr Cys Gln Gln Tyr Tyr Ser Tyr Pro Leu
85 90 95

```
Thr Phe Gly Gly Gly Thr Lys Val Glu Ile Lys Arg
            100                 105


<210> SEQ ID NO 983
<211> LENGTH: 108
<212> TYPE: PRT
<213> ORGANISM: Homo sapiens

<400> SEQUENCE: 983

Glu Ile Val Leu Thr Gln Ser Pro Ser Ser Leu Ser Ala Ala Val Gly
1               5                   10                  15

Asp Arg Val Thr Ile Thr Cys Arg Ala Ser Gln Asn Ile Tyr Ser Tyr
            20                  25                  30

Leu Asn Trp Tyr Gln Gln Lys Leu Gly Lys Ala Pro Asn Leu Leu Ile
        35                  40                  45

Tyr Ala Val Phe Ser Leu Gln Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Ser Pro Leu
                85                  90                  95

Thr Phe Gly Gly Gly Thr Lys Val Glu Ile Lys Arg
            100                 105


<210> SEQ ID NO 984
<211> LENGTH: 108
<212> TYPE: PRT
<213> ORGANISM: Homo sapiens

<400> SEQUENCE: 984

Asp Ile Val Leu Thr Gln Ser Pro Ser Thr Leu Ser Ala Ser Val Gly
1               5                   10                  15

Asp Arg Val Thr Ile Ser Cys Arg Ala Ser Arg Ser Ile Gly Trp Tyr
            20                  25                  30

Leu Asn Trp Tyr Gln Gln Arg Pro Gly Lys Ala Pro Lys Leu Leu Ile
        35                  40                  45

Tyr Ala Ala Ser Ser Leu His Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ala Phe Gly Phe Pro Arg
                85                  90                  95

Thr Phe Gly Gln Gly Thr Lys Val Glu Ile Lys Arg
            100                 105


<210> SEQ ID NO 985
<211> LENGTH: 30
<212> TYPE: PRT
<213> ORGANISM: Homo sapiens

<400> SEQUENCE: 985

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30


<210> SEQ ID NO 986
<211> LENGTH: 5
<212> TYPE: PRT
```

<213> ORGANISM: Homo sapiens

<400> SEQUENCE: 986

Asn Tyr Ala Met Thr
1 5

<210> SEQ ID NO 987
<211> LENGTH: 14
<212> TYPE: PRT
<213> ORGANISM: Homo sapiens

<400> SEQUENCE: 987

Trp Val Arg Gln Ala Pro Gly Lys Gly Leu Glu Trp Val Ser
1 5 10

<210> SEQ ID NO 988
<211> LENGTH: 17
<212> TYPE: PRT
<213> ORGANISM: Homo sapiens

<400> SEQUENCE: 988

Ser Ile Ser Val Gly Gly Ser Asp Thr Tyr Tyr Ala Asp Ser Val Lys
1 5 10 15

Gly

<210> SEQ ID NO 989
<211> LENGTH: 32
<212> TYPE: PRT
<213> ORGANISM: Homo sapiens

<400> SEQUENCE: 989

Arg Phe Thr Val Ser Arg Asp Asn Ser Lys Asn Thr Leu Leu Leu Gln
1 5 10 15

Met Asn Ser Leu Arg Ala Glu Asp Thr Ala Val Tyr Tyr Cys Ala Lys
20 25 30

<210> SEQ ID NO 990
<211> LENGTH: 17
<212> TYPE: PRT
<213> ORGANISM: Homo sapiens

<400> SEQUENCE: 990

Val Arg Thr Lys Tyr Cys Ser Ser Leu Ser Cys Phe Ala Gly Phe Asp
1 5 10 15

Ser

<210> SEQ ID NO 991
<211> LENGTH: 11
<212> TYPE: PRT
<213> ORGANISM: Homo sapiens

<400> SEQUENCE: 991

Trp Gly Gln Gly Thr Arg Val Thr Val Ser Ser
1 5 10

<210> SEQ ID NO 992
<211> LENGTH: 30
<212> TYPE: PRT
<213> ORGANISM: Homo sapiens

<400> SEQUENCE: 992

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 993
<211> LENGTH: 5
<212> TYPE: PRT
<213> ORGANISM: Homo sapiens

<400> SEQUENCE: 993

Asn Tyr Ala Met Thr
1 5

<210> SEQ ID NO 994
<211> LENGTH: 14
<212> TYPE: PRT
<213> ORGANISM: Homo sapiens

<400> SEQUENCE: 994

Trp Val Arg Gln Arg Pro Gly Lys Gly Leu Glu Trp Val Ser
1 5 10

<210> SEQ ID NO 995
<211> LENGTH: 17
<212> TYPE: PRT
<213> ORGANISM: Homo sapiens

<400> SEQUENCE: 995

Ser Ile Ser Val Gly Gly Ser Asp Thr Tyr Tyr Ala Asp Ser Val Lys
1 5 10 15

Gly

<210> SEQ ID NO 996
<211> LENGTH: 32
<212> TYPE: PRT
<213> ORGANISM: Homo sapiens

<400> SEQUENCE: 996

Arg Phe Thr Val Ser Arg Asp Asn Ser Lys Asn Thr Leu Leu Leu Gln
1 5 10 15

Met Asn Ser Leu Arg Ala Glu Asp Thr Ala Val Tyr Tyr Cys Ala Lys
20 25 30

<210> SEQ ID NO 997
<211> LENGTH: 17
<212> TYPE: PRT
<213> ORGANISM: Homo sapiens

<400> SEQUENCE: 997

Val Arg Thr Lys Tyr Cys Ser Ser Leu Ser Cys Phe Ala Gly Phe Asp
1 5 10 15

Ser

<210> SEQ ID NO 998
<211> LENGTH: 11
<212> TYPE: PRT
<213> ORGANISM: Homo sapiens

<400> SEQUENCE: 998

Trp Gly Gln Gly Thr Leu Val Thr Val Ser Ser
1 5 10

<210> SEQ ID NO 999

<211> LENGTH: 30
<212> TYPE: PRT
<213> ORGANISM: Homo sapiens

<400> SEQUENCE: 999

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 1000
<211> LENGTH: 5
<212> TYPE: PRT
<213> ORGANISM: Homo sapiens

<400> SEQUENCE: 1000

Asn Tyr Ala Met Thr
1 5

<210> SEQ ID NO 1001
<211> LENGTH: 14
<212> TYPE: PRT
<213> ORGANISM: Homo sapiens

<400> SEQUENCE: 1001

Trp Val Arg Gln Ala Pro Gly Lys Gly Leu Glu Trp Val Ser
1 5 10

<210> SEQ ID NO 1002
<211> LENGTH: 17
<212> TYPE: PRT
<213> ORGANISM: Homo sapiens

<400> SEQUENCE: 1002

Ser Ile Ser Val Gly Gly Ser Asp Thr Tyr Tyr Ala Asp Ser Val Lys
1 5 10 15

Gly

<210> SEQ ID NO 1003
<211> LENGTH: 32
<212> TYPE: PRT
<213> ORGANISM: Homo sapiens

<400> SEQUENCE: 1003

Arg Phe Thr Val Ser Arg Asp Asn Ser Lys Asn Thr Leu Leu Leu Gln
1 5 10 15

Met Asn Ser Leu Arg Ala Glu Asp Thr Ala Val Tyr Tyr Cys Ala Lys
20 25 30

<210> SEQ ID NO 1004
<211> LENGTH: 17
<212> TYPE: PRT
<213> ORGANISM: Homo sapiens

<400> SEQUENCE: 1004

Val Arg Thr Lys Tyr Cys Ser Ser Leu Ser Cys Phe Ala Gly Phe Asp
1 5 10 15

Ser

<210> SEQ ID NO 1005
<211> LENGTH: 11
<212> TYPE: PRT
<213> ORGANISM: Homo sapiens

<400> SEQUENCE: 1005

Trp Gly Gln Gly Thr Leu Val Thr Val Ser Ser
1 5 10

<210> SEQ ID NO 1006
<211> LENGTH: 30
<212> TYPE: PRT
<213> ORGANISM: Homo sapiens

<400> SEQUENCE: 1006

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 1007
<211> LENGTH: 5
<212> TYPE: PRT
<213> ORGANISM: Homo sapiens

<400> SEQUENCE: 1007

Asn Tyr Arg Met Thr
1 5

<210> SEQ ID NO 1008
<211> LENGTH: 14
<212> TYPE: PRT
<213> ORGANISM: Homo sapiens

<400> SEQUENCE: 1008

Trp Val Arg Gln Arg Pro Gly Lys Gly Leu Glu Trp Val Ser
1 5 10

<210> SEQ ID NO 1009
<211> LENGTH: 17
<212> TYPE: PRT
<213> ORGANISM: Homo sapiens

<400> SEQUENCE: 1009

Ser Ile Ser Val Gly Gly Ser Asp Thr Tyr Tyr Ala Asp Ser Val Lys
1 5 10 15

Gly

<210> SEQ ID NO 1010
<211> LENGTH: 32
<212> TYPE: PRT
<213> ORGANISM: Homo sapiens

<400> SEQUENCE: 1010

Arg Phe Thr Val Ser Arg Asp Asn Ser Lys Asn Thr Leu Leu Leu Gln
1 5 10 15

Met Asn Ser Leu Arg Ala Glu Asp Thr Arg Val Tyr Tyr Cys Ala Lys
20 25 30

<210> SEQ ID NO 1011
<211> LENGTH: 17
<212> TYPE: PRT
<213> ORGANISM: Homo sapiens

<400> SEQUENCE: 1011

Val Arg Thr Lys Tyr Cys Ser Ser Leu Ser Cys Phe Ala Gly Phe Asp
1 5 10 15

Ser

<210> SEQ ID NO 1012
<211> LENGTH: 11
<212> TYPE: PRT
<213> ORGANISM: Homo sapiens

<400> SEQUENCE: 1012

Trp Gly Gln Gly Thr Leu Val Thr Val Ser Ser
1 5 10

<210> SEQ ID NO 1013
<211> LENGTH: 30
<212> TYPE: PRT
<213> ORGANISM: Homo sapiens

<400> SEQUENCE: 1013

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 1014
<211> LENGTH: 5
<212> TYPE: PRT
<213> ORGANISM: Homo sapiens

<400> SEQUENCE: 1014

Asn Tyr Ala Met Thr
1 5

<210> SEQ ID NO 1015
<211> LENGTH: 14
<212> TYPE: PRT
<213> ORGANISM: Homo sapiens

<400> SEQUENCE: 1015

Trp Val Arg Gln Ala Pro Gly Lys Gly Leu Glu Trp Val Ser
1 5 10

<210> SEQ ID NO 1016
<211> LENGTH: 17
<212> TYPE: PRT
<213> ORGANISM: Homo sapiens

<400> SEQUENCE: 1016

Ser Ile Ser Val Gly Gly Ser Asp Thr Tyr Tyr Ala Asp Ser Val Lys
1 5 10 15

Gly

<210> SEQ ID NO 1017
<211> LENGTH: 32
<212> TYPE: PRT
<213> ORGANISM: Homo sapiens

<400> SEQUENCE: 1017

Arg Phe Thr Val Ser Arg Asp Asn Ser Lys Asn Thr Leu Leu Leu Gln
1 5 10 15

Met Asn Ser Leu Arg Arg Glu Asp Thr Ala Val Tyr Tyr Cys Ala Lys
20 25 30

<210> SEQ ID NO 1018

<211> LENGTH: 17
<212> TYPE: PRT
<213> ORGANISM: Homo sapiens

<400> SEQUENCE: 1018

Val Arg Thr Lys Tyr Cys Ser Ser Leu Ser Cys Phe Ala Gly Phe Asp
1               5                   10                  15

Ser

<210> SEQ ID NO 1019
<211> LENGTH: 11
<212> TYPE: PRT
<213> ORGANISM: Homo sapiens

<400> SEQUENCE: 1019

Trp Gly Gln Gly Thr Leu Val Thr Val Ser Ser
1               5                   10

<210> SEQ ID NO 1020
<211> LENGTH: 30
<212> TYPE: PRT
<213> ORGANISM: Homo sapiens

<400> SEQUENCE: 1020

Gln Val Gln Leu Val Gln Ser Gly Gly Gly Leu Ala Gln Pro Gly Gly
1               5                   10                  15

Ser Leu Arg Leu Ser Cys Arg Ala Ser Gly Phe Thr Phe Gly
            20                  25                  30

<210> SEQ ID NO 1021
<211> LENGTH: 5
<212> TYPE: PRT
<213> ORGANISM: Homo sapiens

<400> SEQUENCE: 1021

Ser Tyr Ser Met Asn
1               5

<210> SEQ ID NO 1022
<211> LENGTH: 14
<212> TYPE: PRT
<213> ORGANISM: Homo sapiens

<400> SEQUENCE: 1022

Trp Val Arg Gln Ala Pro Gly Lys Gly Leu Glu Trp Val Ser
1               5                   10

<210> SEQ ID NO 1023
<211> LENGTH: 17
<212> TYPE: PRT
<213> ORGANISM: Homo sapiens

<400> SEQUENCE: 1023

Ser Ile Thr Gly Asn Ser Gly Leu Ile Tyr Tyr Ala Asp Ser Val Lys
1               5                   10                  15

Gly

<210> SEQ ID NO 1024
<211> LENGTH: 32
<212> TYPE: PRT
<213> ORGANISM: Homo sapiens

<400> SEQUENCE: 1024

Arg Phe Thr Val Ser Arg Asp Asn Arg Lys Asn Ser Leu Phe Leu His
1 5 10 15

Met His Ser Leu Arg Arg Asp Asp Thr Arg Val Tyr Tyr Cys Ala Arg
20 25 30

<210> SEQ ID NO 1025
<211> LENGTH: 17
<212> TYPE: PRT
<213> ORGANISM: Homo sapiens

<400> SEQUENCE: 1025

Asp Pro Gly Trp Ile Tyr Ser Asp Thr Ser Ala Ala Gly Trp Phe Asp
1 5 10 15

Pro

<210> SEQ ID NO 1026
<211> LENGTH: 11
<212> TYPE: PRT
<213> ORGANISM: Homo sapiens

<400> SEQUENCE: 1026

Trp Gly His Gly Thr Leu Val Thr Val Ser Ser
1 5 10

<210> SEQ ID NO 1027
<211> LENGTH: 30
<212> TYPE: PRT
<213> ORGANISM: Homo sapiens

<400> SEQUENCE: 1027

Gln Val Gln Leu Val Gln Ser Gly Gly Gly Leu Arg Gln Pro Gly Gly
1 5 10 15

Ser Leu Arg Leu Ser Cys Arg Ala Ser Gly Phe Thr Phe Gly
20 25 30

<210> SEQ ID NO 1028
<211> LENGTH: 5
<212> TYPE: PRT
<213> ORGANISM: Homo sapiens

<400> SEQUENCE: 1028

Ser Tyr Ser Met Asn
1 5

<210> SEQ ID NO 1029
<211> LENGTH: 14
<212> TYPE: PRT
<213> ORGANISM: Homo sapiens

<400> SEQUENCE: 1029

Trp Val Arg Gln Arg Pro Gly Lys Gly Leu Glu Trp Val Ser
1 5 10

<210> SEQ ID NO 1030
<211> LENGTH: 17
<212> TYPE: PRT
<213> ORGANISM: Homo sapiens

<400> SEQUENCE: 1030

Ser Ile Thr Gly Asn Ser Gly Leu Ile Tyr Tyr Ala Asp Ser Val Lys
1 5 10 15

Gly

<210> SEQ ID NO 1031
<211> LENGTH: 32
<212> TYPE: PRT
<213> ORGANISM: Homo sapiens

<400> SEQUENCE: 1031

```
Arg Phe Thr Val Ser Arg Asp Asn Arg Lys Asn Ser Leu Phe Leu His
1               5                   10                  15

Met His Ser Leu Arg Ala Asp Asp Thr Arg Val Tyr Tyr Cys Ala Arg
            20                  25                  30
```

<210> SEQ ID NO 1032
<211> LENGTH: 17
<212> TYPE: PRT
<213> ORGANISM: Homo sapiens

<400> SEQUENCE: 1032

```
Asp Pro Gly Trp Ile Tyr Ser Asp Thr Ser Ala Ala Gly Trp Phe Asp
1               5                   10                  15

Pro
```

<210> SEQ ID NO 1033
<211> LENGTH: 11
<212> TYPE: PRT
<213> ORGANISM: Homo sapiens

<400> SEQUENCE: 1033

```
Trp Gly His Gly Thr Leu Val Thr Val Ser Ser
1               5                   10
```

<210> SEQ ID NO 1034
<211> LENGTH: 30
<212> TYPE: PRT
<213> ORGANISM: Homo sapiens

<400> SEQUENCE: 1034

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ala
            20                  25                  30
```

<210> SEQ ID NO 1035
<211> LENGTH: 5
<212> TYPE: PRT
<213> ORGANISM: Homo sapiens

<400> SEQUENCE: 1035

```
Asp Tyr Tyr Ile His
1               5
```

<210> SEQ ID NO 1036
<211> LENGTH: 14
<212> TYPE: PRT
<213> ORGANISM: Homo sapiens

<400> SEQUENCE: 1036

```
Trp Val Arg Gln Ala Pro Gly Gln Gly Leu Glu Trp Met Gly
1               5                   10
```

<210> SEQ ID NO 1037
<211> LENGTH: 17
<212> TYPE: PRT
<213> ORGANISM: Homo sapiens

<400> SEQUENCE: 1037

Arg Ile Asn Ser Asn Ser Gly Gly Pro Asn Tyr Ala Gln Asn Tyr Gln
1 5 10 15

Gly

<210> SEQ ID NO 1038
<211> LENGTH: 32
<212> TYPE: PRT
<213> ORGANISM: Homo sapiens

<400> SEQUENCE: 1038

Arg Val Thr Met Thr Arg Asp Thr Ser Ile Ser Thr Ala Tyr Met Glu
1 5 10 15

Val Ile Ser Leu Arg Ser Asp Asp Thr Ala Val Tyr Tyr Cys Ala Arg
20 25 30

<210> SEQ ID NO 1039
<211> LENGTH: 17
<212> TYPE: PRT
<213> ORGANISM: Homo sapiens

<400> SEQUENCE: 1039

Glu Ala Ser Phe Gly Trp Ser Tyr Leu Gly His Asp Asp Ala Phe Asp
1 5 10 15

Ile

<210> SEQ ID NO 1040
<211> LENGTH: 11
<212> TYPE: PRT
<213> ORGANISM: Homo sapiens

<400> SEQUENCE: 1040

Trp Gly Gln Gly Thr Met Val Thr Val Ser Ser
1 5 10

<210> SEQ ID NO 1041
<211> LENGTH: 23
<212> TYPE: PRT
<213> ORGANISM: Homo sapiens

<400> SEQUENCE: 1041

Asp Ile Val Met Thr Gln Ser Pro Ser Ser Leu Ser Ala Ser Val Gly
1 5 10 15

Asp Arg Val Thr Ile Thr Cys
20

<210> SEQ ID NO 1042
<211> LENGTH: 11
<212> TYPE: PRT
<213> ORGANISM: Homo sapiens

<400> SEQUENCE: 1042

Arg Ala Ser Gln Ser Ile Ser Ser Tyr Leu Asn
1 5 10

<210> SEQ ID NO 1043
<211> LENGTH: 15
<212> TYPE: PRT
<213> ORGANISM: Homo sapiens

<400> SEQUENCE: 1043

Trp Tyr Gln Gln Lys Pro Gly Lys Ala Pro Lys Leu Leu Ile Tyr
1 5 10 15

<210> SEQ ID NO 1044
<211> LENGTH: 7
<212> TYPE: PRT
<213> ORGANISM: Homo sapiens

<400> SEQUENCE: 1044

Ala Ala Ser Ser Leu Gln Ser
1 5

<210> SEQ ID NO 1045
<211> LENGTH: 32
<212> TYPE: PRT
<213> ORGANISM: Homo sapiens

<400> SEQUENCE: 1045

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Arg Thr Tyr Tyr Cys
20 25 30

<210> SEQ ID NO 1046
<211> LENGTH: 10
<212> TYPE: PRT
<213> ORGANISM: Homo sapiens

<400> SEQUENCE: 1046

Gln Gln Ser Tyr Ser Thr Pro Arg Thr Thr
1 5 10

<210> SEQ ID NO 1047
<211> LENGTH: 11
<212> TYPE: PRT
<213> ORGANISM: Homo sapiens

<400> SEQUENCE: 1047

Phe Gly Gly Gly Thr Lys Val Asp Ile Lys Arg
1 5 10

<210> SEQ ID NO 1048
<211> LENGTH: 23
<212> TYPE: PRT
<213> ORGANISM: Homo sapiens

<400> SEQUENCE: 1048

Glu Ile Val Leu Thr Gln Ser Pro Ser Ser Leu Ser Arg Ser Val Gly
1 5 10 15

Asp Arg Val Thr Ile Thr Cys
20

<210> SEQ ID NO 1049
<211> LENGTH: 11
<212> TYPE: PRT
<213> ORGANISM: Homo sapiens

<400> SEQUENCE: 1049

Arg Ala Ser Gln Ser Ile Ser Ser Tyr Leu Asn
1 5 10

<210> SEQ ID NO 1050
<211> LENGTH: 15
<212> TYPE: PRT

<213> ORGANISM: Homo sapiens

<400> SEQUENCE: 1050

Trp Tyr Gln Gln Lys Pro Gly Lys Ala Pro Lys Leu Leu Ile Tyr
1 5 10 15

<210> SEQ ID NO 1051
<211> LENGTH: 7
<212> TYPE: PRT
<213> ORGANISM: Homo sapiens

<400> SEQUENCE: 1051

Asp Ala Ser Ser Leu Gln Ser
1 5

<210> SEQ ID NO 1052
<211> LENGTH: 32
<212> TYPE: PRT
<213> ORGANISM: Homo sapiens

<400> SEQUENCE: 1052

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 1053
<211> LENGTH: 8
<212> TYPE: PRT
<213> ORGANISM: Homo sapiens

<400> SEQUENCE: 1053

Gln Gln Tyr Ser Thr Pro Pro Thr
1 5

<210> SEQ ID NO 1054
<211> LENGTH: 11
<212> TYPE: PRT
<213> ORGANISM: Homo sapiens

<400> SEQUENCE: 1054

Phe Gly Gln Gly Thr Lys Val Glu Ile Lys Arg
1 5 10

<210> SEQ ID NO 1055
<211> LENGTH: 22
<212> TYPE: PRT
<213> ORGANISM: Homo sapiens

<400> SEQUENCE: 1055

Asp Trp Met Thr Gln Ser Pro Ser Ser Leu Ser Ala Ser Val Gly Asp
1 5 10 15

Arg Val Thr Ile Thr Cys
20

<210> SEQ ID NO 1056
<211> LENGTH: 11
<212> TYPE: PRT
<213> ORGANISM: Homo sapiens

<400> SEQUENCE: 1056

Arg Ala Ser Gln Ser Ile Ser Ser Tyr Leu His
1 5 10

<210> SEQ ID NO 1057
<211> LENGTH: 15
<212> TYPE: PRT
<213> ORGANISM: Homo sapiens

<400> SEQUENCE: 1057

Trp Tyr Gln Gln Lys Pro Gly Lys Arg Thr Lys Leu Leu Ile Ser
1 5 10 15

<210> SEQ ID NO 1058
<211> LENGTH: 7
<212> TYPE: PRT
<213> ORGANISM: Homo sapiens

<400> SEQUENCE: 1058

Asp Ala Ser Ser Ser Gln Ser
1 5

<210> SEQ ID NO 1059
<211> LENGTH: 32
<212> TYPE: PRT
<213> ORGANISM: Homo sapiens

<400> SEQUENCE: 1059

Gly Val Pro Ser Arg Phe Arg Phe Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 1060
<211> LENGTH: 10
<212> TYPE: PRT
<213> ORGANISM: Homo sapiens

<400> SEQUENCE: 1060

Gln Gln Ser Tyr Ser Thr Arg Ala Leu Thr
1 5 10

<210> SEQ ID NO 1061
<211> LENGTH: 11
<212> TYPE: PRT
<213> ORGANISM: Homo sapiens

<400> SEQUENCE: 1061

Phe Gly Gly Gly Thr Lys Val Asp Ile Arg Arg
1 5 10

<210> SEQ ID NO 1062
<211> LENGTH: 22
<212> TYPE: PRT
<213> ORGANISM: Homo sapiens

<400> SEQUENCE: 1062

Asp Trp Met Thr Gln Ser Pro Ser Ser Leu Ser Ala Ser Val Gly Asp
1 5 10 15

Arg Val Thr Ile Thr Cys
20

<210> SEQ ID NO 1063
<211> LENGTH: 11
<212> TYPE: PRT
<213> ORGANISM: Homo sapiens

<400> SEQUENCE: 1063

```
Arg Ala Ser Gln Ser Ile Ser Ser Tyr Leu His
1               5                   10


<210> SEQ ID NO 1064
<211> LENGTH: 14
<212> TYPE: PRT
<213> ORGANISM: Homo sapiens

<400> SEQUENCE: 1064

Trp Tyr Gln Gln Pro Gly Lys Ala Pro Thr Leu Leu Ile Ser
1               5                   10


<210> SEQ ID NO 1065
<211> LENGTH: 7
<212> TYPE: PRT
<213> ORGANISM: Homo sapiens

<400> SEQUENCE: 1065

Asp Ala Ser Ser Ser Gln Ser
1               5


<210> SEQ ID NO 1066
<211> LENGTH: 32
<212> TYPE: PRT
<213> ORGANISM: Homo sapiens

<400> SEQUENCE: 1066

Gly Val Pro Ser Arg Phe Ser Gly Ser Arg Phe Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 1067
<211> LENGTH: 10
<212> TYPE: PRT
<213> ORGANISM: Homo sapiens

<400> SEQUENCE: 1067

Gln Gln Ser Tyr Ser Thr Arg Arg Leu Thr
1               5                   10


<210> SEQ ID NO 1068
<211> LENGTH: 11
<212> TYPE: PRT
<213> ORGANISM: Homo sapiens

<400> SEQUENCE: 1068

Phe Gly Gly Gly Thr Lys Val Glu Ile Arg Arg
1               5                   10


<210> SEQ ID NO 1069
<211> LENGTH: 23
<212> TYPE: PRT
<213> ORGANISM: Homo sapiens

<400> SEQUENCE: 1069

Glu Ile Val Leu Thr Gln Ser Pro Ser Ser Leu Ser Ala Ser Val Gly
1               5                   10                  15

Asp Arg Val Thr Ile Thr Cys
            20


<210> SEQ ID NO 1070
<211> LENGTH: 11
```

<212> TYPE: PRT
<213> ORGANISM: Homo sapiens

<400> SEQUENCE: 1070

Arg Ala Ser Gln Gly Ile Ser Asn Tyr Leu Ala
1 5 10

<210> SEQ ID NO 1071
<211> LENGTH: 15
<212> TYPE: PRT
<213> ORGANISM: Homo sapiens

<400> SEQUENCE: 1071

Trp Tyr Gln Gln Lys Pro Gly Lys Val Pro Lys Leu Leu Ile Tyr
1 5 10 15

<210> SEQ ID NO 1072
<211> LENGTH: 7
<212> TYPE: PRT
<213> ORGANISM: Homo sapiens

<400> SEQUENCE: 1072

Ala Ala Ser Thr Leu Gln Ser
1 5

<210> SEQ ID NO 1073
<211> LENGTH: 31
<212> TYPE: PRT
<213> ORGANISM: Homo sapiens

<400> SEQUENCE: 1073

Gly Val Pro Ser Arg Phe Ser Gly Ser Gly Ser Gly Thr Asp Phe Thr
1 5 10 15

Leu Thr Ser Ser Leu Gln Pro Glu Asp Val Ala Thr Tyr Tyr Cys
20 25 30

<210> SEQ ID NO 1074
<211> LENGTH: 10
<212> TYPE: PRT
<213> ORGANISM: Homo sapiens

<400> SEQUENCE: 1074

Gln Gln Ser Tyr Ser Thr Leu Met Cys Ser
1 5 10

<210> SEQ ID NO 1075
<211> LENGTH: 11
<212> TYPE: PRT
<213> ORGANISM: Homo sapiens

<400> SEQUENCE: 1075

Phe Gly Gln Gly Thr Lys Leu Glu Ile Lys Arg
1 5 10

<210> SEQ ID NO 1076
<211> LENGTH: 23
<212> TYPE: PRT
<213> ORGANISM: Homo sapiens

<400> SEQUENCE: 1076

Asp Ile Val Met Thr Gln Ser Pro Ser Ser Leu Ser Ala Ser Val Gly
1 5 10 15

Asp Arg Val Thr Ile Thr Cys
20

<210> SEQ ID NO 1077
<211> LENGTH: 11
<212> TYPE: PRT
<213> ORGANISM: Homo sapiens

<400> SEQUENCE: 1077

Arg Ala Ser Gln Ser Ile Ser Ser Tyr Leu Asn
1 5 10

<210> SEQ ID NO 1078
<211> LENGTH: 15
<212> TYPE: PRT
<213> ORGANISM: Homo sapiens

<400> SEQUENCE: 1078

Trp Tyr Gln Gln Lys Pro Gly Lys Arg Pro Lys Leu Leu Ile Tyr
1 5 10 15

<210> SEQ ID NO 1079
<211> LENGTH: 7
<212> TYPE: PRT
<213> ORGANISM: Homo sapiens

<400> SEQUENCE: 1079

Ala Ala Ser Ser Leu Gln Ser
1 5

<210> SEQ ID NO 1080
<211> LENGTH: 32
<212> TYPE: PRT
<213> ORGANISM: Homo sapiens

<400> SEQUENCE: 1080

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 1081
<211> LENGTH: 9
<212> TYPE: PRT
<213> ORGANISM: Homo sapiens

<400> SEQUENCE: 1081

Gln Gln Ser Tyr Asp Thr Pro Arg Thr
1 5

<210> SEQ ID NO 1082
<211> LENGTH: 11
<212> TYPE: PRT
<213> ORGANISM: Homo sapiens

<400> SEQUENCE: 1082

Phe Gly Gln Gly Thr Arg Leu Glu Ile Lys Arg
1 5 10

<210> SEQ ID NO 1083
<211> LENGTH: 22
<212> TYPE: PRT
<213> ORGANISM: Homo sapiens

<400> SEQUENCE: 1083

Asp Trp Met Thr Gln Ser Pro Ser Thr Leu Ser Ala Ser Val Gly Asp

```
1               5                   10                  15

Arg Val Thr Ile Thr Cys
            20


<210> SEQ ID NO 1084
<211> LENGTH: 11
<212> TYPE: PRT
<213> ORGANISM: Homo sapiens

<400> SEQUENCE: 1084

Arg Ala Ser Gln Thr Ile Ser Ser Tyr Leu Asn
1               5                   10


<210> SEQ ID NO 1085
<211> LENGTH: 15
<212> TYPE: PRT
<213> ORGANISM: Homo sapiens

<400> SEQUENCE: 1085

Trp Tyr Gln Gln Lys Pro Gly Lys Ala Pro Lys Leu Leu Ile Tyr
1               5                   10                  15


<210> SEQ ID NO 1086
<211> LENGTH: 7
<212> TYPE: PRT
<213> ORGANISM: Homo sapiens

<400> SEQUENCE: 1086

Ala Ala Ser Ser Leu Gln Ser
1               5


<210> SEQ ID NO 1087
<211> LENGTH: 32
<212> TYPE: PRT
<213> ORGANISM: Homo sapiens

<400> SEQUENCE: 1087

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 1088
<211> LENGTH: 9
<212> TYPE: PRT
<213> ORGANISM: Homo sapiens

<400> SEQUENCE: 1088

Gln Gln Ser Tyr Asp Thr Pro Arg Thr
1               5


<210> SEQ ID NO 1089
<211> LENGTH: 11
<212> TYPE: PRT
<213> ORGANISM: Homo sapiens

<400> SEQUENCE: 1089

Phe Gly Gln Gly Thr Arg Leu Glu Ile Lys Arg
1               5                   10


<210> SEQ ID NO 1090
<211> LENGTH: 23
<212> TYPE: PRT
<213> ORGANISM: Homo sapiens
```

<400> SEQUENCE: 1090

Asp Ile Gln Met Thr Gln Ser Pro Ser Phe Leu Ser Ala Ser Val Gly
1 5 10 15

Asp Arg Val Thr Ile Thr Cys
20

<210> SEQ ID NO 1091
<211> LENGTH: 11
<212> TYPE: PRT
<213> ORGANISM: Homo sapiens

<400> SEQUENCE: 1091

Arg Ala Ser Gln Gly Ile Ser Ser Ala Leu Ala
1 5 10

<210> SEQ ID NO 1092
<211> LENGTH: 15
<212> TYPE: PRT
<213> ORGANISM: Homo sapiens

<400> SEQUENCE: 1092

Trp Tyr Gln Gln Lys Pro Gly Lys Ala Pro Lys Leu Leu Ile Tyr
1 5 10 15

<210> SEQ ID NO 1093
<211> LENGTH: 7
<212> TYPE: PRT
<213> ORGANISM: Homo sapiens

<400> SEQUENCE: 1093

Gly Ala Ser Ser Leu Gln Ser
1 5

<210> SEQ ID NO 1094
<211> LENGTH: 32
<212> TYPE: PRT
<213> ORGANISM: Homo sapiens

<400> SEQUENCE: 1094

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 1095
<211> LENGTH: 8
<212> TYPE: PRT
<213> ORGANISM: Homo sapiens

<400> SEQUENCE: 1095

Gln Gln Tyr His Thr Tyr Trp Thr
1 5

<210> SEQ ID NO 1096
<211> LENGTH: 11
<212> TYPE: PRT
<213> ORGANISM: Homo sapiens

<400> SEQUENCE: 1096

Phe Gly Gln Gly Thr Lys Val Glu Ile Lys Arg
1 5 10

<210> SEQ ID NO 1097
<211> LENGTH: 30
<212> TYPE: PRT
<213> ORGANISM: Homo sapiens

<400> SEQUENCE: 1097

Gln Val Gln Leu Val Gln Ser Gly Ala Glu Val Glu Lys Pro Gly Ser
1 5 10 15

Ser Val Lys Val Ser Cys Lys Ala Ser Gly Gly Ser Phe Ser
20 25 30

<210> SEQ ID NO 1098
<211> LENGTH: 5
<212> TYPE: PRT
<213> ORGANISM: Homo sapiens

<400> SEQUENCE: 1098

Ser Tyr Ala Phe Thr
1 5

<210> SEQ ID NO 1099
<211> LENGTH: 14
<212> TYPE: PRT
<213> ORGANISM: Homo sapiens

<400> SEQUENCE: 1099

Trp Val Arg Gln Ala Pro Gly Gln Gly Leu Glu Trp Met Gly
1 5 10

<210> SEQ ID NO 1100
<211> LENGTH: 17
<212> TYPE: PRT
<213> ORGANISM: Homo sapiens

<400> SEQUENCE: 1100

Arg Ile Val Pro Phe Leu Gly Val Pro Tyr Tyr Thr Gln Lys Phe Arg
1 5 10 15

Gly

<210> SEQ ID NO 1101
<211> LENGTH: 32
<212> TYPE: PRT
<213> ORGANISM: Homo sapiens

<400> SEQUENCE: 1101

Arg Val Thr Ile Thr Ala Asp Lys Ala Thr Ser Thr Val Tyr Met Glu
1 5 10 15

Leu Ser Ser Leu Thr Phe Asp Asp Thr Ala Val Tyr Tyr Cys Ala Arg
20 25 30

<210> SEQ ID NO 1102
<211> LENGTH: 14
<212> TYPE: PRT
<213> ORGANISM: Homo sapiens

<400> SEQUENCE: 1102

Asp Lys Arg Thr Tyr Glu Tyr Asn Trp Asn Ser Leu Trp Phe
1 5 10

<210> SEQ ID NO 1103
<211> LENGTH: 11
<212> TYPE: PRT
<213> ORGANISM: Homo sapiens

<400> SEQUENCE: 1103

Trp Gly Arg Gly Thr Leu Val Thr Val Ser Ser
1 5 10

<210> SEQ ID NO 1104
<211> LENGTH: 30
<212> TYPE: PRT
<213> ORGANISM: Homo sapiens

<400> SEQUENCE: 1104

Gln Val Gln Leu Leu Glu Ser Gly Gly Gly Leu Val Gln Pro Gly Arg
1 5 10 15

Ser Leu Arg Leu Ser Cys Arg Gly Ser Gly Phe Thr Phe Gly
20 25 30

<210> SEQ ID NO 1105
<211> LENGTH: 5
<212> TYPE: PRT
<213> ORGANISM: Homo sapiens

<400> SEQUENCE: 1105

Asp Tyr Ala Leu Ser
1 5

<210> SEQ ID NO 1106
<211> LENGTH: 14
<212> TYPE: PRT
<213> ORGANISM: Homo sapiens

<400> SEQUENCE: 1106

Trp Phe Arg Gln Ala Pro Gly Lys Gly Leu Glu Trp Ile Gly
1 5 10

<210> SEQ ID NO 1107
<211> LENGTH: 19
<212> TYPE: PRT
<213> ORGANISM: Homo sapiens

<400> SEQUENCE: 1107

Leu Ile Arg Ser Arg Ala His Gly Gly Thr Ile Glu Tyr Ala Ala Ser
1 5 10 15

Val Lys Gly

<210> SEQ ID NO 1108
<211> LENGTH: 32
<212> TYPE: PRT
<213> ORGANISM: Homo sapiens

<400> SEQUENCE: 1108

Arg Phe Thr Ile Ser Arg Asp Asp Ser Lys Ser Ile Gly Tyr Leu Gln
1 5 10 15

Met Asn Ser Leu Lys Ser Glu Asp Thr Ala Val Tyr Tyr Cys Thr Arg
20 25 30

<210> SEQ ID NO 1109
<211> LENGTH: 22
<212> TYPE: PRT
<213> ORGANISM: Homo sapiens

<400> SEQUENCE: 1109

Asp Ile Leu Tyr Tyr His Asp Ser Ser Asp Tyr Trp Gly Arg Gly His
1 5 10 15

Phe Tyr Tyr Met Asp Val
20

<210> SEQ ID NO 1110
<211> LENGTH: 11
<212> TYPE: PRT
<213> ORGANISM: Homo sapiens

<400> SEQUENCE: 1110

Trp Gly Thr Gly Thr Pro Val Thr Val Ser Ser
1 5 10

<210> SEQ ID NO 1111
<211> LENGTH: 30
<212> TYPE: PRT
<213> ORGANISM: Homo sapiens

<400> SEQUENCE: 1111

Gln Val Gln Leu Val Glu Ser Gly Gly Ala Leu Val Lys Pro Gly Gly
1 5 10 15

Ser Leu Arg Leu Ser Cys Ala Ala Ser Gly Phe Thr Phe Ser
20 25 30

<210> SEQ ID NO 1112
<211> LENGTH: 5
<212> TYPE: PRT
<213> ORGANISM: Homo sapiens

<400> SEQUENCE: 1112

Asp Tyr Tyr Met Ser
1 5

<210> SEQ ID NO 1113
<211> LENGTH: 14
<212> TYPE: PRT
<213> ORGANISM: Homo sapiens

<400> SEQUENCE: 1113

Trp Ile Arg Gln Ala Pro Gly Lys Gly Leu Glu Trp Val Ser
1 5 10

<210> SEQ ID NO 1114
<211> LENGTH: 17
<212> TYPE: PRT
<213> ORGANISM: Homo sapiens

<400> SEQUENCE: 1114

Tyr Ile Ser Ser Ser Ser Ser Tyr Thr Asn Tyr Ala Asp Ser Val Lys
1 5 10 15

Gly

<210> SEQ ID NO 1115
<211> LENGTH: 32
<212> TYPE: PRT
<213> ORGANISM: Homo sapiens

<400> SEQUENCE: 1115

Arg Phe Thr Ile Ser Arg Asp Asn Ala Lys Asn Ser Leu Tyr Leu Gln
1 5 10 15

Met Asn Ser Leu Phe Ala Glu Asp Thr Ala Val Tyr Tyr Cys Ala Arg
20 25 30

<210> SEQ ID NO 1116

<211> LENGTH: 18
<212> TYPE: PRT
<213> ORGANISM: Homo sapiens

<400> SEQUENCE: 1116

Met Arg Gly Tyr Ser Ser Ser Trp His Tyr Ser Tyr Tyr Tyr Val Met
1 5 10 15

Asp Val

<210> SEQ ID NO 1117
<211> LENGTH: 11
<212> TYPE: PRT
<213> ORGANISM: Homo sapiens

<400> SEQUENCE: 1117

Trp Gly Gln Gly Thr Thr Val Thr Val Ser Ser
1 5 10

<210> SEQ ID NO 1118
<211> LENGTH: 32
<212> TYPE: PRT
<213> ORGANISM: Homo sapiens

<400> SEQUENCE: 1118

Gln Val Gln Leu Val Gln Ser Gly Ala Glu Val Lys Lys Pro Gly Glu
1 5 10 15

Ser Leu Val Ile Ser Cys Lys Ala Ser Gly Asp Lys Asp Thr Phe Thr
20 25 30

<210> SEQ ID NO 1119
<211> LENGTH: 5
<212> TYPE: PRT
<213> ORGANISM: Homo sapiens

<400> SEQUENCE: 1119

Ser Phe Trp Ile Ala
1 5

<210> SEQ ID NO 1120
<211> LENGTH: 14
<212> TYPE: PRT
<213> ORGANISM: Homo sapiens

<400> SEQUENCE: 1120

Trp Val Arg Gln Met Pro Gly Lys Gly Leu Glu Trp Met Gly
1 5 10

<210> SEQ ID NO 1121
<211> LENGTH: 17
<212> TYPE: PRT
<213> ORGANISM: Homo sapiens

<400> SEQUENCE: 1121

Ile Ile Tyr Ala Gly Asp Ser Asp Thr Arg Tyr Ser Pro Ser Phe Gln
1 5 10 15

Gly

<210> SEQ ID NO 1122
<211> LENGTH: 32
<212> TYPE: PRT
<213> ORGANISM: Homo sapiens

<400> SEQUENCE: 1122

-continued

His Val Asn Ile Ser Val Asp Arg Ser Thr Asn Thr Ala Tyr Leu Gln
1 5 10 15

Trp Ser Ser Leu Lys Ala Ser Asp Thr Ala Trp Tyr Tyr Cys Ala Arg
20 25 30

<210> SEQ ID NO 1123
<211> LENGTH: 14
<212> TYPE: PRT
<213> ORGANISM: Homo sapiens

<400> SEQUENCE: 1123

His Asp Ser Arg Tyr Lys Tyr Phe Tyr Phe Gly Met Asp Val
1 5 10

<210> SEQ ID NO 1124
<211> LENGTH: 11
<212> TYPE: PRT
<213> ORGANISM: Homo sapiens

<400> SEQUENCE: 1124

Trp Gly Gln Gly Thr Thr Val Thr Val Ser Ser
1 5 10

<210> SEQ ID NO 1125
<211> LENGTH: 32
<212> TYPE: PRT
<213> ORGANISM: Homo sapiens

<400> SEQUENCE: 1125

Gln Val Gln Leu Val Gln Ser Gly Ala Glu Val Lys Lys Pro Gly Glu
1 5 10 15

Ser Leu Val Ile Ser Cys Lys Ala Ser Gly Asp Lys Asp Thr Phe Thr
20 25 30

<210> SEQ ID NO 1126
<211> LENGTH: 5
<212> TYPE: PRT
<213> ORGANISM: Homo sapiens

<400> SEQUENCE: 1126

Ser Phe Trp Ile Ala
1 5

<210> SEQ ID NO 1127
<211> LENGTH: 14
<212> TYPE: PRT
<213> ORGANISM: Homo sapiens

<400> SEQUENCE: 1127

Trp Val Arg Gln Met Pro Gly Lys Gly Leu Glu Trp Met Gly
1 5 10

<210> SEQ ID NO 1128
<211> LENGTH: 17
<212> TYPE: PRT
<213> ORGANISM: Homo sapiens

<400> SEQUENCE: 1128

Ile Ile Tyr Ala Gly Asp Ser Asp Thr Arg Tyr Ser Pro Ser Phe Gln
1 5 10 15

Gly

<210> SEQ ID NO 1129

<211> LENGTH: 32
<212> TYPE: PRT
<213> ORGANISM: Homo sapiens

<400> SEQUENCE: 1129

His Val Asn Ile Ser Val Asp Arg Ser Thr Asn Thr Ala Tyr Leu Gln
1 5 10 15

Trp Ser Ser Leu Lys Ala Ser Asp Thr Arg Met Tyr Tyr Cys Ala Arg
20 25 30

<210> SEQ ID NO 1130
<211> LENGTH: 14
<212> TYPE: PRT
<213> ORGANISM: Homo sapiens

<400> SEQUENCE: 1130

His Asp Ser Arg Tyr Lys Tyr Phe Tyr Phe Gly Met Asp Val
1 5 10

<210> SEQ ID NO 1131
<211> LENGTH: 11
<212> TYPE: PRT
<213> ORGANISM: Homo sapiens

<400> SEQUENCE: 1131

Trp Gly Gln Gly Thr Thr Val Thr Val Ser Ser
1 5 10

<210> SEQ ID NO 1132
<211> LENGTH: 32
<212> TYPE: PRT
<213> ORGANISM: Homo sapiens

<400> SEQUENCE: 1132

Gln Val Gln Leu Val Gln Ser Gly Ala Glu Val Lys Lys Pro Gly Glu
1 5 10 15

Ser Leu Val Ile Ser Cys Lys Ala Ser Gly Asp Lys Asp Thr Phe Thr
20 25 30

<210> SEQ ID NO 1133
<211> LENGTH: 5
<212> TYPE: PRT
<213> ORGANISM: Homo sapiens

<400> SEQUENCE: 1133

Ser Phe Trp Ile Ala
1 5

<210> SEQ ID NO 1134
<211> LENGTH: 14
<212> TYPE: PRT
<213> ORGANISM: Homo sapiens

<400> SEQUENCE: 1134

Trp Val Arg Gln Met Pro Gly Lys Gly Leu Glu Trp Met Gly
1 5 10

<210> SEQ ID NO 1135
<211> LENGTH: 17
<212> TYPE: PRT
<213> ORGANISM: Homo sapiens

<400> SEQUENCE: 1135

Ile Ile Tyr Ala Gly Asp Ser Asp Thr Arg Tyr Ser Pro Ser Phe Gln 1 5 10 15

Gly

<210> SEQ ID NO 1136
<211> LENGTH: 32
<212> TYPE: PRT
<213> ORGANISM: Homo sapiens

<400> SEQUENCE: 1136

His Val Asn Ile Ser Val Asp Arg Ser Thr Asn Thr Ala Tyr Leu Gln
1 5 10 15

Trp Ser Ser Leu Lys Ala Ser Asp Thr Ala Met Tyr Tyr Cys Ala Arg
20 25 30

<210> SEQ ID NO 1137
<211> LENGTH: 14
<212> TYPE: PRT
<213> ORGANISM: Homo sapiens

<400> SEQUENCE: 1137

His Asp Ser Arg Tyr Lys Tyr Phe Tyr Phe Gly Met Asp Val
1 5 10

<210> SEQ ID NO 1138
<211> LENGTH: 11
<212> TYPE: PRT
<213> ORGANISM: Homo sapiens

<400> SEQUENCE: 1138

Trp Gly Gln Gly Thr Thr Val Thr Val Ser Ser
1 5 10

<210> SEQ ID NO 1139
<211> LENGTH: 32
<212> TYPE: PRT
<213> ORGANISM: Homo sapiens

<400> SEQUENCE: 1139

Gln Val Gln Leu Val Gln Ser Gly Ala Glu Val Lys Lys Pro Gly Glu
1 5 10 15

Ser Leu Val Ile Ser Cys Lys Arg Ser Gly Asp Lys Asp Thr Phe Thr
20 25 30

<210> SEQ ID NO 1140
<211> LENGTH: 5
<212> TYPE: PRT
<213> ORGANISM: Homo sapiens

<400> SEQUENCE: 1140

Ser Phe Trp Ile Ala
1 5

<210> SEQ ID NO 1141
<211> LENGTH: 14
<212> TYPE: PRT
<213> ORGANISM: Homo sapiens

<400> SEQUENCE: 1141

Trp Val Arg Gln Met Pro Gly Lys Gly Leu Glu Trp Met Gly
1 5 10

<210> SEQ ID NO 1142
<211> LENGTH: 17

<212> TYPE: PRT
<213> ORGANISM: Homo sapiens

<400> SEQUENCE: 1142

Ile Ile Tyr Ala Gly Asp Ser Asp Thr Arg Tyr Ser Pro Ser Phe Gln
1 5 10 15

Gly

<210> SEQ ID NO 1143
<211> LENGTH: 32
<212> TYPE: PRT
<213> ORGANISM: Homo sapiens

<400> SEQUENCE: 1143

His Val Asn Ile Ser Val Asp Arg Ser Thr Asn Thr Ala Tyr Leu Gln
1 5 10 15

Trp Ser Ser Leu Lys Ala Ser Asp Thr Ala Met Tyr Tyr Cys Ala Arg
20 25 30

<210> SEQ ID NO 1144
<211> LENGTH: 14
<212> TYPE: PRT
<213> ORGANISM: Homo sapiens

<400> SEQUENCE: 1144

His Asp Ser Arg Tyr Lys Tyr Phe Tyr Phe Gly Met Asp Val
1 5 10

<210> SEQ ID NO 1145
<211> LENGTH: 11
<212> TYPE: PRT
<213> ORGANISM: Homo sapiens

<400> SEQUENCE: 1145

Trp Gly Gln Gly Thr Thr Val Thr Val Ser Ser
1 5 10

<210> SEQ ID NO 1146
<211> LENGTH: 31
<212> TYPE: PRT
<213> ORGANISM: Homo sapiens

<400> SEQUENCE: 1146

Gln Val Gln Leu Trp Ser Gly Pro Gly Leu Val Lys Pro Ser Gln Thr
1 5 10 15

Leu Ser Leu Thr Cys Ser Val Ser Gly Gly Ser Ile Asn Ser Asp
20 25 30

<210> SEQ ID NO 1147
<211> LENGTH: 5
<212> TYPE: PRT
<213> ORGANISM: Homo sapiens

<400> SEQUENCE: 1147

Gly Ser Tyr Trp Ser
1 5

<210> SEQ ID NO 1148
<211> LENGTH: 14
<212> TYPE: PRT
<213> ORGANISM: Homo sapiens

<400> SEQUENCE: 1148

Trp Val Arg Gln His Pro Gly Lys Gly Leu Glu Trp Ile Gly
1 5 10

<210> SEQ ID NO 1149
<211> LENGTH: 16
<212> TYPE: PRT
<213> ORGANISM: Homo sapiens

<400> SEQUENCE: 1149

Tyr Ile Tyr Tyr Ser Gly Thr Thr Tyr Phe Asn Pro Ser Leu Lys Ser
1 5 10 15

<210> SEQ ID NO 1150
<211> LENGTH: 32
<212> TYPE: PRT
<213> ORGANISM: Homo sapiens

<400> SEQUENCE: 1150

Arg Leu Thr Met Ser Val Asp Thr Ser Lys Asn Gln Phe Ser Leu Lys
1 5 10 15

Met Thr Ser Val Thr Ala Ala Asp Thr Arg Val Tyr Tyr Cys Ala Arg
20 25 30

<210> SEQ ID NO 1151
<211> LENGTH: 14
<212> TYPE: PRT
<213> ORGANISM: Homo sapiens

<400> SEQUENCE: 1151

Met Ser Gly Ser Arg Ser Tyr Ser Gln Tyr Tyr Phe Asp Ser
1 5 10

<210> SEQ ID NO 1152
<211> LENGTH: 11
<212> TYPE: PRT
<213> ORGANISM: Homo sapiens

<400> SEQUENCE: 1152

Trp Gly Gln Gly Thr Leu Val Thr Val Ser Ser
1 5 10

<210> SEQ ID NO 1153
<211> LENGTH: 30
<212> TYPE: PRT
<213> ORGANISM: Homo sapiens

<400> SEQUENCE: 1153

Gln Val Gln Leu Leu Gln Ser Ala Gly Gly Val Val Gln Pro Gly Arg
1 5 10 15

Ser Leu Arg Leu Ser Cys Ala Ala Ser Gly Phe Ile Phe Arg
20 25 30

<210> SEQ ID NO 1154
<211> LENGTH: 5
<212> TYPE: PRT
<213> ORGANISM: Homo sapiens

<400> SEQUENCE: 1154

Thr Tyr Gly Met His
1 5

<210> SEQ ID NO 1155
<211> LENGTH: 14
<212> TYPE: PRT

<213> ORGANISM: Homo sapiens

<400> SEQUENCE: 1155

Trp Val Arg Gln Ala Pro Gly Lys Gly Leu Glu Trp Val Ala
1               5                   10

<210> SEQ ID NO 1156
<211> LENGTH: 17
<212> TYPE: PRT
<213> ORGANISM: Homo sapiens

<400> SEQUENCE: 1156

Phe Val Ser Ser Asp Gly Asn Asn Lys Phe Tyr Ser Asp Ser Val Lys
1               5                   10                  15

Gly

<210> SEQ ID NO 1157
<211> LENGTH: 32
<212> TYPE: PRT
<213> ORGANISM: Homo sapiens

<400> SEQUENCE: 1157

Arg Phe Thr Ile Pro Arg Asp Asn Ala Lys Asn Thr Leu Tyr Leu Gln
1               5                   10                  15

Met Asn Ser Leu Glu Thr Glu Asp Thr Ala Val Tyr Tyr Cys Ala Lys
            20                  25                  30

<210> SEQ ID NO 1158
<211> LENGTH: 19
<212> TYPE: PRT
<213> ORGANISM: Homo sapiens

<400> SEQUENCE: 1158

Asp Arg Tyr Pro Ile Asp Cys Ser Gly Gly Ser Cys Phe Ser Tyr Gly
1               5                   10                  15

Met Asp Val

<210> SEQ ID NO 1159
<211> LENGTH: 11
<212> TYPE: PRT
<213> ORGANISM: Homo sapiens

<400> SEQUENCE: 1159

Trp Gly Gln Gly Thr Thr Val Thr Val Ser Ser
1               5                   10

<210> SEQ ID NO 1160
<211> LENGTH: 29
<212> TYPE: PRT
<213> ORGANISM: Homo sapiens

<400> SEQUENCE: 1160

Glu Val Gln Leu Val Glu Ser Gly Gly Gly Trp Gln Pro Gly Arg Ser
1               5                   10                  15

Leu Arg Leu Ser Cys Ala Thr Ser Gly Phe Ile Leu Arg
            20                  25

<210> SEQ ID NO 1161
<211> LENGTH: 5
<212> TYPE: PRT
<213> ORGANISM: Homo sapiens

<400> SEQUENCE: 1161

Thr Tyr Gly Met His
1 5

<210> SEQ ID NO 1162
<211> LENGTH: 14
<212> TYPE: PRT
<213> ORGANISM: Homo sapiens

<400> SEQUENCE: 1162

Trp Val Arg Gln Ala Pro Gly Lys Gly Leu Glu Trp Val Ala
1 5 10

<210> SEQ ID NO 1163
<211> LENGTH: 17
<212> TYPE: PRT
<213> ORGANISM: Homo sapiens

<400> SEQUENCE: 1163

Phe Val Ser Ser Asp Gly Asn Asn Lys Phe Tyr Ser Asp Ser Val Lys
1 5 10 15

Gly

<210> SEQ ID NO 1164
<211> LENGTH: 32
<212> TYPE: PRT
<213> ORGANISM: Homo sapiens

<400> SEQUENCE: 1164

Arg Phe Thr Ile Pro Arg Asp Asn Ala Lys Asn Thr Leu Tyr Leu Gln
1 5 10 15

Met Asn Ser Leu Glu Thr Glu Asp Thr Ala Val Tyr Tyr Cys Ala Lys
20 25 30

<210> SEQ ID NO 1165
<211> LENGTH: 19
<212> TYPE: PRT
<213> ORGANISM: Homo sapiens

<400> SEQUENCE: 1165

Asp Arg Tyr Pro Ile Asp Cys Ser Gly Gly Ser Cys Phe Ser Tyr Gly
1 5 10 15

Met Asp Val

<210> SEQ ID NO 1166
<211> LENGTH: 11
<212> TYPE: PRT
<213> ORGANISM: Homo sapiens

<400> SEQUENCE: 1166

Trp Gly Gln Gly Thr Leu Val Thr Val Ser Ser
1 5 10

<210> SEQ ID NO 1167
<211> LENGTH: 29
<212> TYPE: PRT
<213> ORGANISM: Homo sapiens

<400> SEQUENCE: 1167

Glu Val Arg Leu Val Gln Ser Gly Gly Gly Trp Gln Pro Gly Arg Ser
1 5 10 15

Leu Arg Leu Ser Cys Ala Ala Ser Gly Phe Val Phe Arg
20 25

<210> SEQ ID NO 1168
<211> LENGTH: 5
<212> TYPE: PRT
<213> ORGANISM: Homo sapiens

<400> SEQUENCE: 1168

Thr Tyr Gly Met His
1 5

<210> SEQ ID NO 1169
<211> LENGTH: 14
<212> TYPE: PRT
<213> ORGANISM: Homo sapiens

<400> SEQUENCE: 1169

Trp Val Arg Gln Ala Pro Gly Lys Gly Leu Glu Trp Val Ala
1 5 10

<210> SEQ ID NO 1170
<211> LENGTH: 16
<212> TYPE: PRT
<213> ORGANISM: Homo sapiens

<400> SEQUENCE: 1170

Trp Ser Ser Asp Gly Asn Asn Lys Phe Tyr Ser Asp Ser Val Lys Gly
1 5 10 15

<210> SEQ ID NO 1171
<211> LENGTH: 32
<212> TYPE: PRT
<213> ORGANISM: Homo sapiens

<400> SEQUENCE: 1171

Arg Phe Thr Ile Pro Arg Asp Asn Ala Lys Asn Thr Leu Tyr Leu Gln
1 5 10 15

Met Asn Ser Leu Glu Thr Glu Asp Thr Ala Val Tyr Tyr Cys Ala Lys
20 25 30

<210> SEQ ID NO 1172
<211> LENGTH: 19
<212> TYPE: PRT
<213> ORGANISM: Homo sapiens

<400> SEQUENCE: 1172

Asp Arg Tyr Pro Ile Asp Cys Ser Gly Gly Ser Cys Phe Ser Tyr Gly
1 5 10 15

Met Asp Val

<210> SEQ ID NO 1173
<211> LENGTH: 11
<212> TYPE: PRT
<213> ORGANISM: Homo sapiens

<400> SEQUENCE: 1173

Trp Gly Gln Gly Thr Pro Val Thr Val Ser Ser
1 5 10

<210> SEQ ID NO 1174
<211> LENGTH: 30
<212> TYPE: PRT
<213> ORGANISM: Homo sapiens

<400> SEQUENCE: 1174

Glu Val Gln Leu Val Glu Ser Gly Gly Gly Val Val Gln Pro Gly Arg
1 5 10 15

Ser Leu Arg Leu Ser Cys Arg Ala Ser Gly Phe Ile Phe Arg
20 25 30

<210> SEQ ID NO 1175
<211> LENGTH: 5
<212> TYPE: PRT
<213> ORGANISM: Homo sapiens

<400> SEQUENCE: 1175

Thr Tyr Gly Met His
1 5

<210> SEQ ID NO 1176
<211> LENGTH: 14
<212> TYPE: PRT
<213> ORGANISM: Homo sapiens

<400> SEQUENCE: 1176

Trp Val Arg Gln Ala Pro Gly Lys Gly Leu Glu Trp Val Ala
1 5 10

<210> SEQ ID NO 1177
<211> LENGTH: 17
<212> TYPE: PRT
<213> ORGANISM: Homo sapiens

<400> SEQUENCE: 1177

Phe Val Ser Ser Asp Gly Asn Asn Lys Phe Tyr Ser Asp Ser Val Lys
1 5 10 15

Gly

<210> SEQ ID NO 1178
<211> LENGTH: 32
<212> TYPE: PRT
<213> ORGANISM: Homo sapiens

<400> SEQUENCE: 1178

Arg Phe Thr Ile Pro Arg Asp Asn Ala Lys Asn Thr Leu Tyr Leu Gln
1 5 10 15

Met Asn Ser Leu Glu Thr Glu Asp Thr Ala Val Tyr Tyr Cys Ala Lys
20 25 30

<210> SEQ ID NO 1179
<211> LENGTH: 19
<212> TYPE: PRT
<213> ORGANISM: Homo sapiens

<400> SEQUENCE: 1179

Asp Arg Tyr Pro Ile Asp Cys Ser Gly Gly Ser Cys Phe Ser Tyr Gly
1 5 10 15

Met Asp Val

<210> SEQ ID NO 1180
<211> LENGTH: 11
<212> TYPE: PRT
<213> ORGANISM: Homo sapiens

<400> SEQUENCE: 1180

Trp Gly Gln Gly Thr Met Val Thr Val Ser Ser
1 5 10

<210> SEQ ID NO 1181
<211> LENGTH: 30
<212> TYPE: PRT
<213> ORGANISM: Homo sapiens

<400> SEQUENCE: 1181

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg
            20                  25                  30

<210> SEQ ID NO 1182
<211> LENGTH: 5
<212> TYPE: PRT
<213> ORGANISM: Homo sapiens

<400> SEQUENCE: 1182

Thr Tyr Gly Met His
1               5

<210> SEQ ID NO 1183
<211> LENGTH: 14
<212> TYPE: PRT
<213> ORGANISM: Homo sapiens

<400> SEQUENCE: 1183

Trp Val Arg Gln Ala Pro Gly Lys Gly Leu Glu Trp Val Ala
1               5                   10

<210> SEQ ID NO 1184
<211> LENGTH: 17
<212> TYPE: PRT
<213> ORGANISM: Homo sapiens

<400> SEQUENCE: 1184

Phe Val Ser Ser Asp Gly Asn Asn Lys Phe Tyr Ser Asp Ser Val Lys
1               5                   10                  15

Gly

<210> SEQ ID NO 1185
<211> LENGTH: 32
<212> TYPE: PRT
<213> ORGANISM: Homo sapiens

<400> SEQUENCE: 1185

Arg Phe Thr Ile Pro Arg Asp Asn Ala Lys Asn Thr Leu Tyr Leu Gln
1               5                   10                  15

Met Asn Ser Leu Glu Thr Glu Asp Thr Ala Val Tyr Tyr Cys Ala Lys
            20                  25                  30

<210> SEQ ID NO 1186
<211> LENGTH: 19
<212> TYPE: PRT
<213> ORGANISM: Homo sapiens

<400> SEQUENCE: 1186

Asp Arg Tyr Pro Ile Asp Cys Ser Gly Gly Ser Cys Phe Ser Tyr Gly
1               5                   10                  15

Met Asp Val

<210> SEQ ID NO 1187

<211> LENGTH: 11
<212> TYPE: PRT
<213> ORGANISM: Homo sapiens

<400> SEQUENCE: 1187

Trp Gly Gln Gly Thr Met Val Thr Val Ser Ser
1 5 10

<210> SEQ ID NO 1188
<211> LENGTH: 30
<212> TYPE: PRT
<213> ORGANISM: Homo sapiens

<400> SEQUENCE: 1188

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 1189
<211> LENGTH: 5
<212> TYPE: PRT
<213> ORGANISM: Homo sapiens

<400> SEQUENCE: 1189

Ser Tyr Ser Met Asn
1 5

<210> SEQ ID NO 1190
<211> LENGTH: 14
<212> TYPE: PRT
<213> ORGANISM: Homo sapiens

<400> SEQUENCE: 1190

Trp Val Arg Gln Ala Pro Gly Lys Gly Leu Glu Trp Val Ala
1 5 10

<210> SEQ ID NO 1191
<211> LENGTH: 17
<212> TYPE: PRT
<213> ORGANISM: Homo sapiens

<400> SEQUENCE: 1191

Val Ile Trp Tyr Asp Gly Ser Asn Lys Tyr Tyr Ala Asp Ser Val Lys
1 5 10 15

Gly

<210> SEQ ID NO 1192
<211> LENGTH: 32
<212> TYPE: PRT
<213> ORGANISM: Homo sapiens

<400> SEQUENCE: 1192

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 1193
<211> LENGTH: 12
<212> TYPE: PRT
<213> ORGANISM: Homo sapiens

<400> SEQUENCE: 1193

Ser Ser Ile Val Gly Ala Pro Tyr Gly Met Asp Val
1 5 10

<210> SEQ ID NO 1194
<211> LENGTH: 11
<212> TYPE: PRT
<213> ORGANISM: Homo sapiens

<400> SEQUENCE: 1194

Trp Gly Gln Gly Thr Thr Val Thr Val Ser Ser
1 5 10

<210> SEQ ID NO 1195
<211> LENGTH: 30
<212> TYPE: PRT
<213> ORGANISM: Homo sapiens

<400> SEQUENCE: 1195

Gln Val Gln Leu Val Gln Ser Gly Ala Glu Val Lys Lys Pro Gly Ala
1 5 10 15

Ser Val Asn Val Ser Cys Lys Ala Ser Gly Tyr Thr Phe Thr
20 25 30

<210> SEQ ID NO 1196
<211> LENGTH: 5
<212> TYPE: PRT
<213> ORGANISM: Homo sapiens

<400> SEQUENCE: 1196

Gly Tyr Tyr Ile Tyr
1 5

<210> SEQ ID NO 1197
<211> LENGTH: 14
<212> TYPE: PRT
<213> ORGANISM: Homo sapiens

<400> SEQUENCE: 1197

Trp Val Arg Gln Ala Pro Gly Gln Gly Leu Glu Trp Met Gly
1 5 10

<210> SEQ ID NO 1198
<211> LENGTH: 17
<212> TYPE: PRT
<213> ORGANISM: Homo sapiens

<400> SEQUENCE: 1198

Trp Ile Asn Pro Asn Ser Gly Val Thr Lys Tyr Ala Gln Lys Phe Gln
1 5 10 15

Gly

<210> SEQ ID NO 1199
<211> LENGTH: 32
<212> TYPE: PRT
<213> ORGANISM: Homo sapiens

<400> SEQUENCE: 1199

Arg Val Thr Met Thr Ile Asp Thr Ser Thr Asn Thr Ala Tyr Met Glu
1 5 10 15

Leu Asn Arg Leu Arg Ala Asp Asp Thr Ala Val Tyr Tyr Cys Ala Arg
20 25 30

<210> SEQ ID NO 1200
<211> LENGTH: 11
<212> TYPE: PRT
<213> ORGANISM: Homo sapiens

<400> SEQUENCE: 1200

Glu Trp Thr Gln Leu Trp Ser Pro Tyr Asp Tyr
1               5                   10

<210> SEQ ID NO 1201
<211> LENGTH: 11
<212> TYPE: PRT
<213> ORGANISM: Homo sapiens

<400> SEQUENCE: 1201

Trp Gly Gln Gly Thr Thr Val Thr Val Ser Ser
1               5                   10

<210> SEQ ID NO 1202
<211> LENGTH: 23
<212> TYPE: PRT
<213> ORGANISM: Homo sapiens

<400> SEQUENCE: 1202

Glu Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 1203
<211> LENGTH: 11
<212> TYPE: PRT
<213> ORGANISM: Homo sapiens

<400> SEQUENCE: 1203

Arg Ala Ser Gln Gly Val Ser Thr Asp Leu Ala
1               5                   10

<210> SEQ ID NO 1204
<211> LENGTH: 15
<212> TYPE: PRT
<213> ORGANISM: Homo sapiens

<400> SEQUENCE: 1204

Trp Tyr Gln Gln Lys Pro Gly Lys Ser Pro Arg Leu Leu Ile Tyr
1               5                   10                  15

<210> SEQ ID NO 1205
<211> LENGTH: 7
<212> TYPE: PRT
<213> ORGANISM: Homo sapiens

<400> SEQUENCE: 1205

Ala Ala Ser Thr Leu His Ser
1               5

<210> SEQ ID NO 1206
<211> LENGTH: 32
<212> TYPE: PRT
<213> ORGANISM: Homo sapiens

<400> SEQUENCE: 1206

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Phe Cys
            20                  25                  30

<210> SEQ ID NO 1207
<211> LENGTH: 9
<212> TYPE: PRT
<213> ORGANISM: Homo sapiens

<400> SEQUENCE: 1207

Gln Lys Tyr Tyr Thr Ala Pro Leu Thr
1               5

<210> SEQ ID NO 1208
<211> LENGTH: 11
<212> TYPE: PRT
<213> ORGANISM: Homo sapiens

<400> SEQUENCE: 1208

Phe Gly Gly Gly Thr Lys Val Glu Ile Lys Arg
1               5                   10

<210> SEQ ID NO 1209
<211> LENGTH: 23
<212> TYPE: PRT
<213> ORGANISM: Homo sapiens

<400> SEQUENCE: 1209

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 1210
<211> LENGTH: 11
<212> TYPE: PRT
<213> ORGANISM: Homo sapiens

<400> SEQUENCE: 1210

Arg Ala Ser Gln Ser Ile Ser Asn Tyr Leu Asn
1               5                   10

<210> SEQ ID NO 1211
<211> LENGTH: 15
<212> TYPE: PRT
<213> ORGANISM: Homo sapiens

<400> SEQUENCE: 1211

Trp Tyr Gln Lys Lys Pro Gly Trp Ile Pro Arg Leu Leu Met Leu
1               5                   10                  15

<210> SEQ ID NO 1212
<211> LENGTH: 7
<212> TYPE: PRT
<213> ORGANISM: Homo sapiens

<400> SEQUENCE: 1212

Ala Ala Ser Thr Leu His Asp
1               5

<210> SEQ ID NO 1213
<211> LENGTH: 33
<212> TYPE: PRT
<213> ORGANISM: Homo sapiens

<400> SEQUENCE: 1213

Gly Val Pro Ser Arg Phe Ser Gly Ser Gly Ser Gly Gln Ser Asp Phe
1 5 10 15

Thr Leu Thr Ile Asn Gly Leu Gln Pro Glu Asp Phe Ala Thr Tyr Tyr
20 25 30

Cys

<210> SEQ ID NO 1214
<211> LENGTH: 9
<212> TYPE: PRT
<213> ORGANISM: Homo sapiens

<400> SEQUENCE: 1214

Gln Glu Ser Tyr Ser Val Tyr Arg Thr
1 5

<210> SEQ ID NO 1215
<211> LENGTH: 11
<212> TYPE: PRT
<213> ORGANISM: Homo sapiens

<400> SEQUENCE: 1215

Phe Gly Gln Gly Thr Lys Val Glu Ile Lys Arg
1 5 10

<210> SEQ ID NO 1216
<211> LENGTH: 23
<212> TYPE: PRT
<213> ORGANISM: Homo sapiens

<400> SEQUENCE: 1216

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 1217
<211> LENGTH: 11
<212> TYPE: PRT
<213> ORGANISM: Homo sapiens

<400> SEQUENCE: 1217

Arg Ala Ser Gln Ser Val Thr Thr Phe Leu Asn
1 5 10

<210> SEQ ID NO 1218
<211> LENGTH: 15
<212> TYPE: PRT
<213> ORGANISM: Homo sapiens

<400> SEQUENCE: 1218

Trp Tyr Gln Gln Lys Pro Gly Lys Ala Pro Asn Leu Leu Ile Tyr
1 5 10 15

<210> SEQ ID NO 1219
<211> LENGTH: 7
<212> TYPE: PRT
<213> ORGANISM: Homo sapiens

<400> SEQUENCE: 1219

Ala Thr Ser Ser Leu Gln Ser
1 5

<210> SEQ ID NO 1220
<211> LENGTH: 32
<212> TYPE: PRT
<213> ORGANISM: Homo sapiens

<400> SEQUENCE: 1220

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 1221
<211> LENGTH: 9
<212> TYPE: PRT
<213> ORGANISM: Homo sapiens

<400> SEQUENCE: 1221

Gln Gln Ser Tyr Ser Thr Pro Leu Thr
1 5

<210> SEQ ID NO 1222
<211> LENGTH: 11
<212> TYPE: PRT
<213> ORGANISM: Homo sapiens

<400> SEQUENCE: 1222

Phe Gly Gly Gly Thr Lys Leu Glu Ile Lys Arg
1 5 10

<210> SEQ ID NO 1223
<211> LENGTH: 23
<212> TYPE: PRT
<213> ORGANISM: Homo sapiens

<400> SEQUENCE: 1223

Asp Val Val Met Thr Gln Ser Pro Ser Ser Leu Ser Ala Ser Val Gly
1 5 10 15

Asp Arg Ile Thr Ile Thr Cys
20

<210> SEQ ID NO 1224
<211> LENGTH: 11
<212> TYPE: PRT
<213> ORGANISM: Homo sapiens

<400> SEQUENCE: 1224

Gln Ala Gly Gln Asp Ile Ser Asn Phe Leu Asn
1 5 10

<210> SEQ ID NO 1225
<211> LENGTH: 15
<212> TYPE: PRT
<213> ORGANISM: Homo sapiens

<400> SEQUENCE: 1225

Trp Tyr Gln Gln Lys Pro Gly Lys Ala Pro Lys Leu Leu Ile Arg
1 5 10 15

<210> SEQ ID NO 1226
<211> LENGTH: 7
<212> TYPE: PRT
<213> ORGANISM: Homo sapiens

<400> SEQUENCE: 1226

```
Asp Ala Ser Asn Leu Glu Thr
1               5


<210> SEQ ID NO 1227
<211> LENGTH: 32
<212> TYPE: PRT
<213> ORGANISM: Homo sapiens

<400> SEQUENCE: 1227

Gly Val Pro Ser Arg Phe Ser Gly Gly Gly Ser Gly Thr His Phe Thr
1               5                   10                  15

Phe Thr Ile Ser Ser Leu His Pro Glu Asp Ile Ala Thr Tyr Phe Cys
            20                  25                  30


<210> SEQ ID NO 1228
<211> LENGTH: 9
<212> TYPE: PRT
<213> ORGANISM: Homo sapiens

<400> SEQUENCE: 1228

Gln Gln Tyr Asp Asn Leu Pro Tyr Thr
1               5


<210> SEQ ID NO 1229
<211> LENGTH: 11
<212> TYPE: PRT
<213> ORGANISM: Homo sapiens

<400> SEQUENCE: 1229

Phe Gly Gln Gly Thr Lys Leu Glu Ile Lys Arg
1               5                   10


<210> SEQ ID NO 1230
<211> LENGTH: 23
<212> TYPE: PRT
<213> ORGANISM: Homo sapiens

<400> SEQUENCE: 1230

Asp Ile Gln Met Thr Gln Ser Pro Ser Ser Leu Ser Ala Ser Val Gly
1               5                   10                  15

Asp Arg Val Thr Ile Thr Cys
            20


<210> SEQ ID NO 1231
<211> LENGTH: 11
<212> TYPE: PRT
<213> ORGANISM: Homo sapiens

<400> SEQUENCE: 1231

Arg Ala Ser Gln Ser Ile Ser Ser Tyr Leu Asn
1               5                   10


<210> SEQ ID NO 1232
<211> LENGTH: 15
<212> TYPE: PRT
<213> ORGANISM: Homo sapiens

<400> SEQUENCE: 1232

Trp Tyr Gln Gln Glu Pro Gly Lys Ala Pro Lys Leu Leu Ile Tyr
1               5                   10                  15


<210> SEQ ID NO 1233
<211> LENGTH: 7
<212> TYPE: PRT
```

<213> ORGANISM: Homo sapiens

<400> SEQUENCE: 1233

Ser Ala Ser Ser Leu Gln Ser
1 5

<210> SEQ ID NO 1234
<211> LENGTH: 32
<212> TYPE: PRT
<213> ORGANISM: Homo sapiens

<400> SEQUENCE: 1234

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 1235
<211> LENGTH: 10
<212> TYPE: PRT
<213> ORGANISM: Homo sapiens

<400> SEQUENCE: 1235

Gln Gln Ser Tyr Ser Thr Pro Pro Tyr Thr
1 5 10

<210> SEQ ID NO 1236
<211> LENGTH: 11
<212> TYPE: PRT
<213> ORGANISM: Homo sapiens

<400> SEQUENCE: 1236

Phe Gly Gln Gly Thr Lys Leu Glu Ile Lys Arg
1 5 10

<210> SEQ ID NO 1237
<211> LENGTH: 23
<212> TYPE: PRT
<213> ORGANISM: Homo sapiens

<400> SEQUENCE: 1237

Asp Ile Val Met Thr Gln Ser Pro Ser Ser Leu Ser Ala Ser Val Gly
1 5 10 15

Asp Arg Val Thr Ile Thr Cys
20

<210> SEQ ID NO 1238
<211> LENGTH: 11
<212> TYPE: PRT
<213> ORGANISM: Homo sapiens

<400> SEQUENCE: 1238

Arg Ala Ser Gln Ser Ile Ser Ser Tyr Leu Asn
1 5 10

<210> SEQ ID NO 1239
<211> LENGTH: 15
<212> TYPE: PRT
<213> ORGANISM: Homo sapiens

<400> SEQUENCE: 1239

Trp Tyr Gln Gln Lys Pro Gly Lys Ala Pro Lys Leu Leu Ile Tyr
1 5 10 15

<210> SEQ ID NO 1240
<211> LENGTH: 7
<212> TYPE: PRT
<213> ORGANISM: Homo sapiens

<400> SEQUENCE: 1240

Ala Ala Ser Ser Leu Gln Ser
1               5

<210> SEQ ID NO 1241
<211> LENGTH: 32
<212> TYPE: PRT
<213> ORGANISM: Homo sapiens

<400> SEQUENCE: 1241

Gly Val Pro Ser Arg Phe Ser Gly Ser Gly Ser Gly Thr Asp Phe Thr
1               5                   10                  15

Leu Thr Ile Ser Ser Leu Gln Pro Glu Ala Phe Ala Thr Tyr Tyr Cys
            20                  25                  30

<210> SEQ ID NO 1242
<211> LENGTH: 9
<212> TYPE: PRT
<213> ORGANISM: Homo sapiens

<400> SEQUENCE: 1242

Gln Gln Ser Tyr Thr Ala Pro Cys Thr
1               5

<210> SEQ ID NO 1243
<211> LENGTH: 11
<212> TYPE: PRT
<213> ORGANISM: Homo sapiens

<400> SEQUENCE: 1243

Phe Gly Gln Gly Thr Lys Leu Glu Ile Lys Arg
1               5                   10

<210> SEQ ID NO 1244
<211> LENGTH: 24
<212> TYPE: PRT
<213> ORGANISM: Homo sapiens

<400> SEQUENCE: 1244

Asp Val Val Met Thr Gln Ser Pro Cys Leu Pro Cys Leu His Leu Ile
1               5                   10                  15

Gly Asp Arg Val Thr Ile Thr Cys
            20

<210> SEQ ID NO 1245
<211> LENGTH: 11
<212> TYPE: PRT
<213> ORGANISM: Homo sapiens

<400> SEQUENCE: 1245

Arg Ala Ser Gln Ser Ile Arg Asp Tyr Leu Ser
1               5                   10

<210> SEQ ID NO 1246
<211> LENGTH: 15
<212> TYPE: PRT
<213> ORGANISM: Homo sapiens

<400> SEQUENCE: 1246

```
Trp Tyr Gln Gln Glu Pro Gly Lys Ala Pro Lys Leu Leu Ile Tyr
1               5                   10                  15


<210> SEQ ID NO 1247
<211> LENGTH: 7
<212> TYPE: PRT
<213> ORGANISM: Homo sapiens

<400> SEQUENCE: 1247

Ser Ala Ser Ser Leu Gln Ser
1               5


<210> SEQ ID NO 1248
<211> LENGTH: 32
<212> TYPE: PRT
<213> ORGANISM: Homo sapiens

<400> SEQUENCE: 1248

Gly Val Pro Ser Arg Phe Ser Gly Ser Gly Ser Gly Thr Asp Phe Thr
1               5                   10                  15

Leu Thr Ile Thr Asn Leu Gln Pro Glu Asp Phe Ala Thr Tyr Tyr Cys
            20                  25                  30


<210> SEQ ID NO 1249
<211> LENGTH: 10
<212> TYPE: PRT
<213> ORGANISM: Homo sapiens

<400> SEQUENCE: 1249

Leu Glu Lys Tyr Ser Phe Pro Arg Cys Thr
1               5                   10


<210> SEQ ID NO 1250
<211> LENGTH: 11
<212> TYPE: PRT
<213> ORGANISM: Homo sapiens

<400> SEQUENCE: 1250

Phe Gly Gln Gly Thr Lys Leu Asp Ile Lys Arg
1               5                   10


<210> SEQ ID NO 1251
<211> LENGTH: 23
<212> TYPE: PRT
<213> ORGANISM: Homo sapiens

<400> SEQUENCE: 1251

Asp Ile Gln Met Thr Gln Ser Pro Ser Ser Leu Ser Ala Ser Val Gly
1               5                   10                  15

Asp Arg Val Thr Ile Thr Cys
            20


<210> SEQ ID NO 1252
<211> LENGTH: 11
<212> TYPE: PRT
<213> ORGANISM: Homo sapiens

<400> SEQUENCE: 1252

Arg Ala Ser Gln Ser Ile Ser Ser Tyr Leu Asn
1               5                   10


<210> SEQ ID NO 1253
<211> LENGTH: 15
```

<212> TYPE: PRT
<213> ORGANISM: Homo sapiens

<400> SEQUENCE: 1253

Trp Tyr Gln Gln Lys Pro Gly Thr Ala Pro Lys Leu Leu Ile Ser
1 5 10 15

<210> SEQ ID NO 1254
<211> LENGTH: 7
<212> TYPE: PRT
<213> ORGANISM: Homo sapiens

<400> SEQUENCE: 1254

Asp Ala Ser Thr Leu Gln Ser
1 5

<210> SEQ ID NO 1255
<211> LENGTH: 32
<212> TYPE: PRT
<213> ORGANISM: Homo sapiens

<400> SEQUENCE: 1255

Gly Val Pro Ser Arg Phe Ser Gly Ser Gly Ser Gly Thr Glu Phe Thr
1 5 10 15

Leu Thr Ile Ser Asn Leu Gln Pro Glu Asp Phe Ala Thr Tyr Tyr Cys
20 25 30

<210> SEQ ID NO 1256
<211> LENGTH: 9
<212> TYPE: PRT
<213> ORGANISM: Homo sapiens

<400> SEQUENCE: 1256

Gln Gln Phe Asn Ser Tyr Val Trp Thr
1 5

<210> SEQ ID NO 1257
<211> LENGTH: 11
<212> TYPE: PRT
<213> ORGANISM: Homo sapiens

<400> SEQUENCE: 1257

Phe Gly Gln Gly Thr Lys Leu Glu Ile Lys Arg
1 5 10

<210> SEQ ID NO 1258
<211> LENGTH: 23
<212> TYPE: PRT
<213> ORGANISM: Homo sapiens

<400> SEQUENCE: 1258

Asp Ile Val Met Thr Gln Ser Pro Ser Thr Leu Ser Ala Ser Val Gly
1 5 10 15

Asp Arg Val Thr Val Thr Cys
20

<210> SEQ ID NO 1259
<211> LENGTH: 11
<212> TYPE: PRT
<213> ORGANISM: Homo sapiens

<400> SEQUENCE: 1259

Arg Ala Ser Gln Ser Ile Asn Ser Trp Leu Ala
1 5 10

<210> SEQ ID NO 1260
<211> LENGTH: 15
<212> TYPE: PRT
<213> ORGANISM: Homo sapiens

<400> SEQUENCE: 1260

Trp Tyr Gln Gln Lys Pro Gly Lys Ala Pro Lys Leu Leu Ile Tyr
1               5                   10                  15

<210> SEQ ID NO 1261
<211> LENGTH: 7
<212> TYPE: PRT
<213> ORGANISM: Homo sapiens

<400> SEQUENCE: 1261

Glu Ala Ser Ser Leu Glu Ser
1               5

<210> SEQ ID NO 1262
<211> LENGTH: 32
<212> TYPE: PRT
<213> ORGANISM: Homo sapiens

<400> SEQUENCE: 1262

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 1263
<211> LENGTH: 9
<212> TYPE: PRT
<213> ORGANISM: Homo sapiens

<400> SEQUENCE: 1263

Gln Gln Tyr Asp Ser Tyr Trp Leu Thr
1               5

<210> SEQ ID NO 1264
<211> LENGTH: 11
<212> TYPE: PRT
<213> ORGANISM: Homo sapiens

<400> SEQUENCE: 1264

Phe Gly Gly Gly Thr Lys Val Glu Ile Lys Arg
1               5                   10

<210> SEQ ID NO 1265
<211> LENGTH: 23
<212> TYPE: PRT
<213> ORGANISM: Homo sapiens

<400> SEQUENCE: 1265

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 1266
<211> LENGTH: 11
<212> TYPE: PRT
<213> ORGANISM: Homo sapiens

<400> SEQUENCE: 1266

Arg Ala Ser Gln Gly Val Ser Arg Trp Leu Ala
1 5 10

<210> SEQ ID NO 1267
<211> LENGTH: 15
<212> TYPE: PRT
<213> ORGANISM: Homo sapiens

<400> SEQUENCE: 1267

Trp Tyr Gln Gln Arg Pro Gly Glu Ala Pro Lys Leu Leu Ile Tyr
1 5 10 15

<210> SEQ ID NO 1268
<211> LENGTH: 7
<212> TYPE: PRT
<213> ORGANISM: Homo sapiens

<400> SEQUENCE: 1268

Gly Ala Ser Ser Leu Gln Ser
1 5

<210> SEQ ID NO 1269
<211> LENGTH: 32
<212> TYPE: PRT
<213> ORGANISM: Homo sapiens

<400> SEQUENCE: 1269

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 1270
<211> LENGTH: 9
<212> TYPE: PRT
<213> ORGANISM: Homo sapiens

<400> SEQUENCE: 1270

Gln Gln Tyr Asp Ser Phe Pro Leu Thr
1 5

<210> SEQ ID NO 1271
<211> LENGTH: 11
<212> TYPE: PRT
<213> ORGANISM: Homo sapiens

<400> SEQUENCE: 1271

Phe Gly Gly Gly Thr Lys Val Glu Ile Lys Arg
1 5 10

<210> SEQ ID NO 1272
<211> LENGTH: 23
<212> TYPE: PRT
<213> ORGANISM: Homo sapiens

<400> SEQUENCE: 1272

Glu Ile Val Leu Thr Gln Ser Pro Ala Thr Leu Ser Val Ser Pro Gly
1 5 10 15

Glu Arg Ala Thr Leu Ser Cys
20

<210> SEQ ID NO 1273

<211> LENGTH: 11
<212> TYPE: PRT
<213> ORGANISM: Homo sapiens

<400> SEQUENCE: 1273

Arg Ala Ser Gln Ser Val Ser Lys Phe Leu Ala
1 5 10

<210> SEQ ID NO 1274
<211> LENGTH: 15
<212> TYPE: PRT
<213> ORGANISM: Homo sapiens

<400> SEQUENCE: 1274

Trp Tyr Gln Gln Lys Arg Gly Gln Ala Pro Arg Leu Leu Ile Tyr
1 5 10 15

<210> SEQ ID NO 1275
<211> LENGTH: 7
<212> TYPE: PRT
<213> ORGANISM: Homo sapiens

<400> SEQUENCE: 1275

Gly Ala Ser Thr Arg Ala Thr
1 5

<210> SEQ ID NO 1276
<211> LENGTH: 32
<212> TYPE: PRT
<213> ORGANISM: Homo sapiens

<400> SEQUENCE: 1276

Gly Ile Pro Ala Arg Phe Ser Gly Ser Gly Ser Gly Thr Glu Phe Ala
1 5 10 15

Leu Thr Ile Ser Ser Leu Gln Ser Glu Asp Phe Ala Asp Tyr Tyr Cys
20 25 30

<210> SEQ ID NO 1277
<211> LENGTH: 9
<212> TYPE: PRT
<213> ORGANISM: Homo sapiens

<400> SEQUENCE: 1277

Gln Gln Tyr Asp Asn Trp Pro Ile Thr
1 5

<210> SEQ ID NO 1278
<211> LENGTH: 11
<212> TYPE: PRT
<213> ORGANISM: Homo sapiens

<400> SEQUENCE: 1278

Phe Gly Gln Gly Thr Arg Leu Glu Ile Lys Arg
1 5 10

<210> SEQ ID NO 1279
<211> LENGTH: 22
<212> TYPE: PRT
<213> ORGANISM: Homo sapiens

<400> SEQUENCE: 1279

Glu Thr Leu Thr Gln Ser Pro Ala Thr Leu Ser Val Ser Pro Gly Glu
1 5 10 15

Arg Ala Thr Leu Ser Cys

20

<210> SEQ ID NO 1280
<211> LENGTH: 11
<212> TYPE: PRT
<213> ORGANISM: Homo sapiens

<400> SEQUENCE: 1280

Arg Ala Ser Gln Ser Val Gly Ser Thr Leu Ala
1 5 10

<210> SEQ ID NO 1281
<211> LENGTH: 15
<212> TYPE: PRT
<213> ORGANISM: Homo sapiens

<400> SEQUENCE: 1281

Trp Tyr Gln Gln Lys Pro Gly Gln Ala Pro Arg Leu Leu Val Tyr
1 5 10 15

<210> SEQ ID NO 1282
<211> LENGTH: 7
<212> TYPE: PRT
<213> ORGANISM: Homo sapiens

<400> SEQUENCE: 1282

Gly Arg Ser Thr Arg Ala Thr
1 5

<210> SEQ ID NO 1283
<211> LENGTH: 32
<212> TYPE: PRT
<213> ORGANISM: Homo sapiens

<400> SEQUENCE: 1283

Gly Ile Pro Arg Arg Phe Ser Gly Ser Gly Ser Gly Thr Glu Phe Thr
1 5 10 15

Leu Thr Ile Ser Ser Leu Gln Ser Glu Asp Phe Ala Val Tyr Tyr Cys
20 25 30

<210> SEQ ID NO 1284
<211> LENGTH: 9
<212> TYPE: PRT
<213> ORGANISM: Homo sapiens

<400> SEQUENCE: 1284

Gln Gln Tyr Asn Ser Trp Pro Ile Thr
1 5

<210> SEQ ID NO 1285
<211> LENGTH: 11
<212> TYPE: PRT
<213> ORGANISM: Homo sapiens

<400> SEQUENCE: 1285

Phe Gly Gln Gly Thr Arg Leu Glu Ile Lys Arg
1 5 10

<210> SEQ ID NO 1286
<211> LENGTH: 23
<212> TYPE: PRT
<213> ORGANISM: Homo sapiens

<400> SEQUENCE: 1286

```
Glu Ile Val Leu Thr Gln Ser Pro Ser Ser Phe Ser Ala Ser Thr Gly
1               5                   10                  15

Asp Arg Val Thr Ile Thr Cys
            20


<210> SEQ ID NO 1287
<211> LENGTH: 11
<212> TYPE: PRT
<213> ORGANISM: Homo sapiens

<400> SEQUENCE: 1287

Arg Ala Ser Gln Gly Ile Asn Asn Tyr Leu Ala
1               5                   10


<210> SEQ ID NO 1288
<211> LENGTH: 15
<212> TYPE: PRT
<213> ORGANISM: Homo sapiens

<400> SEQUENCE: 1288

Trp Tyr Gln Gln Lys Pro Gly Lys Ala Pro Lys Leu Leu Ile Tyr
1               5                   10                  15


<210> SEQ ID NO 1289
<211> LENGTH: 7
<212> TYPE: PRT
<213> ORGANISM: Homo sapiens

<400> SEQUENCE: 1289

Ala Ala Ser Thr Leu Gln Ser
1               5


<210> SEQ ID NO 1290
<211> LENGTH: 32
<212> TYPE: PRT
<213> ORGANISM: Homo sapiens

<400> SEQUENCE: 1290

Gly Val Pro Ser Arg Phe Ser Gly Gly Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30


<210> SEQ ID NO 1291
<211> LENGTH: 9
<212> TYPE: PRT
<213> ORGANISM: Homo sapiens

<400> SEQUENCE: 1291

Gln Gln Tyr Tyr Ser Tyr Pro Leu Thr
1               5


<210> SEQ ID NO 1292
<211> LENGTH: 11
<212> TYPE: PRT
<213> ORGANISM: Homo sapiens

<400> SEQUENCE: 1292

Phe Gly Gly Gly Thr Lys Val Glu Ile Lys Arg
1               5                   10


<210> SEQ ID NO 1293
<211> LENGTH: 23
<212> TYPE: PRT
```

<213> ORGANISM: Homo sapiens

<400> SEQUENCE: 1293

Glu Ile Val Leu Thr Gln Ser Pro Ser Ser Leu Ser Ala Ala Val Gly
1 5 10 15

Asp Arg Val Thr Ile Thr Cys
20

<210> SEQ ID NO 1294
<211> LENGTH: 11
<212> TYPE: PRT
<213> ORGANISM: Homo sapiens

<400> SEQUENCE: 1294

Arg Ala Ser Gln Asn Ile Tyr Ser Tyr Leu Asn
1 5 10

<210> SEQ ID NO 1295
<211> LENGTH: 15
<212> TYPE: PRT
<213> ORGANISM: Homo sapiens

<400> SEQUENCE: 1295

Trp Tyr Gln Gln Lys Leu Gly Lys Ala Pro Asn Leu Leu Ile Tyr
1 5 10 15

<210> SEQ ID NO 1296
<211> LENGTH: 7
<212> TYPE: PRT
<213> ORGANISM: Homo sapiens

<400> SEQUENCE: 1296

Ala Val Phe Ser Leu Gln Ser
1 5

<210> SEQ ID NO 1297
<211> LENGTH: 32
<212> TYPE: PRT
<213> ORGANISM: Homo sapiens

<400> SEQUENCE: 1297

Gly Val Pro Ser Arg Phe Ser Gly Ser Gly Tyr Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 1298
<211> LENGTH: 9
<212> TYPE: PRT
<213> ORGANISM: Homo sapiens

<400> SEQUENCE: 1298

Gln Gln Ser Ser Ser Ser Pro Leu Thr
1 5

<210> SEQ ID NO 1299
<211> LENGTH: 11
<212> TYPE: PRT
<213> ORGANISM: Homo sapiens

<400> SEQUENCE: 1299

Phe Gly Gly Gly Thr Lys Val Glu Ile Lys Arg
1 5 10

<210> SEQ ID NO 1300
<211> LENGTH: 23
<212> TYPE: PRT
<213> ORGANISM: Homo sapiens

<400> SEQUENCE: 1300

Asp Ile Val Leu Thr Gln Ser Pro Ser Thr Leu Ser Ala Ser Val Gly
1 5 10 15

Asp Arg Val Thr Ile Ser Cys
20

<210> SEQ ID NO 1301
<211> LENGTH: 11
<212> TYPE: PRT
<213> ORGANISM: Homo sapiens

<400> SEQUENCE: 1301

Arg Ala Ser Arg Ser Ile Gly Trp Tyr Leu Asn
1 5 10

<210> SEQ ID NO 1302
<211> LENGTH: 15
<212> TYPE: PRT
<213> ORGANISM: Homo sapiens

<400> SEQUENCE: 1302

Trp Tyr Gln Gln Arg Pro Gly Lys Ala Pro Lys Leu Leu Ile Tyr
1 5 10 15

<210> SEQ ID NO 1303
<211> LENGTH: 7
<212> TYPE: PRT
<213> ORGANISM: Homo sapiens

<400> SEQUENCE: 1303

Ala Ala Ser Ser Leu His Asn
1 5

<210> SEQ ID NO 1304
<211> LENGTH: 32
<212> TYPE: PRT
<213> ORGANISM: Homo sapiens

<400> SEQUENCE: 1304

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 1305
<211> LENGTH: 9
<212> TYPE: PRT
<213> ORGANISM: Homo sapiens

<400> SEQUENCE: 1305

Gln Gln Ala Phe Gly Phe Pro Arg Thr
1 5

<210> SEQ ID NO 1306
<211> LENGTH: 11
<212> TYPE: PRT
<213> ORGANISM: Homo sapiens

<400> SEQUENCE: 1306

```
Phe Gly Gln Gly Thr Lys Val Glu Ile Lys Arg
1               5                   10


<210> SEQ ID NO 1307
<211> LENGTH: 124
<212> TYPE: PRT
<213> ORGANISM: Artificial Sequence
<220> FEATURE:
<223> OTHER INFORMATION: Synthetic amino acid sequence

<400> SEQUENCE: 1307

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Gly Met His Trp Val Arg Gln Ser Pro Gly Lys Gly Leu Glu Trp Val
        35                  40                  45

Ala Val Ile Trp Tyr Asp Gly Arg Asn Pro Tyr Tyr Ala Ala Ser Val
    50                  55                  60

Lys Gly Arg Phe Thr Ile Ser Arg Asp Asn Asp Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Leu Thr Arg Phe His Asp Thr Thr Phe Gly Val Phe Glu
            100                 105                 110

Met Trp Gly Pro Gly Thr Thr Val Thr Val Ser Ser
        115                 120


<210> SEQ ID NO 1308
<211> LENGTH: 106
<212> TYPE: PRT
<213> ORGANISM: Artificial Sequence
<220> FEATURE:
<223> OTHER INFORMATION: Synthetic amino acid sequence

<400> SEQUENCE: 1308

Glu Ile Val Leu Thr Gln Ser Pro Ser Phe Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Leu Tyr Thr
                85                  90                  95

Phe Gly Gln Gly Thr Lys Val Asp Ile Lys
            100                 105


<210> SEQ ID NO 1309
<211> LENGTH: 8
<212> TYPE: PRT
<213> ORGANISM: Artificial Sequence
<220> FEATURE:
<223> OTHER INFORMATION: Synthetic amino acid sequence

<400> SEQUENCE: 1309
```

-continued

```
Gly Phe Thr Phe Ser His Tyr Gly
1               5


<210> SEQ ID NO 1310
<211> LENGTH: 8
<212> TYPE: PRT
<213> ORGANISM: Artificial Sequence
<220> FEATURE:
<223> OTHER INFORMATION: Synthetic amino acid sequence

<400> SEQUENCE: 1310

Ile Trp Tyr Asp Gly Arg Asn Pro
1               5


<210> SEQ ID NO 1311
<211> LENGTH: 17
<212> TYPE: PRT
<213> ORGANISM: Artificial Sequence
<220> FEATURE:
<223> OTHER INFORMATION: Synthetic amino acid sequence

<400> SEQUENCE: 1311

Val Lys Asp Leu Thr Arg Phe His Asp Thr Thr Phe Gly Val Phe Glu
1               5                   10                  15

Met


<210> SEQ ID NO 1312
<211> LENGTH: 6
<212> TYPE: PRT
<213> ORGANISM: Artificial Sequence
<220> FEATURE:
<223> OTHER INFORMATION: Synthetic amino acid sequence

<400> SEQUENCE: 1312

Gln Gly Ile Ser Ser Trp
1               5


<210> SEQ ID NO 1313
<211> LENGTH: 3
<212> TYPE: PRT
<213> ORGANISM: Artificial Sequence
<220> FEATURE:
<223> OTHER INFORMATION: Synthetic amino acid sequence

<400> SEQUENCE: 1313

Ala Ala Ser
1


<210> SEQ ID NO 1314
<211> LENGTH: 6
<212> TYPE: PRT
<213> ORGANISM: Artificial Sequence
<220> FEATURE:
<223> OTHER INFORMATION: Synthetic amino acid sequence

<400> SEQUENCE: 1314

Gln Gln Tyr Ser Ser Leu
1               5
```